United States Patent
Huang et al.

(10) Patent No.: US 9,796,712 B2
(45) Date of Patent: *Oct. 24, 2017

(54) HETEROARYL COMPOUNDS FOR KINASE INHIBITION

(71) Applicant: Ariad Pharmaceuticals, Inc., Cambridge, MA (US)

(72) Inventors: Wei-Sheng Huang, Acton, MA (US); Yongjin Gong, Belmont, MA (US); Feng Li, Winchester, MA (US); Nicholas E. Bencivenga, Malden, MA (US); David C. Dalgarno, Brookline, MA (US); Anna Kohlmann, Winchester, MA (US); William C. Shakespeare, Southborough, MA (US); Ranny M. Thomas, Sharon, MA (US); Xiaotian Zhu, Newton, MA (US); Angela V. West, Franklin, MA (US); Willmen Youngsaye, Boston, MA (US); Yun Zhang, Acton, MA (US); Tianjun Zhou, Belmont, MA (US)

(73) Assignee: ARIAD Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/600,023

(22) Filed: May 19, 2017

(65) Prior Publication Data

US 2017/0253594 A1    Sep. 7, 2017

Related U.S. Application Data

(63) Continuation of application No. 15/319,637, filed as application No. PCT/US2015/030576 on May 13, 2015.

(60) Provisional application No. 62/014,500, filed on Jun. 19, 2014.

(51) Int. Cl.
| | | |
|---|---|---|
| *A61K 31/506* | (2006.01) |
| *C07D 403/14* | (2006.01) |
| *C07D 471/04* | (2006.01) |
| *C07D 405/12* | (2006.01) |
| *C07F 9/6558* | (2006.01) |
| *C07D 401/14* | (2006.01) |
| *C07D 403/04* | (2006.01) |

(52) U.S. Cl.
CPC ......... *C07D 471/04* (2013.01); *C07D 401/14* (2013.01); *C07D 403/04* (2013.01); *C07D 405/12* (2013.01); *C07F 9/65583* (2013.01)

(58) Field of Classification Search
CPC ... C07D 403/14; C07D 403/04; A61K 31/506
USPC ......................................... 544/331; 514/275
See application file for complete search history.

(56) References Cited

U.S. PATENT DOCUMENTS

| | | |
|---|---|---|
| 2005/0288327 A1 | 12/2005 | Uesugi et al. |
| 2009/0306101 A1 | 12/2009 | Solca et al. |
| 2010/0298156 A1 | 11/2010 | Lee-Hoeflich et al. |
| 2011/0263541 A1 | 10/2011 | Luo et al. |
| 2012/0094999 A1 | 4/2012 | Gray et al. |

FOREIGN PATENT DOCUMENTS

| | | |
|---|---|---|
| WO | 8705781 | 10/1987 |
| WO | 8705897 | 10/1987 |
| WO | 8705898 | 10/1987 |
| WO | 2007050347 | 5/2007 |
| WO | 2008032858 | 3/2008 |
| WO | 2010093808 | 8/2010 |
| WO | 2012020215 | 2/2012 |
| WO | 2012068440 | 5/2012 |
| WO | 2012068450 | 5/2012 |
| WO | 2012158658 | 11/2012 |
| WO | 2013014448 | 1/2013 |
| WO | 2012170113 | 11/2013 |
| WO | 2013170115 | 11/2013 |
| WO | 2014160478 | 10/2014 |
| WO | 2015039612 | 3/2015 |
| WO | 2015039613 | 3/2015 |

OTHER PUBLICATIONS

Cross, Darren A.E. et al., AZD9291, an Irreversible EGFR TKI, Overcomes T790M-Mediated Resistance to EGFR Inhibitors in Lung Cancer, Cancer Discovery, vol. 4, Issue 9, pp. 1046-1061, Jun. 3, 2014.

*Primary Examiner* — Charanjit Aulakh
(74) *Attorney, Agent, or Firm* — Honigman Miller Schwartz and Cohn LLP; Lucy X. Yang; Jonathan P. O'Brien

(57) ABSTRACT

Compounds and pharmaceutical compositions that modulate kinase activity, including mutant EGFR and mutant HER2 kinase activity, and compounds, pharmaceutical compositions, and methods of treatment of diseases and conditions associated with kinase activity, including mutant EGFR and mutant HER2 activity, are described herein.

15 Claims, No Drawings

HETEROARYL COMPOUNDS FOR KINASE INHIBITION

CROSS-REFERENCE TO RELATED APPLICATIONS

Priority Claim

This application is a continuation of U.S. patent application Ser. No. 15/319,637 filed Dec. 16, 2016, which is a National Stage entry of PCT/US2015/030576 filed May 13, 2015, which claims priority under 35 U.S.C. §119(e) to U.S. Provisional Patent Application No. 62/014,500, filed Jun. 19, 2014. The entire contents of the aforementioned applications are herein incorporated by reference.

SEQUENCE LISTING

The instant application contains a Sequence Listing which has been submitted electronically in ASCII format and is hereby incorporated by reference in its entirety. Said ASCII copy, created on May 12, 2015, is named 477APCT_SL.txt and is 767 bytes in size.

BACKGROUND

Biological signal transduction refers to the transmission of stimulatory or inhibitory signals into and within a cell leading, often via a cascade of signal transmission events, to a biological response within the cell. Many signal transduction pathways and their biological responses have been studied. Defects in various components of signal transduction pathways have been found to account for a large number of diseases, including numerous forms of cancer, inflammatory disorders, metabolic disorders, vascular and neuronal diseases. These defects can often occur at the gene level, where DNA insertions, deletions or translocations can, for example, cause cells to proliferate uncontrollably in the case of some cancers.

Signal transduction is often mediated by certain proteins called kinases. Kinases can generally be classified into protein kinases and lipid kinases, and certain kinases exhibit dual specificities. Protein kinases are enzymes that catalyze the phosphorylation of other proteins and/or themselves (i.e., autophosphorylation) and can be generally classified based upon their substrate utilization, e.g.: tyrosine kinases which predominantly phosphorylate substrates on tyrosine residues (e.g., KIT, erb2, PDGF receptor, EGF receptor, VEGF receptor, src, and abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Epidermal growth factor receptor (EGFR) belongs to a family of receptor tyrosine kinases (RTKs) that include EGFR/ERBB1, HER2/ERBB2/NEU, HER3/ERBB3, and HER4/ERBB4. The binding of a ligand, such as epidermal growth factor (EGF), induces a conformational change in EGFR that facilitates receptor homo- or heterodimer formation, leading to activation of EGFR tyrosine kinase activity. Activated EGFR then phosphorylates its substrates, resulting in activation of multiple downstream pathways within the cell, including the PI3K-AKT-mTOR pathway, which is involved in cell survival, and the RAS-RAF-MEK-ERK pathway, which is involved in cell proliferation. (Chong et al. Nature Med. 2013; 19(11):1389-1400).

Approximately 10% of patients with NSCLC in the US (10,000 cases/year) and 35% in East Asia are reported to have tumor-associated EGFR mutations. (Lynch et al. N Engl J Med. 2004; 350(21):2129-39). The vast majority of NSCLC cases having an EGFR mutation do not also have a mutation in another oncogene (e.g., KRAS mutations, ALK rearrangements, etc.). EGFR mutations mostly occur within EGFR exons 18-21, which encode a portion of the EGFR kinase domain. EGFR mutations are usually heterozygous, with amplification of mutant allele copy number. Approximately 90% of these mutations are exon 19 deletions or exon 21 L858R point mutations. These mutations increase the kinase activity of EGFR, leading to hyperactivation of downstream pro-survival signaling pathways. (Pao et. al. Nat Rev Cancer 2010; 10:760-774).

Small deletions, insertions or point mutations in the EGFR kinase domain have been cataloged and described at length in the scientific literature. See e.g., Sharma, Nat Re. Cancer 2007; 7:169 (exon 19 mutations characterized by in-frame deletions of amino-acid 747 account for 45% of mutations, exon 21 mutations resulting in L858R substitutions account for 40-45% of mutations, and the remaining 10% of mutations involve exon 18 and 20); Sordella et al., Science 2004; 305:1163; and Mulloy et al., Cancer Res 2007; 67:2325. EGFR mutants also include those with a combination of two or more mutations, such as those described herein. For example, "DT" refers to a T790M gatekeeper point mutation in exon 20 and a five amino acid deletion in exon 19 (delE746_A750). Another common mutation combination is "LT" that includes the T790M gatekeeper point mutation and the L858R point mutation in exon 21.

EGFR exon 20 insertions reportedly comprise approximately 4-9.2% of all EGFR mutant lung tumors (Arcila et al. 2013; 12(2):220-9; Mitsudomi and Yatabe FEBS J. 2010; 277(2):301-8; Oxnard et al. J Thorac Oncol. 2013; 8(2):179-84). Most EGFR exon 20 insertions occur in the region encoding amino acids 767 through 774 of exon 20, within the loop that follows the C-helix of the kinase domain of EGFR (Yasuda et al. Lancet Oncol. 2012; 13(1):e23-31).

EGFR exon 20 insertion mutants, other than A763_Y764insFQEA, are associated in preclinical models, for the most part, with lower sensitivity to clinically achievable doses of the reversible EGFR TKIs, erlotinib (Tarceva) and gefitinib (Iressa), and of the irreversible EGFR TKIs neratinib, afatinib (Gilotrif), and dacomitinib (Engelman et al. Cancer Res. 2007; 67(24):11924-32; Li et al. Oncogene 2008:27(34):4702-11; Yasuda, et al. 2012; Yasuda et al. Sci Transl Med. 2013; 5(216):216ra177; Yuza et al. Cancer Biol Ther. 2007; 6(5):661-7), and of the mutant-selective covalent EGFR TKIs WZ4002 (Zhou et al. Nature 2009; 462 (7276):1070-4) and CO-1686 (Walter et al. Cancer Discov 2013; 3(12):1404-15). The crystal structure of a representative TKI-insensitive mutant (D770_N771insNPG) revealed that it has an unaltered ATP-binding pocket and that, unlike EGFR sensitizing mutations, it activates EGFR without increasing its affinity for ATP (Yasuda et al. 2013).

Patients with tumors harboring EGFR exon 20 insertion mutations involving amino acids A767, S768, D770, P772 and H773 don't respond to gefitinib or erlotinib (Wu et al. Clin Cancer Res. 2008; 14(15):4877-82; Wu et al. Clin Cancer Res. 2011; 17(11):3812-21; Yasuda et al. 2012). In retrospective and prospective analyses of patients with NSCLCs harboring typical EGFR exon 20 insertions, most displayed progressive disease in the course of treatment with gefitinib or erlotinib or afatinib (Yasuda et al. 2012; Yasuda et al. 2013).

HER2 mutations are reportedly present in 2-4% of NSCLC (Buttitta et al. Int J Cancer 2006; 119:2586-2591; Shigematsu et al. Cancer Res 2005; 65:1642-6; Stephens et al. Nature 2004; 431:525-6). The most common mutation is an in-frame insertion within exon 20. In 83% of patients having HER2 associated NSCLC, a four amino acid YVMA insertion mutation occurs at codon 775 in exon 20 of HER2. (Arcila et al. Clin Cancer Res 2012; 18:4910-4918). HER2 mutations appear more common in "never smokers" (defined as less than 100 cigarettes in a patient's lifetime) with adenocarcinoma histology (Buttitta et al. 2006; Shigematsu et al. 2005; Stephens et al. 2004). However, HER2 mutations can also be found in other subsets of NSCLC, including in former and current smokers as well as in other histologies (Buttitta et al. 2006; Shigematsu et al. 2005; Stephens et al. 2004). The exon 20 insertion results in increased HER2 kinase activity and enhanced signaling through downstream pathways, resulting in increased survival, invasiveness, and tumorigenicity (Wang et al. Cancer Cell 2006; 10:25-38). Tumors harboring the HER2 YVMA mutation are largely resistant to known EGFR inhibitors. (Arcila et al. 2012).

Disclosed herein are compounds with inhibitory activity against a) mutant EGFR, such as EGFR having one or more exon 20 insertions, DT or LT, and b) mutant HER2 such as HER2 having a YVMA insertion mutation. Also disclosed are methods for preparing the compounds and pharmaceutical compositions containing them. In addition, methods are disclosed for inhibiting mutant EGFR bearing an exon 20 insertion mutation or bearing a, DT or LT mutation, and for inhibiting mutant HER2, as well as methods of treatment of disease mediated by any of those mutant EGFR or HER2 proteins, including cases that are resistant to known treatments of care

SUMMARY

Compounds are disclosed herein that are capable of inhibiting mutant EGFR proteins, e.g., EGFR having one or more mutations in the exon 20 domain. In some embodiments, compounds disclosed herein selectively inhibit mutant EGFR, such as EGFR having one or more exon 20 mutations, over wild-type EGFR. In other embodiments, the compounds selectively inhibit mutant EGFR, such as EGFR having an exon 20 point mutation together with an exon 19 or exon 21 mutation. Such inhibitors can be effective in ameliorating diseases and disorders associated with mutant EGFR activity.

Compounds disclosed herein are capable of inhibiting mutant HER2, e.g., HER2 having one or more mutations in the exon 20 domain. In some embodiments, the disclosed compounds selectively inhibit mutant HER2, such as HER2 having one or more exon 20 mutations, over wild-type EGFR. Such inhibitors can be effective in ameliorating diseases and disorders associated with mutant HER2 activity.

One aspect of the invention provides compounds of Formula I:

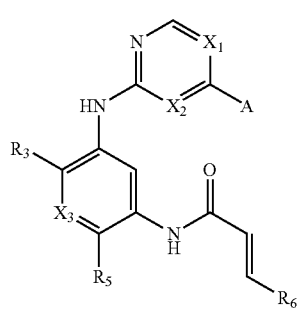

Formula I or a pharmaceutically acceptable form thereof, wherein:
A is selected from

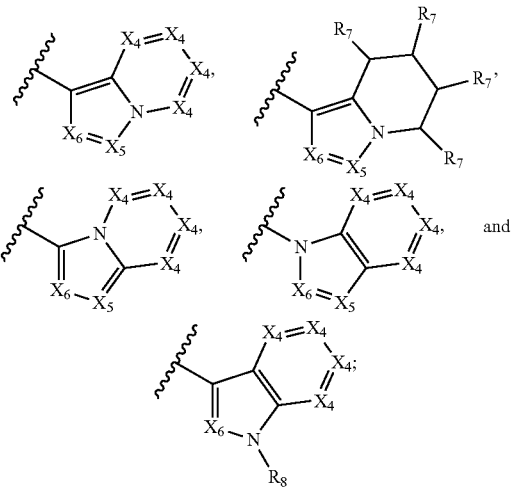

and $X_1$ is selected from N and $CR_1$;
$X_2$ is selected from N and $CR_2$;
$X_3$ is selected from N and $CR_4$;
each $X_4$ is independently selected from N and $CR_7$;
$X_5$ is selected from N and $CR_8$;
$X_6$ is selected from N and $CR_9$;
$R_1$ is selected from H, acyl, alkyl, alkenyl, alkynyl, alkoxy, aryloxy, alkoxycarbonyl, amido, amino, carbonate, carbamate, carbonyl, carboxyl, ester, halo, CN, $NO_2$, hydroxy, phosphate, phosphonate, phosphinate, phosphine oxide, mercapto, thio, alkylthio, arylthio, thiocarbonyl, sulfonyl, sulfonamidyl, sulfoxyl, sulfonate, urea, cycloalkyl, heterocyclyl, aryl, and heteroaryl, each of which is substituted with 0, 1, 2, or 3 $R_{12}$;
$R_2$, $R_3$, and $R_4$ are each independently selected from H, alkyl, alkoxy, halo, CN, and $NO_2$, each of which is substituted with 0, 1, 2, or 3 $R_{12}$;
$R_5$ is selected from H, alkyl, alkenyl, alkynyl, $-NR_{10}R_{11}$, $-OR_{11}$, and $-SR_{11}$, each of which is independently substituted with 0, 1, 2, or 3 $R_{12}$; or when $R_5$ is $-NR_{10}R_{11}$, then $R_{10}$ and $R_{11}$ can be taken together with the nitrogen atom to which they are attached to form a heterocyclyl or heteroaryl group, each of which is substituted with 0, 1, 2, or 3 $R_{12}$;
$R_4$ and $R_5$ can be taken together with the carbon atoms to which they are attached to form a cycloalkyl, heterocyclyl, aryl, or heteroaryl group, each of which is substituted with 0, 1, 2, or 3 $R_{12}$;
$R_6$ is selected from H, acyl, alkyl, amino, halo, CN, cycloalkyl, heterocycloalkyl, aryl, and heteroaryl, each of which is substituted with 0, 1, 2, or 3 $R_{12}$;
each $R_7$ is independently selected from H, alkyl, alkenyl, alkynyl, alkoxy, amido, amino, carbonyl, ester, halo, CN, and $NO_2$, each of which is substituted with 0, 1, 2, or 3 $R_{12}$; and wherein any two adjacent $R_7$ groups can be taken together with the carbon atoms to which they are attached to form a cycloalkyl, heterocyclyl, aryl, or heteroaryl ring, each of which is substituted with 0, 1, 2, or 3 $R_{12}$;
$R_8$ is selected from H, acyl, alkyl, amido, amino, carbamate, carbonyl, and urea, each of which is substituted with 0, 1, 2, or 3 $R_{12}$;
$R_9$ is selected from H, alkyl, alkenyl, alkynyl, alkoxy, amino, amido, ester, halo, CN, $NO_2$, cycloalkyl, heterocyclyl, aryl, and heteroaryl, each of which is substituted with 0, 1, 2, or 3 $R_{12}$;
each $R_{10}$ and $R_{11}$ are independently selected from H, acyl, alkyl, carbonyl, cycloalkyl, heterocycloalkyl, aryl, and heteroaryl, each of which is independently substituted with 0, 1, 2, or 3 $R_{12}$; and each $R_{12}$ is independently selected from acyl, alkyl, alkenyl, alkynyl, alkoxy, aryloxy, alkoxycarbonyl, amido, amino, carbonate, carbamate, carbonyl, ester, halo, CN, $NO_2$, hydroxyl, phosphate, phosphonate, phosphinate, phosphine oxide, thio, alkylthio, arylthio, thiocarbonyl, sulfonyl, sulfonamidyl, sulfoxyl, sulfonate, urea, cycloalkyl, heterocycloalkyl, aryl, and heteroaryl.

In the following embodiments, all variables are as described for Formula I and/or elsewhere below.

Formula I includes a compound of Formula Aa:

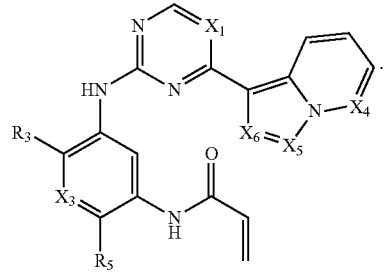

Formula Aa

Formula I includes a compound of Formula Ab:

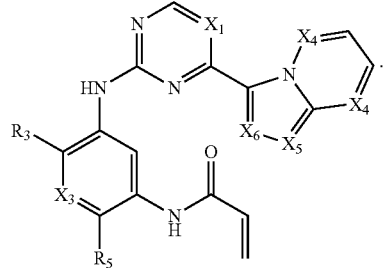

Formula Ab

Formula I includes a compound of Formula Ac:

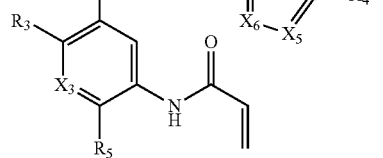

Formula Ac

Formula I includes a compound of Formula Ad:

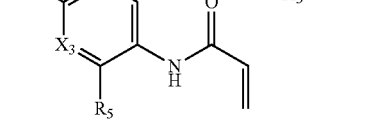

Formula Ad

Formula I includes a compound of Formula Ae:

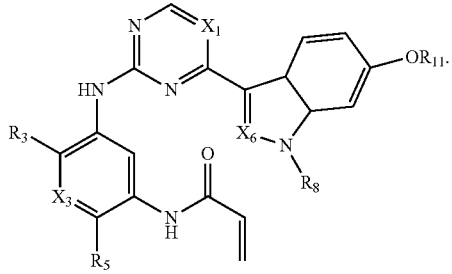

Formula Ae

Formula I includes a compound of Formula Af:

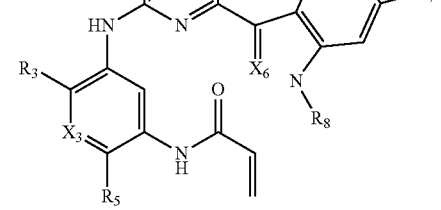

Formula Af

Formula I includes a compound of Formula Ba:

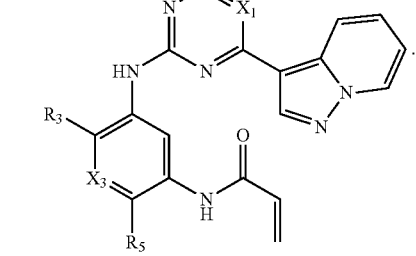

Formula Ba

Formula I includes a compound of Formula Bb:

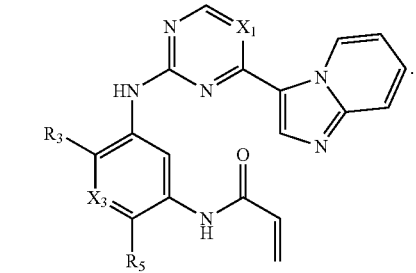

Formula Bb

Formula I includes a compound of Formula Bc:

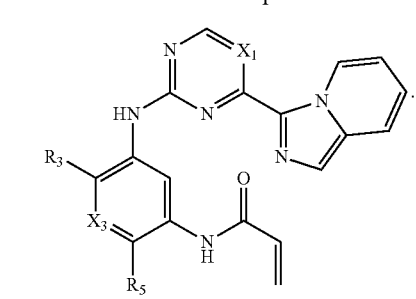

Formula Bc

Formula I includes a compound of Formula Bd:

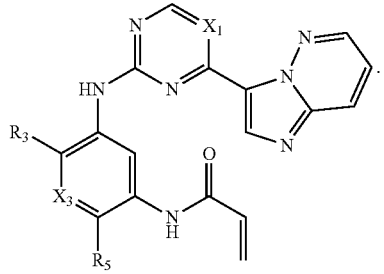
Formula Bd

Formula I includes a compound of Formula Be:

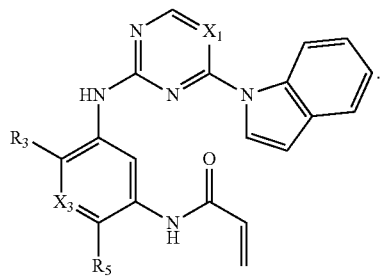
Formula Be

Formula I includes a compound of Formula Bf:

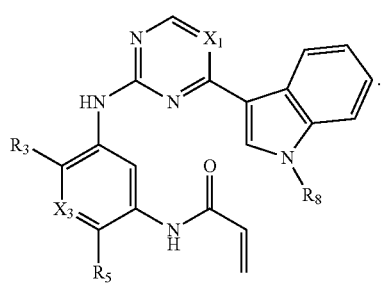
Formula Bf

Formula I includes a compound of Formula Bg:

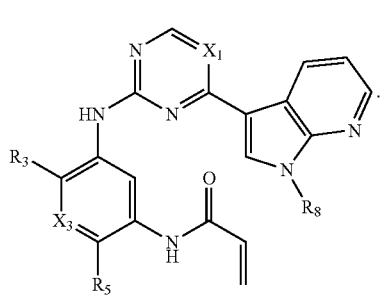
Formula Bg

Formula I includes a compound of Formula Bh:

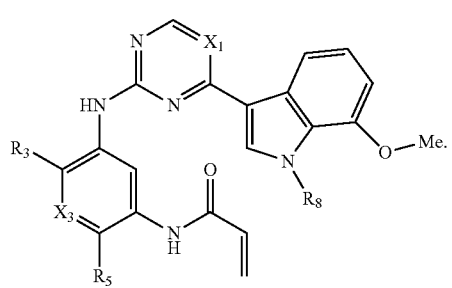
Formula Bh

Formula I includes a compound of Formula Bi:

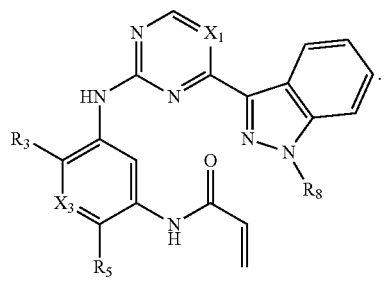
Formula Bi

A method is also disclosed herein for treating cancer associated with one or more insertion or deletion mutations in the exon 20 domain of EGFR or of HER2, comprising administering to a subject in need thereof, a therapeutically effective amount of a compound of Formula I.

A composition (e.g., a pharmaceutical composition) is also disclosed comprising a compound as described herein and one or more pharmaceutically acceptable excipients. In some embodiments, provided herein is a method of inhibiting exon 20 mutant EGFR, comprising contacting the exon 20 mutant EGFR with an effective amount of a compound or pharmaceutical composition as described herein. In some embodiments, a method is provided for inhibiting exon 20 mutant EGFR wherein said exon 20 mutant EGFR is present in a cell. This inhibition can be selective for exon 20 mutant EGFR over wild type. In other aspects, the inhibition can take place in a subject suffering from a disorder selected from various cancers, such as but not limited to, NSCLC, colorectal cancer, pancreatic cancer, and head and neck cancers. In some embodiments, a second therapeutic agent can be administered to the subject.

In one aspect, provided herein are compounds of Formula I:

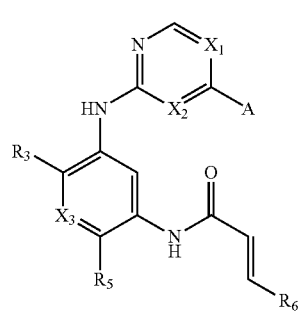
Formula I wherein:
A is selected from

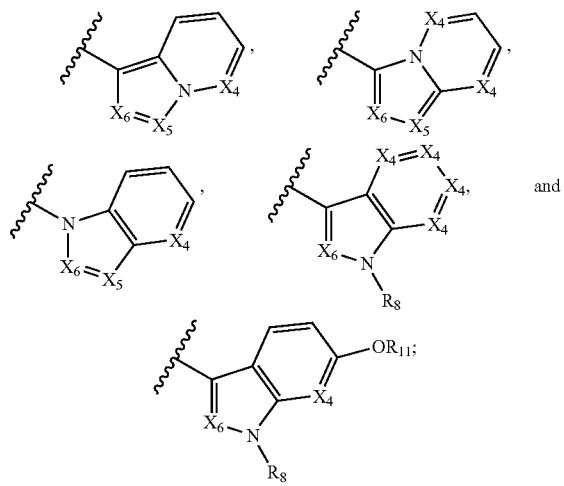

$X_1$ is selected from

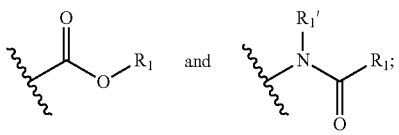

$X_2$ is selected from N and $CR_2$;
$X_3$ is selected from N and $CR_4$;
each $X_4$ is independently selected from N and $CR_7$;
$X_5$ is selected from N and $CR_8$;
$X_6$ is selected from N and $CR_9$;
each $R_1$ is independently selected from alkyl, alkenyl, alkynyl, cycloalkyl, heterocyclyl, aryl, and heteroaryl, each of which is substituted with 0, 1, 2, or 3 $R_{12}$;
$R_1'$ is selected from H and alkyl, each of which is substituted with 0, 1, 2, or 3 $R_{12}$;
$R_2$, $R_3$, and $R_4$ are each independently selected from H, alkyl, alkoxy, halo, CN, and $NO_2$, each of which is substituted with 0, 1, 2, or 3 $R_{12}$;
$R_5$ is selected from H, alkyl, alkenyl, alkynyl, —$NR_{10}R_{11}$, —$OR_{11}$, and —$SR_{11}$, each of which is independently substituted with 0, 1, 2, or 3 $R_{12}$; or when $R_5$ is —$NR_{10}R_{11}$, then $R_{10}$ and $R_{11}$ can be taken together with the nitrogen atom to which they are attached to form a heterocyclyl or heteroaryl group, each of which is substituted with 0, 1, 2, or 3 $R_{12}$;
$R_4$ and $R_5$ can be taken together with the carbon atoms to which they are attached to form a cycloalkyl, heterocyclyl, aryl, or heteroaryl group, each of which is substituted with 0, 1, 2, or 3 $R_{12}$;
$R_6$ is selected from H, acyl, alkyl, amino, halo, CN, cycloalkyl, heterocycloalkyl, aryl, and heteroaryl, each of which is substituted with 0, 1, 2, or 3 $R_{12}$;
each $R_7$ is independently selected from H, alkyl, alkenyl, alkynyl, alkoxy, amido, amino, carbonyl, ester, halo, CN, and $NO_2$, each of which is substituted with 0, 1, 2, or 3 $R_{12}$; and wherein any two adjacent $R_7$ groups can be taken together with the carbon atoms to which they are attached to form a cycloalkyl, heterocyclyl, aryl, or heteroaryl ring, each of which is substituted with 0, 1, 2, or 3 $R_{12}$;

$R_8$ is selected from H, acyl, alkyl, amido, amino, carbamate, carbonyl, and urea, each of which is substituted with 0, 1, 2, or 3 $R_{12}$;
$R_9$ is selected from H, alkyl, alkenyl, alkynyl, alkoxy, amino, amido, ester, halo, CN, $NO_2$, cycloalkyl, heterocyclyl, aryl, and heteroaryl, each of which is substituted with 0, 1, 2, or 3 $R_{12}$;
each $R_{10}$ and $R_{11}$ are independently selected from H, acyl, alkyl, carbonyl, cycloalkyl, heterocycloalkyl, aryl, and heteroaryl, each of which is independently substituted with 0, 1, 2, or 3 $R_{12}$; and
each $R_{12}$ is independently selected from acyl, alkyl, alkenyl, alkynyl, alkoxy, aryloxy, alkoxycarbonyl, amido, amino, carbonate, carbamate, carbonyl, ester, halo, CN, $NO_2$, hydroxyl, phosphate, phosphonate, phosphinate, phosphine oxide, urea, cycloalkyl, heterocycloalkyl, aryl, and heteroaryl.

In the following embodiments, all variables are as described for Formula I and/or in further aspects of the disclosure below.

A method is provided for treating cancer associated with mutant EGFR or mutant HER2, comprising administering to a subject in need thereof, a therapeutically effective amount of a compound of Formula I. In certain embodiments, compounds disclosed herein selectively modulate mutant EGFR, such as, but not limited to, EGFR having one or more insertion, point, or deletion mutations in the exon 19, 20, and/or 21 domain. In other embodiments, compounds disclosed herein selectively modulate mutant HER2, such as, but not limited to, HER2 having one or more insertion, point, or deletion mutations in the exon 20 domain. In some embodiments, compounds disclosed herein selectively modulate mutant EGFR having one or more insertion mutations in the exon 20 domain. In other embodiments, compounds disclosed herein selectively modulate mutant EGFR having one or more deletion mutations in the exon 20 domain. In other embodiments, compounds disclosed herein selectively modulate mutant EGFR having one or more point mutations in the exon 20 domain. In other embodiments, compounds disclosed herein selectively modulate mutant EGFR having one or more insertion or deletion mutations in the exon 19 domain. In other embodiments, compounds disclosed herein selectively modulate mutant EGFR having one or more insertion, deletion or point mutations in the exon 21 domain.

In some embodiments, disclosed compounds selectively inhibit mutant EGFR, having one or more insertion or deletion mutations, over wild-type EGFR. In other embodiments, disclosed compounds selectively inhibit mutant EGFR having an exon 20 point mutation concomitantly with an exon 19 deletion or an exon 21 point mutation. In a further embodiment, disclosed compounds selectively inhibit mutant EGFR having one or more exon 19 deletion mutations. In other embodiments, compounds disclosed herein selectively inhibit mutant EGFR, having an exon 21 point mutation (e.g., L858R). By way of non-limiting example, the ratio of selectivity can be greater than a factor of about 10, greater than a factor of about 20, greater than a factor of about 30, greater than a factor of about 40, greater than a factor of about 50, greater than a factor of about 60, greater than a factor of about 70, greater than a factor of about 80, greater than a factor of about 100, greater than a factor of about 120, or greater than a factor of about 150, where selectivity can be measured by in vitro assays known in the art. Non-limiting examples of assays to measure selectivity include enzymatic assays, cellular proliferation assays, and EGFR phosphorylation assays. In one embodiment, selectivity can be determined by cellular proliferation assays. In another embodiment, selectivity can be determined by EGFR phosphorylation assays. In some embodiments, the mutant EGFR inhibitory activity of a compound as disclosed herein can be less than about 1000 nM, less than about 100 nM, less than about 50 nM, less than about 30 nM, or less than about 10 nM.

In some embodiments, a composition (e.g., a pharmaceutical composition) is provided comprising a compound as described herein and one or more pharmaceutically acceptable excipients. In some embodiments, provided herein is a method of inhibiting exon 20 mutant EGFR, comprising contacting the exon 20 mutant EGFR with an effective amount of a compound or pharmaceutical composition as described herein. In some embodiments, a method is provided for inhibiting exon 20 mutant EGFR wherein said exon 20 mutant EGFR is present in a cell. This inhibition can be selective for exon 20 mutant EGFR over wild type EGFR. In other aspects, the inhibition can take place in a subject suffering from a disorder selected from various cancers, such as but not limited to, NSCLC, colorectal cancer, pancreatic cancer, and head and neck cancers. In some embodiments, a second therapeutic agent can be administered to the subject.

Some embodiments provide a method of preparing a compound as described herein.

Some embodiments provide a reaction mixture comprising a compound as described herein.

Some embodiments provide a kit comprising a compound as described herein.

Some embodiments provide a method for treating a disease or disorder described herein, the method comprising administering a therapeutically effective amount of a compound or pharmaceutical composition described herein to a subject.

Some embodiments provide a method for treating an exon 20 mutant EGFR mediated disorder in a subject, the method comprising administering a therapeutically effective amount of a compound or pharmaceutical composition described herein to a subject.

Some embodiments provide a method for treating an exon 20 mutant HER2 mediated disorder in a subject, the method comprising administering a therapeutically effective amount of a compound or pharmaceutical composition described herein to a subject.

Some embodiments provide a use of a compound or a pharmaceutical composition described herein for the treatment of a disease or disorder described herein in a subject.

Some embodiments provide a use of a compound or a pharmaceutical composition described herein for the treatment of an exon 20 mutant EGFR disorder in a subject.

Some embodiments provide a use of a compound or a pharmaceutical composition described herein for the treatment of an exon 20 mutant HER2 disorder in a subject.

Some embodiments provide a use of a compound or a pharmaceutical composition described herein in the manufacture of a medicament for the treatment of a disease or disorder described herein in a subject.

Some embodiments provide use of a compound or a pharmaceutical composition described herein in the manufacture of a medicament for the treatment of an exon 20 mutant EGFR mediated disorder in a subject.

Some embodiments provide a use of a compound or a pharmaceutical composition described herein in the manufacture of a medicament for the treatment of an exon 20 mutant HER2 mediated disorder in a subject.

INCORPORATION BY REFERENCE

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

DESCRIPTION

One embodiment herein provides compounds, and their pharmaceutically acceptable forms, including, but not limited to, salts, hydrates, solvates, isomers, prodrugs, and isotopically labeled derivatives thereof.

Another embodiment herein provides methods of treating and/or managing various diseases and disorders, which comprises administering to a patient a therapeutically effective amount of a compound provided herein, or a pharmaceutically acceptable form (e.g., salts, hydrates, solvates, isomers, prodrugs, and isotopically labeled derivatives) thereof. Non-limiting examples of diseases and disorders are described herein.

Another embodiment herein provides methods of preventing various diseases and disorders, which comprises administering to a patient in need of such prevention a prophylactically effective amount of a compound provided herein, or a pharmaceutically acceptable form (e.g., salts, hydrates, solvates, isomers, prodrugs, and isotopically labeled derivatives) thereof. Non-limiting examples of diseases and disorders are described herein.

In other embodiments, a compound provided herein, or a pharmaceutically acceptable form (e.g., salts, hydrates, solvates, isomers, prodrugs, and isotopically labeled derivatives) thereof, can be administered in combination with another drug ("second active agent") or treatment. Second active agents include small molecules and large molecules (e.g., proteins and antibodies), non-limiting examples of which are provided herein, as well as stem cells. Other methods or therapies that can be used in combination with the administration of compounds provided herein include, but are not limited to, surgery, blood transfusions, immunotherapy, biological therapy, radiation therapy, and other non-drug based therapies presently used to treat, prevent or manage various disorders described herein.

Also provided herein are pharmaceutical compositions (e.g., single unit dosage forms) that can be used in the methods provided herein. In one embodiment, pharmaceutical compositions comprise a compound provided herein, or a pharmaceutically acceptable form (e.g., salts, hydrates, solvates, isomers, prodrugs, and isotopically labeled derivatives) thereof, and optionally one or more second active agents.

While specific embodiments have been discussed, the specification is illustrative only and not restrictive. Many variations of this disclosure will become apparent to those skilled in the art upon review of this specification.

Unless defined otherwise, all technical and scientific terms used herein have the same meaning as is commonly understood by one of skill in the art to which this specification pertains.

Definitions

As used in the specification and claims, the singular form "a", "an" and "the" includes plural references unless the context clearly dictates otherwise.

As used herein, "agent" or "biologically active agent" or "second active agent" refers to a biological, pharmaceutical, or chemical compound or other moiety. Non-limiting examples include simple or complex organic or inorganic molecules, a peptide, a protein, an oligonucleotide, an antibody, an antibody derivative, an antibody fragment, a vitamin, a vitamin derivative, a carbohydrate, a toxin, or a chemotherapeutic compound, and metabolites thereof. Various compounds can be synthesized, for example, small molecules and oligomers (e.g., oligopeptides and oligonucleotides), and synthetic organic compounds based on various core structures. In addition, various natural sources can provide active compounds, such as plant or animal extracts, and the like. A skilled artisan can readily recognize that there is no limit as to the structural nature of the agents of this disclosure.

The terms "antagonist" and "inhibitor" are used interchangeably, and they refer to a compound or agent having the ability to inhibit a biological function of a target protein or polypeptide, such as by inhibiting the activity or expression of the target protein or polypeptide. Accordingly, the terms "antagonist" and "inhibitor" are defined in the context of the biological role of the target protein or polypeptide. While some antagonists herein specifically interact with (e.g., bind to) the target, compounds that inhibit a biological activity of the target protein or polypeptide by interacting with other members of the signal transduction pathway of that target protein or polypeptide are also specifically included within this definition. Non-limiting examples of biological activity inhibited by an antagonist include those associated with the development, growth, or spread of a tumor, or an undesired immune response as manifested in autoimmune disease.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of cell division. This term also encompasses cell growth by which the cell morphology has changed (e.g., increased in size) consistent with a proliferative signal.

"Administration" of a disclosed compound encompasses the delivery to a subject of a compound as described herein, or a prodrug or other pharmaceutically acceptable derivative thereof, using any suitable formulation or route of administration, as discussed herein.

The term "co-administration," "administered in combination with," and their grammatical equivalents, as used herein, encompasses administration of two or more agents to the subject so that both agents and/or their metabolites are present in the subject at the same time. Co-administration includes simultaneous administration in separate compositions, administration at different times in separate compositions, or administration in a composition in which both agents are present.

The term "effective amount" or "therapeutically effective amount" refers to that amount of a compound or pharmaceutical composition described herein that is sufficient to effect the intended application including, but not limited to, disease treatment, as illustrated below. In some embodiments, the amount is that effective for detectable killing or inhibition of the growth or spread of cancer cells; the size or number of tumors; or other measure of the level, stage, progression or severity of the cancer. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of cell migration. The specific dose will vary depending on, for example, the particular compounds chosen, the species of subject and their age/existing health conditions or risk for health conditions, the dosing regimen to be followed, the severity of the disease, whether it is administered in combination with other agents, timing of administration, the tissue to which it is administered, and the physical delivery system in which it is carried.

As used herein, the terms "treatment", "treating", "palliating" "managing" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

"Signal transduction" is a process during which stimulatory or inhibitory signals are transmitted into and within a cell to elicit an intracellular response. A "modulator" of a signal transduction pathway refers to a compound which modulates the activity of one or more cellular proteins mapped to the same specific signal transduction pathway. A modulator can augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or interact interaction with the target. For example, a compound that selectively inhibits exon 20 mutant EGFR over wild-type EGFR has an activity of at least about 2× against the mutated EGF relative to the compound's activity against the wild-type EGFR isoform (e.g., at least about 3×, about 5×, about 10×, about 20×, about 50×, or about 100×).

"Radiation therapy" means exposing a patient, using routine methods and compositions known to the practitioner, to radiation emitters such as, but not limited to, alpha-particle emitting radionuclides (e.g., actinium and thorium radionuclides), low linear energy transfer (LET) radiation emitters (i.e., beta emitters), conversion electron emitters (e.g., strontium-89 and samarium-153-EDTMP), or high-energy radiation, including without limitation x-rays, gamma rays, and neutrons.

"Subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The term "in vivo" refers to an event that takes place in a subject's body. In vivo also includes events occurring in rodents, such as rats, mice, guinea pigs, and the like.

The term "in vitro" refers to an event that takes places outside of a subject's body. For example, an in vitro assay encompasses any assay conducted outside of a subject. In vitro assays encompass cell-based assays in which cells, alive or dead, are employed. In vitro assays also encompass a cell-free assay in which no intact cells are employed.

As used herein, "pharmaceutically acceptable derivative" denotes any pharmaceutically acceptable salt, ester, enol ether, or salt of such ester, of such compound, or any other adduct or derivative which, upon administration to a subject, is capable of providing (directly or indirectly) a compound as otherwise described herein, or a metabolite or residue (MW about >300) thereof.

As used herein, "pharmaceutically acceptable ester" refers to esters which hydrolyze in vivo and include those that break down readily in the human body to leave the parent compound or a salt thereof. Such esters can act as a prodrug as defined herein. Pharmaceutically acceptable esters include, but are not limited to, alkyl, alkenyl, alkynyl, aryl, aralkyl, and cycloalkyl esters of acidic groups, including, but not limited to, carboxylic acids, phosphoric acids, phosphinic acids, sulfinic acids, sulfonic acids and boronic acids. Examples of esters include formates, acetates, propionates, butyrates, acrylates and ethylsuccinates. The esters can be formed with a hydroxyl or carboxylic acid group of the parent compound.

As used herein, "pharmaceutically acceptable enol ethers" include, but are not limited to, derivatives of formula —C=C(OR) where R can be selected from alkyl, alkenyl, alkynyl, aryl, aralkyl and cycloalkyl. Pharmaceutically acceptable enol esters include, but are not limited to, derivatives of formula —C=C(OC(O)R) where R can be selected from hydrogen, alkyl, alkenyl, alkynyl, aryl, aralkyl and cycloalkyl.

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds. In one embodiment, a "pharmaceutically acceptable form" includes, but is not limited to, pharmaceutically acceptable salts, isomers, prodrugs and isotopically labeled derivatives of disclosed compounds. In some embodiments, a "pharmaceutically acceptable form" includes, but is not limited to, pharmaceutically acceptable salts, stereoisomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. *Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchioric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^+(C_{1-4}alkyl)^4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, —NO$_2$, —ONO, or —ONO$_2$ moieties. Prodrugs can typically be prepared using well known methods, such as those described in *Burger's Medicinal Chemistry and Drug Discovery*, 172-178, 949-982 (Manfred E. Wolff ed., 5th ed., 1995), and *Design of Prodrugs* (H. Bundgaard ed., Elsevier, New York, 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as (C$_{1-8}$)alkyl, (C$_{1-12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 10 carbon atoms, N-(alkoxycarbonyl) aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N— (C$_{1-2}$)alkylamino(C$_{2-3}$)alkyl (such as [3-dimethylaminoethyl), carbamoyl-(C$_{1-2}$)alkyl, N,N-di(C$_{1-2}$)alkylcarbamoyl-(C$_{1-2}$)alkyl and piperidino-, pyrrolidino- or morpholino (C$_{2-3}$)alkyl.

Similarly, if a disclosed compound or a pharmaceutically acceptable form of the compound contains an alcohol functional group, a prodrug can be formed by the replacement of the hydrogen atom of the alcohol group with a group such as (C$_{1-6}$)alkanoyloxymethyl, 1-((C$_{1-6}$)alkanoyloxy)ethyl, 1-methyl-1-((C$_{1-6}$)alkanoyloxy)ethyl, (C$_{1-6}$)alkoxycarbonyloxymethyl, N—(C$_{1-6}$)alkoxycarbonylaminomethyl, succinoyl, (C$_{1-6}$)alkanoyl, α-amino(C$_{1-4}$)alkanoyl, arylacyl, and α-aminoacyl, or α-aminoacyl-α-aminoacyl, where each α-aminoacyl group is independently selected from the naturally occurring L-amino acids, —P(O)(OH)$_2$, —P(O)(O (C$_{1-6}$)alkyl)$_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently selected from (C$_{1-10}$)alkyl, (C$_{3-7}$) cycloalkyl, benzyl, a natural α-aminoacyl or natural α-aminoacyl-natural-α-aminoacyl, —C(OH)C(O)OY$^1$ wherein Y$^1$ is H, (C$_{1-6}$)alkyl or benzyl; —C(OY$^2$)Y$^3$ wherein Y$^2$ is (C$_{1-4}$)alkyl and Y$^3$ is (C$_{1-6}$)alkyl, carboxy (C$_{1-6}$)alkyl, amino(C$_{1-4}$)alkyl or mono-N— or di-N,N— (C$_{1-6}$)alkylaminoalkyl; and —C(Y$^4$)Y$^5$ wherein Y$^4$ is H or methyl and Y$^5$ is mono-N— or di-N—(C$_{1-6}$)alkylamino, morpholino, piperidin-1-yl or pyrrolidin-1-yl.

In certain embodiments, the pharmaceutically acceptable form is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Geometric isomers can be represented by the symbol ----- which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring.

Mixtures of compounds wherein the substituents are disposed on both the same and opposite sides of plane of the ring are designated "cis/trans."

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

The "enantiomeric excess" or "% enantiomeric excess" of a composition can be calculated using the equation shown below. In the example shown below, a composition contains 90% of one enantiomer, e.g., the S enantiomer, and 10% of the other enantiomer, e.g., the R enantiomer.

$$ee=(90-10)/100=80\%.$$

Thus, a composition containing 90% of one enantiomer and 10% of the other enantiomer is said to have an enantiomeric excess of 80%. Some compositions described herein contain an enantiomeric excess of at least about 50%, about 75%, about 90%, about 95%, or about 99% of the S enantiomer. In other words, the compositions contain an enantiomeric excess of the S enantiomer over the R enantiomer. In other embodiments, some compositions described herein contain an enantiomeric excess of at least about 50%, about 75%, about 90%, about 95%, or about 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than 1:1 by weight). For example, an enantiomerically enriched preparation of the S enantiomer means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least about 95% by weight. In certain embodiments, the compound provided herein can be made up of at least about 90% by weight of one enantiomer. In other embodiments, the compound can be made up of at least about 95%, about 98%, or about 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In other embodiments, the compound mixture contains identical chemical entities except for their stereochemical orientations, namely (S)- or (R)-isomers. For example, if a compound disclosed herein has a —CH(R)— unit, and R is not hydrogen, then the —CH(R)— is in an (S)- or (R)-stereochemical orientation for each of the identical chemical entities. In some embodiments, the mixture of identical chemical entities is a racemic mixture of (S)- and (R)-isomers. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric excess greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, *Enantiomers, Racemates and Resolutions* (Jacques, Ed., Wiley Interscience, New York, 1981); Wilen et al., *Tetrahedron* 33:2725 (1977); Stereochemistry of Carbon Compounds (E. L. Eliel, Ed., McGraw-Hill, NY, 1962); and *Tables of Resolving Agents and Optical Resolutions* p. 268 (E. L. EIM, Ed., Univ. of Notre Dame Press, Notre Dame, Ind. 1972).

Optical isomers can be obtained by resolution of the racemic mixtures according to conventional processes, e.g., by formation of diastereoisomeric salts, by treatment with an optically active acid or base. Examples of appropriate acids include, but are not limited to, tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In certain embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The disclosure also embraces pharmaceutically acceptable forms that are "isotopically labeled derivatives" which are compounds that are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, fluorine and chlorine, such as $^{2}$H, $^{3}$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Certain isotopically-labeled disclosed compounds (e.g., those labeled with $^{3}$H and $^{14}$C) are useful in compound and/or substrate tissue distribution assays. Tritiated (i.e., $^{3}$H) and carbon-14 (i.e., $^{14}$C) isotopes can allow for ease of preparation and detectability. Further, substitution with heavier isotopes such as deuterium (i.e., $^{2}$H) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure. In some embodiments, radiolabeled compounds are useful for studying metabolism and/or tissue distribution of the compounds or to alter the rate or path of metabolism or other aspects of biological functioning "Pharmaceutically acceptable carrier" or "pharmaceutically acceptable excipient" includes any and all solvents, dispersion media, coatings, antibacterial and antifungal agents, isotonic and absorption delaying agents and the like. The pharmaceutically acceptable carrier or excipient does not destroy the pharmacological activity of the disclosed compound and is nontoxic when administered in doses sufficient to deliver a therapeutic amount of the compound. The use of such media and agents for pharmaceutically active substances is well known in the art. Except insofar as any conventional media or agent is incompatible with the active ingredient, its use in the therapeutic compositions as disclosed herein is contemplated. Non-limiting examples of pharmaceutically acceptable carriers and excipients include sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc;

cocoa butter and suppository waxes; oils such as peanut oil, cottonseed oil, safflower oil, sesame oil, olive oil, corn oil and soybean oil; glycols, such as polyethylene glycol and propylene glycol; esters such as ethyl oleate and ethyl laurate; agar; buffering agents such as magnesium hydroxide and aluminum hydroxide; alginic acid; isotonic saline; Ringer's solution; ethyl alcohol; phosphate buffer solutions; non-toxic compatible lubricants such as sodium lauryl sulfate and magnesium stearate; coloring agents; releasing agents; coating agents; sweetening, flavoring and perfuming agents; preservatives; antioxidants; ion exchangers; alumina; aluminum stearate; lecithin; self emulsifying drug delivery systems (SEDDS) such as d-atocopherol polyethyleneglycol 1000 succinate; surfactants used in pharmaceutical dosage forms such as Tweens or other similar polymeric delivery matrices; serum proteins such as human serum albumin; glycine; sorbic acid; potassium sorbate; partial glyceride mixtures of saturated vegetable fatty acids; water, salts or electrolytes such as protamine sulfate, disodium hydrogen phosphate, potassium hydrogen phosphate, sodium chloride, and zinc salts; colloidal silica; magnesium trisilicate; polyvinyl pyrrolidone; cellulose-based substances; polyacrylates; waxes; and polyethylene-polyoxypropylene-block polymers. Cyclodextrins such as α-, β-, and γ-cyclodextrin, or chemically modified derivatives such as hydroxyalkylcyclodextrins, including 2- and 3-hydroxypropyl-cyclodextrins, or other solubilized derivatives can also be used to enhance delivery of compounds described herein.

Definitions of specific functional groups and chemical terms are described in more detail below. The chemical elements are identified in accordance with the Periodic Table of the Elements, CAS version, Handbook of Chemistry and Physics, 75th ed., inside cover, and specific functional groups are generally defined as described therein. Additionally, general principles of organic chemistry, as well as specific functional moieties and reactivity, are described in *Organic Chemistry*, Thomas Sorrell, University Science Books, Sansalito, 1999; Smith and March *March's Advanced Organic Chemistry*, 5th ed., John Wiley & Sons, Inc., NewYork, 2001; Larock, *Comprehensive Organic Transformations*, VCH Publishers, Inc., NewYork, 1989; and Carruthers, *Some Modern Methods of Organic Synthesis*, 3rd ed., Cambridge University Press, Cambridge, 1987.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, "alkyl" can be a $C_{1-6}$ alkyl group. In some embodiments, alkyl groups have 1 to 10, 1 to 8, 1 to 6, or 1 to 3 carbon atoms. Representative saturated straight chain alkyls include, but are not limited to, -methyl, -ethyl, -n-propyl, -n-butyl, -n-pentyl, and -n-hexyl; while saturated branched alkyls include, but are not limited to, -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group is optionally substituted by one or more of substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, $—Si(R^a)_3$, $—OR^a$, $—SR^a$, $—OC(O)—R^a$, $—N(R^a)_2$, $—C(O)R^a$, $—C(O)OR^a$, $—OC(O)N(R^a)_2$, $—C(O)N(R^a)_2$, $—N(R^a)C(O)OR^a$, $—N(R^a)C(O)R^a$, $—N(R^a)C(O)N(R^a)_2$, $—N(R^a)C(NR^a)N(R^a)_2$, $—N(R^a)S(O)_tN(R^a)_2$ (where t is 1 or 2), $—P(=O)(R^a)(R^a)$, or $—O—P(=O)(OR^a)_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

"Perhaloalkyl" refers to an alkyl group in which all of the hydrogen atoms have been replaced with a halogen selected from fluoro, chloro, bromo, and iodo. In some embodiments, all of the hydrogen atoms are each replaced with fluoro. In some embodiments, all of the hydrogen atoms are each replaced with chloro. Examples of perhaloalkyl groups include $—CF_3$, $—CF_2CF_3$, $—CF_2CF_2CF_3$, $—CFCl_2$, $—CF_2Cl$ and the like.

"Alkyl-cycloalkyl" refers to an -(alkyl)cycloalkyl radical where alkyl and cycloalkyl are as disclosed herein and which are optionally substituted by one or more of the substituents described as suitable substituents for alkyl and cycloalkyl respectively. The "alkyl-cycloalkyl" is bonded to the parent molecular structure through the alkyl group. The terms "alkenyl-cycloalkyl" and "alkynyl-cycloalkyl" mirror the above description of "alkyl cycloalkyl" wherein the term "alkyl" is replaced with "alkenyl" or "alkynyl" respectively, and "alkenyl" or "alkynyl" are as described herein.

"Alkyl-aryl" refers to an -(alkyl)aryl radical where aryl and alkyl are as disclosed herein and which are optionally substituted by one or more of the substituents described as suitable substituents for aryl and alkyl respectively. The "alkylaryl" is bonded to the parent molecular structure through the alkyl group. The terms "-(alkenyl)aryl" and "-(alkynyl)aryl" mirror the above description of "-(alkyl)aryl" wherein the term "alkyl" is replaced with "alkenyl" or "alkynyl" respectively, and "alkenyl" or "alkynyl" are as described herein.

"Alkyl-heteroaryl" refers to an -(alkyl)heteroaryl radical where heteroaryl and alkyl are as disclosed herein and which are optionally substituted by one or more of the substituents described as suitable substituents for heteroaryl and alkyl respectively. The "alkyl heteroaryl" is bonded to the parent molecular structure through the alkyl group. The terms "-(alkenyl)heteroaryl" and "-(alkynyl)heteroaryl" mirror the above description of "(alkyl) heteroaryl" wherein the term "alkyl" is replaced with "alkenyl" or "alkynyl" respectively, and "alkenyl" or "alkynyl" are as described herein.

"Alkyl-heterocyclyl" refers to an -(alkyl)heterocycyl radical where alkyl and heterocyclyl are as disclosed herein and which are optionally substituted by one or more of the substituents described as suitable substituents for heterocyclyl and alkyl respectively. The "alkyl-heterocyclyl" is bonded to the parent molecular structure through the alkyl group. The terms "-(alkenyl)heterocyclyl" and "-(alkynyl) heterocyclyl" mirror the above description of "(alkyl)heterocyclyl" wherein the term"alkyl" is replaced with"alkenyl" or "alkynyl" respectively, and "alkenyl" or "alkynyl" are as described herein.

"Alkenyl" refers to a straight or branched hydrocarbon chain radical group consisting solely of carbon and hydrogen atoms, containing at least one double bond, and having from two to ten carbon atoms (i.e., $C_{2-10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In certain embodiments, an alkenyl comprises two to eight carbon atoms. In other embodiments, an alkenyl comprises two to six carbon atoms (e.g., $C_{2-6}$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), 2-methylprop-2-enyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$), 2,3-dimethyl-2-butenyl ($C_6$) and the like. Additional examples of alkenyl include heptenyl ($C_7$), octenyl ($C_8$), octatrienyl ($C_8$) and the like. Unless stated otherwise in the specification, an alkenyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Alkynyl" refers to a straight or branched hydrocarbon chain radical group consisting solely of carbon and hydrogen atoms, containing at least one triple bond, having from two to ten carbon atoms (i.e., $C_{2-10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, etc., up to and including 10 carbon atoms. In certain embodiments, an alkynyl comprises two to eight carbon atoms. In other embodiments, an alkynyl has two to six carbon atoms (e.g., $C_{2-6}$ alkynyl). The alkynyl is attached to the parent molecular structure by a single bond, for example, ethynyl, propynyl, butynyl, pentynyl, 3-methyl-4-pentenyl, hexynyl, and the like. Unless stated otherwise in the specification, an alkynyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "alkenoxy" and "alkynoxy" mirror the above description of "alkoxy" wherein the prefix "alk" is replaced with "alken" or "alkyn" respectively, and the parent "alkenyl" or "alkynyl" terms are as described herein.

"Alkoxy" refers to the group —O-alkyl, including from 1 to 10 carbon atoms of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. "Lower alkoxy" refers to alkoxy groups containing one to six carbons. In some embodiments, $C_{1-4}$ alkoxy is an alkoxy group which encompasses both straight and branched chain alkyls of from 1 to 4 carbon atoms. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "alkenoxy" and "alkynoxy" mirror the above description of "alkoxy" wherein the prefix "alk" is replaced with "alken" or "alkyn" respectively, and the parent "alkenyl" or "alkynyl" terms are as described herein.

The term "alkoxycarbonyl" refers to a group of the formula (alkoxy)(C=O)— attached to the parent molecular structure through the carbonyl carbon having from 1 to 10 carbon atoms. Thus, a $C_{1-6}$ alkoxycarbonyl group is an alkoxy group having from 1 to 6 carbon atoms attached through its oxygen to a carbonyl linker. The $C_{1-6}$ designation does not include the carbonyl carbon in the atom count. "Lower alkoxycarbonyl" refers to an alkoxycarbonyl group wherein the alkyl portion of the alkoxy group is a lower alkyl group. In some embodiments, $C_{1-4}$ alkoxy is an alkoxy group which encompasses both straight and branched chain alkoxy groups of from 1 to 4 carbon atoms. Unless stated otherwise in the specification, an alkoxycarbonyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "alkenoxycarbonyl" and "alkynoxycarbonyl" mirror the above description of "alkoxycarbonyl" wherein the prefix "alk" is replaced with "alken" or "alkyn" respectively, and the parent "alkenyl" or "alkynyl" terms are as described herein.

"Acyl" refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, (heteroalkyl)-C(O)—, and (heterocycloalkyl)-C(O)—, wherein the group is attached to the parent molecular structure through the carbonyl functionality. In some embodiments, it is a $C_{1-10}$ acyl radical which refers to the total number of chain or ring atoms of the, for example, alkyl, alkenyl, alkynyl, aryl, cyclohexyl, heteroaryl or heterocycloalkyl portion plus the carbonyl carbon of acyl. For example, a $C_4$-acyl has three other ring or chain atoms plus carbonyl. If the R radical is heteroaryl or heterocycloalkyl, the hetero ring or chain atoms contribute to the total number of chain or ring atoms. Unless stated otherwise in the specification, the "R" of an acyloxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Acyloxy" refers to a R(C=O)O— radical wherein "R" can be alkyl, alkenyl, alkynyl, heteroalkyl, heteroalkenyl, heteroalkynyl, aryl, cyclohexyl, heteroaryl or heterocycloalkyl, which are as described herein. The acyloxy group is attached to the parent molecular structure through the oxygen functionality. In some embodiments, an acyloxy group is a $C_{1-4}$ acyloxy radical which refers to the total number of chain or ring atoms of the alkyl, alkenyl, alkynyl, aryl, cyclohexyl, heteroaryl or heterocycloalkyl portion of the acyloxy group plus the carbonyl carbon of acyl, i.e., a $C_4$-acyloxy has three other ring or chain atoms plus carbonyl. If the R radical is heteroaryl or heterocycloalkyl, the hetero ring or chain atoms contribute to the total number of chain or ring atoms. Unless stated otherwise in the specification, the "R" of an acyloxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Amino" or "amine" refers to a —N($R^b$)$_2$, —N($R^b$)—$R^b$—, or —$R^b$N($R^b$)$R^b$— radical group, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. When a —N($R^b$)$_2$ group has two $R^b$ other than hydrogen, they can be combined with the nitrogen atom to form a 3-, 4-, 5-, 6-, or 7-membered ring. For example, —N($R^b$), is meant to include, but not be limited to, 1-pyrrolidinyl and 4-morpholinyl. Unless stated otherwise in the specification, an amino group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The terms "amine" and "amino" also refer to N-oxides of the groups —$N^+$(H)($R^a$)O—, and —$N^+$($R^a$)($R^a$)O—, $R^a$ as described above, where the N-oxide is bonded to the parent molecular structure through the N atom. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N($R^b$)$_2$, —C(O)N($R^b$)—, —N$R^b$C(O)$R_b$, or —N$R^b$C(O)— where $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, this radical is a $C_{1-4}$ amido or amide radical, which includes the amide carbonyl in the total number of carbons in the radical. When a —C(O)N($R^b$)$_2$ has two $R^b$ other than hydrogen, they can be combined with the nitrogen atom to form a 3-, 4-, 5-, 6-, or 7-membered ring. For example, N($R^b$)$_2$ portion of a —C(O)N($R^b$)$_2$ radical is meant to include, but not be limited to, 1-pyrrolidinyl and 4-morpholinyl. Unless stated otherwise in the specification, an amido $R^b$ group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

The term "amide" or "amido" is inclusive of an amino acid or a peptide molecule. Any amine, hydroxy, or carboxyl side chain on the compounds described herein can be transformed into an amide group. The procedures and specific groups to make such amides are known to those of skill in the art and can readily be found in reference sources such as Greene and Wuts, *Protective Groups in Organic Synthesis*, 3rd Ed., John Wiley & Sons, New York, N.Y., 1999, which is incorporated herein by reference in its entirety.

"Amidino" refers to both the —C(=N$R^b$)N($R^b$), and —N($R^b$)—C(=N$R^b$)— radicals, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Aromatic" or "aryl" refers to a radical with 6 to 14 ring atoms (e.g., $C_{6-14}$ aromatic or $C_{6-14}$ aryl) which has at least one ring having a conjugated pi electron system which is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl" refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Aryloxy" refers to the group —O-aryl, including from 6 to 14 carbon atoms of an aromatic configuration and combinations thereof, attached to the parent molecular structure through an oxygen. Aryl is as described herein. Examples include phenoxy, phenalenyloxy, naphthalenyloxy, tetrahydronaphthyloxy, phenanthrenyloxy, anthracenyloxy, fluorenyloxy, indolyloxy, indanyloxy and the like. "Lower aryloxy" refers to aryloxy groups containing 6 to 10 carbons. Unless stated otherwise in the specification, an alkoxy group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "alkenoxy" and "alkynoxy" mirror the above description of "alkoxy" wherein the prefix "alk" is replaced with "alken" or "alkyn" respectively, and the parent "alkenyl" or "alkynyl" terms are as described herein.

"Aralkyl" or "arylalkyl" refers to an -(alkyl)aryl radical where aryl and alkyl are as disclosed herein and which are optionally substituted by one or more of the substituents described as suitable substituents for aryl and alkyl respectively. The "aralkyl/arylalkyl" is bonded to the parent molecular structure through the alkyl group. The terms "aralkenyl/arylalkenyl" and "aralkynyl/arylalkynyl" mirror the above description of "aralkyl/arylalkyl" wherein the "alkyl" is replaced with "alkenyl" or "alkynyl" respectively, and the "alkenyl" or "alkynyl" terms are as described herein.

"Carbamate" refers to any of the following radicals: —O—(C=O)—N($R^b$)—, —O—(C=O)—N($R^b$)$_2$, —N($R^b$)—(C=O)—O—, and —N($R^b$)—(C=O)—O$R^b$, wherein each $R^b$ is independently selected from alkyl, alkenyl alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Carbonate" refers to a —O—(C=O)—O— radical.

"Carbonyl" refers to a —(C=O)— radical.

"Carboxaldehyde" refers to a —(C=O)H radical.

"Carboxyl" refers to a —(C=O)OH radical.

"Cyano" refers to a —CN radical.

"Cycloalkyl" and "carbocyclyl" each refer to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

"Cycloalkyl-alkyl" refers to a -(cycloalkyl)alkyl radical where cycloalkyl and alkyl are as disclosed herein and which are optionally substituted by one or more of the substituents described as suitable substituents for cycloalkyl and alkyl respectively. The "cycloalkyl-alkyl" is bonded to the parent molecular structure through the cycloalkyl group. The terms "cycloalkyl-alkenyl" and "cycloalkyl-alkynyl" mirror the above description of "cycloalkyl-alkyl" wherein the term "alkyl" is replaced with "alkenyl" or "alkynyl" respectively, and "alkenyl" or "alkynyl" are as described herein.

"Cycloalkyl-heterocycloalkyl" refers to a -(cycloalkyl) heterocycylalkyl radical where cycloalkyl and heterocycloalkyl are as disclosed herein and which are optionally substituted by one or more of the substituents described as suitable substituents for heterocycloalkyl and cycloalkyl respectively. The "cycloalkyl-heterocycloalkyl" is bonded to the parent molecular structure through the cycloalkyl group.

"Cycloalkyl-heteroaryl" refers to a -(cycloalkyl) heteroaryl radical where cycloalkyl and heteroaryl are as disclosed herein and which are optionally substituted by one or more of the substituents described as suitable substituents for heteroaryl and cycloalkyl respectively. The "cycloalkylheteroaryl" is bonded to the parent molecular structure through the cycloalkyl group.

As used herein, a "covalent bond" or "direct bond" refers to a single bond joining two groups.

"Ester" refers to a radical of formula —C(O)O$R^b$ or —$R_b$OC(O)—, where $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl. Any amine, hydroxy, or carboxyl side chain on the compounds described herein can be esterified. The procedures and specific groups to make such esters are known to those of skill in the art and can readily be found in reference sources such as Greene and Wuts, *Protective Groups in Organic Synthesis,* 3rd Ed., John Wiley & Sons, New York, N.Y., 1999, which is incorporated herein by reference in its entirety. Unless stated otherwise in the specification, an ester group can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R_a^b$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Ether" refers to a —O—$R^b$—O— radical where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups are as defined herein and can be optionally further substituted as defined herein.

"Heteroalkyl", "heteroalkenyl" and "heteroalkynyl" include alkyl, alkenyl and alkynyl radicals, respectively, which have one or more skeletal chain atoms selected from an atom other than carbon, e.g., oxygen, nitrogen, sulfur, phosphorus or combinations thereof. A numerical range can be given, e.g., $C_{1-4}$ heteroalkyl which refers to the chain length in total, which in this example is 4 atoms long. For example, a —$CH_2OCH_2CH_3$ radical is referred to as a "$C_4$" heteroalkyl, which includes the heteroatom center in the atom chain length description. Connection to the parent molecular structure can be through either a heteroatom or a carbon in the heteroalkyl chain. For example, an N-containing heteroalkyl moiety refers to a group in which at least one of the skeletal atoms is a nitrogen atom. One or more heteroatom(s) in the heteroalkyl radical can be optionally oxidized. One or more nitrogen atoms, if present, can also be optionally quaternized. For example, heteroalkyl also includes skeletal chains substituted with one or more nitrogen oxide (—O—) substituents. Exemplary heteroalkyl groups include, without limitation, ethers such as methoxyethanyl (—$CH_2CH_2OCH_3$), ethoxymethanyl (—$CH_2OCH_2CH_3$), (methoxymethoxy)ethanyl (—$CH_2CH_2OCH_2OCH_3$), (methoxymethoxy) methanyl (—$CH_2OCH_2OCH_3$) and (methoxyethoxy)methanyl (—$CH_2OCH_2CH_2OCH_3$) and the like; amines such as (—$CH_2CH_2NHCH_3$, —$CH_2CH_2N(CH_3)_2$, —$CH_2NHCH_2CH_3$, —$CH_2N(CH_2CH_3)(CH_3)$) and the like. Heteroalkyl, heteroalkenyl, and heteroalkynyl groups can each be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —$Si(R^a)_3$, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, —$N(R^a)C(NR^a)N(R^a)_2$, —$N(R^a)S(O)_tN(R^a)_2$ (where t is 1 or 2), —$P(=O)(R^a)(R^a)$, or —O—$P(=O)(OR^a)_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Heteroalkyl-aryl" refers to a -(heteroalkyl)aryl radical where heteroalkyl and aryl are as disclosed herein and which are optionally substituted by one or more of the substituents described as suitable substituents for heteroalkyl and aryl respectively. The "heteroalkyl-aryl" is bonded to the parent molecular structure through an atom of the heteroalkyl group.

"Heteroalkyl-heteroaryl" refers to a -(heteroalkyl)heteroaryl radical where heteroalkyl and heteroaryl are as disclosed herein and which are optionally substituted by one or more of the substituents described as suitable substituents for heteroalkyl and heteroaryl respectively. The "heteroalkylheteroaryl" is bonded to the parent molecular structure through an atom of the heteroalkyl group.

"Heteroalkyl-heterocycloalkyl" refers to a -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl respectively. The "heteroalkyl-heterocycloalkyl" is bonded to the parent molecular structure through an atom of the heteroalkyl group.

"Heteroalkyl-cycloalkyl" refers to a -(heteroalkyl)cycloalkyl radical where heteroalkyl and cycloalkyl are as disclosed herein and which are optionally substituted by one or more of the substituents described as suitable substituents for heteroalkyl and cycloalkyl respectively. The "heteroalkylcycloalkyl" is bonded to the parent molecular structure through an atom of the heteroalkyl group.

"Heteroaryl" or, alternatively, "heteroaromatic" refers to a refers to a radical of a 5-18 membered monocyclic or polycyclic (e.g., bicyclic, tricyclic, tetracyclic and the like) aromatic ring system (e.g., having 6, 10 or 14 π electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno [2,3-d]pyrimidinyl, 5,6-dihydrobenzo [h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo [3,2-c]pyridinyl, 5,6,7,8,9,10-hexahydrocycloocta[d] pyrimidinyl, 5,6,7,8,9,10-hexahydrocycloocta[d] pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d] pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo [4,5]thieno [2,3-d]pyrimdinyl, 6,7,8,9-tetrahydro-5H-cyclohepta[4,5]thieno [2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno [2,3-c]pridinyl, and thiophenyl (i.e., thienyl). Unless stated otherwise in the specification, a heteroaryl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Heteroaryl-alkyl" refers to a -(heteroaryl)alkyl radical where heteroaryl and alkyl are as disclosed herein and which are optionally substituted by one or more of the substituents described as suitable substituents for heteroaryl and alkyl respectively. The "heteroaryl alkyl" is bonded to the parent molecular structure through any atom of the heteroaryl group.

"Heteroaryl-heterocycloalkyl" refers to an -(heteroaryl) heterocycloalkyl radical where heteroaryl and heterocycloalkyl are as disclosed herein and which are optionally substituted by one or more of the substituents described as suitable substituents for heteroaryl and heterocycloalkyl respectively. The "heteroaryl-heterocycloalkyl" is bonded to the parent molecular structure through an atom of the heteroaryl group.

"Heteroaryl-cycloalkyl" refers to an -(heteroaryl)cycloalkyl radical where heteroaryl and cycloalkyl are as disclosed herein and which are optionally substituted by one or more of the substituents described as suitable substituents for heteroaryl and cycloalkyl respectively. The "heteroaryl-cycloalkyl" is bonded to the parent molecular structure through a carbon atom of the heteroaryl group.

"Heterocyclyl", "heterocycloalkyl" or "heterocarbocyclyl" each refer to any 3 to 18-membered non-aromatic radical monocyclic or polycyclic moiety comprising at least one heteroatom selected from nitrogen, oxygen, phosphorous and sulfur. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or both rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, etc., up to and including 18 ring atoms. For example, bivalent radicals derived from univalent heterocyclyl radicals whose names end in "-yl" by removal of one hydrogen atom from the atom with the free valence are named by adding "-ene" to the name of the corresponding univalent radical, e.g., a piperidine group with two points of attachment is a piperidylene.

An N-containing heterocyclyl moiety refers to an non-aromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocycyl ring, as defined above, is fused with one or more carbocycyl groups wherein the point of attachment is either on the carbocycyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 5-14 membered non-aromatic ring system having ring carbon atoms and 1-4 ring heteroatoms, wherein each heteroatom is independently selected from nitrogen, oxygen, phosphorous and sulfur ("5-14 membered heterocyclyl"). In some embodiments, a heterocyclyl group is a 3-10 membered non-aromatic ring system having ring carbon atoms and 1-4 ring heteroatoms, wherein each heteroatom is independently selected from nitrogen, oxygen, phosphorous and sulfur ("3-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorous and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorous and sulfur ("5-6 membered heterocyclyl"). In some embodiments, the 5-6 membered heterocyclyl has 1-3 ring heteroatoms selected from nitrogen, oxygen phosphorous and sulfur. In some embodiments, the 5-6 membered heterocyclyl has 1-2 ring heteroatoms selected from nitrogen, oxygen, phosphorous and sulfur. In some embodiments, the 5-6 membered heterocyclyl has 1 ring heteroatom selected from nitrogen, oxygen, phosphorous and sulfur.

Exemplary 3-membered heterocyclyls containing 1 heteroatom include, without limitation, azirdinyl, oxiranyl, and thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl, thiazolidinyl, and dithiolanyl. Exemplary 5-membered heterocyclyls containing 3 heteroatoms include, without limitation, triazolinyl, diazolonyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6 membered heterocyclyl groups containing 2 heteroatoms include, without limitation, piperazinyl, morpholinyl, thiomorpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, benzoxanyl, benzopyrrolidinyl, benzopiperidinyl, benzoxolanyl, benzothiolanyl, benzothianyl, tetrahydroindolyl, tetrahydroquinolinyl, tetrahydroisoquinolinyl, decahydroquinolinyl, decahydroisoquinolinyl, 3-1H-benzimidazol-2-one, (1-substituted)-2-oxo-benzimidazol-3-yl, octahydrochromenyl, octahydroisochromenyl, decahydronaphthyridinyl, decahydro-1,8-naphthyridinyl, octahydropyrrolo[3,2-b]pyrrole, phenanthridinyl, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo [3,2-b]pyranyl, 5,7-dihydro-4H-thieno [2,3-c]pyranyl, 2,3-dihydro-1H-pyrrolo[2,3-b]pyridinyl, hydrofuro[2,3-b]pyridinyl, 4,5,6,7 tetrahydro-1H-pyrrolo[2,3-b]pyridinyl, 4,5,6,7-tetrahydrofuro [3,2-c]pyridinyl, 4,5,6,7-tetrahydrothieno[3,2-b]pyridinyl, 1,2,3,4-tetrahydro-1,6-naphthyridinyl, and the like.

Unless stated otherwise in the specification, a heterocyclyl moiety can be optionally substituted by one or more substituents which independently include: acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Heterocyclyl-alkyl" refers to a -(heterocyclyl)alkyl radical where heterocyclyl and alkyl are as disclosed herein and which are optionally substituted by one or more of the substituents described as suitable substituents for heterocyclyl and alkyl respectively. The "heterocyclyl-alkyl" is bonded to the parent molecular structure through any atom of the heterocyclyl group. The terms "heterocyclyl-alkenyl" and "heterocyclyl-alkynyl" mirror the above description of "heterocyclyl-alkyl" wherein the term "alkyl" is replaced with "alkenyl" or "alkynyl" respectively, and "alkenyl" or "alkynyl" are as described herein.

"Imino" refers to the "—(C=N)—$R^b$ radical where $R^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Phosphate" refers to a —O—P(=O)(O$R^b$)$_2$ radical, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, when $R^b$ is hydrogen and depending on the pH, the hydrogen can be replaced by an appropriately charged counter ion.

"Phosphonate" refers to a —O—(P=O)($R^b$)(O$R^b$) radical, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, when $R^b$ is hydrogen and depending on the pH, the hydrogen can be replaced by an appropriately charged counter ion.

"Phosphinate" refers to a —P(=O)($R^b$)(O$R^b$) radical, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, when $R^b$ is hydrogen and depending on the pH, the hydrogen can be replaced by an appropriately charged counter ion.

"Phosphine oxide" refers to a —P(=O)($R^b$)($R^b$) radical, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, when $R^b$ is hydrogen and depending on the pH, the hydrogen can be replaced by an appropriately charged counter ion.

"Silyl" refers to a —Si($R^b$)$_3$ radical where each $R^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfanyl", "sulfide", and "thio" each refer to the radical —S—$R^b$, wherein $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. For instance, an "alkylthio" refers to the "alkyl-S—" radical, and "arylthio" refers to the "aryl-S—" radical, each of which are bound to the parent molecular group through the S atom. The terms "sulfide", "thiol", "mercapto", and "mercaptan" can also each refer to the group —$R^b$SH.

"Sulfinyl" or "sulfoxide" refer to the —S(O)—$R^b$ radical, wherein for "sulfinyl", $R^b$ is H and for "sulfoxide", $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfonyl" or "sulfone" refer to the —S($O_2$)—$R^b$ radical, wherein $R^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfonamidyl" or "sulfonamido" refer to the following radicals: —S(=O)$_2$—($R^b$)$_2$, —N($R^b$)—S(=O)$_2$—$R^b$, —S(=O)$_2$—N($R^b$)—, or —N($R^b$)—S(=O)$_2$—, where each $R_b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. The $R^b$ groups in —S(=O)$_2$—($R^b$)$_2$ can be taken together with the nitrogen to which they are attached to form a 4-, 5-, 6-, or 7-membered heterocyclyl ring. In some embodiments, the term designates a $C_{1-4}$ sulfonamido, wherein each $R^b$ in the sulfonamido contains 1 carbon, 2 carbons, 3 carbons, or 4 carbons total.

"Sulfoxyl" or "sulfoxide" refer to a —S(=O)$_2$OH radical.

"Sulfonate" refers to a —S(=O)$_2$—O$R^b$ radical, wherein $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Thiocarbonyl" refers to a —(C=S)— radical.

"Urea" refers to a —N($R^b$)—(C=O)—N($R^b$)$_2$ or —N($R^b$)—(C=O—N($R^b$)— radical, where each $R^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

Where substituent groups are specified by their conventional chemical Formulae, written from left to right, they equally encompass the chemically identical substituents that would result from writing the structure from right to left, e.g., —$CH_2O$— is equivalent to —O$CH_2$—.

A "leaving group or atom" is any group or atom that will, under the reaction conditions, cleave from the starting material, thus promoting reaction at a specified site. Suitable non-limiting examples of such groups unless otherwise specified include halogen atoms, mesyloxy, p-nitrobenzensulphonyloxy, trifluoromethyloxy, and tosyloxy groups.

"Protecting group" has the meaning conventionally associated with it in organic synthesis, i.e., a group that selectively blocks one or more reactive sites in a multifunctional compound such that a chemical reaction can be carried out selectively on another unprotected reactive site and such that the group can readily be removed after the selective reaction is complete. Non-limiting embodiments of functional groups that can be masked with a protecting group include an amine, hydroxy, thiol, carboxylic acid, and aldehyde. For example, a hydroxy protected form is where at least one of the hydroxy groups present in a compound is protected with a hydroxy protecting group. A variety of protecting groups are disclosed, for example, in T. H. Greene and R G. M. Wuts, *Protective Groups in Organic Synthesis*, Third Edition, John Wiley & Sons, New York (1999), incorporated herein by reference in its entirety. For additional background information on protecting group methodologies (materials, methods and strategies for protection and deprotection) and other synthetic chemistry transformations useful in producing the compounds described herein, see in R. Larock, Comprehensive organic Transformations, VCH Publishers (1989); T. W. Greene and P. G. M. Wuts, Protective Groups in Organic Synthesis, 3rd. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995). These references are incorporated herein by reference in their entirety.

The terms "substituted" or "substitution" mean that at least one hydrogen present on a group atom (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents include one or more group(s) individually and independently selected from acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo, haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, —Si($R^a$)$_3$, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$N($R^a$)$_2$ (where t is 1 or 2), —P(=O)($R^a$)($R^a$), or —O—P(=O)(O$R^a$)$_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein. For example, a cycloalkyl substituent can have a halide substituted at one or more ring carbons, and the like. The protecting groups that can form the protective derivatives of the above substituents are known to those of skill in the art and can be found in references such as Greene and Wuts, above.

Suitable substituents include, but are not limited to, haloalkyl and trihaloalkyl, alkoxyalkyl, halophenyl, -M-heteroaryl, -M-heterocycle, -M-aryl, -M-O$R^a$, -M-S$R^a$, -M-N($R^a$)$_2$, -M-OC(O)N($R^a$)$_2$, -M-C(=N$R^a$)N($R^a$)$_2$, -M-C(=N$R^a$)O$R^a$, -M-P(O)($R^a$)$_2$, Si($R^a$)$_3$, -M-N$R^a$C(O)$R^a$, -M-N$R^a$C(O)O$R^a$, -M-C(O)$R^a$, -M-C(=S)$R^a$, -M-C(=S)N$R^a$$R^a$, -M-C(O)N($R^a$)$_2$, -M-C(O)N$R^a$-M-N($R^a$)$_2$, -M-N$R^a$C(N$R^a$)N($R^a$)$_2$, -M-N$R^a$C(S)N($R^a$)$_2$, -M-S(O)$_2$$R^a$, -M C(O)$R^a$, -M-OC(O)$R^a$, -MC(O)S$R^a$, -M-S(O)$_2$N($R^a$)$_2$, —C(O)-M-C(O)$R^a$, -MCO$_2$$R^a$, -MC(=O)N($R^a$)$_2$, -M-C(=NH)N($R^a$)$_2$, and -M-OC(=NH)N($R^a$)$_2$ (wherein M is a $C_{1-6}$ alkyl group).

When a ring system (e.g., cycloalkyl, heterocyclyl, aryl, or heteroaryl) is substituted with a number of substituents varying within an expressly defined range, it is understood that the total number of substituents does not exceed the normal available valencies under the existing conditions. Thus, for example, a phenyl ring substituted with "p" substituents (where "p" ranges from 0 to 5) can have 0 to 5 substituents, whereas it is understood that a pyridinyl ring substituted with "p" substituents has a number of substituents ranging from 0 to 4. The maximum number of substituents that a group in the disclosed compounds can have can be easily determined. The substituted group encompasses only those combinations of substituents and variables that result in a stable or chemically feasible compound. A stable compound or chemically feasible compound is one that, among other factors, has stability sufficient to permit its preparation and detection. In some embodiments, disclosed compounds are sufficiently stable that they are not substantially altered when kept at a temperature of 40° C. or less, in the absence of moisture (e.g., less than about 10%, less than about 5%, less than about 2%, less than about 1%, or less than about 0.5%) or other chemically reactive conditions, for e.g., at least about 3 days, at least about a week, at least about 2 weeks, at least about 4 weeks, or at least about 6 weeks.

The terms "combine, combining, to combine, combination" refer to the action of adding at least one chemical substance to another chemical substance(s) either sequentially or simultaneously. In some embodiments, bringing these chemical substances together can result in transformation of the initial chemical substances into one or more different chemical substances. This transformation can occur through one or more chemical reactions, e.g., where covalent bonds are formed, broken, rearranged and the like. A non-limiting example can include hydrolysis of an ester into an alcohol and carboxylic acid which can result from the combination of the ester with a suitable base. In another non-limiting example, an aryl fluoride can be combined with an amine to provide an aryl amine through a substitution process. These terms also include changes in association of charged chemical substances and creation of charged chemical substances, such as, but not limited to, N-oxide formation, acid addition salt formation, basic addition salt formation, and the like. These terms include the creation and/or transformation of radical chemical substances and isotopically labeled chemical substances.

The terms "convert, converting, to convert, conversion" refer to a subset of "combination" and its grammatical equivalents, where the action of one or more reagents transforms one or more functional groups on a chemical substance to other functional group(s). For example, a conversion includes, but is not limited to, transforming a nitro functional group on a chemical substance to an amine with a reducing agent. Conversions also include changes in charged chemical substances, radical chemical substances and isotopically labeled chemical substances. However, the term "convert" does not include alteration of conserved bonds in disclosed genuses and compounds.

Compounds

In one aspect, provided herein are compounds of Formula I:

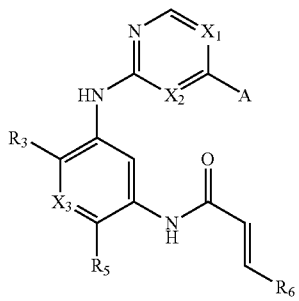

Formula I wherein:

A is selected from

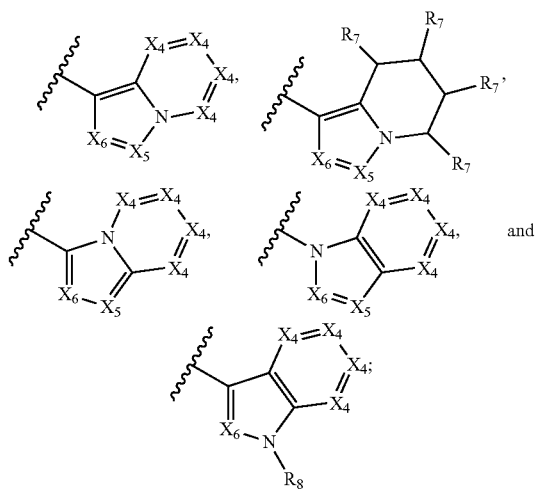

and $X_1$ is selected from N and $CR_1$;
$X_2$ is selected from N and $CR_2$;
$X_3$ is selected from N and $CR_4$;
each $X_4$ is independently selected from N and $CR_7$;
$X_5$ is selected from N and $CR_8$;
$X_6$ is selected from N and $CR_9$;

$R_1$ is selected from H, acyl, alkyl, alkenyl, alkynyl, alkoxy, aryloxy, alkoxycarbonyl, amido, amino, carbonate, carbamate, carbonyl, carboxyl, ester, halo, CN, $NO_2$, hydroxy, phosphate, phosphonate, phosphinate, phosphine oxide, mercapto, thio, alkylthio, arylthio, thiocarbonyl, sulfonyl, sulfonamidyl, sulfoxyl, sulfonate, urea, cycloalkyl, heterocyclyl, aryl, and heteroaryl, each of which is substituted with 0, 1, 2, or 3 $R_{12}$;

$R_2$, $R_3$, and $R_4$ are each independently selected from H, alkyl, alkoxy, halo, CN, and $NO_2$, each of which is substituted with 0, 1, 2, or 3 $R_{12}$;

$R_5$ is selected from H, alkyl, alkenyl, alkynyl, —$NR_{10}R_{11}$, —$OR_{11}$, and —$SR_{11}$, each of which is independently substituted with 0, 1, 2, or 3 $R_{12}$; or when $R_5$ is —$NR_{10}R_{11}$, then $R_{10}$ and $R_{11}$ can be taken together with the nitrogen atom to which they are attached to form a heterocyclyl or heteroaryl group, each of which is substituted with 0, 1, 2, or 3 $R_{12}$;

$R_4$ and $R_5$ can be taken together with the carbon atoms to which they are attached to form a cycloalkyl, heterocyclyl, aryl, or heteroaryl group, each of which is substituted with 0, 1, 2, or 3 $R_{12}$;

$R_6$ is selected from H, acyl, alkyl, amino, halo, CN, cycloalkyl, heterocycloalkyl, aryl, and heteroaryl, each of which is substituted with 0, 1, 2, or 3 $R_{12}$;

each $R_7$ is independently selected from H, alkyl, alkenyl, alkynyl, alkoxy, amido, amino, carbonyl, ester, halo, CN, and $NO_2$, each of which is substituted with 0, 1, 2, or 3 $R_{12}$; and wherein any two adjacent $R_7$ groups can be taken together with the carbon atoms to which they are attached to form a cycloalkyl, heterocyclyl, aryl, or heteroaryl ring, each of which is substituted with 0, 1, 2, or 3 $R_{12}$;

$R_8$ is selected from H, acyl, alkyl, amido, amino, carbamate, carbonyl, and urea, each of which is substituted with 0, 1, 2, or 3 $R_{12}$;

$R_9$ is selected from H, alkyl, alkenyl, alkynyl, alkoxy, amino, amido, ester, halo, CN, $NO_2$, cycloalkyl, heterocyclyl, aryl, and heteroaryl, each of which is substituted with 0, 1, 2, or 3 $R_{12}$;

each $R_{10}$ and $R_{11}$ are independently selected from H, acyl, alkyl, carbonyl, cycloalkyl, heterocycloalkyl, aryl, and heteroaryl, each of which is independently substituted with 0, 1, 2, or 3 $R_{12}$; and each $R_{12}$ is independently selected from acyl, alkyl, alkenyl, alkynyl, alkoxy, aryloxy, alkoxycarbonyl, amido, amino, carbonate, carbamate, carbonyl, ester, halo, CN, $NO_2$, hydroxyl, phosphate, phosphonate, phosphinate, phosphine oxide, thio, alkylthio, arylthio, thiocarbonyl, sulfonyl, sulfonamidyl, sulfoxyl, sulfonate, urea, cycloalkyl, heterocycloalkyl, aryl, and heteroaryl.

In some embodiments, the compound of Formula I can be a compound of Formula Aa:

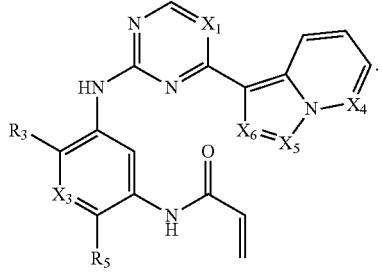

Formula Aa

In some embodiments, the compound of Formula I can be a compound of Formula Ab:

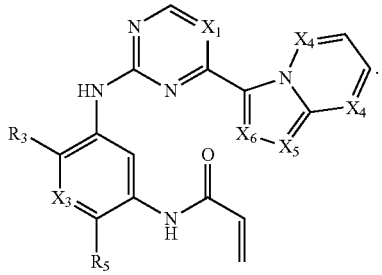

Formula Ab

In some embodiments, the compound of Formula I can be a compound of Formula Ac:

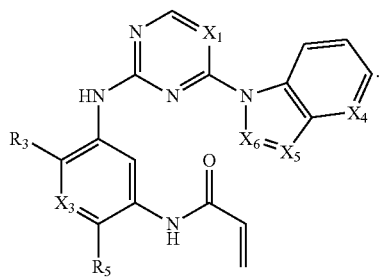

Formula Ac

In some embodiments, the compound of Formula I can be a compound of Formula Ad:

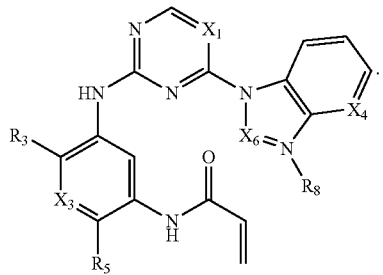

Formula Ad

In some embodiments, the compound of Formula I can be a compound of Formula Ae:

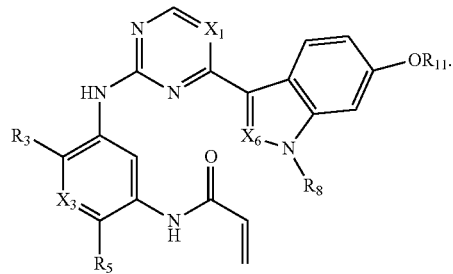

Formula Ae

In some embodiments, the compound of Formula I can be a compound of Formula Af:

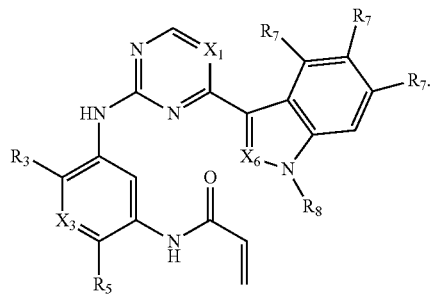

Formula Af

In some embodiments, the compound of Formula I can be a compound of Formula Ba:

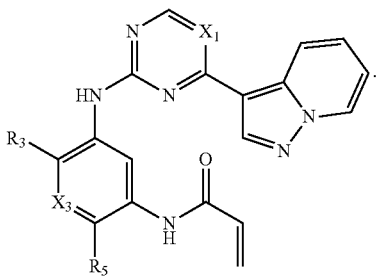

Formula Ba

In some embodiments, the compound of Formula I can be a compound of Formula Bb:

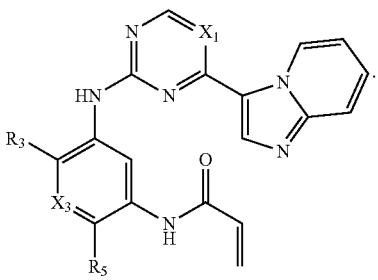

Formula Bb

In some embodiments, the compound of Formula I can be a compound of Formula Bc:

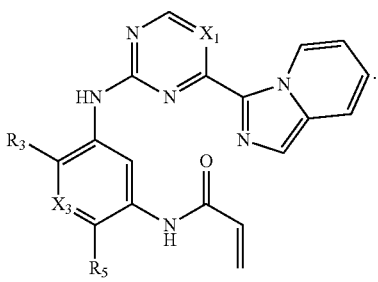

Formula Bc

In some embodiments, the compound of Formula I can be a compound of Formula Bd:

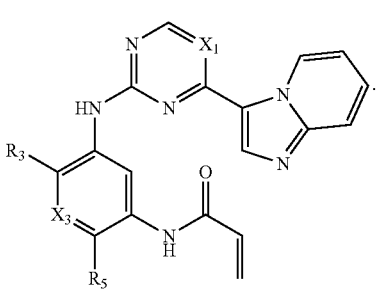

Formula Bd

In some embodiments, the compound of Formula I can be a compound of Formula Be:

Formula Be

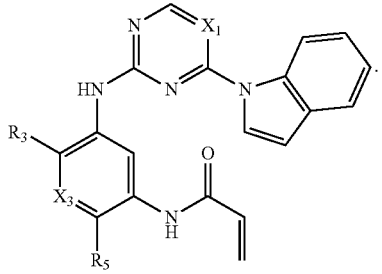

In some embodiments, the compound of Formula I can be a compound of Formula Bf:

Formula Bf

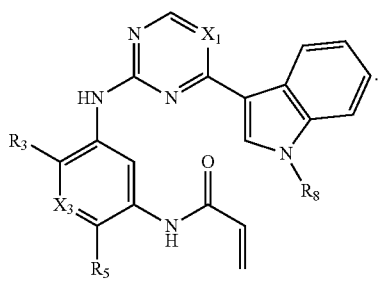

In some embodiments, the compound of Formula I can be a compound of Formula Bg:

Formula Bg

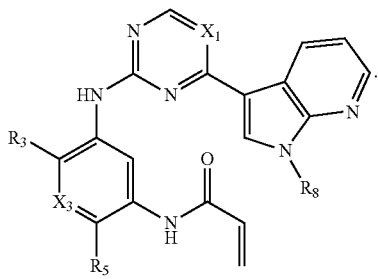

In some embodiments, the compound of Formula I can be a compound of Formula Bh:

Formula Bh

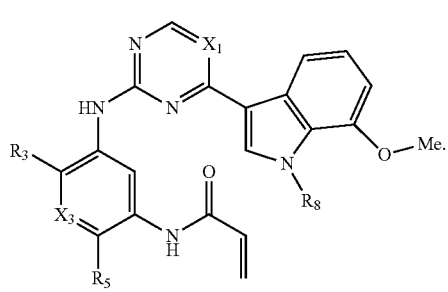

In some embodiments, the compound of Formula I can be a compound of Formula Bi:

Formula Bi

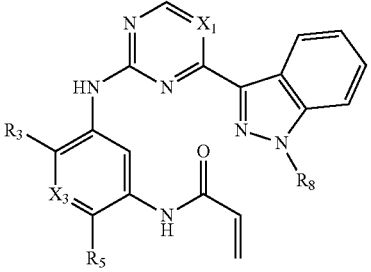

The following embodiments apply to any and all compounds of Formula I, including, but not limited to, Formulae Aa, Ab, Ac, Ad, Ae, Af, Ba, Bb, Bc, Bd, Be, Bf, Bg, Bh and Bi.

In some embodiments, $X_1$ can be N. In other embodiments, $X_1$ can be $CR_1$. In some embodiments, $X_2$ can be N. In other embodiments, $X_2$ can be $CR_2$, where $R_2$ is H. In some embodiments, $X_1$ can be N, and $X_2$ can be N. In some embodiments, $X_1$ can be $CR_1$, and $X_2$ can be N. In other embodiments, $X_1$ can be N, and $X_2$ can be $CR_2$, where $R_2$ is H. In further embodiments, $X_1$ can be $CR_1$, and $X_2$ can be $CR_2$, where $R_2$ is H. In some embodiments, $X_3$ can be N. In other embodiments, $X_3$ can be $CR_4$, where $R_4$ is H. In some embodiments, $X_1$ can be $CR_1$, $X_2$ can be N, and $X_3$ can be N. In some embodiments, $X_1$ can be $CR_1$, $X_2$ can be N, and $X_3$ can be $CR_4$, where $R_4$ is H. In further embodiments, $X_1$ can be N, $X_2$ can be N, and $X_3$ can be N. In some embodiments, $X_1$ can be N, $X_2$ can be N, and $X_3$ can be $CR_4$, where $R_4$ is H.

In some embodiments, A can be

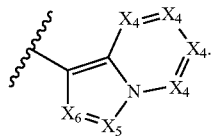

In some embodiments, A can be

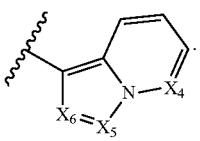

In some embodiments, A can be

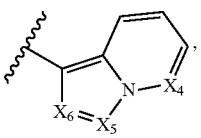

and $X_4$ can be N. In some embodiments, A can be

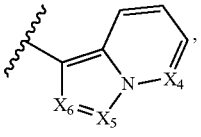

and $X_4$ can be $CR_7$, where $R_7$ is selected from H alkyl, alkoxy, amido, and CN. In further embodiments, A can be

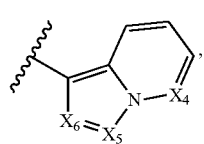

and $X_4$ can be $CR_7$, where $R_7$ is alkoxy, and the alkoxy is —OMe. In some embodiments, A can be

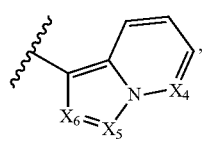

and $X_5$ can be N. In other embodiments, A can be

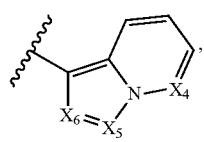

and $X_5$ can be $CR_8$, where $R_8$ is selected from H and alkyl. In further embodiments, A can be

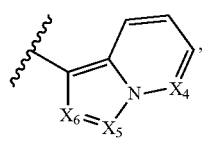

$X_5$ can be $CR_8$, where $R_8$ is alkyl, and the alkyl is Me. In some embodiments, A can be

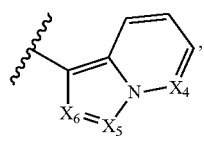

and $X_6$ can be N. In other embodiments, A can be

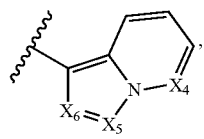

and $X_6$ can be $CR_9$, where $R_9$ is selected from H, heterocyclyl, aryl, and heteroaryl, each of which is substituted with 0, 1, or 2 $R_{12}$. In other embodiments, A can be

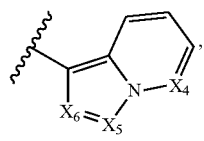

$X_6$ can be $CR_9$, where $R_9$ is selected from

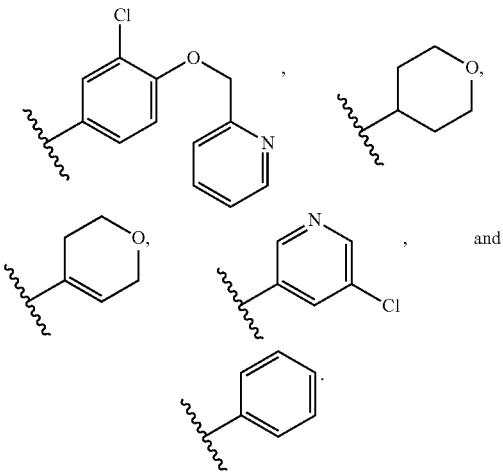

In some embodiments, A can be

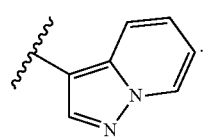 [SMILES: *c1cnn2ccccc12]

In some embodiments, A can be

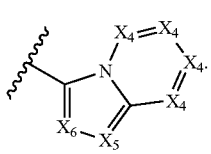

In some embodiments, A can be

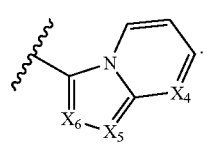

In some embodiments, A can be

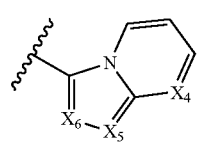

and $X_4$ can be N. In some embodiments, A can be

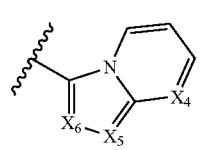

and $X_4$ can be $CR_7$, where $R_7$ is selected from H alkyl, alkoxy, amido, and CN. In further embodiments, A can be

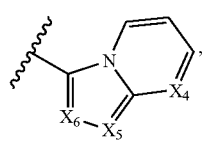

and $X_4$ can be $CR_7$, where $R_7$ is alkoxy, and the alkoxy is —OMe. In some embodiments, A can be

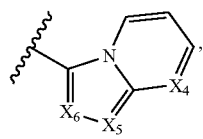

and $X_5$ can be N. In other embodiments, A can be

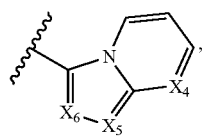

and $X_5$ can be $CR_8$, where $R_8$ is selected from H and alkyl. In further embodiments, A can be

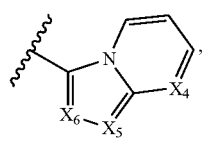

$X_5$ can be $CR_8$, where $R_8$ is alkyl, and the alkyl is Me. In some embodiments, A can be

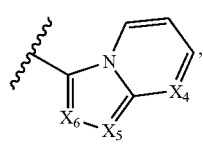

and $X_6$ can be N. In other embodiments, A can be

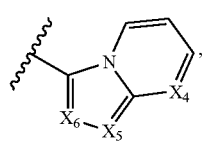

and $X_6$ can be $CR_9$, where $R_9$ is selected from H, heterocyclyl, aryl, and heteroaryl, each of which is substituted with 0, 1, or 2 $R_{12}$. In other embodiments, A can be $X_6$ can be $CR_9$, where $R_9$ is selected from

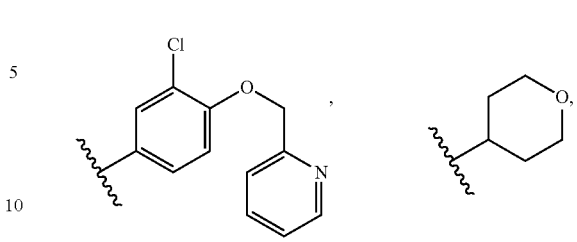

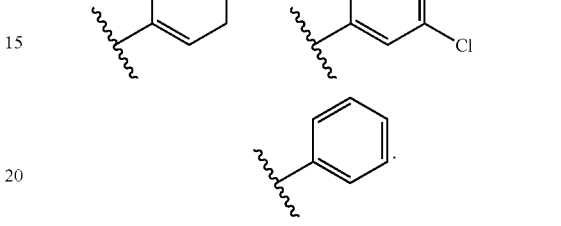

In some embodiments, A can be

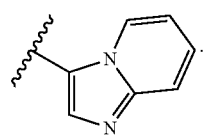 [SMILES: *c1cnc2ccccn12]

In other embodiments, A can be

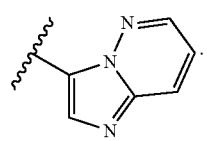 [SMILES: *c1cnc2cccnn12]

In further embodiments, A can be

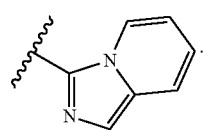 [SMILES: *c1ncc2ccccn12]

In some embodiments, A can be

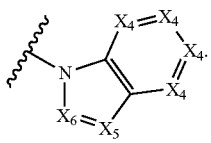

In some embodiments, A can be

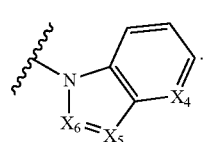

In some embodiments, A can be

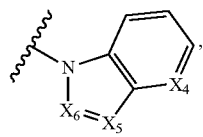

and $X_4$ can be N. In some embodiments, A can be

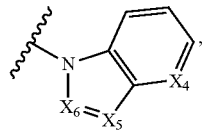

and $X_4$ can be $CR_7$, where $R_7$ is selected from H alkyl, alkoxy, amido, and CN. In further embodiments, A can be

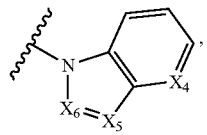

and $X_4$ can be $CR_7$, where $R_7$ is alkoxy, and the alkoxy is —OMe. In some embodiments, A can be

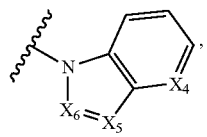

and $X_5$ can be N. In other embodiments, A can be

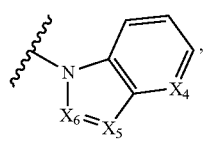

and $X_5$ can be $CR_8$, where $R_8$ is selected from H and alkyl. In further embodiments, A can be

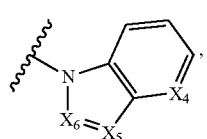

$X_5$ can be $CR_8$, where $R_8$ is alkyl, and the alkyl is Me. In some embodiments, A can be

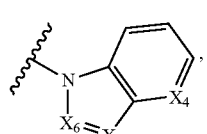

and $X_6$ can be N. In other embodiments, A can be

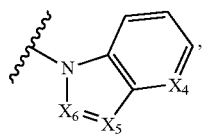

and $X_6$ can be $CR_9$, where $R_9$ is selected from H, heterocyclyl, aryl, and heteroaryl, each of which is substituted with 0, 1, or 2 $R_{12}$. In other embodiments, A can be

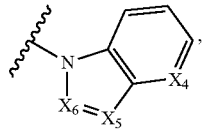

$X_6$ can be $CR_9$, where $R_9$ is selected from

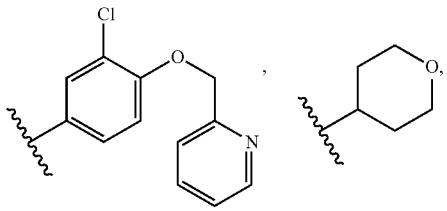

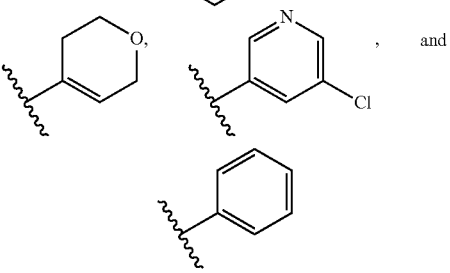

, and

In some embodiments, A can be

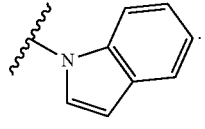 [SMILES: *n1ccc2ccccc21]

In some embodiments, A can be

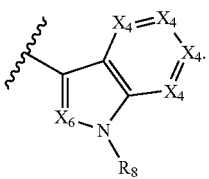

In some embodiments, A can be

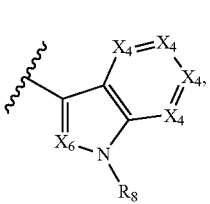

and each $X_4$ can be $CR_7$, where $R_7$ is H. In other embodiments, A can be

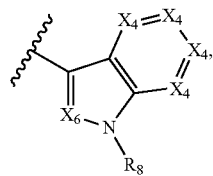

$X_4$ can be $CR_7$, where any two adjacent $R_7$ groups can be taken together with the carbon atoms to which they are attached to form a cycloalkyl, heterocyclyl, aryl, or heteroaryl ring, each of which can be substituted with 0, 1, 2, or 3 $R_{12}$. In other embodiments, A can be selected from

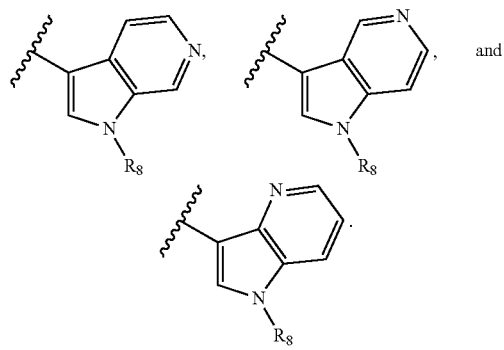

and

In some embodiments, A can be

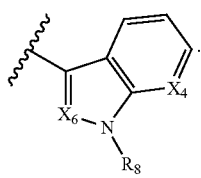

In some embodiments, A can be

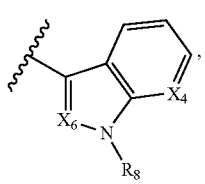

and $X_4$ can be N. In some embodiments, A can be

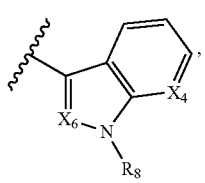

and $X_4$ can be $CR_7$, where $R_7$ is selected from H alkyl, alkoxy, amido, ester, cyclohexyl, and CN. In some embodiments, A can be

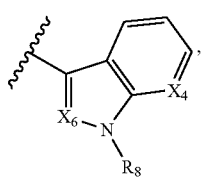

and $X_4$ can be $CR_7$, where $R_7$ is selected from H alkyl, alkoxy, amido, and CN. In further embodiments, A can be and $X_4$ can be $CR_7$, where $R_7$ is alkoxy, and the alkoxy is —OMe. In other embodiments, A can be

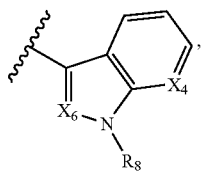

and $R_8$ can be selected from H and alkyl, where the alkyl is substituted with 0 or 1 $R_{12}$, and $R_{12}$ is amino. In further embodiments, A can be and $R_8$ can be alkyl, where the alkyl is Me or Et. In further embodiments, A can be and $R_8$ can be alkyl, where the alkyl where the alkyl is substituted with 0 or 1 $R_{12}$, where $R_{12}$ is amido or hydroxy. In some embodiments, A can be

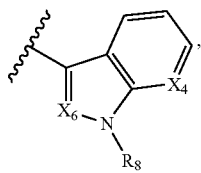

and $R_8$ can be H. In some embodiments, A can be

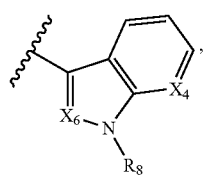

and $X_6$ can be N. In other embodiments, A can be

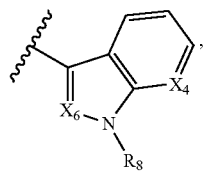

and $X_6$ can be $CR_9$, where $R_9$ is selected from H, CN, alkyl, ester, amido, heterocyclyl, aryl, and heteroaryl, each of which is substituted with 0, 1, or 2 $R_{12}$. In other embodiments, A can be

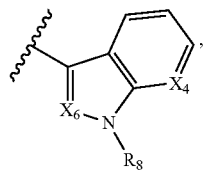

and $X_6$ can be $CR_9$, where $R_9$ is selected from H, heterocyclyl, aryl, and heteroaryl, each of which is substituted with 0, 1, or 2 $R_{12}$. In other embodiments, A can be

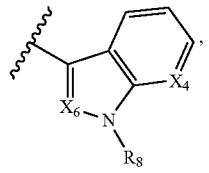

$X_6$ can be $CR_9$,

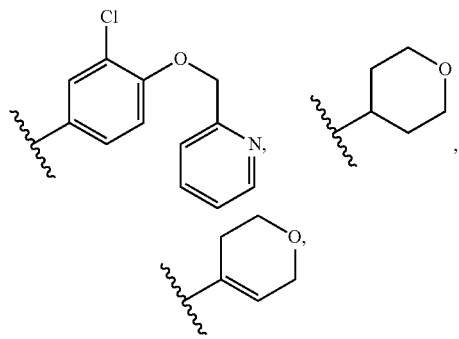

where $R_9$ is selected from

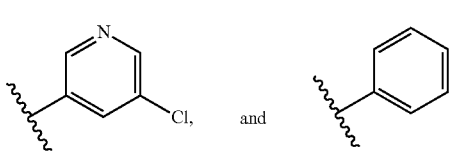

In some embodiments, A can be

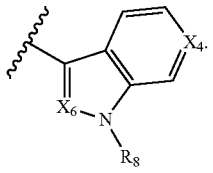

In some embodiments, A can be

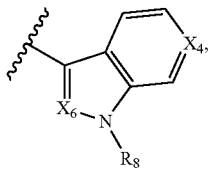

and $X_4$ is $CR_7$, and $R_7$ is selected from cyano, ester, and heteroaryl. In other embodiments, A can be

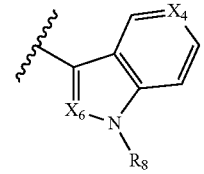

and $X_4$ is $CR_7$, and $R_7$ is ester. In further embodiments, A can be

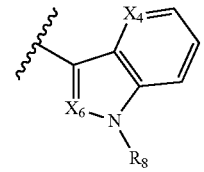

and $X_4$ is $CR_7$, and $R_7$ is ester.

In some embodiments, A can be

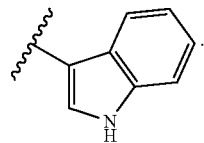 [SMILES: *c1c[nH]c2ccccc12]

In other embodiments, A can be

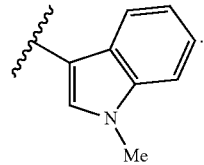 [SMILES: *c1nn(C)c2ccccc12]

In further embodiments, A can be

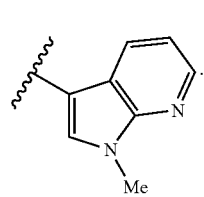

In further embodiments, A can be

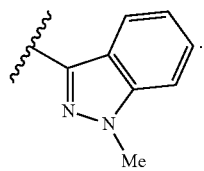

In some embodiments, A can be

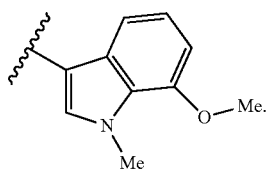 [SMILES: *c1cn(C)c2c(OC)cccc12]

In some embodiments, A can be

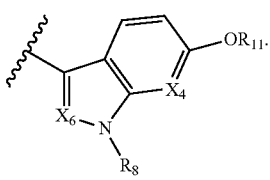

In some embodiments, A can be

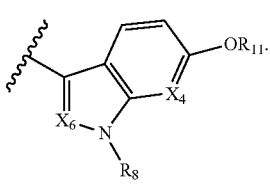

In some embodiments, A can be

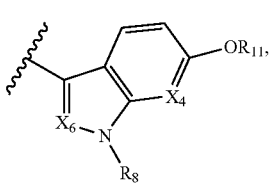

and $X_4$ can be N. In some embodiments, A can be

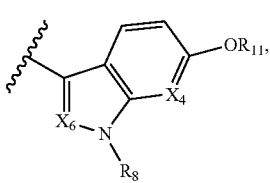

and $X_4$ can be $CR_7$, where $R_7$ is selected from H alkyl, alkoxy, amido, and CN. In further embodiments, A can be

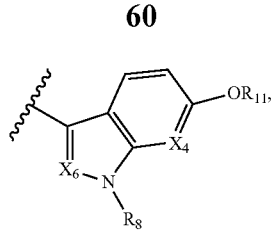

and $X_4$ can be $CR_7$, where $R_7$ is alkoxy. In further embodiments, A can be

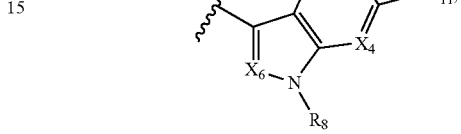

and $X_4$ can be $CR_7$, where $R_7$ is alkoxy, and the alkoxy is —OMe. In other embodiments, A can be

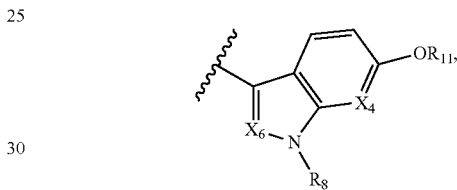

and $R_8$ can be selected from H and alkyl. In further embodiments, A can be

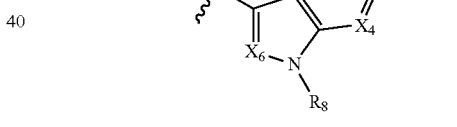

and $R_8$ can be alkyl, where the alkyl is Me. In some embodiments, A can be

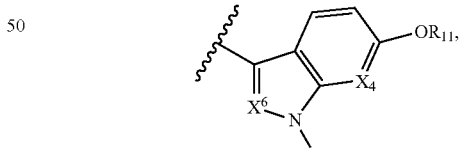

and $R_8$ can be H. In some embodiments, A can be

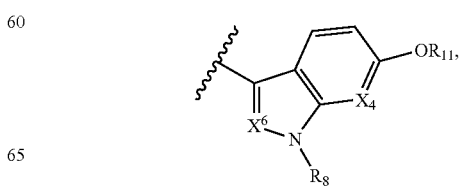

and $X_6$ can be N. In other embodiments, A can be
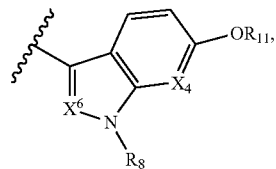
and $X_6$ can be $CR_9$, where $R_9$ is selected from H, heterocyclyl, aryl, and heteroaryl, each of which is substituted with 0, 1, or 2 $R_{12}$. In other embodiments, A can be
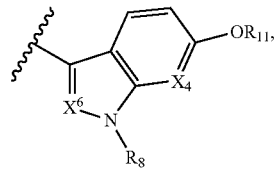
$X_6$ can be $CR_9$, where $R_9$ is selected from
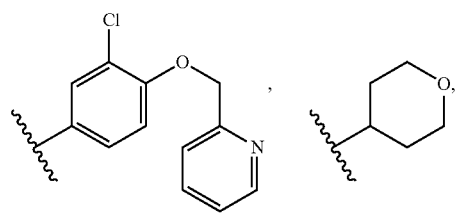
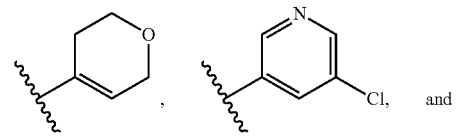, and
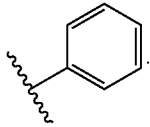.
In some embodiments, A can be
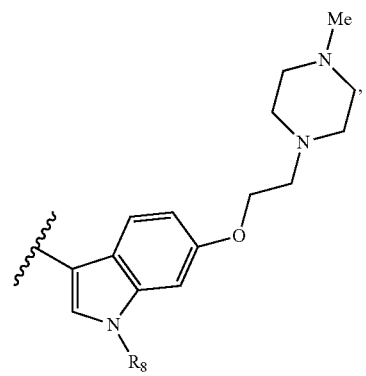
selected from
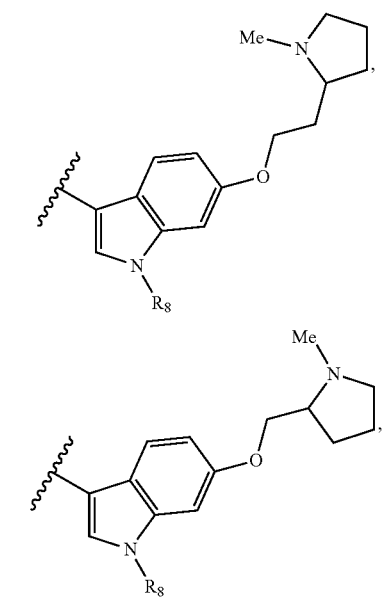
In other embodiments, A can be
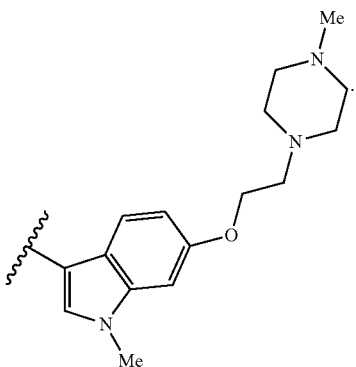 [SMILES: *c1cn(C)c2cc(OCCN3CCN(C)CC3)ccc12]

In further embodiments, A can be

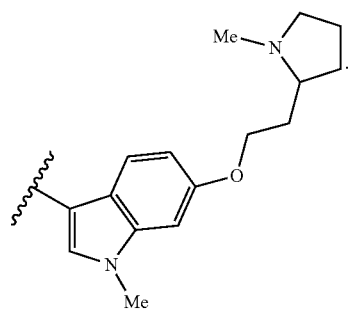 [SMILES: *c1cn(C)c2cc(OCCC3CCCN3C)ccc12]

In other embodiments, A can be

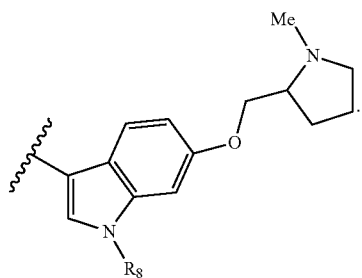

In some embodiments, A can be

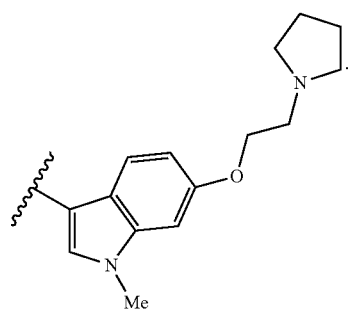 [SMILES: *c1cn(C)c2cc(OCCN3CCCC3)ccc12]

In further embodiments, A can be

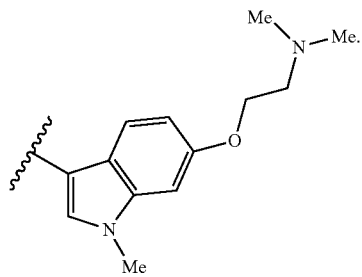 [SMILES: *c1cn(C)c2cc(OCCN(C)C)ccc12]

In some embodiments, $R_1$ can be selected from H, alkyl, alkenyl, alkynyl, amido, amino, ester, halo, CN, cycloalkyl, urea, phosphine oxide, heterocyclyl, aryl, and heteroaryl, each of which is substituted with 0, 1, 2, or 3 $R_{12}$. In some embodiments, $R_1$ can be selected from H, alkyl, alkenyl, alkynyl, amido, amino, ester, halo, CN, cycloalkyl, heterocyclyl, aryl, and heteroaryl, each of which is substituted with 0, 1, 2, or 3 $R_{12}$. In other embodiments, $R_1$ can be selected from H, alkyl, amido, ester, halo, and CN, each of which is substituted with 0, 1, or 2 $R_{12}$. In further embodiments, $R_1$ can be ester or amido, each of which is substituted with 1 or 2 $R_{12}$.

In some embodiments, $R_1$ can be ester substituted with one $R_{12}$. In some embodiments, the ester is selected from

[structures of various esters]

In other embodiments, the ester can be selected from

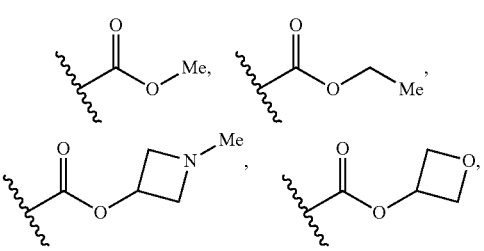

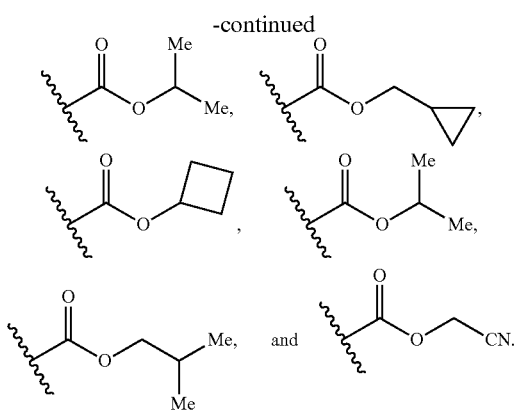

In further embodiments, the ester can be selected from

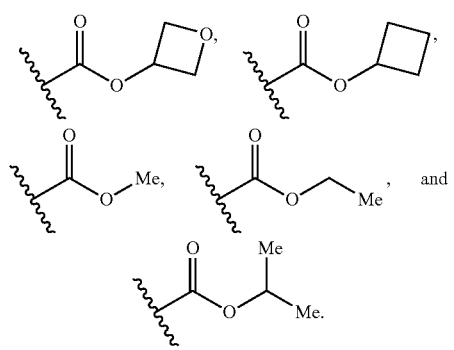

In other embodiments, the ester can be selected from

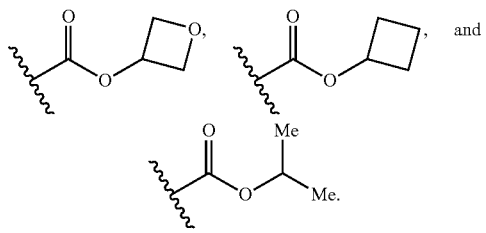

In other embodiments, $R_1$ can be amide substituted with 1 or 2 $R_{12}$. In further embodiments, the amide can be selected from

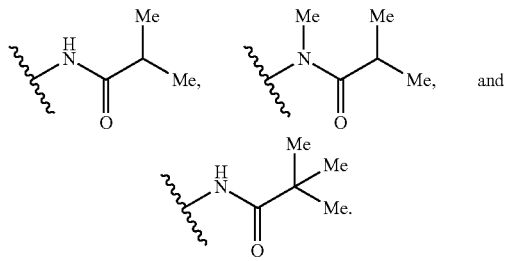

In a further embodiment, the amide can be

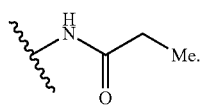 [SMILES: *NC(=O)CC]

In some embodiments, $R_3$ can be selected from H, alkyl, alkoxy, and halo. In other embodiments, $R_3$ can be alkoxy. In further embodiments, $R_3$ can be alkoxy, where the alkoxy is —OMe.

In some embodiments, $R_5$ can be selected from H, alkynyl, —$NR_{10}R_{11}$, and —$OR_{11}$, each of which is independently substituted with 0, 1, 2, or 3 $R_{12}$; or when $R_5$ is —$NR_{10}R_{11}$, then $R_{10}$ and $R_{11}$ can be taken together with the nitrogen atom to which they are attached to form a heterocyclyl or heteroaryl group, each of which is substituted with 0, 1, 2, or 3 $R_{12}$. In other embodiments, $R_5$ can be —$NR_{10}R_{11}$, where $R_{10}$ is alkyl, $R_{11}$ is alkyl substituted with 1 or 2 $R_{12}$, and $R_{12}$ is amino or heterocyclyl. In some embodiments, $R_5$ can be —$NR_{10}R_{11}$, and $R_{10}$ and $R_{11}$ are taken together with the nitrogen atom to which they are attached to form a heterocyclyl or heteroaryl group, substituted with 0 or 1 $R_{12}$. In other embodiments, $R_5$ can be —$OR_{11}$, where $R_{11}$ is alkyl substituted with 0, 1 or 2 $R_{12}$, and each $R_{12}$ is independently selected from heterocyclyl, heterocyclylalkyl, alkoxyalkyl, and aminoalkyl. In further embodiments, $R_5$ can be alkynyl, where the alkynyl is substituted with one $R_{12}$, and $R_{12}$ alkylamino.

In some embodiments, $R_5$ can be selected from

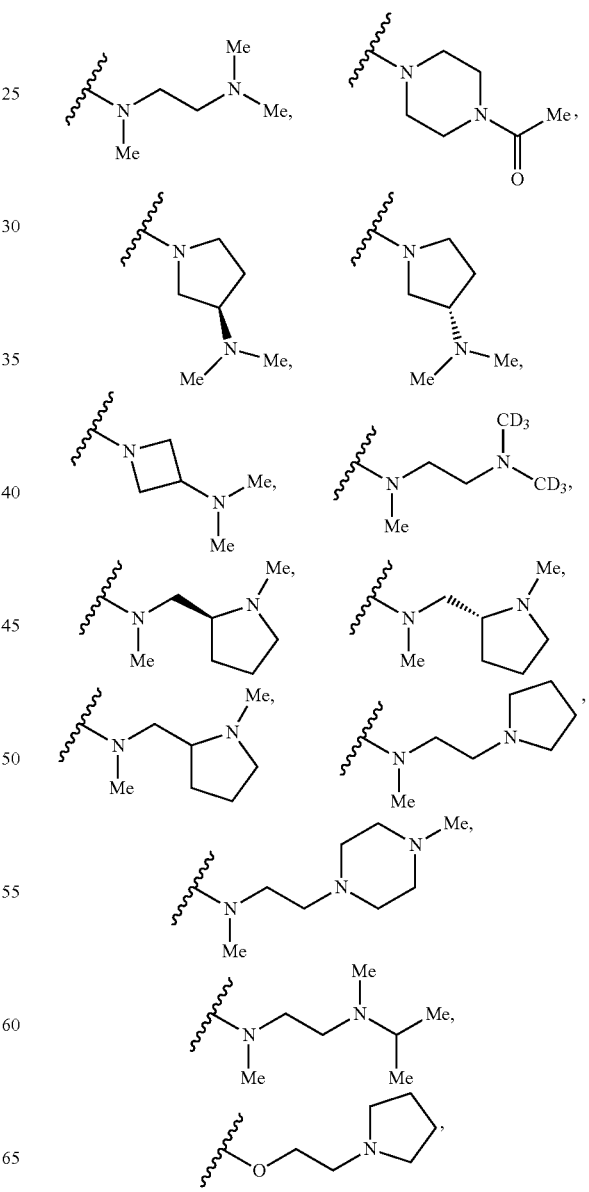

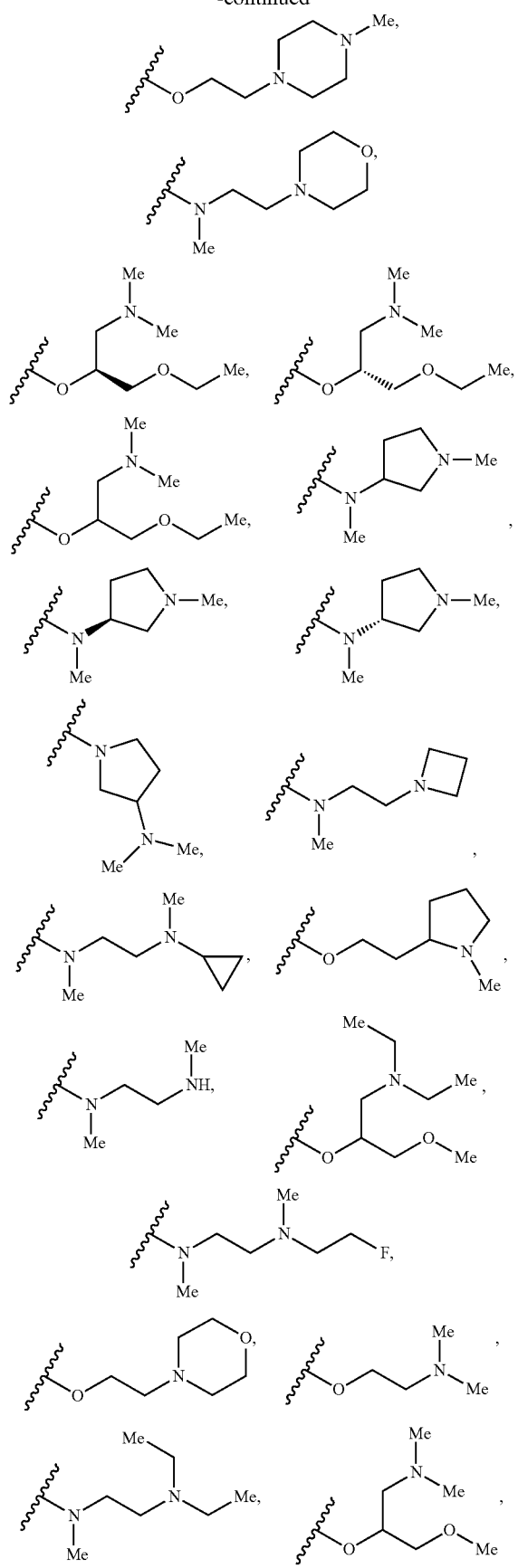
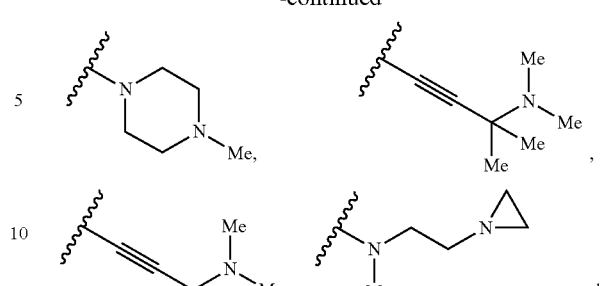
In other embodiments, $R_5$ can be selected from

-continued

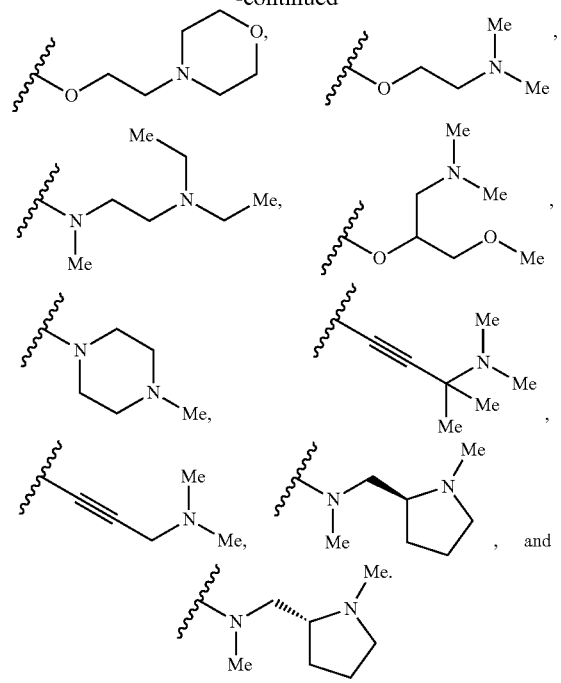

In some embodiments, $R_5$ can be selected from

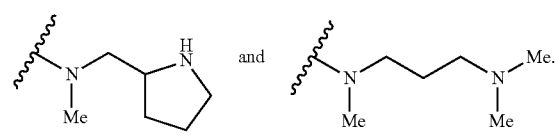 [SMILES: *N(C)CC1CCCN1 ; *N(C)CCCN(C)C]

In further embodiments, $R_5$ can be selected from

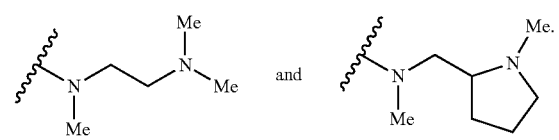 [SMILES: *N(C)CCN(C)C ; *N(C)CC1CCCN1C]

In some embodiments, $R_6$ can be H or alkyl substituted with 0 or 1 $R_{12}$. In some embodiments, $R_6$ can be H. In other embodiments, $R_6$ can be alkyl substituted with one $R_{12}$, and $R_{12}$ is amino. In other embodiments, $R_6$ can be alkyl substituted with one $R_{12}$, and $R_{12}$ is heterocyclyl. In some embodiments, $R_6$ can be selected from alkyl, CN, and halo.

In some embodiments, each $R_7$ can be independently selected from H, alkyl, alkenyl, alkynyl, alkoxy, amido, amino, carbonyl, ester, halo, CN, $NO_2$ and heteroaryl, each of which is substituted with 0, 1, 2, or 3 $R_{12}$; and wherein any two adjacent $R_7$ groups can be taken together with the carbon atoms to which they are attached to form a cycloalkyl, heterocyclyl, aryl, or heteroaryl ring, each of which is substituted with 0, 1, 2, or 3 $R_{12}$. In other embodiments, $R_8$ can be selected from H, acyl, alkyl, cycloalkyl, amido, amino, carbamate, carbonyl, and urea, each of which is substituted with 0, 1, 2, or 3 $R_{12}$.

In some embodiments, the compound of Formula I can have the following aspects:

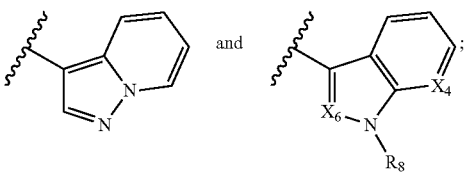

A is selected from R
$X_1$ is selected from N and $CR_1$;
$X_2$ is N;
$X_3$ is $CR_4$;
$X_4$ is selected from N and $CR_7$;
$X_6$ is $CR_9$;
$R_1$ is selected from H, alkyl, and ester;
$R_3$ is alkoxy;
$R_4$ is H;
$R_5$ is $—NR_{10}R_{11}$;
$R_6$ is H;
$R_7$ is selected from H and alkoxy;
$R_8$ is selected from H and alkyl;
$R_9$ is selected from H, aryl, and heteroaryl, each of which is substituted with 0 or 1 $R_{12}$, and $R_{12}$ is halo;
$R_{10}$ is alkyl; and
$R_{11}$ is alkyl substituted with one $R_{12}$, and $R_{12}$ is substituted with amino or heterocyclyl.

In some embodiments, the compound of Formula I can have the following aspects:

A is selected from $R_8$

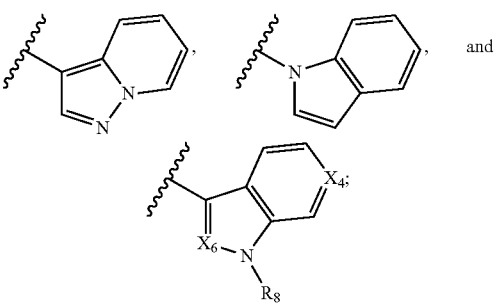

$X_1$ is $CR_1$;
$X_2$ is N;
$X_3$ is $CR_4$;
$X_4$ is $CR_7$;
$X_6$ is $CR_9$;
$R_1$ is selected from H, ester, halo, and CN;
$R_3$ is alkoxy;
$R_4$ is H;
$R_5$ is selected from H, alkynyl, $—NR_{10}R_{11}$, and $—OR_{11}$, each of which is independently substituted with 0, 1, or 2 $R_{12}$, and $R_{12}$ is amino, alkoxy, or heterocyclyl; or when $R_5$ is $—NR_{10}R_{11}$, then $R_{10}$ and $R_{11}$ can be taken together with the nitrogen atom to which they are attached to form a heterocyclyl or heteroaryl group, each of which is substituted with 1 $R_{12}$, and $R_{12}$ is alkyl or amino;
$R_6$ is H;
$R_7$ is selected from H and alkoxy substituted with one $R_{12}$, and $R_{12}$ is amino or heterocyclyl;
$R_8$ is alkyl;
$R_9$ is selected from H and aryl substituted with 2 $R_{12}$, and $R_{12}$ is alkoxy or halo; and $R_{10}$ and $R_{11}$ are each independently alkyl, each of which is independently substituted with 0, 1, or 2 $R_{12}$, and $R_{12}$ is amino, alkoxy, or heterocyclyl.

In some aspects, the compound of Formula I can have the following aspects:

A is selected from

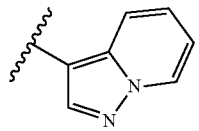 and 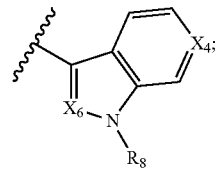

$X_1$ is selected from N and $CR_1$;
$X_2$ is N;
$X_3$ is $CR_4$;
$X_4$ is $CR_7$;
$X_6$ is $CR_9$;
$R_1$ is selected from H, ester, halo, and CN;
$R_3$ is alkoxy;
$R_4$ is H;
$R_5$ is selected from H, alkynyl, —$NR_{10}R_{11}$, and —$OR_{11}$, each of which is independently substituted with 0, 1, or 2 $R_{12}$, and $R_{12}$ is amino, alkoxy, or heterocyclyl; or when $R_5$ is —$NR_{10}R_{11}$, then $R_{10}$ and $R_{11}$ can be taken together with the nitrogen atom to which they are attached to form a heterocyclyl or heteroaryl group, each of which is substituted with 1 $R_{12}$, and $R_{12}$ is alkyl or amino;
$R_6$ is H;
$R_7$ is selected from H and alkoxy;
$R_8$ is selected from H and alkyl;
$R_9$ is selected from H, heterocyclyl, and aryl;
$R_{10}$ and $R_{11}$ are each independently alkyl, each of which is independently substituted with 0, 1, or 2 $R_{12}$, and $R_{12}$ is amino, alkoxy, or heterocyclyl.

In some embodiments, the compound of Formula I can have the following aspects:

A is selected from

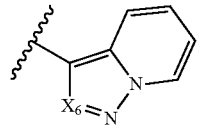 and 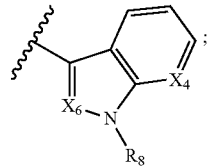;

$X_1$ is $CR_1$;
$X_2$ is N;
$X_3$ is $CR_4$;
$X_4$ is selected from N and $CR_7$;
$X_6$ is $CR_9$;
$R_1$ is selected from H, alkyl, and ester;
$R_3$ is alkoxy;
$R_4$ is H;
$R_5$ is selected from —$NR_{10}R_{11}$ and —$OR_{11}$.
$R_6$ is H;
$R_7$ is alkoxy;
$R_8$ is selected from H and alkyl;
$R_9$ is selected from H, aryl, and heteroaryl, each of which is substituted with 0 or 1 $R_{12}$, and $R_{12}$ is halo;
$R_{10}$ is alkyl; and
$R_{11}$ is alkyl substituted with one $R_{12}$, and $R_{12}$ is substituted with alkoxy, amino or heterocyclyl.

In other embodiments, the compound of Formula I can have the following aspects:

A is selected from

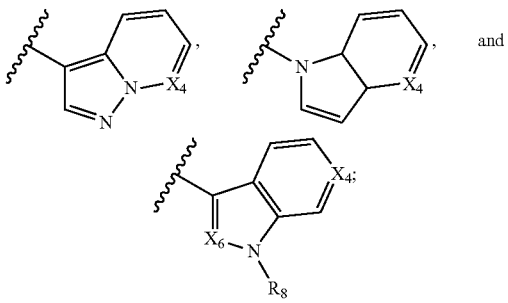

$X_1$ is $CR_1$;
$X_2$ is N;
$X_3$ is $CR_4$;
$X_4$ is $CR_7$;
$X_6$ is $CR_9$;
$R_1$ is selected from H, ester, amido, halo, and CN;
$R_3$ is alkoxy;
$R_4$ is H;
$R_5$ is selected from H, alkynyl, —$NR_{10}R_{11}$, and —$OR_{11}$, each of which is independently substituted with 0, 1, or 2 $R_{12}$, and $R_{12}$ is amino, alkoxy, or heterocyclyl; or when $R_5$ is —$NR_{10}R_{11}$, then $R_{10}$ and $R_{11}$ can be taken together with the nitrogen atom to which they are attached to form a heterocyclyl or heteroaryl group, each of which is substituted with 1 $R_{12}$, and $R_{12}$ is alkyl or amino;
$R_6$ is H;
$R_7$ is selected from H and alkoxy;
$R_8$ is alkyl;
$R_9$ is selected from H and aryl substituted with 2 $R_{12}$, and $R_{12}$ is alkoxy or halo; and
$R_{10}$ and $R_{11}$ are each independently alkyl, each of which is independently substituted with 0, 1, or 2 $R_{12}$, and $R_{12}$ is amino, alkoxy, or heterocyclyl.

Provided herein are compounds of Formula I selected from:

N-(3-((5-chloro-4-(6-(2-(pyrrolidin-1-yl)ethoxy)-1H-indol-3-yl)pyrimidin-2-yl)amino)-4-methoxyphenyl)acrylamide;

N-(5-((5-chloro-4-(pyrazolo[1,5-a]pyridin-3-yl)pyrimidin-2-yl)amino)-2-(2-(dimethylamino)ethoxy)-4-methoxyphenyl)acrylamide;

N-(3-((5-cyano-4-(1-methyl-6-(2-(1-methylpyrrolidin-2-yl)ethoxy)-1H-indol-3-yl)pyrimidin-2-yl)amino)-4-methoxyphenyl)acrylamide;

N-(2-((2-(dimethylamino)ethyl)(methyl)-amino)-4-methoxy-5-((4-(1-methyl-1H-indol-3-yl)-5-(N-methylisobutyramido)-pyrimidin-2-yl)amino)phenyl)acrylamide;

N-(3-((5-cyano-4-(1-methyl-6-(2-(pyrrolidin-1-yl)ethoxy)-1H-indol-3-yl)pyrimidin-2-yl)amino)-4-methoxyphenyl)acrylamide;

N-(2-((2-(dimethylamino)ethyl)(methyl)amino)-5-((5-isobutyramido-4-(1-methyl-1H-indol-3-yl)pyrimidin-2-yl)amino)-4-methoxyphenyl)acrylamide;

N-(3-((5-cyano-4-(6-(3-(dimethylamino)propoxy)-1-methyl-1H-indol-3-yl)pyrimidin-2-yl)amino)-4-methoxyphenyl)acrylamide;

N-(2-((2-(dimethylamino)ethyl)(methyl)amino)-4-methoxy-5-((4-(1-methyl-1H-indol-3-yl)pyrimidin-2-yl)amino)phenyl)acrylamide;

N-(4-methoxy-2-(methylamino)ethyl)amino)-5-((4-(1-methyl-1H-indol-3-yl)pyrimidin-2-yl)amino)phenyl)acrylamide;

N-(2-((2-(dimethylamino)ethyl)(methyl)amino)-4-methoxy-5-((4-(1-methyl-2-(tetrahydro-2H-pyran-4-yl)-1H-indol-3-yl)-1,3,5-triazin-2-yl)amino)phenyl)acrylamide; and N-(2-((2-(dimethylamino)ethyl)(methyl)amino)-4-methoxy-5-((4-(1-methyl-2-phenyl-1H-indol-3-yl)pyrimidin-2-yl)amino)phenyl)acrylamide;

or a pharmaceutically acceptable form thereof.

Provided herein are compounds of Formula I selected from:

N-(2-((2-(dimethylamino)ethyl)(methyl)amino)-4-methoxy-5-((4-(1-methyl-2-phenyl-1H-indol-3-yl)-1,3,5-triazin-2-yl)amino)phenyl)acrylamide;

Sec-butyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;

Isobutyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;

isopropyl 2-((5-acrylamido-4-((2-(dimethylamino)ethyl)(methyl)amino)-2-methoxyphenyl)amino)-4-(1H-indol-1-yl)pyrimidine-5-carboxylate;

N-(5-((4-(1H-indol-3-yl)pyrimidin-2-yl)amino)-2-((2-(dimethylamino)ethyl)(methyl)amino)-4-methoxyphenyl)acrylamide;

isopropyl 2-((5-acrylamido-2-methoxy-4-(methyl(2-(methylamino)ethyl)-amino)phenyl)amino)-4-(1-methyl-1H-indol-3-yl)pyrimidine-5-carboxylate;

Isopropyl 2-((5-acrylamido-4-((2-(dimethylamino)ethyl)(methyl)amino)-2-methoxyphenyl)amino)-4-(7-methoxy-1-methyl-1H-indol-3-yl)pyrimidine-5-carboxylate;

Cyclopropylmethyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;

Cyclobutyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;

N-(5-((4-(2-(5-chloropyridin-3-yl)-1-methyl-1H-indol-3-yl)pyrimidin-2-yl)amino)-2-((2-(dimethylamino)ethyl)(methyl)amino)-4-methoxyphenyl)acrylamide;

Isopropyl 2-((5-acrylamido-4-((2-(dimethylamino)ethyl)(methyl)amino)-2-methoxyphenyl)amino)-4-(pyrazolo[1,5-a]pyridin-3-yl)pyrimidine-5-carboxylate;

Methyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;

Oxetan-3-yl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;

Isopropyl 2-((5-acrylamido-4-((2-(dimethylamino)ethyl)(methyl)amino)-2-methoxyphenyl)amino)-4-(1-methyl-1H-pyrrolo[2,3-b]pyridin-3-yl)pyrimidine-5-carboxylate;

Isopropyl 2-((5-acrylamido-2-methoxy-4-(methyl((1-methylpyrrolidin-2-yl)methyl)amino)phenyl)amino)-4-(1-methyl-1H-indol-3-yl)pyrimidine-5-carboxylate;

Ethyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;

Isopropyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate; and Isopropyl 2-((5-acrylamido-4-((2-(dimethylamino)ethyl)(methyl)amino)-2-methoxyphenyl)amino)-4-(1H-indol-3-yl)pyrimidine-5-carboxylate;

Methyl 2-((5-acrylamido-2-methoxy-4-(methyl((1-methylpyrrolidin-2-yl)methyl)amino)phenyl)amino)-4-(1-methyl-1H-indol-3-yl)pyrimidine-5-carboxylate;

N-(5-((5-chloro-4-(pyrazolo[1,5-a]pyridin-3-yl)pyrimidin-2-yl)amino)-2-((2-(dimethylamino)ethyl)(methyl)amino)-4-methoxyphenyl)acrylamide; and N-(5-((4-(2-(3,6-dihydro-2H-pyran-4-yl)-1-methyl-1H-indol-3-yl)-1,3,5-triazin-2-yl)amino)-2-((2-(dimethylamino)ethyl)(methyl)amino)-4-methoxyphenyl)acrylamide;

or a pharmaceutically acceptable form thereof.

Provided herein are compounds of Formula I selected from:

N-(3-((5-cyano-4-(1-methyl-6-((1-methylpyrrolidin-2-yl)methoxy)-1H-indol-3-yl)pyrimidin-2-yl)amino)-4-methoxyphenyl)acrylamide;

N-(3-((5-chloro-4-(1-methyl-6-(2-(4-methylpiperazin-1-yl)ethoxy)-1H-indol-3-yl)pyrimidin-2-yl)amino)-4-methoxyphenyl)acrylamide;

Isopropyl 2-((5-acrylamido-4-((2-(dimethylamino)ethyl)(methyl)amino)-2-methoxyphenyl)amino)-4-(1H-indol-1-yl)pyrimidine-5-carboxylate;

N-(2-((2-(dimethylamino)ethyl)(methyl)amino)-4-methoxy-5-((4-(1-methyl-1H-indol-3-yl)-5-pivalamidopyrimidin-2-yl)amino)phenyl)acrylamide;

N-(5-((5-chloro-4-(pyrazolo[1,5-a]pyridin-3-yl)pyrimidin-2-yl)amino)-2-(3-(dimethylamino)pyrrolidin-1-yl)-4-methoxyphenyl)acrylamide; and N-(5-((4-(2-(3-chloro-4-(pyridin-2-ylmethoxy)phenyl)-1-methyl-1H-indol-3-yl)pyrimidin-2-yl)amino)-2-((2-(dimethylamino)ethyl)(methyl)amino)-4-methoxyphenyl)acrylamide;

or a pharmaceutically acceptable form thereof.

In another aspect, provided herein are compounds of Formula I

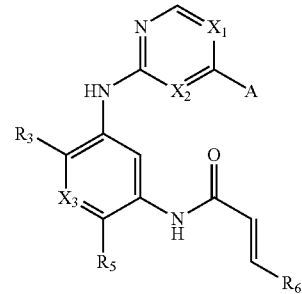

Formula I wherein:

A is selected from

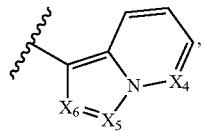 , 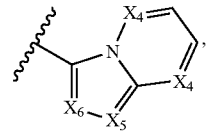 ,

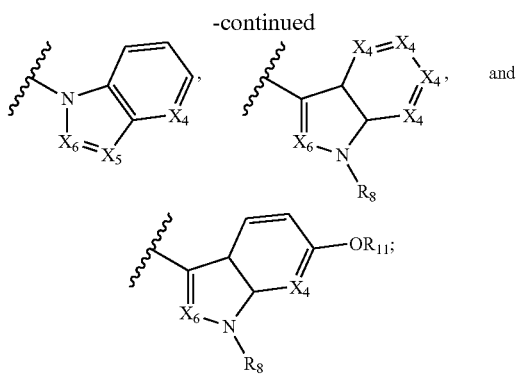

$X_1$ is selected from

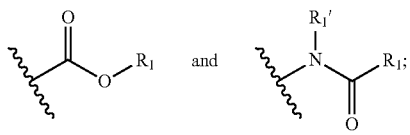

$X_2$ is selected from N and $CR_2$;
$X_3$ is selected from N and $CR_4$;
each $X_4$ is independently selected from N and $CR_7$;
$X_5$ is selected from N and $CR_8$;
$X_6$ is selected from N and $CR_9$;
each $R_1$ is independently selected from alkyl, alkenyl, alkynyl, cycloalkyl, heterocyclyl, aryl, and heteroaryl, each of which is substituted with 0, 1, 2, or 3 $R_{12}$;
$R_1'$ is selected from H and alkyl, each of which is substituted with 0, 1, 2, or 3 $R_{12}$;
$R_2$, $R_3$, and $R_4$ are each independently selected from H, alkyl, alkoxy, halo, CN, and $NO_2$, each of which is substituted with 0, 1, 2, or 3 $R_{12}$;
$R_5$ is selected from H, alkyl, alkenyl, alkynyl, $-NR_{10}R_{11}$, $-OR_{11}$, and $-SR_{11}$, each of which is independently substituted with 0, 1, 2, or 3 $R_{12}$; or when $R_5$ is $-NR_{10}R_{11}$, then $R_{10}$ and $R_{11}$ can be taken together with the nitrogen atom to which they are attached to form a heterocyclyl or heteroaryl group, each of which is substituted with 0, 1, 2, or 3 $R_{12}$;
$R_4$ and $R_5$ can be taken together with the carbon atoms to which they are attached to form a cycloalkyl, heterocyclyl, aryl, or heteroaryl group, each of which is substituted with 0, 1, 2, or 3 $R_{12}$;
$R_6$ is selected from H, acyl, alkyl, amino, halo, CN, cycloalkyl, heterocycloalkyl, aryl, and heteroaryl, each of which is substituted with 0, 1, 2, or 3 $R_{12}$;
each $R_7$ is independently selected from H, alkyl, alkenyl, alkynyl, alkoxy, amido, amino, carbonyl, ester, halo, CN, and $NO_2$, each of which is substituted with 0, 1, 2, or 3 $R_{12}$; and wherein any two adjacent $R_7$ groups can be taken together with the carbon atoms to which they are attached to form a cycloalkyl, heterocyclyl, aryl, or heteroaryl ring, each of which is substituted with 0, 1, 2, or 3 $R_{12}$;
$R_8$ is selected from H, acyl, alkyl, amido, amino, carbamate, carbonyl, and urea, each of which is substituted with 0, 1, 2, or 3 $R_{12}$;
$R_9$ is selected from H, alkyl, alkenyl, alkynyl, alkoxy, amino, amido, ester, halo, CN, $NO_2$, cycloalkyl, heterocyclyl, aryl, and heteroaryl, each of which is substituted with 0, 1, 2, or 3 $R_{12}$;
each $R_{10}$ and $R_{11}$ are independently selected from H, acyl, alkyl, carbonyl, cycloalkyl, heterocycloalkyl, aryl, and heteroaryl, each of which is independently substituted with 0, 1, 2, or 3 $R_{12}$; and each $R_{12}$ is independently selected from acyl, alkyl, alkenyl, alkynyl, alkoxy, aryloxy, alkoxycarbonyl, amido, amino, carbonate, carbamate, carbonyl, ester, halo, CN, $NO_2$, hydroxyl, phosphate, phosphonate, phosphinate, phosphine oxide, urea, cycloalkyl, heterocycloalkyl, aryl, and heteroaryl.

The following embodiments apply to any and all compounds of Formula I, where $X_1$ is

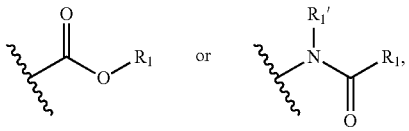

including, but not limited to, Formulae Aa, Ab, Ac, Ad, Ae, Ba, Bb, Bc, Bd, Be, Bf, Bg, and Bh.

In some embodiments, $X_1$ can be

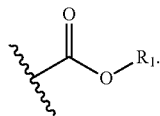

In further embodiments, $X_1$ can be

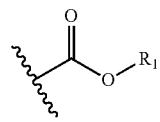

and $R_1$ can be selected from alkyl, cycloalkyl, heterocyclyl, aryl and heteroaryl, each of which is substituted with 0 or 1 $R_{12}$. In other embodiments, $X_1$ can be

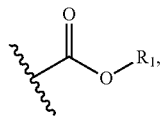

and $R_1$ can be alkyl substituted with 0 or 1 $R_{12}$. In other embodiments, $X_1$ can be

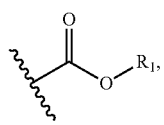

and $R_1$ can be cycloalkyl substituted with 0 or 1 $R_{12}$. In other embodiments, $X_1$ can be

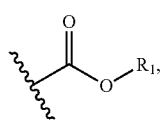

and $R_1$ can be heterocyclyl substituted with 0 or 1 $R_{12}$.

In other embodiments, $X_1$ can be

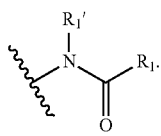

In some embodiments, $X_1$ can be

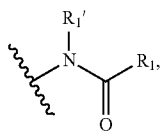

$R_1'$ can be H, and $R_1$ can be alkyl substituted with 0 or 1 $R_{12}$. In some embodiments, $X_1$ can be

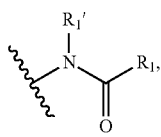

$R_1'$ can be alkyl, and $R_1$ can be alkyl substituted with 0 or 1 $R_{12}$. In some embodiments, $X_2$ can be N. In other embodiments, $X_2$ can be $CR_2$, where $R_2$ is H. In some embodiments, $X_1$ can be N, and $X_2$ can be N. In some embodiments, $X_1$ can be $CR_1$, and $X_2$ can be N.

In other embodiments, $X_1$ can be

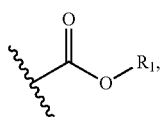

and $X_2$ can be $CR_2$, where $R_2$ is H. In further embodiments, $X_1$ can be

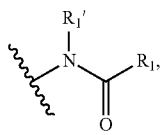

and $X_2$ can be $CR_2$, where $R_2$ is H. In some embodiments, $X_3$ can be N. In other embodiments, $X_3$ can be $CR_4$, where $R_4$ is H.

In some embodiments, $X_1$ can be

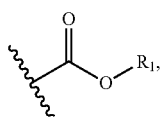

$X_2$ can be N, and $X_3$ can be N. In some embodiments, $X_1$ can be

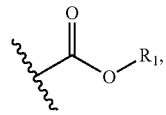

$X_2$ can be N, and $X_3$ can be $CR_4$, where $R_4$ is H. In further embodiments, $X_1$ can be

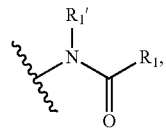

$X_2$ can be N, and $X_3$ can be N. In some embodiments, $X_1$ can be

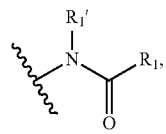

$X_2$ can be N, and $X_3$ can be $CR_4$, where $R_4$ is H.

In some embodiments, $X_1$ can be selected from

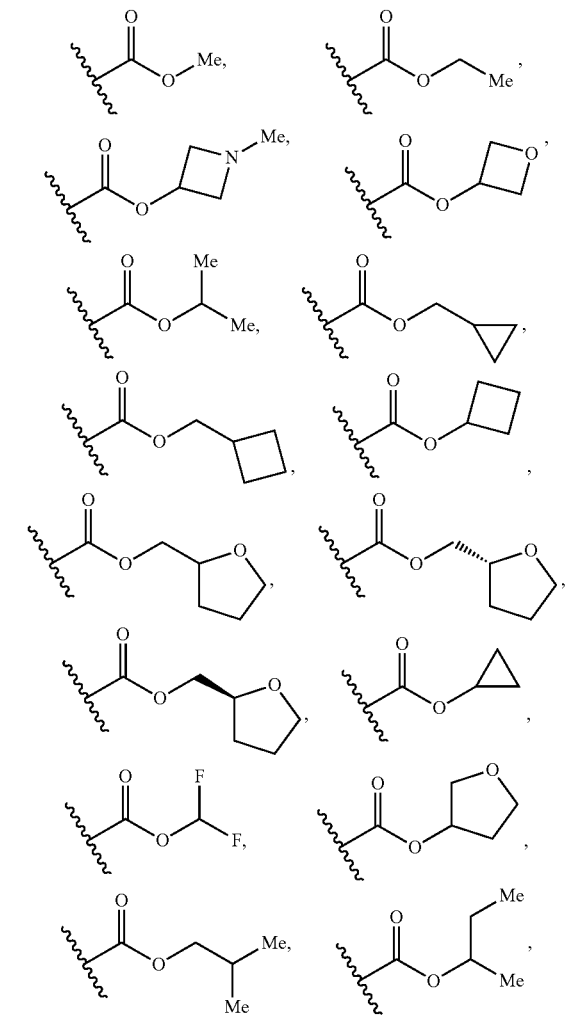

-continued

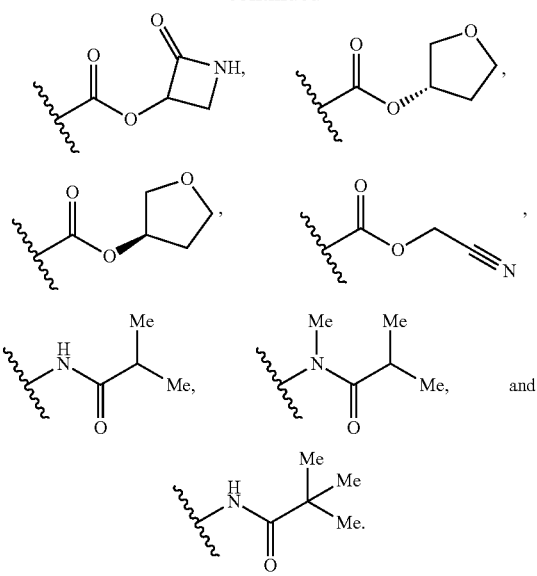

In other embodiments, $X_1$ can be selected from

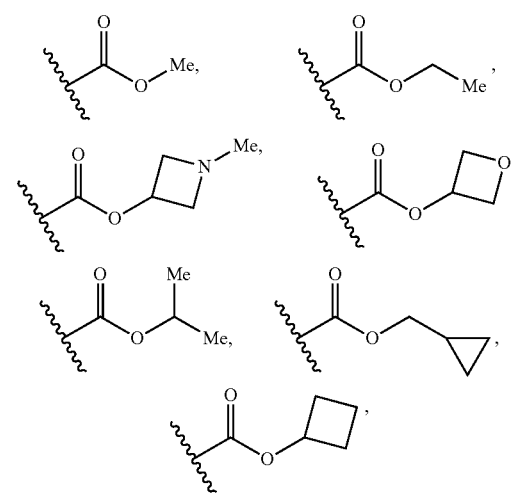

In further embodiments, $X_1$ can be selected from

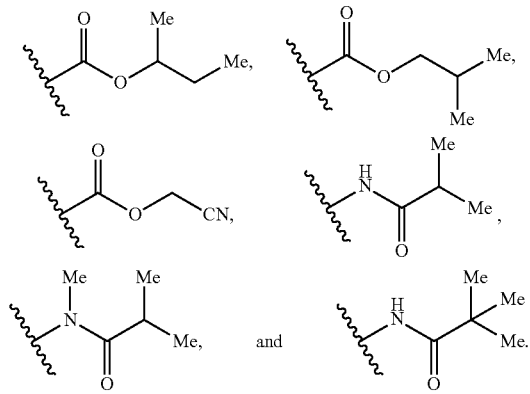

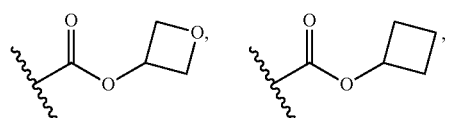

-continued

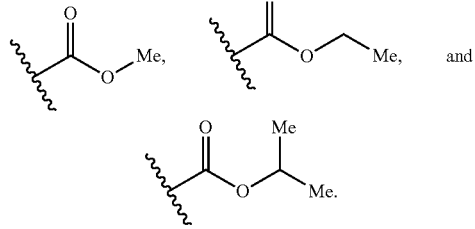

In other embodiments, the $X_1$ can be selected from

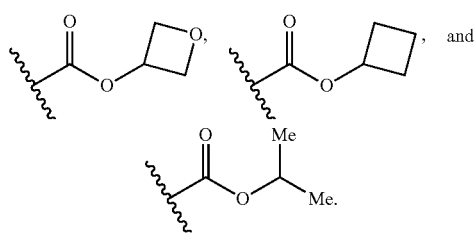

In further embodiments, $X_1$ can be selected from

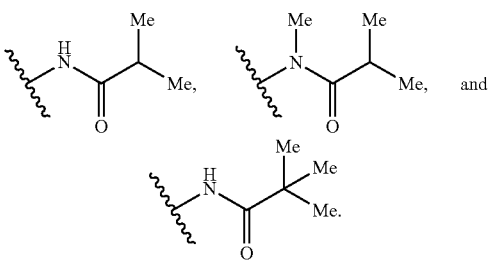

In some embodiments, the compound of Formula I can have the following aspects:

A is selected from

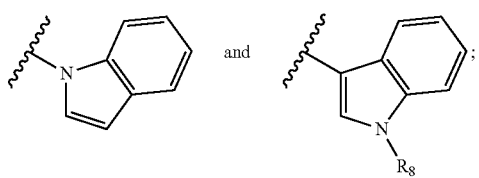

$X_1$ is

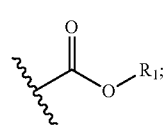

$X_2$ is N;
$X_3$ is $CR_4$;
$R_1$ is selected from alkyl and heterocyclyl;
$R_3$ is alkoxy;
$R_4$ is H;
$R_5$ is —$NR_{10}R_{11}$;

R$_6$ is H;
R$_8$ is alkyl;
R$_{10}$ is alkyl, and
R$_{11}$ is alkyl substituted with one R$_{12}$, and R$_{12}$ is amino or heterocyclyl.

In some embodiments, the compound of Formula I can have the following aspects:

A is selected from

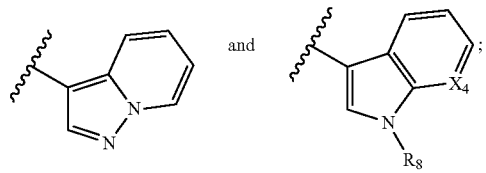

X$_1$ is

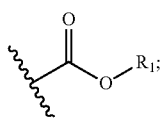

X$_2$ is N;
X$_3$ is CR$_4$;
X$_4$ is selected from N and CR$_7$;
R$_1$ is alkyl, cycloalkyl, and heterocyclyl;
R$_3$ is alkoxy;
R$_4$ is H;
R$_5$ is —NR$_{10}$R$_{11}$;
R$_6$ is H;
R$_7$ is selected from H and alkoxy;
R$_8$ is selected from H and alkyl;
R$_{10}$ is alkyl, and
R$_{11}$ is alkyl substituted with one R$_{12}$, and R$_{12}$ is amino or heterocyclyl.

In some embodiments, the compound of Formula I can have the following aspects:

A is selected from

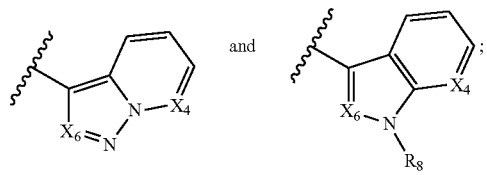

X$_1$ is selected from

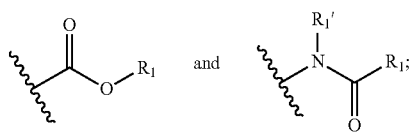

X$_2$ is N;
X$_3$ is CR$_4$;
X$_4$ is selected from N and CR$_7$;
R$_1$ is selected from alkyl, cycloalkyl, and heterocyclyl;
R$_1$' is H;
R$_3$ is alkoxy;
R$_4$ is H;
R$_5$ is selected from —NR$_{10}$R$_{11}$ and —OR$_{11}$;
R$_6$ is H;
R$_7$ is selected from H and alkoxy;
R$_8$ is selected from H and alkyl;
R$_{10}$ is alkyl, and
R$_{11}$ is alkyl substituted with one R$_{12}$, and R$_{12}$ is amino or heterocyclyl.

In further embodiments, the compound of Formula I can have the following aspects:

A is selected from

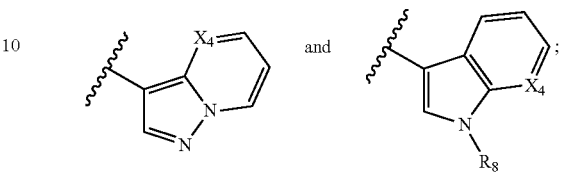

X$_1$ is selected from

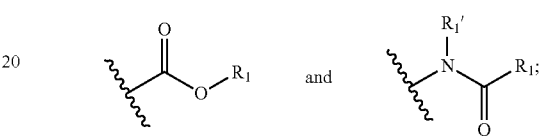

X$_2$ is N;
X$_3$ is CR$_4$;
X$_4$ is N;
R$_1$ is alkyl;
R$_1$' is H;
R$_3$ is alkoxy;
R$_4$ is H;
R$_5$ is —NR$_{10}$R$_{11}$;
R$_6$ is H;
R$_8$ is selected from H and alkyl;
R$_{10}$ is alkyl, and
R$_{11}$ is alkyl substituted with one R$_{12}$, and R$_{12}$ is amino or heterocyclyl.

Provided herein are compounds of Formula I selected from:

Sec-butyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;
Isobutyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;
Isopropyl 2-((5-acrylamido-4-((2-(dimethylamino)ethyl)(methyl)amino)-2-methoxyphenyl)amino)-4-(7-methoxy-1-methyl-1H-indol-3-yl)pyrimidine-5-carboxylate;
Cyclopropylmethyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;
N-(2-((2-(dimethylamino)ethyl)(methyl)amino)-5-((5-isobutyramido-4-(1-methyl-1H-indol-3-yl)pyrimidin-2-yl)amino)-4-methoxyphenyl)acrylamide;
Cyclobutyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;
Isopropyl 2-((5-acrylamido-4-((2-(dimethylamino)ethyl)(methyl)amino)-2-methoxyphenyl)amino)-4-(pyrazolo[1,5-a]pyridin-3-yl)pyrimidine-5-carboxylate;
Methyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;
Oxetan-3-yl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;

Isopropyl 2-((5-acrylamido-4-((2-(dimethylamino)ethyl)(methyl)amino)-2-methoxyphenyl)amino)-4-(1-methyl-1H-pyrrolo[2,3-b]pyridin-3-yl)pyrimidine-5-carboxylate;
N-(2-((2-(dimethylamino)ethyl)(methyl)-amino)-4-methoxy-5-((4-(1-methyl-1H-indol-3-yl)-5-(N-methylisobutyramido)-pyrimidin-2-yl)amino)phenyl)acrylamide;
N-(2-((2-(dimethylamino)ethyl)(methyl)amino)-4-methoxy-5-((4-(1-methyl-1H-indol-3-yl)-5-pivalamidopyrimidin-2-yl)amino)phenyl)acrylamide;
Isopropyl 2-((5-acrylamido-2-methoxy-4-(methyl((1-methylpyrrolidin-2-yl)methyl)amino)phenyl)amino)-4-(1-methyl-1H-indol-3-yl)pyrimidine-5-carboxylate;
Ethyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;
Isopropyl 2-((5-acrylamido-4-((2-(dimethylamino)ethyl)(methyl)amino)-2-methoxyphenyl)amino)-4-(1H-indol-1-yl)pyrimidine-5-carboxylate;
Isopropyl 2-((5-acrylamido-2-methoxy-4-(methyl(2-(methylamino)ethyl)-amino)phenyl)amino)-4-(1-methyl-1H-indol-3-yl)pyrimidine-5-carboxylate;
Isopropyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;
Isopropyl 2-((5-acrylamido-4-((2-(dimethylamino)ethyl)(methyl)amino)-2-methoxyphenyl)amino)-4-(1H-indol-3-yl)pyrimidine-5-carboxylate; and
Methyl 2-((5-acrylamido-2-methoxy-4-(methyl((1-methylpyrrolidin-2-yl)methyl)amino)phenyl)amino)-4-(1-methyl-1H-indol-3-yl)pyrimidine-5-carboxylate;
or a pharmaceutically acceptable form thereof.

In another aspect, provided herein are compounds of Formula I

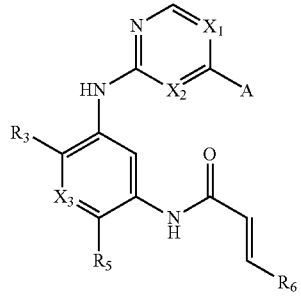

Formula I wherein:
A is

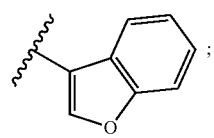 [SMILES: *c1coc2ccccc12]

;

$X_1$ is

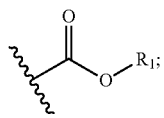

;

$X_2$ is N;
$X_3$ is $CR_4$;

$R_1$ is alkyl;
$R_3$ is alkoxy;
$R_4$ is H;
$R_5$ is $-NR_{10}R_{11}$
$R_6$ is H;
$R_{10}$ is alkyl, and
$R_{11}$ is alkyl substituted with one $R_{12}$, and $R_{12}$ is heterocyclyl.

Provided herein are compounds of Formula I, such as Isopropyl (R)-2-((5-(acryloyl-2-azanyl)-2-methoxy-4-(methyl((1-methylpyrrolidin-2-yl)methyl)amino)phenyl)-2-azanyl)-4-(benzofuran-3-yl)pyrimidine-5-carboxylate, or a pharmaceutically acceptable form thereof.

In another aspect, provided herein are compounds of Formula I

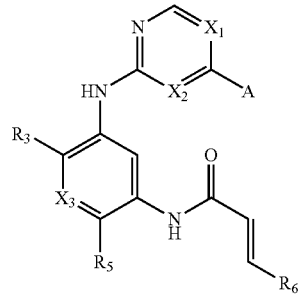

Formula I wherein:
A is

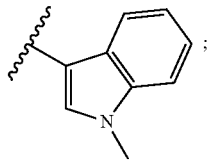 [SMILES: *c1cn(C)c2ccccc12]

;

$X_1$ is

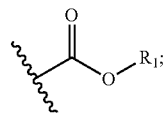

;

$X_2$ is N;
$X_3$ is $CR_4$;
$R_1$ is alkyl;
$R_3$ and $R_4$ are taken together with the carbon atoms to which they are attached to form a cycloalkyl or heterocyclyl group;
$R_5$ is $-NR_{10}R_{11}$
$R_6$ is H;
$R_{10}$ is alkyl, and
$R_{11}$ is alkyl substituted with one $R_{12}$, and $R_{12}$ is amino.

Exemplary compounds of Formula I include, but are not limited to,
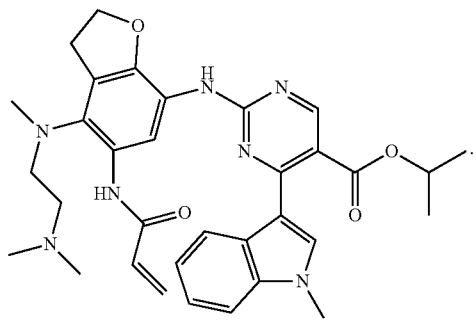 [SMILES: C=CC(=O)Nc1cc(Nc2ncc(C(=O)OC(C)C)c(-c3cn(C)c4ccccc34)n2)c2c(c1N(C)CCN(C)C)CCO2]
Further provided herein are compounds of Formula I, such as
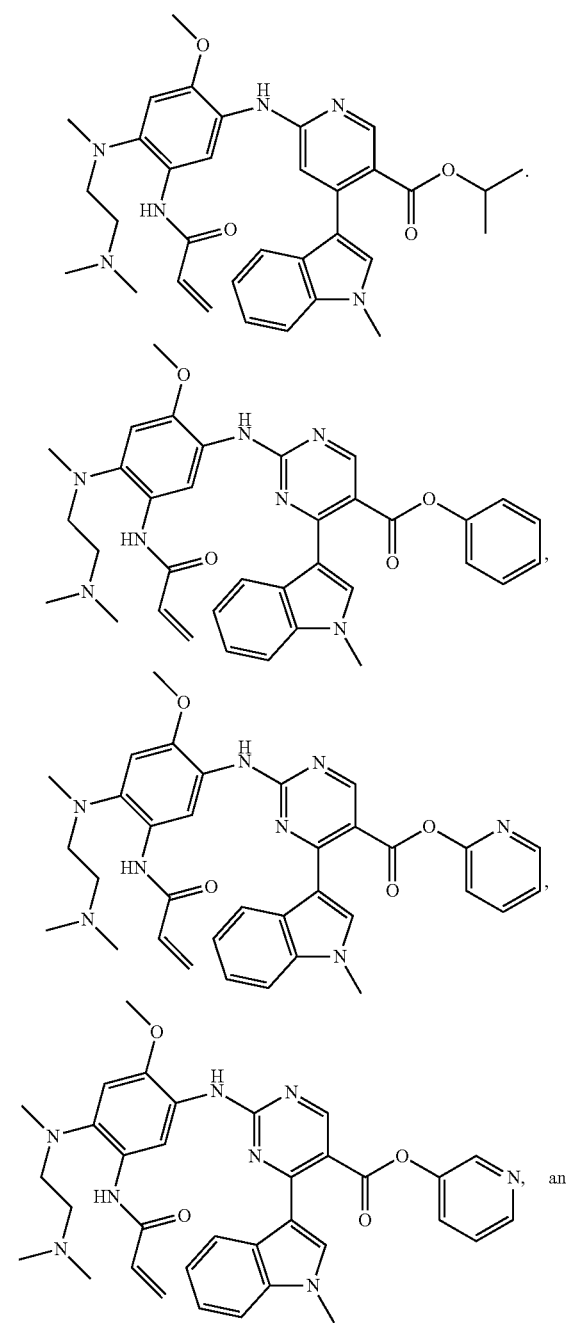
-continued
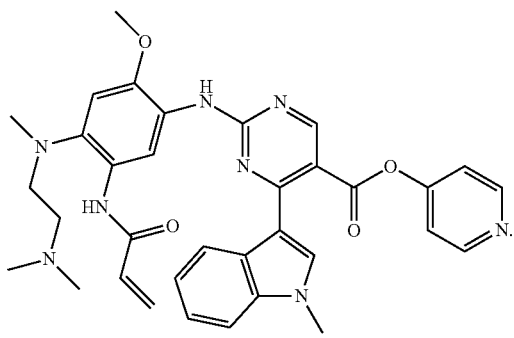
In some embodiments, the compound of Formula I can be selected from
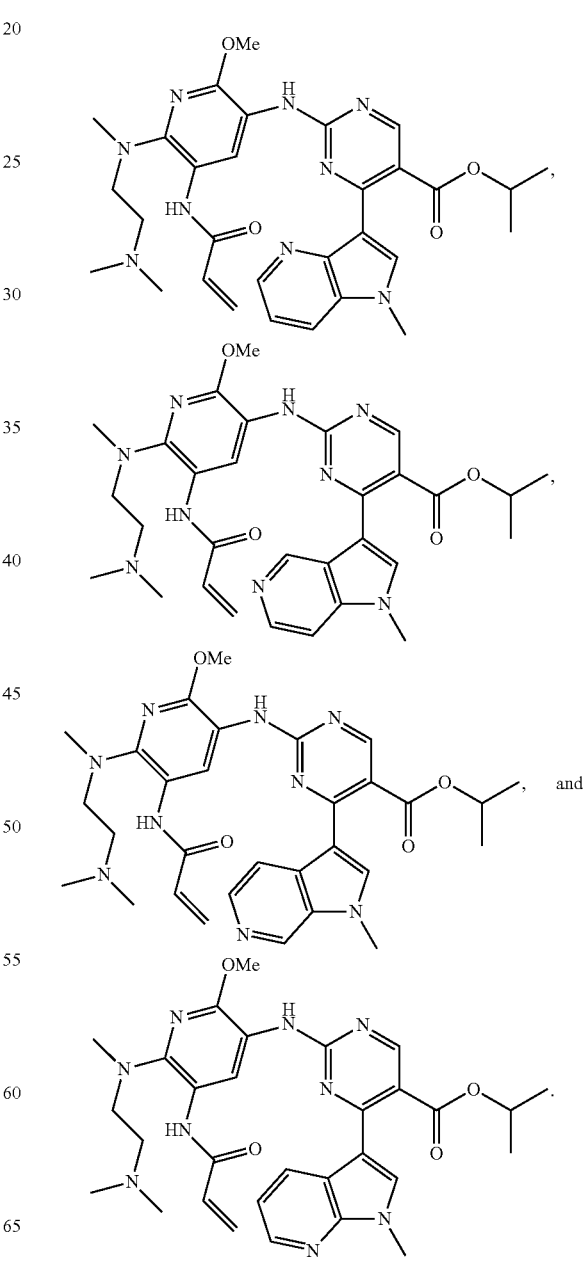

Provided herein are compounds of Formula I, such as

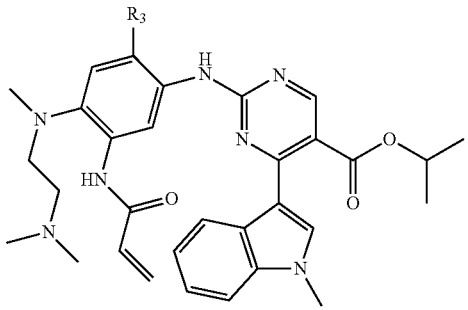

wherein R₃ is selected from alkyl, alkoxy, cyano and halo. In some embodiments, R₃ is selected from methyl, ethyl, propyl, methoxy, ethoxy, propoxy, fluoro, chloro and CN.

In some embodiments, X₃ is N and R₃ is alkoxy. In other embodiments, X₃ is CR₄, and R₄ is selected from alkyl and halo, such as methyl, chloro, and fluoro. Exemplary compounds are given below:

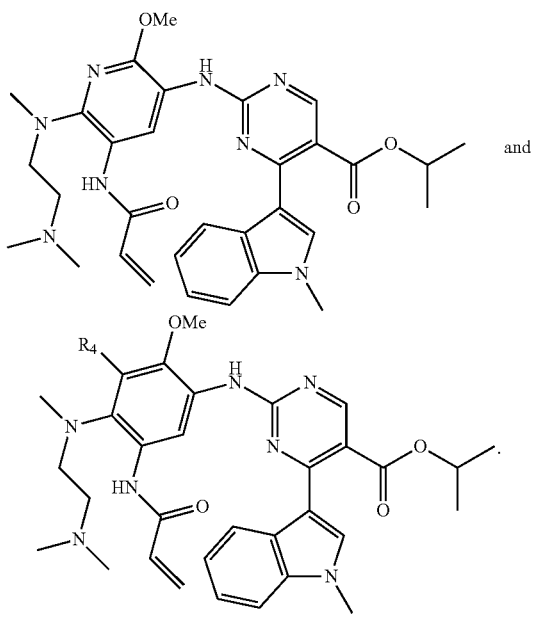

Provided herein are compounds of Formula I where R₅ is selected from the following amino groups:

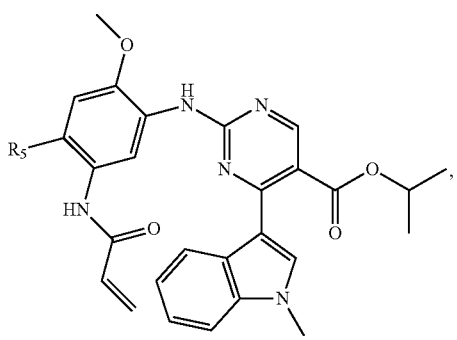

where R₅ is selected from

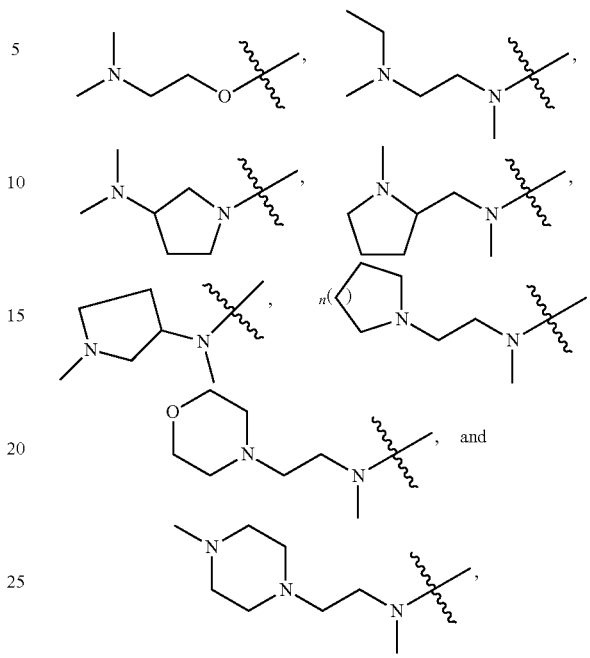

where n is 0-4.

In some embodiments, the compounds described herein can have a molecular weight of less than about 800, less than about 700, less than about 600, or less than about 500 mass units (not including the weight of any solvate, or of any counter-ion in the case of a salt).

Provided herein are compounds of Formula I selected from:
Isopropyl 2-((5-acrylamido-4-((2-(dimethylamino)ethyl)(methyl)amino)-2-methoxyphenyl)amino)-4-(1-methyl-1H-indazol-3-yl)pyrimidine-5-carboxylate;
N-(2-((2-(dimethylamino)ethyl)(methyl)amino)-4-methoxy-5-((4-(1-methyl-1H-indazol-3-yl)-5-propionamidopyrimidin-2-yl)amino)phenyl)acrylamide;
Isopropyl (R)-2-((5-acrylamido-2-methoxy-4-(methyl((1-methylpyrrolidin-2-yl)methyl)amino)phenyl)amino)-4-(1H-indol-1-yl)pyrimidine-5-carboxylate;
Isopropyl (R)-2-((5-acrylamido-2-methoxy-4-(methyl((1-methylpyrrolidin-2-yl)methyl)amino)phenyl)amino)-4-(benzofuran-3-yl)pyrimidine-5-carboxylate;
Methyl (R)-2-((5-acrylamido-2-methoxy-4-(methyl((1-methylpyrrolidin-2-yl)methyl)amino)phenyl)amino)-4-(1H-indol-1-yl)pyrimidine-5-carboxylate;
Isopropyl (R)-2-((5-acrylamido-2-methoxy-4-(methyl((1-methylpyrrolidin-2-yl)methyl)amino)phenyl)amino)-4-(1H-indol-3-yl)pyrimidine-5-carboxylate;
Ethyl (R)-2-((5-acrylamido-2-methoxy-4-(methyl((1-methylpyrrolidin-2-yl)methyl)amino)phenyl)amino)-4-(1-methyl-1H-indol-3-yl)pyrimidine-5-carboxylate;
Isopropyl 2-((5-acrylamido-4-((2-(dimethylamino)ethyl)(methyl)amino)-2-methoxyphenyl)amino)-4-(1H-pyrrolo[2,3-b]pyridin-3-yl)pyrimidine-5-carboxylate;
Isopropyl 2-((5-acrylamido-4-(2-(dimethylamino)ethoxy)-2-methoxyphenyl)amino)-4-(1-methyl-1H-indol-3-yl)pyrimidine-5-carboxylate;
Methyl 2-((5-acrylamido-4-(3-(dimethylamino)prop-1-yn-1-yl)-2-methoxyphenyl)amino)-4-(1-methyl-1H-indol-3-yl)pyrimidine-5-carboxylate;

Methyl 2-((5-acrylamido-4-(3-(dimethylamino)propyl)-2-methoxyphenyl)amino)-4-(1-methyl-1H-indol-3-yl)pyrimidine-5-carboxylate; and N-(5-((4-(1-(2-amino-2-oxoethyl)-1H-indol-3-yl)pyrimidin-2-yl)amino)-2-((2-(dimethylamino)ethyl)(methyl)amino)-4-methoxyphenyl)acrylamide;

or a pharmaceutically acceptable form thereof.

Provided herein are compounds of Formula I selected from:

N-(5-((4-(1-(2-amino-2-oxoethyl)-1H-indol-3-yl)-5-ethyl-pyrimidin-2-yl)amino)-2-((2-(dimethylamino)ethyl)(methyl)amino)-4-methoxyphenyl)acrylamide;

N-(2-((2-(dimethylamino)ethyl)(methyl)amino)-5-((5-ethyl-4-(1-(2-(methylamino)-2-oxoethyl)-1H-indol-3-yl)pyrimidin-2-yl)amino)-4-methoxyphenyl)acrylamide;

Methyl 2-((5-acrylamido-4-fluoro-2-methoxyphenyl)amino)-4-(1-(dimethylamino)-1H-indol-3-yl)pyrimidine-5-carboxylate;

Isopropyl 2-((5-acrylamido-2-methoxy-4-(methyl(2-(methylamino)ethyl)-amino)phenyl)amino)-4-(1-methyl-1H-indol-3-yl)pyrimidine-5-carboxylate;

Isopropyl 2-((5-acrylamido-2-methoxy-4-(methyl(2-(methylamino)ethyl)amino)phenyl)amino)-4-(1-methyl-1H-pyrrolo[2,3-b]pyridin-3-yl)pyrimidine-5-carboxylate;

Methyl 2-((5-acrylamido-4-((2-(dimethylamino)ethyl)(methyl)amino)-2-methoxyphenyl)amino)-4-(1-(dimethylamino)-1H-indol-3-yl)pyrimidine-5-carboxylate;

Isopropyl 2-((5-acrylamido-4-((2-(dimethylamino)ethyl)(methyl)amino)-2-methoxyphenyl)amino)-4-(1-ethyl-1H-indol-3-yl)pyrimidine-5-carboxylate;

Isopropyl 4-(1-acetyl-1H-indol-3-yl)-2-((5-acrylamido-4-((2-(dimethylamino)ethyl)(methyl)amino)-2-methoxyphenyl)amino)pyrimidine-5-carboxylate;

Isopropyl 2-((5-acrylamido-4-((2-(dimethylamino)ethyl)(methyl)amino)-2-methoxyphenyl)amino)-4-(1-cyclopropyl-1H-indol-3-yl)pyrimidine-5-carboxylate; and Methyl 3-(2-((5-acrylamido-4-((2-(dimethylamino)ethyl)(methyl)amino)-2-methoxyphenyl)amino)pyrimidin-4-yl)-1-methyl-1H-indole-4-carboxylate;

or a pharmaceutically acceptable form thereof.

Provided herein are compounds of Formula I selected from:

Methyl 3-(2-((5-acrylamido-4-((2-(dimethylamino)ethyl)(methyl)amino)-2-methoxyphenyl)amino)pyrimidin-4-yl)-1-methyl-1H-indole-5-carboxylate;

Methyl 3-(2-((5-acrylamido-4-((2-(dimethylamino)ethyl)(methyl)amino)-2-methoxyphenyl)amino)pyrimidin-4-yl)-1-methyl-1H-indole-6-carboxylate;

Methyl 3-(2-((5-acrylamido-4-((2-(dimethylamino)ethyl)(methyl)amino)-2-methoxyphenyl)amino)pyrimidin-4-yl)-1-methyl-1H-indole-6-carboxylate;

Isopropyl 3-(2-((5-acrylamido-4-((2-(dimethylamino)ethyl)(methyl)amino)-2-methoxyphenyl)amino)pyrimidin-4-yl)-1-methyl-1H-indole-6-carboxylate;

Isopropyl 3-(2-((5-acrylamido-4-((2-(dimethylamino)ethyl)(methyl)amino)-2-methoxyphenyl)amino)pyrimidin-4-yl)-1-methyl-1H-indole-7-carboxylate;

Methyl 3-(2-((5-acrylamido-4-((2-(dimethylamino)ethyl)(methyl)amino)-2-methoxyphenyl)amino)pyrimidin-4-yl)-1-methyl-1H-indole-2-carboxylate;

Isopropyl 3-(2-((5-acrylamido-4-((2-(dimethylamino)ethyl)(methyl)amino)-2-methoxyphenyl)amino)pyrimidin-4-yl)-1-methyl-1H-indole-2-carboxylate;

N-(5-((4-(2-cyano-1-methyl-1H-indol-3-yl)pyrimidin-2-yl)amino)-2-((2-(dimethylamino)ethyl)(methyl)amino)-4-methoxyphenyl)acrylamide;

N-(5-((4-(6-cyano-1-methyl-1H-indol-3-yl)pyrimidin-2-yl)amino)-2-((2-(dimethylamino)ethyl)(methyl)amino)-4-methoxyphenyl)acrylamide; and 3-(2-((5-acrylamido-4-((2-(dimethylamino)ethyl)(methyl)amino)-2-methoxyphenyl)amino)pyrimidin-4-yl)-1-methyl-1H-indole-2-carboxamide;

or a pharmaceutically acceptable form thereof.

Provided herein are compounds of Formula I selected from:

3-(2-((5-acrylamido-4-((2-(dimethylamino)ethyl)(methyl)amino)-2-methoxyphenyl)amino)pyrimidin-4-yl)-N,1-dimethyl-1H-indole-2-carboxamide;

3-(2-((5-acrylamido-4-((2-(dimethylamino)ethyl)(methyl)amino)-2-methoxyphenyl)amino)pyrimidin-4-yl)-N,N,1-trimethyl-1H-indole-2-carboxamide;

3-(2-((5-acrylamido-4-((2-(dimethylamino)ethyl)(methyl)amino)-2-methoxyphenyl)amino)pyrimidin-4-yl)-N-(2-methoxyethyl)-1-methyl-1H-indole-2-carboxamide;

Isopropyl 2-((5-acrylamido-4-((2-(dimethylamino)ethyl)(methyl)amino)-2-methoxyphenyl)amino)-4-(imidazo[1,2-a]pyridin-3-yl)pyrimidine-5-carboxylate;

N-(2-((2-(dimethylamino)ethyl)(methyl)amino)-4-methoxy-5-((4-(1-methyl-6-(1-methyl-1H-pyrazol-4-yl)-1H-indol-3-yl)pyrimidin-2-yl)amino)phenyl)acrylamide;

N-(2-((2-(dimethylamino)ethyl)(methyl)amino)-5-((5-(dimethylphosphoryl)-4-(1-methyl-1H-indol-3-yl)pyrimidin-2-yl)amino)-4-methoxyphenyl)acrylamide;

Isopropyl 2-((5-acrylamido-4-((2-(dimethylamino)ethyl)(methyl)amino)-2-methoxyphenyl)amino)-4-(3-methyl-1H-indol-1-yl)pyrimidine-5-carboxylate;

N-(5-((5-cyano-4-(1-methyl-1H-indazol-3-yl)pyrimidin-2-yl)amino)-2-((2-(dimethylamino)ethyl)(methyl)amino)-4-methoxyphenyl)acrylamide;

N-(2-((2-(dimethylamino)ethyl)(methyl)amino)-4-methoxy-5-((4-(1-methyl-1H-indol-3-yl)-5-(3-methylureido)pyrimidin-2-yl)amino)phenyl)acrylamide; and N-(2-((2-(dimethylamino)ethyl)(methyl)amino)-4-methoxy-5-((4-(1-methyl-2-((2-oxoazetidin-1-yl)methyl)-1H-indol-3-yl)pyrimidin-2-yl)amino)phenyl)acrylamide;

or a pharmaceutically acceptable form thereof.

Provided herein are compounds of Formula I selected from:

Methyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;

Isopropyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;

Isopropyl 2-((5-acrylamido-4-((2-(dimethylamino)ethyl)(methyl)amino)-2-methoxyphenyl)amino)-4-(1H-indol-1-yl)pyrimidine-5-carboxylate;

Isopropyl 2-((5-acrylamido-2-methoxy-4-(methyl((1-methylpyrrolidin-2-yl)methyl)amino)phenyl)amino)-4-(1-methyl-1H-indol-3-yl)pyrimidine-5-carboxylate;

Isobutyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate;

Isopropyl 2-((5-acrylamido-4-((2-(dimethylamino)ethyl)(methyl)amino)-2-methoxyphenyl)amino)-4-(7-methoxy-1-methyl-1H-indol-3-yl)pyrimidine-5-carboxylate;

Isopropyl 2-((5-acrylamido-4-((2-(dimethylamino)ethyl)(methyl)amino)-2-methoxyphenyl)amino)-4-(1-methyl-1H-pyrrolo[2,3-b]pyridin-3-yl)pyrimidine-5-carboxylate;

N-(2,4-dimethoxy-5-((4-(1-methyl-1H-indol-3-yl)-5-pivalamidopyrimidin-2-yl)amino)phenyl)acrylamide; and Isopropyl 2-((5-acrylamido-2-methoxy-4-(methyl(2-(methylamino)ethyl)-amino)phenyl)amino)-4-(1-methyl-1H-indol-3-yl)pyrimidine-5-carboxylate;
or a pharmaceutically acceptable form thereof.

Provided herein is the compound Methyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate or a pharmaceutically acceptable form thereof.

Provided herein is the compound Isopropyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate or a pharmaceutically acceptable form thereof.

Provided herein is the compound Isopropyl 2-((5-acrylamido-4-((2-(dimethylamino)ethyl)(methyl)amino)-2-methoxyphenyl)amino)-4-(1H-indol-1-yl)pyrimidine-5-carboxylate or a pharmaceutically acceptable form thereof.

Provided herein is the compound Isopropyl 2-((5-acrylamido-2-methoxy-4-(methyl((1-methylpyrrolidin-2-yl)methyl)amino)phenyl)amino)-4-(1-methyl-1H-indol-3-yl)pyrimidine-5-carboxylate or a pharmaceutically acceptable form thereof.

Provided herein is the compound Isopropyl 2-((5-acrylamido-4-((2-(dimethylamino)ethyl)(methyl)amino)-2-methoxyphenyl)amino)-4-(7-methoxy-1-methyl-1H-indol-3-yl)pyrimidine-5-carboxylate or a pharmaceutically acceptable form thereof.

Provided herein is the compound Isopropyl 2-((5-acrylamido-4-((2-(dimethylamino)ethyl)(methyl)amino)-2-methoxyphenyl)amino)-4-(1-methyl-1H-pyrrolo[2,3-b]pyridin-3-yl)pyrimidine-5-carboxylate or a pharmaceutically acceptable form thereof.

Provided herein is the compound N-(2,4-dimethoxy-5-((4-(1-methyl-1H-indol-3-yl)-5-pivalamidopyrimidin-2-yl)amino)phenyl)acrylamide or a pharmaceutically acceptable form thereof.

Provided herein is the compound Isopropyl 2-((5-acrylamido-2-methoxy-4-(methyl(2-(methylamino)ethyl)-amino)phenyl)amino)-4-(1-methyl-1H-indol-3-yl)pyrimidine-5-carboxylate or a pharmaceutically acceptable form thereof.

Activity

As used herein, the term "mutant EGFR" refers to epidermal growth factor receptor having one or more mutations in any of its exons and includes, but is not limited to, EGFR having one or more mutations in the exon 20 domain. Exon 20 insertion mutations include, but are not limited to, ASV and NPG. Mutant EGFR also includes the exon 20 T790M gatekeepeer point mutation. The T790M mutation can occur in combination with one or more other mutations (including insertions, deletions and point mutations) in any EGFR exon. Non-limiting exemplary mutation combinations include the T790M gatekeeper mutation along with the exon 19 (delE746_A750) mutation (DT) and the T790M gatekeeper mutation along with the L858R mutation (LT) in exon 21. The term "mutant EGFR" is also inclusive of mutations in exons that are not exon 20. Examples include, but are not limited to, the exon 19 (delE746_A750) mutation (D) and the exon 21 point mutation L858R (L).

As used herein, the term "exon 20 mutant EGFR" refers to one or more of the known exon 20 mutations, such as ASV, NPG, and T790M. In some embodiments, the exon 20 mutation can be ASV. In another embodiment, the exon 20 mutation can be NPG. In some embodiments, the exon 20 mutation can be T790M. In some instances, the T790M mutation can be combined with one or more other EGFR mutations, such as D and L, to give the DT and LT mutations.

As used herein, the term "mutant HER2" refers to human epidermal growth factor receptor 2 having one or more mutations in any of its exons and includes, but is not limited to, HER2 having one or more mutations in the exon 20 domain ("exon 20 mutant HER2"). Exon 20 insertion mutations include, but are not limited to, YVMA. Exon 20 point mutations include, but are not limited to G776M.

In some embodiments, one or more compounds described herein bind to EGFR. In some embodiments, one or more compounds described herein bind to EGFR having one or more mutations (e.g., bind selectively). In some embodiments, the $IC_{50}$ of a subject compound for mutant EGFR inhibition can be less than about 100 nM, less than about 50 nM, less than about 10 nM, less than about 1 nM, less than about 0.5 nM, or less than about 1 pM.

In some embodiments, the $IC_{50}$ of a subject compound for mutant EGFR having one or more mutations in exon 20 can be less than about 100 nM, less than about 50 nM, less than about 10 nM, less than about 1 nM, less than about 0.5 nM, or less than about 1 pM. In some embodiments, the $IC_{50}$ value can be less than about 1 µM, less than about 500 nM, or less than about 250 nM. In some embodiments, the mutant EGFR has one or more of the following insertions in the exon 20 domain: ASV or NPG. In other embodiments, the mutant EGFR has either or both of the DT and/or LT mutations.

In some embodiments, the compounds disclosed herein inhibit EGFR, or an exon 20 mutant thereof, with an $IC_{50}$ value at least about 10 times lower, at least about 50 times lower, at least about 100 times lower, or at least about 500 times lower than the $IC_{50}$ of another tyrosine kinase. In some embodiments, non-limiting exemplary compounds exhibit one or more inhibitory activities disclosed herein. For example, one or more subject compounds bind with greater affinity to exon 20 mutant EGFR as compared to wild-type EGFR.

In some embodiments, the inhibitory activity of compounds disclosed herein against mutant EGFR can be greater than the activity of other known inhibitors. For example, disclosed compounds can inhibit mutant EGFR at least as well, about 2 times more potently, or about 10 times more potently as erlotinib or gefitinib.

In some embodiments, one or more compounds described herein bind to HER2. In some embodiments, one or more compounds described herein bind to HER2 having one or more mutations (e.g., bind selectively). In some embodiments, the $IC_{50}$ of a subject compound for mutant HER2 inhibition can be less than about 100 nM, less than about 50 nM, less than about 10 nM, less than about 1 nM, less than about 0.5 nM, or less than about 1 pM.

In some embodiments, the $IC_{50}$ of a subject compound for mutant HER2 having one or more mutations in exon 20 can be less than about 100 nM, less than about 50 nM, less than about 10 nM, less than about 1 nM, less than about 0.5 nM, or less than about 1 pM. In some embodiments, the $IC_{50}$ value can be less than about 1 pM, less than about 500 nM, or less than about 250 nM. In some embodiments, the mutant HER2 has the YVMA insertion in the exon 20 domain.

In some embodiments, the compounds disclosed herein inhibit HER2, or an exon 20 mutant thereof, with an $IC_{50}$ value at least about 10 times lower, at least about 50 times lower, at least about 100 times lower, or at least about 500 times lower than the $IC_{50}$ of another tyrosine kinase. In some embodiments, non-limiting exemplary compounds exhibit one or more inhibitory activities disclosed herein. For example, one or more subject compounds bind with greater affinity to exon 20 mutant HER2 as compared to wild-type EGFR. In some embodiments, the inhibitory activity of compounds disclosed herein against mutant HER2 can be greater than the activity of other known inhibitors.

In some embodiments, the compounds are also useful as standards and reagents for characterizing various kinases, including, but not limited to, EGFR family kinases, as well as for studying the role of such kinases in biological and pathological phenomena; for studying intracellular signal transduction pathways mediated by such kinases, for the comparative evaluation of new kinase inhibitors; and for studying various cancers in cell lines and animal models.

Pharmaceutical Compositions

In some embodiments, provided herein are pharmaceutical compositions comprising one or more compounds as disclosed herein, or a pharmaceutically acceptable form thereof (e.g., pharmaceutically acceptable salts, hydrates, solvates, isomers, prodrugs, and isotopically labeled derivatives), and one or more pharmaceutically acceptable excipients, carriers, including inert solid diluents and fillers, diluents, including sterile aqueous solution and various organic solvents, permeation enhancers, solubilizers and adjuvants. In some embodiments, a pharmaceutical composition described herein includes a second active agent such as an additional therapeutic agent, (e.g., a chemotherapeutic).

As described herein, the disclosed compositions comprise a disclosed compound together with a pharmaceutically acceptable carrier, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired. Except insofar as any conventional carrier medium is incompatible with the compounds provided herein, such as by producing any undesirable biological effect or otherwise interacting in a deleterious manner with any other component(s) of the pharmaceutical composition, the carrier is contemplated to be within the scope of this disclosure.

1. Formulations

Pharmaceutical compositions can be specially formulated for administration in solid or liquid form, including those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Methods of preparing these formulations or compositions include the step of bringing into association a compound described herein and/or the chemotherapeutic with the carrier and, optionally, one or more accessory ingredients. In general, the formulations are prepared by uniformly and intimately bringing into association a compound as disclosed herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, N.Y., 1990; Katzung, ed., *Basic and Clinical Pharmacology*, Ninth Edition, McGraw Hill, 2003; Goodman and Gilman, eds., *The Pharmacological Basis of Therapeutics*, Tenth Edition, McGraw Hill, 2001; *Remington's Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

In some embodiments, the concentration of one or more of the compounds provided in the disclosed pharmaceutical compositions can be less than about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% w/w, w/v or v/v.

In some embodiments, the concentration of one or more of the compounds as disclosed herein can be greater than about 90%, about 80%, about 70%, about 60%, about 50%, about 40%, about 30%, about 20%, about 19.75%, about 19.50%, about 19.25% about 19%, about 18.75%, about 18.50%, about 18.25%, about 18%, about 17.75%, about 17.50%, about 17.25%, about 17%, about 16.75%, about 16.50%, about 16.25%, about 16%, about 15.75%, about 15.50%, about 15.25%, about 15%, about 14.75%, about 14.50%, about 14.25%, about 14%, about 13.75%, about 13.50%, about 13.25%, about 13%, about 12.75%, about 12.50%, about 12.25%, about 12%, about 11.75%, about 11.50%, about 11.25%, about 11%, about 10.75%, about 10.50%, about 10.25%, about 10%, about 9.75%, about 9.50%, about 9.25%, about 9%, about 8.75%, about 8.50%, about 8.25%, about 8%, about 7.75%, about 7.50%, about 7.25%, about 7%, about 6.75%, about 6.50%, about 6.25%, about 6%, about 5.75%, about 5.50%, about 5.25%, about 5%, about 4.75%, about 4.50%, about 4.25%, about 4%, about 3.75%, about 3.50%, about 3.25%, about 3%, about 2.75%, about 2.50%, about 2.25%, about 2%, about 1.75%, about 1.50%, about 1.25%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001% w/w, w/v, or v/v. In some embodiments, the concentration of one or more of the compounds as disclosed herein can be in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v, v/v. In some embodiments, the concentration of one or more of the compounds as disclosed herein can be in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds as disclosed herein can be equal to or less than about 10 g, about 9.5 g, about 9.0 g, about 8.5 g, about 8.0 g, about 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g. In some embodiments, the amount of one or more of the compounds as disclosed herein can be more than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g. about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g, about 1.5 g, about 2 g, about 2.5, about 3 g, about 3.5, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g.

In some embodiments, the amount of one or more of the compounds as disclosed herein can be in the range of about 0.0001-about 10 g, about 0.0005-about 9 g, about 0.001-about 0.5 g, about 0.001-about 2 g, about 0.001-about 8 g, about 0.005-about 2 g, about 0.005-about 7 g, about 0.01-about 6 g, about 0.05-about 5 g, about 0.1-about 4 g, about 0.5-about 4 g, or about 1-about 3 g.

1A. Formulations for Oral Administration

In some embodiments, provided herein are pharmaceutical compositions for oral administration containing a compound as disclosed herein, and a pharmaceutical excipient suitable for oral administration. In some embodiments, provided herein are pharmaceutical compositions for oral administration containing: (i) an effective amount of a disclosed compound; optionally (ii) an effective amount of one or more second agents; and (iii) one or more pharmaceutical excipients suitable for oral administration. In some embodiments, the pharmaceutical composition further contains: (iv) an effective amount of a third agent.

In some embodiments, the pharmaceutical composition can be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more ingredients. In general, the pharmaceutical compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient can be mixed with an inert solid diluent, for example, calcium carbonate, calcium phosphate or kaolin, or as soft gelatin capsules wherein the active ingredient can be mixed with water or an oil medium, for example, peanut oil, liquid paraffin or olive oil.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, microcrystalline cellulose, diluents, granulating agents, lubricants, binders, and disintegrating agents can be used in the case of oral solid preparations, in some embodiments without employing the use of lactose. In some embodiments, compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol for subsequent formulation. For example, suitable carriers include powders, capsules, and tablets, with the solid oral preparations. In some embodiments, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions as provided herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds disclosed herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms include, but are not limited to, agaragar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein can be combined with various sweetening or flavoring agents, coloring matter or dyes and, for example, emulsifying and/or suspending agents, together with such diluents as water, ethanol, propylene glycol, glycerin and various combinations thereof.

Surfactants which can be used to form pharmaceutical compositions and dosage forms include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least about 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or nonionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and diacetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-1 actylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oil-soluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

In one embodiment, the pharmaceutical composition can include a solubilizer to ensure good solubilization and/or dissolution of a compound as provided herein and to minimize precipitation of the compound. This can be especially important for pharmaceutical compositions for nonoral use, e.g., pharmaceutical compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydxoxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydxoxyethylpyrrolidone, polyvinylpyrrolidone, hydroxypropyl methylcellulose, hydxoxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included can vary with the composition. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the pharmaceutical composition to a subject using conventional techniques, such as distillation or evaporation. Thus, if present, the solubilizer can be in a weight ratio of about 10%, about 25%, about 50%, about 100%, or up to about 200% by weight, based on the combined weight of the drug, and other excipients. If desired, very small amounts of solubilizer can also be used, such as about 5%, 2%, 1% or even less. Typically, the solubilizer can be present in an amount of about 1% to about 100%, more typically about 5% to about 25% by weight.

The pharmaceutical composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, oils, odorants, opacifiers, suspending agents, binders, fillers, plasticizers, lubricants, and mixtures thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chiorhexidine, chiorobutanol, chiorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, betacarotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative can be an anti-oxidant. In other embodiments, the preservative can be a chelating agent.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukni nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Oil/aqueous emulsion formulations can include an emulsifier, or it can comprise a mixture of at least one emulsifier with a fat or an oil or with both a fat and an oil. In some embodiments, a hydrophilic emulsifier can be included together with a lipophilic emulsifier which acts as a stabilizer. In one embodiment, both an oil and a fat can be used. Together, the emulsifier(s) with or without stabilizer(s) create an emulsifying wax, and the wax together with the oil and fat form an emulsifying ointment base. This ointment base forms the oily dispersed phase of the cream formulations. Emulsifiers and emulsion stabilizers suitable for use in the disclosed formulations include Tween 60, Span 80, cetostearyl alcohol, myristyl alcohol, glyceryl monostearate, sodium lauryl sulfate, glyceryl distearate alone or with a wax, or other materials well known in the art. In some cases, the solubility of the active compound in the oil(s) likely to be used in the pharmaceutical emulsion formulations can be low. Straight or branched chain, mono- or dibasic alkyl esters can aid solubility, such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters can be used. These can be used alone or in combination depending on the properties required. Alternatively, high melting point lipids such as white soft paraffin and/or liquid paraffin or other mineral oils can be used.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

1B. Formulations for Parenteral Administration

In some embodiments, provided herein are pharmaceutical compositions for parenteral administration containing a compound as disclosed herein, and one or more pharmaceutical excipients suitable for parenteral administration. In some embodiments, provided herein are pharmaceutical compositions for parenteral administration containing: (i) an effective amount of a disclosed compound; optionally (ii) an effective amount of one or more second agents; and (iii) one or more pharmaceutical excipients suitable for parenteral administration. In some embodiments, the pharmaceutical composition further contains: (iv) an effective amount of a third agent.

The forms in which the disclosed pharmaceutical compositions can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, benzyl alcohol, and the like (and suitable mixtures thereof), cyclodextrin derivatives, sodium chloride, tragacanth gum, buffers, and vegetable oils can also be employed.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

In some embodiments, the active ingredient can also be administered by injection as a composition with suitable carriers including saline, dextrose, or water, or with cyclodextrin (e.g., Captisol), cosolvent solubilization (e.g., propylene glycol) or micellar solubilization (e.g., Tween 80).

Sterile injectable solutions are prepared by incorporating a compound as disclosed herein in the required amount in the appropriate solvent with various other ingredients as enumerated above, as appropriate, followed by filtered sterilization. Generally, dispersions are prepared by incorporating the various sterilized active ingredients into a sterile vehicle which contains the basic dispersion medium and the appropriate other ingredients from those enumerated above. In the case of sterile powders for the preparation of sterile injectable solutions, certain methods of preparation are vacuum-drying and freeze-drying techniques which yield a powder of the active ingredient plus any additional ingredient from a previously sterile-filtered solution thereof.

The sterile injectable preparation can also be a sterile injectable solution or suspension in a non-toxic parenterally acceptable diluent or solvent, for example as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed, including synthetic mono- or diglycerides. In addition, fatty acids such as oleic acid find use in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Injectable compositions can contain from about 0.1 to about 5% w/w of a compound as disclosed herein.

1C. Formulations for Topical Administration

In some embodiments, provided herein are pharmaceutical compositions for topical (e.g., transdermal) administration containing a compound as disclosed herein, and one or more pharmaceutical excipients suitable for topical administration. In some embodiments, provided herein are pharmaceutical compositions for topical administration containing: (i) an effective amount of a disclosed compound; optionally (ii) an effective amount of one or more second agents; and (iii) one or more pharmaceutical excipients suitable for topical administration. In some embodiments, the pharmaceutical composition further contains: (iv) an effective amount of a third agent.

Pharmaceutical compositions provided herein can be formulated into preparations in solid, semi-solid, or liquid forms suitable for local or topical administration, such as gels, water soluble jellies, linements, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation can provide more immediate exposure of the active ingredient to the chosen area. For example, an ointment formulation can have either a paraffinic or a water-miscible base. Alternatively, the active ingredient can be formulated in a cream with an oil-in-water cream base. The aqueous phase of the cream base can include, for example at least about 30% w/w of a polyhydric alcohol such as propylene glycol, butane-1,3-diol, mannitol, sorbitol, glycerol, polyethylene glycol and mixtures thereof.

The pharmaceutical compositions also can comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the disclosed methods employs transdermal delivery devices ("patches"). Such transdermal patches can be used to provide continuous or discontinuous infusion of a compound as provided herein in controlled amounts, either with or without another agent. Patchs can be either of the reservoir and porous membrane type or of a solid matrix variety. In either case, the active agent can be delivered continuously from the reservoir or microcapsules through a membrane into the active agent permeable adhesive, which is in contact with the skin or mucosa of the recipient. If the active agent is absorbed through the skin, a controlled and predetermined flow of the active agent can be administered to the recipient. In the case of microcapsules, the encapsulating agent can also function as the membrane.

The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Suitable devices for use in delivering intradermal pharmaceutically acceptable compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Topically-administrable formulations can, for example, comprise from about 1% to about 10% (w/w) of a disclosed compound, although the concentration of the compound of Formula I can be as high as the solubility limit of the compound in the solvent. In some embodiments, topically-administrable formulations can, for example, include from about 0.001% to about 10% (w/w) compound, about 1% to about 9% (w/w) compound, such as from about 1% to about 8% (w/w), further such as from about 1% to about 7% (w/w), further such as from about 1% to about 6% (w/w), further such as from about 1% to about 5% (w/w), further such as from about 1% to about 4% (w/w), further such as from about 1% to about 3% (w/w), further such as from about 1% to about 2% (w/w), and further such as from about 0.1% to about 1% (w/w) compound. In some embodiments, the topical formulation includes about 0.1 mg to about 150 mg administered one to four, such as one or two times daily. Formulations for topical administration can further comprise one or more of the additional pharmaceutically acceptable excipients described herein.

1D. Formulations for Inhalation Administration

In some embodiments, provided herein are pharmaceutical compositions for inhalation administration containing a compound as disclosed herein, and one or more pharmaceutical excipients suitable for topical administration. In some embodiments, provided herein are pharmaceutical compositions for inhalation administration containing: (i) an effective amount of a disclosed compound; optionally (ii) an effective amount of one or more second agents; and (iii) one or more pharmaceutical excipients suitable for inhalation administration. In some embodiments, the pharmaceutical composition further contains: (iv) an effective amount of a third agent.

Pharmaceutical compositions for inhalation or insufflation include solutions and suspensions in pharmaceutically acceptable, aqueous or organic solvents, or mixtures thereof and powders. The liquid or solid pharmaceutical compositions can contain suitable pharmaceutically acceptable excipients as described herein. For example, suitable excipients include, but are not limited to, saline, benzyl alcohol and fluorocarbons. In some embodiments, the pharmaceutical compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder pharmaceutical compositions can be administered, e.g., orally or nasally, from devices that deliver the formulation in an appropriate manner.

1E. Formulations for Ocular Administration

In some embodiments, provided herein are pharmaceutical compositions for opthalmic administration containing a compound as disclosed herein, and one or more pharmaceutical excipients suitable for ophthalmic administration. Pharmaceutical compositions suitable for ocular administration can be presented as discrete dosage forms, such as drops or sprays each containing a predetermined amount of an active ingredient, a solution, or a suspension in an aqueous or non-aqueous liquid, an oil-in-water emulsion, or a water-in-oil liquid emulsion. Other administration forms include intraocular injection, intravitreal injection, topically, or through the use of a drug eluting device, microcapsule, implant, or microfluidic device. In some cases, the compounds as disclosed herein are administered with a carrier or excipient that increases the intraocular penetrance of the compound such as an oil and water emulsion with colloid particles having an oily core surrounded by an interfacial film. It is contemplated that all local routes to the eye can be used including topical, subconjunctival, periocular, retrobulbar, subtenon, intracameral, intravitreal, intraocular, subretinal, juxtascleral and suprachoroidal administration. Systemic or parenteral administration can be feasible including, but not limited to, intravenous, subcutaneous, and oral delivery. An exemplary method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

Eye drops can be prepared by dissolving the active ingredient in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chiorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondritin sulfate, etc.; e.g., sodium polyacrylate, carboxyvinyl polymer, crosslinked polyacrylate, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art).

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent can be selected from an alkylamine, a tertiary alkyl amine, a quarternary ammonium compound, a cationiclipid, an amino alcohol, a biguanidine salt, a cationic compound or a mixture thereof. In some cases, the cationic agent can be a biguanidine salt such as chlorhexidine, polyaminopropyl biguanidine, phenformin, alkylbiguanidine, or a mixture thereof. In some cases, the quaternary ammonium compound can be a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chiorallyl methenamine halide, rnyristylalkonium halide, stearalkonium halide or a mixture of two or more thereof. In some cases, cationic agent can be a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase can be mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising poluoxyl-40 hydrogenated castor oil, polyoxyl-60 hydrogenated castor oil or polyoxyl-100 hydrogenated castor oil.

In some embodiments, the amount of a compound as disclosed herein in the formulation can be about 0.5% to about 20%, 0.5% to about 10%, or about 1.5% w/w.

1F. Formulations for Controlled Release Administration

In some embodiments, provided herein are pharmaceutical compositions for controlled release administration containing a compound as disclosed herein, and one or more pharmaceutical excipients suitable for controlled release administration. In some embodiments, provided herein are pharmaceutical compositions for controlled release administration containing: (i) an effective amount of a disclosed compound; optionally (ii) an effective amount of one or more second agents; and (iii) one or more pharmaceutical excipients suitable for controlled release administration. In some embodiments, the pharmaceutical composition further contains: (iv) an effective amount of a third agent.

Active agents such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and U.S. Pat. Nos. 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active agents using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active agents provided herein. Thus, the pharmaceutical compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. In some embodiments, the use of a controlled release preparation in medical treatment can be characterized by a minimum of drug substance being employed to cure or control the disease, disorder, or condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

In some embodiments, controlled release formulations are designed to initially release an amount of a compound as disclosed herein that promptly produces the desired therapeutic effect, and gradually and continually release other amounts of the compound to maintain this level of therapeutic or prophylactic effect over an extended period of time. In order to maintain this constant level of the compound in the body, the compound should be released from the dosage form at a rate that will replace the amount of drug being metabolized and excreted from the body. Controlled release of an active agent can be stimulated by various conditions including, but not limited to, pH, temperature, enzymes, water, or other physiological conditions or compounds.

In certain embodiments, the pharmaceutical composition can be administered using intravenous infusion, an implantable osmotic pump, a transdermal patch, liposomes, or other modes of administration. In one embodiment, a pump can be used (see, Sefton, *CRC Crit. Ref Biomed. Eng.* 14:201 (1987); Buchwald et al., *Surgery* 88:507 (1980); Sandek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, 115-138 (vol. 2, 1984). Other controlled release systems are discussed in the review by Langer, *Science* 249:1527-1533 (1990). The one or more active agents can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydxogels of esters of acrylic and methacrylic acid, collagen, cross-linked polyvinylalcohol and cross-linked partially hydxolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The one or more active agents then diffuse through the outer polymeric membrane in a release rate controlling step. The percentage of active agent in such parenteral compositions can depend on the specific nature thereof, as well as the needs of the subject.

2. Dosage

A compound described herein can be delivered in the form of pharmaceutically acceptable compositions which comprise a therapeutically effective amount of one or more compounds described herein and/or one or more additional therapeutic agents such as a chemotherapeutic, formulated together with one or more pharmaceutically acceptable excipients. In some embodiments, only a compound provided herein without an additional therapeutic agent can be included in the dosage form. In some instances, the compound described herein and the additional therapeutic agent are administered in separate pharmaceutical compositions and can (e.g., because of different physical and/or chemical characteristics) be administered by different routes (e.g., one therapeutic can be administered orally, while the other can be administered intravenously). In other instances, the compound described herein and the additional therapeutic agent can be administered separately, but via the same route (e.g., both orally or both intravenously). In still other instances, the compound described herein and the additional therapeutic agent can be administered in the same pharmaceutical composition.

The selected dosage level will depend upon a variety of factors including, for example, the activity of the particular compound employed, the severity of the condition, the route of administration, the time of administration, the rate of excretion or metabolism of the particular compound being employed, the rate and extent of absorption, the duration of the treatment, administration of other drugs, compounds and/or materials used in combination with the particular compound employed, the age, sex, weight, condition, general health and prior medical history of the patient being treated, and like factors well known in the medical arts.

The dosage level can also be informed by in vitro or in vivo assays which can optionally be employed to help identify optimal dosage ranges. A rough guide to effective doses can be extrapolated from dose-response curves derived from in vitro or animal model test systems.

In general, a suitable daily dose of a compound described herein and/or a chemotherapeutic will be that amount of the compound which, in some embodiments, can be the lowest dose effective to produce a therapeutic effect. Such an effective dose will generally depend upon the factors described above. Generally, doses of the compounds described herein for a patient, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.1 mg to about 125 mg per day, or about 0.0001 mg to about 500 mg per day, or about 0.001 mg to about 500 mg per day, or about 0.01 mg to about 1000 mg per day, or about 0.01 mg to about 500 mg per day, or about 0.1 mg to about 500 mg per day, or about 1 mg to about 25 mg per day, or about 1 mg to about 50 mg per day, or about 5 mg to about 40 mg per day. An exemplary dosage can be about 10 to about 30 mg per day. In some embodiments, for a 70 kg human, a suitable dose would be about 0.05 to about 7 g/day, such as about 0.05 to about 2 g/day.

Actual dosage levels of the active ingredients in the pharmaceutical compositions described herein can be varied so as to obtain an amount of the active ingredient which is effective to achieve the desired therapeutic response for a particular patient, composition, and mode of administration, without being toxic to the patient. In some instances, dosage levels below the lower limit of the aforesaid range can be more than adequate, while in other cases still larger doses can be employed without causing any harmful side effect, e.g., by dividing such larger doses into several small doses for administration throughout the day.

In some embodiments, the compounds can be administered daily, every other day, three times a week, twice a week, weekly, bi-weekly, or another intermittent schedule. The dosing schedule can include a "drug holiday," i.e., the drug can be administered for two weeks on, one week off, or three weeks on, one week on, or four weeks on, one week off, etc., or continuously, without a drug holiday. The compounds can be administered orally, rectally, parenterally, intravenously, intraperitoneally, topically, transdermally, intramuscularly, subcutaneously, intracisternally, intravaginally, intranasally, sublingually, bucally, or by any other route.

In some embodiments, a compound as provided herein can be administered in multiple doses. Dosing can be about once, twice, three times, four times, five times, six times, or more than six times per day. Dosing can be about once a month, about once every two weeks, about once a week, or about once every other day. In another embodiment, a compound as disclosed herein and another agent are administered together about once per day to about 6 times per day. For example, the compound can be administered one or more times per day on a weekly basis (e.g., every Monday) indefinitely or for a period of weeks, e.g., 4-10 weeks. Alternatively, it can be administered daily for a period of days (e.g., 2-10 days) followed by a period of days (e.g., 1-30 days) without administration of the compound, with that cycle repeated indefinitely or for a given number of repetitions, e.g., 4-10 cycles. As an example, a compound provided herein can be administered daily for 5 days, then discontinued for 9 days, then administered daily for another 5 day period, then discontinued for 9 days, and so on, repeating the cycle indefinitely, or for a total of 4-10 times. In another embodiment, the administration of a compound as provided herein and an agent continues for less than about 7 days. In yet another embodiment, the administration continues for more than about 6, about 10, about 14, about 28 days, about two months, about six months, or about one year. In some cases, continuous dosing can be achieved and maintained as long as necessary.

Administration of the pharmaceutical compositions as disclosed herein can continue as long as necessary. In some embodiments, an agent as disclosed herein can be administered for more than about 1, about 2, about 3, about 4, about 5, about 6, about 7, about 14, or about 28 days. In some embodiments, an agent as disclosed herein can be administered for less than about 28, about 14, about 7, about 6, about 5, about 4, about 3, about 2, or about 1 day. In some embodiments, an agent as disclosed herein can be administered chronically on an ongoing basis, e.g., for the treatment of chronic effects.

Since the compounds described herein can be administered in combination with other treatments (such as additional chemotherapeutics, radiation or surgery), the doses of each agent or therapy can be lower than the corresponding dose for single-agent therapy. The dose for single agent therapy can range from, for example, about 0.0001 to about 200 mg, or about 0.001 to about 100 mg, or about 0.01 to about 100 mg, or about 0.1 to about 100 mg, or about 1 to about 50 mg per kilogram of body weight per day.

When a compound provided herein is administered in a pharmaceutical composition that comprises one or more agents, and one or more of the agents has a shorter half-life than the compound provided herein, unit dose forms of the agent(s) and the compound provided herein can be adjusted accordingly.

3. Kits

In some embodiments, provided herein are kits. The kits can include a compound or pharmaceutical composition as described herein, in suitable packaging, and written material that can include instructions for use, discussion of clinical studies, listing of side effects, and the like. Kits are well suited for the delivery of solid oral dosage forms such as tablets or capsules. Such kits can also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information can be based on the results of various studies, for example, studies using experimental animals involving in vivo models and studies based on human clinical trials.

In some embodiments, a memory aid can be provided with the kit, e.g., in the form of numbers next to the tablets or capsules whereby the numbers correspond with the days of the regimen which the tablets or capsules so specified should be ingested. Another example of such a memory aid can be a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several tablets or capsules to be taken on a given day.

The kit can further contain another agent. In some embodiments, the compound as disclosed herein and the agent are provided as separate pharmaceutical compositions in separate containers within the kit. In some embodiments, the compound as disclosed herein and the agent are provided as a single pharmaceutical composition within a container in the kit. Suitable packaging and additional articles for use (e.g., measuring cup for liquid preparations, foil wrapping to minimize exposure to air, and the like) are known in the art and can be included in the kit. In other embodiments, kits can further comprise devices that are used to administer the active agents. Examples of such devices include, but are not limited to, syringes, drip bags, patches, and inhalers. Kits described herein can be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules can be removed from the blister pack by manually applying pressure on the recesses whereby an opening is formed in the sheet at the place of the recess. The tablet or capsule can then be removed via said opening.

Kits can further comprise pharmaceutically acceptable vehicles that can be used to administer one or more active agents. For example, if an active agent is provided in a solid form that must be reconstituted for parenteral administration, the kit can comprise a sealed container of a suitable vehicle in which the active agent can be dissolved to form a particulate free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

Therapeutic Methods

As used herein, a "mutant EGFR-mediated disorder" refers to a disease or condition involving an aberrant EGFR-mediated signaling pathway associated with the EGFR having one or more mutations in any of its exons and includes having one or more mutations in the exon 20 domain. In one embodiment, the mutant EGFR has one or more mutations in the exon 20 domain. In another embodiment, the mutant EGFR-mediated disorder can be associated with EGFR having one or more mutations in the exon 20 domain.

As used herein, a "mutant HER2-mediated disorder" refers to a disease or condition involving an aberrant HER2-mediated signaling pathway associated with the EGFR having one or more mutations in any of its exons and includes having one or more mutations in the exon 20 domain. In one embodiment, the mutant HER2 has one or more mutations in the exon 20 domain. In another embodiment, the mutant HER2-mediated disorder can be associated with HER2 having one or more mutations in the exon 20 domain.

In some embodiments, a method is provided for inhibiting mutant EGFR activity by contacting the mutant EGFR with an effective amount of a compound, or a pharmaceutically acceptable form (e.g., pharmaceutically acceptable salts, hydrates, solvates, isomers, prodrugs, and isotopically labeled derivatives) thereof, or a pharmaceutical composition as provided herein, in some cases in solution, to inhibit the mutant EGFR kinase activity. In some embodiments, methods are provided for inhibiting the mutant EGFR activity by contacting a cell, tissue, or organ that expresses the mutant EGFR with a compound provided herein. In some embodiments, methods are provided for inhibiting the mutant EGFR activity in a subject (including mammals such as humans) by administering into the subject an effective amount of a compound as provided herein to inhibit or reduce the activity of the mutant EGFR in the subject. In some embodiments, the kinase activity can be inhibited (e.g., reduced) by more than about 25%, about 30%, about 40%, about 50%, about 60%, about 70%, about 80%, or about 90% when contacted with a compound provided herein as compared to the kinase activity without such contact. In some embodiments, the kinase can be exon 20 mutant EGFR. For instance, the mutant EGFR can be exon 20 mutant EGFR.

In EGFR kinase, the exon 20 domain lies in a loop beginning at the C-terminal side of the kinase's C-helix. (Yasuda 2012) Exon 20 in HER2 is in a similar position. While the C-helix forms a portion of the active site, the exon 20 loop exerts a more indirect conformational motion when mutated. The conformational change affects the C-helix such that the active site pocket is altered in a subtle manner. Without being bound by any one theory, this conformational change can enable selective inhibition of exon 20 mutant EGFR and/or exon 20 mutant HER2 relative to wild-type EGFR.

In some embodiments, the exon 20 mutant EGFR has insertion mutations in its exon 20 domain. Insertion mutations have been documented for at least residues 762-774 of EGFR, with those involving amino acids A767, S768, V769, D770, P772 and H773 displaying a lack of response when treated with known inhibitors, such as gefitinib or erlotinib. (Yasuda 2012). Other types of mutations can occur in the exon 20 domain, such as the T790M "gatekeeper" point mutation, which lies in the active site of EGFR. T790M mutations can occur in conjunction with deletion mutations such as DT and other point mutations such as LT. Disclosed compounds can have inhibitory activity against T790M mutated EGFR and activity against exon 20 insertion mutants.

In one embodiment, the disclosed compounds show inhibitory activity towards one or more of the EGFR exon 20 insertion mutants shown in Table 1. The relative frequency is derived from a survey of published clinical trials in which the EGFR mutation(s) in the patient were determined. (Yasuda 2012).

TABLE 1

| EGFR amino acid | Insertion Mutation | Relative Frequency |
| --- | --- | --- |
| 767 | Ala767_Ser768insThrLeuAla | 2.5% |
| 768 | Ser768_Val769insValAlaSer | 5.7% |
|  | Ser768_Val769insAlaTrpThr |  |
| 769 | Val769_Asp770insAlaSerVal | 20.5% |
|  | Val769_Asp770insGlyVal |  |
|  | Val769_Asp770insCysVal |  |
|  | Val769_Asp770insAspAsnVal |  |
|  | Val769_Asp770insGlySerVal |  |
|  | Val769_Asp770insGlyValVal |  |
|  | Val769_Asp770insMetAlaSerValAsp |  |
|  | (SEQ ID NO: 1) |  |
| 770 | Asp770_Asn771insSerValAsp | 28.7% |
|  | Asp770_Asn771insAsnProGly |  |
|  | Asp770_Asn771insAlaProTrp |  |
|  | Asp770_Asn771insAsp |  |
|  | Asp770_Asn771insAspGly |  |
|  | Asp770_Asn771insGly |  |
|  | Asp770_Asn771insGlyLeu |  |
|  | Asp770_Asn771insAsn |  |
|  | Asp770_Asn771insAsnProHis |  |
|  | Asp770_Asn771insSerValPro |  |
|  | Asp770_Asn771insSerValGln |  |
|  | Asp770_Asn771insMetAlaThrPro |  |
|  | (SEQ ID NO: 2) |  |
|  | delAsp770insGlyTyr |  |

TABLE 1-continued

| EGFR amino acid | Insertion Mutation | Relative Frequency |
|---|---|---|
| 771 | Asn771_Pro772insHis<br>Asn771_Pro772insAsn<br>delAsn771insGlyTyr<br>delAsn771insGlyPhe | 4.1% |
| 772 | Pro772_His773insProArg<br>Pro772_His773insTyrAsnPro<br>Pro772_His773insX<br>Pro772_His773insAspProHis<br>Pro772_His773insAspAsnPro<br>Pro772_His773insGlnVal<br>Pro772_His773insThrProHis<br>Pro772_His773insAsn<br>Pro772_His773insVal | 17.2% |
| 773 | His773_Val774insAsnProHis<br>His773_Val774insHis<br>His773_Val774insProHis<br>His773_Val774insGlyAsnProHis<br>(SEQ ID NO: 3)<br>His773_Val774insGly<br>His773_Val774insGlyHis | 14% |
| 774 | Val774_Cys775insHisVal | 3.3% |

In another embodiment, the compounds disclosed herein show inhibitory activity towards the exon 20 mutant EGFR Val769_Asp770insAlaSerVal and/or the Asp770_Asn771insAsnProGly insertion mutations. In some embodiments, the compounds disclosed herein show inhibitory activity towards one or more of the exon 20 mutant EGFR Asp770_Asn771 insSVD, the His773_Val774insNPH, and the Ala763_Tyr764insFQEA (SEQ ID NO: 4) insertion mutations. Provided herein, methods of treatment for a mutant EGFR-mediated disorder include subjects who have an exon 20 insertion mutation as listed in Table 1. In other embodiments, the exon 20 insertion mutation can be selected from Val769_Asp770insAlaSerVal and/or the Asp770_Asn771 insAsnProGly. In other embodiments, the exon 20 insertion mutation can be selected from Asp770_Asn771insSVD, His773_Val774insNPH, and Ala763_Tyr764insFQEA (SEQ ID NO: 4).

In some embodiments, methods are disclosed for inhibiting mutant HER2 activity (e.g., selectively modulating) by contacting the HER2 with an effective amount of a compound, or a pharmaceutically acceptable form (e.g., pharmaceutically acceptable salts, hydrates, solvates, isomers, prodrugs, and isotopically labeled derivatives) thereof, or a pharmaceutical composition as provided herein, to inhibit the HER2 activity. In some embodiments, the mutant HER2 has one or more exon 20 mutations. In some embodiments, methods are provided for inhibiting kinase activity by contacting the kinase with a solution containing an effective amount of the compound to inhibit the HER2. In some embodiments, methods are provided for inhibiting the HER2 kinase activity by contacting a cell, tissue, or organ that express the kinase with a compound provided herein. In some embodiments, methods of inhibiting kinase activity in a subject by administering into the subject an effective amount of a compound as provided herein. In some embodiments, the kinase activity can be inhibited (e.g., reduced) by more than about 25%, about 30%, about 40%, about 50%, about 60%, about 70%, about 80%, or about 90% when contacted with a compound provided herein as compared to the kinase activity without such contact. In some embodiments, the kinase can be exon 20 mutant HER2. In some embodiments, provided herein are methods of inhibiting mutant HER2 activity in a subject (including mammals such as humans) by contacting said subject with an amount of a compound as provided herein sufficient to inhibit or reduce the activity of the mutant HER2 in said subject. For instance, the mutant HER2 can be exon 20 mutant HER2.

In some embodiments, the exon 20 mutant HER2 has insertion mutations in its exon 20 domain that have been documented for at least residues 770-831 of HER2. (Arcila 2012; Shigematsu et. al. Cancer Res 2005; 65:1642-46). In one embodiment, the disclosed compounds show inhibitory activity towards one or more of the HER2 exon 20 insertion mutants shown in Table 2.

TABLE 2

| HER2 amino acid | Point and Insertion Mutations | Relative Frequency |
|---|---|---|
| 775 | Ala775_Gly776insTyrValMetAla (SEQ ID NO: 5) | 80% |
| 776 | Gly776>ValCys | 8% |
| 780 | Pro780_Tyr781insGlySerPro | 4% |
| 776 and 777 | Gly776Cys and Val777_Gly778insCysGly | 4% |

In another embodiment, the compounds disclosed herein show inhibitory activity towards the Ala775_Gly776insTyrValMetAla (SEQ ID NO: 5) exon 20 mutant HER2 insertion mutations. The disclosed methods of treatment for a mutant HER2-mediated disorder are applicable to those subjects, among others, who have exon 20 insertion mutation Ala775_Gly776insTyrValMetAla (SEQ ID NO: 5) or another exon 20 insertion mutation listed in Table 2.

In some embodiments, the compounds disclosed herein show inhibitory activity against the wild type receptor tyrosine kinases that include EGFR/ERBB1, HER2/ERBB2/NEU, HER3/ERBB3, and HER4/ERBB4.

In one embodiment, provided herein is a method of treating a mutant EGFR-mediated disorder in a subject, the method comprising administering a therapeutically effective amount of a compound or a pharmaceutical composition as provided herein. In some embodiments, provided herein is a method of ameliorating a mutant EGFR-mediated disorder in a subject, the method comprising administering a therapeutically effective amount of a compound or a pharmaceutical composition as provided herein. In some embodiments, provided herein is a method for inhibiting mutant EGFR, the method comprising contacting a cell expressing mutant EGFR in vitro or in vivo with an effective amount of the compound or composition provided herein. In all these embodiments, the mutant can be, for example, an exon 20 insertion mutant. In another aspect, in all the above embodiments the mutant can be an exon 20 point mutation, optionally accompanied by another mutation such as D or L.

In some embodiments, provided herein are methods of treating a mutant EGFR-mediated disorder, such as where the mutation is an exon 20 insertion, that is resistant to another anti-cancer agent(s) (e.g., erlotinib, gefitinib, neratinib, afatinib, dacomitinib), the method involving administering a therapeutic effective amount of a compound of Formula I to a subject in need thereof.

Without being limited by a particular theory, EGFR having one or more exon 20 insertion mutations has been associated with lung cancer (e.g., non-small cell lung cancer NSCLC, lung adenocarcinoma), colorectal cancer, pancreatic cancer, and head and neck cancers. Exon 20 insertion mutations are most prevalent in NSCLC: 15% of western Europeans, 30% East Asians, and 50% of non-smokers.

(Yasuda 2012). In head and neck cancers, current therapies targeting mutant EGFR include cetuximab, a chimeric mouse-human IgG1antibody. (Chong et al. 2013). Exon 20 mutant EGFR colorectal cancer has been treated using cetuximab and panitumumab, a fully humanized IgG2 antibody. Id. Exon 20 mutant EGFR pancreatic cancer has been treated with erlotinib. Id. EGFR having the T790M point mutation, optionally accompanied by exon 19 D and/or exon 21 L mutations, have been associated with NSCLC where the cancer has developed resistance to one or more other TKI's such as erlotinib and gefitinib.

Without being limited by a particular theory, HER2 having one or more exon 20 insertion mutations has been associated with lung cancer (e.g., NSCLC), breast cancer, ovarian cancer, uterine cancer, and stomach cancer. (Santin et al. Int J Gynaecol Obstet 2008; 102:128-31). Current therapies include Herceptin and pertuzamab. HER2 mutations are present in about 2-4% of NSCLC: 80-84% of those patients have the YVMA exon 20 insertion mutation. (Arcila 2012).

In some embodiments, provided herein are methods of using a compound of Formula I, or a pharmaceutically acceptable form (e.g., pharmaceutically acceptable salts, hydrates, solvates, isomers, prodrugs, and isotopically labeled derivatives) thereof, or pharmaceutical compositions as provided herein to treat disease conditions, including, but not limited to, diseases associated with one or more types of mutant EGFR or mutant HER2. In some embodiments, the disclosure relates to a method of treating a hyperproliferative disorder in a subject that comprises administering to said subject a therapeutically effective amount of a compound, or a pharmaceutically acceptable form (e.g., pharmaceutically acceptable salts, hydrates, solvates, isomers, prodrugs, and isotopically labeled derivatives) thereof, or a pharmaceutical composition as provided herein.

Compounds and pharmaceutical compositions are disclosed herein for the manufacture of a medicament for treating a mutant EGFR or mutant HER2 disorder in a subject in need thereof. Also provided are compounds and pharmaceutical compositions for the treatment of a mutant EGFR-mediated disorder or mutant HER2-mediated disorder in a subject in need thereof. In all of the above embodiments, the mutant can be an exon 20 insertion mutation. In another aspect, in all the above embodiments the mutant can be an exon 20 point mutation, optionally accompanied by another mutation such as D or L.

Patients that can be treated with compounds, or a pharmaceutically acceptable form (e.g., pharmaceutically acceptable salts, hydrates, solvates, isomers, prodrugs, and isotopically labeled derivatives) thereof, or pharmaceutical compositions as provided herein, according to the methods as provided herein include, but are not limited to, patients that have been diagnosed as having lung cancer, colorectal cancer, pancreatic cancer and head and neck cancers. In other embodiments, a patient can be diagnosed with lung cancer, breast cancer, ovarian cancer, uterine cancer, and stomach cancer. Efficacy of a compound provided herein in treating, preventing and/or managing the disease or disorder can be tested using various animal models known in the art. See, e.g., Yasuda 2012.

In some embodiments, a symptom associated with a disease or disorder provided herein can be reduced by at least about 10%, at least about 20%, at least about 30%, at least about 40%, at least about 50%, at least about 60%, at least about 70%, at least about 80%, at least about 90%, or at least about 95% relative to a control level. The control level includes any appropriate control as known in the art. For example, the control level can be the pre-treatment level in the sample or subject treated, or it can be the level in a control population (e.g., the level in subjects who do not have the disease or disorder or the level in samples derived from subjects who do not have the disease or disorder). In some embodiments, the decrease can be statistically significant, for example, as assessed using an appropriate parametric or non-parametric statistical comparison.

In some embodiments, treatment of a mutant EGFR-mediated disorder or a mutant HER2-mediated disorder involves administering (as a monotherapy or in combination with one or more other anti-cancer agents, one or more agents for ameliorating side effects, radiation, etc) a therapeutically effective amount of a compound disclosed herein to a human or animal in need of it in order to inhibit, slow or reverse the growth, development or spread of cancer, including solid tumors or other forms of cancer such as leukemias, in the subject. Such administration constitutes a method for the treatment or prophylaxis of diseases mediated by one or more kinases inhibited by one of the disclosed compounds or a pharmaceutically acceptable form thereof. In one embodiment, the mutant can be an exon 20 insertion mutation.

Combination Therapy

In some embodiments, provided herein are methods for combination therapies in which an agent known to modulate other pathways, or other components of the same pathway, or even overlapping sets of target enzymes are used in combination with a compound as provided herein, or a pharmaceutically acceptable form (e.g., pharmaceutically acceptable salts, hydrates, solvates, isomers, prodrugs, and isotopically labeled derivatives) thereof. In one aspect, such therapy includes, but is not limited to, the combination of the subject compound with chemotherapeutic agents, therapeutic antibodies, and radiation treatment, to provide a synergistic or additive therapeutic effect.

When administered as a combination, the therapeutic agents can be formulated as separate compositions that are administered at the same time or sequentially at different times, or the therapeutic agents can be given as a single composition. The phrase "combination therapy", in referring to the use of a disclosed compound together with another pharmaceutical agent, means the coadministration of each agent in a substantially simultaneous manner as well as the administration of each agent in a sequential manner, in either case, in a regimen that will provide beneficial effects of the drug combination. Coadministration includes, inter alia, the simultaneous delivery, e.g., in a single tablet, capsule, injection or other dosage form having a fixed ratio of these active agents, as well as the simultaneous delivery in multiple, separate dosage forms for each agent respectively. Thus, the administration of disclosed compounds can be in conjunction with additional therapies known to those skilled in the art in the prevention or treatment of cancer, such as radiation therapy or cytostatic agents, cytotoxic agents, other anti-cancer agents and other drugs to amerliorate symptoms of the cancer or side effects of any of the drugs.

If formulated as a fixed dose, such combination products employ the disclosed compounds within suitable dosage ranges. Compounds provided herein can also be administered sequentially with other anticancer or cytotoxic agents when a combination formulation is inappropriate. As defined herein, combination therapy is not limited in the sequence of administration; disclosed compounds can be administered prior to, simultaneously with, or after administration of the other anticancer or cytotoxic agent.

In some embodiments, pharmaceutical compositions disclosed herein can include a compound as described herein or a pharmaceutically acceptable salt thereof; an additional agent selected from a kinase inhibitory agent (small molecule, polypeptide, antibody, etc.), an immunosuppressant, an anticancer agent, an anti-viral agent, antiinflammatory agent, antifungal agent, antibiotic, or an anti-vascular hyperproliferation compound; and any pharmaceutically acceptable carrier, adjuvant or vehicle.

Alternate pharmaceutical compositions disclosed herein include a compound as described herein or a pharmaceutically acceptable salt thereof; and a pharmaceutically acceptable carrier, adjuvant or vehicle. Such compositions can optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

In one aspect, a compound as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can present synergistic or additive efficacy when administered in combination with agents that inhibit other kinase(s) production or activity. Such combination can reduce undesired side effect of the compounds and compositions described herein, if such effect occurs.

In some embodiments, treatment can be provided in combination with one or more other cancer therapies, include surgery, radiotherapy (e.g., gamma-radiation, neutron beam radiotherapy, electron beam radiotherapy, proton therapy, brachytherapy, and systemic radioactive isotopes, etc.), endocrine therapy, biologic response modifiers (e.g., interferons, interleukins, and tumor necrosis factor (TNF)), hyperthermia, cryotherapy, agents to attenuate any adverse effects (e.g., antiemetics), and other cancer chemotherapeutic drugs. The other agent(s) can be administered using a formulation, route of administration and dosing schedule the same or different from that used with the compounds provided herein.

For treatment of mutant EGFR-mediated diseases and mutant HER2-mediated diseases, a compound as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can be used in combination with commonly prescribed drugs including, but not limited to, anti-cancer drugs (e.g., anti-proliferative agents, anti-angiogenic agents and other chemotherapeutic agents). In another aspect, provided herein is a pharmaceutical composition for inhibiting abnormal cell growth in a subject which comprises an amount of a compound as provided herein, or a pharmaceutically acceptable form (e.g., pharmaceutically acceptable salts, hydrates, solvates, isomers, prodrugs, and isotopically labeled derivatives) thereof, in combination with an amount of an anti-cancer agent (e.g., a chemotherapeutic agent). Many chemotherapeutics are presently known in the art and can be used in combination with the compounds as provided herein. In some embodiments, the chemotherapeutic can be selected from mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, antibiotics, immunological agents, interferon-type agents, and anti-androgens. Non-limiting examples include chemotherapeutic agents, cytotoxic agents, and non-peptide small molecules such as Gleevec® (Imatinib Mesylate), Velcade® (bortezomib), Casodex (bicalutamide), Iressa®, and Adriamycin as well as a host of chemotherapeutic agents. Non-limiting examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; BTK inhibitors such as ibrutinib (PCI-32765) and AVL-292; HDAC inhibitors such as vorinostat, romidepsin, panobinostat, valproic acid, belinostat, mocetinostat, abrexinostat, entinostat, SB939, resminostat, givinostat, CUDC-101, AR-42, CHR-2845, CHR-3996, 4SC-202, CG200745, ACY-1215 and kevetrin; JAK-STAT inhibitors such as lestaurtinib, tofacitinib, ruxolitinib, pacritinib, CYT387, baricitinib, fostamatinib, GLPG0636, TG101348, INCB16562 and AZDI480; nitrogen mustards such as bedamustine, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pralatrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; ellip700tinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethyla-mine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France) and ABRAXANE® (paclitaxel protein-bound particles); retinoic acid; esperamicins; capecitabine; and pharmaceutically acceptable forms (e.g., pharmaceutically acceptable salts, hydrates, solvates, isomers, prodrugs, and isotopically labeled derivatives) of any of the above. Also included as suitable chemotherapeutic cell conditioners are anti-hormonal agents that act to regulate or inhibit hormone action on tumors such as anti-estrogens including, for example, tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandlonate; camptothecin-11 (CPT-11); topoisomerase inhibitor RFS 2000; and difluoromethylornithine (DMFO).

Where desired, the compounds or pharmaceutical compositions as provided herein can be used in combination with commonly prescribed anti-cancer drugs such as, but not limited to, Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, Crizotinib, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126, and Zosuquidar.

Other chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A(2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP), ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TK1258, CHIR-258), BIBW 2992 (TOVOKTM®), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP 11981, tivozanib (AV-951), OSI-930, MM-121, XL-184, XL-647, and/or XL228), proteasome inhibitors (e.g., bortezomib (Velcade®)), mTOR inhibitors (e.g., rapamycin, temsirolimus (CCI-779), everolimus (RAD-001), ridaforolimus, AP23573 (ARIAD), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, caminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, caminomycin-aminopterin, and hexamethyl melamine.

In some embodiments, the anti-cancer agent can be selected from, but not limited to, one or more of the following anti-metabolite agents: 5-FU-fibrinogen, acanthifolic acid, aminothiadiazole, brequinar sodium, carmofur, CibaGeigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(21-furanidyl) fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC- 612567, Warner-Lambert PALA, pentostatin, piritrexim, plicamycin, Asahi Chemical PL-AC, Takeda TAC788, thioguanine, tiazofurin, Erbamont TIF, trimetrexate, tyrosine kinase inhibitors, Taiho UFT and uricytin.

In some embodiments, the anti-cancer agent can be selected from, but not limited to, one or more of the following alkylating-type agents: Shionogi 254-S, aldophosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D 384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G M, Chinoin GYKI-17230, hepsulfam, ifosfamide, iproplatin, lomustine, mafosfamide, mitolactolf Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

In some embodiments, the anti-cancer agent can be selected from, but not limited to, one or more of the following antibiotic-type agents: Taiho 4181-A, aclarubicin, actinomycin D, actinoplanone, Erbamont ADR-456, aeroplysinin derivative, Ajinomoto AN II, Ajinomoto AN3, Nippon Soda anisomycins, anthracycline, azino-mycin-A, bisucaberin, Bristol-Myers BL-6859, Bristol-Myers BMY-25067, Bristol-Myers BNY-25551, Bristol-Myers BNY-26605, BristolMyers BNY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko, DC89-AI, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-AI, esperamicin-Alb, Erbamont FCE21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-1, rapamycin, rhizoxin, rodorubicin, sibanomicin, siwenmycin, Sumitomo SM5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

In some embodiments, the anti-cancer agent can be selected from, but not limited to, one or more of the following antineoplastic agents, including tubulin interacting agents, topoisomerase II inhibitors, topoisomerase I inhibitors and hormonal agents: β-carotene, β-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5. antineoplaston AS2-1F Henkel APD, aphidicolin glycinate, asparaginase, Avarol, baccharin, batracylin, benfluron, benzotript, Ipsen-Beaufour BIM-23015, bisantrene, BristoMyers BNY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, WarnerLambert CI-937, Warner-Lambert CI-941, Warner-Lambert CI958, clanfenur, claviridenone, ICN compound 1259, ICN compound 4711, Contracan, Yakult Honsha CPT-11, crisnatol, curaderm, cytochalasin B. cytarabine, cytocytin, Merz D-609, DABIS maleate, dacarbazine, datelliptinium, didemnin-B, dihaematoporphirin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704t gallium nitrate, genkwadaphnin, Chugai GLA-43, Glaxo GR-63178, grifolan NMF5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU 1121 Lilly LY-186641, NCI (US) MAP, marycin, Merrel Dow MDL-27048, Medco MEDR-340, merbarone, merocyanlne derivatives, methylanilinoacridine, Molecular Genetics MG1136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, WarnerLambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM.

In some embodiments, the additional therapeutic agent can be selected from, but not limited to, acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon1, interferon alpha, natural, interferon beta, interferon beta-Ia, interferon beta-Ib, interferon gamma, natural interferon gamma-Ia, interferon gamma-Ib, interleukin-I beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama. vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinidel filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM iodine 131 MAb (Techniclone), polymorphic epithelial mucin-yttrium 90 MAb (Antisoma), marimastat, menogaril, mitumomab, motexafin, gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN)y SU 6668 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

In some embodiments, the additional therapeutic agent can be selected from, but not limited to, anti-cancer alkylating or intercalating agent (e.g., mechlorethamine, chlorambucil, Cyclophosphamide, Melphalan, and Ifosfamide); antimetabolite (e.g., Methotrexate); purine antagonist or pyrimidine antagonist (e.g., 6-Mercaptopurine, 5-Fluorouracil, Cytarabile, and Gemcitabine); spindle poison (e.g., Vinblastine, Vincristine, Vinorelbine and Paclitaxel); podophyllotoxin (e.g., Etoposide, Irinotecan, Topotecan); antibiotic (e.g., Doxorubicin, Bleomycin and Mitomycin); nitrosourea (e.g., Carmustine, Lomustine); inorganic ion (e.g., Cisplatin, Carboplatin, Oxaliplatin or oxiplatin); enzyme (e.g., Asparaginase); hormone (e.g., Tamoxifen, Leuprolide, Flutamide and Megestrol); mTOR inhibitor (e.g., Sirolimus (rapamycin), Temsirolimus (CC1779), Everolimus (RAD001), AP23573 or other compounds disclosed in U.S. Pat. No. 7,091,213); proteasome inhibitor (such as Velcade, another proteasome inhibitor (see e.g., WO 02/096933) or another NF-kB inhibitor, including, e.g., an IkK inhibitor); other kinase inhibitors (e.g., an inhibitor of Src, BRC/Abl, kdr, flt3, aurora-2, glycogen synthase kinase 3 ("GSK-3"), EGF-R kinase (e.g., Iressa, Tarceva, etc.), VEGF-R kinase, PDGF-R kinase, etc.); an antibody, soluble receptor or other receptor antagonist against a receptor or hormone implicated in a cancer (including receptors such as EGFR, ErbB2, VEGFR, PDGFR, and IGF-R; and agents such as Herceptin, Avastin, Erbitux, etc.); etc.

Examples of other therapeutic agents are noted elsewhere herein and include among others, Zyloprim, alemtuzmab, altretamine, amifostine, nastrozole, antibodies against prostate-specific membrane antigen (such as MLN-591, MLN591RL and MLN2704), arsenic trioxide, bexarotene, bleomycin, busulfan, capecitabine, Gliadel Wafer, celecoxib, chlorambucil, cisplatin-epinephrine gel, cladribine, cytarabine liposomal, daunorubicin liposomal, daunorubicin, daunomycin, dexrazoxane, docetaxel, doxorubicin, Elliott's B Solution, epirubicin, estramustine, etoposide phosphate, etoposide, exemestane, fludarabine, 5-FU, fulvestrant, gemcitabine, gemtuzumab-ozogamicin, goserelin acetate, hydroxyurea, idarubicin, idarubicin, Idamycin, ifosfamide, imatinib mesylate, irinotecan (or other topoisomerase inhibitor, including antibodies such as MLN576 (XR11576)), letrozole, leucovorin, leucovorin levamisole, liposomal daunorubicin, melphalan, L-PAM, mesna, methotrexate, methoxsalen, mitomycin C, mitoxantrone, MLN518 or MLN608 (or other inhibitors of the flt-3 receptor tyrosine kinase, or PDFG-R), itoxantrone, paclitaxel, Pegademase, pentostatin, porfimer sodium, Rituximab (RITUXAN®), talc, tamoxifen, temozolamide, teniposide, VM-26, topotecan, toremifene, 2C4 (or other antibody which interferes with HER2-mediated signaling), tretinoin, ATRA, valrubicin, vinorelbine, or pamidronate, zoledronate or another bisphosphonate.

Exemplary biotherapeutic agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. Herceptin (trastuzumab), T-DM1, AVASTIN (bevacizumab), ERBITUX (cetuximab), Vectibix (panitumumab), Rituxan (rituximab), and Bexxar (tositumomab)).

In some embodiments, the chemotherapeutic agent can be selected from HSP90 inhibitors. The HSP90 inhibitor can be a geldanamycin derivative, e.g., a benzoquinone or hygroquinone ansamycin HSP90 inhibitor (e.g., IPI-493 and/or IPI-504). Non-limiting examples of HSP90 inhibitors include IPI-493, IPI-504, 17-AAG (also known as tanespimycin or CNF-1010), BIIB-021 (CNF-2024), BIIB-028, AUY-922 (also known as VER-49009), SNX-5422, STA-9090, AT-13387, XL-888, MPC-3100, CU-0305, 17-DMAG, CNF-1010, Macbecin (e.g., Macbecin I, Macbecin II), CCT-018159, CCT 129397, PU-H71, or PF-04928473 (SNX-2112).

In some embodiments, the chemotherapeutic can be selected from PI3K inhibitors. In some embodiments, the PI3K inhibitor can be an inhibitor of delta and gamma isoforms of PI3K. In some embodiments, the PI3K inhibitor can be an inhibitor of alpha isoforms of PI3K. In other embodiments, the PI3K inhibitor can be an inhibitor of one or more alpha, beta, delta and gamma isoforms of PI3K. Exemplary PI3K inhibitors that can be used in combination are described in, e.g., WO 09/088,990, WO 09/088,086, WO 2011/008302, WO 2010/036380, WO 2010/006086, WO 09/114,870, WO 05/113556; US 2009/0312310, and US 2011/0046165. Additional PI3K inhibitors that can be used in combination include, but are not limited to, AMG-319, GSK 2126458, GDC-0980, GDC-0941, Sanofi XL147, XL499, XL756, XL147, PF-46915032, BKM 120, CAL-101 (GS-1101), CAL 263, SF1126, PX-886, and a dual PI3K inhibitor (e.g., Novartis BEZ235).

In some embodiments, provided herein is a method for using the a compound as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, in combination with radiation therapy in inhibiting abnormal cell growth or treating the hyperproliferative disorder in the subject. Techniques for administering radiation therapy are known in the art, and these techniques can be used in the combination therapy described herein. The administration of the compound as provided herein in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, 1-131, 1-125, Y-90, Re-186, Re-188, Sm-153, Bi-212, P-32, and radioactive isotopes of Lu). Suitable radiation sources for use as a cell conditioner as provided herein include both solids and liquids. By way of non-limiting example, the radiation source can be a radionuclide, such as 1-125, 1-131, Yb 169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can render abnormal cells more sensitive to treatment with radiation for purposes of killing and/or inhibiting the growth of such cells. Accordingly, provided herein is a method for sensitizing abnormal cells in a subject to treatment with radiation which comprises administering to the subject an amount of a compound as provided herein or pharmaceutically acceptable forms (e.g., pharmaceutically acceptable salts, hydrates, solvates, isomers, prodrugs, and isotopically labeled derivatives) thereof, which amount is effective in sensitizing abnormal cells to treatment with radiation. The amount of the compound used in this method can be determined according to the means for ascertaining effective amounts of such compounds described herein.

The compounds as provided herein, or a pharmaceutically acceptable form (e.g., pharmaceutically acceptable salts, hydrates, solvates, isomers, prodrugs, and isotopically labeled derivatives) thereof, or pharmaceutical compositions as provided herein, can be used in combination with an amount of one or more substances selected from anti-angiogenesis agents, signal transduction inhibitors, and anti-proliferative agents, glycolysis inhibitors, or autophagy inhibitors.

Anti-angiogenesis agents, such as MMP-2 (matrixmetalloproteinase 2) inhibitors, MMP-9 (matrix-metalloproteinase 9) inhibitors, and COX-11 (cyclooxygenase 11) inhibitors, can be used in conjunction with a compound as provided herein and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172, WO 96/27583, European Patent Application No. 97304971.1, European Patent Application No. 99308617.2, WO 98/07697, WO 98/03516 (published Jan. 29, 1998), WO 98/34918, WO 98/34915, WO 98/33768, WO 98/30566, European Patent Publication 606,046, European Patent Publication 931,788, WO 90/05719, WO 99/52910, WO 99/52889, WO99/29667, PCT International Application No. PCT/IB98/01113, European Patent Application No. 99302232.1, Great Britain Patent Application No. 9912961.1, U.S. Provisional Application No. 60/148,464, U.S. Pat. No. 5,863,949, U.S. Pat. No. 5,861,510, and European Patent Publication 780,386, all of which are incorporated herein in their entireties by reference. In some embodiments, MMP-2 and MMP-9 inhibitors are those that have little or no activity inhibiting MMP-1. Other embodiments include those that selectively inhibit MMP-2 and/or AMP-9 relative to the other matrixmetalloproteinases (i.e., MAP-I, MMP-3, MMP-4, MMP-5, MMP-6, MMP-7, MMP-8, MMP-10, MMP-II, MMP-12, and MMP-13). Some non-limiting examples of MMP inhibitors are AG-3340, RO 32-3555, and RS 13-0830.

Autophagy inhibitors include, but are not limited to, chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including, but not limited to ATG5 (which are implicated in autophagy), can also be used.

Medicaments which can be administered in conjunction with the compounds as provided herein, or a pharmaceutically acceptable form (e.g., pharmaceutically acceptable salts, hydrates, solvates, isomers, prodrugs, and isotopically labeled derivatives) thereof, include any suitable drugs usefully delivered by inhalation for example, analgesics, (e.g., codeine, dihydromorphine, ergotamine, fentanyl or morphine); anginal preparations, (e.g., diltiazem; antiallergics, e.g. cromoglycate, ketotifen or nedocromil); anti-infectives, (e.g., cephalosporins, penicillins, streptomycin, sulphonamides, tetracyclines or pentamidine); antihistamines, (e.g., methapyrilene; anti-inflammatories, e.g., beclomethasone, flunisolide, budesonide, tipredane, triamcinolone acetonide or fluticasone); antitussives, (e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol); diuretics, (e.g., amiloride); anticholinergics (e.g., ipratropium, atropine or oxitropium); hormones, (e.g., cortisone, hydrocortisone or prednisolone); xanthines (e.g., aminophylline, choline theophyllinate, lysine theophyllinate or theophylline); and therapeutic proteins and peptides, (e.g., insulin or glucagon). It will be clear to a person skilled in the art that, where appropriate, the medicaments can be used in the form of salts (e.g., as alkali metal or amine salts or as acid addition salts) or as esters (e.g., lower alkyl esters) to optimize the activity and/or stability of the medicament.

Other exemplary therapeutic agents useful for a combination therapy include, but are not limited to, agents as described above, radiation therapy, hormone antagonists, hormones and their releasing factors, thyroid and antithyroid drugs, estrogens and progestins, androgens, adxenocorticotropic hormone; adxenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water soluble vitamins, vitamin B complex, ascorbic acid, fat soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, [β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents, agents affecting the renal conservation of water, rennin, angiotensin, agents useful in the treatment of myocardial ischemia, anti-hypertensive agents, angiotensin converting enzyme inhibitors, [β-adrenergic receptor antagonists, agents for the treatment of hypercholesterolemia, and agents for the treatment of dyslipidemia.

Other therapeutic agents contemplated herein include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents include, but are not limited to, those used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include, but are not limited to, antimicrobial agents, sulfonamides, trimethoprim-sulfamethoxazole quinolones, and agents for urinary tract infections, penicillins, cephalosporins, and other β-Lactam antibiotics, an agent containing an aminoglycoside, protein synthesis inhibitors, drugs used in the chemotherapy of tuberculosis, mycobacteriumavium complex disease, and leprosy, antifungal agents, antiviral agents including nonretroviral agents and antiretroviral agents.

Examples of therapeutic antibodies that can be combined with a subject compound include, but are not limited to, anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs. Further therapeutic agents that can be combined with a subject compound can be found in Goodman and Gilman's "*The Pharmacological Basis of Therapeutics*" Tenth Edition edited by Hardman, Limbird and Gilman or the Physician's Desk Reference, both of which are incorporated herein by reference in their entirety.

The compounds described herein can be used in combination with the agents provided herein or other suitable agents, depending on the condition being treated. Hence, in some embodiments, the compounds as provided herein will be co-administered with other agents as described above. When used in combination therapy, the compounds described herein can be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound as provided herein and any of the agents described above can be simultaneously administered, wherein both the agents are present in separate formulations. In another alternative, a compound as provided herein can be administered just followed by and any of the agents described above, or vice versa. In the separate administration protocol, a compound as provided herein and any of the agents described above can be administered a few minutes apart, or a few hours apart, or a few days apart.

Administration of the compounds as provided herein can be effected by any method that enables delivery of the compounds to the site of action. An effective amount of a compound as provided herein can be administered in either single or multiple doses by any of the accepted modes of administration of agents having similar utilities, including rectal, buccal, intranasal and transdermal routes, by intraarterial injection, intravenously, intraperitoneally, parenterally, intramuscularly, subcutaneously, orally, topically, as an inhalant, or via an impregnated or coated device such as a stent, for example, or an artery-inserted cylindrical polymer.

When a compound as provided herein is administered in a pharmaceutical composition that comprises one or more agents, and the agent has a shorter half-life than the compound as provided herein, unit dose forms of the agent and the compound as provided herein can be adjusted accordingly.

EXAMPLES

The examples and preparations provided below further illustrate and exemplify the compounds as disclosed herein and methods of preparing such compounds. It is to be understood that the scope of the present disclosure is not limited in any way by the scope of the following examples and preparations. In the following examples, molecules with a single chiral center, unless otherwise noted, exist as a racemic mixture. Those molecules with two or more chiral centers, unless otherwise noted, exist as a racemic mixture of diastereomers. Single enantiomers/diastereomers can be obtained by methods known to those skilled in the art.

The chemical entities described herein can be synthesized according to one or more illustrative schemes herein and/or techniques well known in the art. Unless specified to the contrary, the reactions described herein take place at atmospheric pressure, generally within a temperature range from about −10° C. to about 200° C. Further, except as otherwise specified, reaction times and conditions are intended to be approximate, e.g., taking place at about atmospheric pressure within a temperature range of about −10° C. to about 200° C. over a period that can be, for example, about 1 to about 24 hours; reactions left to run overnight in some embodiments can average a period of about 16 hours.

The terms "solvent," "organic solvent," or "inert solvent" each mean a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane "DCM"), diethyl ether, methanol, N-methylpyrrolidone ("NMP"), pyridine and the like. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. See, e.g., Carey et al. Advanced Organic Chemistry, 3$^{rd}$ Ed., 1990 New York: Plenum Press; Mundy et al., Name Reactions and Reagents in Organic Synthesis, 2$^{nd}$ Ed., 2005 Hoboken, N.J.: J. Wiley & Sons. Specific illustrations of suitable separation and isolation procedures are given by reference to the examples hereinbelow. However, other equivalent separation or isolation procedures can also be used.

When desired, the (R)- and (S)-isomers of the nonlimiting exemplary compounds, if present, can be resolved by methods known to those skilled in the art, for example by formation of diastereoisomeric salts or complexes which can be separated, for example, by crystallization; via formation of diastereoisomeric derivatives which can be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Aldrich Chemical Company (Milwaukee, Wis.) or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein. The skilled artisan will understand that standard atom valencies apply to all compounds disclosed herein in genus or named compound form unless otherwise specified.

The following abbreviations have the definitions set forth below:
Boc: tert-butyl carbonate
2-BuOH: 2-butanol (sec-butyl alcohol)
DABCO: 1,4-diazabicyclo[2.2.2]octane
dba: dibenzylideneacetone
DCE: 1,2-dichloroethane
DCM: dichloromethane
DCC: dicyclohexylcarbodiimide
Diglyme: diethylene glycol dimethyl ether
DIPEA: diisopropylethylamine
DMAP: 4-(dimethylamino)pyridine
DMF: N,N-dimethylformamide
DMSO: dimethylsulfoxide
dppe: ethylenebis(diphenylphosphine)
dppf: 1,1'-bis(diphenylphosphino)ferrocene
dppp: 1,3-bis(diphenylphosphino)propane
EDCl: N-(3-Dimethylaminopropyl)-N'-ethylcarbodiimide hydrochloride
EtOAc: ethyl acetate
EtOH: ethanol
Glyme: 1,2-dimethoxyethane HATU: 1-[Bis(dimethylamino)methylene]-1H-1,2,3-triazolo[4,5-b]pyridinium 3-oxid hexafluorophosphate
HBTU: N,N,N',N'-Tetramethyl-O-(1H-benzotriazol-1-yl)uronium hexafluorophosphate
HMDS: hexamethyldisilizane
HOBt: 1-hydroxybenzotriazole hydrate
IPA: iso-propanol
MeCN: acetonitrile
MeOH: methanol
2-MeTHF: 2-methyltetrahydrofuran
MsCl: methanesulfonyl chloride
NMR: nuclear magnetic resonance
PPh$_3$: triphenylphosphine
PTSA: p-toluenesulfonic acid monohydrate
TBTU: N,N,N',N'-Tetramethyl-O-(benzotriazol-1-yl)uronium tetrafluoroborate
TFA: trifluoroacetic acid
THF: tetrahydrofuran
T3P: propylphosphonic anhydride
XantPhos: 4,5-Bis(diphenylphosphino)-9,9-dimethylxanthene General Synthetic Methods In one embodiment, the compound of Formula I-1 can be combined with a compound of Formula I-2 to form a compound of Formula II-1:

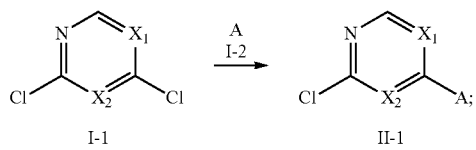

wherein:

A is selected from

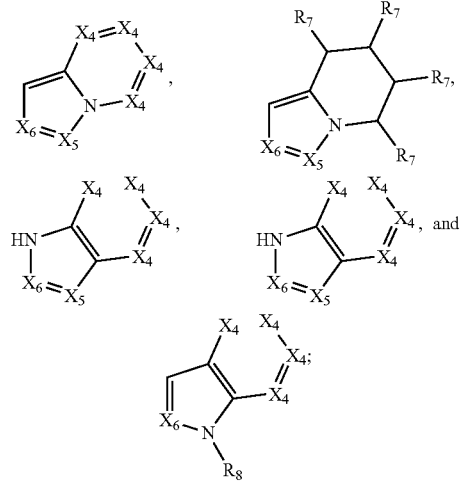

$X_1$ is selected from N and $CR_1$;
$X_2$ is selected from N and $CR_2$;
each $X_4$ is independently selected from N and $CR_7$;
$X_5$ is selected from N and $CR_8$;
$X_6$ is selected from N and $CR_9$;
$R_1$ is selected from H, acyl, alkyl, alkenyl, alkynyl, alkoxy, aryloxy, alkoxycarbonyl, amido, amino, carbonate, carbamate, carbonyl, carboxyl, ester, halo, CN, NO$_2$, hydroxy, phosphate, phosphonate, phosphinate, phosphine oxide, mercapto, thio, alkylthio, arylthio, thiocarbonyl, sulfonyl, sulfonamidyl, sulfoxyl, sulfonate, urea, cycloalkyl, heterocyclyl, aryl, and heteroaryl, each of which is substituted with 0, 1, 2, or 3 $R_{12}$;

each $R_7$ is independently selected from H, alkyl, alkenyl, alkynyl, alkoxy, amido, amino, carbonyl, ester, halo, CN, and NO$_2$, each of which is substituted with 0, 1, 2, or 3 $R_{12}$; and wherein any two adjacent $R_7$ groups can be taken together with the carbon atoms to which they are attached to form a cycloalkyl, heterocyclyl, aryl, or heteroaryl ring, each of which is substituted with 0, 1, 2, or 3 $R_{12}$;

$R_8$ is selected from H, acyl, alkyl, amido, amino, carbamate, carbonyl, and urea, each of which is substituted with 0, 1, 2, or 3 $R_{12}$;

$R_9$ is selected from H, alkyl, alkenyl, alkynyl, alkoxy, amino, amido, ester, halo, CN, NO$_2$, cycloalkyl, heterocyclyl, aryl, and heteroaryl, each of which is substituted with 0, 1, 2, or 3 $R_{12}$; and each $R_{12}$ is independently selected from acyl, alkyl, alkenyl, alkynyl, alkoxy, aryloxy, alkoxycarbonyl, amido, amino, carbonate, carbamate, carbonyl, ester, halo, CN, NO$_2$, hydroxyl, phosphate, phosphonate, phosphinate, phosphine oxide, thio, alkylthio, arylthio, thiocarbonyl, sulfonyl, sulfonamidyl, sulfoxyl, sulfonate, urea, cycloalkyl, heterocycloalkyl, aryl, and heteroaryl.

In some embodiments, $X_1$ can be $CR_1$, and $X_2$ can be N. In one embodiment, $X_2$ can be N, and $R_1$ can be selected from amido and ester. In another embodiment, $X_2$ can be N, and $R_1$ can be selected from H, alkyl, ester, halo, CN, and heteroaryl. In some embodiments, A can be

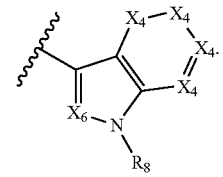

In other embodiments, $X_1$ can be selected from

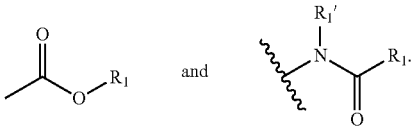

Compounds of Formulae I-1 and I-2 can be coupled using a metal-catalyzed process, such as, but not limited to, those in Price and Nachtsheim (Price Organic Reactions. 2011:1-82; Nachtsheim Beilstein J. Org. Chem. 2010; 6:1-24). Non-limiting examples of a metal catalyst include AlCl$_3$ and FeCl$_3$. In one embodiment, the metal catalyst can be AlCl$_3$. The ratio of equivalents of the metal catalyst relative to that of the compound of Formula I-1 can range from about 0.75 to about 2.50, such as about 0.75 to about 1.30, such as about 0.90 to about 1.30, such as about 1.50 to about 2.50, such as about 1.75 to about 2.25, and further such as about 1.05 to about 1.15. The equivalents of the compound of Formula I-2 relative to that of the compound of Formula I-1 can range from about 0.75 to about 3.0, such as about 1.5 to about 3.0, such as about 1.5 to about 2.5, such as about 0.75 to about 1.50, such as about 0.75 to about 1.25, and further such as about 1.75 to about 2.25.

Reaction times can vary from about 1 h to about 5 h, such as about 2 h to about 5 h, and further such as about 2 h to about 4 h, to convert compounds of Formulae I-1 and 1-2 to the compound of Formula II-1. Reaction temperatures can range from about 40° C. to about 120° C., such as about 60° C. to about 100° C., such as about 50° C. to about 60° C., and further such as about 70° C. to about 90° C. Suitable solvents include, but are not limited to, THF, DCE, glyme, dioxane and diglyme. In some embodiments, DCE can be the solvent. In other embodiments, glyme is the solvent.

Step b): Formation of III-1 from II-1 and II-2

In one embodiment, the compound of Formula II-1 can be combined with a compound of Formula II-2 to form a compound of Formula III-1:

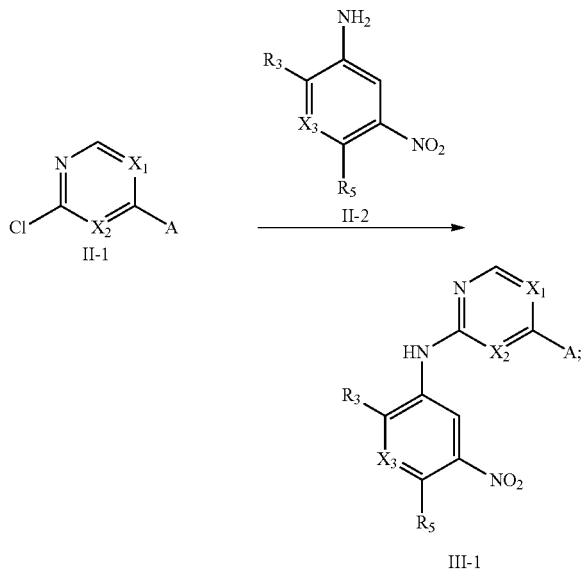

wherein: for the compounds of Formula II-1, II-2 and III-1,
$X_3$ is selected from N and $CR_4$;
$R_3$ and $R_4$ are each independently selected from H, alkyl, alkoxy, halo, CN, and $NO_2$, each of which is substituted with 0, 1, 2, or 3 $R_{12}$; $R_4$ and $R_5$ can be taken together with the carbon atoms to which they are attached to form a cycloalkyl, heterocyclyl, aryl, or heteroaryl group, each of which is substituted with 0, 1, 2, or 3 $R_{12}$;
$R_5$ is selected from H, alkyl, alkenyl, alkynyl, $—NR_{10}R_{11}$, $—OR_{11}$, and $—SR_{11}$, each of which is independently substituted with 0, 1, 2, or 3 $R_{12}$; or when $R_5$ is $—NR_{10}R_{11}$, then $R_{10}$ and $R_{11}$ can be taken together with the nitrogen atom to which they are attached to form a heterocyclyl or heteroaryl group, each of which is substituted with 0, 1, 2, or 3 $R_{12}$; and
the variables A, $X_1$, $X_2$, $X_4$, $X_5$, $X_6$, $R_1$, $R_2$, $R_7$, $R_8$, $R_{10}$, $R_{11}$, and $R_{12}$ are as disclosed above and herein.

In some embodiments, $X_1$ can be $CR_1$, and $X_2$ can be N. In one embodiment, $X_2$ can be N, $R_1$ can be selected from amido and ester, and $R_3$ can be alkoxy. In another embodiment, $X_2$ can be N, $R_3$ can be alkoxy, and $R_1$ can be selected from H, alkyl, ester, halo, CN, and heteroaryl. In another embodiment, $R_5$ can be selected from halo and $—NR_{10}R_{11}$.
In some embodiments, A can be

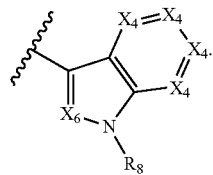

In other embodiments, $X_1$ can be selected from

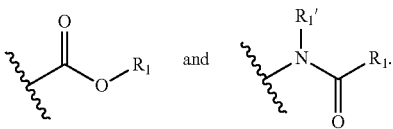

Compounds of Formulae II-1 and II-2 can be combined using a Pd-catalyzed process, such as, but not limited to, those described in Hartwig (Hartwig et al. J. Am. Chem. Soc. 2006; 128:3584-3591). Non-limiting examples of Pd-catalysts include $Pd(OAc)_2$ and XantPhos, $Pd_2dba_3$ and XantPhos, and $PdCl_2(dppf)$. In one embodiment, the Pd-catalyst is $Pd(OAc)_2$ and XantPhos. The ratio of equivalents of the Pd-catalyst catalyst relative to that of the compound of Formula II-1 can range from about 0.05 to about 0.30, such as about 0.10 to about 0.25, and further such as about 0.20 to about 0.30. Suitable bases for this process include, but are not limited to, $Cs_2CO_3$, $NaO^tBu$, LiHMDS, $K_3PO_4$, $K_2CO_3$, NaOMe, and KOH. In one embodiment, the base is $Cs_2CO_3$. The ratio of equivalents of base relative to that of the compound of Formula II-1 can range from about 1.0 to about 1.5, such as about 1.1 to about 1.3, and further such as about 1.15 to about 1.25. The ratio of equivalents of the compound of Formula II-2 to that of the compound of Formula II-1 can range from about 1.0 to about 1.5, such as about 1.2 to about 1.4, and further such as about 1.25 to about 1.35.

Non-limiting exemplary solvents for this process includes DMF, toluene, dioxane and DME. In one embodiment, the solvent is DMF. Reaction times can vary from about 1 h to about 24 h, such as about 8 h to about 20 h, and further such as about 14 h to about 18 h to afford the compound of Formula III-1. Reaction temperatures can range from about 50° C. to about 150° C., such as about 75° C. to about 125° C., and further such as about 90° C. to about 110° C.

In some embodiments, compounds of Formulae II-1 and II-2 can be combined using an acid-catalyzed process. Non-limiting examples of acid catalysts include PTSA, TFA and HCl. In one embodiment, the acid catalyst is PTSA. Non-limiting examples of solvents for this process include dioxane, THF and sec-butanol. In one embodiment, the solvent is dioxane. In another embodiment, the solvent is sec-butanol. The ratio of equivalents of the compound of Formula II-2 to that of the compound of Formula II-1 can range from about 1.0 to about 3.0, such as about 1.5 to about 2.5, and further such as about 1.75 to about 2.25. The ratio of equivalents of the acid relative to that of the compound of Formula II-1 can range from about 2.0 to about 4.0, such as about 2.5 to about 3.5, and further such as about 2.75 to about 3.25. Reaction temperatures for this process can range from about 50° C. to about 150° C., such as about 75° C. to about 125° C., and further such as about 90° C. to about 110° C. Reaction times can vary from about 1 h to about 24 h, such as about 8 h to about 20 h, and further such as about 14 h to about 18 h to afford the compound of Formula III-1.

Additionally, compounds of Formulae II-1 and II-2 can be combined using a base-mediated process. Non-limiting examples of bases include potassium carbonate, sodium carbonate, cesium carbonate, and potassium phosphate. In one embodiment, the base is potassium carbonate. A non-limiting list of solvents includes MeCN, DMF, dioxane, and THF. In some embodiments, the solvent is MeCN. The ratio of equivalents of the compound of Formula II-1 to that of the compound of Formula II-2 can range from about 0.75 to about 1.25, such as about 0.90 to about 1.10, and further such as about 0.95 to about 1.05. In one embodiment, the ratio of equivalents of the compound of Formula II-1 to that of the compound of Formula II-2 is from about 0.95 to about 1.05. The ratio of the equivalents of base to that of the compound of Formula II-1 or 11-2 can range from about 5 to about 1.5, such as about 5 to about 2, such as about 3.5 to about 2, such as about 3.5 to about 2.5, and further such as about 3.25 to about 2.75. In some embodiments, the ratio of the equivalents of base to that of the compound of Formula II-1 or 11-2 can range from about 3.25 to about 2.75. Reaction temperatures for this process can range from about 50° C. to about 150° C., such as about 75° C. to about 125° C., such as about 75° C. to about 85° C., and further such as about 90° C. to about 110° C. Reaction times can vary from about 1 h to about 24 h, such as about 8 h to about 20 h, and further such as about 14 h to about 18 h to afford the compound of Formula III-1.

Step c1): Formation of IV-1 from III-1 and HNR$_{10}$R$_{11}$

In one embodiment, a compound of Formula III-1 can be combined with HNR$_{10}$R$_{11}$ to form a compound of Formula IV-1:

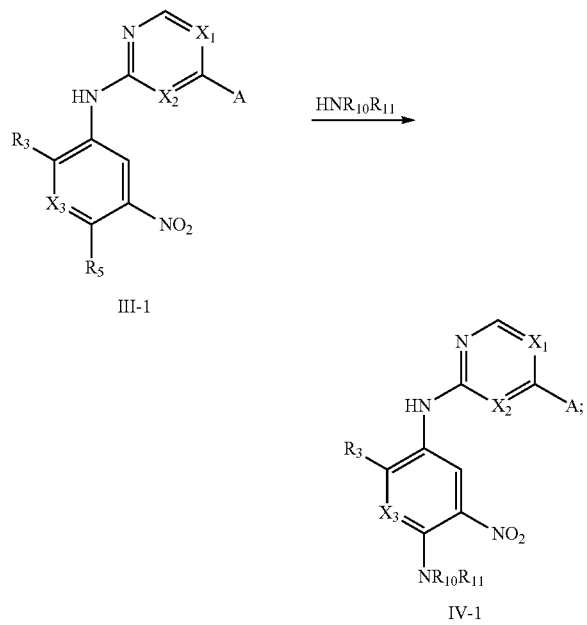

wherein:
for the compound of Formula III-1, R$_5$ is halo; and
for the compounds of Formula III-1 and IV-1, the variables A, X$_1$, X$_2$, X$_3$, X$_4$, X$_5$, X$_6$, R$_1$, R$_2$, R$_3$, R$_4$, R$_5$, R$_7$, R$_8$, R$_9$, R$_{10}$, R$_{11}$, and R$_{12}$ are as disclosed above and herein.

In one embodiment, X$_1$ can be CR$_1$, X$_2$ can be N, R$_3$ can be alkoxy. In another embodiment, X$_2$ can be N, R$_3$ can be alkoxy, and X$_4$ can be CR$_4$, where R$_4$ is H. In some embodiments R$_{10}$ is alkyl, and R$_{11}$ is alkyl substituted with one R$_{12}$, and R$_{12}$ is amino. In some embodiments, A can be

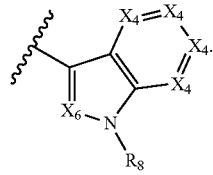

In other embodiments, X$_1$ can be selected from

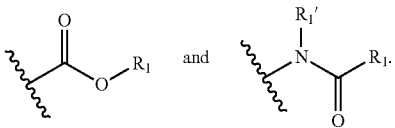

The reaction can be performed in the presence of a base, such as, but not limited to, K$_2$CO$_3$, Na$_2$CO$_3$, K$_3$PO$_4$, Cs$_2$CO$_3$, NaOtBu, KOtBu, NaOH, and KOH. In one embodiment, K$_2$CO$_3$ is the base. The ratio of equivalents of the base relative to that of the compound of Formula III-1 can range from about 1 to about 4, such as about 2 to about 4, and further such as about 3 to about 4. In some embodiments, the ratio of equivalents of the base relative to that of the compound of Formula III-1 can be about 3.5 to about 4.

The ratio of equivalents of HNR$_{10}$R$_{11}$ relative to that of the compound of Formula III-1 can range from about 1 to about 4, such as about 1.5 to about 3.5, such as about 2 to about 3, and further such as about 2.5 to about 2.75. In one embodiment, the ratio of equivalents of HNR$_{10}$R$_{11}$ relative to that of the compound of Formula III-1 can be about 2.5 to about 2.75. Suitable solvents include, but are not limited to, THF, 2-MeTHF, MeCN, DMF and sec-butanol. In one embodiment, the solvent is MeCN. In another embodiment, the solvent is DMF. Reaction times can vary from about 1 h to about 24 h, such as about 2 h to about 12 h, and further such as about 4 h to about 8 h. In one embodiment, the reaction time is about 1 h to about 3 h. Reaction temperatures can vary from about 50° C. to about 120° C., such as about 60° C. to about 80° C., such as about 80° C. to about 120° C., and further such as about 95° C. to about 105° C.

Step C2): Formation of IV-2 from III-1 and HOR$_{11}$

In one embodiment, a compound of Formula III-1 can be combined with HOR$_{11}$ to form a compound of Formula IV-2:

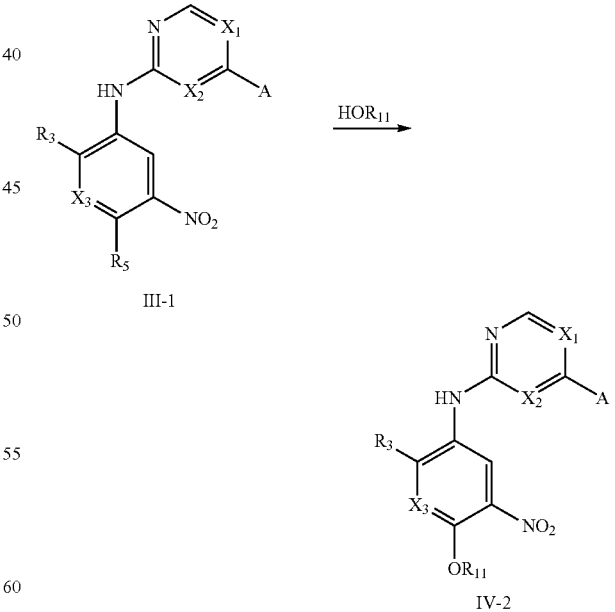

wherein:
for the compound of Formula III-1, R$_5$ is halo; and
for the compounds of Formula III-1 and IV-2, the variables A, X$_1$, X$_2$, X$_3$, X$_4$, X$_5$, X$_6$, X$_7$, R$_1$, R$_2$, R$_3$, R$_4$, R$_5$, R$_7$, R$_8$, R$_9$, R$_{11}$, and R$_{12}$ are as disclosed above and herein.

In one embodiment, $X_1$ can be $CR_1$ and $X_2$ can be N. In another embodiment, $X_2$ can be N, $R_3$ can be alkoxy, and $X_3$ can be $CR_4$, where $R_4$ is H. In another embodiment, $R_{11}$ can be alkyl substituted with one $R_{12}$, and $R_{12}$ is H. In some embodiments, A can be

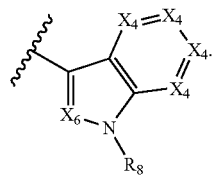

In other embodiments, $X_1$ can be selected from

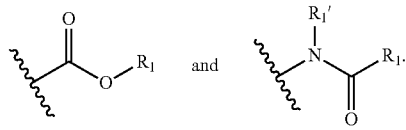

The reaction can be performed in the presence of a base, such as, but not limited to, NaH, KH and LiH. In one embodiment, the base is NaH. The ratio of equivalents of the base relative to that of the compound of Formula III-1 can range from about 1 to about 4, such as about 2 to about 4, and further such as about 3 to about 4. In some embodiments, the equivalents of base relative to that of the compound of Formulae III-1 is about 2.75 to about 3.25.

The ratio of equivalents of $HOR_{11}$ relative to that of the compound of Formulae III-1 can range from about 1 to about 2, such as about 1.2 to about 1.8, and further such as about 1.5 to about 1.75. Suitable solvents include, but are not limited to, THF, 2-MeTHF, DMF and dioxane. In one embodiment, the solvent is THF. In another embodiment, the solvent is DMF. In one embodiment, the base and $HOR_{11}$ can be first combined and stirred at about 20° C. to about 25° C., for about 10 min to about 15 min. Then, the compound of Formula III-1 is added. When addition is complete, the reaction time can vary from about 1 h to about 24 h, such as about 2 h to about 20 h, such as about 12 h to about 18 h, and further such as about 8 h to about 20 h. Reaction temperatures can vary from about 30° C. to about 80° C., such as about 40° C. to about 60° C., and further such as about 45° C. to about 55° C.

Step d): Formation of V-1 from III-1, IV-1, or IV-2

In one embodiment, a compound of any one of Formulae II-1, IV-1, or IV-2 can be converted to a compound of Formula V-1:

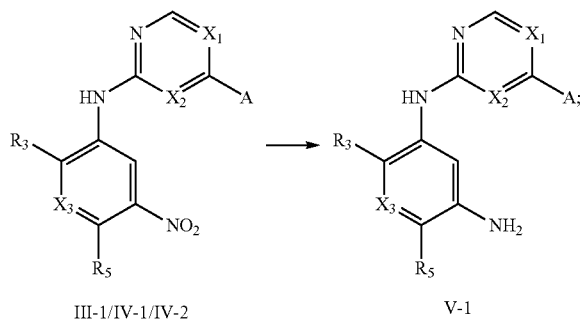

wherein:

for a compound of any one of Formulae III-1, IV-1, IV-2 and V-1, the variables A, $X_1$, $X_2$, $X_3$, $X_4$, $X_5$, $X_6$, $X_7$, $R_1$, $R_2$, $R_3$, $R_4$, $R_5$, $R_7$, $R_8$, $R_9$, $R_{10}$, $R_{11}$, and $R_{12}$ are as defined above.

In some embodiments, $X_1$ can be $CR_1$, where $R_1$ is amido or ester. In one embodiment, $X_2$ can be N and $R_5$ can be selected from $-NR_{10}R_{11}$ and $-OR_{11}$. In another embodiment, $X_2$ can be N, $R_3$ can be alkoxy, and $X_3$ can be $CR_4$, where $R_4$ is H. In some embodiments, A can be

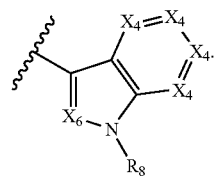

In other embodiments, $X_1$ can be selected from

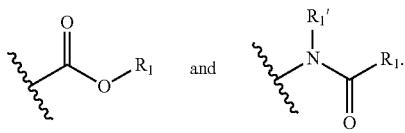

In one embodiment, the conversion of the compound of any one of Formulae III-1, IV-1, or IV-2 to the compound of Formula V-1 can occur through the hydrogenation of the nitro group to give the amino group of the compound of Formula V-1. In the presence of $H_2$, suitable hydrogenation catalysts include, but are not limited to, Raney Ni, $Pd(OH)_2$, $PtO_2$, and Pd/C. In one embodiment, Pd/C is the hydrogenation catalyst. The hydrogenation catalyst loading can be selected from about 2% Pd/C, about 4% Pd/C, about 6% Pd/C, about 8% Pd/C, about 15% Pd/C, and about 20% Pd/C. In one embodiment, the hydrogenation catalyst loading is about 10% Pd/C. The ratio of equivalents of the hydrogenation catalyst to that of the compound of Formulae III-1, IV-1, or IV-2 can be from about 0.01 to about 0.25, such as about 0.05 to about 0.15, and further such as about 0.05 to about 0.20. In one embodiment, the ratio of the hydrogenation catalyst to that of the compound of Formulae III-1, IV-1, or IV-2 is about 0.075 to about 0.125. In another embodiment, the ratio of the hydrogenation catalyst to that of the compound of Formulae III-1, IV-1, or IV-2 can be about 0.125 to about 0.175.

In another embodiment, the conversion of the compound of Formula III-1, IV-1, or IV-2 to a compound of Formula V-1 can occur through the reduction of the nitro group to afford the V-1 amino group by employing an oxidizable metal and a proton source. Examples of oxidizable metals include, but are not limited to, iron, stannous chloride, zinc, and Raney nickel. Non-limiting examples of proton sources include hydrochloric acid, acetic acid, formic acid, and ammonium chloride. In one embodiment, the oxidizable metal is zinc. In another embodiment, the proton source is ammonium chloride. Exemplary combinations can include iron and hydrochloric acid, stannous chloride and hydrochloric acid, zinc and ammonium chloride, and Raney nickel and formic acid. The ratio of equivalents of the compound of Formulae III-1, IV-1, or IV-2 to that of the zinc metal can be from about 1/4 to about 1/10, such as about 1/4 to about 1/8, such as about 1/6 to about 1/10, and further such as about 1/5 to about 1/7. The ratio of equivalents of the compound of Formulae III-1, IV-1, or IV-2 to that of ammonium chloride can be from about 1/6 to about 1/18, such as about 1/6 to about 1/10, such as about 1/8 to about 1/18, such as about 1/10 to about 1/18, such as about 1/8 to about 1/16, and further such as about 1/8 to about 1/12.

Reaction times can vary from about 10 min to about 24 h, such as about 30 min to about 4 h, such as about 30 min to about 2 h, such as about 2 h to about 20 h, such as about 15 min to about 4 h, such as about 15 min to about 2 h, such as about 15 min to about 1 h, and further such as about 15 min to about 45 min. Suitable solvents include, but are not limited to, acetone, MeOH, THF, EtOH, DMF, and EtOAc. Suitable solvent mixtures include, but are not limited to, acetone/water, MeOH/water, THF/water, EtOH/water, DMF/water and EtOAc/water. In some embodiments, the solvent mixture can be selected from acetone/water and MeOH/water. In one embodiment, the solvent mixture is acetone/water. Reaction temperatures can vary from about 15° C. to about 50° C., such as about 15° C. to about 40° C., such as about 15° C. to about 35° C., such as about 15° C. to about 30° C., such as about 20° C. to about 30° C., and further such as about 20° C. to about 25° C.

Step e): Formation of I from V-1 and V-2 or V-3

In one embodiment, a compound of Formula V-1 can be combined with a compound of either Formula V-2 or V-3 to form a compound of Formula I:

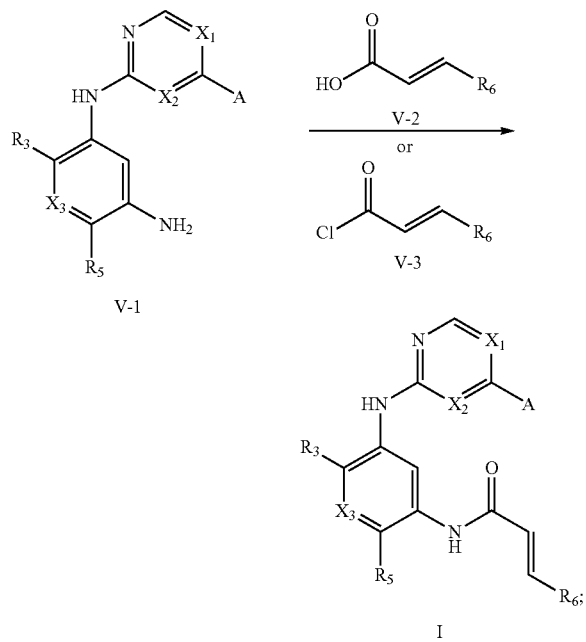

wherein:

for the compound of any one of Formulae V-2, V-3, or I, $R_6$ can be selected from H, acyl, alkyl, amino, halo, CN, cycloalkyl, heterocycloalkyl, aryl, and heteroaryl, each of which is substituted with 0, 1, 2, or 3 $R_{12}$; and for a compound of any one of Formulae V-1, V-2, V-3, and I, the variables A, $X_1$, $X_2$, $X_3$, $X_4$, $X_5$, $X_6$, $X_7$, $R_1$, $R_2$, $R_3$, $R_4$, $R_5$, $R_7$, $R_8$, $R_9$, $R_{10}$, $R_{11}$, and $R_{12}$ are as defined above.

In some embodiments, $X_1$ can be $CR_1$, where $R_1$ is amido or ester. In one embodiment, $X_2$ can be N and $R_5$ can be selected from —$NR_{10}R_{11}$ and —$OR_{11}$. In another embodiment, $X_2$ can be N, $R_3$ can be alkoxy, and $X_3$ can be $CR_4$, where $R_4$ is H. In other embodiments, $R_6$ can be H. In some embodiments, A can be

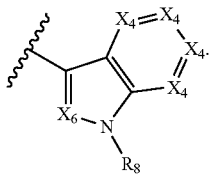

In other embodiments, $X_1$ can be selected from

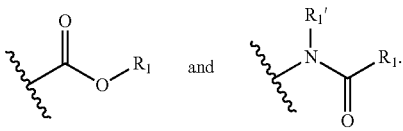

In one embodiment, the compounds of Formulae V-1 and V-2 can be combined using a coupling reagent and a base to form a compound of Formula I. Examples of coupling reagents include, but are not limited to, DCC, EDCl, HATU, HBTU, TBTU, and T3P. In one embodiment, the coupling reagent is EDCl. The ratio of equivalents of the coupling reagent to that of the compound of Formula V-1 can range from about 1.75 to about 2.25, such as about 1.75 to about 2.0, such as about 1.90 to about 2.25, and further such as about 1.95 to about 2.05. Non-limiting examples of bases include piperidine, triethylamine, diisopropylamine, and diisopropylethylamine. In one embodiment, the base is triethylamine. The ratio of the base to that of the compound of Formula V-1 can range from about 0.75 to about 3.5, such as about 1 to about 3, such as about 1.5 to about 2.5, and further such as about 1.75 to about 2.25. In one embodiment, the ratio of the base to that of the compound of Formula V-1 is about 1.75 to about 2.25.

A coupling catalyst can optionally be added to the reaction. In one embodiment, a coupling catalyst is added to the combination. In another embodiment, no coupling catalyst is added to the combination. Suitable coupling catalysts include, but are not limited to, pyridine, N-methylimidazole, imidazole, DABCO, 4-(dimethylamino)pyridine, and 4-(pyrrolidino)pyridine. A non-limiting example of a suitable coupling catalyst is 4-(dimethylamino)pyridine. The ratio of equivalents of the coupling catalyst to that of the compound of Formula V-1 can range from about 0.01 to about 0.25, such as about 0.01 to about 0.20, such as about 0.05 to about 0.15, and further such as about 0.05 to about 0.10. In one embodiment, the ratio of the coupling catalyst to that of the compound of the compound of Formula V-1 ranges from about 0.05 to about 0.10. The ratio of equivalents of the compound of Formula V-2 to that of the compound of Formula V-1 can range from about 1.75 to about 2.25, such as about 1.75 to about 2.0, such as about 1.90 to about 2.25, and further such as about 1.95 to about 2.05. In one embodiment, the ratio of equivalents of the compound of Formula V-2 to that of the compound of Formula V-1 ranges from about 1.95 to about 2.05.

Reaction times can vary from about 15 min to about 24 h, such as about 15 min to about 2 h, such as about 6 h to about 8 h, such as about 8 h to about 16 h, and further such as about 16 h to about 24 h. Reaction temperatures can vary from about 15° C. to about 50° C., such as about 15° C. to about 40° C., such as about 15° C. to about 35° C., such as about 15° C. to about 30° C., such as about 20° C. to about 30° C., and further such as about 20° C. to about 25° C. Suitable solvents include, but are not limited to, DCM, DMF, THF, diethyl ether, MeCN, and EtOAc. In some embodiments, DCM is the solvent. In other embodiments, DMF is the solvent.

In another embodiment, the compound of Formula V-1 can be combined with a compound of Formula V-3 to form a compound of Formula I. The compounds of Formulae V-1 and V-3 can be combined in the presence of a base. Non-limiting examples of the base include diisopropylamine, triethylamine, piperidine and diisopropylethylamine. In some embodiments, the base is triethylamine. The ratio of equivalents of the compound of Formula V-3 to that of the compound of Formula V-1 can range from 0.75 to about 1.25, such as about 0.75 to about 1.0, such as about 0.90 to about 1.25, and further such as about 0.95 to about 1.05. In some embodiments, the ratio of the compound of Formula V-3 to that of the compound of Formula V-1 is about 0.95 to about 1.05.

Suitable solvents include, but are not limited to, DMF, DCM, THF, MeCN, pyridine, diethyl ether, and EtOAc. In one embodiment, the solvent is DCM. In another embodiment, the solvent is DMF. Reaction temperatures can range from about −10° C. to about 25° C., such as about −10° C. to about 10° C., such as about −5° C. to about 25° C., such as about −5° C. to about 10° C., such as about 20° C. to about 25° C., and further such as about −5° C. to about 5° C. In some embodiments, the combination includes adding the compound of Formula V-3 to the compound of V-1. In some embodiments, the reaction temperature can be about −5° C. to about 5° C. until the compound of Formula V-3 addition is complete, and then the reaction temperature is adjusted to about 20° C. to about 25° C. Reaction times can vary from about 15 min to about 24 h, such as about 15 min to about 2 h, such as about 30 min to about 1 h, such as about 6 h to about 8 h, such as about 8 h to about 16 h, and further such as about 16 h to about 24 h.

Step f): Formation of VI-1 from I and $H_mZ$

In some embodiments, a compound of Formula I can be combined with an acid of Formula $H_mZ$ to form an acid addition salt of Formula VI-1:

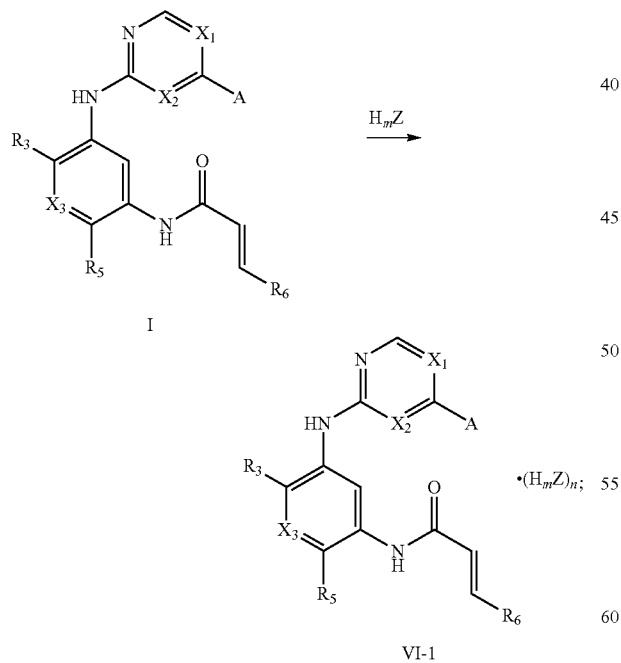

wherein:

for the compound of any one of Formulae I and VI-1, the variables A, $X_1$, $X_2$, $X_3$, $X_4$, $X_5$, $X_6$, $X_7$, $R_1$, $R_2$, $R_3$, $R_4$, $R_5$, $R_6$, $R_7$, $R_8$, $R_9$, $R_{10}$, $R_{11}$, and $R_{12}$, are as disclosed above and herein;

Z is an anionic form of a Bronsted-Lowry acid;

m is 1, 2, or 3; and n is 1, 2, or 3.

In some embodiments, $X_1$ can be $CR_1$, where $R_1$ is amido or ester. In one embodiment, $X_2$ can be N and $R_5$ can be selected from $—NR_{10}R_{11}$ and $—OR_{11}$. In another embodiment, $X_2$ can be N, $R_3$ can be alkoxy, and $X_3$ can be $CR_4$, where $R_4$ is H. In other embodiments, $R_6$ can be H. In some embodiments, A can be

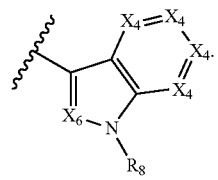

In other embodiments, $X_1$ can be selected from

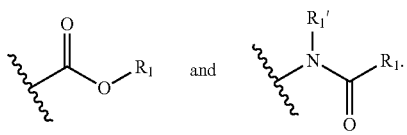

As used herein, a "Bronsted-Lowry acid" is a compound that is able to donate one or more protons to an acceptor base. An "anionic form" of a Bronsted-Lowry acid is the partially or fully deprotonated conjugate base of a given Bronstead-Lowry acid. For example, compounds of Formula I contain one or more nitrogen atoms that can serve as a base to accept a proton from a Bronsted-Lowry acid. The variable "n" serves to indicate the range of compound of Formula I:acid stoichiometries. The Bronsted-Lowry acids themselves can contain one or more acidic protons for donation, which is signified by the variable "m". Values for the acid $(H_mZ)_n$ include, but are not limited to the following:

Z is Cl⁻ and m is 1;

Z is Br⁻ and m is 1;

Z is $MeSO_2^-$ and m is 1;

Z is $PhSO_2^-$ and m is 1;

Z is 4-methylphenyl$SO_2^-$ and m is 1;

Z is $—OC(O)—C(O)O^-$ and m is 2;

Z is $—OC(O)—CH_2—C(O)O^-$ and m is 2;

Z is

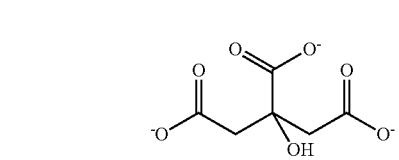

and m is 3;

Z is $SO_4^{3-}$ and m is 3; and

Z is $PO_4^{3-}$ and m is 3.

In some embodiments, Z is Cl⁻, m is 1, and n is 1 or 2. In other embodiments, Z is Cl⁻, m is 1, and n is 1 or 2. In some embodiments, Z is $MeSO_2^-$, m is 1, and n is 1 or 2. In other embodiments, Z is

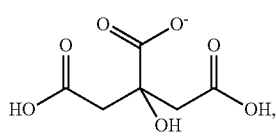 [SMILES: O=C(O)CC(O)(CC(=O)O)C(=O)[O-]]

m is 1, and n is 1 or 2.

Non-limiting examples of "H$_m$Z" acids are described by Berge et al. in J. Pharmaceutical Sciences (1977) 66:1-19, such as adipic acid, alginic acid, ascorbic acid, aspartic acid, benzenesulfonic acid, benzoic acid, sulfuric acid, boric acid, camphoric acid, camphorsulfonic acid, citric acid, cyclopentanepropionic acid, gluconic acid, dodecylsulfuric acid, ethanesulfonic acid, formic acid, fumaric acid, glucoheptonic acid, glycerophosphoric acid, gluconic acid, heptanoic acid, hexanoic acid, hydroiodic acid, 2-hydroxy-ethanesulfonic acid, lactobionic acid, lauric acid, dodecylsulfonic acid, malic acid, maleic acid, malonic acid, methanesulfonic acid, 2-naphthalenesulfonic acid, nicotinic acid, nitric acid, oleic acid, oxalic acid, palmitic acid, pamoic acid, petcinic acid, peroxymonosulfuric acid, 3-phenylpropionic acid, picric acid, pivalic acid, propionic acid, stearic acid, succinic acid, tartric acid, thiocyanic acid, p-toluenesulfonic acid, undecanoic acid, valeric acid, and the like. In one embodiment, non-limiting examples of "H$_m$Z" acids, where m is 1, include hydrochloric acid, methanesulfonic acid, hydrobromic acid, benzenesulfonic acid, tosic acid, and the like. In another embodiment, non-limiting examples of "H$_m$Z" acids, where m can be an integer greater than 1, include oxalic acid (m is 2), phosphoric acid (m is 3), citric acid (m is 3), malonic acid (m is 2), sulfuric acid (m is 2), and the like. Non-limiting examples of acid addition salts of Formula V-1 include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

In some embodiments, the compound of Formula I can be first dissolved or suspended in a solvent. In some embodiments, the solvent can be an alcohol, such as, but not limited to, MeOH, EtOH, IPA, or 2-BuOH. In other embodiments, the solvent can be a non-alcoholic solvent, such as, but not limited to, DCM, EtOAc, THF, diethyl ether, acetone, heptane, or acetonitrile. In a further embodiment, the solvent can be a mixture of two or more of any of the aforementioned solvents.

After addition of the compound of Formula I to the solvent system, the mixture can be heated to a temperature from about 30° C. to about 100° C., such as about 30° C. to about 75° C., such as about 50° C. to about 100° C., such as about 35° C. to about 55° C., such as about 45° C. to about 55° C., such as about 50° C. to about 75° C., and further such as about 60° C. to 85° C. Subsequently, H$_m$Z can be added, neat or as a mixture in a solvent, and the resulting mixture can be stirred from about 1 h to about 5 h, such as about 1 h to about 3 h, and further such as about 1 h to about 2 h. The ratio of H$_m$Z to that of the compound of Formula I can range from about 0.75 to about 3.5, such as about 1 to about 3, such as about 1 to about 2, such as about 1 to about 1.5, such as about 1 to about 1.25, such as about 1 to about 1.15, and further such as about 0.95 to about 1.05. The mixture can then be cooled to a temperature from about −10° C. to about rt, such as about 0° C. to about rt, such as about 0° C. to about 10° C., and further such as about 15° C. to about rt. In one embodiment, the mixture can be cooled to about rt. A non-limiting example would be an initial temperature of the compound of Formula I in a given solvent at about 55° C., addition of H$_m$Z in a solvent, stirring for about 1.5 h and cooling to about rt.

Non-limiting methods of inducing crystallization include cooling, addition of an anti-solvent, scratching the crystallization vessel with an implement, by adding one or more seed crystals, or any combination of these methods. In one embodiment, the mixture can be cooled to induce crystallization. In another embodiment, an anti-solvent can be added to induce crystallization. In another embodiment, crystallization can be induced by cooling and adding an anti-solvent. Non-limiting examples of anti-solvents include heptane, hexane, pentane and dibutyl ether. In one embodiment, heptane can be added. Upon crystallization, the mixture can be filtered to isolate the compound of Formula VI-1. In some embodiments, the compound of Formula VI-1 can be isolated by decanting the mother liquor, evaporation of volatile solvents in the mixture, solid-liquid centrifugation, and using a solid-phase crystallization base to induce crystallization followed by removal from the base. The stoichiometry, n, of the resulting acid addition salt can be determined by using any one of the many analytical methods known to a person skilled in the art such as, but not limited to, mass spectral analysis, elemental analysis, and NMR spectroscopy.

Exemplary Preparation Sequences for the Compound of Formula I

In one non-limiting embodiment, a compound of Formula I can be formed using the following sequence of general method steps as described above: step a), step b), step c1), step d), and then step e). In another non-limiting embodiment, a compound of Formula I can be formed using the following sequence of general method steps as described above: step a), step b), step c2), step d) and then step e). In a further non-limiting embodiment, a compound of Formula I can be formed using the following sequence of general method steps as described above: step a), step b), step d), and then step e).

Intermediate A1

4-fluoro-2-methoxyaniline

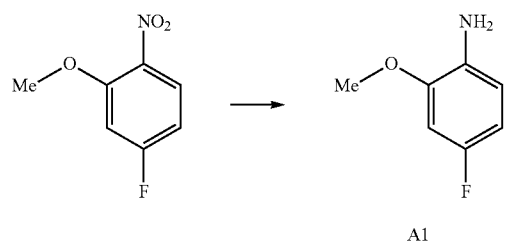 [SMILES: COc1cc(F)ccc1[N+](=O)[O-] ; COc1cc(F)ccc1N ; "A1"]

A1

To a solution of 4-fluoro-2-methoxy-1-nitrobenzene (100 g, 0.584 mol) in MeOH (1.5 L) was added 10%-Pd/C (10 g). The mixture was stirred under a hydrogen atmosphere at rt overnight. Subsequently, the mixture was filtered and the filtrate was concentrated in vacuo to afford 4-fluoro-2-methoxyaniline (A1) as a brown oil.

Intermediate A2

4-fluoro-2-methoxy-5-nitroaniline

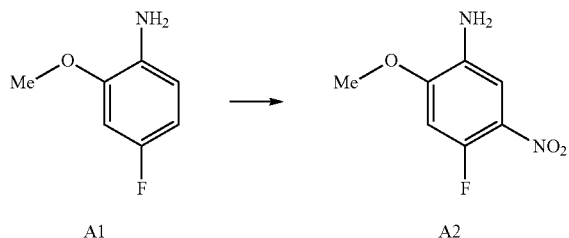

To a concentrated sulfuric acid solution (800 mL) was added 4-fluoro-2-methoxyaniline (A3) (79.4 g, 0.562 mol) at −10° C., then guanidine nitrate (68.7 g, 0.562 mol) over the course of 1 h. The mixture was stirred at 0° C. for 2 h. Subsequently, the mixture was treated with sodium bicarbonate until the pH was 7. The mixture was then filtered and the filtrate was extracted with DCM (5 L×2). The isolated organic layer was dried over sodium sulfate, filtered and concentrated in vacuo to afford 4-fluoro-2-methoxy-5-nitroaniline (A2) as a brown solid.

Intermediate A3

N1-(2-(dimethylamino)ethyl)-5-methoxy-N1-methyl-2-nitrobenzene-1,4-diamine

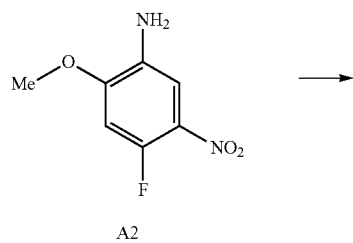

-continued

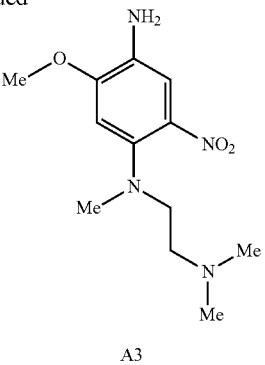

4-Fluoro-2-methoxy-5-nitroaniline (A4) (2 g, 10.8 mmol) was combined with N1,N1,N2-trimethylethane-1,2-diamine (1.2 g, 11.8 mmol) and potassium carbonate (3.0 g, 21.6 mmol) in MeCN (20 mL). The mixture was stirred at 80° C. for 2 h. Upon cooling, the mixture was filtered and the filtrate was concentrated in vacuo to afford N1-(2-(dimethylamino)ethyl)-5-methoxy-N1-methyl-2-nitrobenzene-1,4-diamine (A3) as a red oil.

Intermediate A4

(R)-1-(dimethylamino)-3-ethoxypropan-2-ol

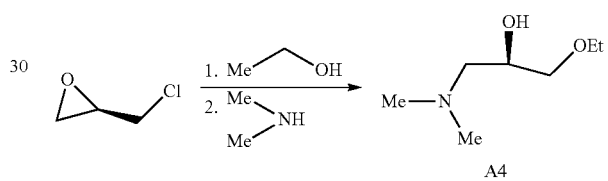

Step 1: To a solution of (R)-(2-chloromethyl)oxirane (5 g, 54.1 mmol) and tetra-n-butylammonium bromide (870 mg, 5 mol-%) in EtOH (3.5 mL) was added sodium hydroxide (2.4 g) at 0° C. The mixture was then stirred at rt overnight. Subsequently, the mixture was filtered, washed with DCM, and the filtrate was concentrated in vacuo.

Step 2: The resulting residue was stirred with a solution of dimethylamine in THF (30 mL, 2.0 M) at rt for 3 h. The mixture was then concentrated in vacuo and the resulting residue was purified by flash column chromatography on silica gel (5% MeOH/DCM) to afford (R)-1-(dimethylamino)-3-ethoxypropan-2-ol as a colorless liquid.

The following intermediate compounds, as shown in Table 3, were synthesized in analogous fashion to Step 2 of intermediate A4.

TABLE 3

| Intermediate A | Epoxide | Amine |
|---|---|---|
| A5 | | |
| A6 | | |

Intermediate A7

Isopropyl 2,4-dichloropyrimidine-5-carboxylate

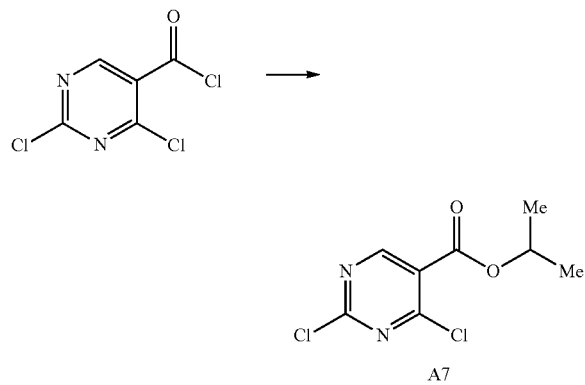

A solution of 2,4-dichloropyrimidine-5-carbonyl chloride (2.00 g, 9.45 mmol) in THF (4.7 mL) was cooled to −78° C. before IPA (0.80 mL) was added. The mixture was warmed to rt and stirred overnight. The mixture was then concentrated in vacuo and purified by flash column chromatography on silica gel (0%→10% EtOAc/heptane) to afford isopropyl 2,4-dichloropyrimidine-5-carboxylate (A7) as a colorless oil.

Intermediate A8

7-methoxy-1-methyl-1H-indole

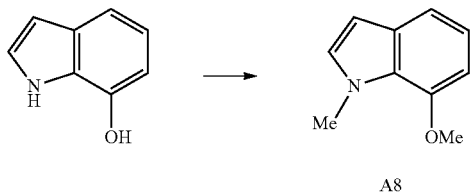 [SMILES: Oc1cccc2cc[nH]c12 ; COc1cccc2ccn(C)c12 ; "A8"]

To a solution of 7-hydroxy-1H-indole (1.00 g, 7.5 mmol) in DMF (25 mL) was added potassium carbonate (5.19 g, 37.6 mmol), followed by iodomethane (1.40 mL, 22.5 mmol). The mixture was heated to 60° C. and stirred overnight. The mixture was then cooled to 0° C. and sodium hydride (0.90 g, 22.5 mmol) was added. The mixture was warmed to rt and stirred for 10 min before adding additional iodomethane (1.40 mL, 22.5 mmol). The resulting mixture was heated to 60° C. and stirred for an additional 2 h. Upon cooling, the mixture was cooled to rt and diluted with water (50 mL) and EtOAc (50 mL). The layers were separated and the aqueous phase was extracted with EtOAc (3×50 mL). The combined organic layers were washed with water (2×50 mL) and brine (50 mL), then dried over sodium sulfate, filtered, and concentrated under reduced pressure to afford 7-methoxy-1-methyl-1H-indole (A8).

Intermediate A9

N-(2,4-dichloropyrimidin-5-yl)-2,2,2-trifluoroacetamide

A solution of 5-amino-2,4-dichloropyrimidine (2.00 g, 12.2 mmol) in DCM (41 mL) was treated with trifluoroacetic anhydride (1.87 mL, 13.4 mmol). The resulting mixture was stirred at rt for 30 min, then concentrated in vacuo. The resulting residue was suspended in heptane, filtered, and air-dried to afford N-(2,4-dichloropyrimidin-5-yl)-2,2,2-trifluoroacetamide (A9).

Intermediate A10

1H-indol-1-amine

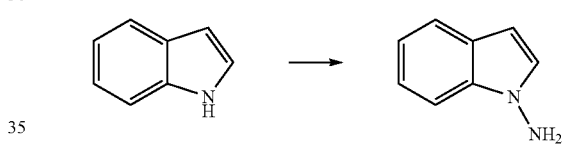

To a solution of indole (5.7 g, 49 mmol) in DMF (100 mL) was added sodium hydride (1.6 g, 60% mineral oil dispersion) at rt, and the mixture was stirred for 1 h at rt. Subsequently, a solution of chloramine in diethyl ether (320 mL) was added to the mixture, and stirred for 2 h at rt. To the resulting mixture was added aqueous sodium thiosulfate, followed by water (100 mL). The mixture was extracted with DCM, and the combined organic layers were dried over magnesium sulfate, filtered, and concentrated in vacuo. The resulting residue was purified by flash column chromatography on silica gel (0→50% EtOAc/heptane) to afford 1H-indol-1-amine (A10) as brown solid.

Intermediate A11

N,N-dimethyl-1H-indol-1-amine

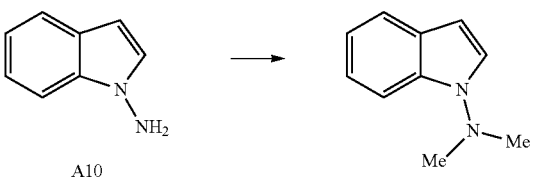

To a solution of 1H-indol-1-amine (A10) (2.64 g, 20 mmol) in DMF (20 mL) was added iodomethane (2.0 mL)

and potassium carbonate (4.0 g), and the resulting mixture was stirred at rt for 2 days. Subsequently, the mixture was filtered, and the filtrate was concentrated in vacuo. The resulting residue was purified by flash column chromatography on silica gel (0→50% EtOAc/heptane) to afford N,N-dimethyl-1H-indol-1-amine (A11) as light brown solid.

Intermediate A12

1-ethyl-1H-indole

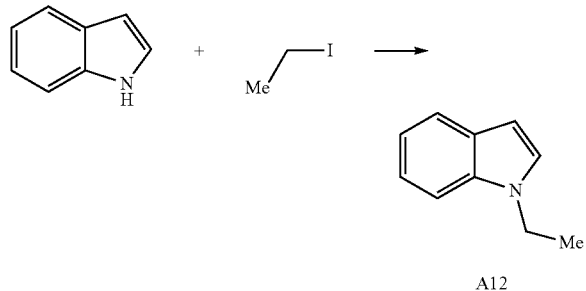

To a mixture of indole (1.17 g, 10 mmol) in DMF (10 mL) was added sodium hydride (480 mg, 12 mmol, 60% dispersion in mineral oil), and the mixture was stirred at rt for 30 min before adding iodoethane (0.96 ml, 12 mmol) at 0° C. The mixture was stirred overnight before diluting with water (20 mL). The resulting mixture was extracted with DCM (3×10 mL) and the combined organic layers were dried over magnesium sulfate, filtered, and concentrated in vacuo. The resulting residue was purified by flash column chromatography on silica gel (0→20% EtOAc/DCM) to afford 1-ethyl-1H-indole (A12).

Intermediate A13

1-cyclopropyl-1H-indole

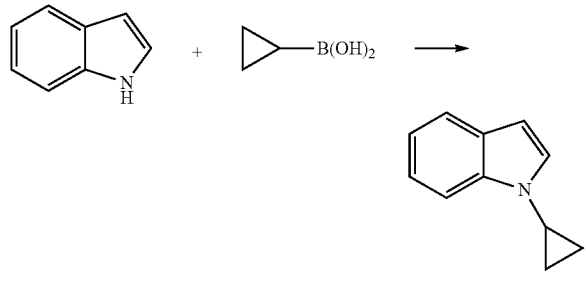

To a mixture of indole (585 mg, 5.0 mmol), cyclopropylboronic acid (860 mg, 10 mmol), and sodium carbonate (1.06 g, 10 mmol), in DCE (20 mL), was added a suspension of 2,2'-bipyridine (781 mg, 5.0 mmol) and copper(II) acetate (908 mg, 5.0 mmol), in DCE (15 mL), and the resulting mixture was stirred at 70° C. for 4 h. Upon cooling, the mixture was filtered and the filtrate was concentrated in vacuo. The resulting residue was purified by flash column chromatography on silica gel (0→25% EtOAc/heptane) to afford 1-cyclopropyl-1H-indole (A13) as yellow oil.

Intermediate A14 isopropyl (E)-4-(2-butoxyvinyl)-2-chloropyrimidine-5-carboxylate

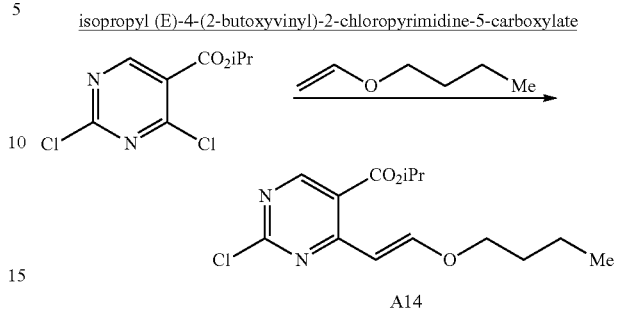

A mixture of isopropyl 2,4-dichloropyrimidine-5-carboxylate (50 mg, 0.21 mmol), 1-(vinyloxy)butane (63 mg, 0.63 mmol), palladium(II) acetate (4 mg, 0.015 mmol), and TEA (0.032 mL), in PEG-400 (2 mL), was stirred at 80° C. for 5 h. Upon cooling, the mixture was diluted with water and extracted with DCM. The combined organic layers were dried over sodium sulfate, filtered, and concentrated in vacuo. The resulting residue was purified by flash column chromatography on silica gel (0→10% EtOAc/heptane) to afford isopropyl (E)-4-(2-butoxyvinyl)-2-chloropyrimidine-5-carboxylate (A14).

Intermediate A15 isopropyl 2-chloro-4-(imidazo[1,2-a]pyridin-3-yl)pyrimidine-5-carboxylate

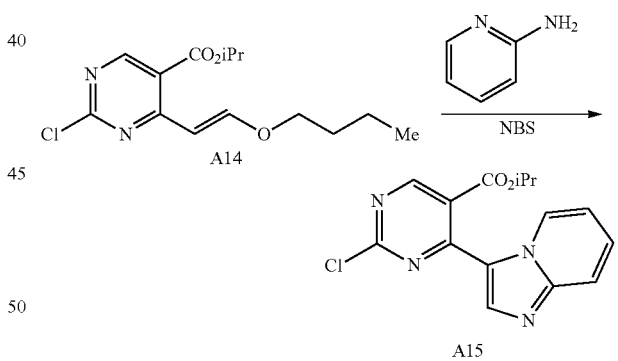

To a mixture of isopropyl (E)-4-(2-butoxyvinyl)-2-chloropyrimidine-5-carboxylate (A14) (100 mg, 0.37 mmol) in dioxane (3 mL) and water (1 mL), was added NBS (66 mg, 0.37 mmol), and the resulting mixture was stirred at rt for 1 h before adding pyridin-2-amine (35 mg, 0.37 mmol). The mixture was then stirred at 85° C. for 2 h. Upon cooling, the mixture was diluted with water and extracted with EtOAc. The combined organic layers were dried over sodium sulfate, filtered, and concentrated in vacuo. The resulting residue was purified by flash column chromatography on silica gel (0→25% EtOAc/DCM) to afford isopropyl 2-chloro-4-(imidazo[1,2-a]pyridin-3-yl)pyrimidine-5-carboxylate (A15) as a yellow solid.

Intermediate A16

6-(1-methyl-1H-pyrazol-4-yl)-1H-indole

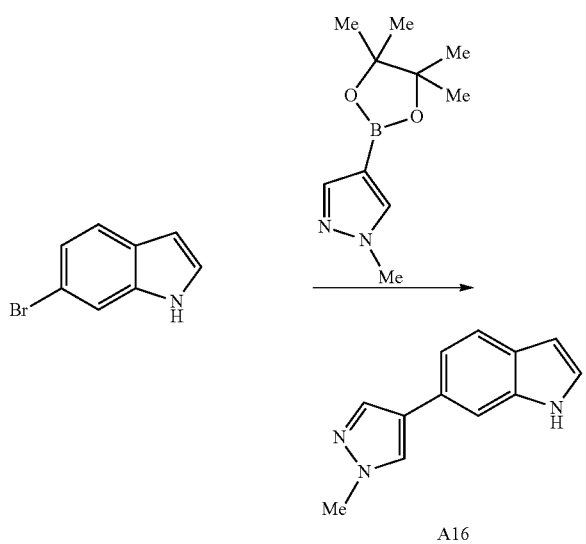

A mixture of 6-bromo-1H-indole (300 mg, 1.53 mmol), 1-methyl-4-(4,4,5,5-tetramethyl-1,3,2-dioxaborolan-2-yl)-1H-pyrazole (478 mg, 2.3 mmol), tetrakis(triphenylphosphine)palladium(0) (92 mg, 0.08 mmol), and potassium carbonate (2.3 g, 1.7 mmol), in DMF (3 mL), was stirred at 90° C. for 3 h. Upon cooling, the mixture was diluted with water and extracted with DCM. The combined organic layers were dried over magnesium sulfate, filtered, and concentrated in vacuo. The resulting residue was purified by flash column chromatography on silica gel (0→50% EtOAc/heptane) to afford 6-(1-methyl-1H-pyrazol-4-yl)-1H-indole (A16) as yellow solid.

Intermediate A17

(2,4-dimethoxypyrimidin-5-yl)dimethylphosphine oxide

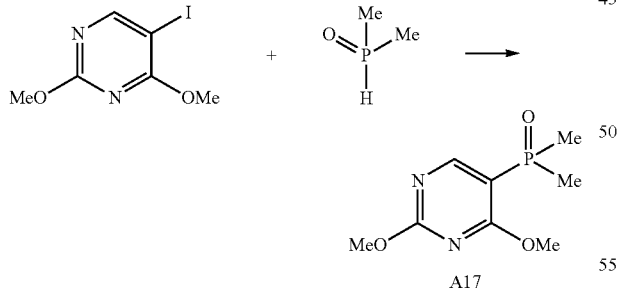

A mixture of 5-iodo-2,4-dimethoxypyrimidine (2.26 g, 10 mmol), dimethylphosphine oxide (1.17 g, 15 mmol), palladium acetate (0.67 g, 1.0 mmol), XPhos (1.16 g, 2.0 mmol), and cesium carbonate (4.9 g, 15 mmol), in DMF (20 mL), was stirred at 60° C. for 1 h. Upon cooling, the mixture was filtered, and the filtrate was concentrated in vacuo. The resulting residue was purified by flash column chromatography on silica gel (15% MeOH/DCM) to afford (2,4-dimethoxypyrimidin-5-yl)dimethylphosphine oxide as white solid.

Intermediate A18

(2,4-dihydroxypyrimidin-5-yl)dimethylphosphine oxide

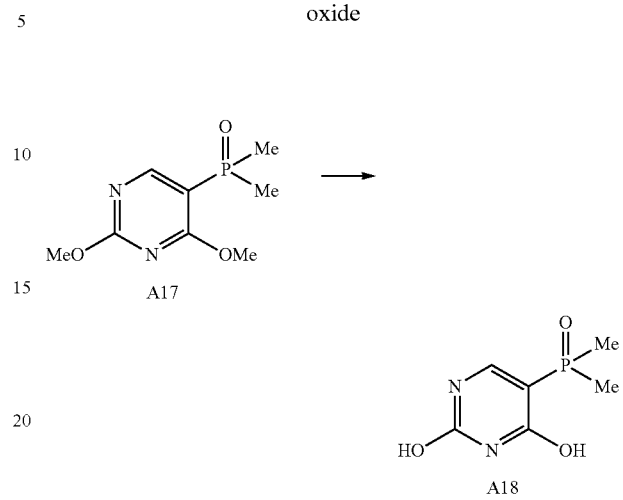

To a solution of (2,4-dimethoxypyrimidin-5-yl)dimethylphosphine oxide (A17) (140 mg, 0.65 mmol) in DCM (6 mL) was added TMSI (0.19 mL) at rt, and stirred for 0.5 h at rt. Subsequently, MeOH (0.4 mL) was added to the mixture, and the resulting mixture was purified by flash column chromatography on silica gel (20% MeOH/DCM) to afford (2,4-dihydroxypyrimidin-5-yl)dimethylphosphine oxide (A18) as white solid.

Intermediate A19

(2,4-dichloropyrimidin-5-yl)dimethylphosphine oxide

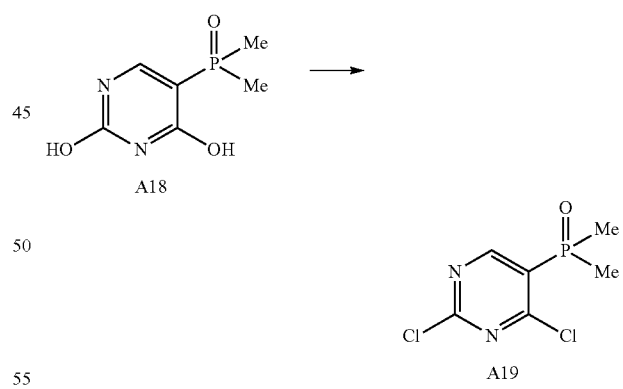

A mixture of (2,4-dihydroxypyrimidin-5-yl)dimethylphosphine oxide (A18) (0.6 g, 3.19 mmol) in phosphorus(V) oxychloride (5 mL) was stirred at 140° C. for 3 h. Upon cooling, the mixture was poured onto ice and aqueous sodium bicarbonate was added. The mixture was extracted with DCM and the combined organic layers were concentrated in vacuo. The resulting residue was purified by flash column chromatography on silica gel (10% MeOH/DCM) to afford (2,4-dichloropyrimidin-5-yl)dimethylphosphine oxide (A18) as yellow solid.

Intermediate A20

1-Methyl-3-(tributylstannyl)-1H-indazole

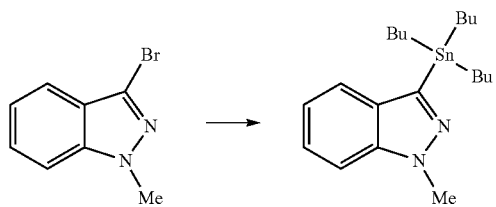

To a mixture of 3-bromo-1-methyl-1H-indazole (1.00 g, 4.74 mmol) and tetrakis(triphenylphosphine)palladium(0) (0.55 g, 0.47 mmol), in 1,4-dioxane (47 mL), was added hexabutylditin (4.78 mL, 9.48 mmol), and the resulting mixture was stirred at 100° C. overnight. Upon cooling, aqueous potassium fluoride (1 M, 25 mL) was added, the mixture was stirred at rt for 15 min and then filtered through a pad of Celite, before rinsing with EtOAc. The filtrate was washed with water (2×25 mL). The combined aqueous layers were extracted with EtOAc (50 mL), and the combined organic layers were dried over magnesium sulfate, filtered, and concentrated in vacuo. The resulting residue was purified by flash column chromatography on silica gel (0→10% EtOAc/heptane) to afford 1-methyl-3-(tributylstannyl)-1H-indazole (A20) as a clear, colorless oil.

Intermediate A21 tert-Butyl 3-(trimethylstannyl)-1H-pyrrolo[2,3-b]pyridine-1-carboxylate

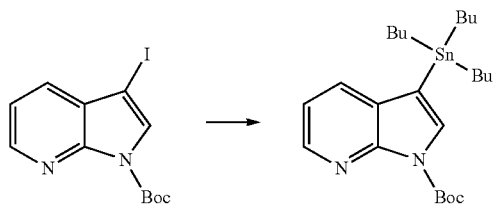

A mixture of tert-butyl 3-iodo-1H-pyrrolo[2,3-b]pyridine-1-carboxylate (250 mg, 0.73 mmol) in THF (2.1 mL) was cooled to −78° C., before adding trimethyltin chloride (724 mg, 3.63 mmol), followed by n-BuLi (2.5 M in hexanes, 0.87 mL, 2.18 mmol). The mixture was warmed to rt and stirred for 6 h. Subsequently, MeOH was added and the resulting mixture was concentrated in vacuo. The resulting residue was purified by flash column chromatography on silica gel (0→20% EtOAc/heptane) to afford tert-butyl 3-(trimethylstannyl)-1H-pyrrolo[2,3-b]pyridine-1-carboxylate (A21) as a clear, colorless oil.

Intermediate B1

1-methyl-6-(2-(4-methylpiperazin-1-yl)ethoxy)-1H-indole

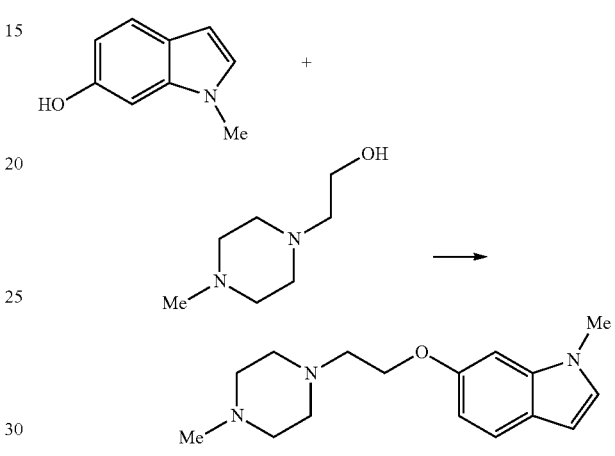

To a solution of 2-(4-methylpiperazin-1-yl)ethanol (1.926 g, 13.38 mmol) in THF (10 mL) at 0° C. was added methanesulfonyl chloride (0.54 ml, 13.38 mmol), and then stirred at rt for 2 h. To a solution of 1-methyl-1H-indol-6-ol (390 mg, 2.67 mmol) in DMF (4 mL) was added sodium hydride (192 mg, 8.0 mmol) at 0° C. and stirred for 30 min, and was then added to the aforementioned THF solution at 0° C. The resulting mixture was stirred at rt overnight, and subsequently concentrated in vacuo. The resulting residue was purified by flash column chromatography on silica gel to afford 1-methyl-6-(2-(4-methylpiperazin-1-yl)ethoxy)-1H-indole (B1).

The following intermediate compounds, as shown in Table 4, were synthesized in analogous fashion to intermediate B1.

TABLE 4

| Intermediate B | Alcohol | Hydroxyindole |
|---|---|---|
| B2 | | |
| B3 | | |

TABLE 4-continued

| Intermediate B | Alcohol | Hydroxyindole |
|---|---|---|
| B4 | | |
| B5 | | |
| B6 | | |

Intermediate C1 tert-butyl 2-(3,6-dihydro-2H-pyran-4-yl)-1H-indole-1-carboxylate

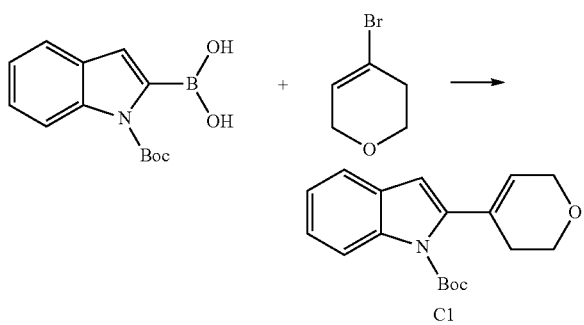

A flask charged with N-boc-2-indole boronic acid (3.00 g, 11.5 mmol), 4-bromo-3,6-dihydro-2H-pyran (2.44 g, 14.5 mmol), and tetrakis(tripheylphosphine)palladium(0) (1.33 g, 1.15 mmol) was evacuated and purged with nitrogen three times. 1,4-dioxane (38 mL) was then added, followed by a solution of sodium carbonate (2 M, 17.3 mL, 34.6 mmol). The mixture was sparged with nitrogen, then stirred at 100° C. for 2 h. Upon cooling to rt, the mixture was diluted with EtOAc (50 mL) and water (100 mL). The layers were separated and the aqueous phase was extracted with EtOAc (3×50 mL). The combined organic layers were washed with brine (100 mL), then dried over sodium sulfate, filtered, and concentrated in vacuo. The resulting residue was purified by flash column chromatography on silica gel (0%→10% EtOAc/heptane) to afford tert-butyl 2-(3,6-dihydro-2H-pyran-4-yl)-1H-indole-1-carboxylate (C1) as a yellow oil.

The following intermediate compounds, as shown in Table 5, were synthesized in analogous fashion to intermediate C1.

TABLE 5

| Intermediate C | Bromide |
|---|---|
| C2 | |
| C3 | |

TABLE 5-continued

| Intermediate C | Bromide |
|---|---|
| 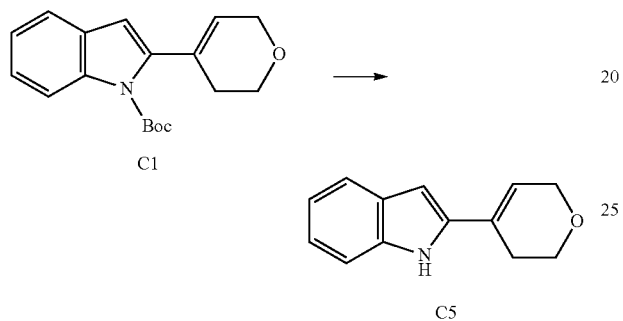<br>C4 | 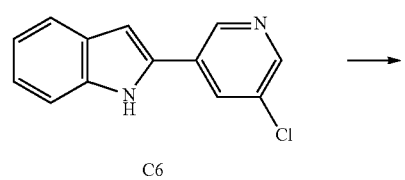 |

Intermediate C5

2-(3,6-dihydro-2H-pyran-4-yl)-1H-indole

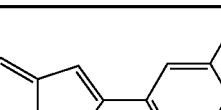

A solution of tert-butyl 2-(3,6-dihydro-2H-pyran-4-yl)-1H-indole-1-carboxylate (2.84 g, 9.5 mmol) in DCM (32 mL) was cooled to 0° C., and then treated with neat TFA (36.3 mL, 474 mmol). The mixture was then stirred at rt for 1H. Subsequently, the mixture was cooled to 0° C. and aqueous sodium hydroxide (4N) was added until the mixture pH was greater than 10. The mixture was further diluted with DCM. The layers were then separated, and the aqueous phase was extracted with DCM (3×50 mL). The combined organics were then washed with saturated sodium bicarbonate (75 mL) and brine (75 mL), then dried over sodium sulfate, filtered, and concentrated in vacuo. The resulting residue was purified by flash column chromatography on silica gel (0%→30% EtOAc/heptane) to afford 2-(3,6-dihydro-2H-pyran-4-yl)-1H-indole (C5) as a pale orange solid.

The following compounds, as shown in Table 6, were prepared in analogous fashion to intermediate C5.

TABLE 6

| Intermediate C | Indole |
|---|---|
| 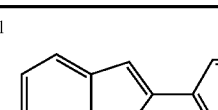<br>C6 | 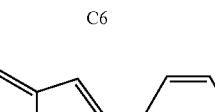<br>C2 |
| 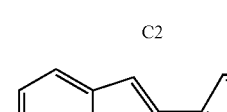<br>C7 | <br>C4 |

Intermediate D1

2-(5-chloropyridin-3-yl)-3-(2-chloropyrimidin-4-yl)-1H-indole

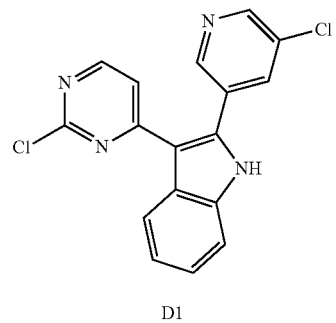

A solution of 2-(5-chloropyridin-3-yl)-1H-indole (C6) (1.8 g, 7.78 mmol) in anhydrous DCE (15 mL) was cooled to 0° C., and methylmagnesium bromide (4 mL, 2 M in THF) was added dropwise. The mixture was stirred at 0° C. for 10 min before 2,6-dichloropyrimidine (1.74 g, 11.66 mmol) was added and the resulting mixture was stirred at reflux for 14 h. Upon cooling to rt, MeOH (10 mL) was added to the mixture. The resulting mixture was concentrated in vacuo, and the resulting residue was diluted with DCM and water. The organic phase was isolated, dried over anhydrous sodium sulfate, filtered, and concentrated in vacuo. The resulting residue was then was purified by flash column chromatography on silica gel (0%→50% EtOAc/heptane) to afford 2-(5-chloropyridin-3-yl)-3-(4-chloropyrimidin-2-yl)-1H-indole (D1) as a yellow solid.

The following compounds, as shown in Table 7, were prepared in analogous fashion to intermediate D1.

TABLE 7

| Intermediate D | Indole | Pyrimidine/triazine |
|---|---|---|
| D2 | C3 | 2,4-dichloropyrimidine |
| D3 | C7 | 2,4-dichloropyrimidine |
| D4 | C5 | 2,4-dichloro-1,3,5-triazine |
| D5 | C7 | 2,4-dichloro-1,3,5-triazine |

TABLE 7-continued
| Intermediate D | Indole | Pyrimidine/triazine |
|---|---|---|
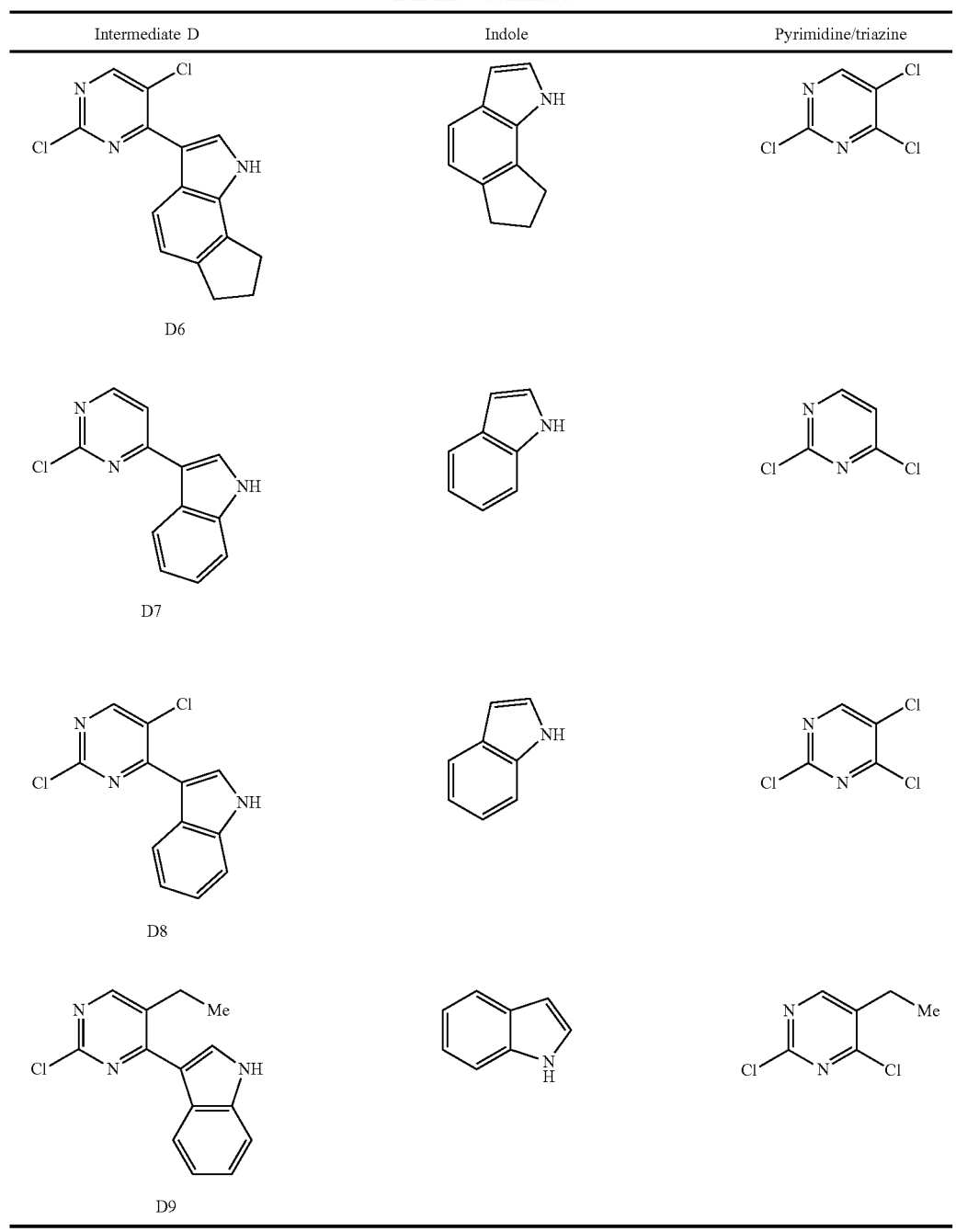
Intermediate E1
isopropyl
2-chloro-4-(1H-indol-1-yl)pyrimidine-5-carboxylate
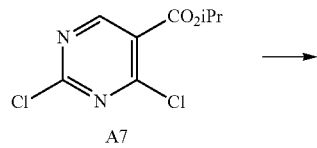
-continued
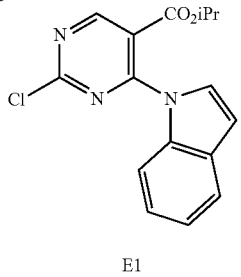
Indole (120 mg, 1 mmol) was dissolved in DMF (3 mL) and the mixture was treated with sodium hydride (45 mg, 1.1 mmol, 60% dispersion in oil) at 0° C. for 15 min. Isopropyl 2,4-dichloropyrimidine-5-carboxylate (A7) (220 mg, 1.1 mmol) was added to the mixture and the resulting mixture was stirred at rt for 16 h. Subsequently, water was added and the mixture was concentrated in vacuo. The resulting residue was dissolved in EtOAc and water. The organic phase was isolated, dried over anhydrous sodium sulfate, and concentrated in vacuo. The resulting residue was then purified by flash column chromatography on silica gel (0%→10% EtOAc/heptane) to afford methyl 2-chloro-4-(1H-indol-1-yl)pyrimidine-5-carboxylate as a white solid.

The following compounds, as shown in Table 8, were prepared in analogous fashion to intermediate E1.

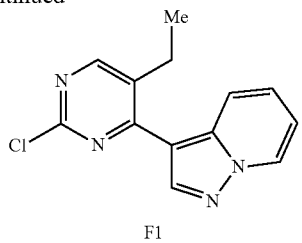

F1

A solution of 5-ethyl-2,4-dichloropyrimidine (160 mg, 0.90 mmol), pyrazolo[1,5-a]pyridin-3-ylboronic acid pinacol ester (287 mg, 1.17 mmol), and [1,1'-bis(diphenylphosphino)ferrocene]dichloropalladium(II) (40 mg, 0.054 mmol) in DMF (9.0 mL) was added, followed by aqueous sodium carbonate (2.0 mL, 4.0 mmol). The mixture was then heated to 100° C. and stirred for 14 h. Upon cooling, the mixture was concentrated in vacuo, and the resulting residue was diluted with 20% (v/v) MeOH in EtOAc (5 mL) and filtered through a Celite pad with additional 20% (v/v) MeOH in EtOAc (20 mL). The filtrate was then concentrated in vacuo and the resulting residue was purified by flash column chromatography on silica gel (0%→5% MeOH/DCM) to afford 3-(2-chloro-5-ethylpyrimidin-4-yl)pyrazolo[1,5-a]pyridine (F1) as a white solid.

TABLE 8

| Intermediate E | Pyrimidine | Indole |
|---|---|---|
| E2 | A7 | (indole) |
| E3 | A7 | (3-methylindole) |

Intermediate F1

3-(2-chloro-5-ethylpyrimidin-4-yl)pyrazolo[1,5-a]pyridine

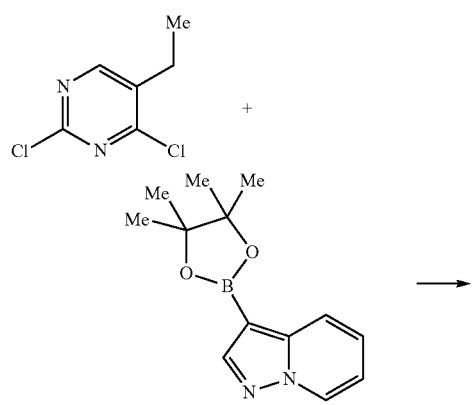

The following intermediate compounds, as shown in Table 9, were synthesized in analogous fashion to intermediate F1.

TABLE 9
| Intermediate F | Boron reagent | Pyrimidine |
|---|---|---|
| 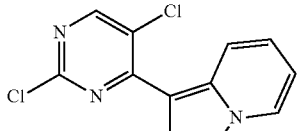 F2 | 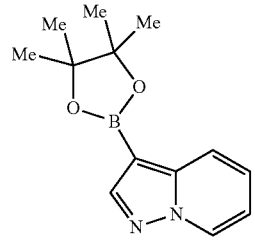 [SMILES: CC1(C)OB(c2cnn3ccccc23)OC1(C)C] | 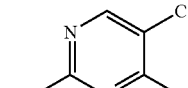 |
| 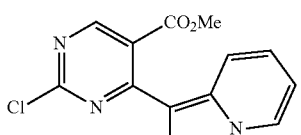 F3 | 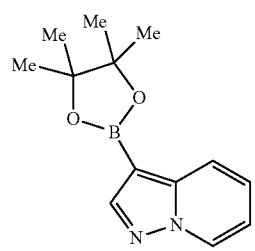 [SMILES: CC1(C)OB(c2cnn3ccccc23)OC1(C)C] | 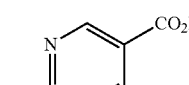 |
| 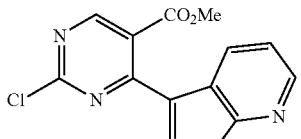 F4 | 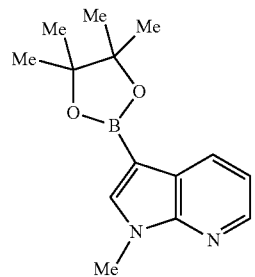 [SMILES: Cn1cc(B2OC(C)(C)C(C)(C)O2)c2cccnc21] | 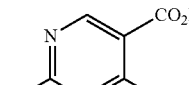 |
| 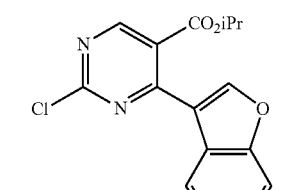 F5 | 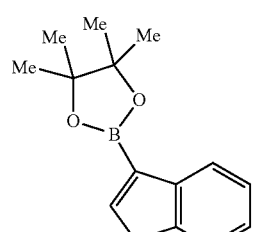 | 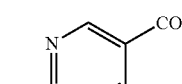 A7 |
| 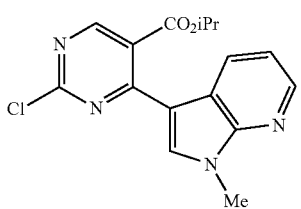 F6 | 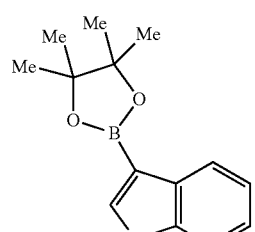 | 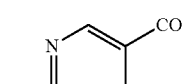 A7 |

Intermediate F7

Isopropyl 2-chloro-4-(1-methyl-1H-indazol-3-yl)pyrimidine-5-carboxylate

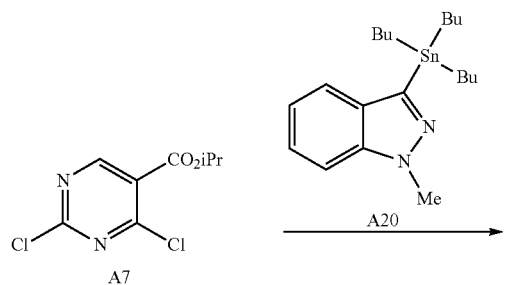

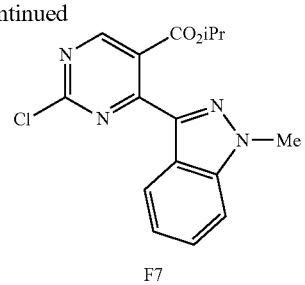

F7

To a mixture of isopropyl 2,4-dichloropyrimidine-5-carboxylate (A7) (0.31 g, 1.32 mmol) and 1-methyl-3-(tributylstannyl)-1H-indazole (A20) (0.67 g, 1.59 mmol), in 1,4-dioxane (24 mL), was added tris(dibenzylideneacetone)dipalladium(0) (0.60 g, 0.66 mmol). The resulting mixture was stirred at 80° C. for 30 min. Upon cooling, the mixture was concentrated in vacuo, and the resulting residue was purified by flash column chromatography on silica gel (0→20% EtOAc/heptane) to afford isopropyl 2-chloro-4-(1-methyl-1H-indazol-3-yl)pyrimidine-5-carboxylate (F7) as an off-white solid.

The following intermediate compounds, as shown in Table 10, were synthesized in analogous fashion to intermediate F7.

TABLE 10

| Intermediate F | Tin reagent | Pyrimidine |
|---|---|---|
| F8 | A20 | |
| F9 | A21 | A7 |
| F10 | A20 | |

Intermediate G1

Methyl 2-chloro-4-(1-methyl-1H-indol-3-yl)pyrimidine-5-carboxylate

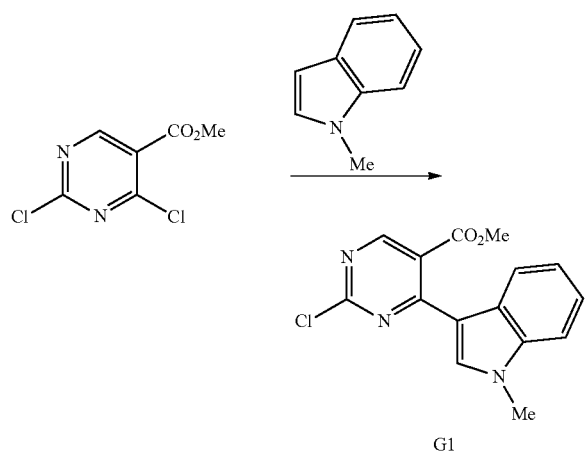

A solution of methyl 2,4-dichloropyrimidine-5-carboxylate (2.07 g, 10 mmol) in DCE (15 mL) was cooled to 0° C. before aluminum chloride (2.7 g, 20 mmol) was added. The resulting mixture was warmed to rt and stirred for 15 min before adding 1-methyl-indole (1.32 g, 10 mmol). The resulting mixture was stirred at 55° C. for 1.5 h, then cooled to 0° C. MeOH (5 mL) and water (10 mL) were added, and the resulting mixture was stirred at rt for 30 min. Additional water (20 mL) was added and the layers were separated. The aqueous phase was extracted with DCM (4×30 mL) and the combined organic layers were dried over magnesium sulfate, filtered, and concentrated in vacuo. The resulting residue was purified by flash column chromatography on silica gel (0%→20% EtOAc/DCM) to afford methyl 2-chloro-4-(1-methyl-1H-indol-3-yl)pyrimidine-5-carboxylate (G1) as yellow solid.

The following intermediate compounds, as shown in Table 11, were synthesized in analogous fashion to intermediate G1.

TABLE 11

| Intermediate G | Indole | Pyrimidine |
|---|---|---|
| G2 | B1 | |
| G3 | B2 | |

TABLE 11-continued

| Intermediate G | Indole | Pyrimidine |
|---|---|---|
| G4 | B3 | |
| G5 | B4 | |
| G6 | B6 | |
| G7 | B5 | |

TABLE 11-continued
| Intermediate G | Indole | Pyrimidine |
|---|---|---|
| 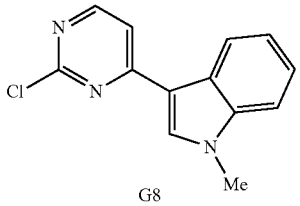 G8 | 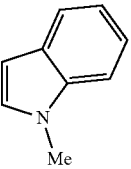 | 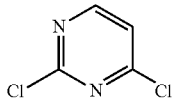 |
| 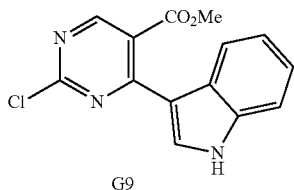 G9 | 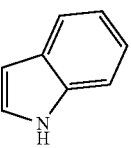 | 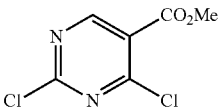 [SMILES: COC(=O)c1cnc(Cl)nc1Cl] |
| 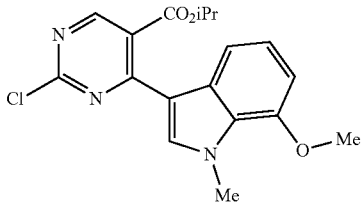 G10 | 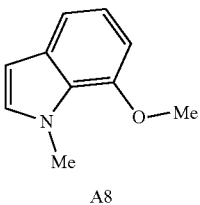 A8 | 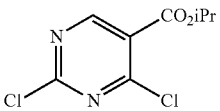 |
| 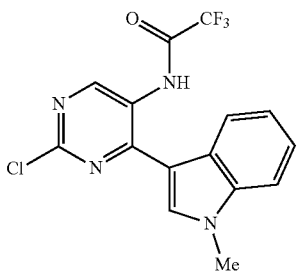 G11 | 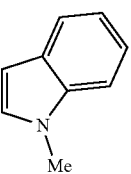 | 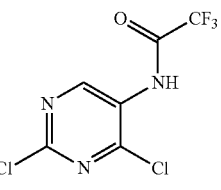 A9 |
| 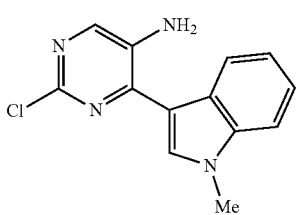 G12 | 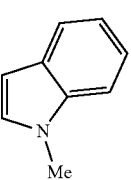 | 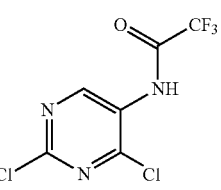 A9 |
| 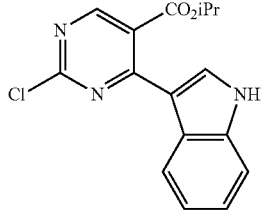 G13 | 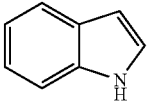 | 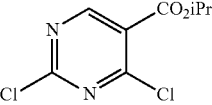 A7 |

TABLE 11-continued
| Intermediate G | Indole | Pyrimidine |
|---|---|---|
| 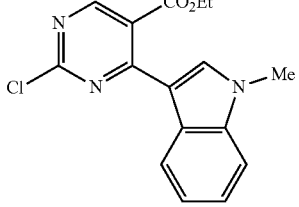 G14 | 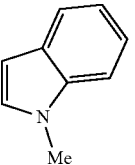 | 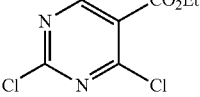 |
| 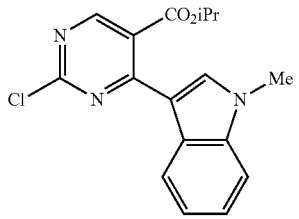 G15 | 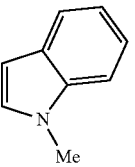 | 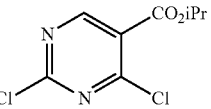 A7 |
| 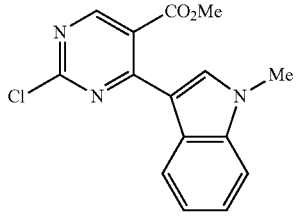 G16 | 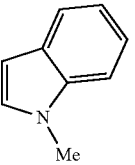 | 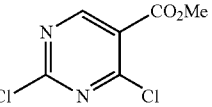 |
| 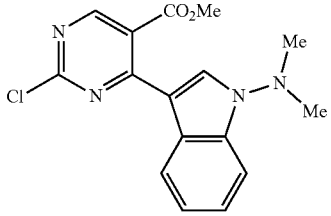 G17 | 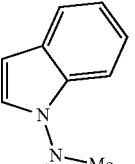 A11 | 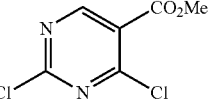 |
| 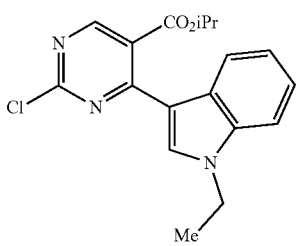 G18 | 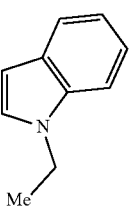 A12 | 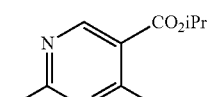 A7 |

TABLE 11-continued
| Intermediate G | Indole | Pyrimidine |
|---|---|---|
| 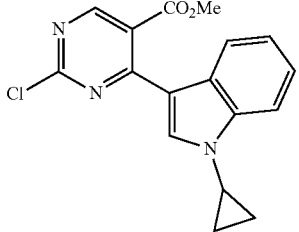<br>G19 | 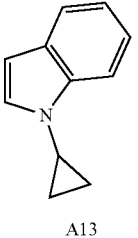<br>A13 | 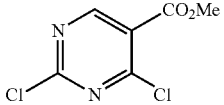 |
| 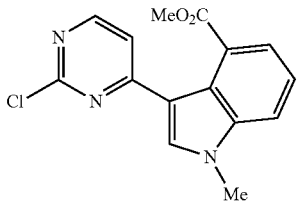<br>G20 | 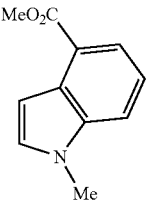 | 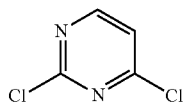 |
| 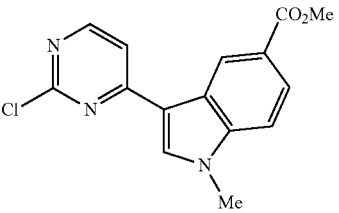<br>G21 | 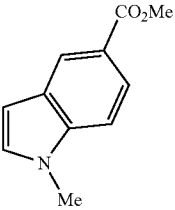 [SMILES: COC(=O)c1ccc2c(ccn2C)c1] | 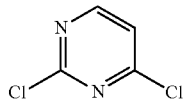 |
| 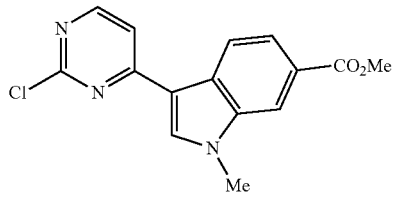<br>G22 | 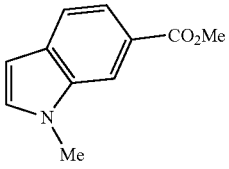 [SMILES: COC(=O)c1ccc2ccn(C)c2c1] | 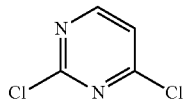 |
| 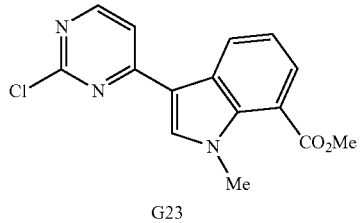 [SMILES: COC(=O)c1cccc2c(-c3ccnc(Cl)n3)cn(C)c12]<br>G23 | 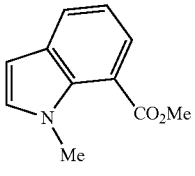 [SMILES: COC(=O)c1cccc2ccn(C)c12] | 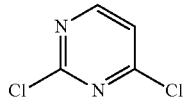 |
| 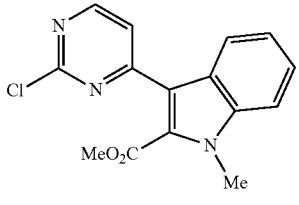<br>G24 | 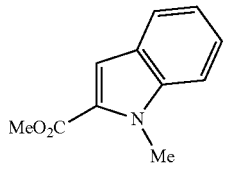 [SMILES: COC(=O)c1cc2ccccc2n1C] | 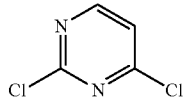 |

TABLE 11-continued
| Intermediate G | Indole | Pyrimidine |
|---|---|---|
| 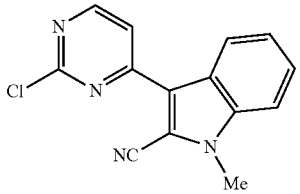 G25 | 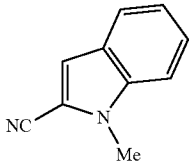 [SMILES: Cn1c(C#N)cc2ccccc21] | 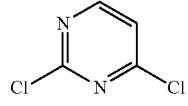 |
| 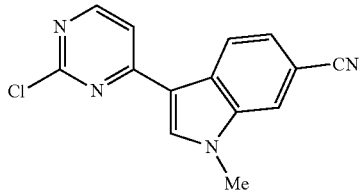 G26 | 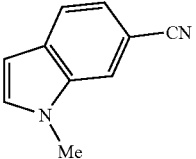 [SMILES: Cn1ccc2ccc(C#N)cc21] | 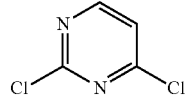 |
| 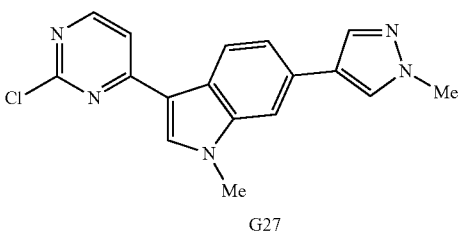 G27 | 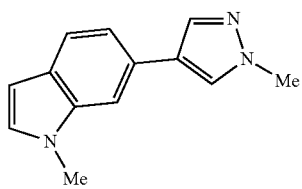 H9 | 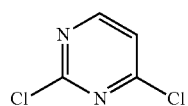 |
| 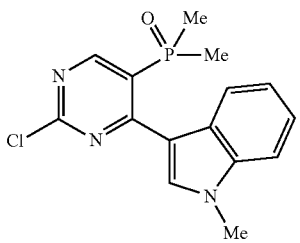 G28 | 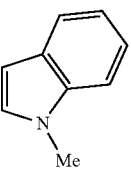 | 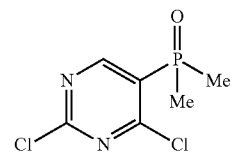 A19 |
| 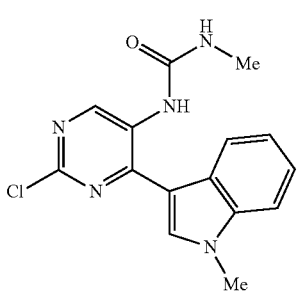 G29 | 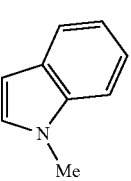 | 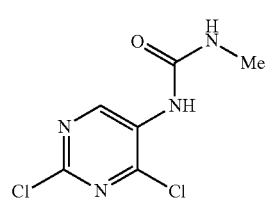 [SMILES: CNC(=O)Nc1cnc(Cl)nc1Cl] |

Example H1

3-(4-chloro-1,3,5-triazin-2-yl)-2-(3,6-dihydro-2H-pyran-4-yl)-1-methyl-1H-indole

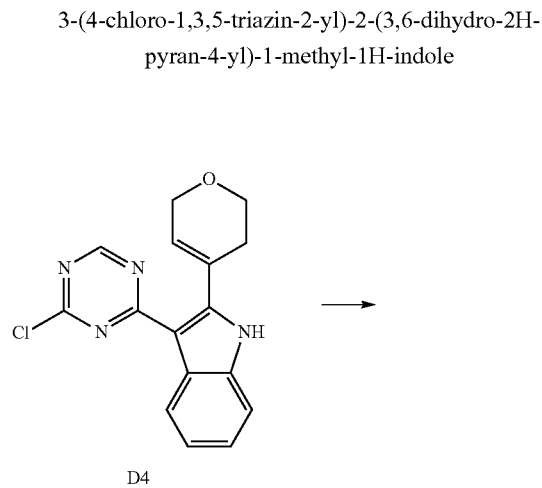

3-(4-chloro-1,3,5-triazin-2-yl)-2-(3,6-dihydro-2H-pyran-4-yl)-1H-indole (D4) (374 mg, 1.2 mmol) was suspended in DMF (2.2 mL) and cooled to 0° C. Sodium hydride (62 mg, 1.55 mmol) was added and the resulting mixture was warmed to rt and stirred for 15 min. The mixture was then treated with iodomethane (97 uL, 1.55 mmol, 1.3 equiv) and stirred at rt for 30 min. Tert-butanol (1 mL) was added, and the resulting mixture was diluted with EtOAc (20 mL) and water (15 mL). The layers were separated and the aqueous phase was extracted with EtOAc (3×10 mL). The combined organic layers were washed with brine (15 mL), dried over sodium sulfate, filtered, and concentrated in vacuo. The resulting residue was purified by flash column chromatography on silica gel (0%→20% EtOAc/heptane) to afford 3-(4-chloro-1,3,5-triazin-2-yl)-2-(3,6-dihydro-2H-pyran-4-yl)-1-methyl-1H-indole (H1) as a white powder.

The following intermediate compounds, as shown in Table 12, were prepared in analogous fashion to intermediate H1.

TABLE 12

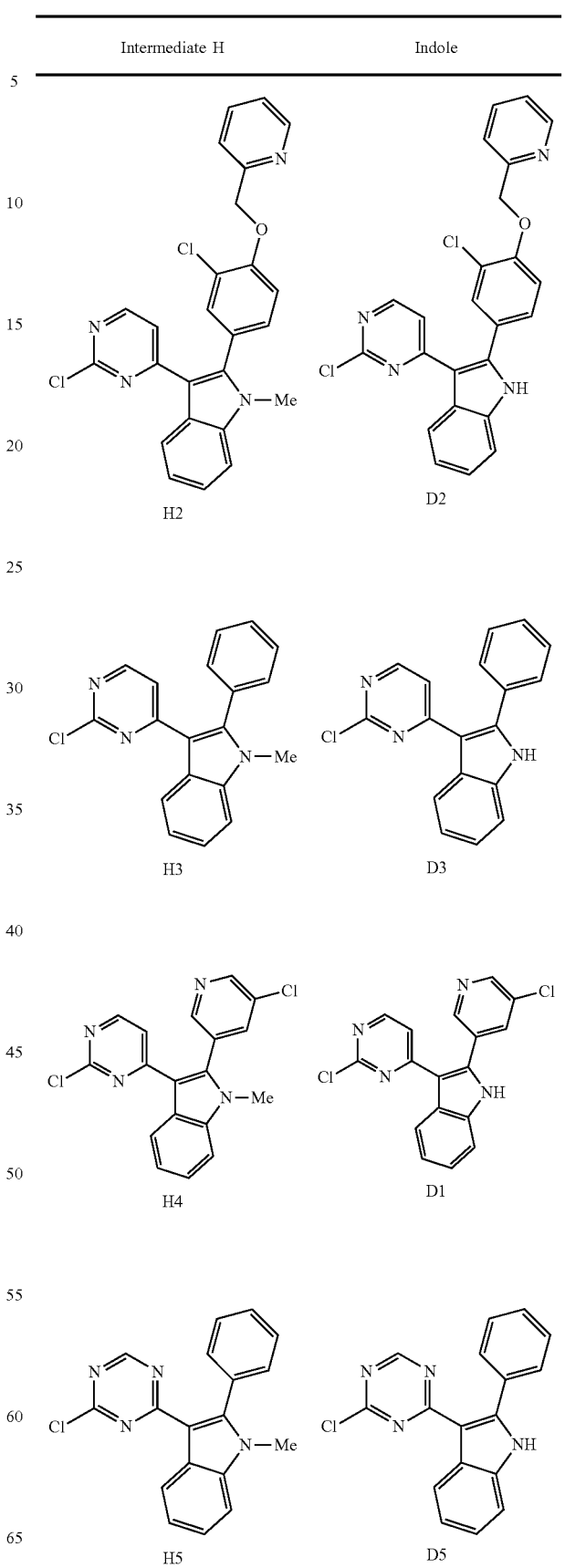

TABLE 12-continued

| Intermediate H | Indole |
|---|---|
| H6 | D6 |
| H7 | D7 |
| H8 | D8 |
| H9 | A16 |

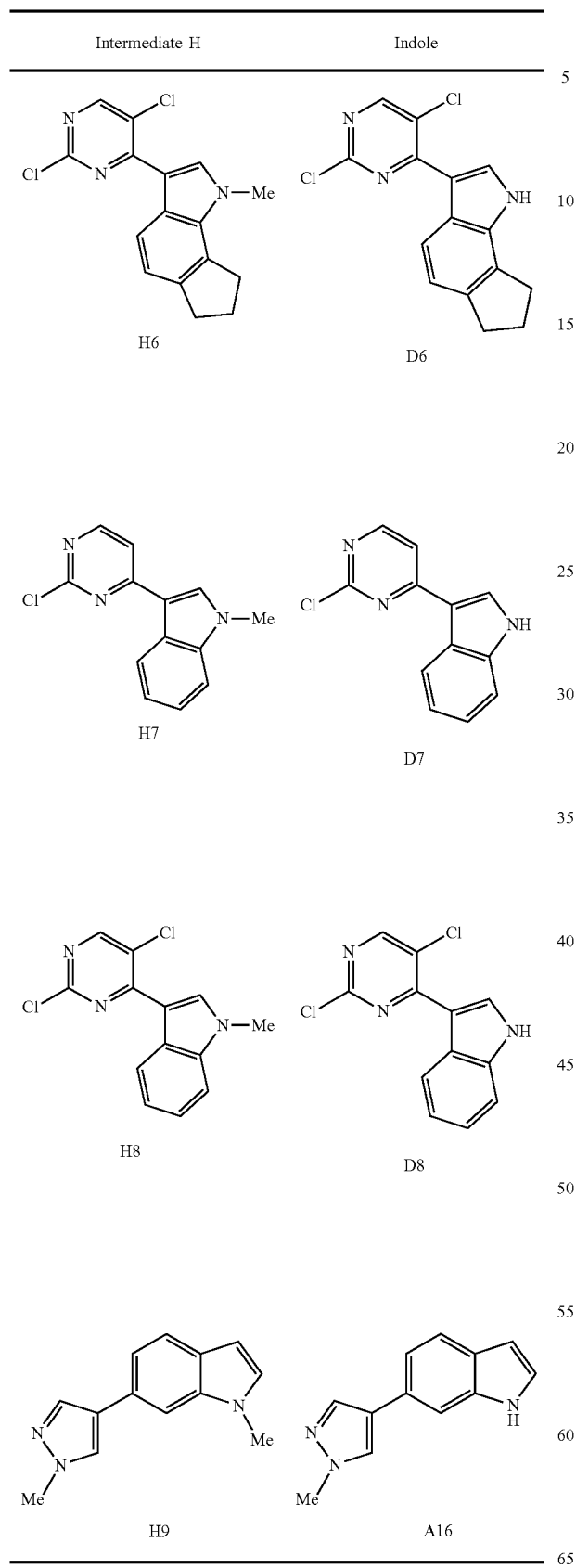

Intermediate H10 isopropyl 4-(1-acetyl-1H-indol-3-yl)-2-((4-((2-(dimethylamino)ethyl)(methyl)amino)-2-methoxy-5-nitrophenyl)amino)pyrimidine-5-carboxylate

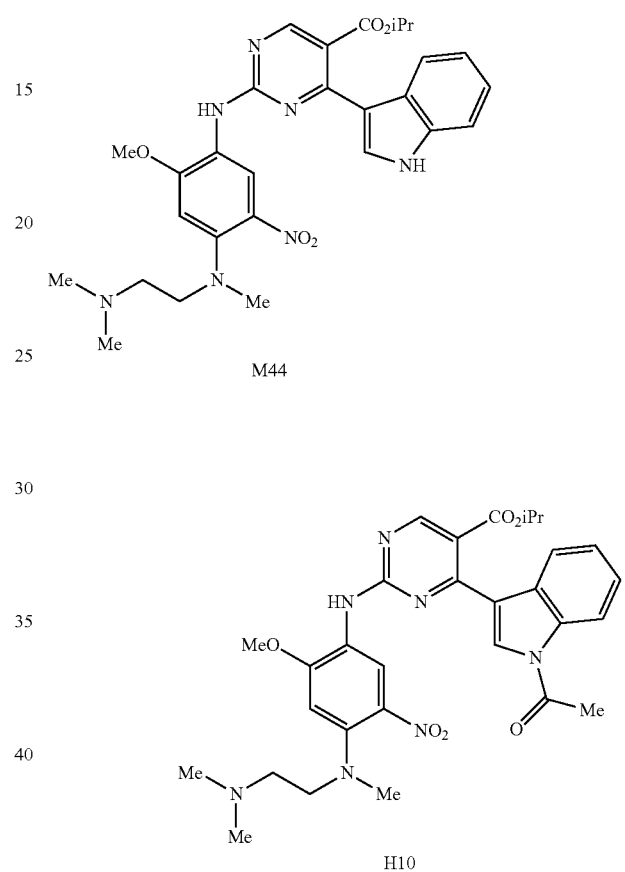

To a solution of isopropyl 2-((4-((2-(dimethylamino)ethyl)(methyl)amino)-2-methoxy-5-nitrophenyl)amino)-4-(1H-indol-3-yl)pyrimidine-5-carboxylate (M44) (200 mg, 0.36 mmol) in DCE (5 mL), was added acetic anhydride (40 mg, 0.4 mmol), followed by trimethylamine (0.055 mL, 0.4 mmol). The resulting mixture was stirred at rt overnight. Subsequently, saturated aqueous potassium carbonate was added, and the resulting mixture was extracted with DCM. The combined organic layers were dried over magnesium sulfate, filtered, and concentrated in vacuo. The resulting residue was purified by flash column chromatography on silica gel (0→20% MeOH/DCM) to afford isopropyl 4-(1-acetyl-1H-indol-3-yl)-2-((4-((2-(dimethylamino)ethyl)(methyl)amino)-2-methoxy-5-nitrophenyl)amino)pyrimidine-5-carboxylate (H10) as a red solid.

Intermediate I1

4-(2-(3,6-dihydro-2H-pyran-4-yl)-1-methyl-1H-indol-3-yl)-N-(4-fluoro-2-methoxy-5-nitrophenyl)-1,3,5-triazin-2-amine

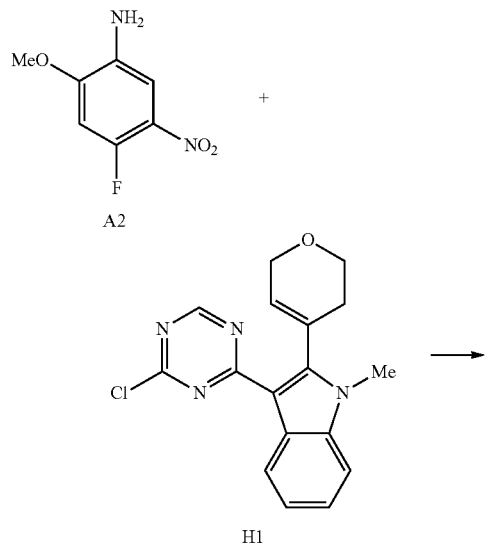

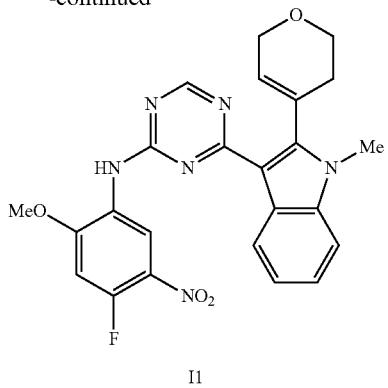

A mixture of 3-(4-chloro-1,3,5-triazin-2-yl)-2-(3,6-dihydro-2H-pyran-4-yl)-1-methyl-1H-indole (H1) (263 mg, 0.80 mmol), 4-fluoro-2-methoxy-5-nitroaniline (A2) (150 mg, 0.80 mmol) and potassium carbonate (334 mg, 2.40 mmol) in MeCN (2.7 mL) was stirred overnight at 80° C. The mixture was cooled to rt, then filtered through a pad of Celite, which was rinsed with EtOAc. The filtrate was concentrated in vacuo to afford 4-(2-(3,6-dihydro-2H-pyran-4-yl)-1-methyl-1H-indol-3-yl)-N-(4-fluoro-2-methoxy-5-nitrophenyl)-1,3,5-triazin-2-amine (I1).

The following intermediate compounds, as shown in Table 13, were prepared in analogous fashion to intermediate I1.

TABLE 13

| Intermediate I | Heteroaryl chloride | Aniline |
|---|---|---|
| I2 | D5 | A2 |
| I3 | G10 | A2 |

TABLE 13-continued
| Intermediate I | Heteroaryl chloride | Aniline |
|---|---|---|
| 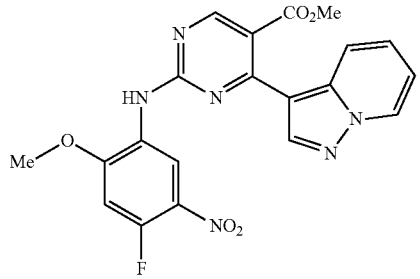 I4 | 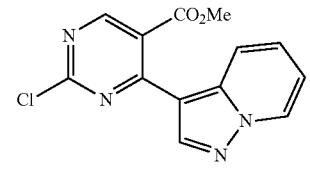 F3 | 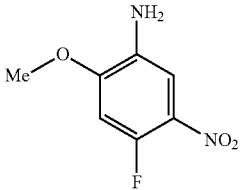 A2 |
| 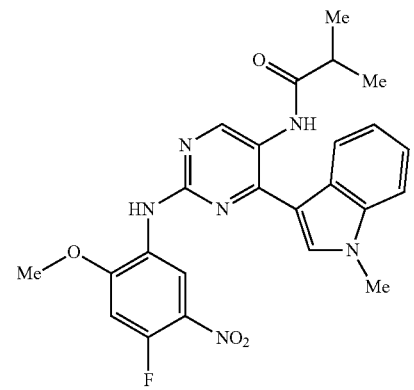 I5 | 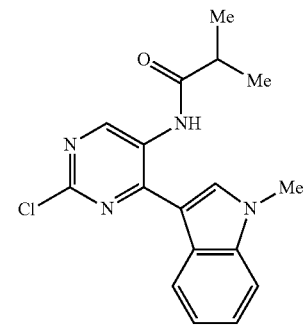 L1 | 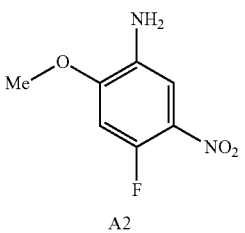 A2 |
| 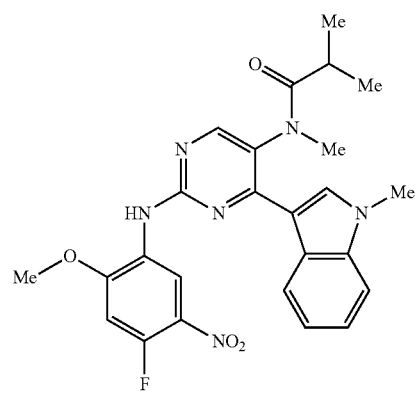 I6 | 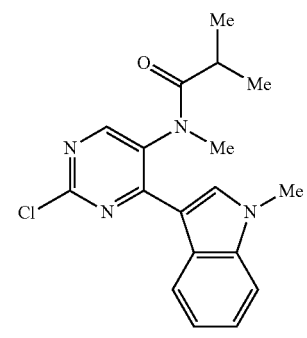 L2 | 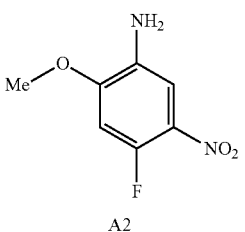 A2 |
| 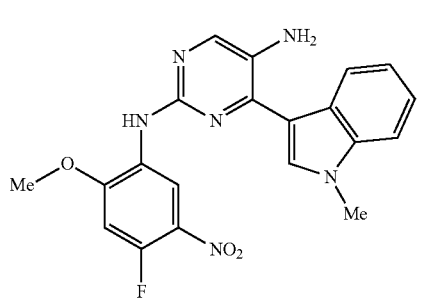 I7 | 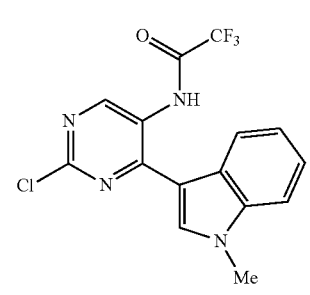 G11 | 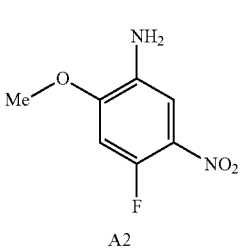 A2 |

Intermediate J1

N1-(2-(dimethylamino)ethyl)-N4-(5-ethyl-4-(pyrarazolo[1,5-a]pyridin-3-yl)pyrimidin-2-yl)-5-methoxy-N1-methyl-2-nitrobenzene-1,4-diamine

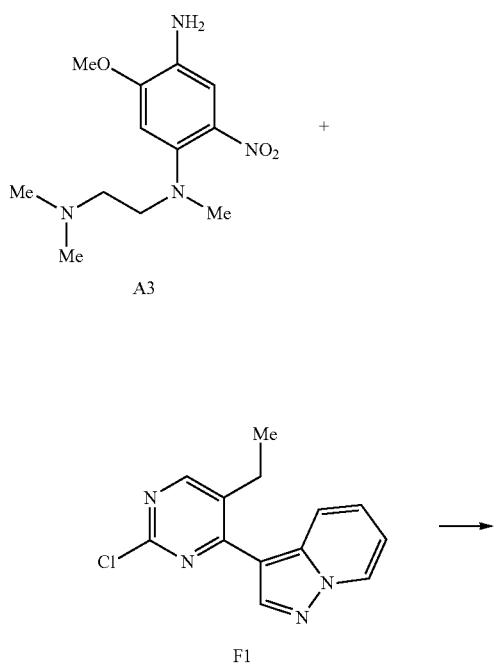

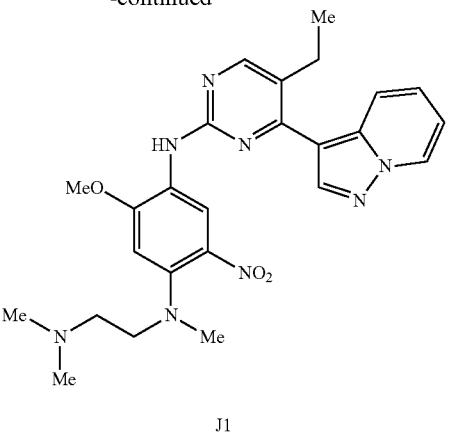

A mixture of 3-(2-chloro-5-ethylpyrimidin-4-yl)pyrazolo[1,5-a]pyridine (F1) (61 mg, 0.24 mmol), N1-(2-(dimethylamino)ethyl)-5-methoxy-N$^1$-methyl-2-nitrobenzene-1,4-diamine (A3) (53 mg, 0.20 mmol), tris(dibenzylideneacetone)dipalladium(0) (18 mg, 0.02 mmol), Xantphos (23 mg, 0.04 mmol), and cesium carbonate (77 mg, 0.24 mmol) in dioxane (1 mL) was stirred at 100° C. overnight. Upon cooling, the mixture was concentrated in vacuo. The resulting residue was purified by flash column chromatography on silica gel (0%→15% MeOH/DCM) to afford N1-(2-(dimethylamino)-ethyl)-N4-(5-ethyl-4-(pyrazolo[1,5-a]pyridin-3-yl)pyrimidin-2-yl)-5-methoxy-N1-methyl-2-nitrobenzene-1,4-diamine (J1) as a red solid.

The following intermediate compounds, as shown in Table 14, were synthesized in analogous fashion to intermediate J1.

TABLE 14

| Intermediate J | Chloropyrimidine | Aniline |
|---|---|---|
| J2 | H2 | A3 |

TABLE 14-continued
| Intermediate J | Chloropyrimidine | Aniline |
|---|---|---|
| 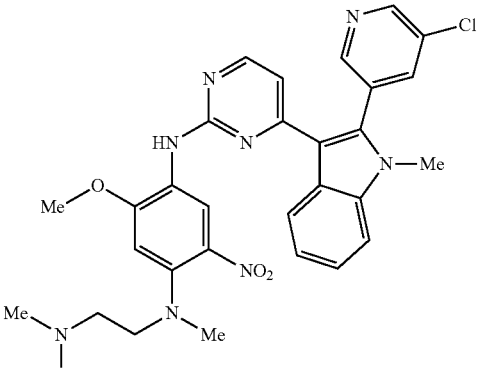 J3 | 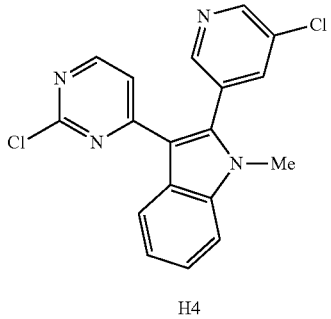 H4 | 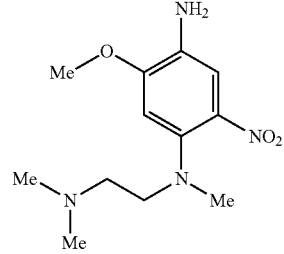 A3 |
| 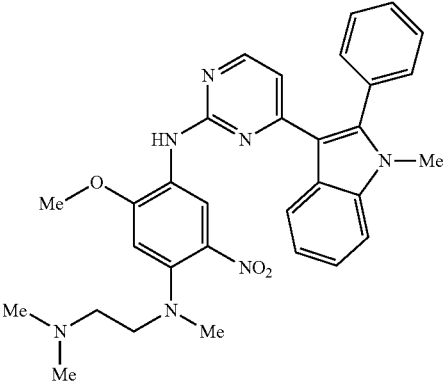 J4 | 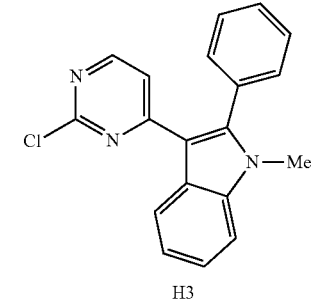 H3 | 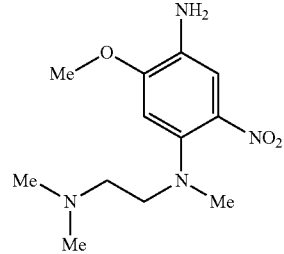 A3 |
| 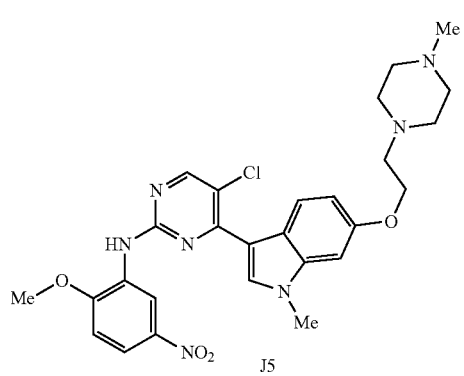 J5 | 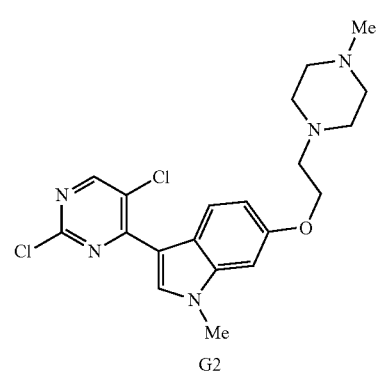 G2 | 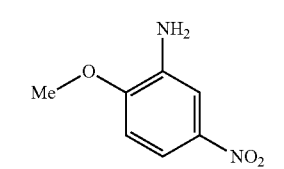 |

Intermediate K1

5-chloro-N-(4-fluoro-2-methoxy-5-nitrophenyl)-4-(1-methyl-1,6,7,8-tetrahydrocyclopenta[g]indol-3-yl)pyrimidin-2-amine

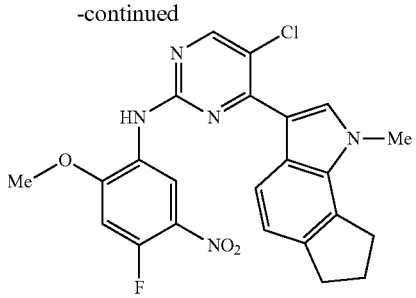

K1

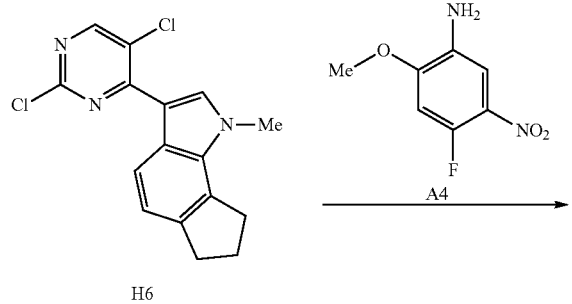

A mixture of intermediate 3-(2,5-dichloropyrimidin-4-yl)-1-methyl-1,6,7,8-tetrahydrocyclopenta[g]indole (H6) (1.43 g, 4.5 mmol), 4-fluoro-2-methoxy-5-nitroaniline (A4) (1.0 g, 5.4 mmol) and pTSA (3.42 g, 18 mmol) in dioxane (10 mL) was heated at 100° C. for 48 h. Upon cooling, the mixture was concentrated in vacuo and the resulting residue was purified by flash column chromatography on silica gel (5% MeOH/DCM) to afford 5-chloro-N-(4-fluoro-2-methoxy-5-nitrophenyl)-4-(1-methyl-1,6,7,8-tetrahydrocyclopenta[g]indol-3-yl)pyrimidin-2-amine (K1) as a brown residue.

The following intermediate compounds, as shown in Table 15, were synthesized in analogous fashion to intermediate K1.

TABLE 15

| Intermediate K | Chloropyrimidine | Aniline |
|---|---|---|
| K2 | H8 | |
| K3 | G1 | A2 |
| K4 | G3 | |

TABLE 15-continued
| Intermediate K | Chloropyrimidine | Aniline |
|---|---|---|
| 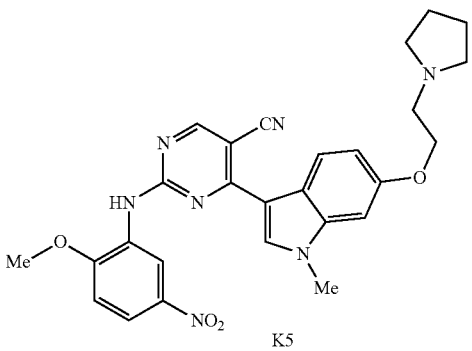 K5 | 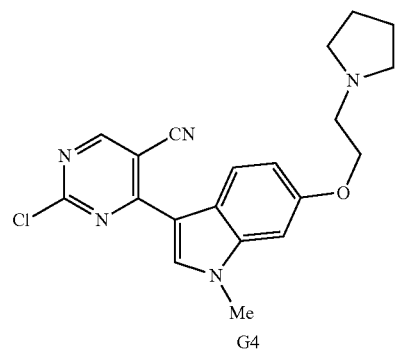 G4 | 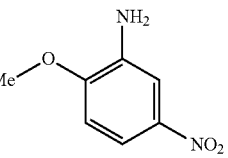 |
| 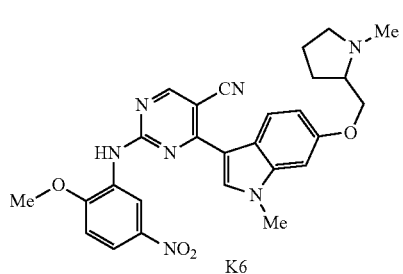 K6 | 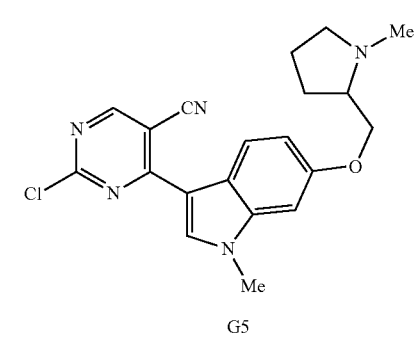 G5 | 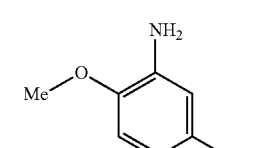 |
| 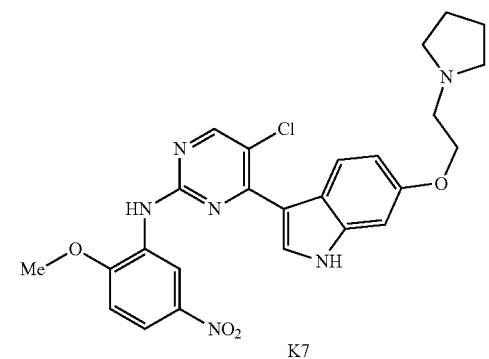 K7 | 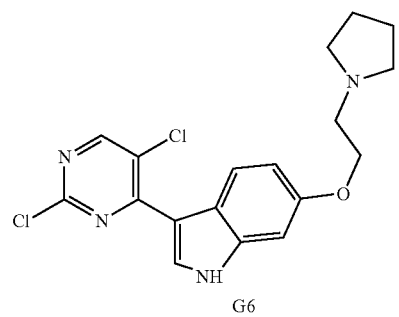 G6 | 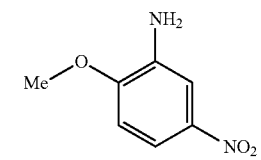 |
| 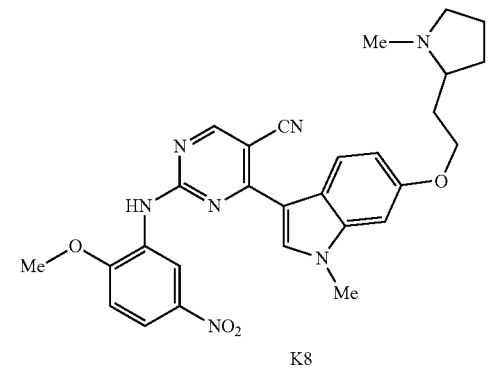 K8 | 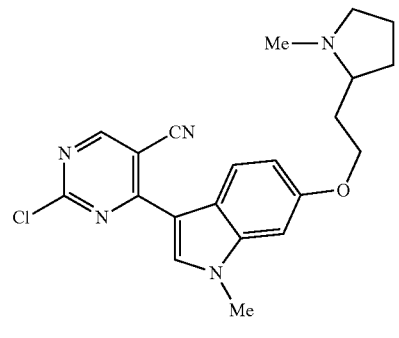 G7 | 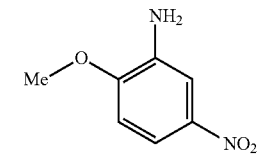 [SMILES: COc1ccc([N+](=O)[O-])cc1N] |

TABLE 15-continued
| Intermediate K | Chloropyrimidine | Aniline |
|---|---|---|
| 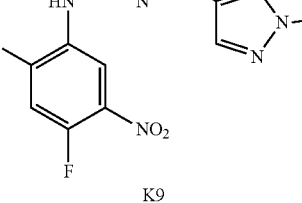 K9 | 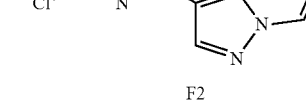 F2 | 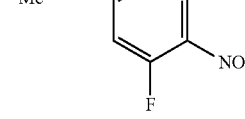 |
| 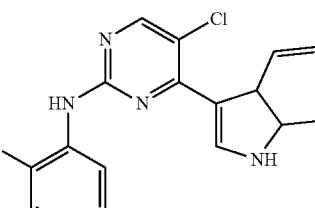 K10 | 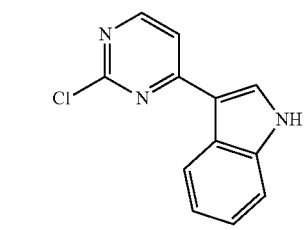 D7 | 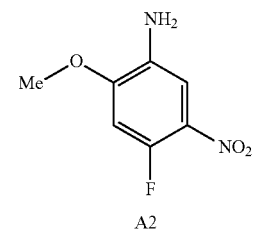 A2 |
| 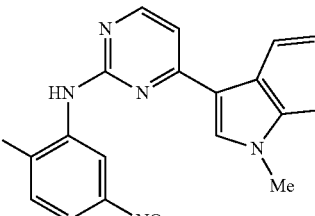 K11 | 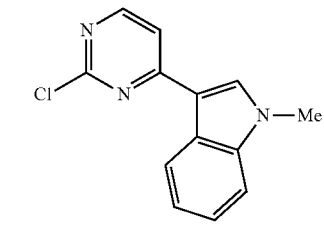 H7 | 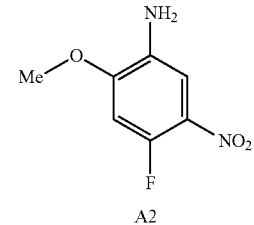 A2 |
| 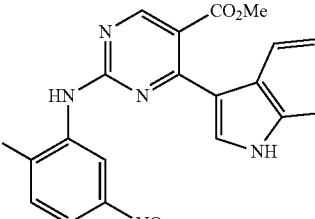 K12 | 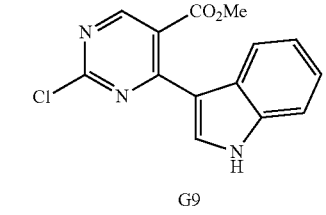 G9 | 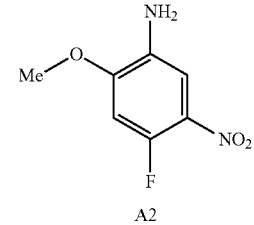 A2 |
| 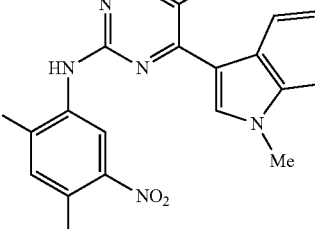 K13 | 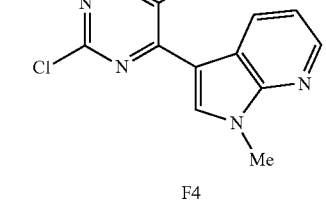 F4 | 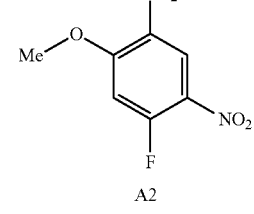 A2 |

TABLE 15-continued

| Intermediate K | Chloropyrimidine | Aniline |
|---|---|---|
| K14 | E1 | A2 |
| K15 | H8 | A2 |
| K16 | F7 | A2 |
| K17 | F8 | A2 |

TABLE 15-continued
| Intermediate K | Chloropyrimidine | Aniline |
|---|---|---|
| 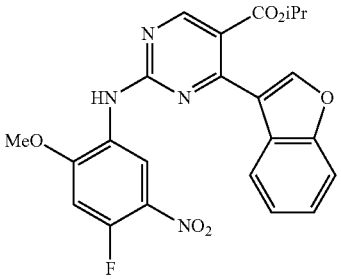 K18 | 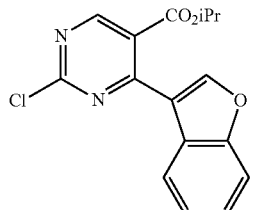 F5 | 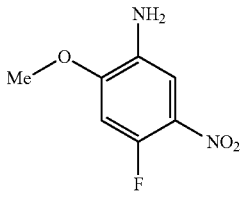 A2 |
| 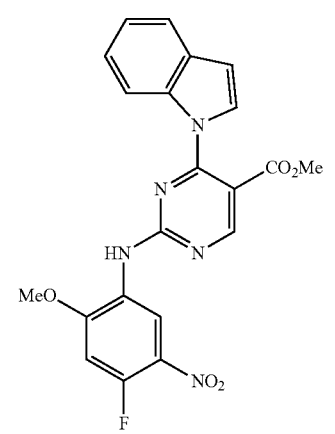 K19 | 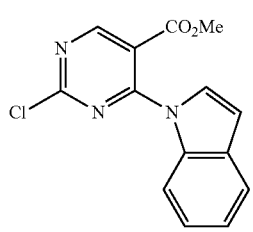 E2 | 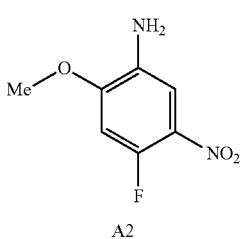 A2 |
| 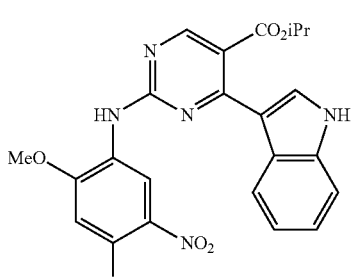 K20 | 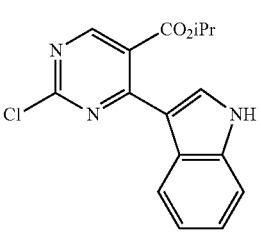 G13 | 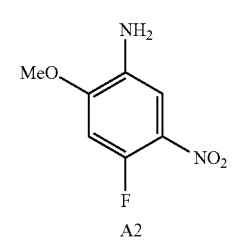 A2 |
| 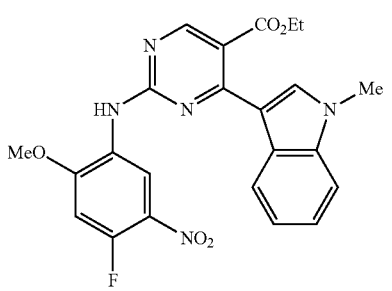 K21 | 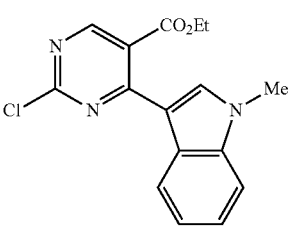 G14 | 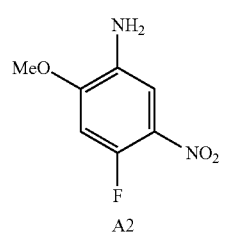 A2 |

TABLE 15-continued
| Intermediate K | Chloropyrimidine | Aniline |
|---|---|---|
| 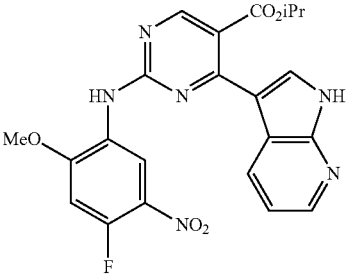 K22 | 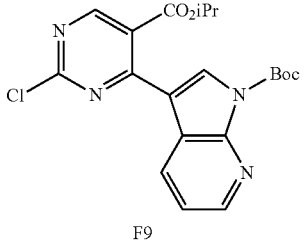 F9 | 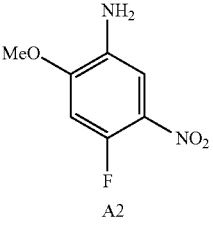 A2 |
| 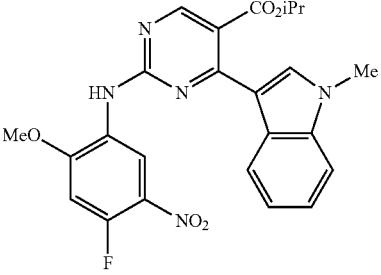 K23 | 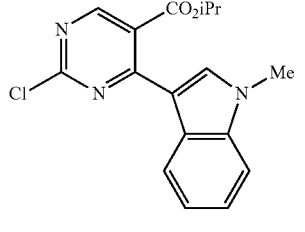 G15 | 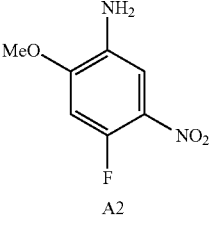 A2 |
| 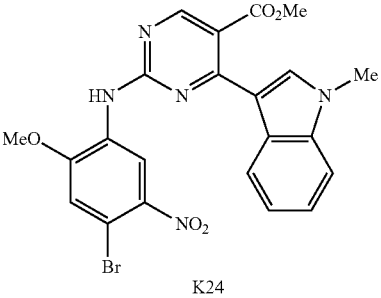 K24 | 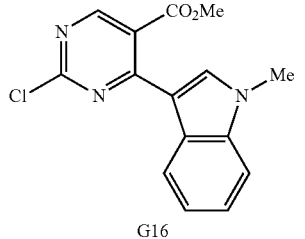 G16 | 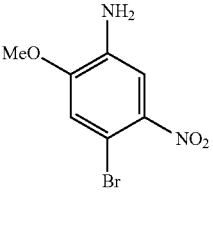 |
| 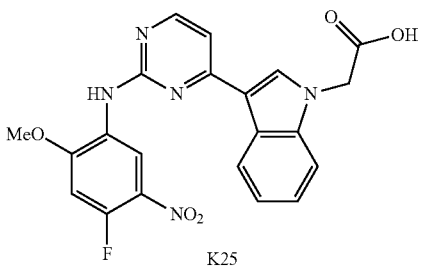 K25 | 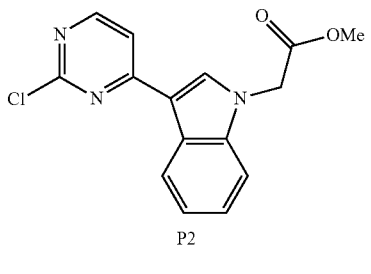 P2 | 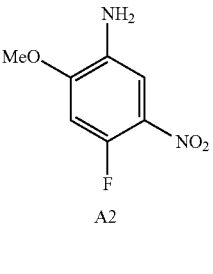 A2 |
| 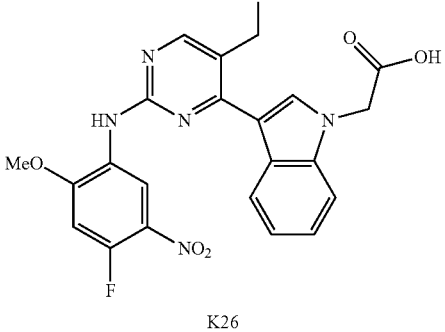 K26 | 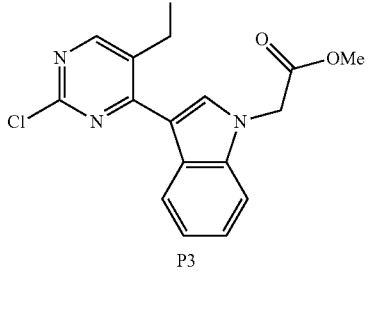 P3 | 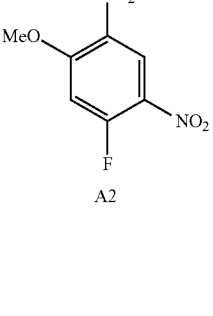 A2 |

TABLE 15-continued
| Intermediate K | Chloropyrimidine | Aniline |
|---|---|---|
| 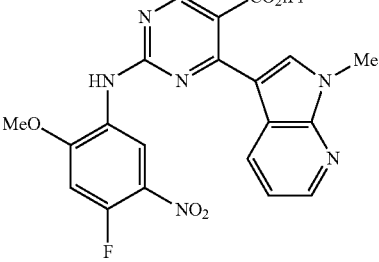<br>K27 | 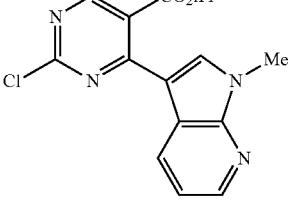<br>F6 | 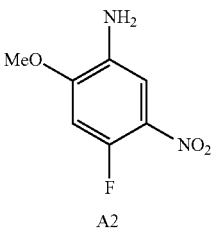<br>A2 |
| 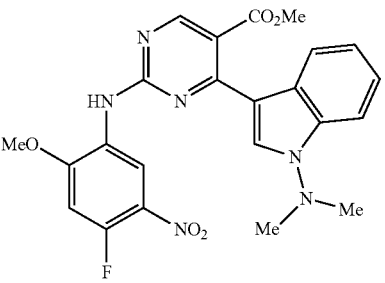<br>K28 | 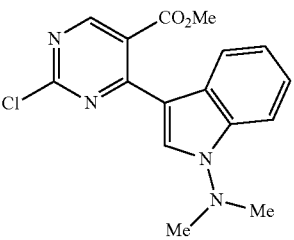<br>G17 | 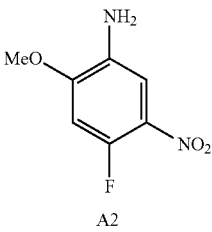<br>A2 |
| 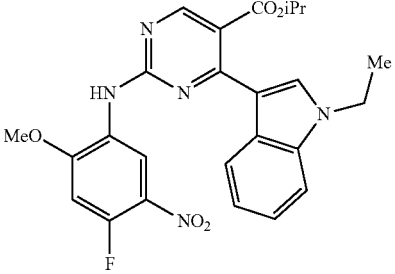<br>K29 | 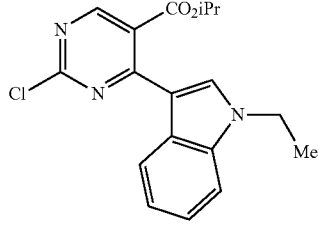<br>G18 | 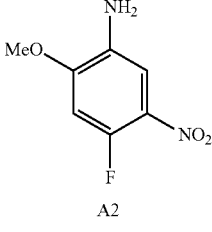<br>A2 |
| 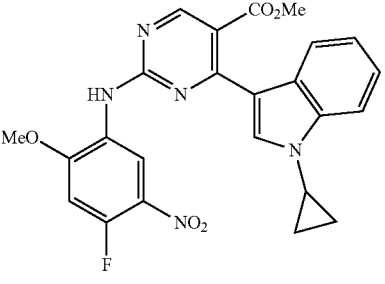<br>K30 | 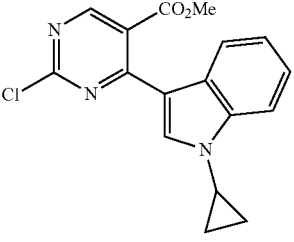<br>G19 | 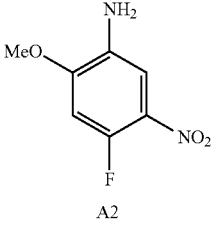<br>A2 |
| 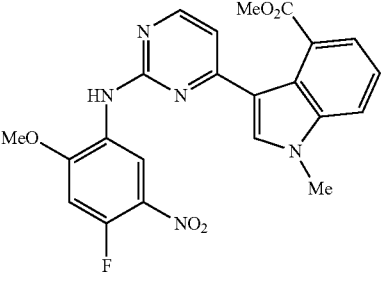<br>K31 | 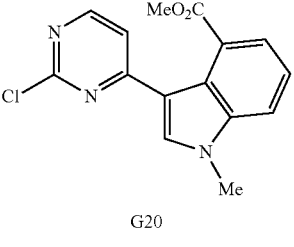 [SMILES: COC(=O)c1cccc2c1c(-c1ccnc(Cl)n1)cn2C]<br>G20 | 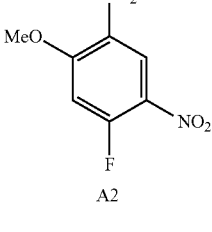<br>A2 |

TABLE 15-continued
| Intermediate K | Chloropyrimidine | Aniline |
|---|---|---|
| 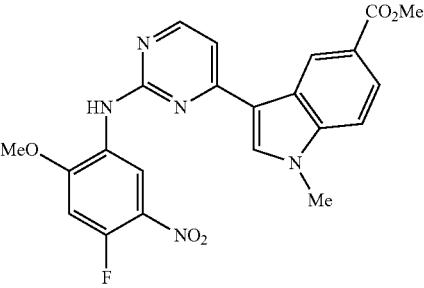 K32 | 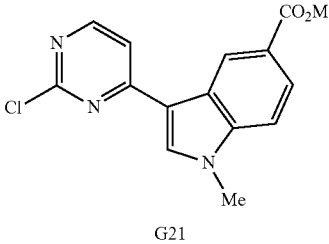 G21 | 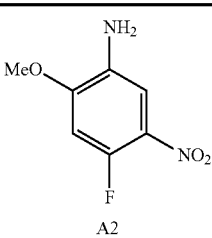 A2 |
| 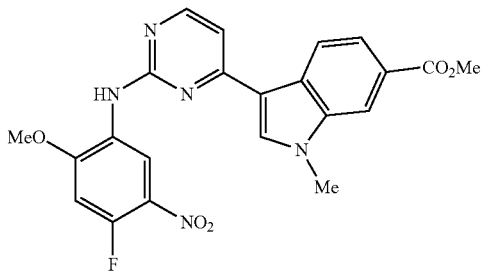 K33 | 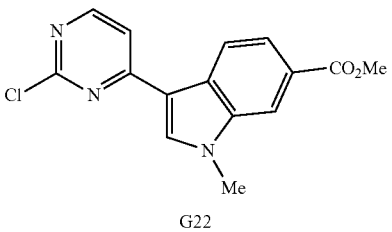 G22 | 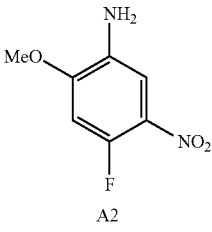 A2 |
| 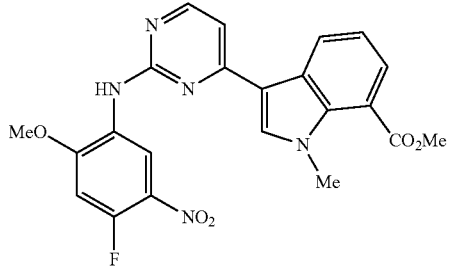 K34 | 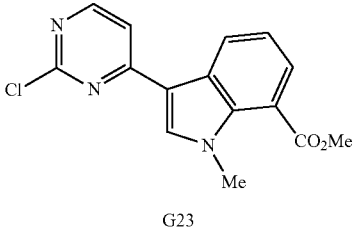 G23 | 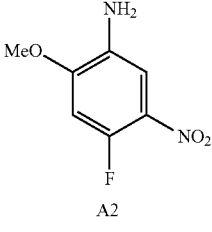 A2 |
| 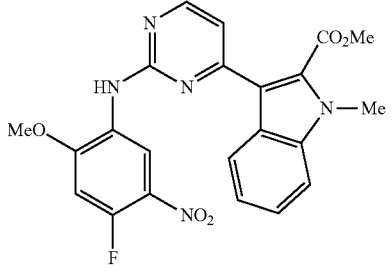 K35 | 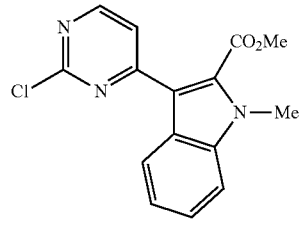 G24 | 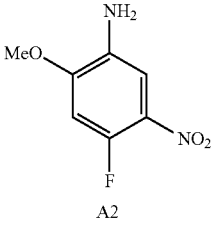 A2 |
| 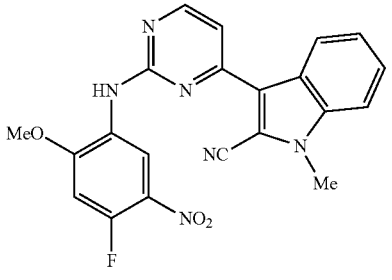 K36 | 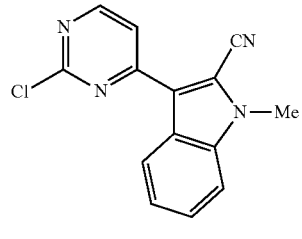 G25 | 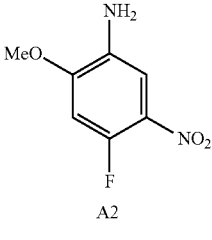 A2 |

TABLE 15-continued
| Intermediate K | Chloropyrimidine | Aniline |
|---|---|---|
| 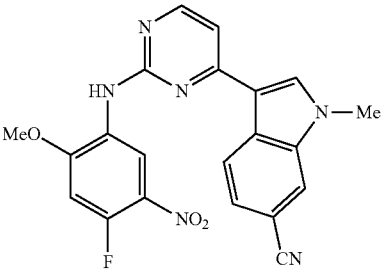 K37 | 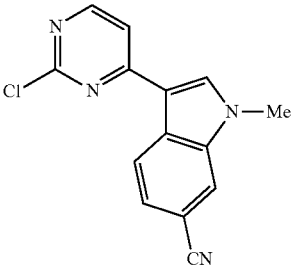 G26 | 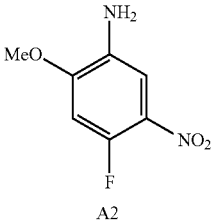 A2 |
| 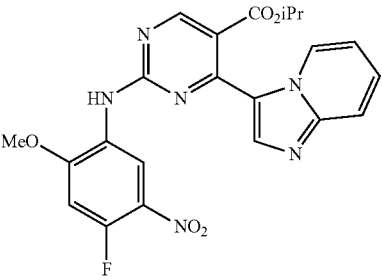 K38 | 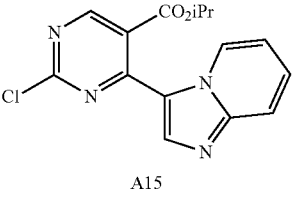 A15 | 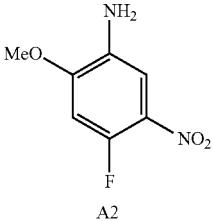 A2 |
| 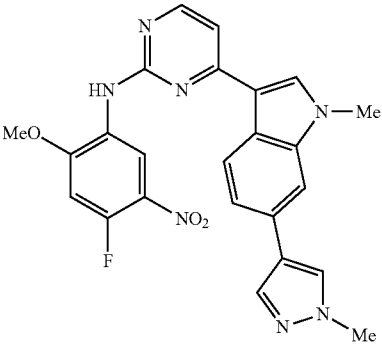 K39 | 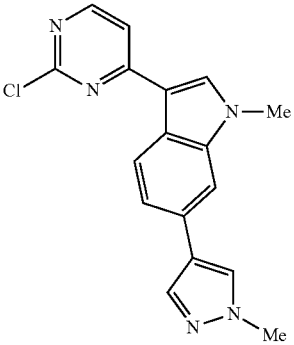 G27 | 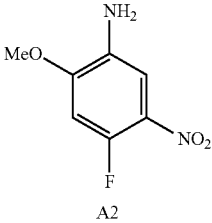 A2 |
| 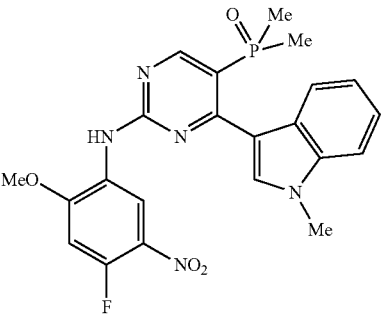 K40 | 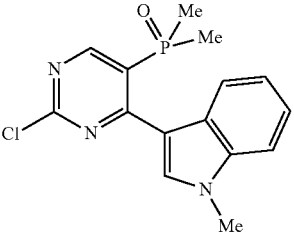 G28 | 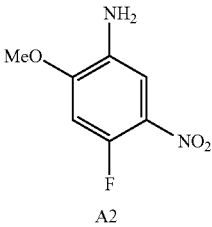 A2 |

TABLE 15-continued
| Intermediate K | Chloropyrimidine | Aniline |
|---|---|---|
| 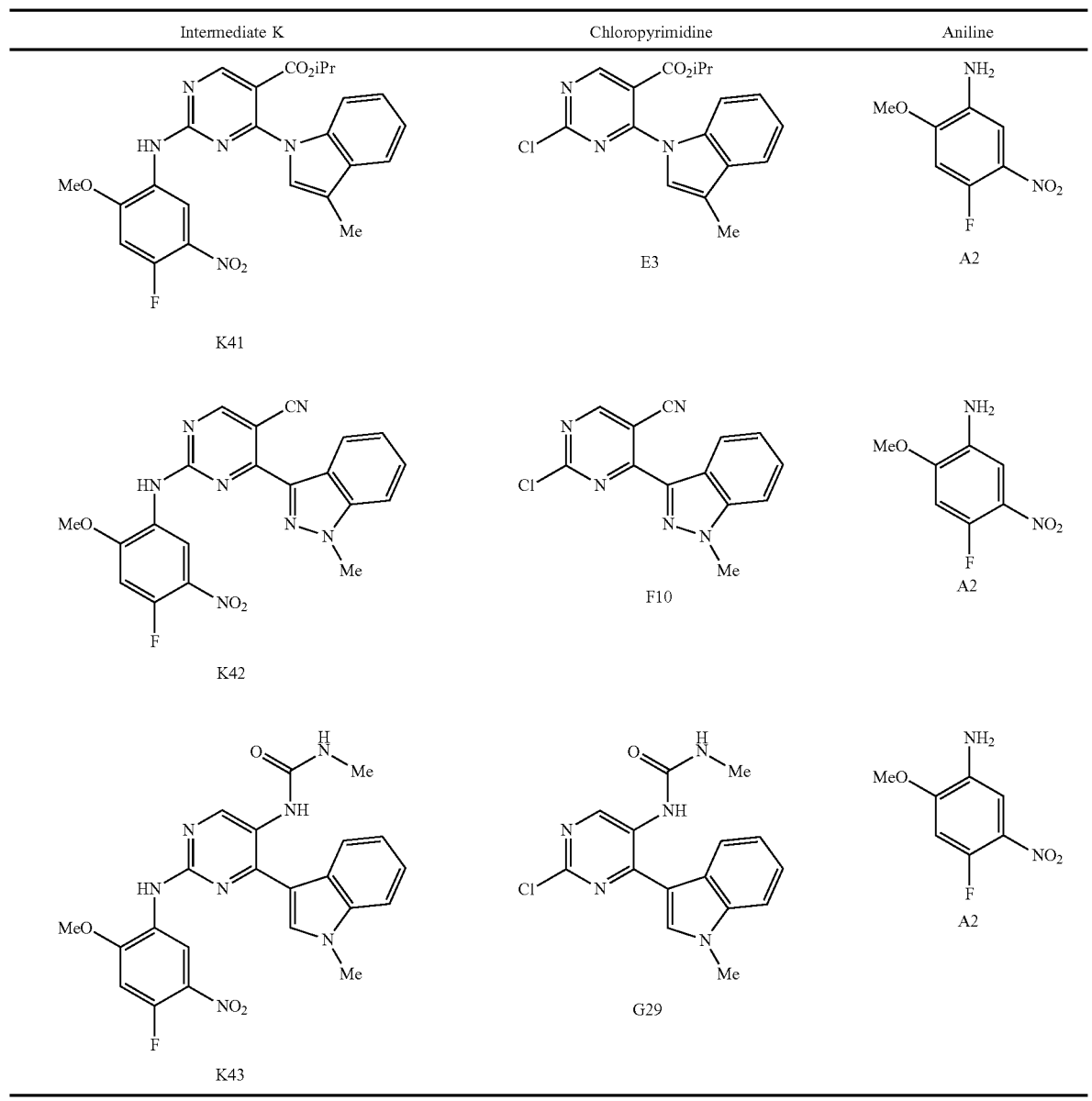 K41 | E3 | A2 |
| K42 | F10 | A2 |
| K43 | G29 | A2 |
Intermediate L1
N-(2-chloro-4-(1-methyl-1H-indol-3-yl)pyrimidin-5-yl)isobutyramide
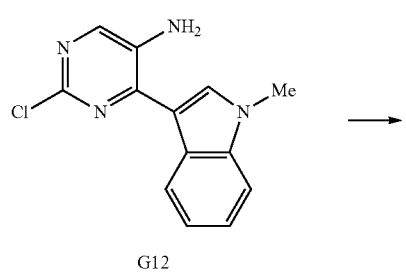
G12
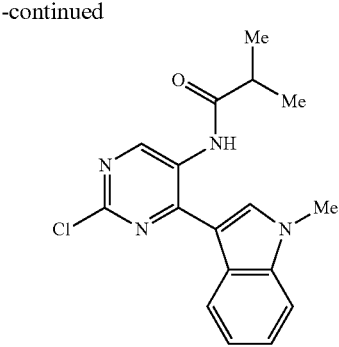
L1
2-chloro-4-(1-methyl-1H-indol-3-yl)pyrimidin-5-amine (G12) (150 mg, 0.58 mmol) was suspended in DCM (5.8 mL) and treated with isobutyryl chloride (67 uL, 0.64 mmol) and triethylamine (161 uL, 1.16 mmol). The mixture was stirred at rt for 1 h before adding water (5 mL). The layers were separated, and the aqueous layer was extracted with DCM (3×5 mL). The combined organic layers were dried over magnesium sulfate, filtered, and concentrated in vacuo to give N-(2-chloro-4-(1-methyl-1H-indol-3-yl)pyrimidin-5-yl)isobutyramide (L1) as a pink solid.

Intermediate L2

N-(2-chloro-4-(1-methyl-1H-indol-3-yl)pyrimidin-5-yl)-N-methylisobutyramide

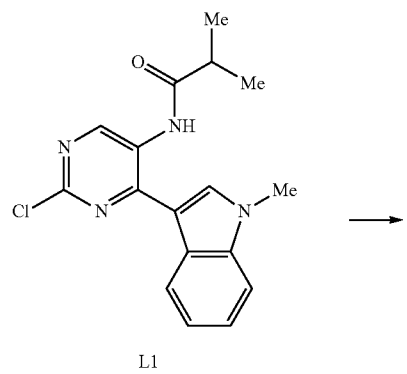

L1

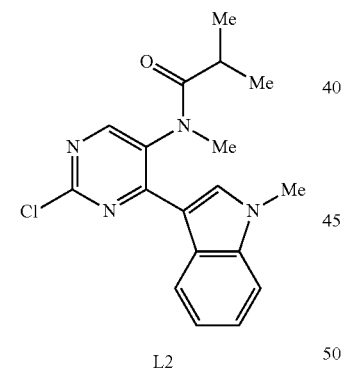

L2

A solution of N-(2-chloro-4-(1-methyl-1H-indol-3-yl)pyrimidin-5-yl)isobutyramide (L1) (166 mg, 0.50 mmol, 1.0 equiv) in MeCN (2.0 mL) was treated with cesium carbonate (329 mg, 1.0 mmol, 2.0 equiv), and then iodomethane (41 uL, 0.65 mmol, 1.3 equiv). The mixture was stirred for 15 h at rt. Subsequently, the mixture was diluted with DCM (10 mL) and filtered through Celite with additional DCM. The filtrate was then concentrated in vacuo. The resulting residue was purified by flash column chromatography on silica gel (0%→75% EtOAc in heptane) to afford N-(2-chloro-4-(1-methyl-1H-indol-3-yl)pyrimidin-5-yl)-N-methylisobutyramide (L2) as a red solid.

Intermediates L3 & L4

N-(2-((4-fluoro-2-methoxy-5-nitrophenyl)amino)-4-(1-methyl-1H-indol-3-yl)pyrimidin-5-yl)pivalamide N-(2-((2,4-dimethoxy-5-nitrophenyl)amino)-4-(1-methyl-1H-indol-3-yl)pyrimidin-5-yl)pivalamide

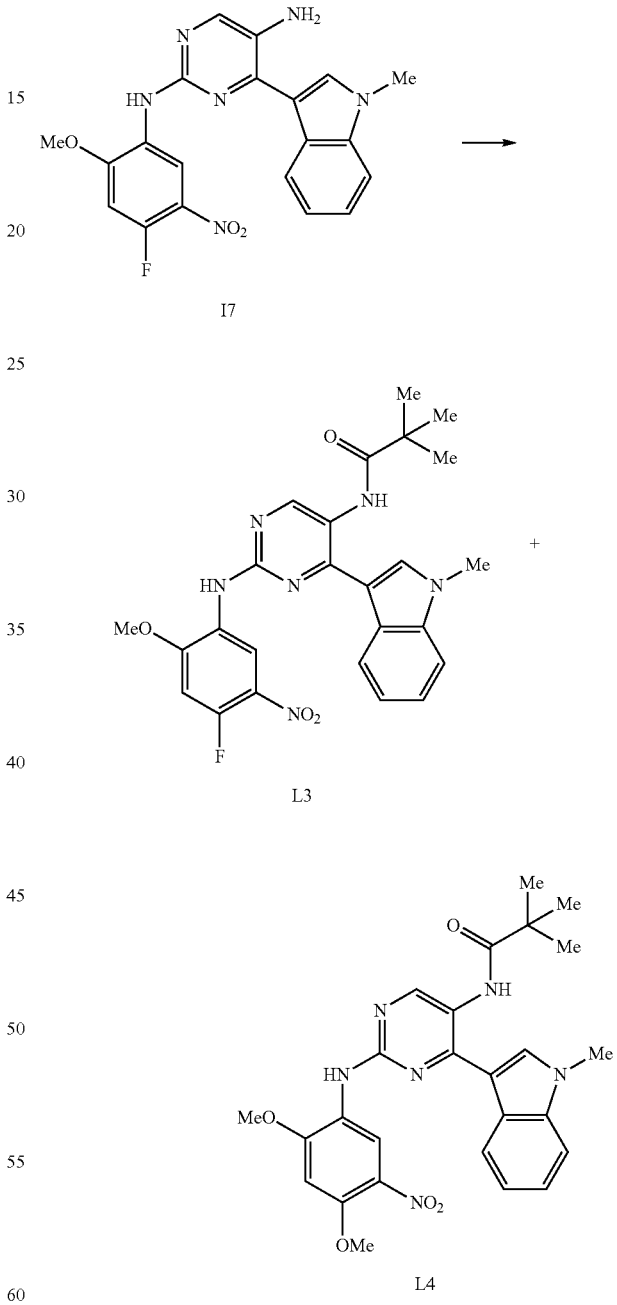

N2-(4-fluoro-2-methoxy-5-nitrophenyl)-4-(1-methyl-1H-indol-3-yl)pyrimidine-2,5-diamine (17) (150 mg, 0.37 mmol) was suspended in DCM (1.8 mL) and treated with trimethylacetyl chloride (50 uL, 0.40 mmol) and triethylamine (102 uL, 0.74 mmol). The mixture was stirred at rt for 1 h. MeOH (1 mL) and potassium carbonate (102 mg, 0.74 mmol) were added to the mixture and stirred at rt for an additional 30 min. The mixture was concentrated in vacuo and purified by flash column chromatography on silica gel (0%→80% EtOAc in heptane) to afford N-(2-((4-fluoro-2-methoxy-5-nitrophenyl)amino)-4-(1-methyl-1H-indol-3-yl)pyrimidin-5-yl)pivalamide (L3) and N-(2-((2,4-dimethoxy-5-nitrophenyl)amino)-4-(1-methyl-1H-indol-3-yl)pyrimidin-5-yl)pivalamide (L4).

Intermediate L5

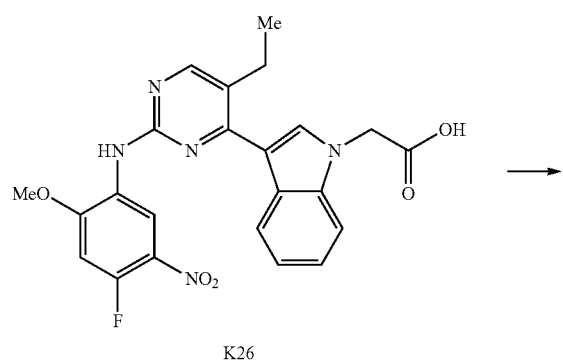

K26

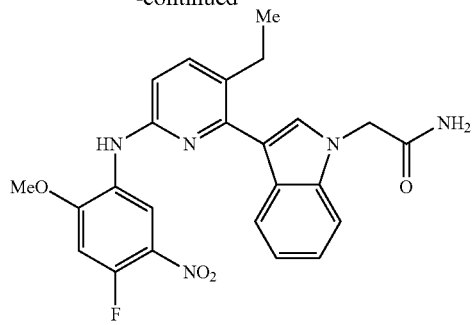

L5

To a solution of 2-(3-(5-ethyl-2-((4-fluoro-2-methoxy-5-nitrophenyl)amino)pyrimidin-4-yl)-1H-indol-1-yl)acetic acid (K26) (0.34 g, 0.73 mmol) in DMF (3.6 mL) was added 1-hydroxybenzotriazole hydrate (0.33 g, 2.19 mmol), N-(3-dimethylaminopropyl)-N'-ethylcarbodiimide hydrochloride (0.42 g, 2.19 mmol), ammonium chloride (0.39 g, 7.30 mmol), and then diisopropylethylamine (0.64 ml, 3.65 mmol). The resulting mixture was stirred overnight at rt. Subsequently, brine (50 mL) was added to the mixture, and the precipitates were collected by vacuum filtration. The collected solids were washed with water (100 mL), and then dried in vacuo at 60° C. to afford 2-(3-(3-ethyl-6-((4-fluoro-2-methoxy-5-nitrophenyl)amino)pyridin-2-yl)-1H-indol-1-yl)acetamide (L5) as a brown solid.

The following compounds in Table 16 were prepared in analogous fashion to Intermediate L5.

TABLE 16

| Compound | Acid | Amine |
|---|---|---|
| L6 | K25 | NH4Cl |
| L7 | K26 | H2NMe |

219
Intermediate L8

3-(2-((4-((2-(dimethylamino)ethyl)(methyl)amino)-2-methoxy-5-nitrophenyl)amino)pyrimidin-4-yl)-1-methyl-1H-indole-2-carboxylic acid

220
Intermediate L9

3-(2-((4-((2-(dimethylamino)ethyl)(methyl)amino)-2-methoxy-5-nitrophenyl)amino)pyrimidin-4-yl)-1-methyl-1H-indole-2-carboxamide

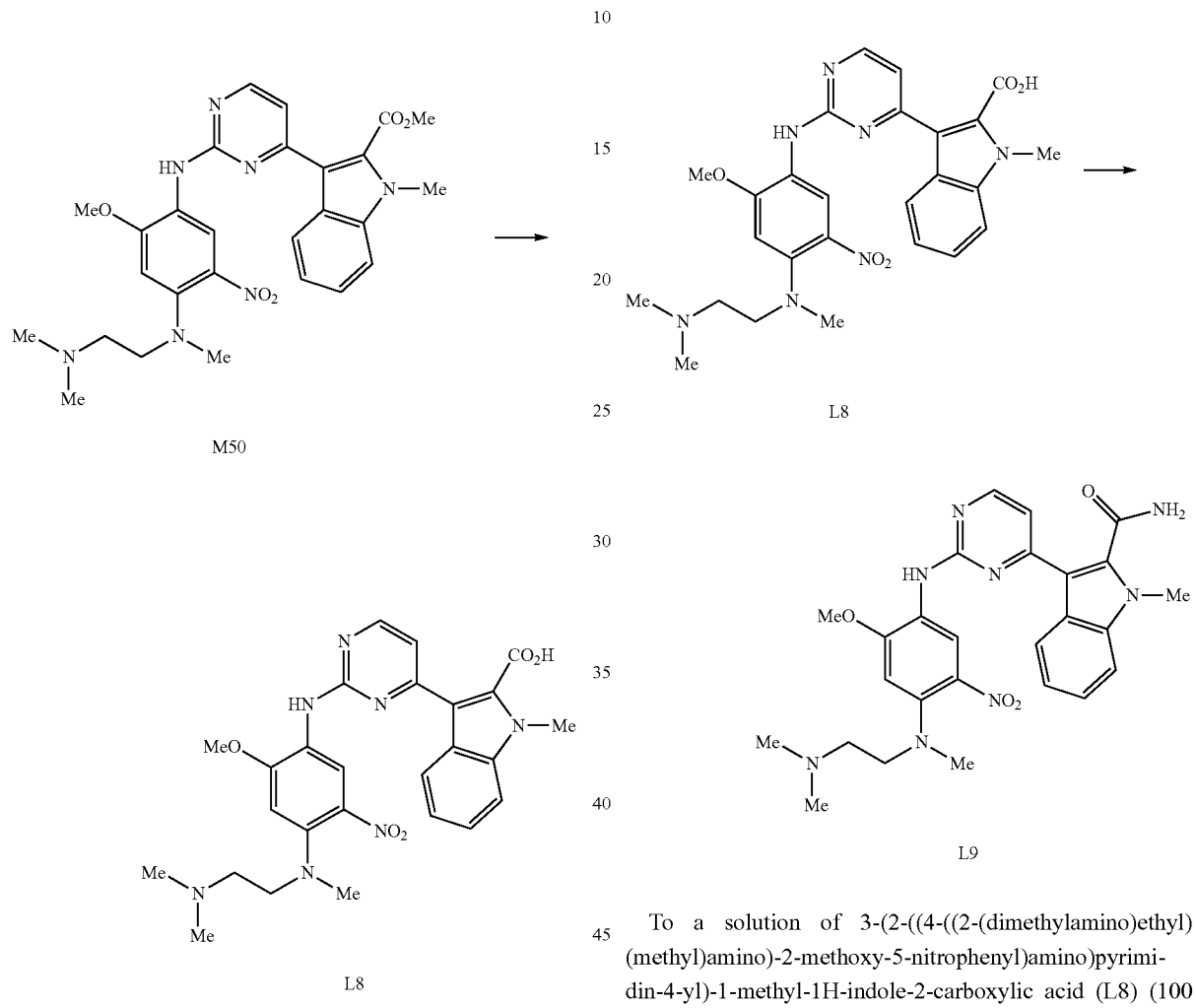

To a mixture of methyl 3-(2-((4-((2-(dimethylamino)ethyl)(methyl)amino)-2-methoxy-5-nitrophenyl)amino)pyrimidin-4-yl)-1-methyl-1H-indole-2-carboxylate (M50) (2.5 g, 4.7 mmol) in MeOH (10 mL) was added aqueous sodium hydroxide (7 mL, 2 N), and the resulting mixture was stirred at 70° C. for 1 h. Upon cooling, HCl (1 N) was added to the mixture until the pH was approximately 5. Subsequently, the mixture was concentrated in vacuo, and the resulting residue was diluted with MeOH and filtered. The filtrate was concentrated in vacuo to afford 3-(2-((4-((2-(dimethylamino)ethyl)(methyl)amino)-2-methoxy-5-nitrophenyl)amino)pyrimidin-4-yl)-1-methyl-1H-indole-2-carboxylic acid (L8) as a red solid.

To a solution of 3-(2-((4-((2-(dimethylamino)ethyl)(methyl)amino)-2-methoxy-5-nitrophenyl)amino)pyrimidin-4-yl)-1-methyl-1H-indole-2-carboxylic acid (L8) (100 mg, 0.19 mmol) in DMF (3 mL), was added HOBt (39 mg, 0.29 mmol) and EDCl (56 mg, 0.29 mmol). The resulting solution was stirred at rt for 20 min before ammonia in dioxane (0.95 mL, 0.4 M in THF) was added, followed by the addition of TEA (0.079 mL, 0.57 mmol). Subsequently, the mixture was stirred at rt for 1 h. The mixture was then diluted with water and extracted with EtOAc, and the combined organic layers were dried over magnesium sulfate, filtered, and concentrated in vacuo to afford 3-(2-((4-((2-(dimethylamino)ethyl)(methyl)amino)-2-methoxy-5-nitrophenyl)amino)pyrimidin-4-yl)-1-methyl-1H-indole-2-carboxamide (L9) as a red solid.

The following intermediate compounds, as shown in Table 17, were synthesized in analogous fashion to Intermediate L9.

TABLE 17
| Intermediate L | Acid | Amine |
|---|---|---|
| 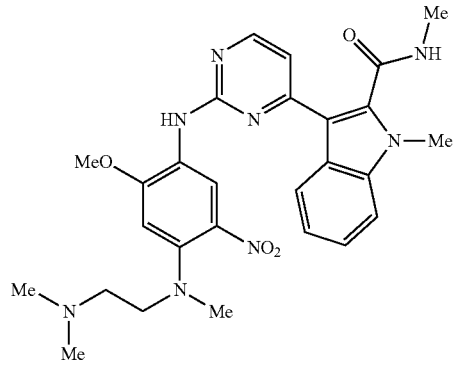 L10 | 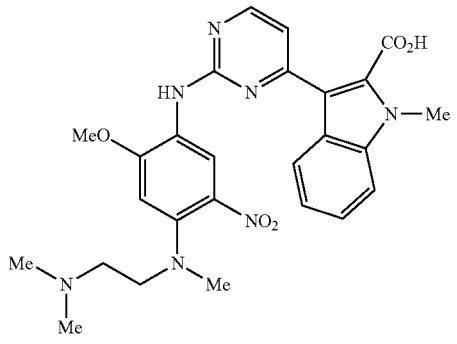 L8 | 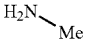 |
| 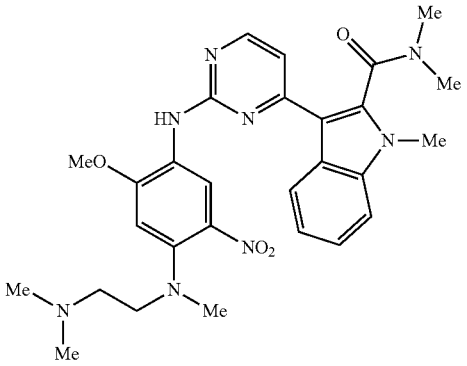 L11 | 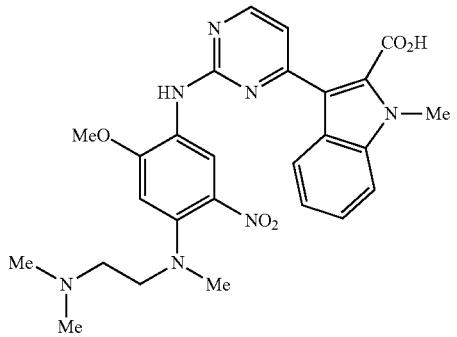 L8 |  |
| 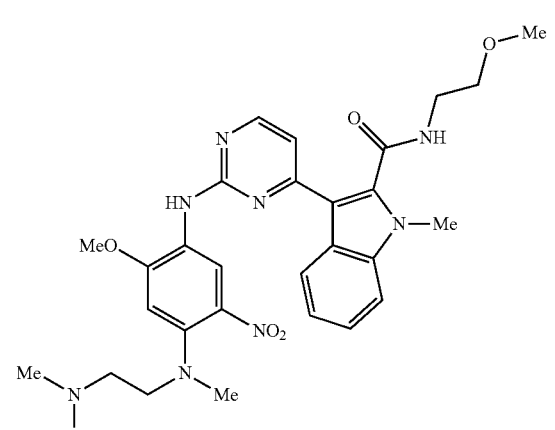 L12 | 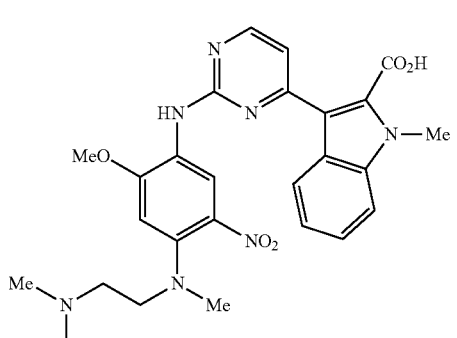 L8 | 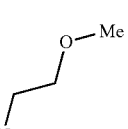 |

Intermediate M1 le;4qN1-(4-(2-(3,6-dihydro-2H-pyran-4-yl)-1-methyl-1H-indol-3-yl)-1,3,5-triazin-2-yl)-N4-(2-(dimethylamino)ethyl)-2-methoxy-N4-methyl-5-nitrobenzene-1,4-diamine

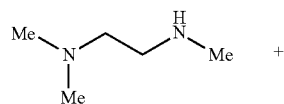

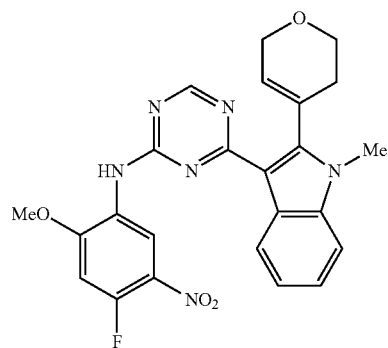

I1

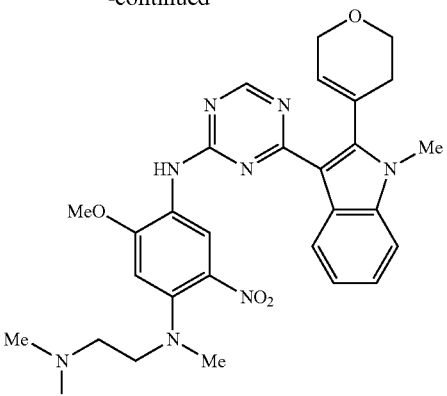

M1

A mixture of 4-(2-(3,6-dihydro-2H-pyran-4-yl)-1-methyl-1H-indol-3-yl)-N-(4-fluoro-2-methoxy-5-nitrophenyl)-1,3,5-triazin-2-amine (11) (383 mg, 0.80 mmol) and N,N,N'-trimethylethylenediamine (114 uL, 0.88 mmol) in MeCN (1.1 mL) was treated with potassium carbonate (334 mg, 2.40 mmol). The resulting mixture was stirred for 90 min at 80° C. Upon cooling, the mixture was filtered through a pad of Celite and rinsed with EtOAc. The filtrate was concentrated in vacuo and the resulting residue was purified by flash column chromatography on silica gel (0%→5% 1.4 N ammonia in MeOH/DCM) to afford N1-(4-(2-(3,6-dihydro-2H-pyran-4-yl)-1-methyl-1H-indol-3-yl)-1,3,5-triazin-2-yl)-N4-(2-(dimethylamino)ethyl)-2-methoxy-N4-methyl-5-nitrobenzene-1,4-diamine (M1) as a red oil.

The following intermediate compounds, as shown in Table 18, were synthesized in analogous fashion to intermediate M1.

TABLE 18

| Intermediate M | Aryl fluroide | Amine |
|---|---|---|
| M2 | I2 | (structure) |

TABLE 18-continued
| Intermediate M | Aryl fluroide | Amine |
|---|---|---|
| 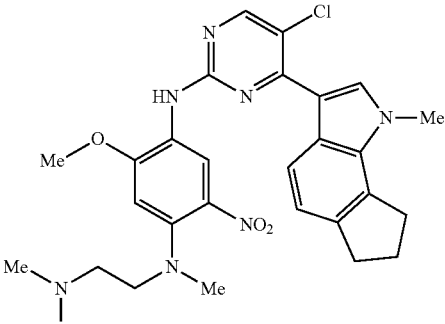 M3 | 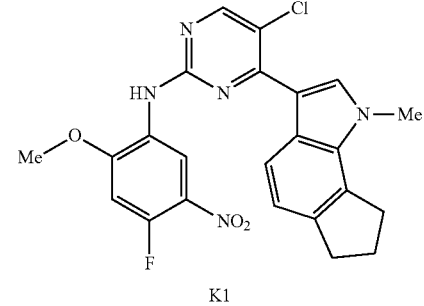 K1 | 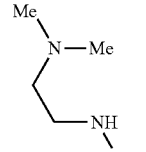 |
| 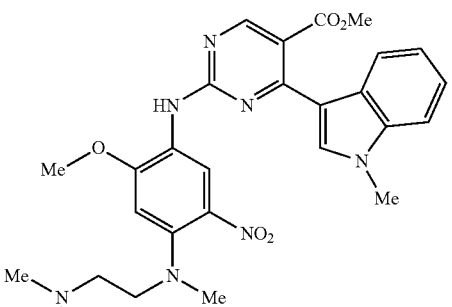 M4 | 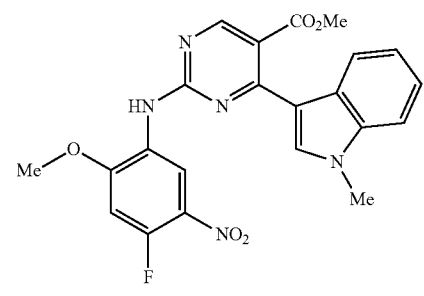 K3 | 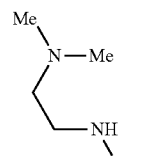 |
| 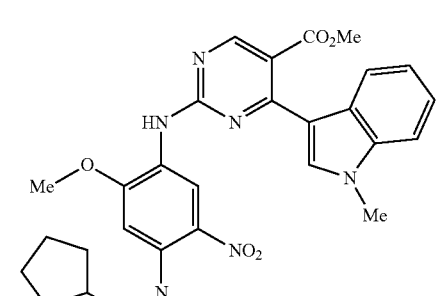 M5 | 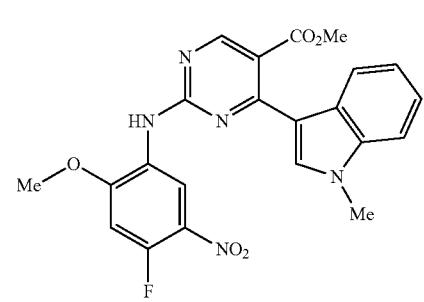 K3 | 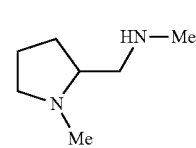 |
| 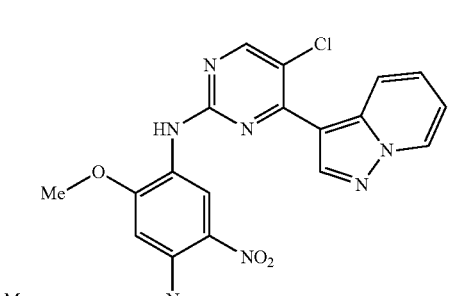 M6 | 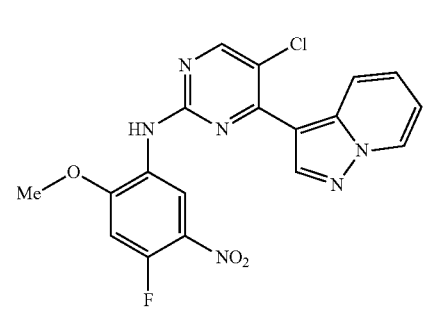 K9 | 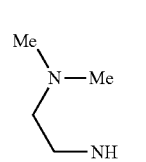 |

TABLE 18-continued

| Intermediate M | Aryl fluroide | Amine |
|---|---|---|
| M7 | K9 | Me-NH, N-Me (3-(dimethylamino)azetidine) |
| M8 | K9 | 1-methylpiperazine |
| M9 | K9 | N,N-diethyl-N'-methylethylenediamine |
| M10 | K9 | N-methyl-2-(4-methylpiperazin-1-yl)ethanamine |

TABLE 18-continued
| Intermediate M | Aryl fluroide | Amine |
|---|---|---|
| 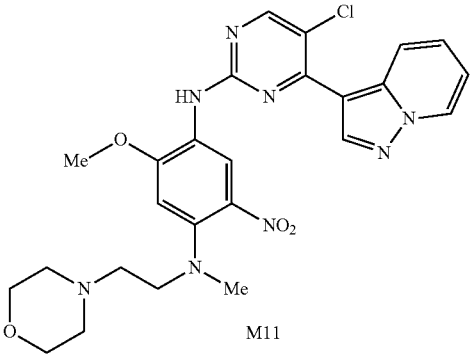 M11 | 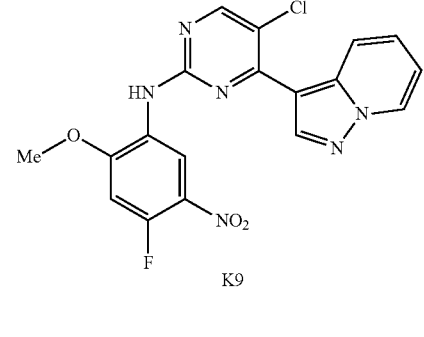 K9 | 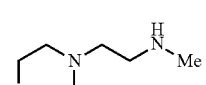 |
| 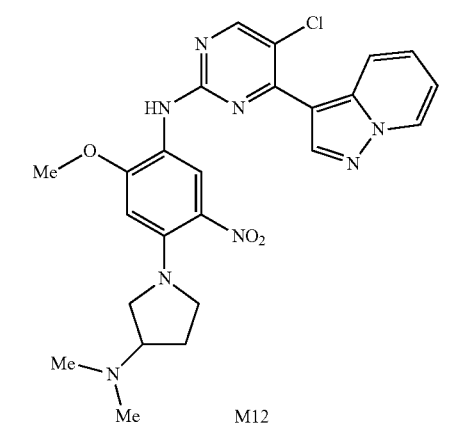 M12 | 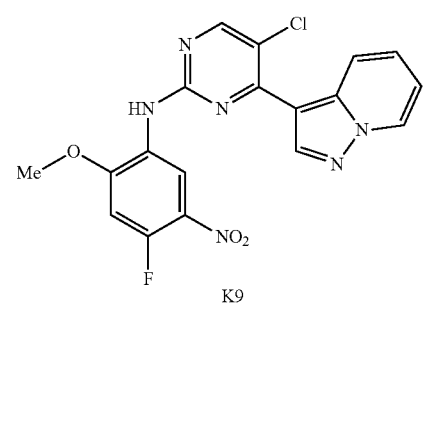 K9 | 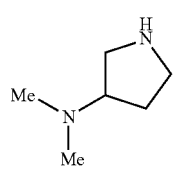 |
| 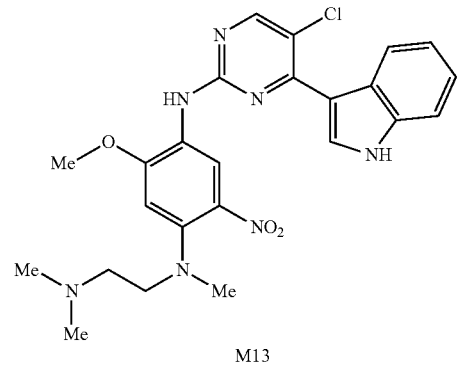 M13 | 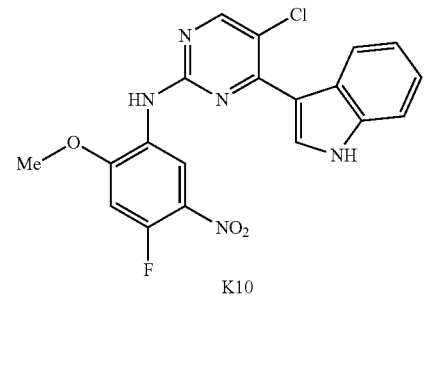 K10 | 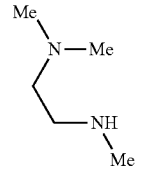 |
| 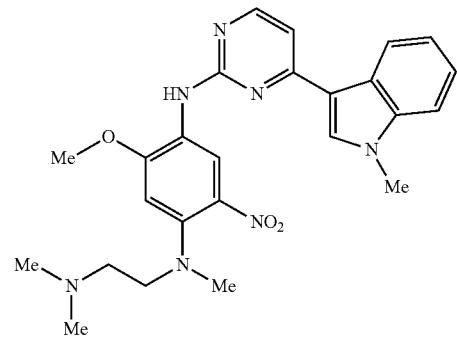 M14 | 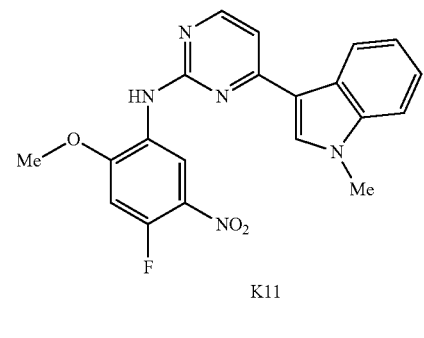 K11 | 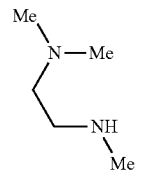 |

TABLE 18-continued
| Intermediate M | Aryl fluroide | Amine |
|---|---|---|
| 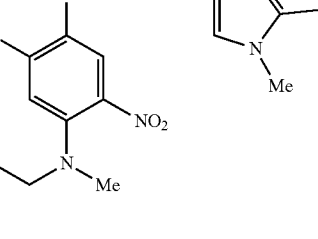 M15 | 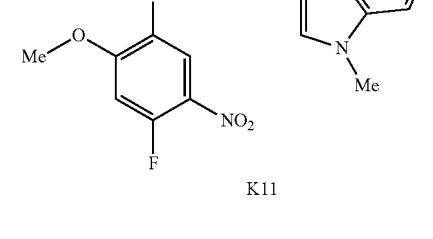 K11 | 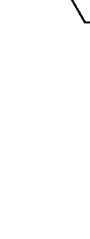 |
| 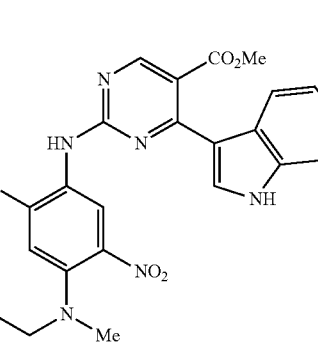 M16 | 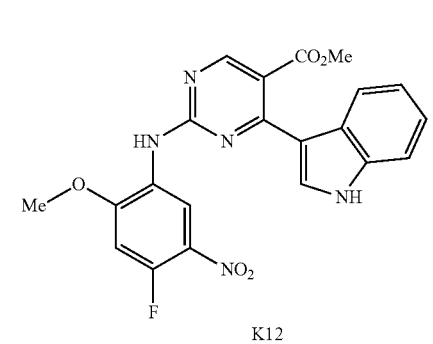 K12 | 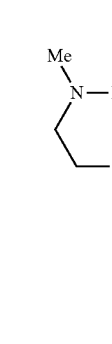 |
| 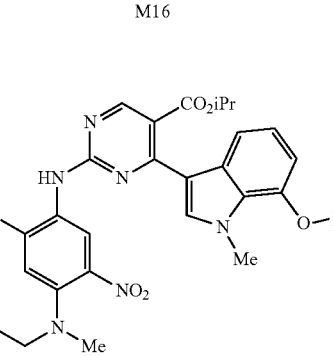 M17 | 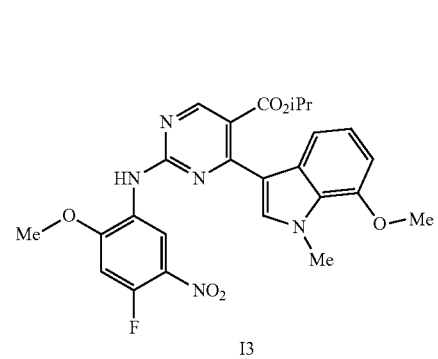 I3 | 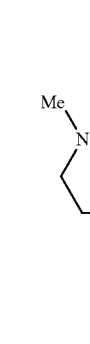 |
| 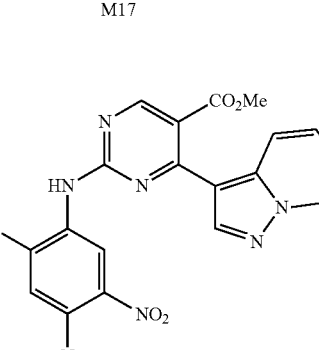 M18 | 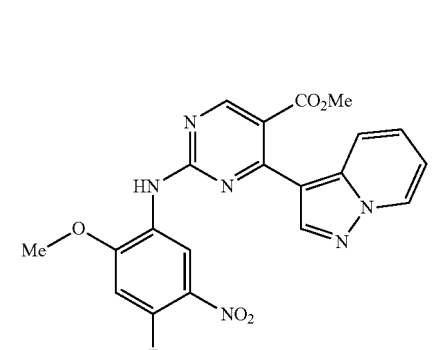 I4 | 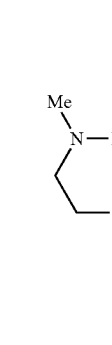 |

TABLE 18-continued
| Intermediate M | Aryl fluroide | Amine |
|---|---|---|
| 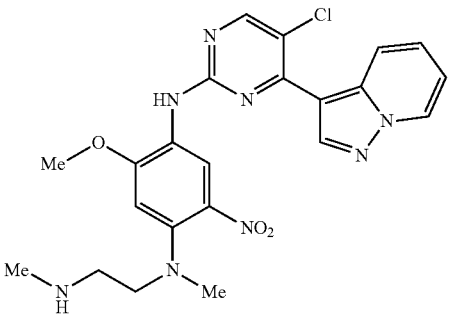 M19 | 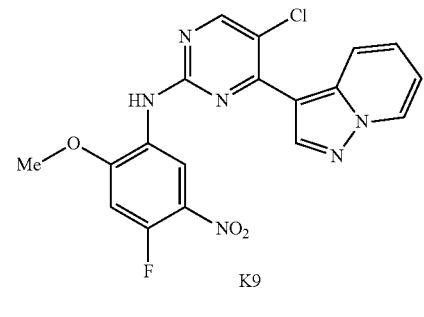 K9 | 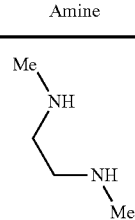 |
| 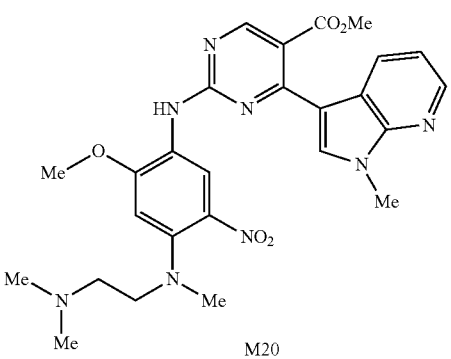 M20 | 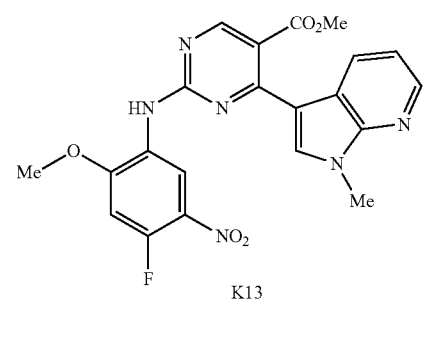 K13 | 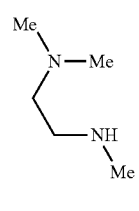 |
| 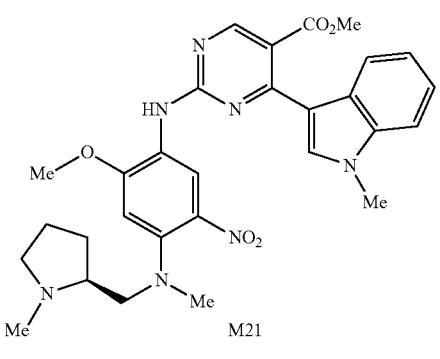 M21 | 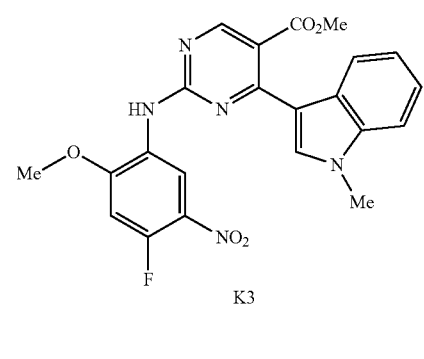 K3 | 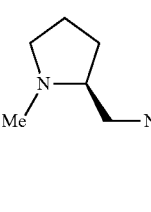 |
| 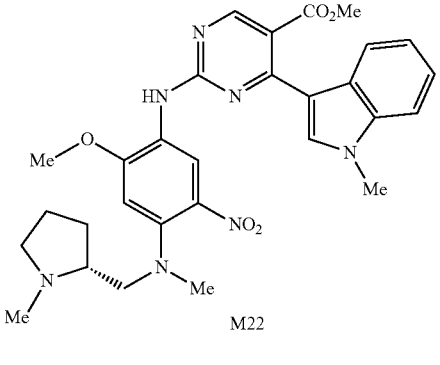 M22 | 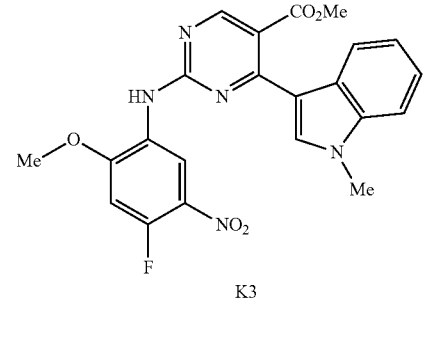 K3 | 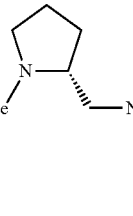 |

TABLE 18-continued
| Intermediate M | Aryl fluroide | Amine |
|---|---|---|
| 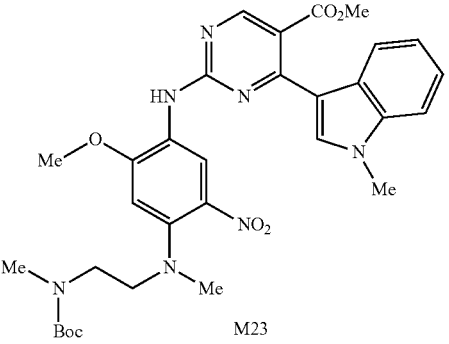 M23 | 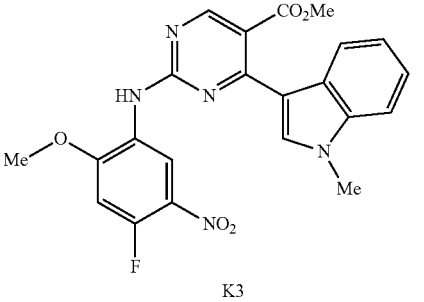 K3 | 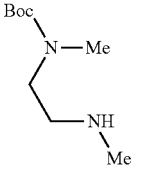 |
| 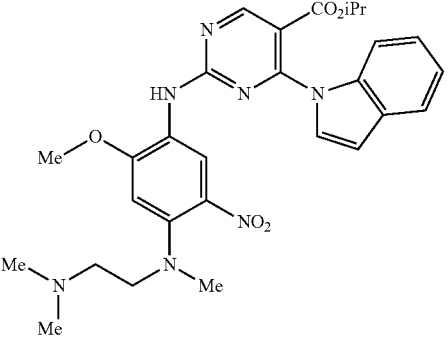 M24 | 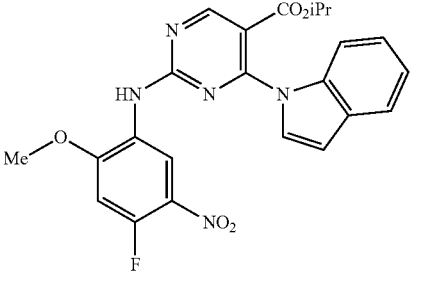 K14 | 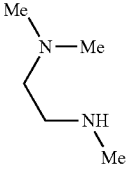 |
| 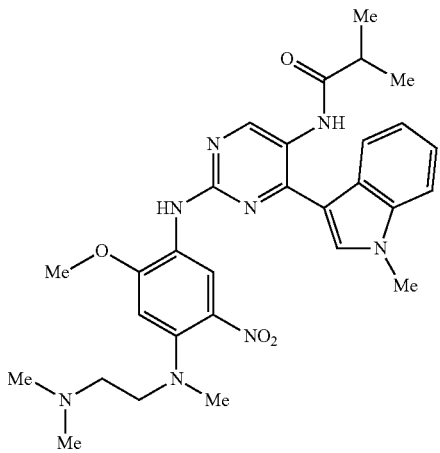 M25 | 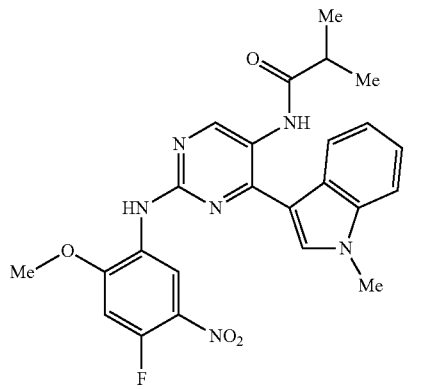 L1 | 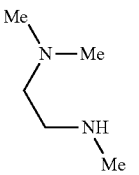 |

TABLE 18-continued
| Intermediate M | Aryl fluroide | Amine |
|---|---|---|
| 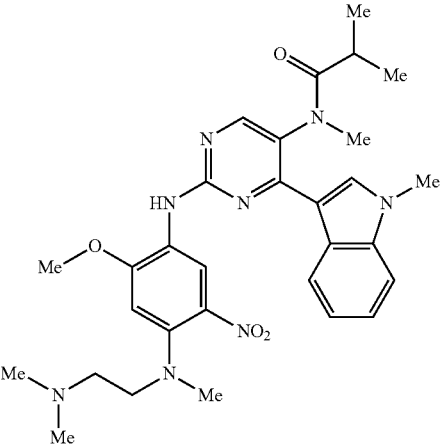<br>M26 | 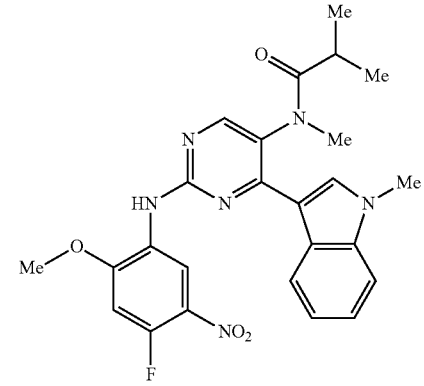<br>L2 | 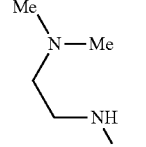 |
| 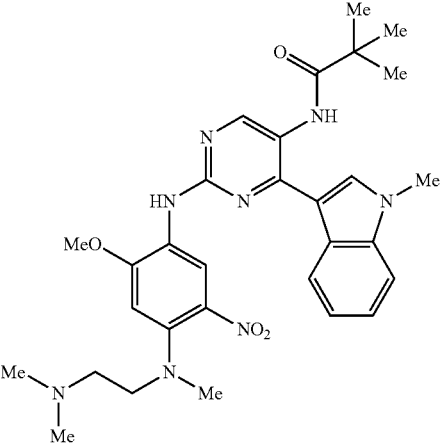<br>M27 | 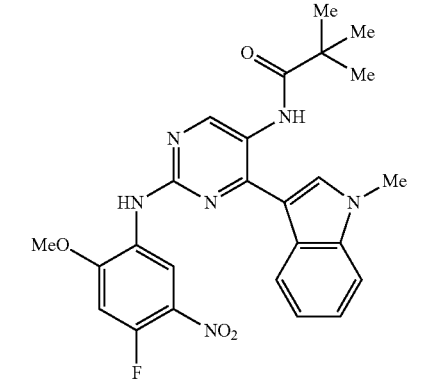<br>L3 | 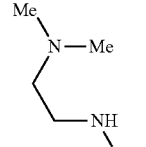 |
| 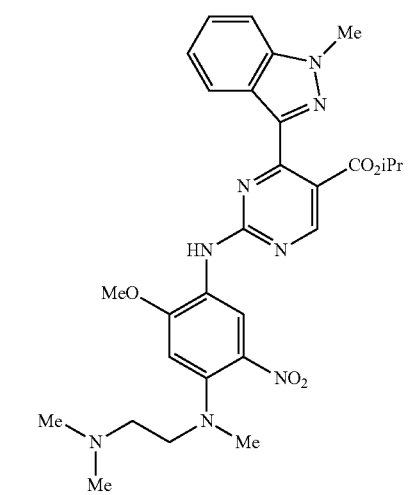<br>M28 | 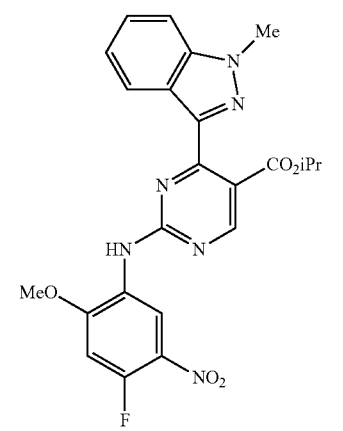<br>K16 | 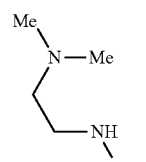 |

TABLE 18-continued
| Intermediate M | Aryl fluroide | Amine |
|---|---|---|
| M29 | K17 | 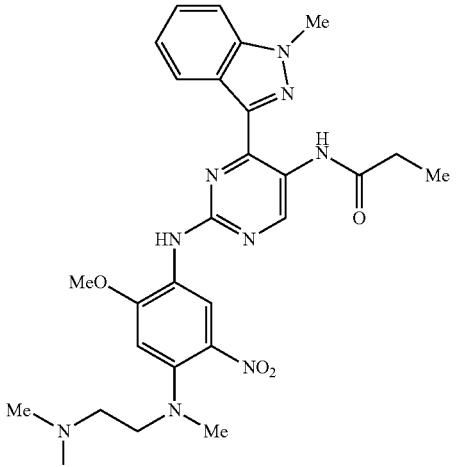 |
| M30 | K14 | 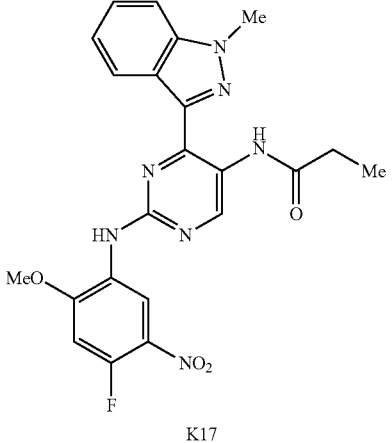 [SMILES: CCC(=O)Nc1cnc(Nc2cc([N+](=O)[O-])c(F)cc2OC)nc1-c1nn(C)c2ccccc12 ; "K17"] |
| M31 | K18 | 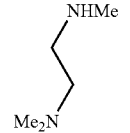 |

TABLE 18-continued
| Intermediate M | Aryl fluroide | Amine |
|---|---|---|
| 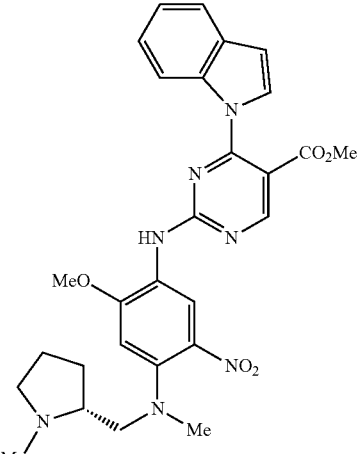<br>M32 | 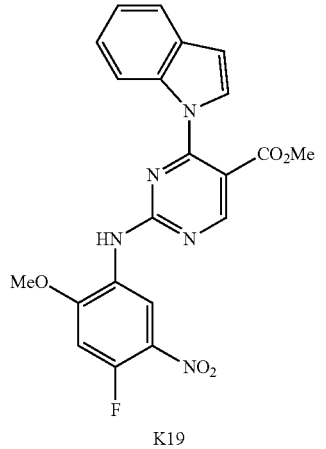<br>K19 | 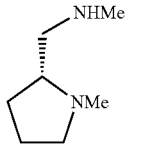 |
| 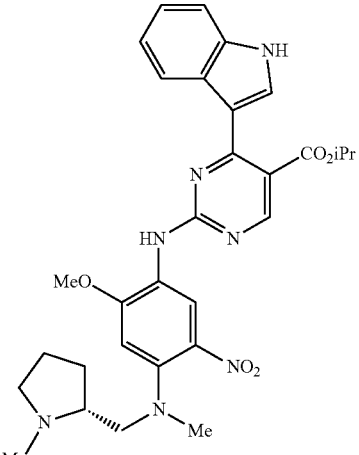<br>M33 | 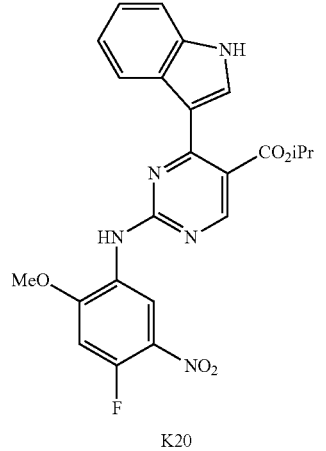<br>K20 | 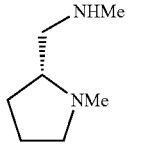 |
| 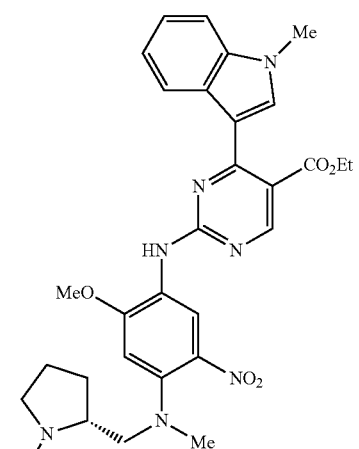<br>M34 | 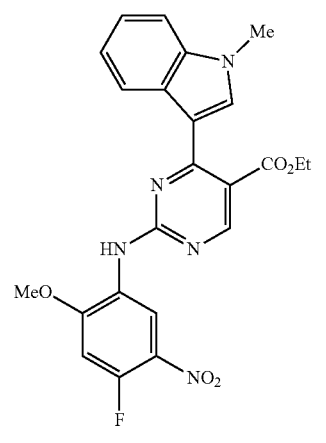<br>K21 | 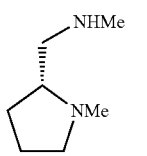 |

TABLE 18-continued
| Intermediate M | Aryl fluroide | Amine |
|---|---|---|
| 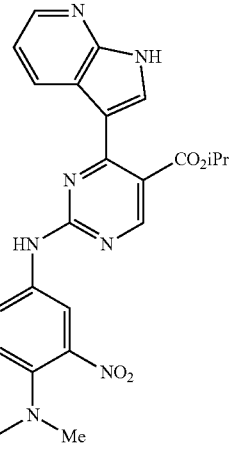 M35 | 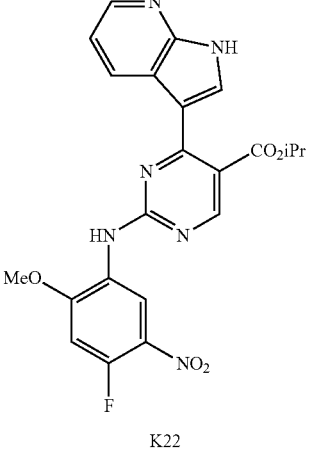 K22 | 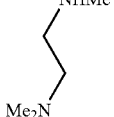 |
| 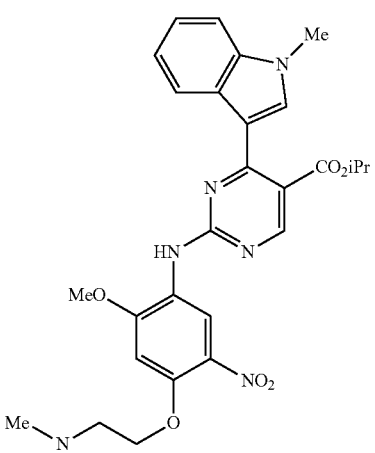 M36 | 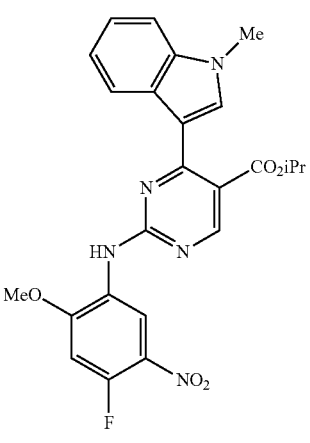 K23 | 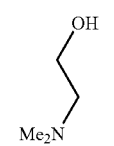 |
| 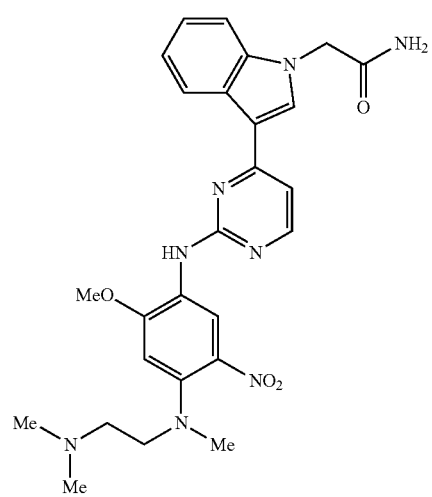 M37 | 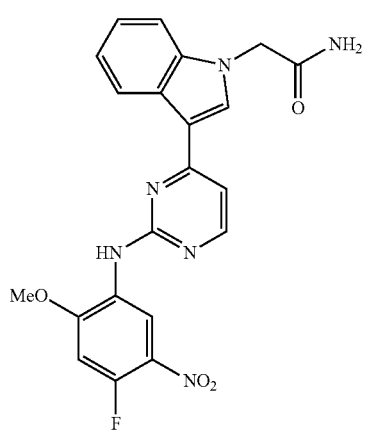 L6 | 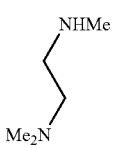 |

TABLE 18-continued
| Intermediate M | Aryl fluroide | Amine |
|---|---|---|
| 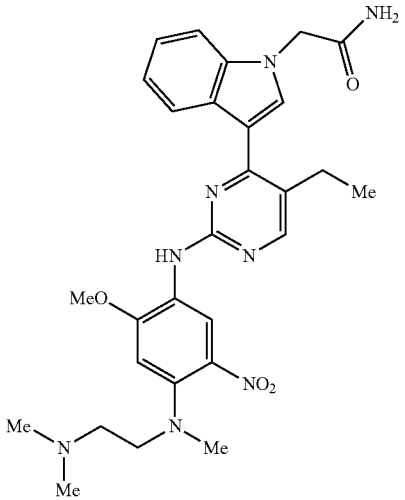 M38 | 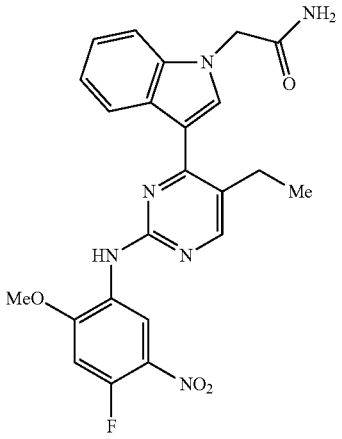 L5 | 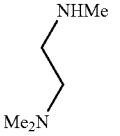 |
| 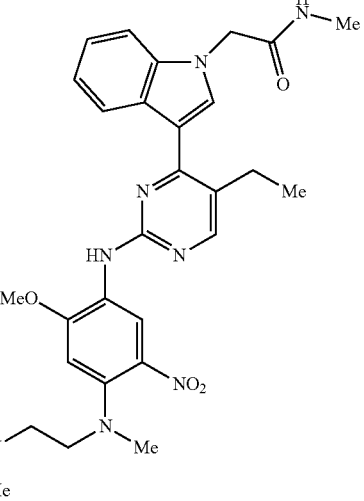 M39 | 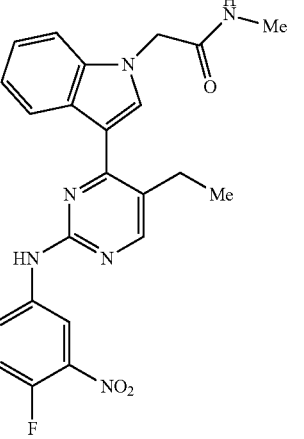 L7 | 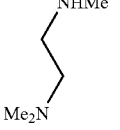 |
| 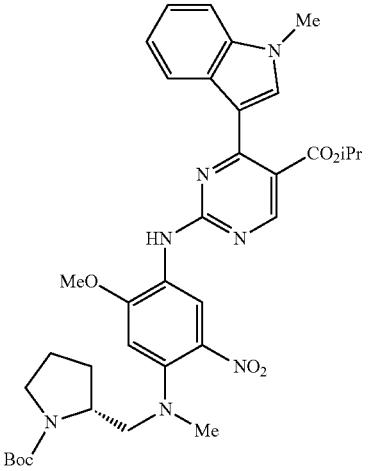 M40 | 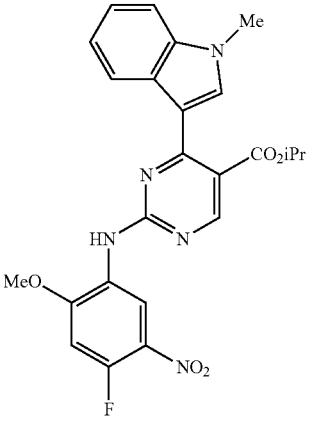 K23 | 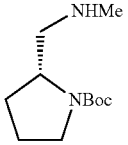 |

TABLE 18-continued
| Intermediate M | Aryl fluroide | Amine |
| --- | --- | --- |
| 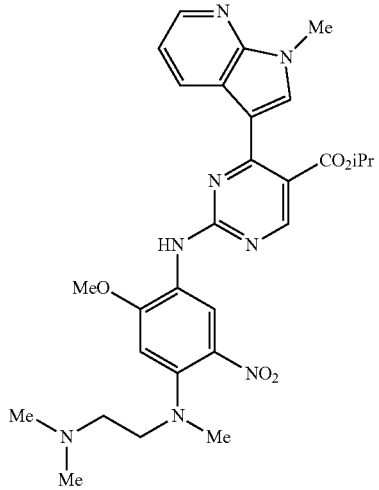<br>M41 | 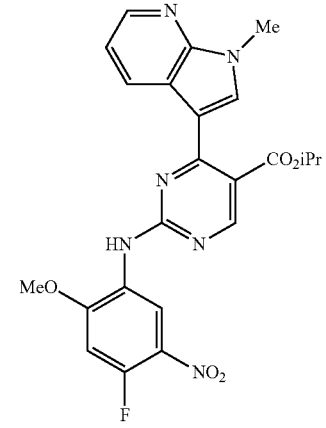<br>K27 | 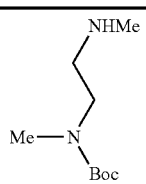 |
| 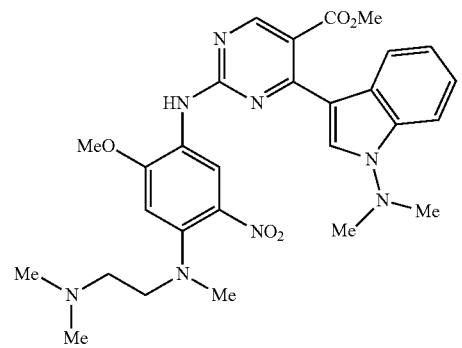<br>M42 | 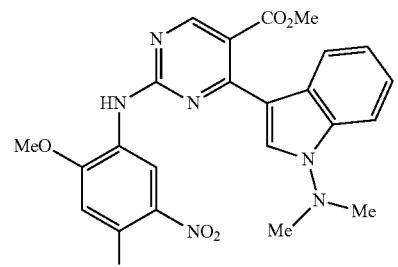<br>K28 | 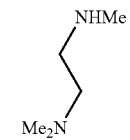 |
| 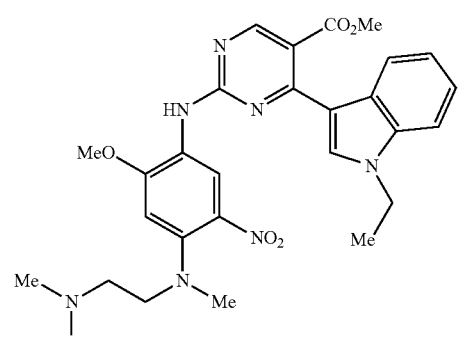<br>M43 | 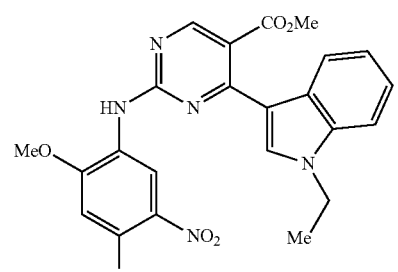<br>K29 | 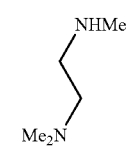 |

TABLE 18-continued
| Intermediate M | Aryl fluroide | Amine |
|---|---|---|
| 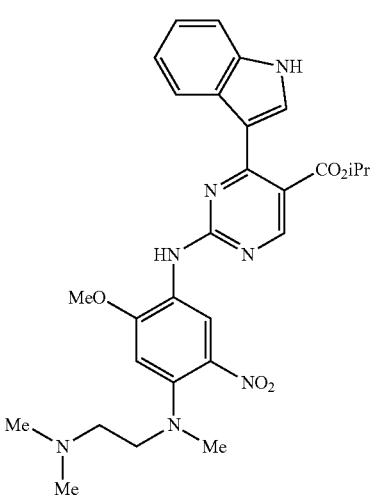<br>M44 | 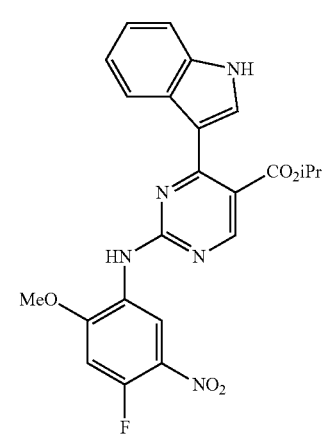<br>K20 | 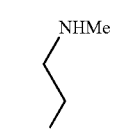 |
| 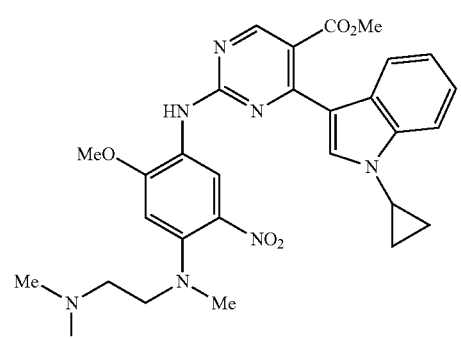<br>M45 | 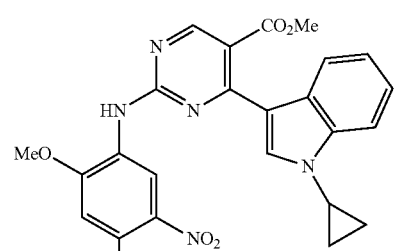<br>K30 | 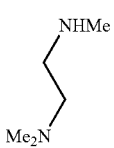 |
| 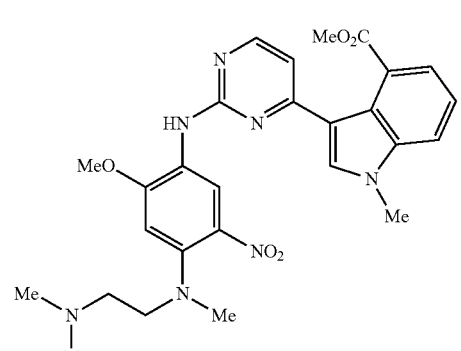<br>M46 | 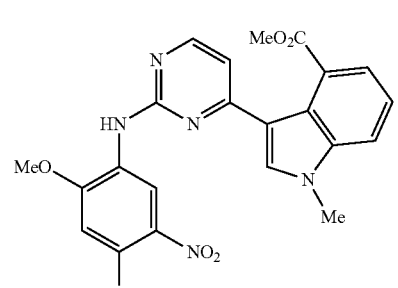<br>K31 | 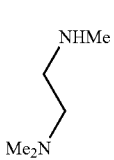 |

TABLE 18-continued
| Intermediate M | Aryl fluroide | Amine |
|---|---|---|
| 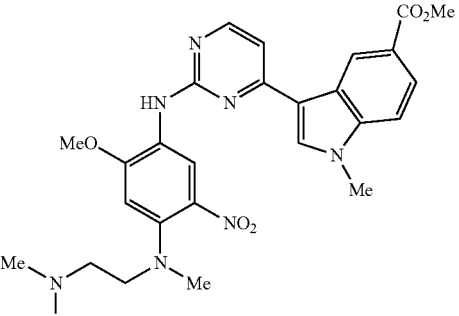<br>M47 | 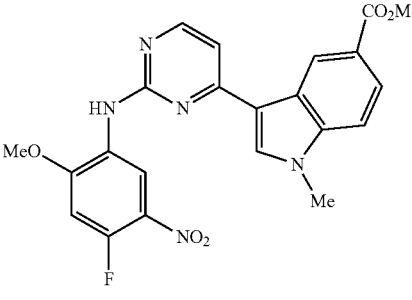<br>K32 | 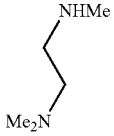 |
| 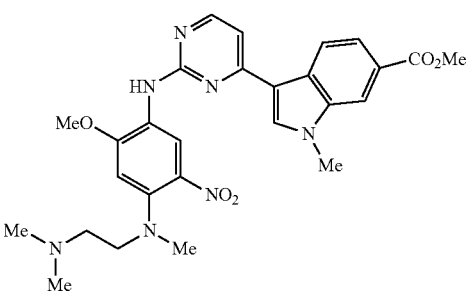<br>M48 | 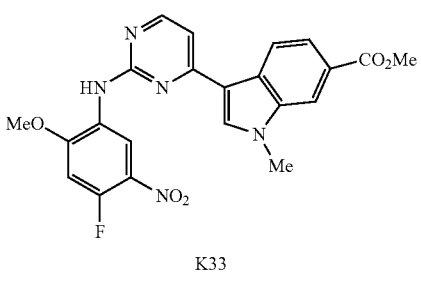 [SMILES: COC(=O)c1ccc2c(-c3ccnc(Nc4cc([N+](=O)[O-])c(F)cc4OC)n3)cn(C)c2c1 ; "K33"]<br>K33 | 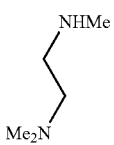 |
| 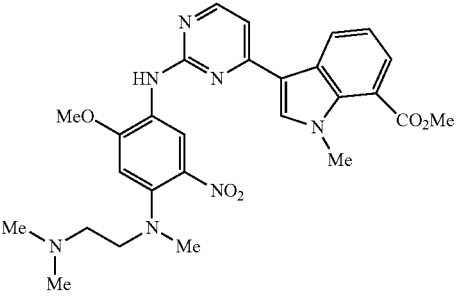<br>M49 | 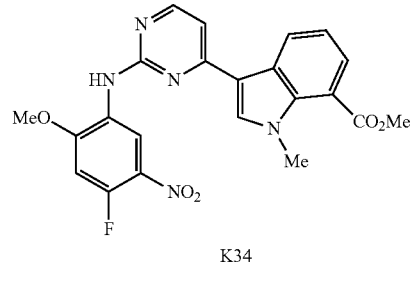 [SMILES: COC(=O)c1cccc2c(-c3ccnc(Nc4cc([N+](=O)[O-])c(F)cc4OC)n3)cn(C)c12 ; "K34"]<br>K34 | 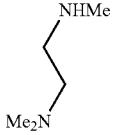 |
| 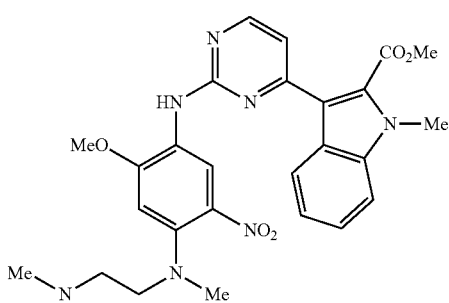<br>M50 | 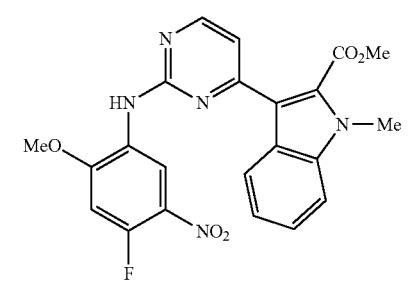<br>K35 | 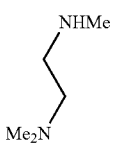 |

TABLE 18-continued

| Intermediate M | Aryl fluroide | Amine |
|---|---|---|
| M51 | K36 | NHMe, Me2N |
| M52 | K37 | NHMe, Me2N |
| M53 | K38 | NHMe, Me2N |
| M54 | K39 | NHMe, Me2N |

TABLE 18-continued
| Intermediate M | Aryl fluroide | Amine |
|---|---|---|
| 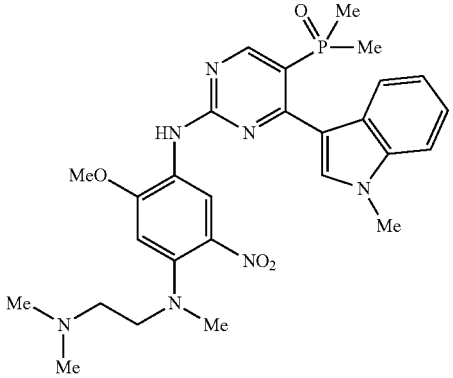 M55 | 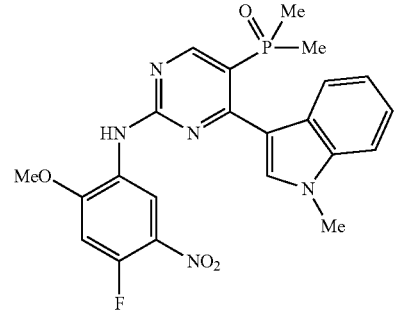 K40 | 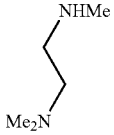 |
| 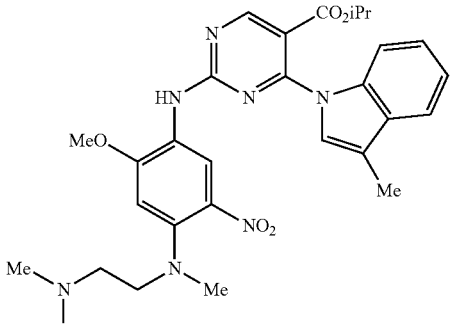 M56 | 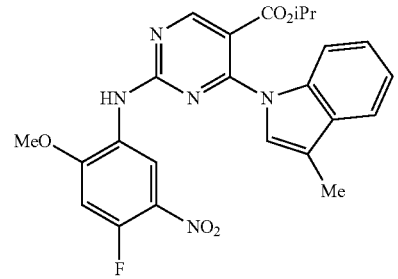 K41 | 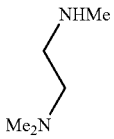 |
| 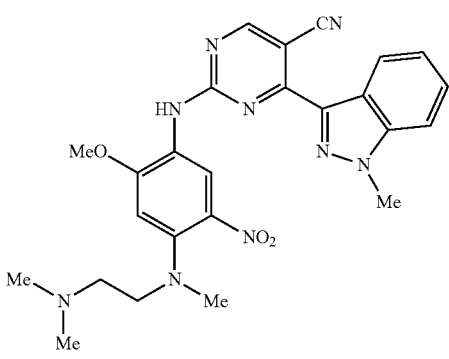 M57 | 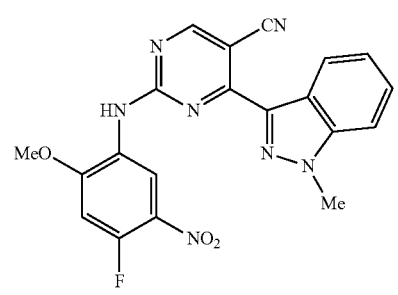 K42 | 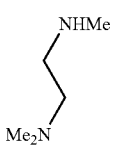 |

TABLE 18-continued

| Intermediate M | Aryl fluroide | Amine |
|---|---|---|
| 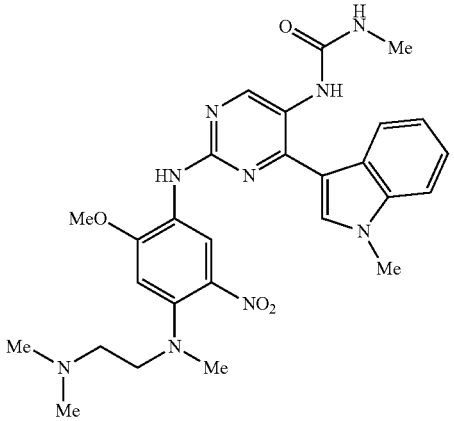 M58 | 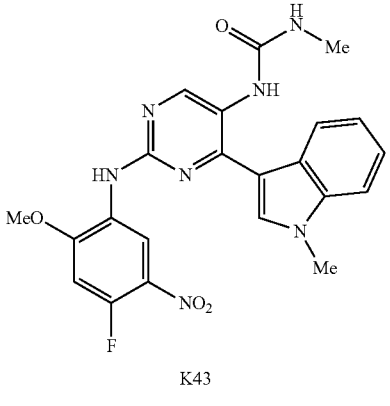 K43 | 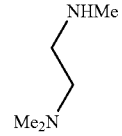 |

Intermediate N1

(R)-5-chloro-N-(4-((1-(dimethylamino)-3-ethoxy-propan-2-yl)oxy)-2-methoxy-5-nitrophenyl)-4-(1-methyl-1H-indol-3-yl)pyrimidin-2-amine

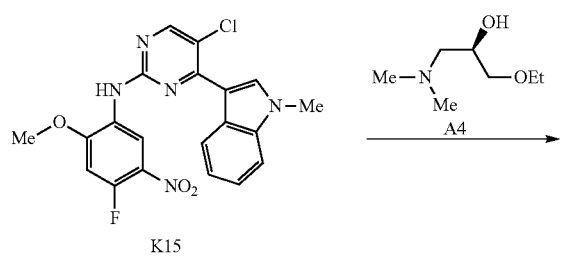

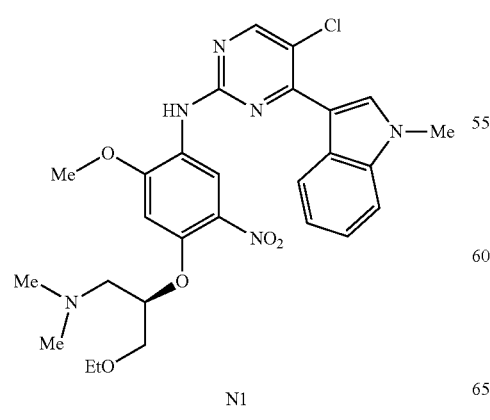

N1

To a solution of (R)-1-(dimethylamino)-3-ethoxypropan-2-ol (A4) (131 mg, 0.9 mmol) in DMF (5 mL) was added sodium hydride (72 mg, 1.8 mmol, 60% dispersion in oil) at rt. After stirring at rt for 10 min, 5-chloro-N-(4-fluoro-2-methoxy-5-nitrophenyl)-4-(1-methyl-1H-indol-3-yl)pyrimidin-2-amine (K15) (190 mg, 0.45 mmol) was added, the mixture was stirred at rt for 4 h. Subsequently, the mixture was concentrated in vacuo, and the resulting residue was dissolved in DCM and washed with saturated ammonium chloride. The aqueous phase was extracted with DCM (2×20 mL) and the organic layers were combined, dried over sodium sulfate, filtered and concentrated in vacuo. The resulting residue was purified by flash column chromatography on silica gel (5% MeOH/DCM) to afford (R)-5-chloro-N-(4-((1-(dimethylamino)-3-ethoxypropan-2-yl)oxy)-2-methoxy-5-nitrophenyl)-4-(1-methyl-1H-indol-3-yl)pyrimidin-2-amine (N1).

The following intermediate compounds, as shown in Table 19, were synthesized in analogous fashion to intermediate N1.

TABLE 19
| Intermediate N | Aryl fluroide | Alcohol |
|---|---|---|
| 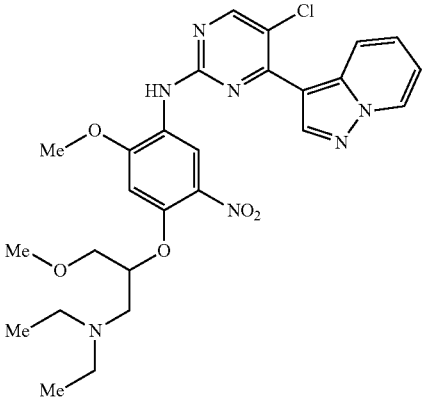<br>N2 | 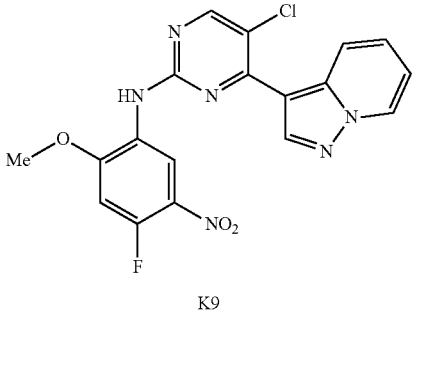<br>K9 | 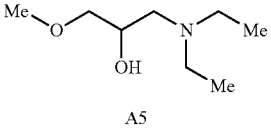<br>A5 |
| 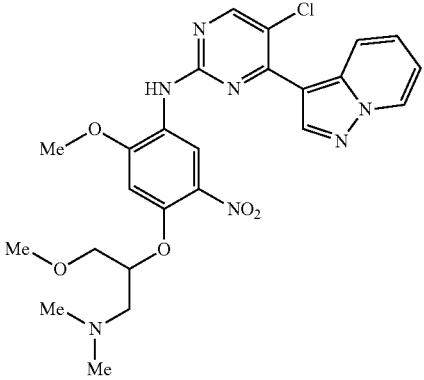<br>N3 | 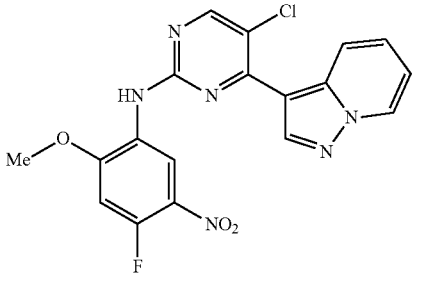<br>K9 | 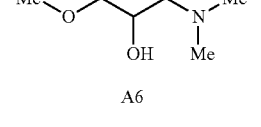<br>A6 |
| 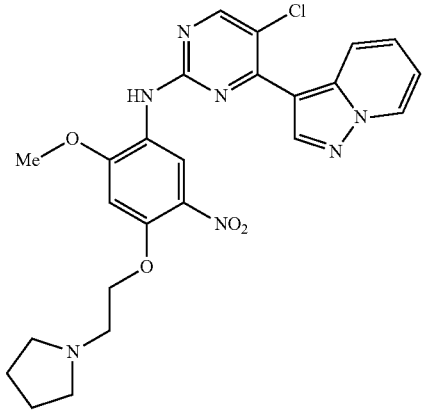<br>N4 | 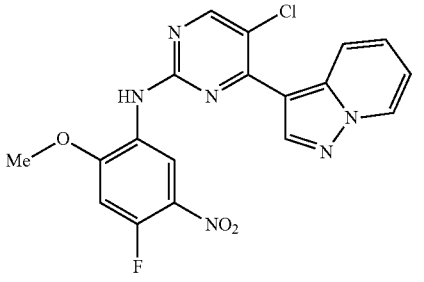<br>K9 | 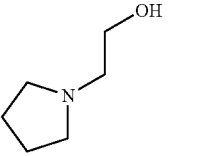 |

TABLE 19-continued

| Intermediate N | Aryl fluroide | Alcohol |
|---|---|---|
| N5 | K9 | |
| N6 | K9 | |

Intermediate O1

5-chloro-N-(4-(3-(dimethylamino)prop-1-yn-1-yl)-2-methoxy-5-nitrophenyl)-4-(1-methyl-1H-indol-3-yl)pyrimidin-2-amine

O1

To a mixture of N-(4-bromo-2-methoxy-5-nitrophenyl)-5-chloro-4-(1-methyl-1H-indol-3-yl)pyrimidin-2-amine (K2) (110 mg, 0.22 mmol), bis(triphenylphosphine)-palladium(II) dichloride (8 mg, 0.011 mmol), and copper(I) iodide (4 mg, 0.022 mmol) in DMF (3 mL) was added N,N-diisopropylethylamine (0.06 mL, 0.36 mmol) and N,N-dimethylpropargylamine (30 mg, 0.060 mL, 0.36 mmol). The resulting mixture was heated at 90° C. overnight. Upon cooling, the mixture was concentrated in vacuo and the resulting residue was purified by flash column chromatography on silica gel (5% MeOH/DCM) to afford 5-chloro-N-(4-(3-(dimethylamino)prop-1-yn-1-yl)-2-methoxy-5-nitrophenyl)-4-(1-methyl-1H-indol-3-yl)pyrimidin-2-amine (O1) as a brown residue.

The following intermediate compounds, as shown in Table 20, were synthesized in analogous fashion to intermediate 01.

TABLE 20

| Intermediate O | Aryl bromide | Alkyne |
|---|---|---|
| 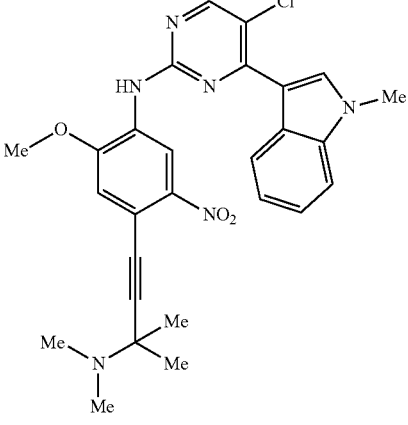 O2 | 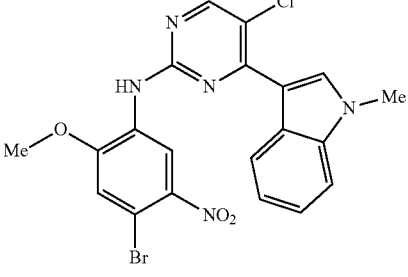 K2 | 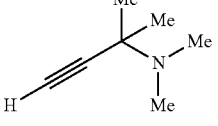 |
| 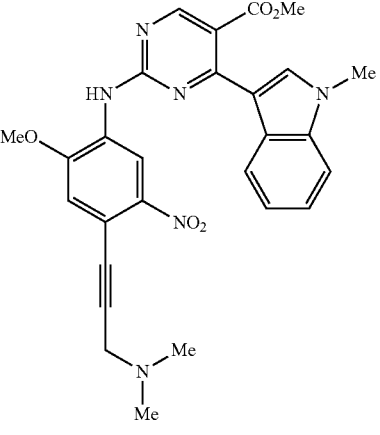 O3 | 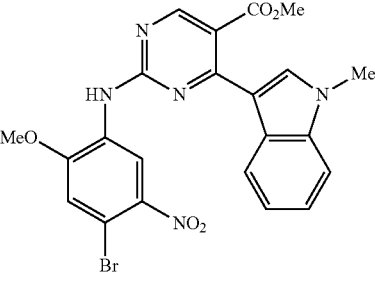 K24 | 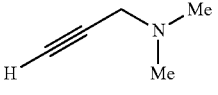 |

Intermediate P1

N1-(5-chloro-4-(pyrazolo[1,5-a]pyridin-3-yl)pyrimidin-2-yl)-N4-(2-((2-fluoroethyl)(methyl)amino)ethyl)-2-methoxy-N4-methyl-5-nitrobenzene-1,4-diamine

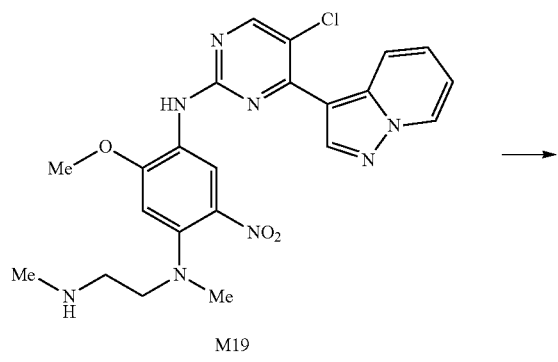

M19

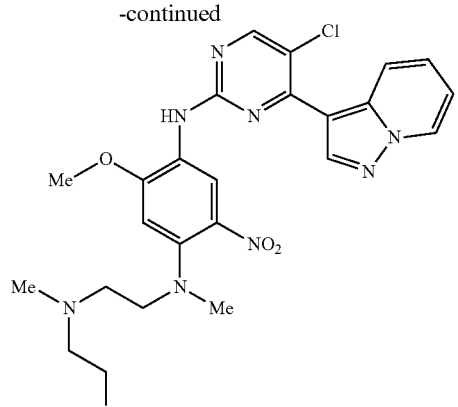

P1

To a solution of N1-(5-chloro-4-(pyrazolo[1,5-a]pyridin-3-yl)pyrimidin-2-yl)-2-methoxy-N4-methyl-N4-(2-(methylamino)ethyl)-5-nitrobenzene-1,4-diamine (M19) (0.2 g, 0.42 mmol) in DMF (2 mL) was added 1-bromo-2-fluoroethane (0.1 g, 0.79 mmol) and sodium bicarbonate (87 mg, 0.83 mmol) at rt. The resulting mixture was heated at 80° C. overnight. Upon cooling, the mixture was concentrated in vacuo and the resulting residue was purified by flash column chromatography on silica gel to afford N1-(5-chloro-4-(pyrazolo[1,5-a]pyridin-3-yl)pyrimidin-2-yl)-N4-(2-((2-fluoroethyl)(methyl)-amino)ethyl)-2-methoxy-N4-methyl-5-nitrobenzene-1,4-diamine (P1).

The following compounds in Table 21 were prepared in analogous fashion to Intermediate P1.

TABLE 21

| Compound | Heterocycle | Halide |
|---|---|---|
| P2 | D7 | |
| P3 | D9 | |

Intermediate Q1 ethyl 2-((4-((2-(dimethylamino)ethyl)(methyl)amino)-2-methoxy-5-nitrophenyl)amino)-4-(1-methyl-1H-indol-3-yl)pyrimidine-5-carboxylate

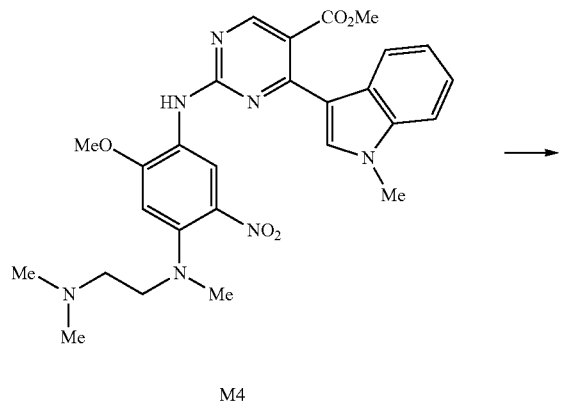

M4

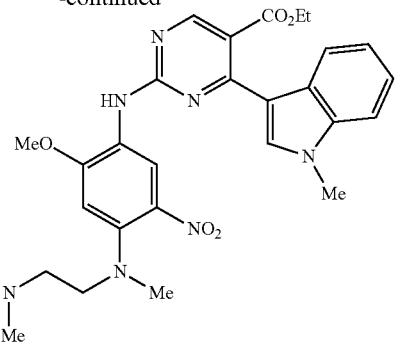

Q1

To a mixture of methyl 2-((4-((2-(dimethylamino)ethyl)(methyl)amino)-2-methoxy-5-nitrophenyl)amino)-4-(1-methyl-1H-indol-3-yl)pyrimidine-5-carboxylate (M4) (110 mg, 0.21 mmol) in EtOH (3.0 mL) was added sodium hydride (10 mg, 0.26 mmol, 60% dispersion in mineral oil). The resulting mixture was then heated to reflux for 5 min. Upon cooling, the mixture was filtered and rinsed with EtOH to afford ethyl 2-((4-((2-(dimethylamino)ethyl)(methyl)amino)-2-methoxy-5-nitrophenyl)amino)-4-(1-methyl-1H-indol-3-yl)pyrimidine-5-carboxylate (Q1) as a red solid.

The following intermediate compounds, as shown in Table 22, were synthesized in analogous fashion to intermediate Q1.

TABLE 22

| Intermediate Q | Ester | Alcohol |
|---|---|---|
| Q2 | M4 | iPrOH |
| Q3 | M4 | (oxetan-3-ol) |

TABLE 22-continued
| Intermediate Q | Ester | Alcohol |
|---|---|---|
| 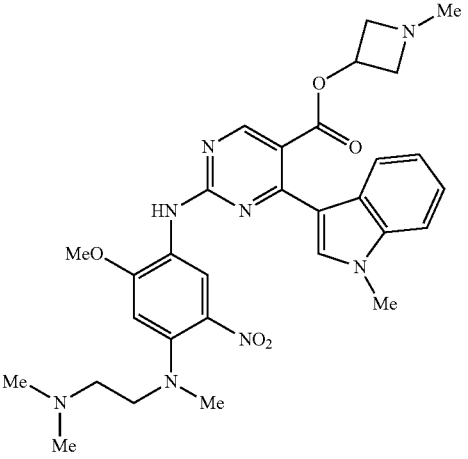 Q4 | 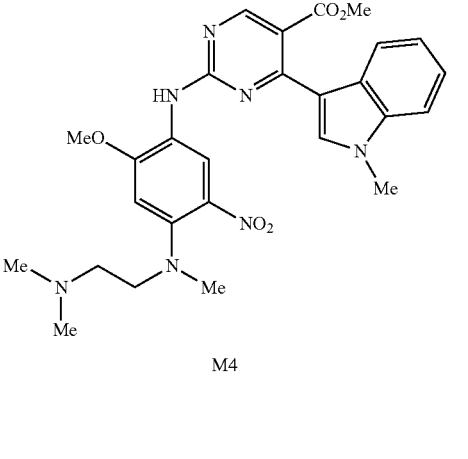 M4 | 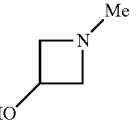 |
| 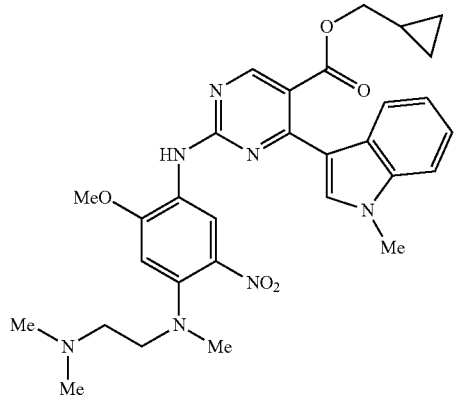 Q5 | 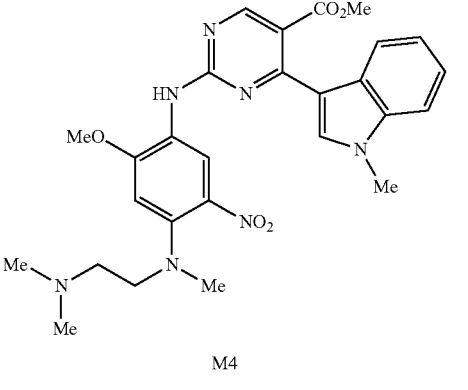 M4 | 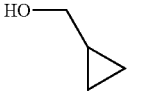 |
| 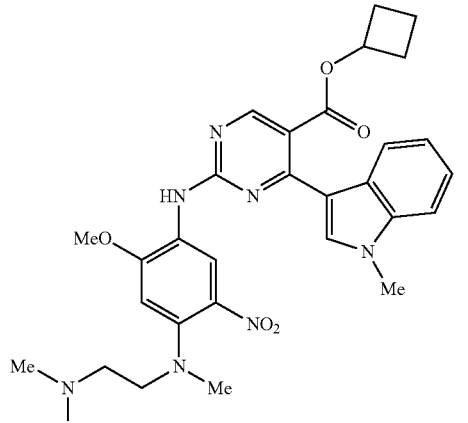 Q6 | 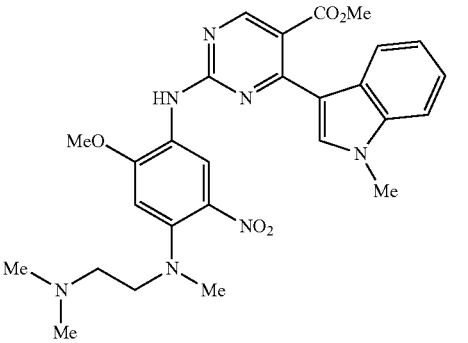 M4 | 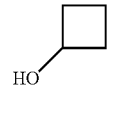 |

TABLE 22-continued

| Intermediate Q | Ester | Alcohol |
| --- | --- | --- |
| Q8 | M5 | iPrOH |
| Q9 | M4 | isobutanol (HOCH2CH(Me)Me) |
| Q10 | M4 | sec-butanol |

TABLE 22-continued
| Intermediate Q | Ester | Alcohol |
| --- | --- | --- |
| 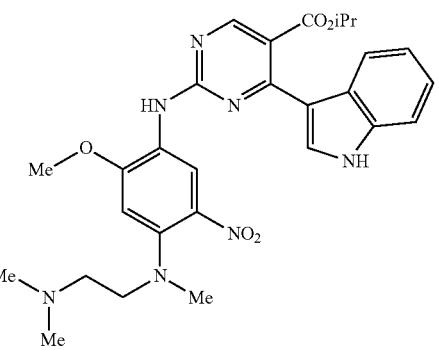 Q11 | 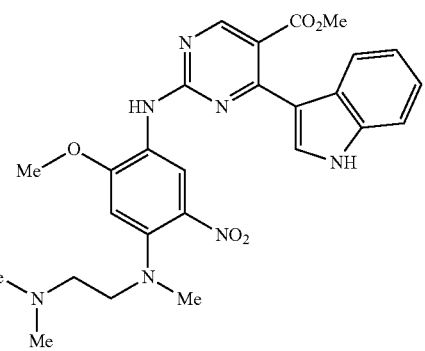 M16 | iPrOH |
| 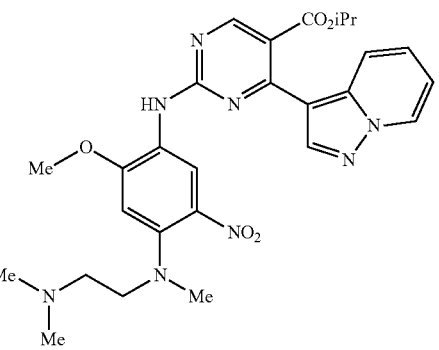 Q12 | 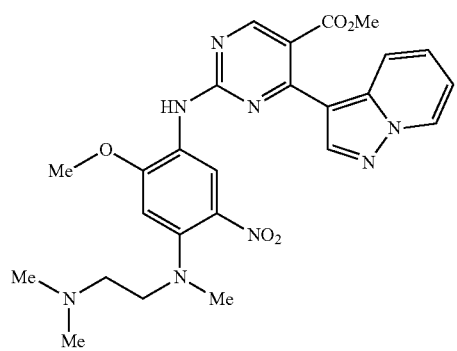 M18 | iPrOH |
| 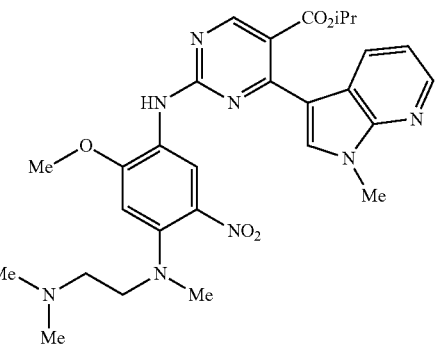 Q13 | 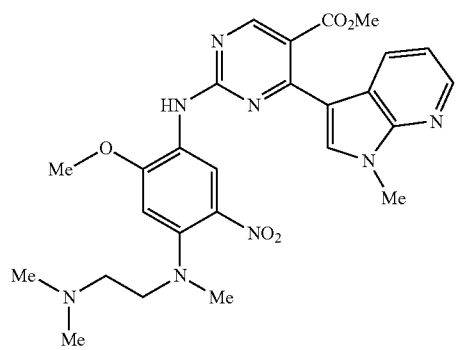 M20 | iPrOH |
| 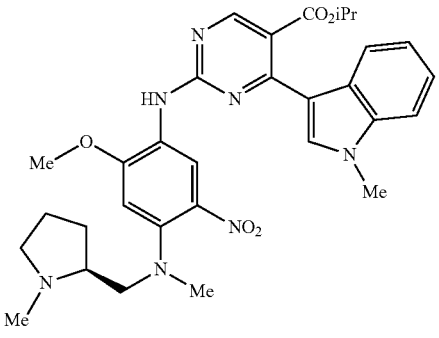 Q14 | 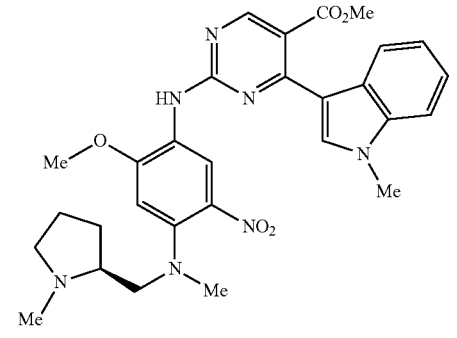 M21 | iPrOH |

TABLE 22-continued

| Intermediate Q | Ester | Alcohol |
|---|---|---|
| Q15 | M22 | iPrOH |
| Q16 | M4 | HOCH₂CN |
| Q17 | M4 | (S)-3-hydroxytetrahydrofuran |

TABLE 22-continued
| Intermediate Q | Ester | Alcohol |
|---|---|---|
| 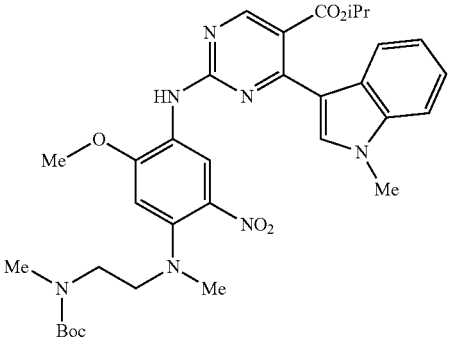 Q18 | 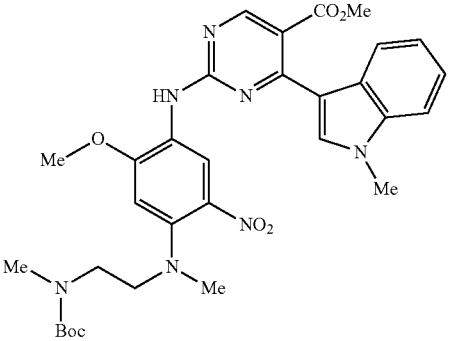 M23 | iPrOH |
| 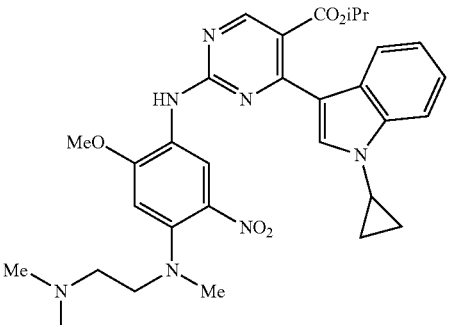 Q19 | 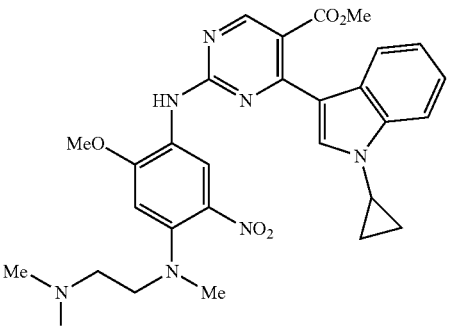 M45 | iPrOH |
| 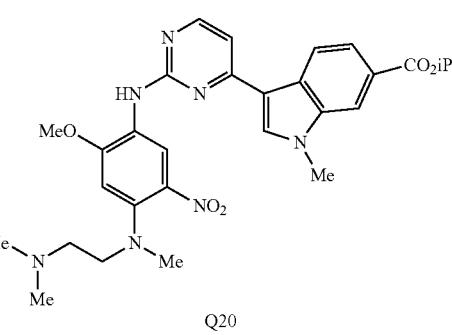 Q20 | 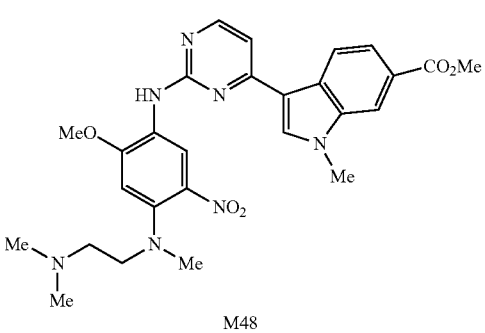 M48 | iPrOH |
| 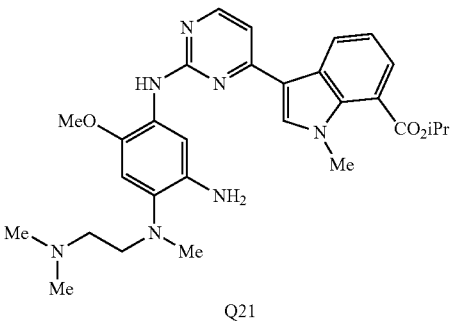 Q21 | 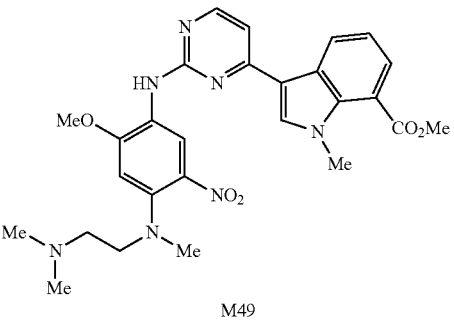 M49 | iPrOH |

TABLE 22-continued

| Intermediate Q | Ester | Alcohol |
|---|---|---|
| 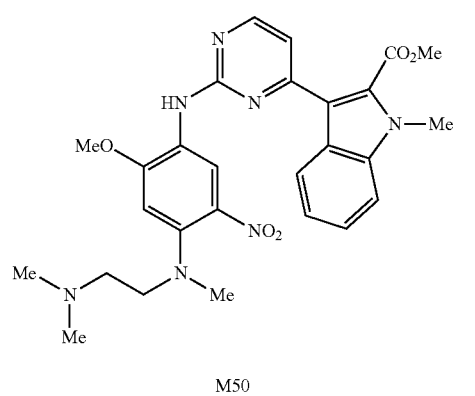 Q22 | M50 | iPrOH |

Intermediate Q23

(3-(2-((4-((2-(dimethylamino)ethyl)(methyl)amino)-2-methoxy-5-nitrophenyl)amino)pyrimidin-4-yl)-1-methyl-1H-indol-2-yl)methanol

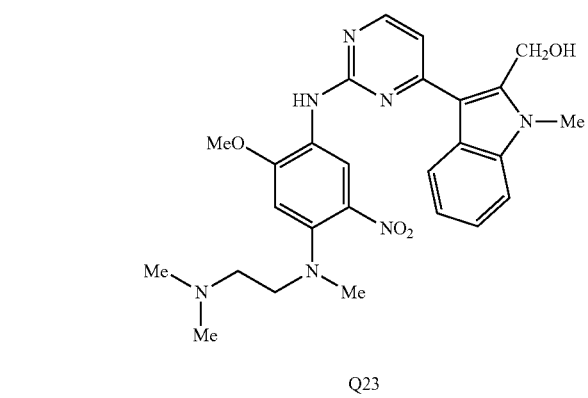

M50

Q23

To a mixture of methyl 3-(2-((4-((2-(dimethylamino)ethyl)(methyl)amino)-2-methoxy-5-nitrophenyl)amino)pyrimidin-4-yl)-1-methyl-1H-indole-2-carboxylate (M50) (533 mg, 1 mmol) in DCM (20 mL), at −78° C., was added DIBAL (1 M in DCM, 3 mL) dropwise. The resulting mixture was stirred for 1 h before adding saturated aqueous ammonium chloride and extracting with DCM. The combined organic layers were dried over magnesium sulfate, filtered, and concentrated in vacuo. The resulting residue was purified by flash column chromatography (25% MeOH/DCM) to afford (3-(2-((4-((2-(dimethylamino)ethyl)(methyl)amino)-2-methoxy-5-nitrophenyl)amino)pyrimidin-4-yl)-1-methyl-1H-indol-2-yl)methanol (Q23) as a red solid.

Intermediate Q24

3-(2-((4-((2-(dimethylamino)ethyl)(methyl)amino)-2-methoxy-5-nitrophenyl)amino)pyrimidin-4-yl)-1-methyl-1H-indole-2-carbaldehyde

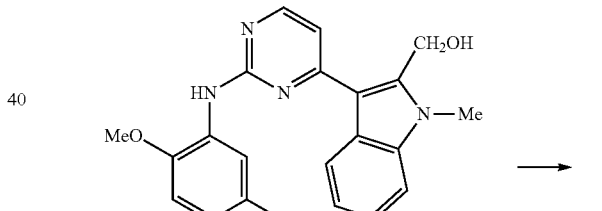

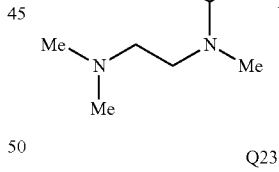

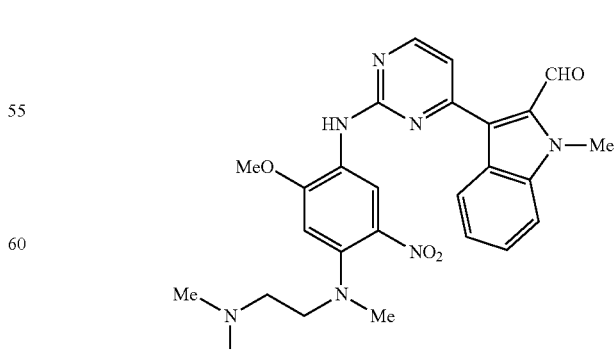

Q24

To a stirred solution of DMSO (77 mg, 0.99 mmol) in DCM (3 mL), at −78° C., was added oxalyl chloride (2 M in DCM, 0.25 mL) dropwise, and the mixture was stirred for 30 min. Subsequently, a mixture of (3-(2-((4-((2-(dimethylamino)ethyl)(methyl)amino)-2-methoxy-5-nitrophenyl)amino)pyrimidin-4-yl)-1-methyl-1H-indol-2-yl)methanol (170 mg, 0.33 mmol) in DCM (2 mL) was added, and the mixture was stirred for 1 h. To that mixture was added TEA (100 mg, 0.99 mmol) before warming to rt. Saturated sodium bicarbonate was added to the mixture, which was then extracted with DCM. The combined organic layers were dried over magnesium sulfate, filtered, and concentrated in vacuo. The resulting residue was purified by flash column chromatography on silica gel (25% MeOH/DCM) to afford 3-(2-((4-((2-(dimethylamino)ethyl)(methyl)amino)-2-methoxy-5-nitrophenyl)amino)pyrimidin-4-yl)-1-methyl-1H-indole-2-carbaldehyde (Q24) as a red solid.

Intermediate Q25 methyl 3-(((3-(2-((4-((2-(dimethylamino)ethyl)(methyl)amino)-2-methoxy-5-nitrophenyl)amino)pyrimidin-4-yl)-1-methyl-1H-indol-2-yl)methyl)amino)propanoate

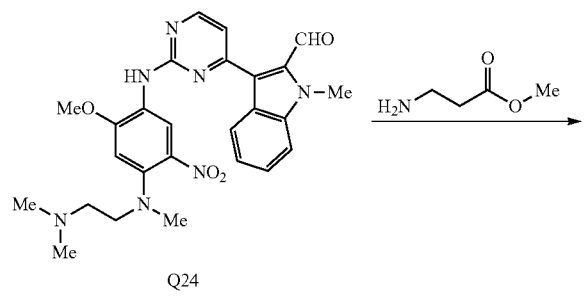

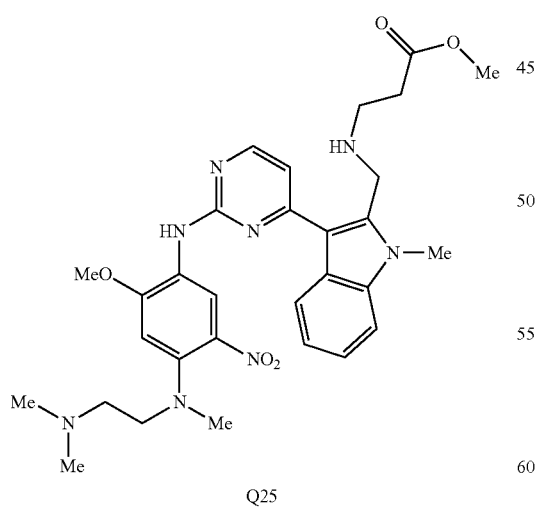

To methyl 3-aminopropanoate hydrochloride (58 mg, 0.42 mmol) in, DCE (5 mL), was added TEA (42 mg, 0.42 mmol), and the mixture was stirred at 70° C. for 20 minutes. Upon cooling, 3-(2-((4-((2-(dimethylamino)ethyl)(methyl)amino)-2-methoxy-5-nitrophenyl)amino)pyrimidin-4-yl)-1-methyl-1H-indole-2-carbaldehyde (Q24) (140 mg, 0.28 mmol) was added, and the mixture was stirred at rt for 1 h. Subsequently, saturated aqueous sodium bicarbonate was added to the mixture, which was then extracted with DCM. The combined organic layers were dried over magnesium sulfate, filtered, and concentrated under reduced pressure. The resulting residue was purified by flash column chromatography on silica gel (20% MeOH/DCM) to afford methyl 3-(((3-(2-((4-((2-(dimethylamino)ethyl)(methyl)amino)-2-methoxy-5-nitrophenyl)amino)pyrimidin-4-yl)-1-methyl-1H-indol-2-yl)methyl)amino)propanoate (Q25) as a red solid.

Intermediate Q26

1-((3-(2-((4-((2-(dimethylamino)ethyl)(methyl)amino)-2-methoxy-5-nitrophenyl)amino)pyrimidin-4-yl)-1-methyl-1H-indol-2-yl)methyl)azetidin-2-one

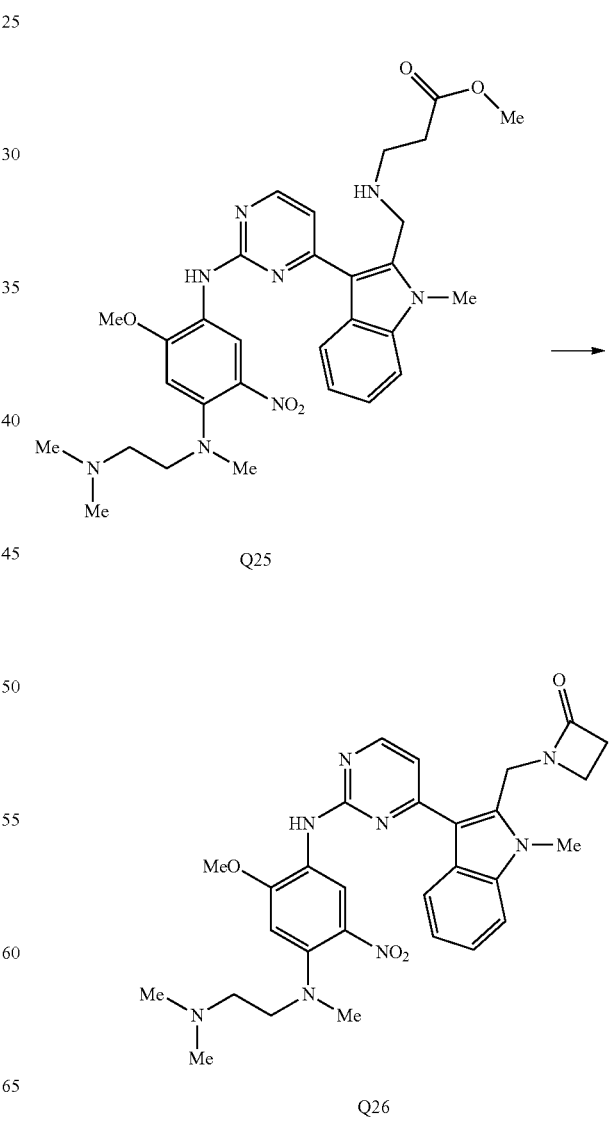

To methyl 3-(((3-(2-((4-((2-(dimethylamino)ethyl)(methyl)amino)-2-methoxy-5-nitrophenyl)amino)pyrimidin-4-yl)-1-methyl-1H-indol-2-yl)methyl)amino)propanoate (Q25) (159 mg, 0.27 mmol) in DCE (3 mL), at −78° C., was added trimethylaluminum (2 M in PhMe, 0.13 mL). Subsequently, the mixture was heated to 90° C., and stirred for 3 h. Upon cooling, saturated aqueous sodium bicarbonate was added, and the resulting mixture was extracted with DCM. The combined organic layers were dried over magnesium sulfate, filtered, and concentrated in vacuo. The resulting residue was purified by flash chromatography (25% MeOH/DCM) to afford 1-((3-(2-((4-((2-(dimethylamino)ethyl)(methyl)amino)-2-methoxy-5-nitrophenyl)amino)pyrimidin-4-yl)-1-methyl-1H-indol-2-yl)methyl)azetidin-2-one (Q26) as a red solid.

Intermediate R1

N1-(2-(dimethylamino)ethyl)-N4-(5-ethyl-4-(pyrazolo[1,5-a]pyridin-3-yl)pyrimidin-2-yl)-5-methoxy-N1-methyl benzene-1,2,4-triamine

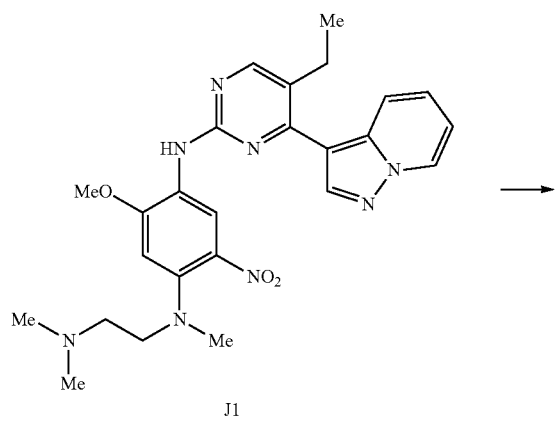

J1

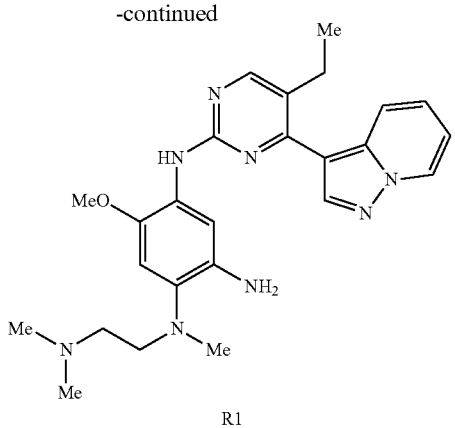

R1

A solution of N1-(2-(dimethylamino)ethyl)-N4-(5-ethyl-4-(pyrazolo[1,5-a]pyridin-3-yl)pyrimidin-2-yl)-5-methoxy-N1-methyl-2-nitrobenzene-1,4-diamine (J1) (69 mg, 0.14 mmol) in acetone (1.4 mL) was treated with zinc powder (37 mg, 0.56 mmol) and saturated aqueous ammonium chloride solution (0.2 mL, 1.4 mmol). The resulting mixture was stirred at rt for 30 min. The mixture was then filtered through a pad of Celite, and the collected solids were rinsed with MeOH. The filtrate was concentrated in vacuo to afford N1-(2-(dimethylamino)-ethyl)-N4-(5-ethyl-4-(pyrazolo[1,5-a]pyridin-3-yl)pyrimidin-2-yl)-5-methoxy-N1-methyl-benzene-1,2,4-triamine (R1).

The following intermediate compounds, as shown in Table 23, were synthesized in analogous fashion to intermediate R1.

TABLE 23

| Intermediate R | Nitro compound |
| --- | --- |
| R2 | M1 |

TABLE 23-continued
| Intermediate R | Nitro compound |
|---|---|
| 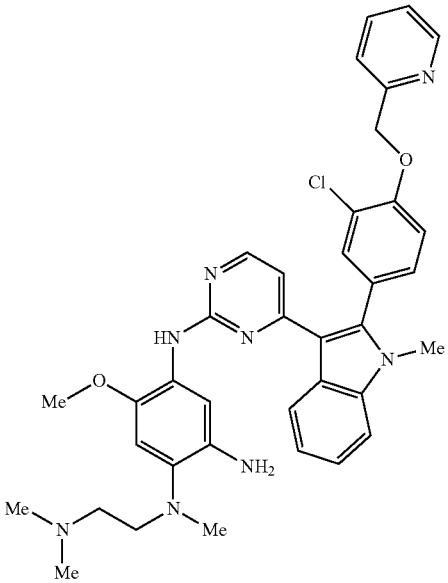 R3 | 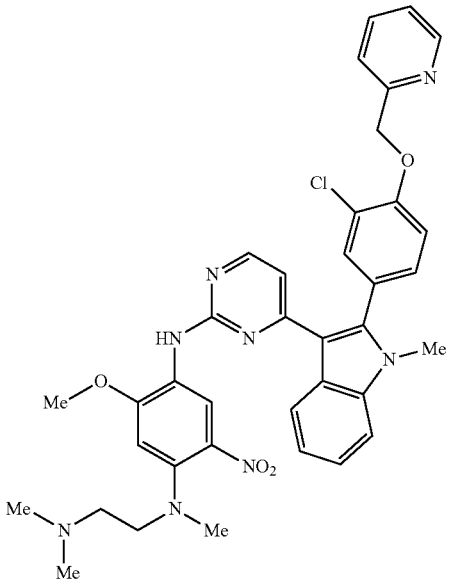 J2 |
| 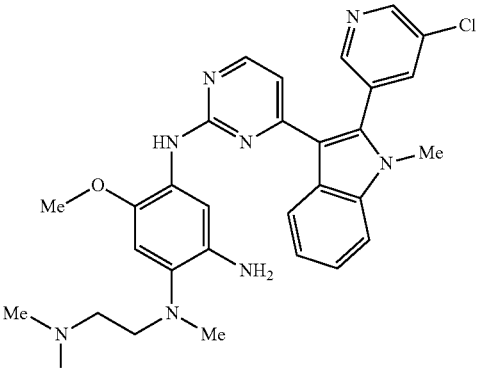 R4 | 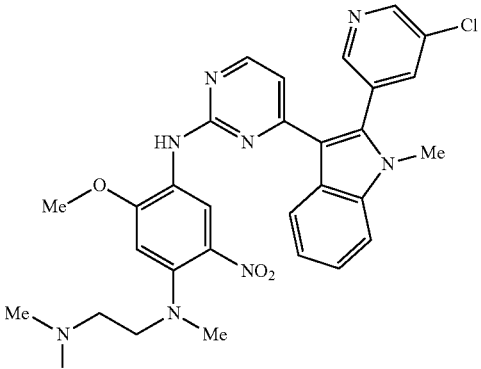 J3 |
| 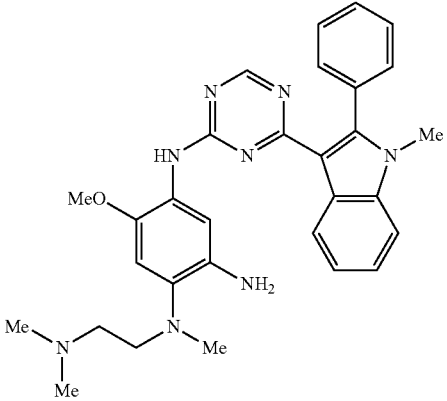 R5 | 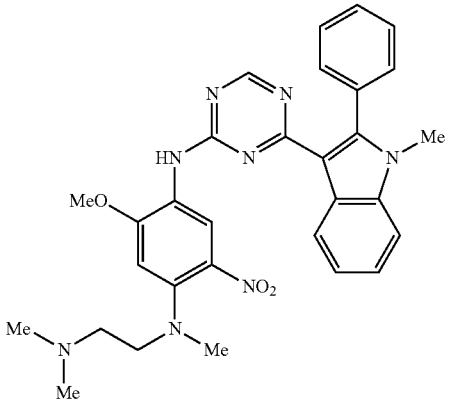 M2 |

TABLE 23-continued
| Intermediate R | Nitro compound |
|---|---|
| 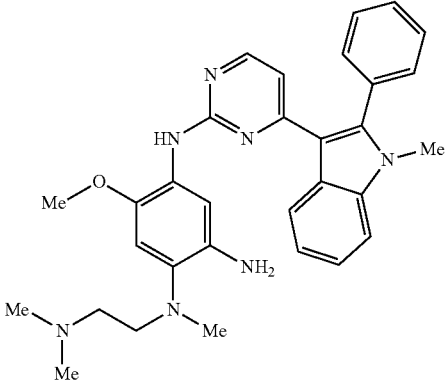<br>R6 | 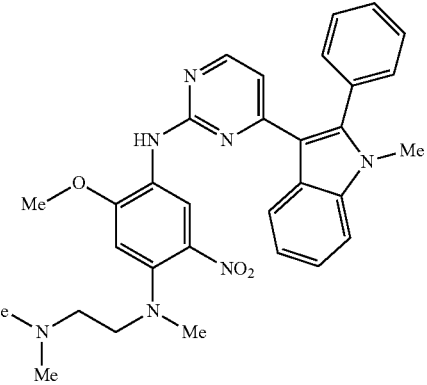<br>J4 |
| 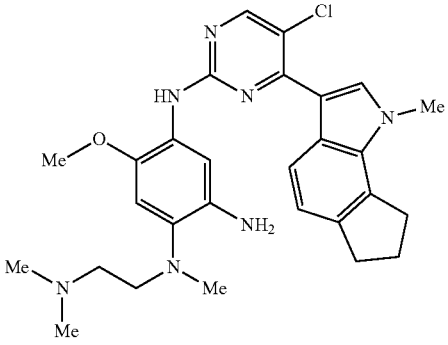<br>R7 | 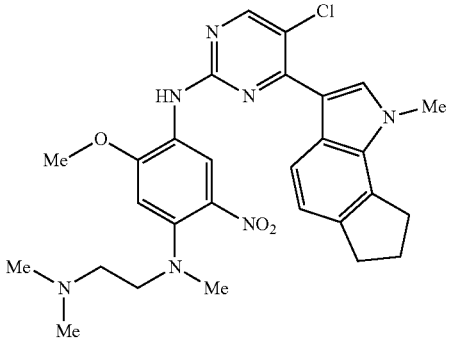<br>M3 |
| 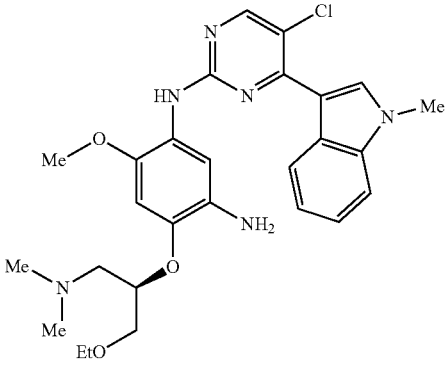<br>R8 | 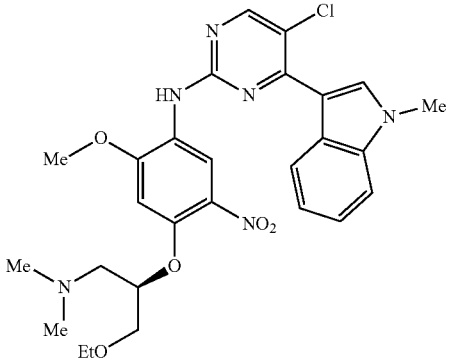<br>N1 |

TABLE 23-continued
| Intermediate R | Nitro compound |
|---|---|
| 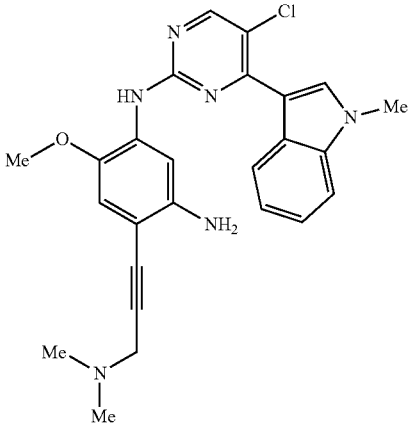<br>R9 | 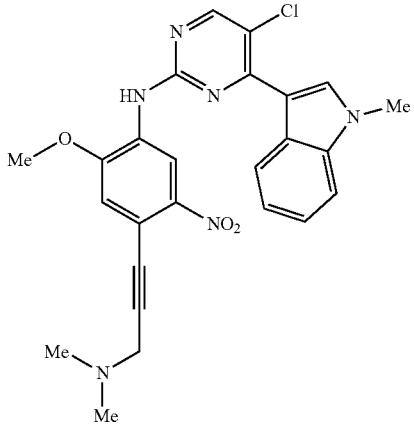<br>O1 |
| 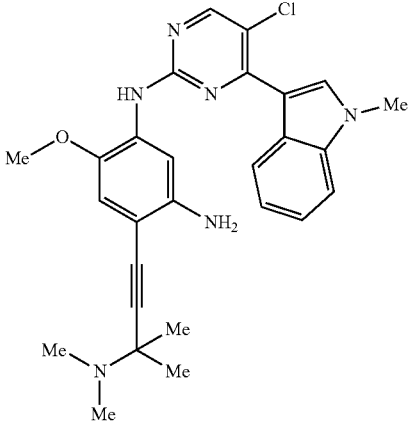<br>R10 | 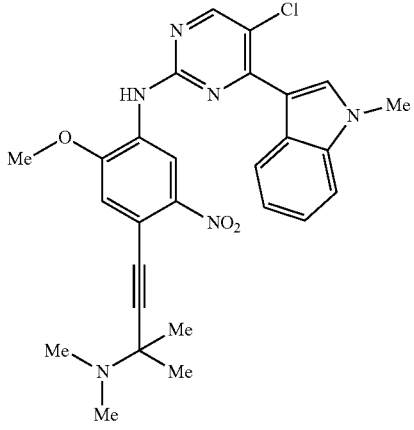<br>O2 |
| 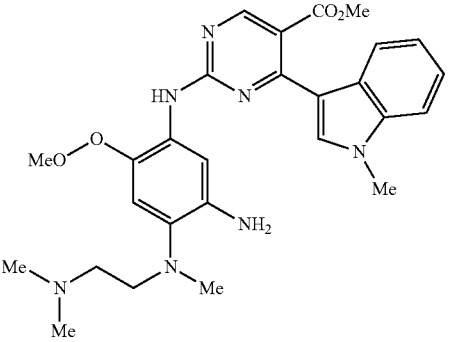<br>R11 | 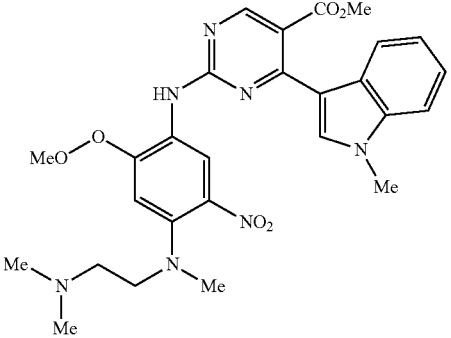<br>M4 |

TABLE 23-continued
| Intermediate R | Nitro compound |
| --- | --- |
| 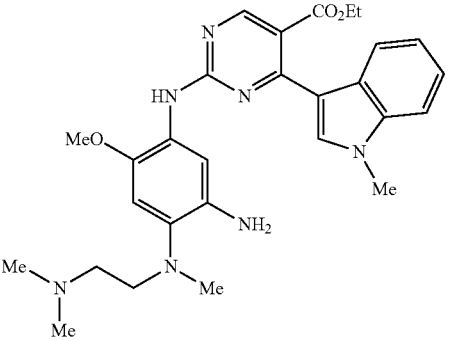 R12 | 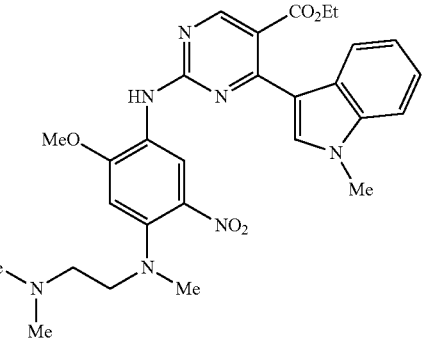 Q1 |
| 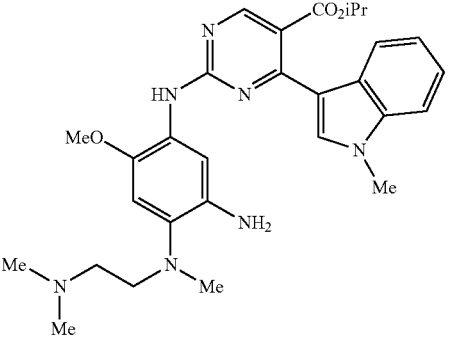 R13 | 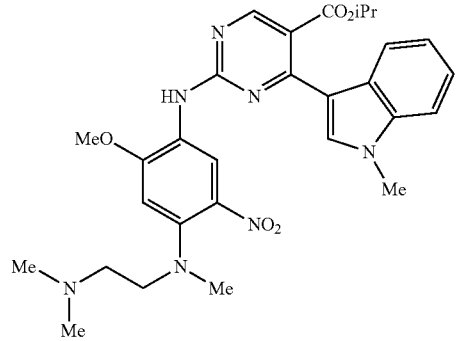 Q2 |
| 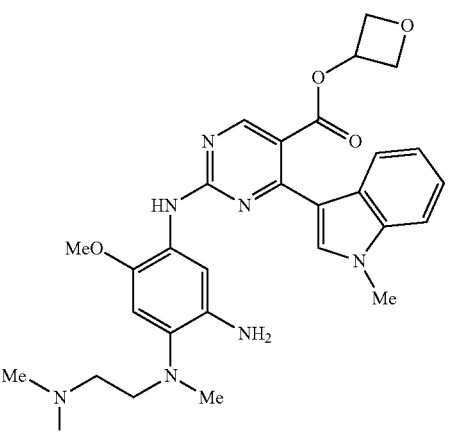 R14 | 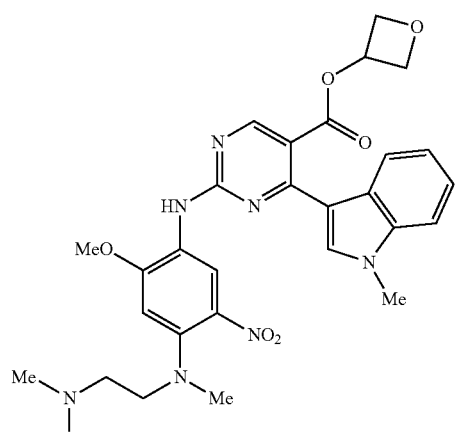 Q3 |

TABLE 23-continued
| Intermediate R | Nitro compound |
|---|---|
| 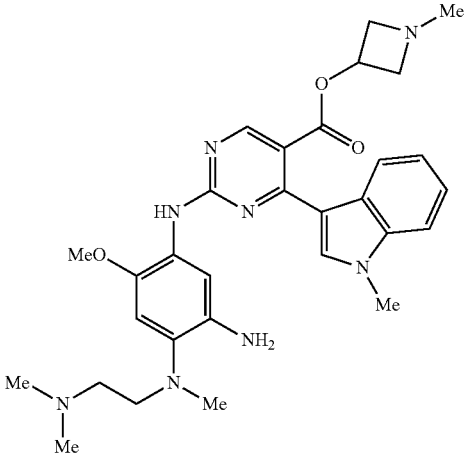<br>R15 | 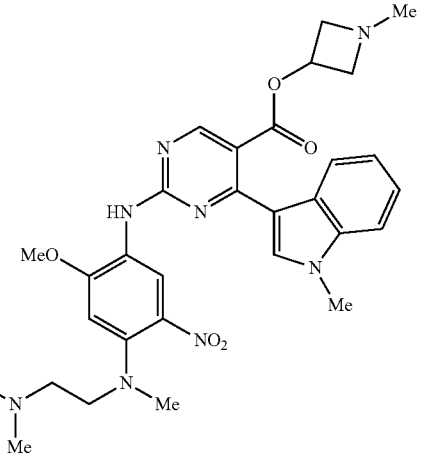<br>Q4 |
| 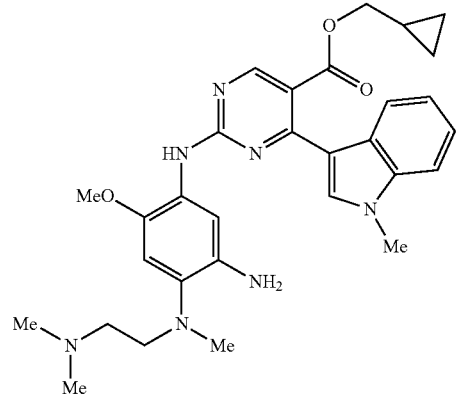<br>R16 | 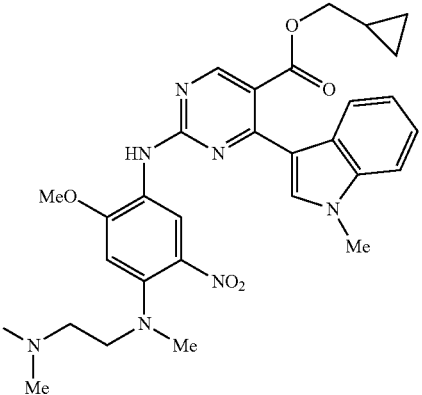<br>Q5 |
| 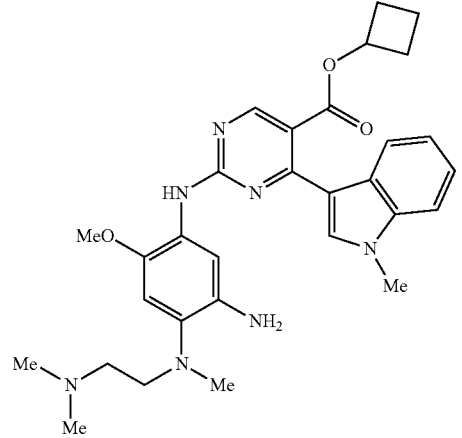<br>R17 | 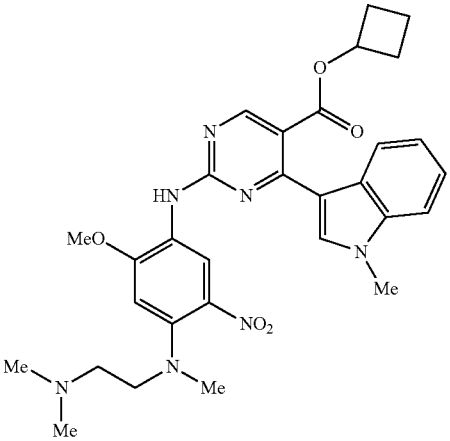<br>Q6 |

TABLE 23-continued
| Intermediate R | Nitro compound |
|---|---|
| 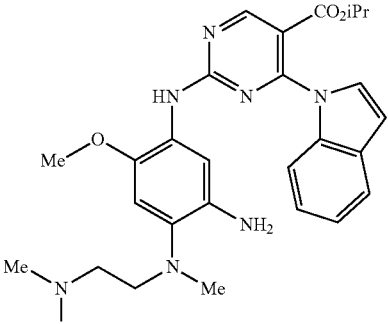 R18 | 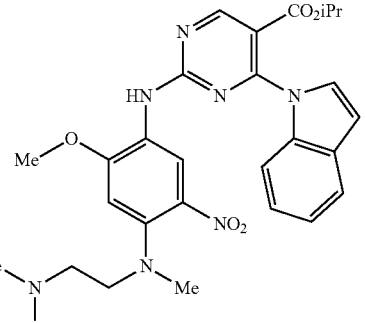 M24 |
| 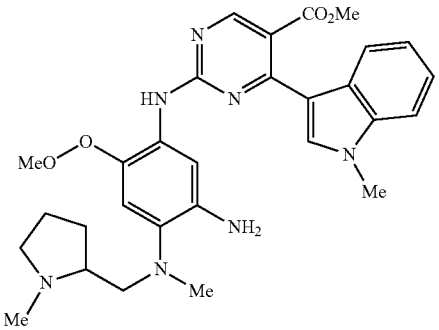 R19 | 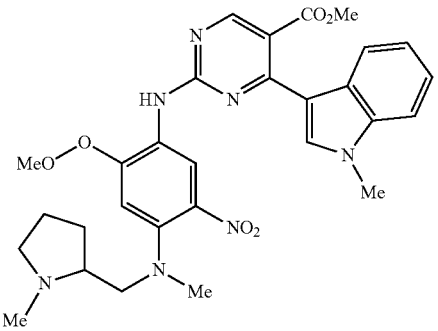 M5 |
| 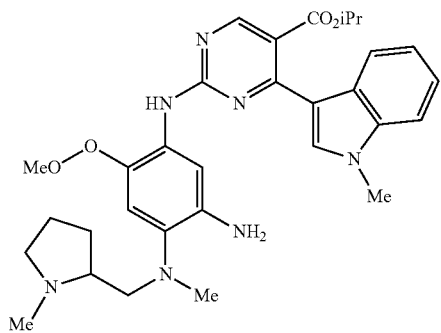 R20 | 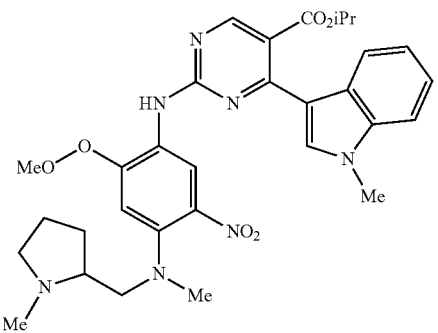 Q8 |

TABLE 23-continued
| Intermediate R | Nitro compound |
|---|---|
| 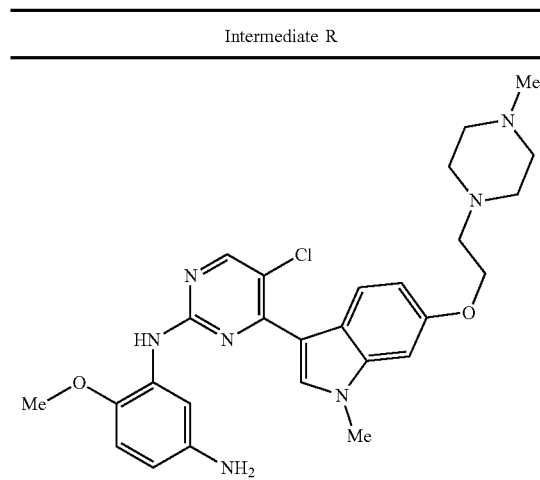<br>R21 | 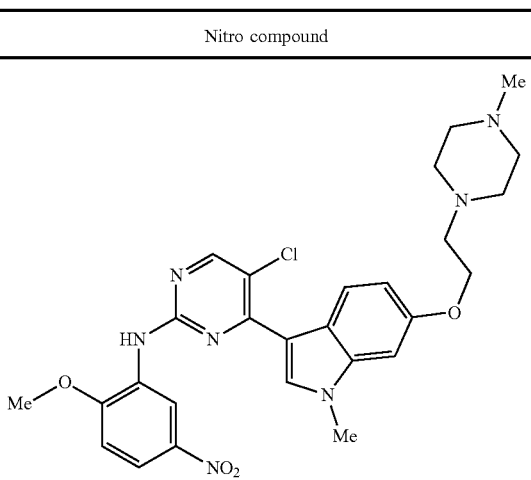<br>J5 |
| 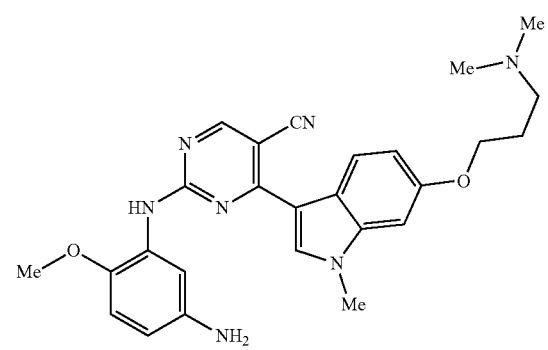<br>R22 | 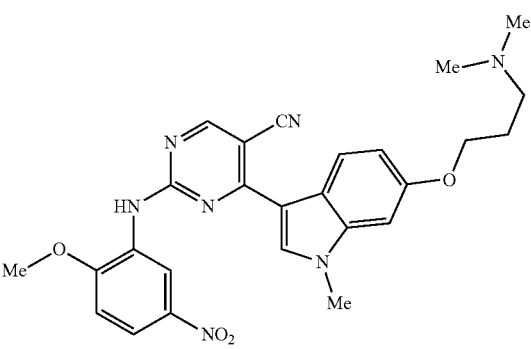<br>K4 |
| 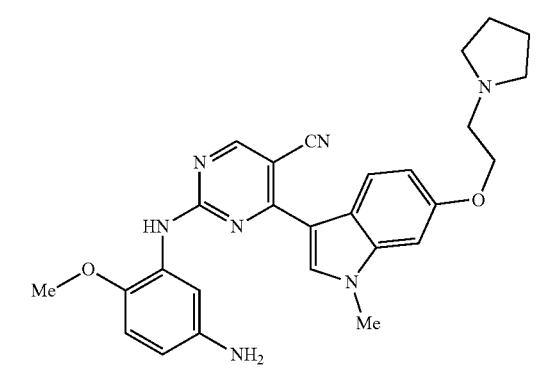<br>R23 | 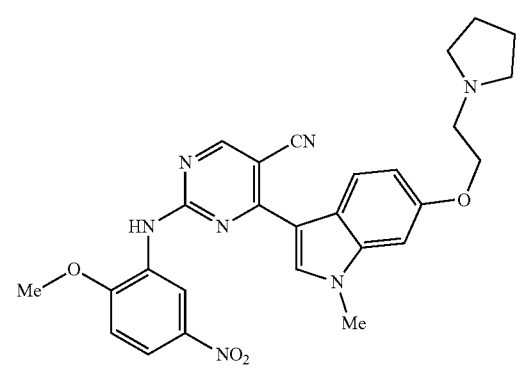<br>K5 |

TABLE 23-continued

| Intermediate R | Nitro compound |
|---|---|
| R24 | K6 |
| R25 | K7 |
| R26 | K8 |

TABLE 23-continued

| Intermediate R | Nitro compound |
| --- | --- |
| R27 | N2 |
| R28 | N3 |
| R29 | N4 |

TABLE 23-continued
| Intermediate R | Nitro compound |
|---|---|
| 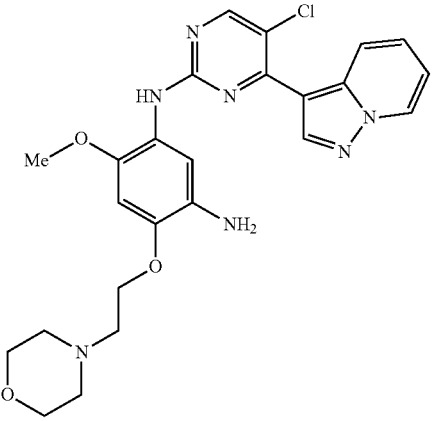<br>R30 | 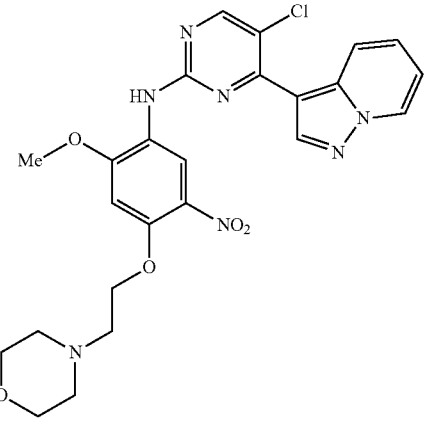<br>N5 |
| 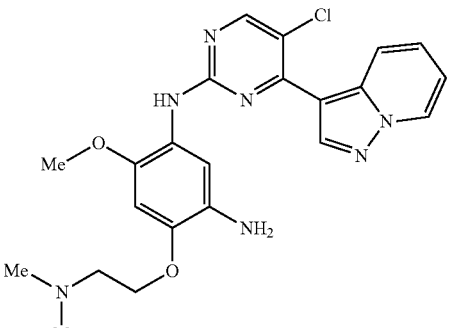<br>R31 | 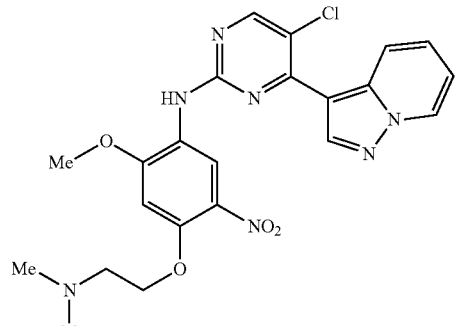<br>N6 |
| 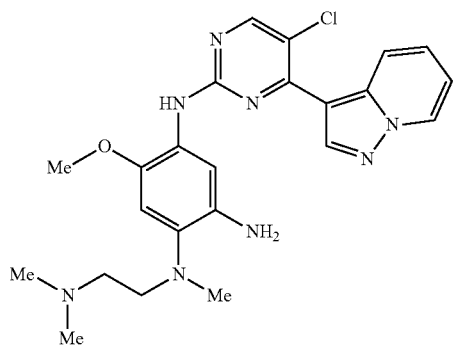<br>R32 | 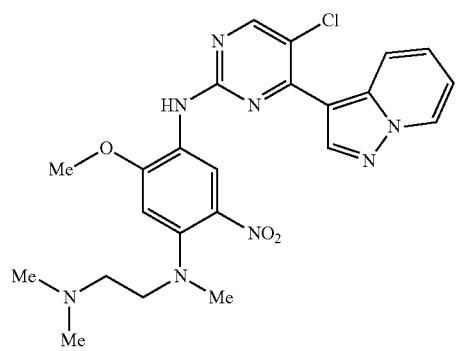<br>M6 |

TABLE 23-continued
| Intermediate R | Nitro compound |
|---|---|
| 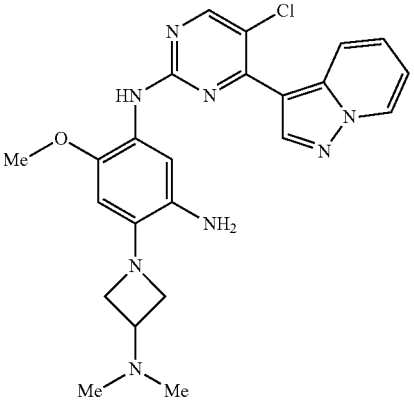<br>R33 | 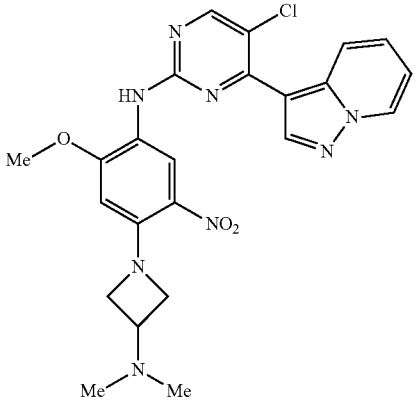<br>M7 |
| 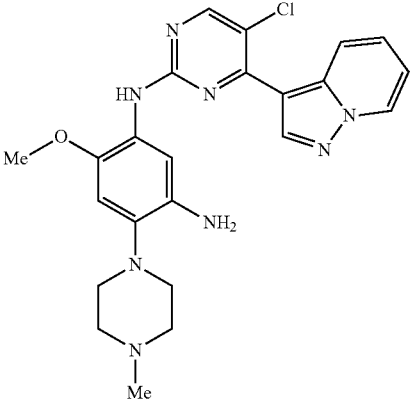<br>R34 | 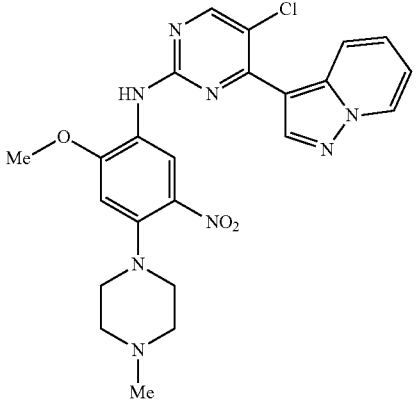<br>M8 |
| 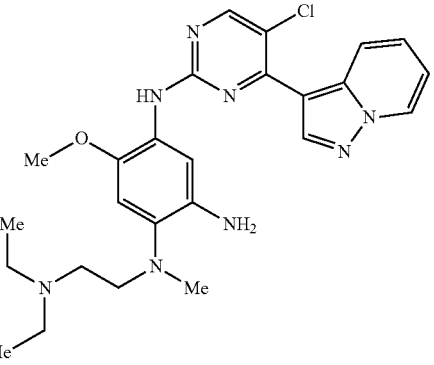<br>R35 | 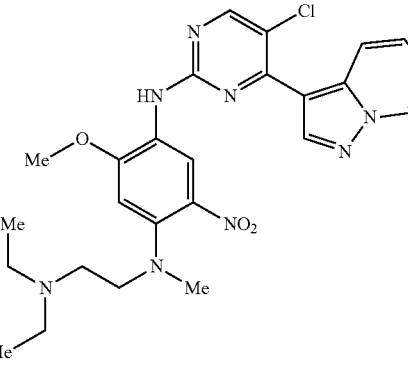<br>M9 |

TABLE 23-continued

| Intermediate R | Nitro compound |
|---|---|
| R36 | M10 |
| R37 | M11 |
| R38 | M12 |

TABLE 23-continued
| Intermediate R | Nitro compound |
|---|---|
| 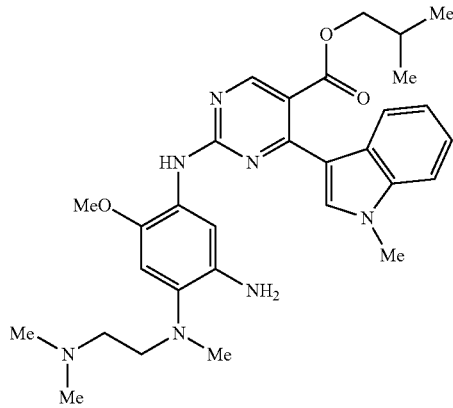<br>R39 | 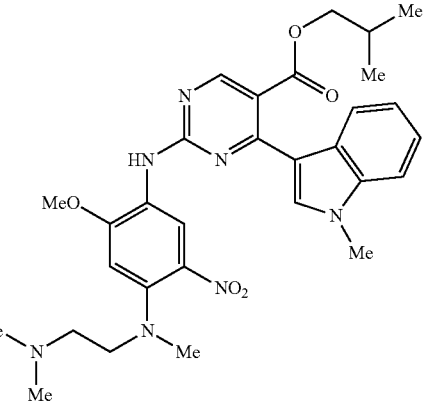<br>Q9 |
| 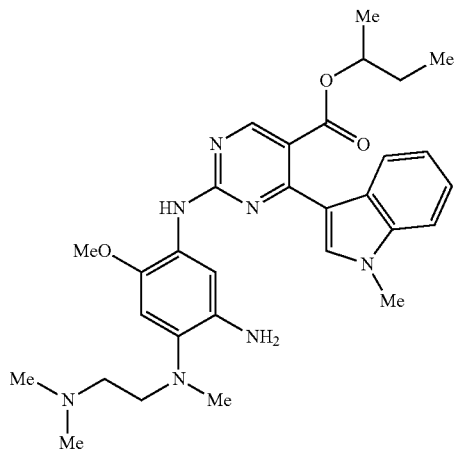<br>R40 | 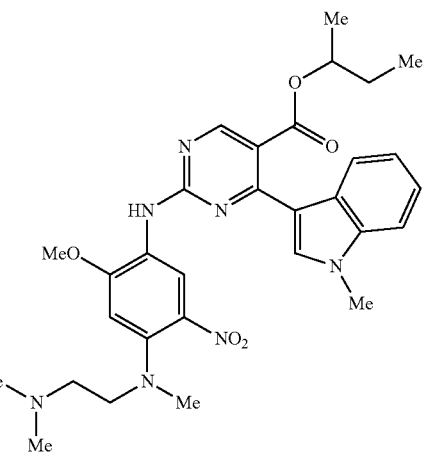<br>Q10 |
| 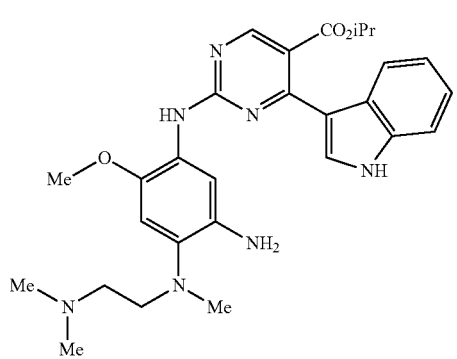<br>R41 | 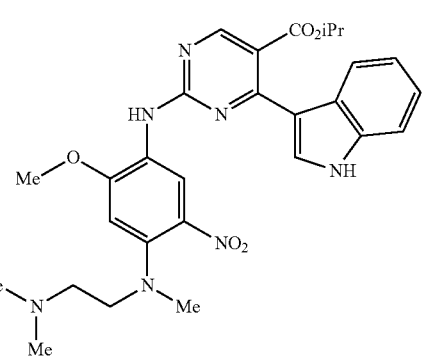<br>Q11 |

TABLE 23-continued
| Intermediate R | Nitro compound |
|---|---|
| 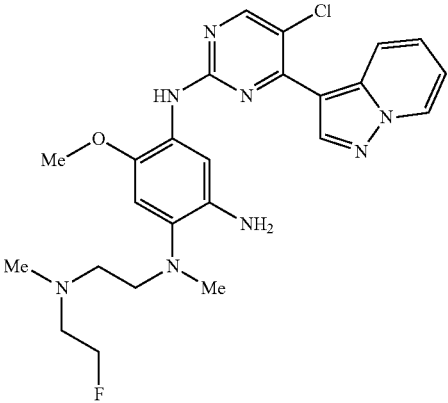 R42 | 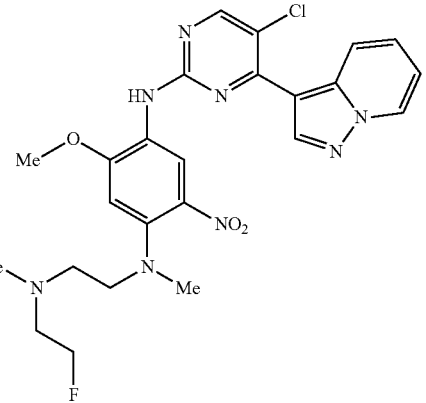 P1 |
| 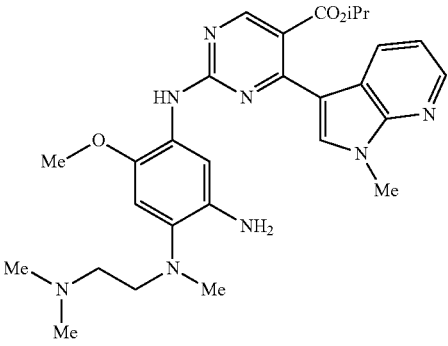 R43 | 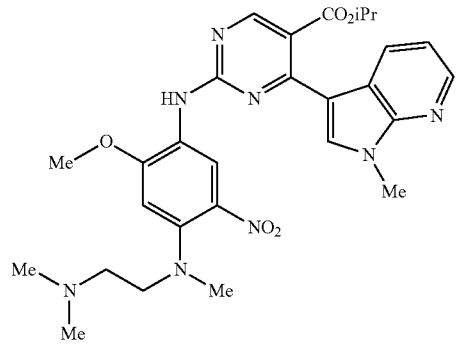 Q13 |
| 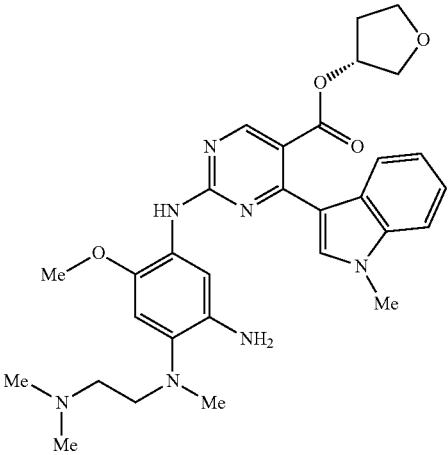 R44 | 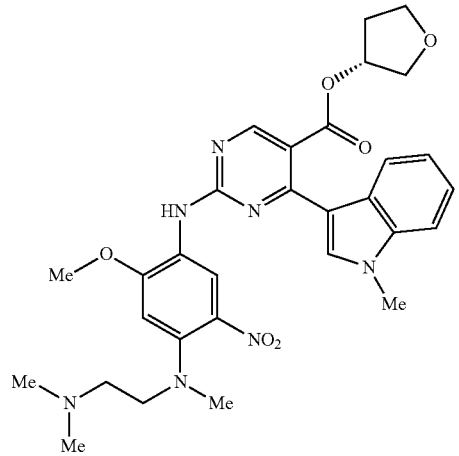 Q17 |

TABLE 23-continued
| Intermediate R | Nitro compound |
|---|---|
| 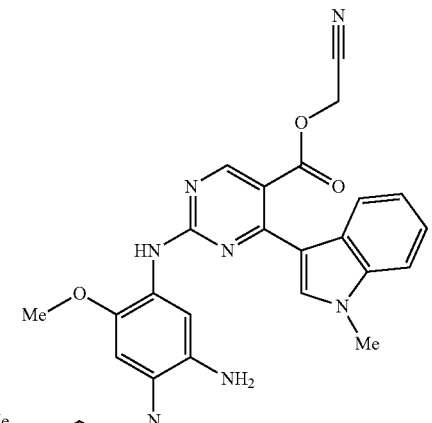<br>R45 | 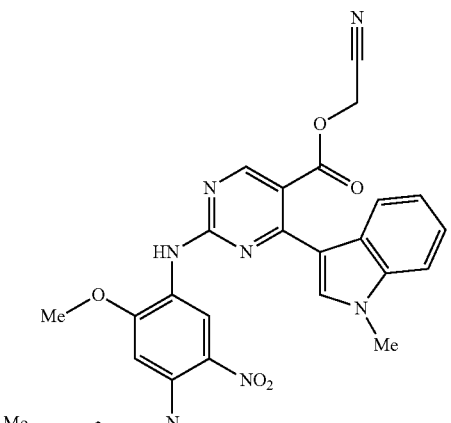<br>Q16 |
| 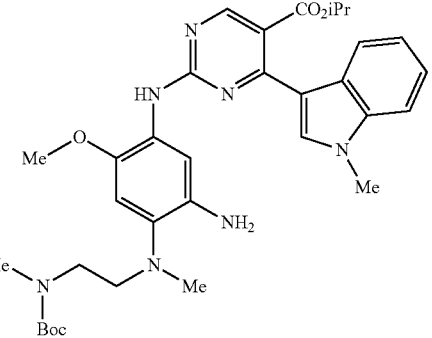<br>R46 | 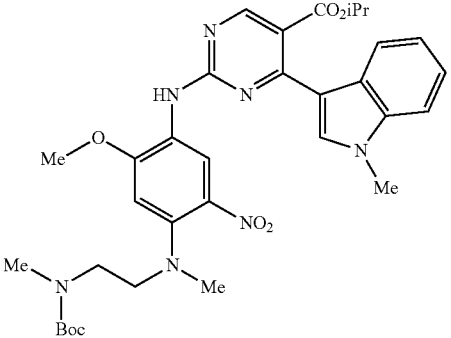<br>Q18 |
| 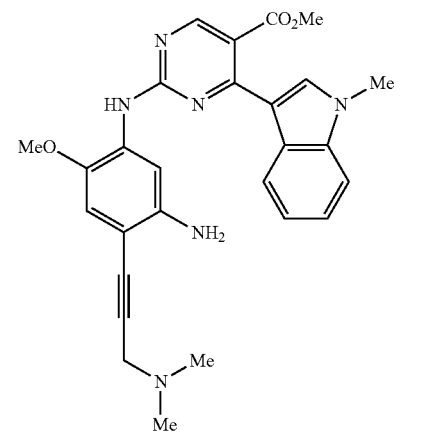<br>R47 | 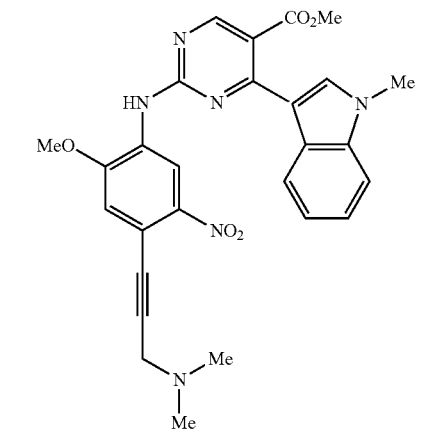<br>O3 |

TABLE 23-continued

| Intermediate R | Nitro compound |
|---|---|
| R48 | K28 |
| R49 | M42 |
| R50 | M57 |

Intermediate S1

N1-(2-(dimethylamino)ethyl)-5-methoxy-N1-methyl-N4-(4-(1-methyl-2-(tetrahydro-2H-pyran-4-yl)-1H-indol-3-yl)-1,3,5-triazin-2-yl)benzene-1,2,4-triamine

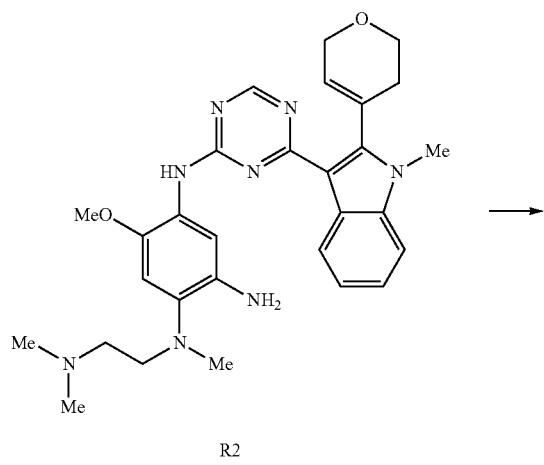

R2

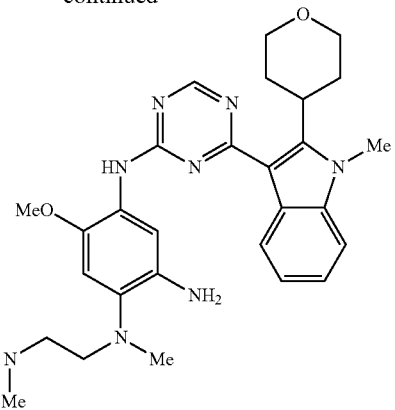

S2

To a microwave vial was added N4-(4-(2-(3,6-dihydro-2H-pyran-4-yl)-1-methyl-1H-indol-3-yl)-1,3,5-triazin-2-yl)-N1-(2-(dimethylamino)ethyl)-5-methoxy-N1-methyl-benzene-1,2,4-triamine (R2) (79 mg, 0.15 mmol), MeOH (1.0 mL), palladium on carbon (10 wt-%, 85 mg, 0.08 mmol), and ammonium formate (93 mg, 1.5 mmol). The resulting mixture was microwaved for 60 min at 80° C. The mixture was then filtered through a Celite pad and rinsed with 20% MeOH in DCM. The filtrate was concentrated in vacuo, and the resulting residue was purified by flash column chromatography on silica gel (0%→10% MeOH/DCM) to afford N1-(2-(dimethylamino)ethyl)-5-methoxy-N1-methyl-N4-(4-(1-methyl-2-(tetrahydro-2H-pyran-4-yl)-1H-indol-3-yl)-1,3,5-triazin-2-yl)benzene-1,2,4-triamine (S1) as a red viscous oil.

The following intermediate compounds, as shown in Table 24, were synthesized in analogous fashion to intermediate S1.

TABLE 24

| Intermediate S | Nitro compound |
|---|---|
| S2 | M13 |
| S3 | M15 |

TABLE 24-continued
| Intermediate S | Nitro compound |
|---|---|
| 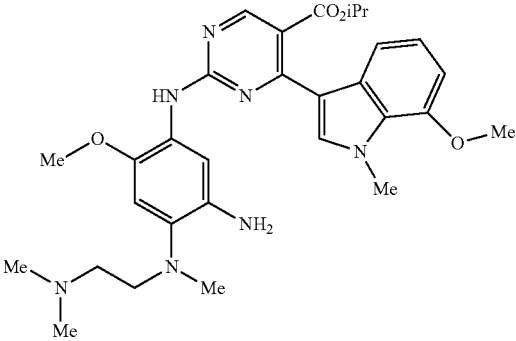<br>S4 | 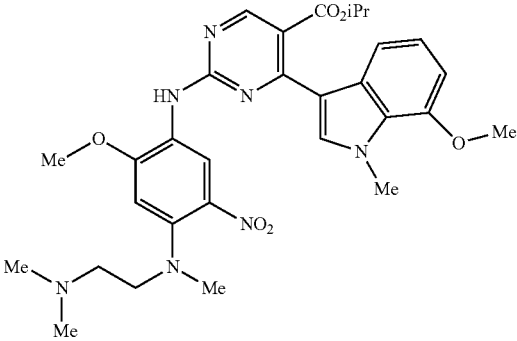<br>M17 |
| 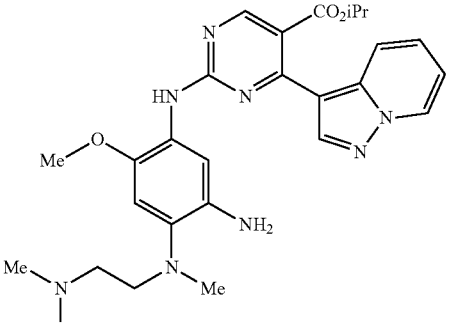<br>S5 | 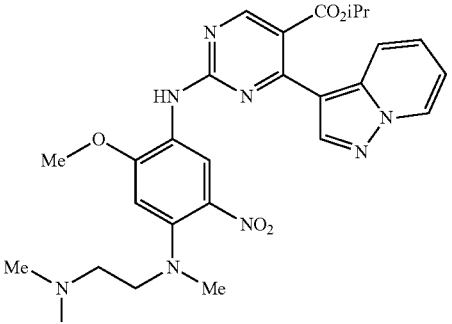<br>Q12 |
| 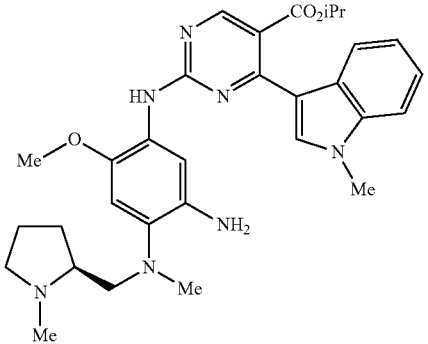<br>S6 | 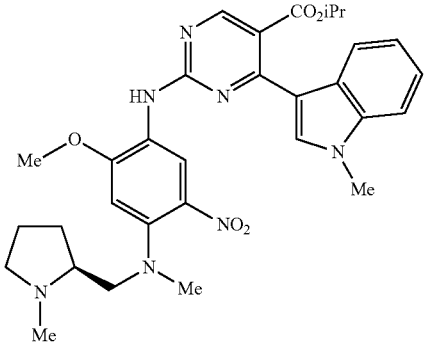<br>Q14 |
| 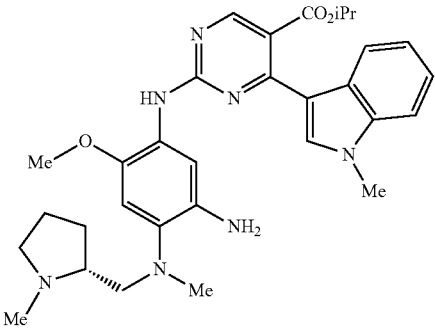<br>S7 | 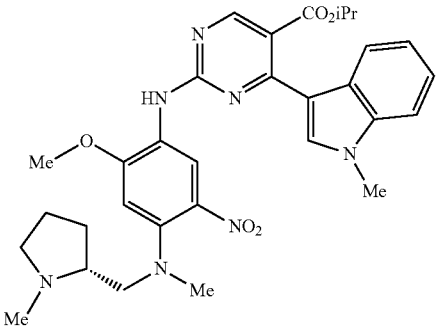<br>Q15 |

TABLE 24-continued
| Intermediate S | Nitro compound |
|---|---|
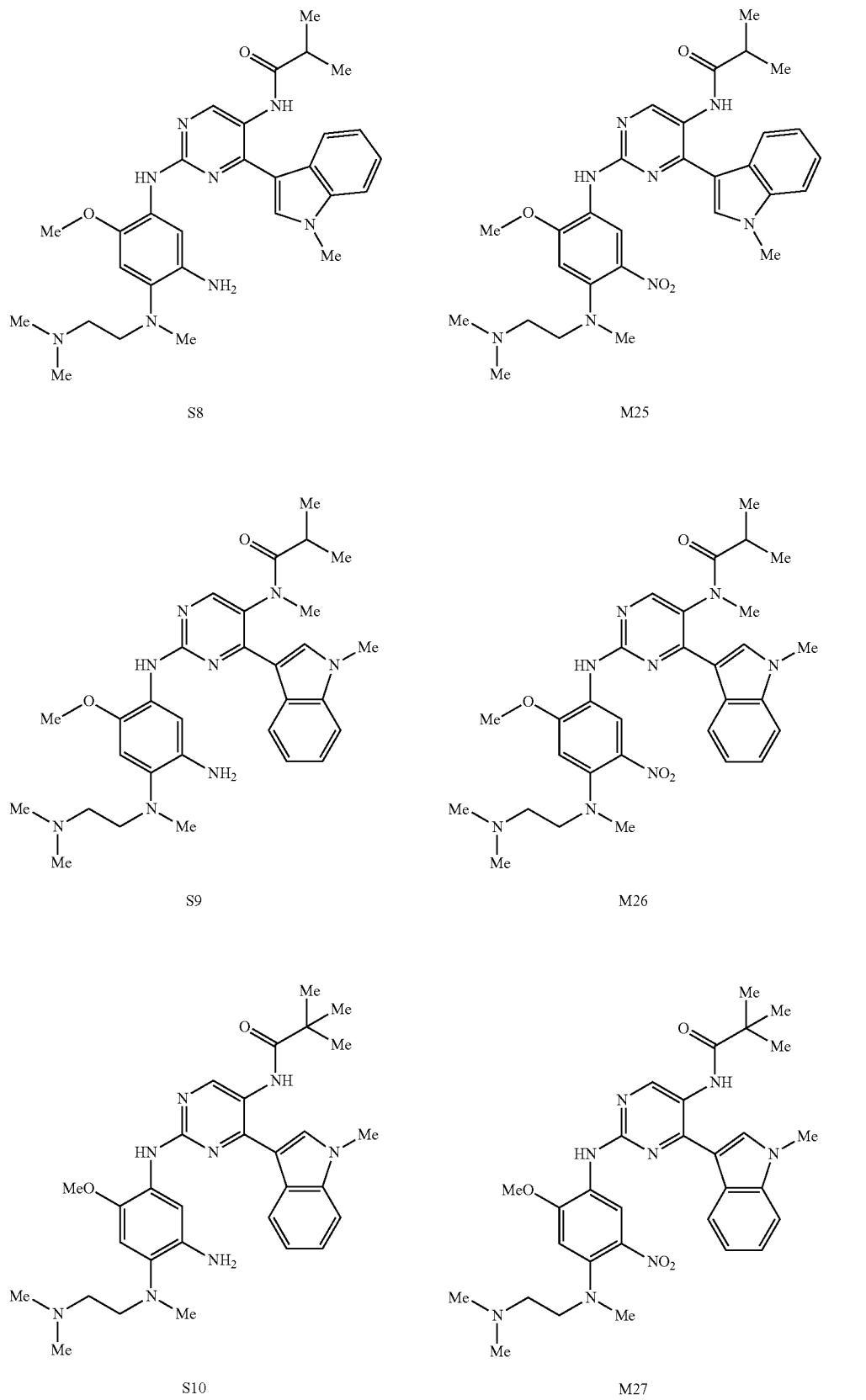

TABLE 24-continued

| Intermediate S | Nitro compound |
|---|---|

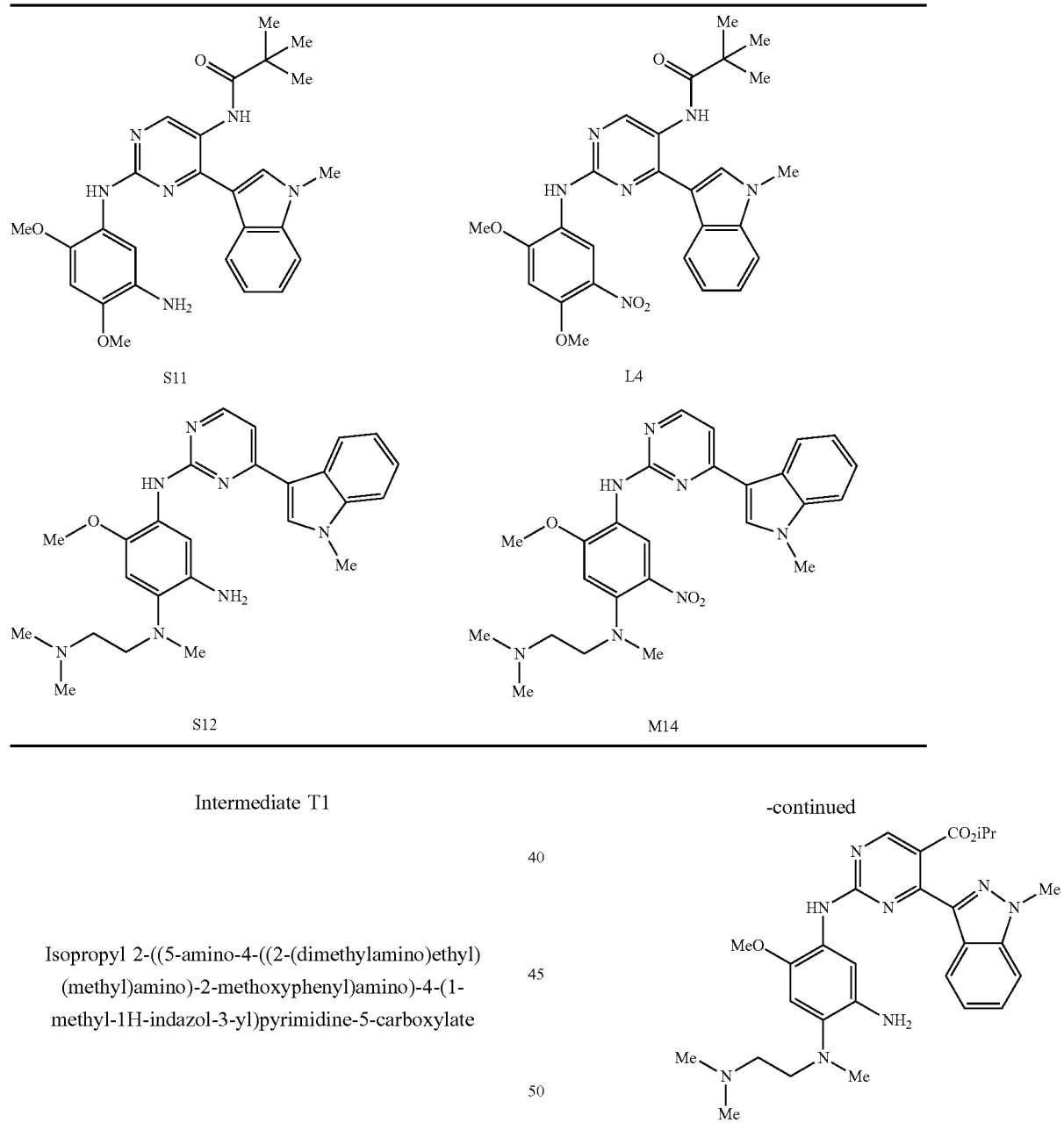

S11

L4

S12

M14

Intermediate T1

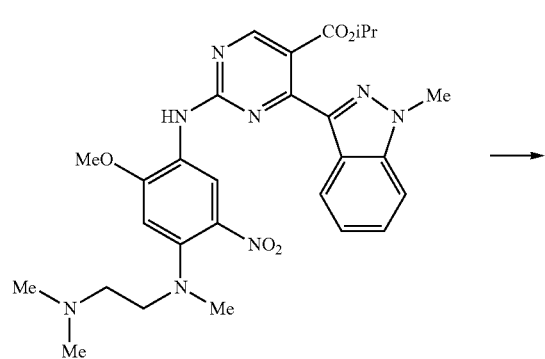

Isopropyl 2-((5-amino-4-((2-(dimethylamino)ethyl)(methyl)amino)-2-methoxyphenyl)amino)-4-(1-methyl-1H-indazol-3-yl)pyrimidine-5-carboxylate To a solution of isopropyl 2-((4-((2-(dimethylamino)ethyl)(methyl)amino)-2-methoxy-5-nitrophenyl)amino)-4-(1-methyl-1H-indazol-3-yl)pyrimidine-5-carboxylate (M28) (70 mg, 0.12 mmol) in MeOH (1.2 mL) was added Pd/C (10 wt.-%, 13 mg, 0.01 mmol), and the resulting mixture was stirred at rt under a hydrogen atmosphere for 1 h. Subsequently, the mixture was diluted with DCM (5 mL), and then filtered through a pad Celite, rinsing with additional DCM (30 mL). The filtrate was concentrated in vacuo to afford isopropyl 2-((5-amino-4-((2-(dimethylamino)ethyl)(methyl)amino)-2-methoxyphenyl)amino)-4-(1-methyl-1H-indazol-3-yl)pyrimidine-5-carboxylate as a yellow residue.

The following intermediate compounds, as shown in Table 25, were synthesized in analogous fashion to intermediate R1.

TABLE 25
| Intermediate T | Nitro compound |
|---|---|
| 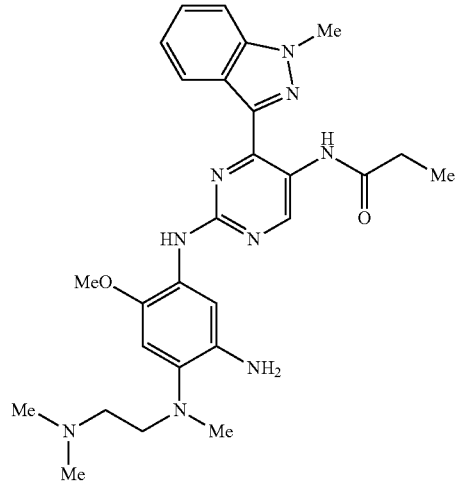<br>T2 | 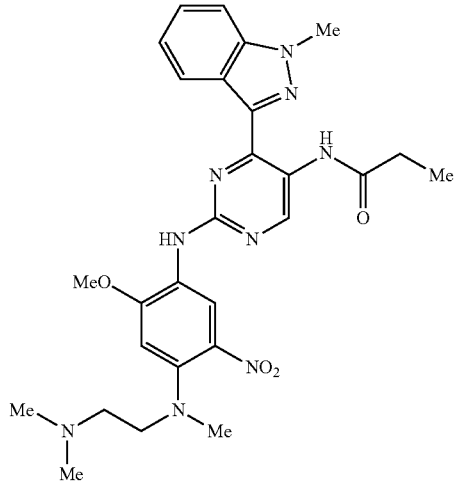<br>M29 |
| 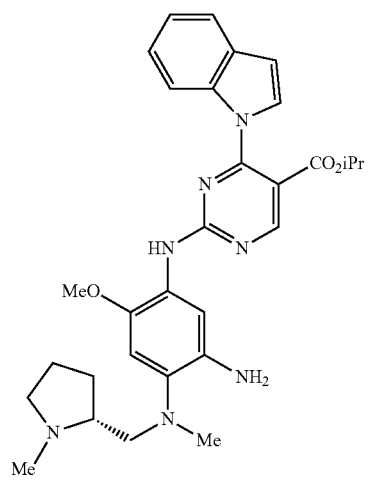<br>T3 | 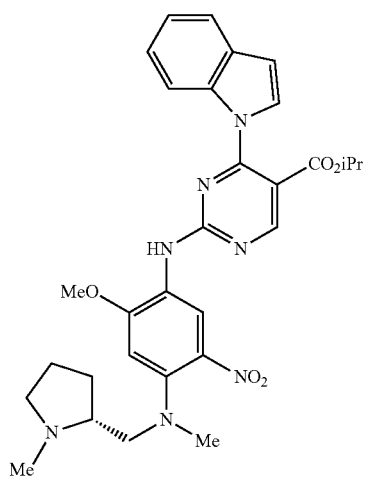<br>M30 |
| 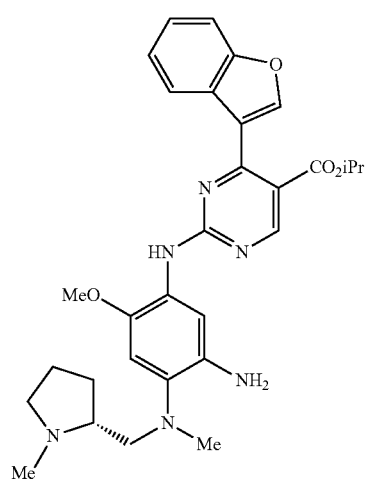<br>T4 | 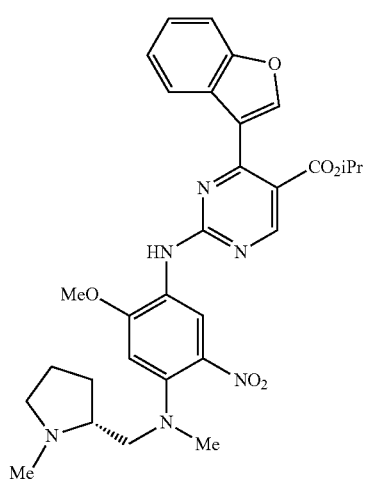<br>M31 |

TABLE 25-continued
| Intermediate T | Nitro compound |
|---|---|
| 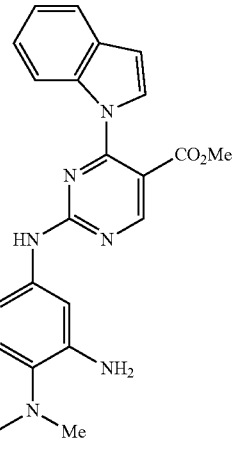<br>T5 | 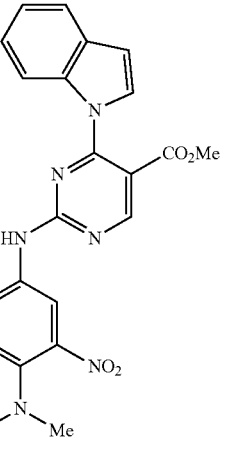<br>M32 |
| 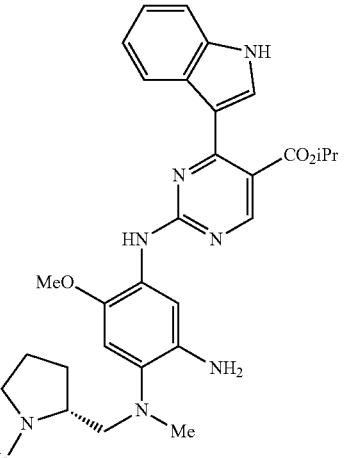<br>T6 | 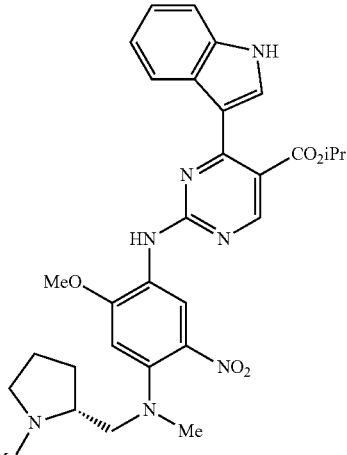<br>M33 |
| 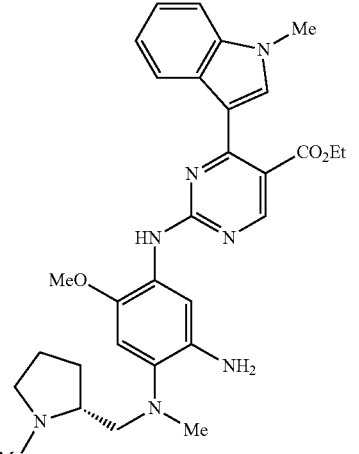<br>T7 | 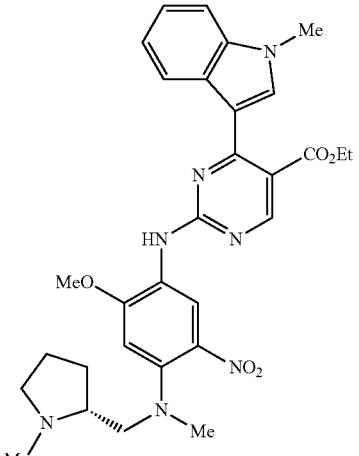<br>M34 |

TABLE 25-continued
| Intermediate T | Nitro compound |
|---|---|
| 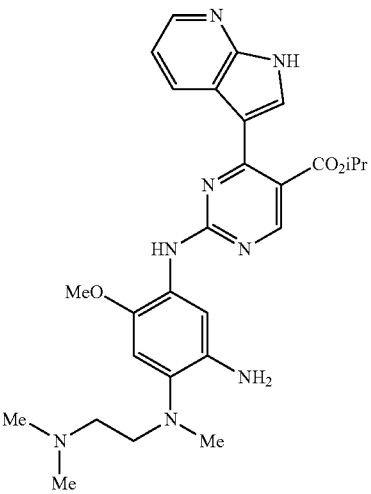 | 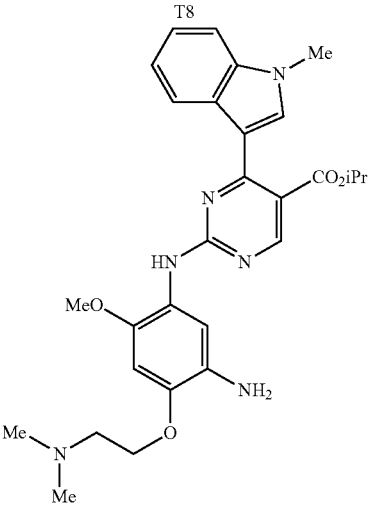 M35 |
| 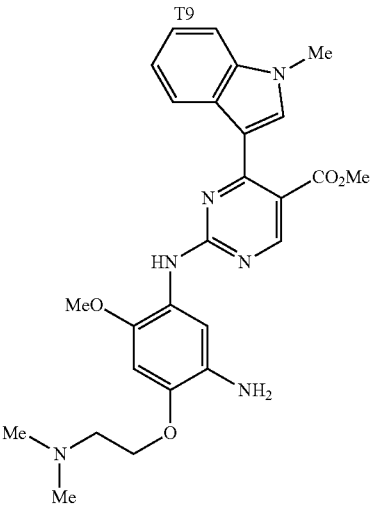 T8 | 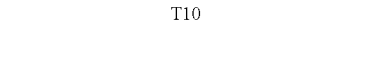 M36 |
| 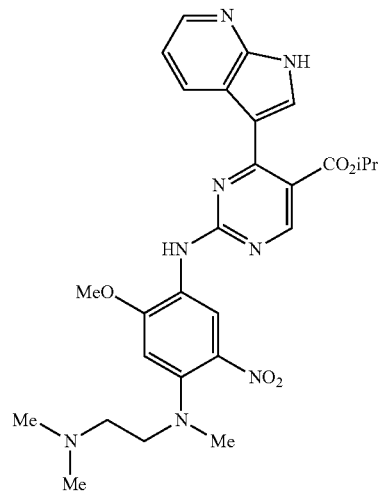 T9 | 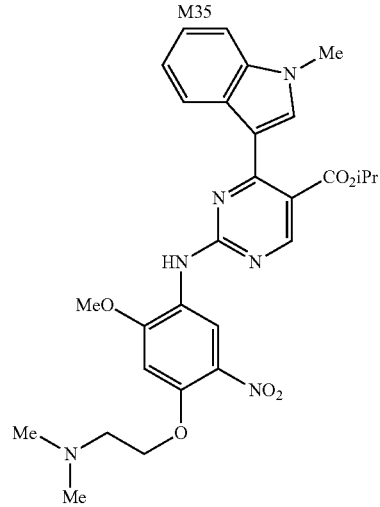 O3 |
| T10 | |
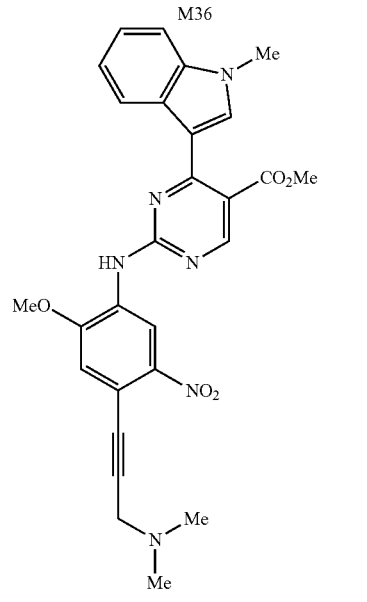

TABLE 25-continued
| Intermediate T | Nitro compound |
|---|---|
| 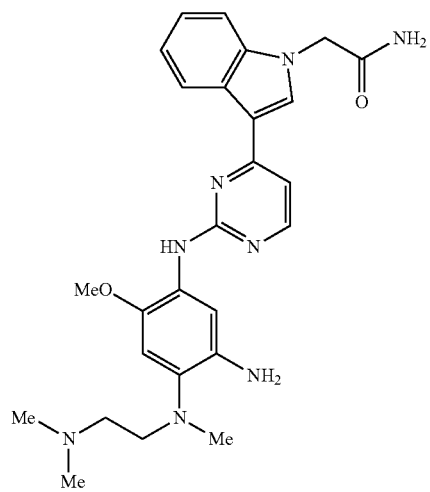 T11 | 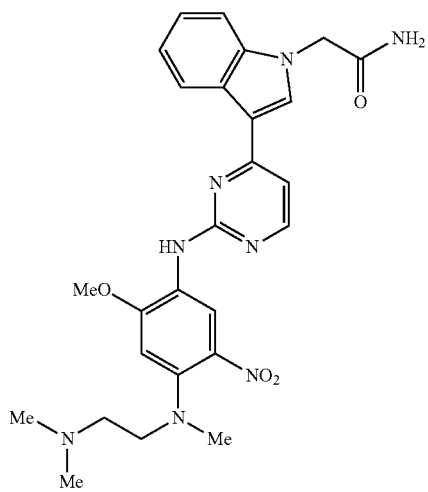 M37 |
| 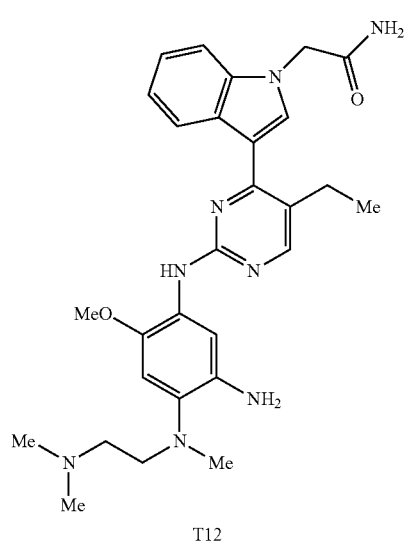 T12 | 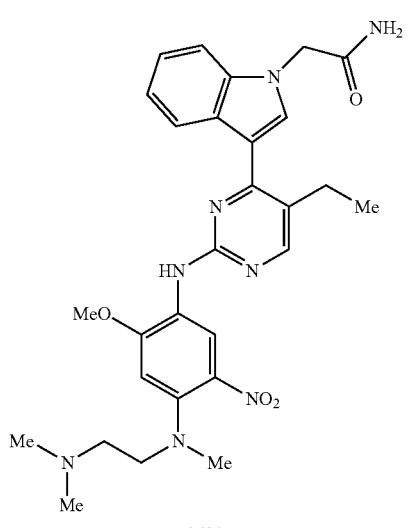 M38 |
| 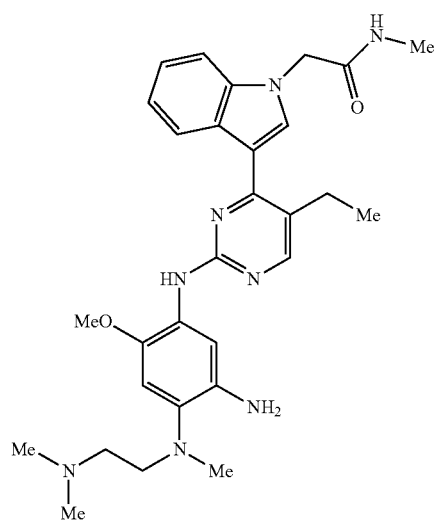 T13 | 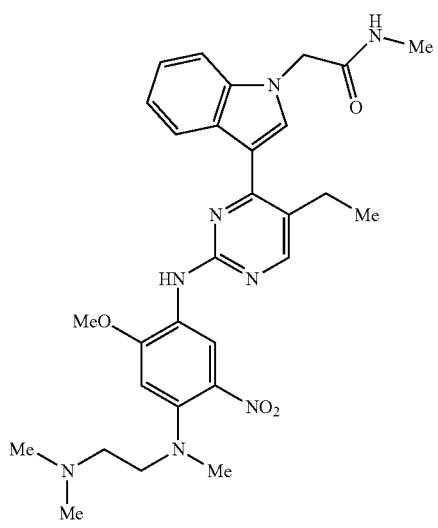 M39 |

TABLE 25-continued

| Intermediate T | Nitro compound |
|---|---|
| T14 | M40 |
| T15 | M41 |
| T16 | M43 |

TABLE 25-continued
| Intermediate T | Nitro compound |
|---|---|
| 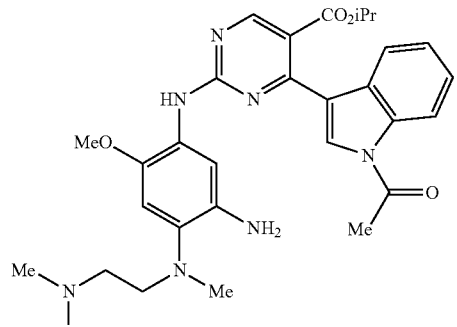 T17 | 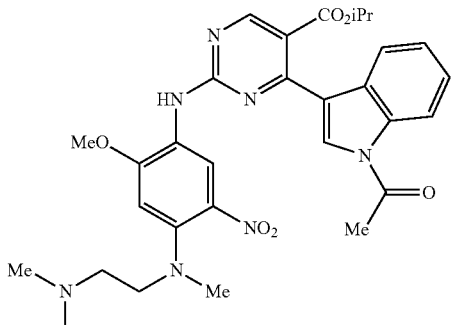 10 |
| 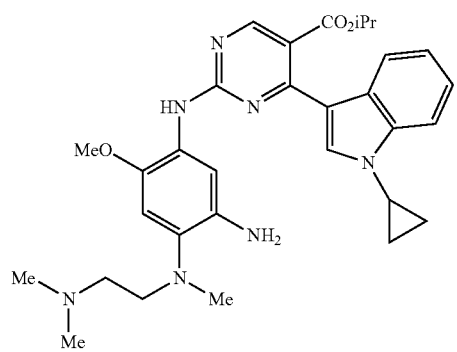 T18 | 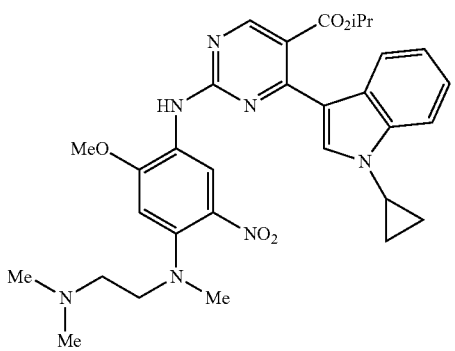 Q19 |
| 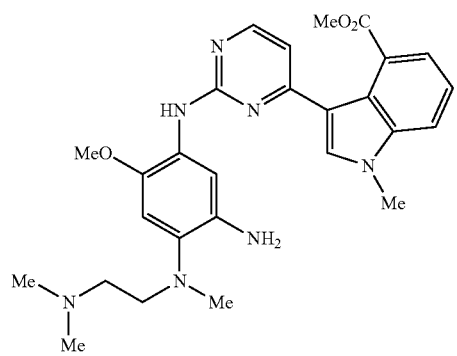 T19 | 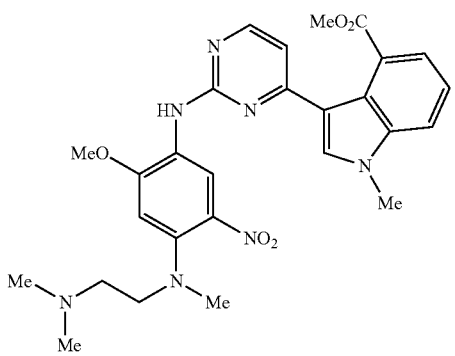 M46 |
| 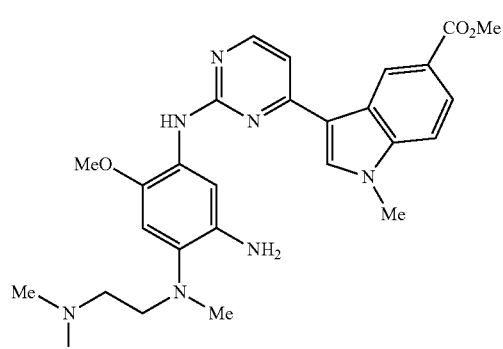 T20 | 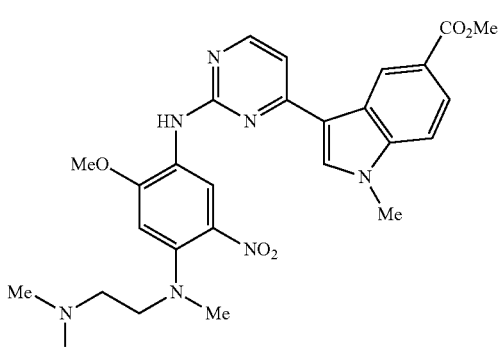 M47 |

TABLE 25-continued

| Intermediate T | Nitro compound |
| --- | --- |
| T21 | M48 |
| T22 | M49 |
| T23 | Q20 |
| T24 | Q21 |

TABLE 25-continued
| Intermediate T | Nitro compound |
|---|---|
| 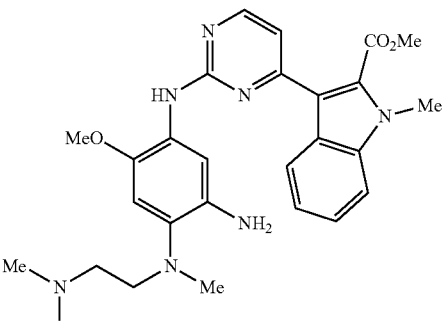<br>T25 | 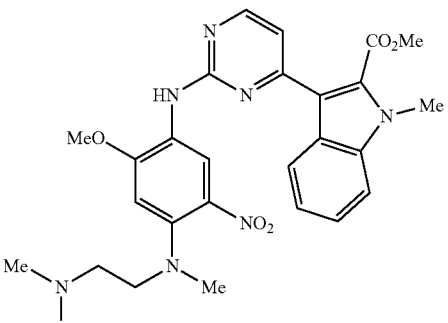<br>M50 |
| 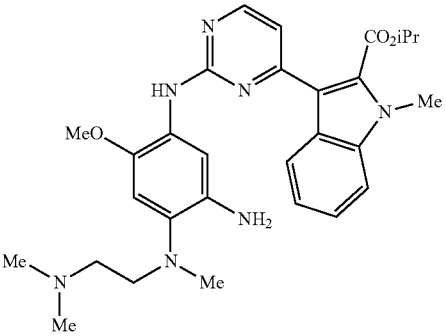<br>T26 | 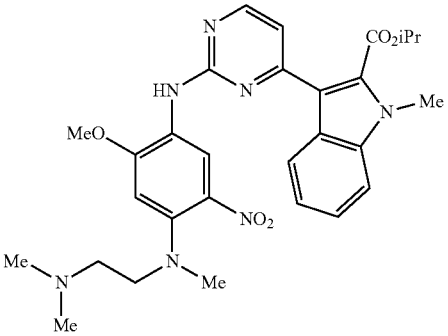<br>Q22 |
| 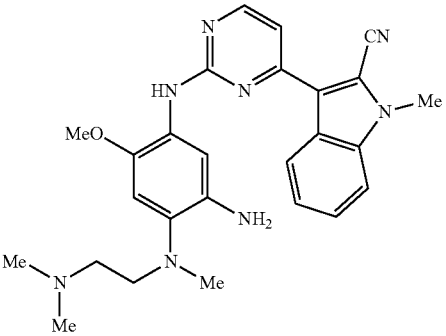<br>T27 | 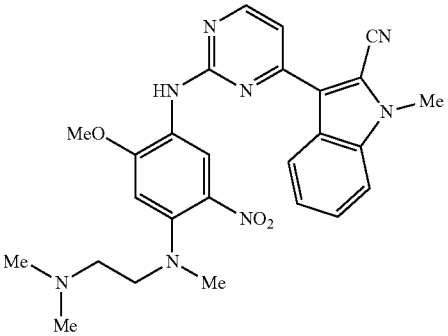<br>M51 |
| 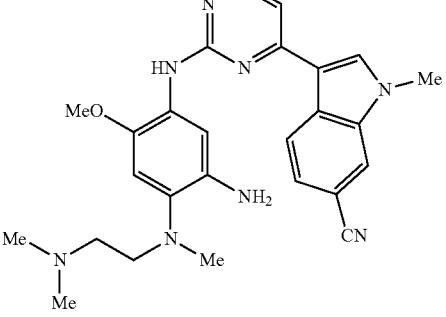<br>T28 | 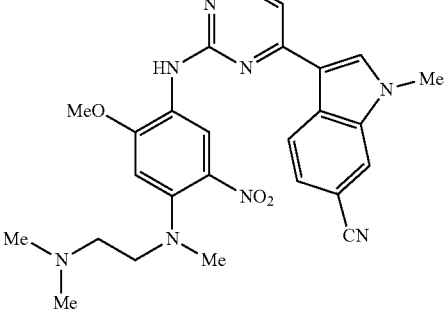<br>M52 |

TABLE 25-continued
| Intermediate T | Nitro compound |
|---|---|
| 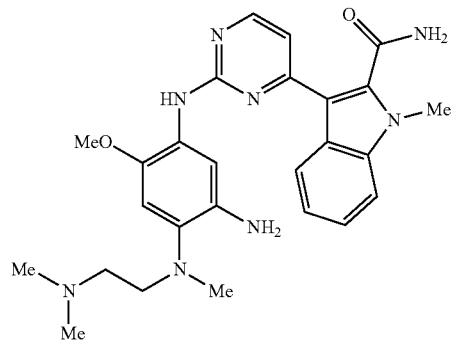<br>T29 | 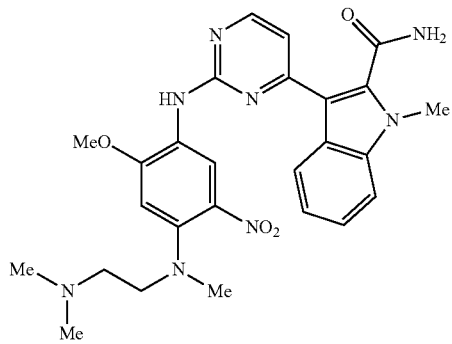<br>L9 |
| 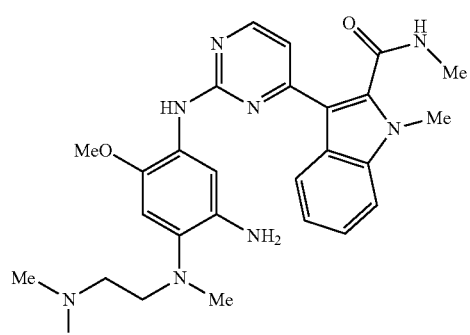<br>T30 | 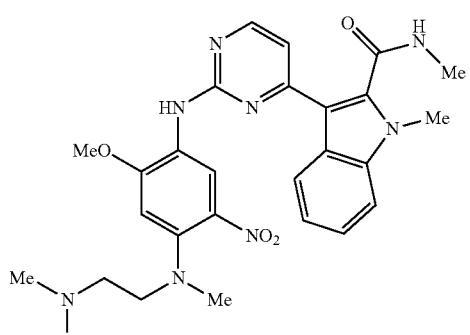<br>L10 |
| 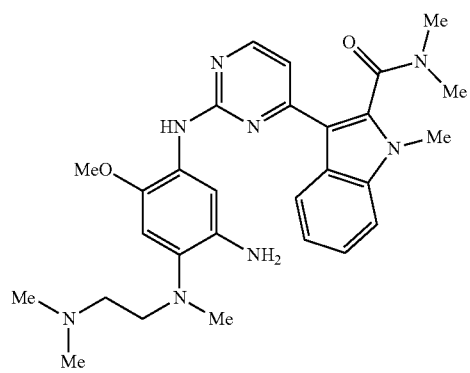<br>T31 | 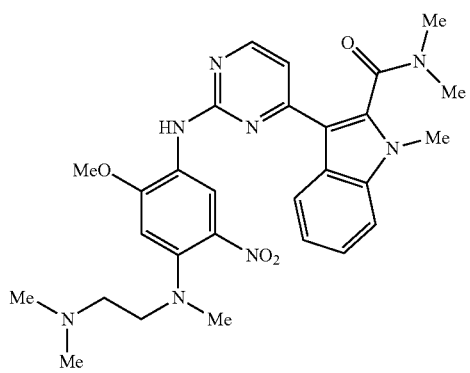<br>L11 |

TABLE 25-continued
| Intermediate T | Nitro compound |
|---|---|
| 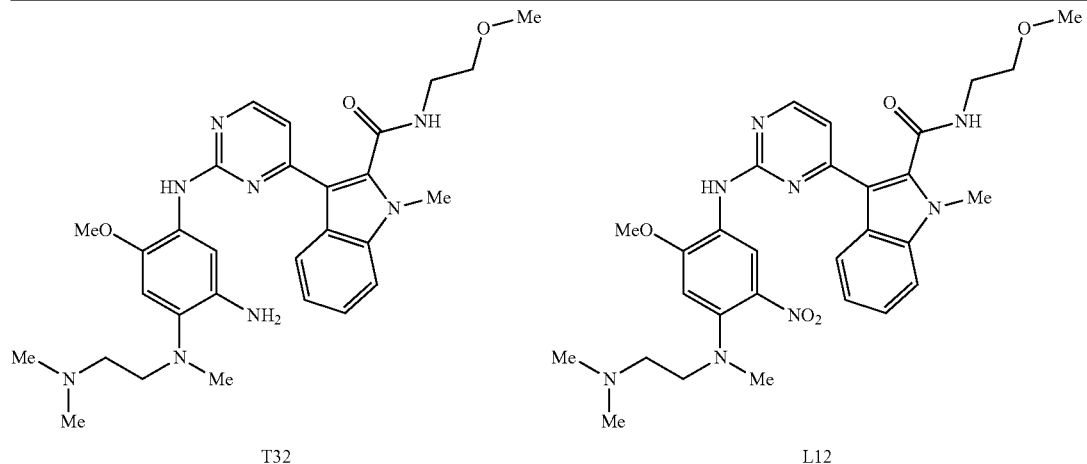 T32 | L12 |
| 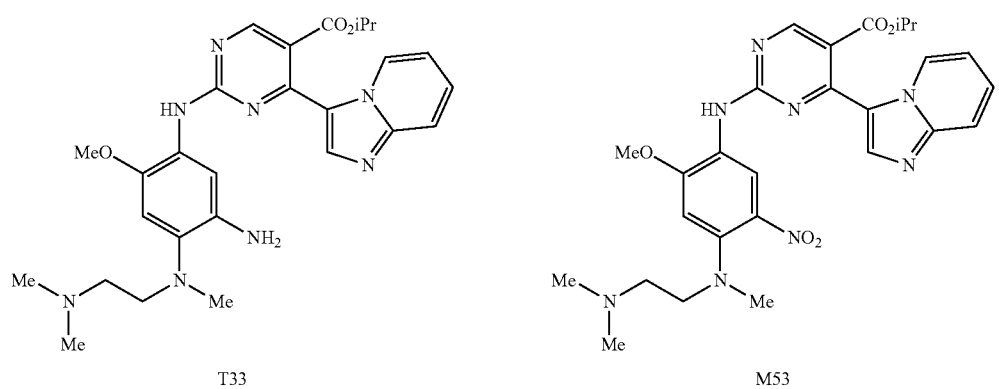 T33 | M53 |
| 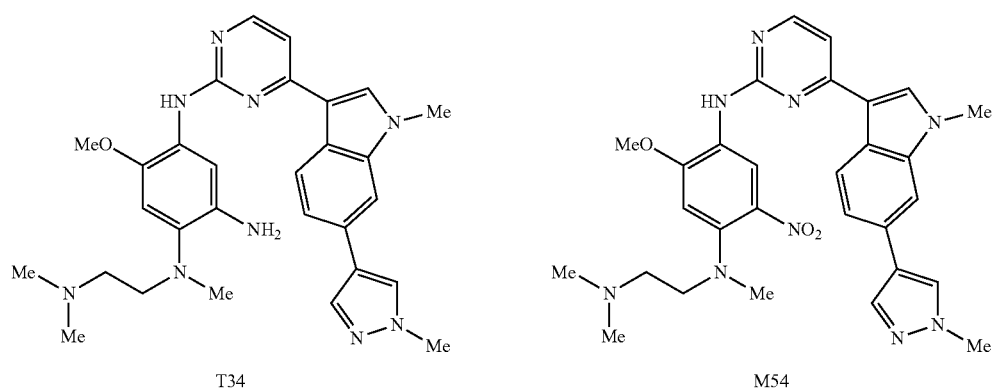 T34 | M54 |

TABLE 25-continued
| Intermediate T | Nitro compound |
|---|---|
| 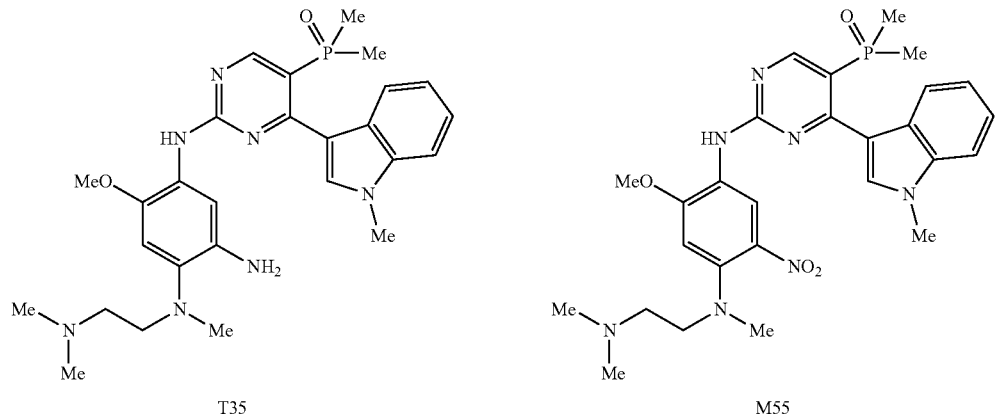T35 | M55 |
| 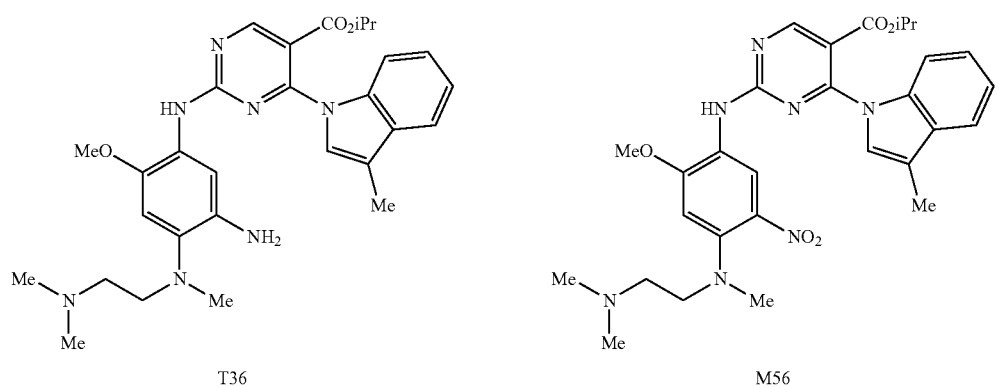T36 | M56 |
| 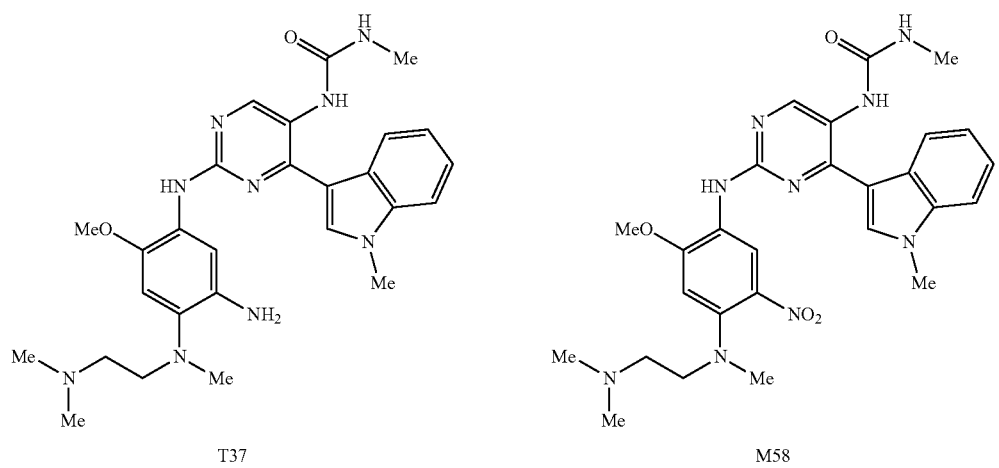T37 | M58 |

TABLE 25-continued

| Intermediate T | Nitro compound |
|---|---|
| 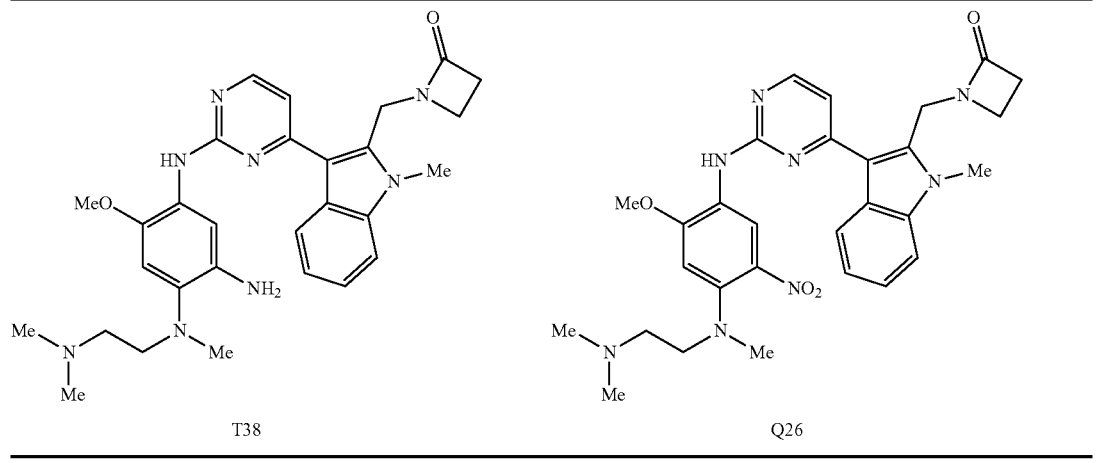 T38 | Q26 |

Example 1

N-(2-((2-(dimethylamino)ethyl)(methyl)amino)-5-((5-ethyl-4-(pyrazolo[1,5-a]pyridin-3-yl)pyrimidin-2-yl)amino)-4-methoxyphenyl)acrylamide

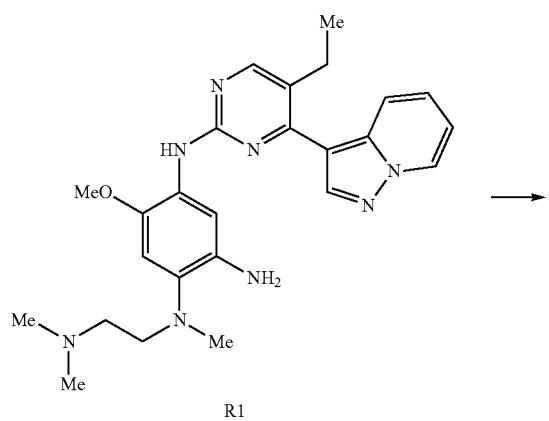

R1

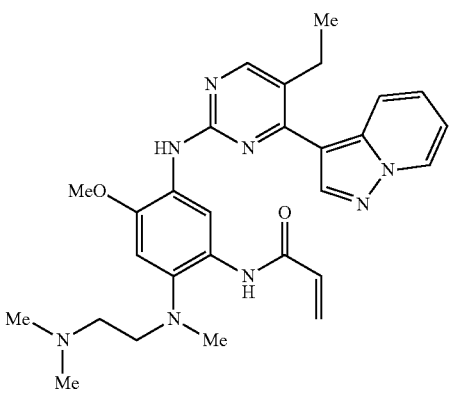

Example 1

A solution of N1-(2-(dimethylamino)ethyl)-N4-(5-ethyl-4-(pyrazolo[1,5-a]pyridin-3-yl)pyrimidin-2-yl)-5-methoxy-N-methylbenzene-1,2,4-triamine (R1) (64 mg, 0.14 mmol) in DCM (1.4 mL) was treated with EDCl (54 mg, 0.28 mmol), Hunig's base (73 uL, 0.42 mmol), and acrylic acid (19 uL, 0.28 mmol). The mixture was concentrated in vacuo and the product was purified by preparative TLC (5% MeOH/DCM) to afford N-(2-((2-(dimethylamino)ethyl)(methyl)amino)-5-((5-ethyl-4-(pyrazolo[1,5-a]pyridin-3-yl)pyrimidin-2-yl)amino)-4-methoxyphenyl)acrylamide (Example 1) as an orange solid. $^1$H NMR (CDCl$_3$): δ 10.01 (br. s., 1H), 9.48 (s, 1H), 8.50 (dt, J=6.9, 1.1 Hz, 1H), 8.40 (m, 2H), 8.33 (s, 1H), 7.41 (s, 1H), 7.21-7.25 (m, 1H), 6.83-6.89 (m, 1H), 6.78 (s, 1H), 6.24-6.41 (m, 2H), 5.66 (dd, J=9.9, 1.7 Hz, 1H), 3.86 (s, 3H), 2.85-2.91 (m, 2H), 2.81 (q, J=7.4 Hz, 2H), 2.70 (s, 3H), 2.27-2.31 (m, 3H), 2.25 (s, 6H), 1.28 (t, J=7.5 Hz, 3H). ESI-MS m/z: 515.2 [M+H]$^+$.

The following example compounds, as shown in Table 26, were synthesized in analogous fashion to Example 1.

TABLE 26

| Ex. | Compound | Amine compound |
|---|---|---|
| 2 | 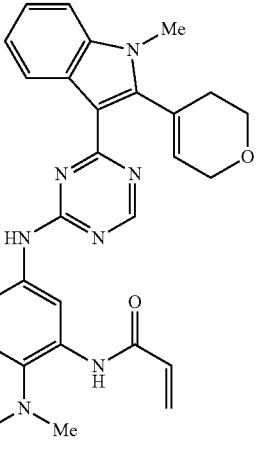<br>N-(5-((4-(2-(3,6-dihydro-2H-pyran-4-yl)-1-methyl-1H-indol-3-yl)-1,3,5-triazin-2-yl)amino)-2-((2-(dimethylamino)ethyl)(methyl)amino)-4-methoxyphenyl)acrylamide<br>$^1$H NMR: (CDCl$_3$) δ 10.09 (br. s., 1H), 9.46 (br. s., 1H), 8.74-8.80 (m, 1H), 8.66 (d, J = 7.9 Hz, 1H), 7.46 (br. s., 1H), 7.20-7.37 (m, 2H), 6.81 (s, 1H), 6.41 (d, J = 16.8 Hz, 1H), 6.24-6.35 (m, 1H), 5.81 (br. s., 1H), 5.62-5.70 (m, 1H), 4.40 (d, J = 2.3 Hz, 2H), 4.02 (br. s., 2H), 3.89 (s, 3H), 3.75 (s, 3H), 2.82-2.95 (m, 2H), 2.72 (s, 3H), 2.47 (br. s., 2H), 2.24-2.34 (m, 8H) ESI-MS m/z: 583.5 [M + H]$^+$ | 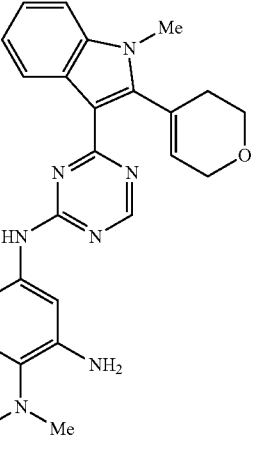<br>R2 |
| 3 | 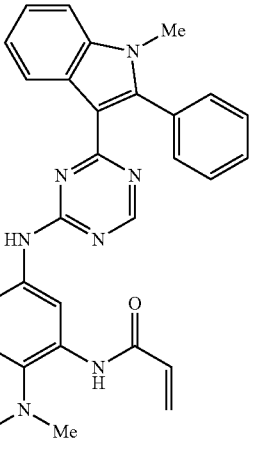<br>N-(2-((2-(dimethylamino)ethyl)(methyl)amino)-4-methoxy-5-((4-(1-methyl-2-phenyl-1H-indol-3-yl)-1,3,5-triazin-2-yl)amino)phenyl)acrylamide<br>$^1$H NMR: (CDCl$_3$) δ 10.04 (br. s., 1H), 9.34 (br. s., 1H), 8.66 (d, J = 8.4 Hz, 1H), 8.59 (br. s., 1H), 7.37-7.48 (m, 6H), 7.27-7.35 (m, 2H), 7.14 (s, 1H), 6.77 (s, 1H), 6.35-6.44 (m, 1H), 6.23-6.34 (m, 1H), 5.64-5.73 (m, 1H), 3.85 (s, 3H), 3.61 (s, 3H), 2.86 (t, J = 5.5 Hz, 2H), 2.70 (s, 3H), 2.30 (obs. m., 2H), 2.26 (s, 6H)<br>ESI-MS m/z: 577.3 [M + H]$^+$ | 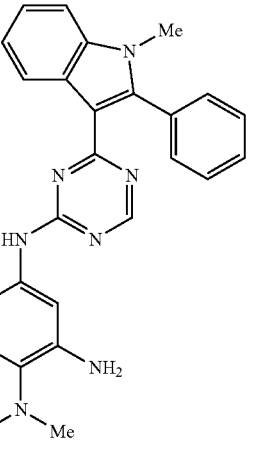<br>R5 |

TABLE 26-continued

| Ex. | Compound | Amine compound |
|---|---|---|
| 4 | 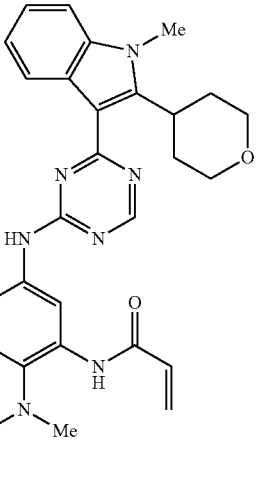<br>N-(2-((2-(dimethylamino)ethyl)(methyl)amino)-4-methoxy-5-((4-(1-methyl-2-(tetrahydro-2H-pyran-4-yl)-1H-indol-3-yl)-1,3,5-triazin-2-yl)amino)phenyl)acrylamide<br>$^1$H NMR: (TFA salt) (CDCl$_3$) δ 11.14 (br. s., 1H), 9.04 (s, 1H), 8.86 (br. s., 1H), 8.59 (br. s., 1H), 8.39 (d, J = 7.0 Hz, 1H), 7.30 (s, 3H), 7.17 (br. s., 1H), 6.85 (dd, J = 16.8, 10.3 Hz, 1H), 6.78 (s, 1H), 6.35 (d, J = 16.3 Hz, 1H), 5.70 (d, J = 10.9 Hz, 1H), 4.91 (br. s., 1H), 3.97 (obs. m, 2H), 3.93 (s, 3H), 3.84 (s, 3H), 3.30-3.34 (m, 2H), 3.20-3.25 (m, 2H), 3.22 (br. s., 32), 2.85 (s, 6H), 2.68 (s, 3H), 2.23 (br. s., 2H), 1.67 (d, J = 11.2 Hz, 2H)<br>ESI-MS m/z: 585.3 [M + H]$^+$ | S1 |
| 5 | 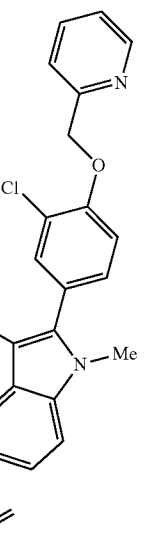<br>N-(5-((4-(2-(3-chloro-4-(pyridin-2-ylmethoxy)phenyl)-1-methyl-1H-indol-3-yl)pyrimidin-2-yl)amino)-2-((2-(dimethylamino)ethyl)(methyl)amino)-4-methoxyphenyl)acrylamide<br>$^1$H NMR: (MeOH-d$_4$): δ 8.50-8.64 (m, 2H), 8.31 (d, J = 7.9 Hz, 1H), 8.10 (d, J = 5.4 Hz, 1H), 7.95 (td, J = 7.7, 1.8 Hz, 1H), 7.76 (d, J = 7.9 Hz, 1H), 7.49-7.57 | R3 |

| Ex. | Compound | Amine compound |
|---|---|---|
| | (m, 2H), 7.41-7.46 (m, 1H), 7.37-7.41 (m, 1H), 7.32-7.35 (m, 1H), 7.29 (ddd, J = 8.3, 7.1, 1.2 Hz, 1H), 7.18 (td, J = 7.6, 0.9 Hz, 1H), 6.95 (s, 1H), 6.38-6.52 (m, 3H), 5.81-5.90 (m, 1H), 5.37 (s, 2H), 4.02 (s, 3H), 3.67 (s, 3H), 3.48 (br. s., 2H), 3.26 (br. s., 2H), 2.85 (br. s., 6H), 2.71 (s, 3H)<br>ESI-MS m/z: 717.3 [M + H]⁺ | |
| 6 | 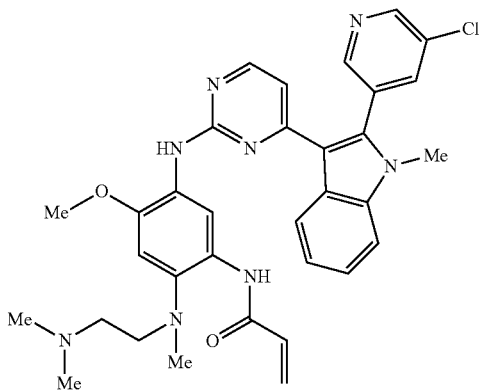 [SMILES: C=CC(=O)Nc1cc(Nc2nccc(-c3c(-c4cncc(Cl)c4)n(C)c4ccccc34)n2)c(OC)cc1N(C)CCN(C)C]<br>N-(5-((4-(2-(5-chloropyridin-3-yl)-1-methyl-1H-indol-3-yl)pyrimidin-2-yl)amino)-2-((2-(dimethylamino)ethyl)(methyl)amino)-4-methoxyphenyl)acrylamide<br>¹H NMR (CDCl₃): δ 9.99-10.04 (m, 1H), 10.01 (br. s., 1H), 9.45-9.48 (m, 1H), 9.45-9.48 (m, 1H), 9.46 (s, 1H), 8.65 (d, J = 2.4 Hz, 1H), 8.56 (d, J = 1.8 Hz, 1H), 8.34 (d, J = 5.3 Hz, 1H), 8.29 (d, J = 7.8 Hz, 1H), 7.82-7.86 (m, 1H), 7.42 (d, J = 8.4 Hz, 1H), 6.79 (s, 1H), 6.50 (d, J = 5.3 Hz, 1H), 6.26-6.45 (m, 2H), 5.67 (dd, J = 9.9, 1.8 Hz, 1H), 3.89 (s, 3H), 3.68 (s, 3H), 2.90 (t, J = 5.6 Hz, 2H), 2.72 (s, 3H), 2.26-2.35 (m, 8H)<br>ESI-MS m/z: 611.5 [M + H]⁺ | 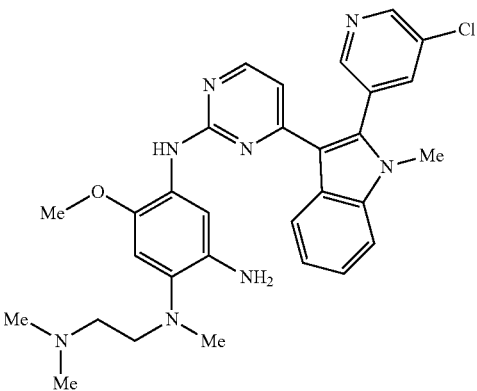<br>R4 |
| 7 | 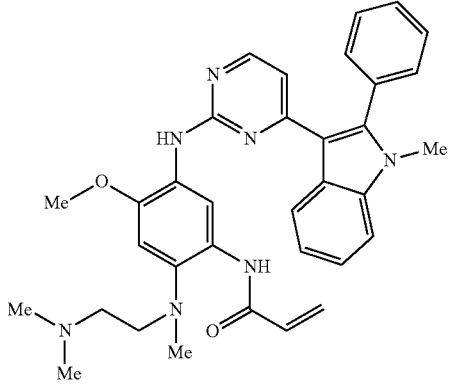 [SMILES: C=CC(=O)Nc1cc(Nc2nccc(-c3c(-c4ccccc4)n(C)c4ccccc34)n2)c(OC)cc1N(C)CCN(C)C]<br>N-(2-((2-(dimethylamino)ethyl)(methyl)amino)-4-methoxy-5-((4-(1-methyl-2-phenyl-1H-indol-3-yl)pyrimidin-2-yl)amino)phenyl)acrylamide<br>¹H NMR: (CDCl₃): δ: 9.93 (br. s., 1H), 9.40 (s, 1H), 8.28-8.55 (m, 1H), 7.88-8.15 (m, 1H), 7.38-7.42 (m, 4H), 7.16-7.35 (m, 5H), 6.70 (s, 1H), 6.16-6.34 (m, 2H), 6.07 (d, J = 5.4 Hz, 1H), 5.56 | 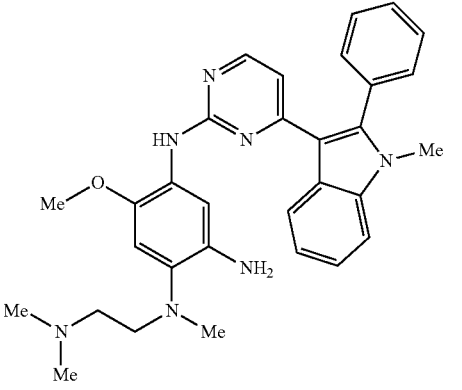<br>R6 |

TABLE 26-continued

| Ex. | Compound | Amine compound |
|---|---|---|
| | (dd, J = 9.7, 2.0 Hz, 1H), 3.79 (s, 3H), 3.52 (s, 3H), 2.80 (t, J = 5.6 Hz, 2H), 2.61 (s, 3H), 2.15-2.27 (m, 9H) ESI-MS m/z: 576.3 [M + H]⁺ | |
| 8 | 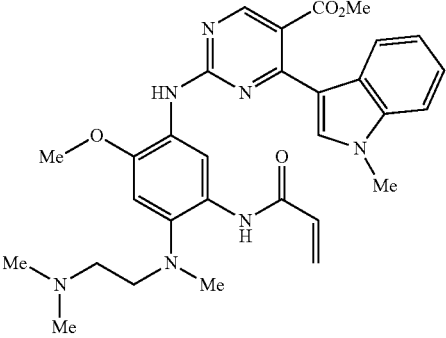 [SMILES: C=CC(=O)Nc1cc(Nc2ncc(C(=O)OC)c(-c3cn(C)c4ccccc34)n2)c(OC)cc1N(C)CCN(C)C]<br>methyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate<br>¹H NMR (CDCl₃) δ 10.19 (br. s., 1H), 9.79 (s, 1H), 8.92 (s, 1H), 8.82 (br. s., 1H), 7.94 (s, 1H), 7.53 (d, J = 12.42 Hz, 1H), 7.36 (d, J = 7.71 Hz, 1H), 7.19-7.31 (m, 2H), 6.81 (s, 1H), 6.44-6.53 (m, 1H), 6.38 (d, J = 8.78 Hz, 1H), 5.71-5.77 (m, 1H), 3.98 (s, 3H), 3.90 (s, 3H), 3.65 (s, 3H), 2.90 (br. s., 2H), 2.69-2.76 (m, 3H), 2.28 (br. s., 8H)<br>ESI-MS m/z: 559.3 [M + H]⁺ | 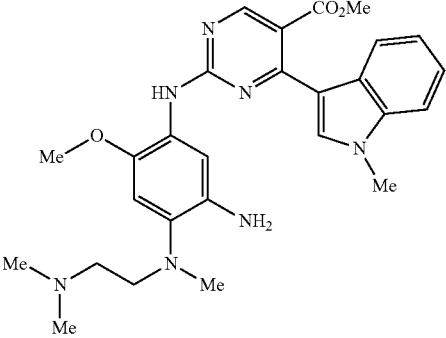<br>R11 |
| 9 | 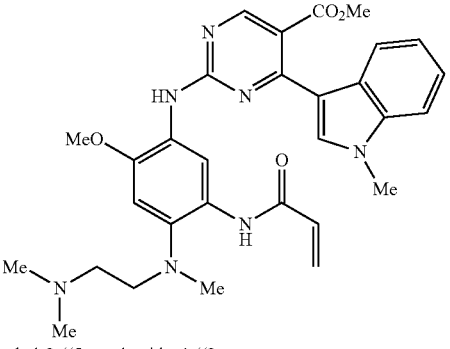<br>ethyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate<br>¹H NMR (CDCl₃) δ 10.16 (br. s., 1H), 9.80 (s, 1H), 8.93 (s, 1H), 8.77 (br. s., 1H), 7.93 (s, 1H), 7.54 (br. s., 1H), 7.16-7.37 (m, 3H), 6.81 (s, 1H), 6.44-6.54 (m, 1H), 6.40 (br. s., 1H), 5.74 (d, J = 11.92 Hz, 1H), 4.07-4.19 (m, 2H), 3.97 (s, 3H), 3.88-3.92 (s, 3H), 2.92 (m, 2H), 2.73 (s, 3H), 2.30-2.56 (m, 8H), 0.84-1.08 (m, 3H)<br>ESI-MS m/z: 573.3 [M + H]⁺ | 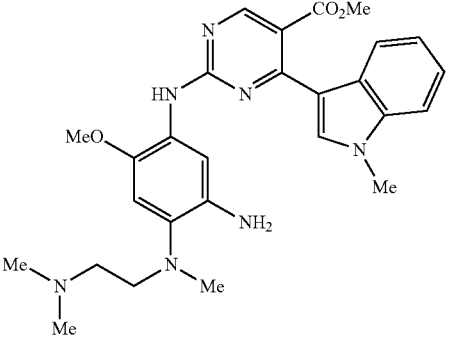<br>R12 |

TABLE 26-continued

| Ex. | Compound | Amine compound |
|---|---|---|
| 10 | 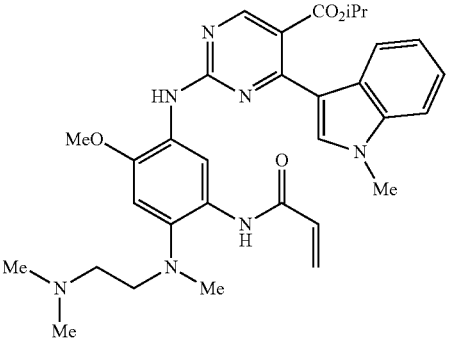<br>isopropyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate<br>$^1$H NMR (CDCl$_3$) δ 10.15 (s, 1H), 9.80 (s, 1H), 8.91 (s, 1H), 8.70 (br. s., 1H), 7.91 (s, 1H), 7.48-7.71 (m, 1H), 7.15 7.37 (m, 3H), 6.81 (s, 1H), 6.49 (dd, J = 17.07, 1.88 Hz, 1H), 6.36 (dd, J = 16.94, 10.04 Hz, 1H), 5.73 (dd, J = 10.04, 1.88 Hz, 1H), 5.02 (dt, J = 12.45, 6.26 Hz, 1H), 4.00 (s, 3H), 3.90 (s, 3H), 2.86-2.93 (m, 2H), 2.76 (s, 3H), 2.26-2.31 (m, 8H), 1.05 (d, J = 6.15 Hz, 6H))<br>ESI-MS m/z: 586.3 [M + H]$^+$ | 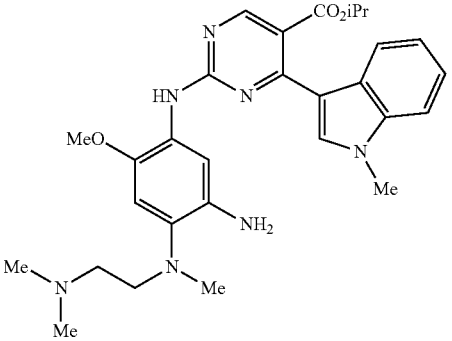<br>R13 |
| 11 | 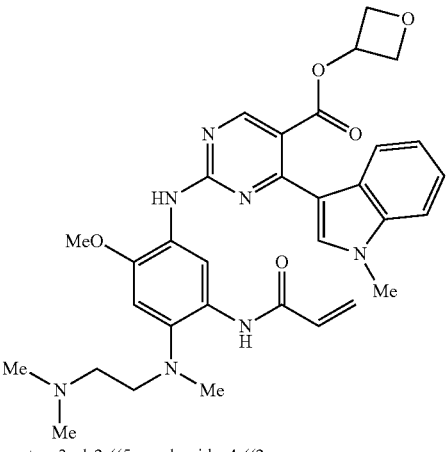<br>oxetan-3-yl 2-((5-acrylamido-4-((2-(dimethylamino)ethyl)(methyl)amino)-2-methoxyphenyl)amino)-4-(1-methyl-1H-indol-3-yl)pyrimidine-5-carboxylate<br>$^1$H NMR: (CDCl$_3$) δ 10.11 (s, 1H), 9.72 (s, 1H), 8.87 (br. s., 1H), 8.78 (br. s., 1H), 7.89 (s, H), 7.36 (br. s., 1 H), 7.19-7.20 (m, 1H), 7.14 (t, J = 7.16 Hz, 1H), 7.02-7.09 (m, 1H), 6.73 (s, 1H), 6.41 (dd, J = 16.64 Hz, 1H), 6.28 (dd, J = 16.94, 10.04 Hz, 1H), 5.65 (dd, J = 10.04, 1.88 Hz, 1H), 5.44-5.52 (m, 1H), 4.56 (t, J = 6.71 Hz, 2H), 4.21 (br. s., 2H), 3.79-3.90 (m, 6H), 2.77-2.84 (m, 2H), 2.63 (s, 3H), 2.10-2.29 (m, 9H)<br>ESI-MS m/z: 600.4 [M + H]$^+$ | 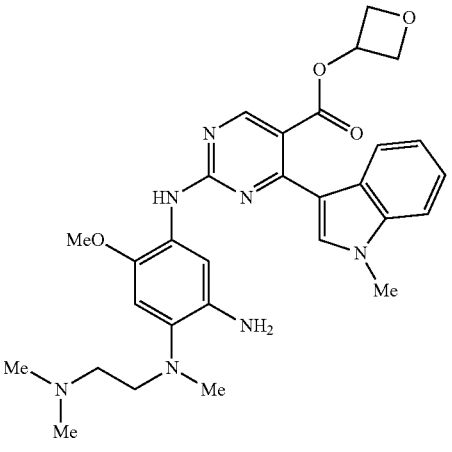<br>R14 |

TABLE 26-continued

| Ex. | Compound | Amine compound |
|---|---|---|
| 12 | 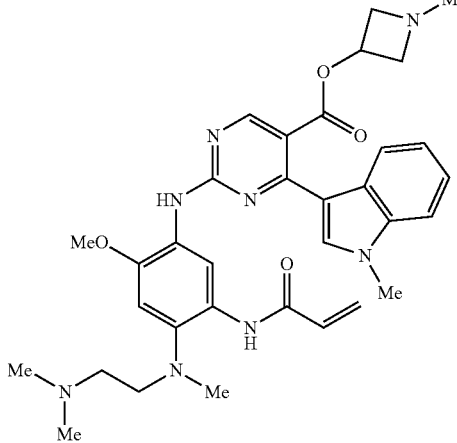<br>1-methylazetidin-3-yl 2-((5-acrylamido-4-((2-(dimethylamino)ethyl)(methyl)amino)-2-methoxyphenyl)amino)-4-(1-methyl-1H-indol-3-yl)pyrimidine-5-carboxylate<br>$^1$H NMR: (MeOH-d$_4$) δ 8.64 (br. s., 1H), 8.33-8.37 (m, 1H), 7.99-8.09 (m, 1H), 7.60 (s, 1H), 7.37 (d, J = 8.28 Hz, 1H), 7.15 (t, J = 7.19 Hz, 1H), 7.01-7.09 (m, 1H), 6.87 (s, 1H), 6.29-6.41 (m, 2H), 5.71-5.78 (m, 1H), 3.88-3.92 (m, 3H), 3.76-3.80 (m, 3H), 3.35-3.55 (m, 1H), 3.24-3.33 (m, 2H), 2.98-3.11 (m, 2H), 2.95 (br. s., 2H), 2.56-2.66 (m, 6H), 2.41 (br. s., 2H), 2.30 (s, 3H), 1.46-1.68 (m, 2H)<br>ESI-MS m/z: 613.4 [M + H]$^+$ | 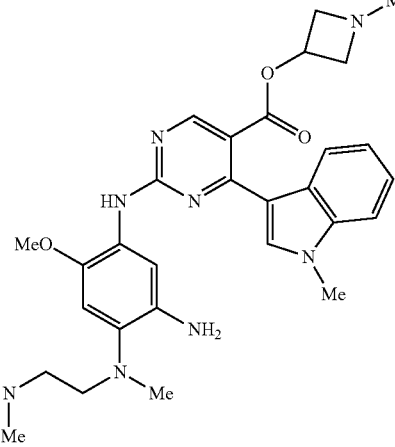<br>R15 |
| 13 | 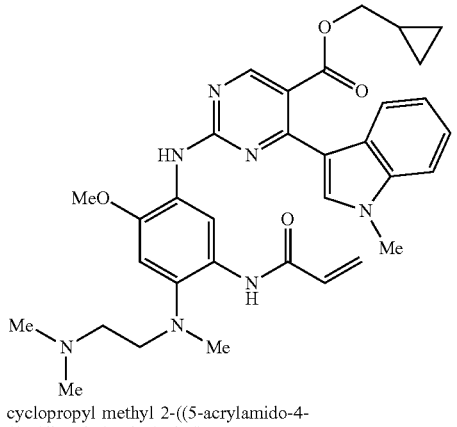<br>cyclopropyl methyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate<br>$^1$H NMR: (CDCl$_3$) δ 10.12 (br. s., 1H), 9.80 (s, 1H), 8.94 (s, 1H), 8.76 (br. s., 1H), 7.89-7.99 (m, 1H), 7.56 (d, J = 7.78 Hz, 1H), 7.14-7.38 (m, 3H), 6.81 (s, 1H), 6.37-6.57 (m, 2H), 5.71-5.77 (m, 1H), 3.86-4.00 (m, 7H), 2.93 (br. s., 2H), 2.70-2.75 (m, 3H), 2.32 (br. s., 8H), 0.37 (d, J = 7.40 Hz, 2H)<br>ESI-MS m/z: 598.4 [M + H]$^+$ | 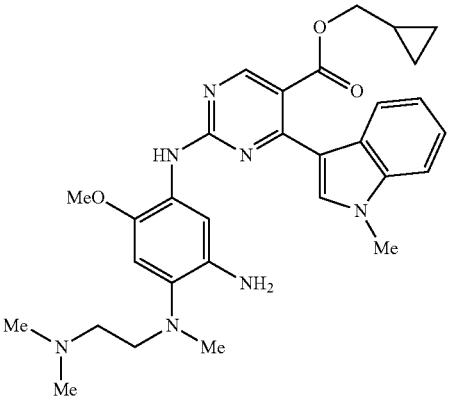 [SMILES: C=CC(=O)Nc1cc(Nc2ncc(C(=O)OCC3CC3)c(-c3cn(C)c4ccccc34)n2)c(OC)cc1N(C)CCN(C)C]<br>R16 |

| Ex. | Compound | Amine compound |
|---|---|---|
| 14 | 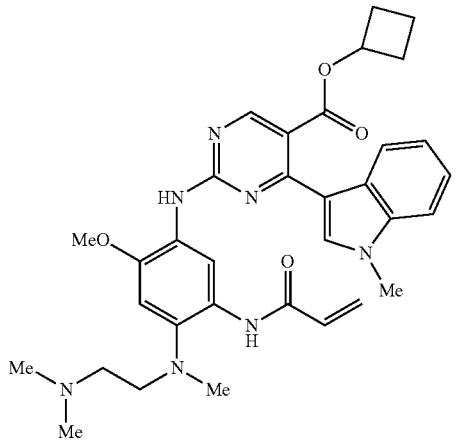 [SMILES: C=CC(=O)Nc1cc(Nc2ncc(C(=O)OC3CCC3)c(-c3cn(C)c4ccccc34)n2)c(OC)cc1N(C)CCN(C)C]<br>cyclobutyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate<br><sup>1</sup>H NMR: (CDCl$_3$) δ 9.80 (s, 1H), 8.94 (s, 1H), 8.76 (br. s., 1H), 7.89-7.99 (m, 1H), 7.56 (d, J = 7.78 Hz, 1H), 7.14-7.38 (m, 3H), 6.81 (s, 1H), 6.37-6.57 (m, 1H), 5.71-5.77 (m, 1H), 4.95-5.05 (m, 1H), 3.86-4.00 (m, 6H), 2.93 (br. s., 2H), 2.20-2.75 (m, 11H), 1.88-2.02 (m, 2H), 1.78 (br. s., 1H), 1.24-1.35 (m, H)<br>ESI-MS m/z: 598.4 [M + H]$^+$ | 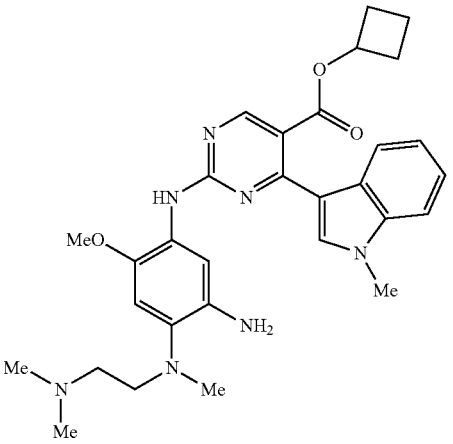<br>R17 |
| 15 | 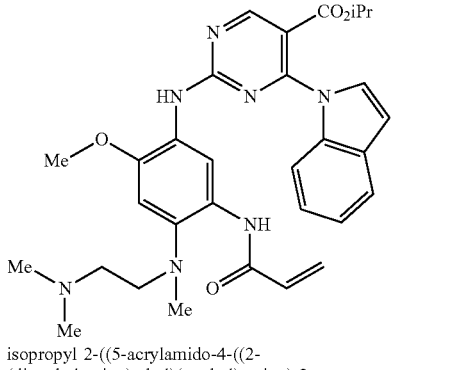<br>isopropyl 2-((5-acrylamido-4-((2-(dimethylamino)ethyl)(methyl)amino)-2-methoxyphenyl)amino)-4-(1H-indol-1-yl)pyrimidine-5-carboxylate<br><sup>1</sup>H NMR (CDCl$_3$): δ 9.95 (br. s., 1H), 9.48 (s, 1H), 8.97 (br. s., 1H), 7.83 (s, 2H), 7.32-7.57 (m, 2H), 7.07 (q, J = 7.0 Hz, 2H), 6.70 (s, 1H), 6.62 (d, J = 3.9 Hz, 1H), 6.40 (br. s., 2H), 5.53-5.74 (m, 1H), 4.75-4.91 (m, 1H), 3.80 (s, 3H), 2.85 (br. s., 2H), 2.63 (s, 3H), 2.19-2.40 (m, 8H), 0.84 (br. s., 6H)<br>ESI-MS m/z: 572.3 [M + H]$^+$ | 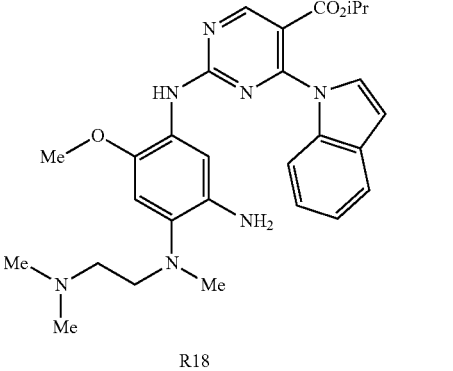<br>R18 |

TABLE 26-continued

| Ex. | Compound | Amine compound |
|---|---|---|
| 16 | 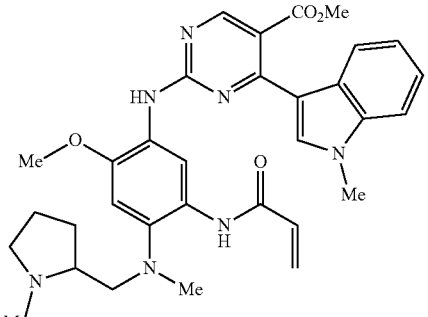<br>methyl 2-((5-acrylamido-2-methoxy-4-(methyl((1-methylpyrrolidin-2-yl)methyl)amino)phenyl)amino)-4-(1-methyl-1H-indol-3-yl)pyrimidine-5-carboxylate<br>$^1$H NMR: (MeOH-d$_4$) δ 9.30 (br. s., 1H), 8.78 (s, 1H), 8.31 (br. s., 1H), 7.68 (d, J = 7.40 Hz, 1H), 7.46 (d, J = 8.45 Hz, 1H), 7.23 (t, J = 7.22 Hz, 1H), 7.10-7.16 (m, 1H), 7.01 (s, 1H), 6.56 (dd, J = 17.00, 10.10 Hz, H), 6.41 (dd, J = 16.91, 1.63 Hz, 1H), 5.83 (dd, J = 10.10, 1.69 Hz, 1H), 3.96 (s, 3H), 3.94 (s, 3H), 3.70 (s, 3H), 3.05-3.24 (m, 2H), 2.92-2.87 (m, 1H), 2.76 (s, 3H), 2.69-2.71 (m, 1H), 2.50 (s, 3H), 2.29-2.47 (m, 1H), 1.96-2.20 (m, 1H), 1.73-1.92 (m, 2H), 1.53-1.71 (m, 1H)<br>ESI-MS m/z: 584.4 [M + H]$^+$ | 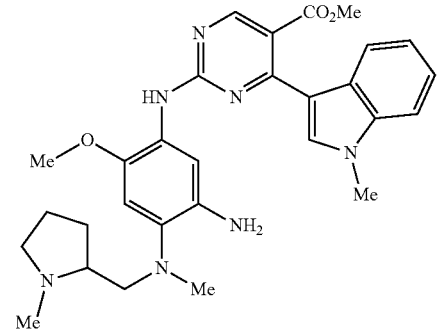<br>R19 |
| 17 | 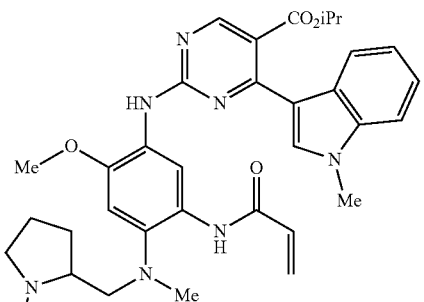<br>isopropyl 2-((5-acrylamido-2-methoxy-4-(methyl((1-methylpyrrolidin-2-yl)methyl)amino)phenyl)amino)-4-(1-methyl-1H-indol-3-yl)pyrimidine-5-carboxylate<br>$^1$H NMR: (MeOH-d$_4$) δ 9.33 (br. s., 1H), 8.75 (s, 1H), 8.29 (br. s., 1H), 7.67 (d, J = 7.78 Hz, 1H), 7.47 (d, J = 8.16 Hz, 1H), 7.24 (t, J = 7.65 Hz, 1H), 7.10-7.16 (m, 1H), 7.01 (s, 1H), 6.51-6.60 (m, 1H),<br>6.45 (dd, J = 16.94 Hz, 1.76 Hz, 1H), 5.84 (dd, J = 10.04, 1.63 3H), 5.00-5.05 (m, 1H), 3.96 (s, 3H), 3.94 (s, 3H), 3.13-3.15 (m, 2H), 2.92 (m, 1H), 2.76 (s, 3H),<br>2.68-2.81 (m, 1H), 2.51 (s, 3H), 2.41-2.58 (m, 1H), 1.98-2.20 (m, 1H), 1.73-1.92 (m, 2H), 1.50-1.72 (m, 1H), 1.10 (s, 3H), 1.08 (s, 3H)<br>ESI-MS m/z: 612.4 [M + H]$^+$ | 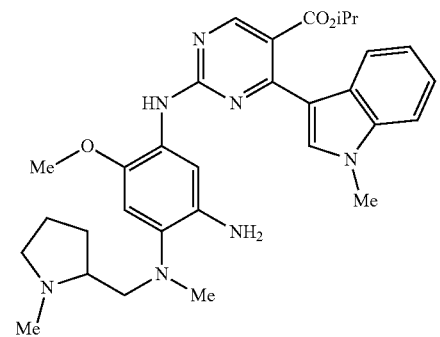<br>R20 |

TABLE 26-continued

| Ex. | Compound | Amine compound |
|---|---|---|

18

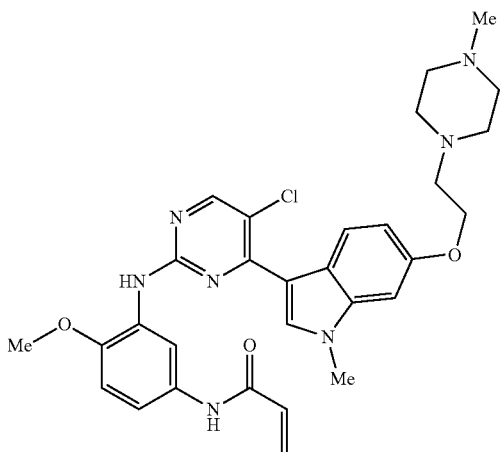 [SMILES: C=CC(=O)Nc1ccc(OC)c(Nc2ncc(Cl)c(-c3cn(C)c4cc(OCCN5CCN(C)CC5)ccc34)n2)c1]

N-(3-((5-chloro-4-(1-methyl-6-(2-(4-methylpiperazin-1-yl)ethoxy)-1H-indol-3-yl)pyrimidin-2-yl)amino)-4-methoxyphenyl)acrylamide $^1$H NMR: (DMSO-d$_6$) δ 8.54 (s, 1H), 8.48 (d, 1H), 8.14 (s, 1H), 7.79 (s, 2H), 7.15 (s,1H), 6.90 (d, 3H), 6.34 (d, 1H), 6.08 (m, 1H), 5.69 (d, 1H), 4.21 (s, 2H), 3.91 (s, 6H), 2.90 (m, 9H), 2.48 (s, 3H)

ESI-MS m/z: 576 [M + H]$^+$

R21

19

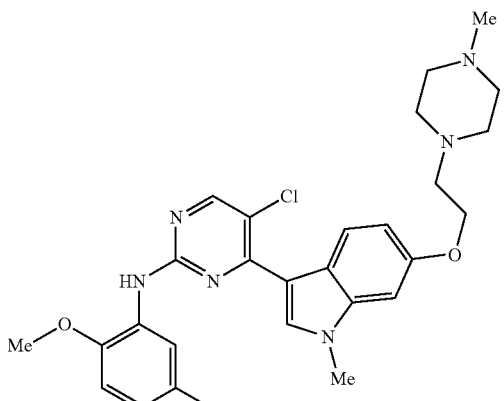

N-(3-((5-cyano-4-(6-(3-(dimethylamino)propoxy)-1-methyl-1H-indol-3-yl)pyrimidin-2-yl)amino)-4-methoxyphenyl)acrylamide $^1$H NMR: (DMSO-d$_6$) δ 10.10 (s, 1H), 9.40 (s, 1H), 8.68 (s, 1H), 8.39 (s, 1H), 7.83 (s, 1H), 7.65 (d, J = 9.2, 1H), 7.10 (m, 2H), 6.63 (s, 1H), 6.41 (dd, J = 10, 16.8, 1H), 6.22 (d, J = 16.8, 1H), 5.72 (d, J = 10, 1H), 4.09 (s, 2H), 3.87 (s, 3H), 3.74 (s, 3H), 3.10 (m, 2H), 2.74 (m, 6H) 2.10 (s, 2H)

ESI-MS m/z: 526 [M + H]$^+$

R22

TABLE 26-continued

| Ex. | Compound | Amine compound |
|---|---|---|
| 20 | 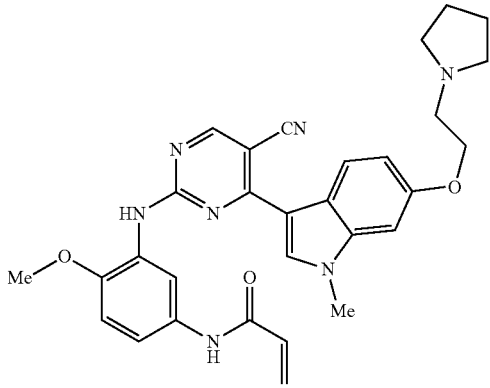 [SMILES: C=CC(=O)Nc1ccc(OC)c(Nc2ncc(C#N)c(-c3cn(C)c4cc(OCCN5CCCC5)ccc34)n2)c1] N-(3-((5-cyano-4-(1-methyl-6-(2-(pyrrolidin-1-yl)ethoxy)-1H-indol-3-yl)pyrimidin-2-yl)amino)-4-methoxyphenyl)acrylamide<br>$^1$H NMR: (DMSO-d$_6$) δ 10.16 (s, 1H), 10.13 (br s, 1H), 9.46 (s, 1H), 8.70 (s, 1H), 8.42 (s, 1H), 7.82 (s, 1H), 7.67 (s, 1H), 7.12 (m, 2H), 6.69 (br, 1H), 6.42 (dd, J = 10, 16.8, 1H), 6.22 (dd, J = 2.0, 16.8, 1H), 6.22 (dd, J = 2.0, 10.0, 1H), 4.36 (s, 2H), 3.61 (m, 4H), 3.12 (m, 2H), 1.96 (m, 4H)<br>ESI-MS m/z: 538 [M + H]$^+$ | R23 |
| 21 | 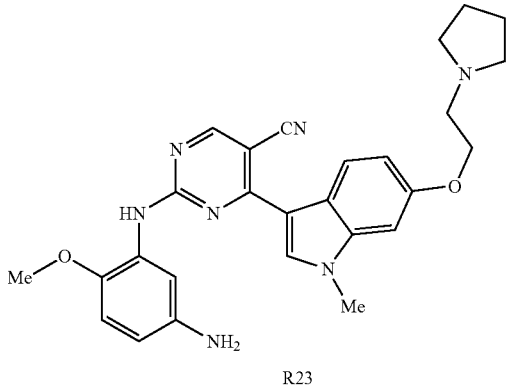 N-(3-((5-cyano-4-(1-methyl-6-((1-methylpyrrolidin-2-yl)methoxy)-1H-indol-3-yl)pyrimidin-2-yl)amino)-4-methoxyphenyl)acrylamide<br>$^1$H NMR: (DMSO-d$_6$) δ 10.08 (s, 1H), 9.37 (s, 1H), 8.68 (s, 1H), 8.38 (s, 1H), 7.86 (s, 1H), 7.62 (d, 1H), 7.12 (m, 2H), 6.60 (s, 1H), 6.43 (m, 1H), 6.23 (d, 1H), 5.71 (d, 1H), 4.03 (s, 1H), 3.88 (s, 4H), 3.75 (s, 3H), 2.99 (m, 1H), 2.50 (m, 1H), 2.39 (s, 3H), 2.22 (m, 1H), 2.01 (m, 1H), 1.69 (m, 3H)<br>ESI-MS m/z: 538 [M + H]$^+$ | R24 |

TABLE 26-continued

| Ex. | Compound | Amine compound |
|---|---|---|
| 22 | N-(3-((5-chloro-4-(6-(2-(pyrrolidin-1-yl)ethoxy)-1H-indol-3-yl)pyrimidin-2-yl)amino)-4-methoxyphenyl)acrylamide<br>$^1$H NMR: (DMSO-d$_6$) δ 11.65 (s, 1H), 10.01 (s, 1H), 8.43-8.37 (m, 2H), 8.17 (d, 1H), 8.00 (d, 1H), 7.55 (dd, 1H), 7.06 (d, 1H), 6.93 (d, 1H), 6.60 (dd, 1H), 6.40 (dd, 1H), 6.21 (dd, 1H), 5.69 (dd, 1H), 4.06 (t, 2H), 3.78 (s, 3H), 2.80 (t, 2H), 2.52 (s, 4H), 1.71-1.67 (m, 4H)<br>ESI-MS m/z: 532.5 [M + H]$^+$ | R25 |
| 23 | N-(3-((5-cyano-4-(1-methyl-6-(2-(1-methylpyrrolidin-2-yl)ethoxy)-1H-indol-3-yl)pyrimidin-2-yl)amino)-4-methoxyphenyl)acrylamide<br>$^1$H NMR: (DMSO-d$_6$) δ 10.12 (s, 1H), 9.39 (s, 1H), 8.68 (s, 1H), 8.39 (s, 1H), 7.84 (s, 1H), 7.64 (d, J = 8.4, 1H), 7.10 (m, 2H), 6.63 (s, 1H), 6.42 (dd, J = 10, 16.8, 1H), 6.22 (d, J = 16.8, 1H), 5.72 (d, J = 10, 1H), 4.12 (m, 2H), 3.87 (s, 3H), 3.74 (s, 3H), 2.74 (m, 4H), 2.33 (m, 2H), 1.93 (m, 4H), 1.73 (m, 2H)<br>ESI-MS m/z: 552 [M + H]$^+$ | R26 |

TABLE 26-continued

| Ex. | Compound | Amine compound |
|---|---|---|
| 24 | 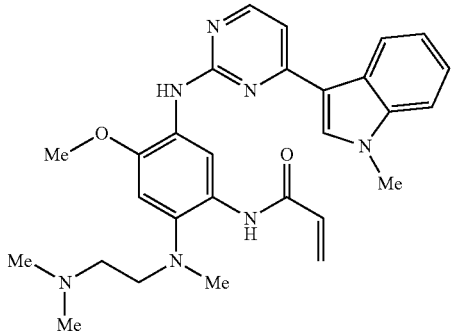 [SMILES: C=CC(=O)Nc1cc(Nc2nccc(-c3cn(C)c4ccccc34)n2)c(OC)cc1N(C)CCN(C)C]<br>N-(2-((2-(dimethylamino)ethyl)(methyl)amino)-4-methoxy-5-((4-(1-methyl-1H-indol-3-yl)pyrimidin-2-yl)amino)phenyl)acrylamide<br>$^1$H NMR: (MeOH-d$_4$) δ 9.42 (s, 1H), 8.61 (s, 1H), 8.27 (d, J = 5.27 Hz, 1H), 8.15 (d, J = 7.72 Hz, 1H), 7.44 (d, J = 7.91 Hz, 1H), 7.18-7.27 (m, 3H), 6.97 (s, 1H), 6.60 (dd, J = 16.94, 10.16 Hz, 1H), 6.40 (d, J = 16.94 Hz, 1H), 5.80 (d, J = 10.35 Hz, 1H), 3.95 (s, 3H), 3.91 (s, 3H), 3.04 (t, J = 5.74 Hz, 2H), 2.70 (s, 3H), 2.43 (t, J = 5.65 Hz, 2H), 2.29 (s, 6H)<br>ESI-MS m/z: 501.2 [M + H]$^+$ | 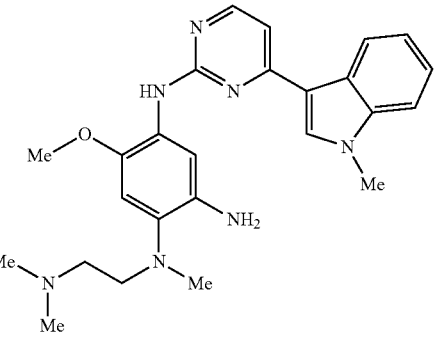<br>S12 |
| 25 | 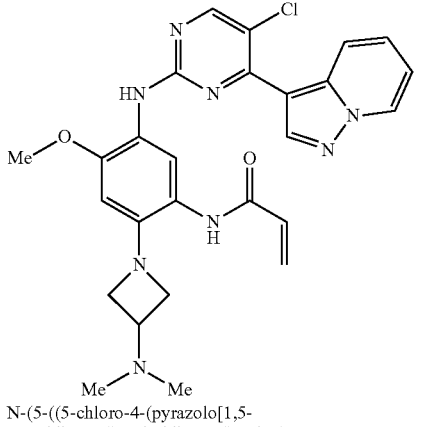<br>N-(5-((5-chloro-4-(pyrazolo[1,5-a]pyridin-3-yl)pyrimidin-2-yl)amino)-2-(3-(dimethylamino)azetidin-1-yl)-4-methoxyphenyl)acrylamide<br>$^1$H NMR: (DMSO-d$_6$) δ 9.28 (s, 1H), 8.93 (s, 1H), 8.82 (d, 1H), 8.50 (s, 1H), 8.35 (s, 2H), 7.41-7.35 (m, 1H), 7.11-7.10 (m, 1H), 6.46-6.42 (m, 1H), 6.25 (s, 1H), 6.16 (dd, 1H), 5.68-5.65 (m, 1H), 3.98 (t, 2H), 3.76 (s, 3H), 3.58 (t, 2H), 3.09-3.08 (m, 1H), 2.09 (s, 6H)<br>ESI-MS m/z: 519.2 [M + H]$^+$ | 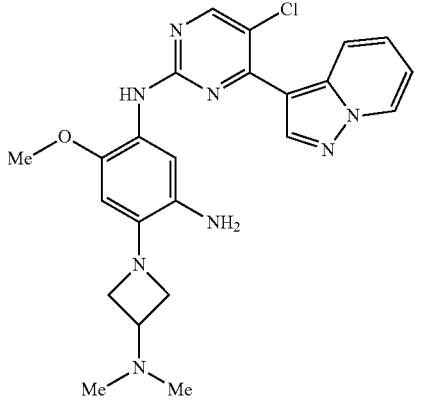<br>R33 |

TABLE 26-continued

| Ex. | Compound | Amine compound |
|---|---|---|
| 26 | 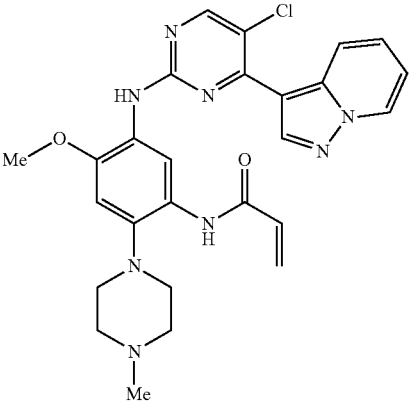 [SMILES: C=CC(=O)Nc1cc(Nc2ncc(Cl)c(-c3cnn4ccccc34)n2)c(OC)cc1N1CCN(C)CC1]<br>N-(5-((5-chloro-4-(pyrazolo[1,5-a]pyridin-3-yl)pyrimidin-2-yl)amino)-4-methoxy-2-(4-methylpiperazin-1-yl)phenyl)acrylamide<br>$^1$H NMR: (DMSO-$d_6$) δ 9.00 (s, 1H), 8.95 (s, 1H), 8.82 (d, 1H), 8.67 (s, 1H), 8.39-8.33 (m, 2H), 8.11 (s, 1H), 7.34 (t, 1H), 7.12 (t, 1H), 6.89 (s, 1H), 6.64-6.57 (m, 1H), 6.16 (d, 1H), 5.70 (d, 1H), 3.77 (s, 3H), 2.90 (s, 4H), 2.56 (s, 4H), 2.27 (s, 3H)<br>ESI-MS m/z: 519.4 [M + H]$^+$ | 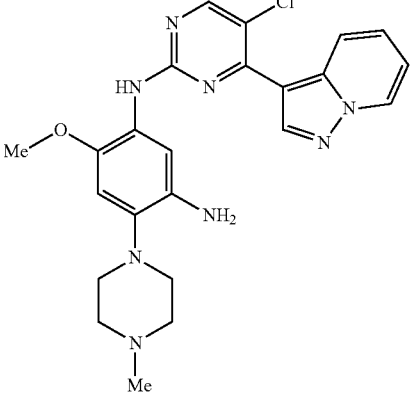<br>R34 |
| 27 | 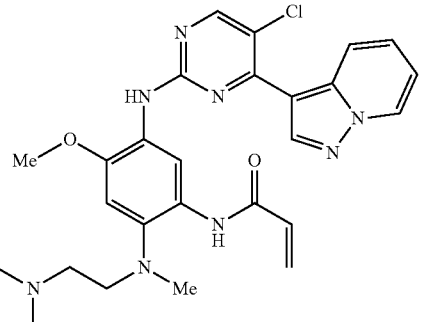<br>N-(5-((5-chloro-4-(pyrazolo[1,5-a]pyridin-3-yl)pyrimidin-2-yl)amino)-4-methoxy-2-(methyl(2-(4-methylpiperazin-1-yl)ethyl)amino)phenyl)acrylamide<br>$^1$H NMR: (DMSO-$d_6$) δ 9.31 (s, 1H), 8.94 (s, 1H), 8.82 (d, 1H), 8.68 (s, 1H), 8.38 (m, 2H), 8.23 (s, 1H), 7.31 (m, 1H), 7.09 (m, 1H), 6.99 (s, 1H), 6.59 (m, 1H), 6.17 (d, 1H), 5.71 (d, 1H), 3.77 (s, 3H), 3.00 (m, 2H), 2.70 (m, 3H), 2.35 (m, 10H), 2.13 (s, 3H)<br>ESI-MS m/z: 576.4 [M + H]$^+$ | 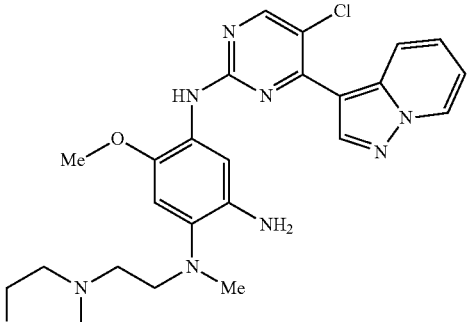<br>R36 |

TABLE 26-continued

| Ex. | Compound | Amine compound |
|---|---|---|
| 28 | 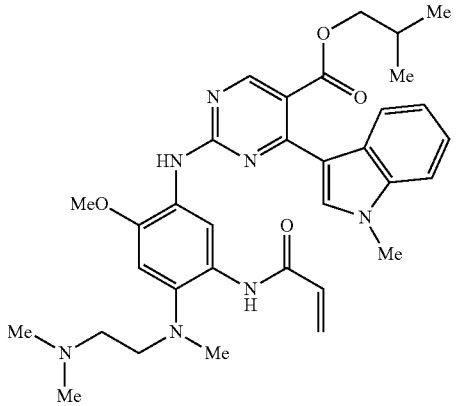 [SMILES: C=CC(=O)Nc1cc(Nc2ncc(C(=O)OCC(C)C)c(-c3cn(C)c4ccccc34)n2)c(OC)cc1N(C)CCN(C)C]<br>isobutyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate<br>$^1$H NMR: (CDCl$_3$) δ 9.74 (s, 1H), 9.23 (br. s., 1H), 8.83 (s, 1H), 8.58 (br. s., 1H), 7.81 (s, 1H), 7.45 (br. s., 1H), 7.05-7.27 (m, 3H), 6.76 (br. s., 1H), 6.63 (s, 1H), 6.42 (dd, J = 16.81, 1.88 Hz, 1H), 5.64-5.70 (m, 1H), 3.84 (s, 3H), 3.80 (s, 3H), 3.74 (d, J = 6.53 Hz, 2H), 3.06 (br. s., 2H), 2.88 (br. s., 1H), 2.56-2.73 (br. s., 9H), 1.39-1.72 (m, 2H), 0.53 (d, J = 6.65 Hz, 6H)<br>ESI-MS m/z: 600.4 [M + H]$^+$ | 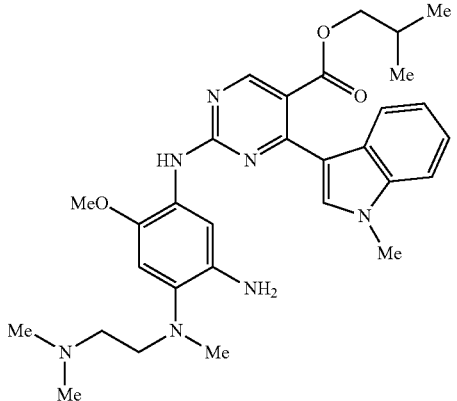<br>R39 |
| 29 | 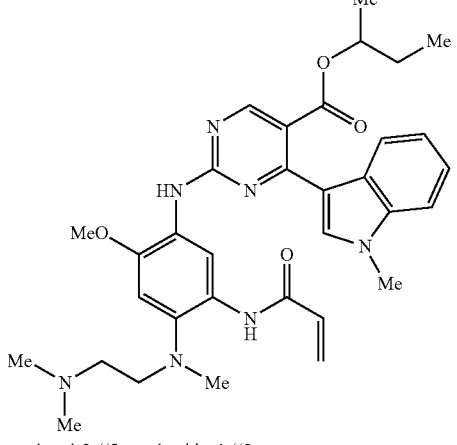<br>sec-butyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate<br>$^1$H NMR: (CDCl$_3$) δ 9.72 (s, 1H), 8.73-8.90 (m, 1H), 8.55 (br. s., 1H), 7.81 (s, 1H), 7.51 (br. s., 1H), 7.03-7.29 (m, 3H), 6.59-6.73 (m, 1H), 6.53 (br. s., 1H), 6.38-6.48 (m, 1H), 5.62-5.69 (m, 1H), 4.80 (s, 3H), 4.85 (s, 3H), 2.93 (br. s., 2H), 2.66 (s, 3H), 2.30-2.58 (br. s., 8H), 1.23-1.42 (m, 2H), 0.99 (d, J = 6.15 Hz, 3H), 0.62-0.79 (m, 3H)<br>ESI-MS m/z: 600.4 [M + H]$^+$ | 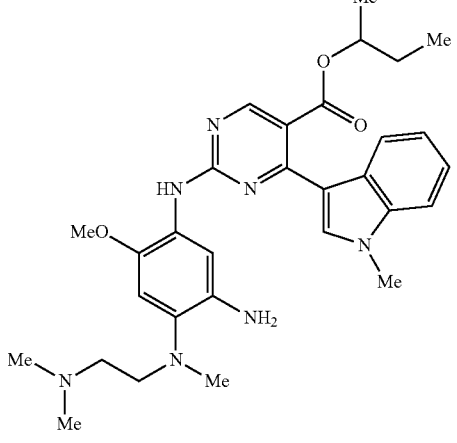<br>R40 |

TABLE 26-continued

| Ex. | Compound | Amine compound |
|---|---|---|
| 30 | 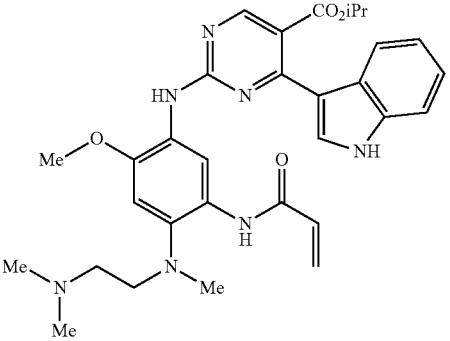<br>isopropyl 2-((5-acrylamido-4-((2-(dimethylamino)ethyl)(methyl)amino)-2-methoxyphenyl)amino)-4-(1H-indol-3-yl)pyrimidine-5-carboxylate<br>$^1$H NMR: (CDCl$_3$) δ 10.11 (br. s., 1H), 9.63 (s, 1H), 9.24 (br. s., 1H), 8.84 (s, 1H), 8.23 (br. s., 1H), 7.83 (s, 1H), 7.61 (br. s., 1H), 7.20-7.27 (m, 1H), 6.94-7.10 (m, 2H), 6.70 (s, 1H), 6.15-6.47 (m, 2H), 5.61 (d, J = 11.54 Hz, 1H), 4.91 (dt, J = 12.49, 6.18 Hz, 1H), 3.78 (s, 3H), 2.80 (t, J = 5.46 Hz, 2H), 2.62 (s, 3H), 2.17-2.29 (m, 8H), 0.96 (d, J = 5.90 Hz, 6H)<br>ESI-MS m/z: 572.5 [M + H]$^+$ | 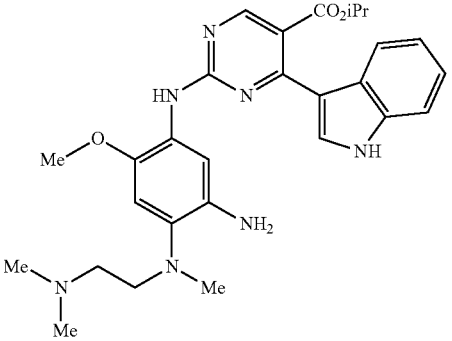<br>R41 |
| 31 | 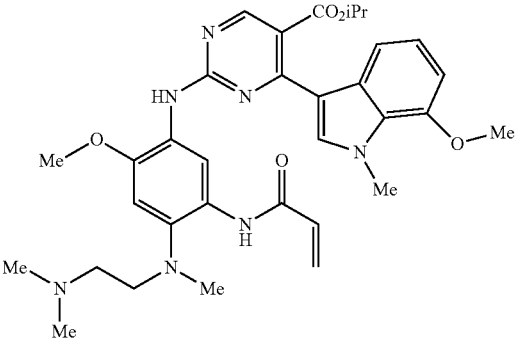<br>isopropyl 2-((5-acrylamido-4-((2-(dimethylamino)ethyl)(methyl)amino)-2-methoxyphenyl)amino)-4-(7-methoxy-1-methyl-1H-indol-3-yl)pyrimidine-5-carboxylate<br>$^1$H NMR: (CDCl$_3$) δ 10.14 (br. s., 1H), 9.76 (s, 1H), 8.86 (s, 1H), 8.48 (br. s., 1H), 7.88 (s, 1H), 7.11 (br. s., 1H), 6.97 (t, J = 7.9 Hz, 1H), 6.78 (s, 1H), 6.58 (d, J = 7.8 Hz, 1H), 6.46 (dd, J = 16.9, 1.9 Hz, 1H), 6.28-6.40 (m, 1H), 5.65-5.73 (m, 1H), 4.93-5.04 (m, 1H), 4.18 (s, 3H), 3.90 (s, 3H), 3.86 (s, 3H), 2.76-2.95 (m, 2H), 2.69 (s, 3H), 2.21-2.30 (obs. m., 2H), 2.25 (s, 6H), 1.04 (d, J = 6.0 Hz, 6H)<br>ESI-MS m/z: 616.6 [M + H]$^+$ | 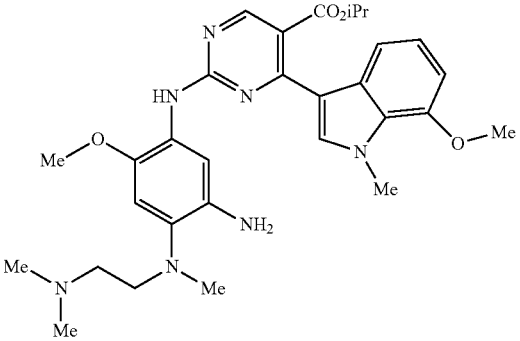<br>S4 |

TABLE 26-continued

| Ex. | Compound | Amine compound |
|---|---|---|
| 32 | isopropyl 2-((5-acrylamido-4-((2-(dimethylamino)ethyl)(methyl)amino)-2-methoxyphenyl)amino)-4-(pyrazolo[1,5-a]pyridin-3-yl)pyrimidine-5-carboxylate<br>$^1$H NMR: (CDCl$_3$) δ 10.08 (br. s., 1H), 9.54 (s, 1H), 8.98 (s, 1H), 8.52 (s, 1H), 8.49 (d, J = 6.9 Hz, 1H), 8.14 (d, J = 8.9 Hz, 1H), 7.21-7.25 (m, 1H), 6.80-6.85 (m, 1H), 6.80 (s, 1H), 6.43 (dd, J = 16.9, 1.6 Hz, 1H), 6.24-6.35 (m, 1H), 5.69 (dd, J = 10.1, 1.6 Hz, 1H), 5.12-5.22 (m, 1H), 3.87 (s, 3H), 2.81-2.92 (m, 2H), 2.71 (m, 3H), 2.28-2.32 (m, 2H), 2.26 (s, 6H), 1.26 (d, J = 6.4 Hz, 6H)<br>ESI-MS m/z: 573.5 [M + H]$^+$ | S5 |
| 33 | N-(5-((5-chloro-4-(pyrazolo[1,5-a]pyridin-3-yl)pyrimidin-2-yl)amino)-2-((2-((2-fluoroethyl)(methyl)amino)ethyl)(methyl)amino)-4-methoxyphenyl)acrylamide<br>$^1$H NMR: (CDCl$_3$) δ 9.31-9.44 (m, 2H), 8.87 (s, 1H), 8.43-8.51 (m, 2H), 8.38 (s, 1H), 7.37 (s, 1H), 7.19-7.21 (m, 1H), 6.82 (td, J = 6.8, 1.0 Hz, 1H), 6.73 (s, 1H), 6.19-6.37 (m, 2H), 5.60 (dd, J = 9.1, 2.2 Hz, 1H), 4.39-4.59 (m, 2H), 3.81 (s, 3H), 2.85 (t, J = 5.7 Hz, 2H), 2.74 (t, J = 4.8 Hz, 1H), 2.62-2.69 (m, 4H), 2.42 (t, J = 5.6 Hz, 2H), 2.26 (s, 3H)<br>ESI-MS m/z: 553.2 [M + H]$^+$ | R42 |

TABLE 26-continued

| Ex. | Compound | Amine compound |
|---|---|---|
| 34 | 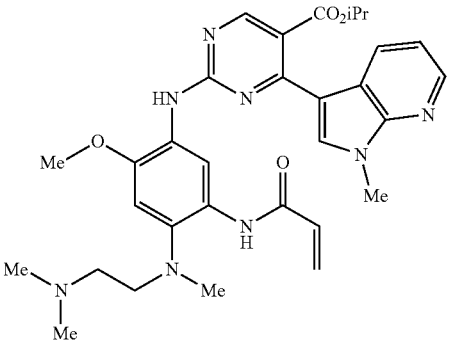<br>isopropyl 2-((5-acrylamido-4-((2-(dimethylamino)ethyl)(methyl)amino)-2-methoxyphenyl)amino)-4-(1-methyl-1H-pyrrolo[2,3-b]pyridin-311)pyrimidine-5-carboxylate<br>$^1$H NMR: (CDCl$_3$) δ 10.06 (br. s., 1H), 9.70 (s, 1H), 8.53-9.06 (m, 2H), 8.25 (dd, J = 4.7, 1.4 Hz, 1H), 7.84 (s, 2H), 7.01 (dd, J = 7.9, 4.6 Hz, 1H), 6.72 (s, 1H), 6.16-6.54 (m, 2H), 5.54-5.75 (m, 1H), 4.96 (dt, J = 12.5, 6.2 Hz, 1H), 3.96 (s, 3H), 3.81 (s, 3H), 2.82 (br. s., 2H), 2.63 (s, 3H), 2.22 (br. s., 8H), 1.02 (d, J = 6.0 Hz, 6H)<br>ESI-MS m/z: 587.5 [M + H]$^+$ | 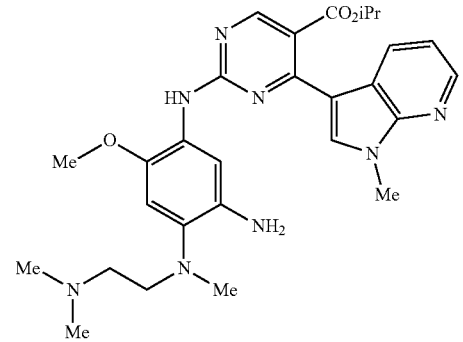<br>R43 |
| 35 | 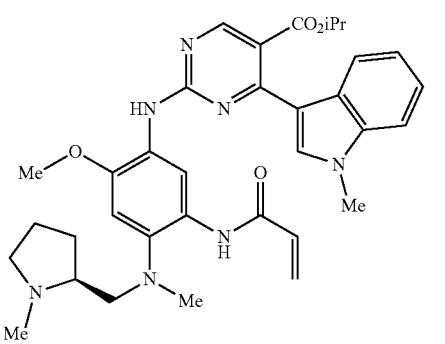<br>(S)-isopropyl 2-((5-acrylamido-2-methoxy-4-(methyl((1-methylpyrrolidin-2-yl)methyl)amino)phenyl)amino)-4-(1-methyl-1H-indol-3-yl)pyrimidine-5-carboxylate<br>$^1$H NMR: (CDCl$_3$) δ 12.17 (br. s., 1H), 9.91 (s,1H), 9.34 (s,1H), 8.88 (s, 1H), 8.66 (s, 1H), 7.92 (s, 1H), 7.53 (d, J = 8.4 Hz, 1H), 7.28-7.34 (m, 1H), 7.19-7.23 (m,1H), 7.11-7.15 (m, 1H), 6.70 (s, 1H), 6.52 (dd, J = 2, 16.8 Hz, 1H), 5.78 (dd, J = 2, 10.4 Hz, 1H), 4.97-5.01 (m, 1H), 3.93 (s, 3H), 3.89 (s, 4H), 3.25-3.40 (m, 3H), 2.76 (s, 4H), 2.57 (s, 3H), 2.15-2.21 (m, 2H), 2.04-2.05 (m, 1H), 1.84-1.85 (m, 1H), 1.05 (d, J = 6.0 Hz, 3H), 0.97 (d, J = 4.8 Hz, 3H)<br>ESI-MS m/z: 613 [M + H]$^+$ | 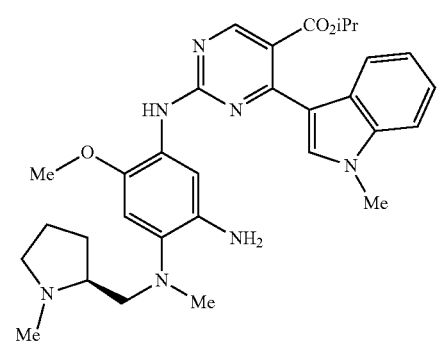<br>S6 |

TABLE 26-continued

| Ex. | Compound | Amine compound |
|---|---|---|
| 36 | 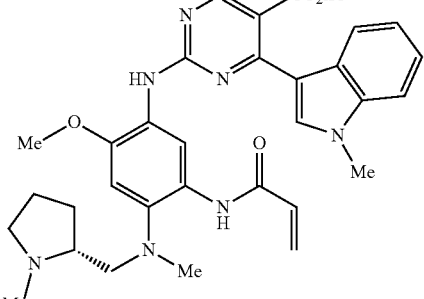<br>(R)-isopropyl 2-((5-acrylamido-2-methoxy-4-(methyl((1-methylpyrrolidin-2-yl)methyl)amino)phenyl)amino)-4-(1-methyl-1H-indol-3-yl)pyrimidine-5-carboxylate<br><sup>1</sup>H NMR: (CDCl<sub>3</sub>) δ 9.68-9.78 (m, 2 H), 8.81 (s, 1H) 8.57 (br. s., 1H), 7.77 (s, 1H), 7.50 (br. s., 1H), 7.07-7.27 (m, 3H), 6.66 (s, 1H), 6.37-6.44 (m, 1H), 6.29 (dd, J = 16.94, 10.04 Hz, 1H), 5.65 (dd, J = 9.91, 1.88 Hz, 1H), 4.92 (dt, J = 12.45, 6.26 Hz, 1H), 3.85 (s, 3H), 3.80 (s, 3H), 2.98-3.05 (m, 1H), 2.82 (dd, J = 12.80, 8.16 Hz, 1H), 2.43-2.67 (m, 8H), 2.25 (td, J = 9.32, 7.34 Hz, 1H), 1.88 (dq, J = 12.56, 8.78 Hz, 1H), 1.57-1.69 (m, 2H), 1.53 (s, 6H), 1.25-1.45 (m, 1H), 1.18 (s, 1H), 0.96 (d, J = 15.18 Hz, 3H), 0.94 (d, J = 15.81 Hz, 3H)<br>ESI-MS m/z: 613 [M + H]<sup>+</sup> | 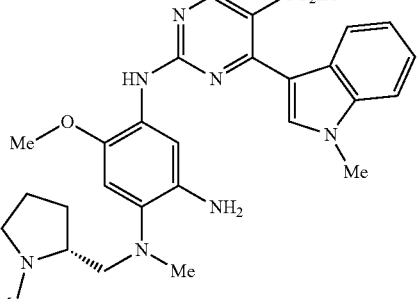<br>S7 |
| 37 | 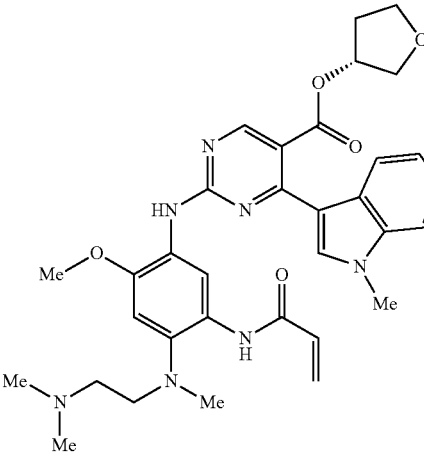<br>(R)-tetrahydrofuran-3-yl 2-((5-acrylamido-4-((2-(dimethylamino)ethyl)-(methyl)amino)-2-methoxyphenyl)amino)-4-(1-methyl-1H-indol-3-yl)pyrimidine-5-carboxylate<br><sup>1</sup>H NMR: (CDCl<sub>3</sub>) δ 10.10 (s, 1H), 9.68-9.73 (m, 1H), 8.84 (s, 1H), 7.86 (s, 1H), 7.43 (d, J = 15.56 Hz, 1H), 7.05-7.30 (m, 3H), 6.72 (s, 1H), 6.34-6.44 (m, 1H), 6.16-6.34 (m, 2H), 5.61-5.68 (m, 1H), 5.17-5.27 (m, 1H), 4.91 (dd, J = 6.27 Hz, 2H), 3.74-3.93 (m, 6H), 3.52-3.66 (m, 2H), 3.43 (d, J = 8.78 Hz, 1H), 3.31 (br. s., 1H), 2.76-2.84 (m, 2H), 2.63 (s, 3H), 2.11-2.27 (m, 8H)<br>ESI-MS m/z: 614 [M + H]<sup>+</sup> | 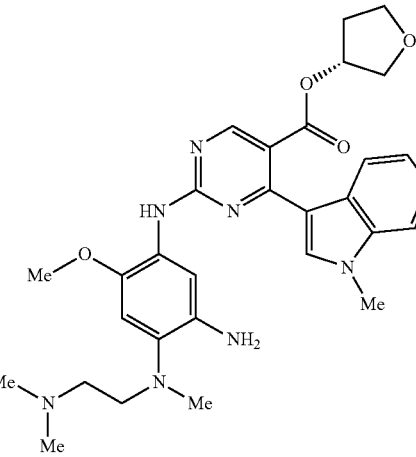<br>R44 |

TABLE 26-continued

| Ex. | Compound | Amine compound |
|---|---|---|
| 38 | 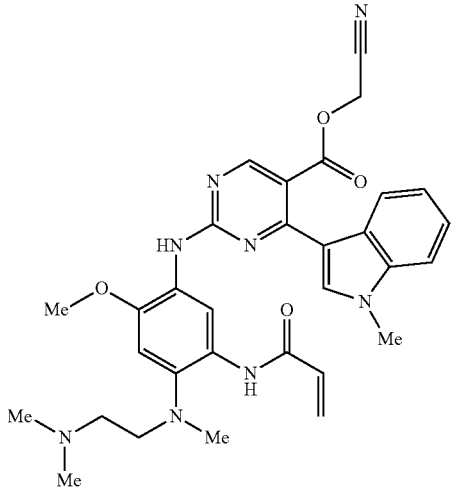 [SMILES: C=CC(=O)Nc1cc(Nc2ncc(C(=O)OCC#N)c(-c3cn(C)c4ccccc34)n2)c(OC)cc1N(C)CCN(C)C]<br>cyanomethyl 2-((5-acrylamido-4-((2-(dimethylamino)ethyl)(methyl)amino)-2-methoxyphenyl)amino)-4-(1-methyl-1H-indol-3-yl)pyrimidine-5-carboxylate<br>$^1$H NMR: (CDCl$_3$) δ 10.20 (br. s., 1H), 9.78 (s, 1H), 8.80-9.05 (m, 2H), 8.02 (s, 1H), 7.34-7.45 (m, 2H), 7.19-7.32 (m, 2H), 6.82 (s, 1H), 6.44-6.54 (m, 1H), 6.32-6.44 (m, 1H), 5.71-5.78 (m, 1H), 4.68 (s, 2H), 3.89-4.01 (m, 6H), 2.98 (s, 1H), 2.86-2.95 (m, 2H), 2.67-2.79 (m, 3H), 2.20-2.40 (m, 8H)<br>ESI-MS m/z: 583 [M + H]$^+$ | 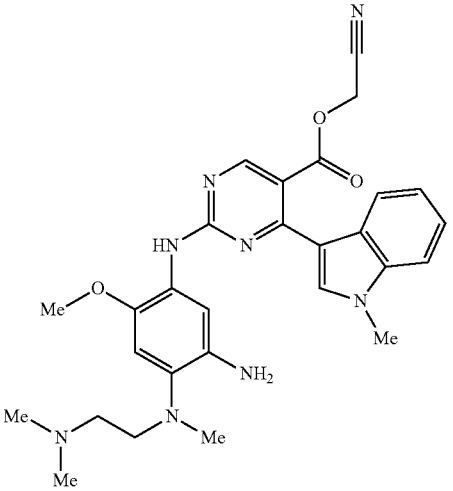<br>R45 |
| 39 | 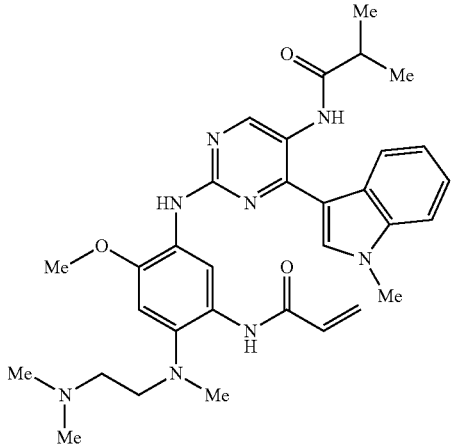 [SMILES: C=CC(=O)Nc1cc(Nc2ncc(NC(=O)C(C)C)c(-c3cn(C)c4ccccc34)n2)c(OC)cc1N(C)CCN(C)C]<br>N-(2-((2-(dimethylamino)ethyl)-(methyl)amino)-5-((5-isobutyramido-4-(1-methyl-1H-indol-3-yl)pyrimidin-2-yl)amino)-4-methoxyphenyl)-acrylamide<br>$^1$H NMR: (CDCl$_3$) δ 9.74 (s, 1H), 9.24 (s, 1H), 8.57 (br. s., 1H), 7.66 (s, 1H), 7.54 (d, J = 7.9 Hz, 1H), 7.40 (d, J = 8.2 Hz, 1H), 7.26-7.30 (m, 2H), 7.14-7.21 (m, 1H), 6.70 (br. s., 1H), 6.44 (d, J = 15.4 Hz, 1H), 5.70 (d, J = 12.0 Hz, 1H), 3.96 (s, 3H), 3.85 (s, 3H), 2.98 (br. s., 2H), 2.68 (s, 3H), 2.25-2.62 (m, 9H), 1.15 (d, J = 6.8 Hz, 6H)<br>ESI-MS m/z: 585.5 [M + H]$^+$ | 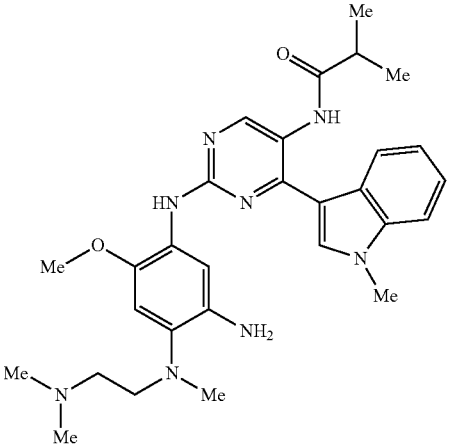<br>S8 |

TABLE 26-continued

| Ex. Compound | Amine compound |
|---|---|
| 40 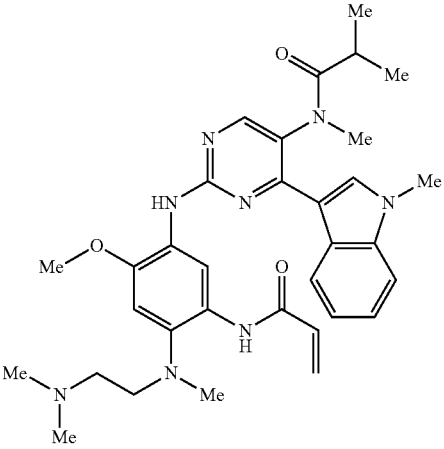 [SMILES: C=CC(=O)Nc1cc(Nc2ncc(N(C)C(=O)C(C)C)c(-c3cn(C)c4ccccc34)n2)c(OC)cc1N(C)CCN(C)C] N-(2-((2-(dimethylamino)ethyl)-(methyl)-amino)-4-methoxy-5-((4-(1-methyl-1H-indol-3-yl)-5-(N-methylisobutyramido)-pyrimidin-2-yl)amino)phenyl)acrylamide<br>$^1$H NMR: (CDCl$_3$) δ 10.10 (br. s., 1H), 9.51 (s, 1H), 8.77 (d, J = 7.8 Hz, 1H), 8.29 (s, 1H), 7.62 (s, 1H), 7.46 (s, 1H), 7.27-7.37 (m, 3H), 6.82 (s, 1H), 6.28-6.42 (m, 2H), 5.64-5.69 (m, 1H), 3.91 (s, 3H), 3.83 (s, 3H), 3.23 (s, 3H), 2.90 (t, J = 5.5 Hz, 2H), 2.72 (s, 3H), 2.58 (m, 1H), 2.32-2.37 (m, 2H), 2.29 (s, 6H), 1.06 (d, J = 6.8 Hz, 3H), 0.85 (d, J = 6.7 Hz, 3H)<br>ESI-MS m/z: 599.5 [M + H]$^+$ | S9 |
| 41 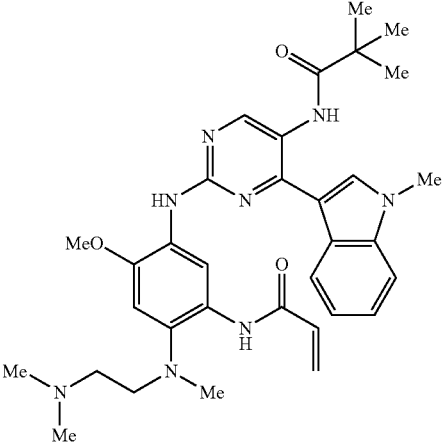 [SMILES: C=CC(=O)Nc1cc(Nc2ncc(NC(=O)C(C)(C)C)c(-c3cn(C)c4ccccc34)n2)c(OC)cc1N(C)CCN(C)C] N-(2-((2-(dimethylamino)ethyl)-(methyl)amino)-4-methoxy-5-((4-(1-methyl-1H-indol-3-yl)-5-pivalamidopyrimidin-2-yl)amino)phenyl)acrylamide<br>$^1$H NMR: (CDCl$_3$) δ 9.74 (s, 1H), 9.27 (s, 1H), 8.50 (s, 1H), 7.65 (s, 1H), 7.47-7.54 (m, 2H), 7.39 (d, J = 8.2 Hz, 1H), 7.24-7.28 (obs. m., 3H), 7.15-7.20 (m, 1H), 6.67 (s, 1H), 6.47 (d, J = 1.9 Hz, 1H), 5.69-5.74 (m, 1H), 5.69-5.74 (m, 1H), 3.94 (s, 3H), 3.85 (s, 3H), 3.07 (br. s., 2H), 2.68 (s, 3H), 2.51 (br. s., 8H), 1.11 (s, 9H)<br>ESI-MS m/z: 599.5 [M + H]$^+$ | S10 |

TABLE 26-continued

| Ex. | Compound | Amine compound |
|---|---|---|
| 42 | 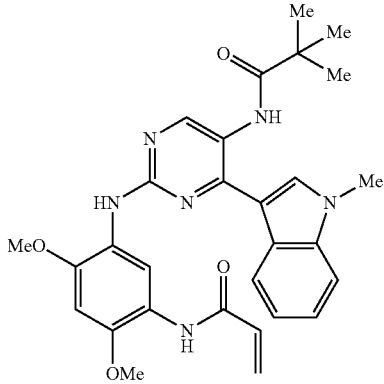 [SMILES: C=CC(=O)Nc1cc(Nc2ncc(NC(=O)C(C)(C)C)c(-c3cn(C)c4ccccc34)n2)c(OC)cc1OC]<br>N-(2,4-dimethoxy-5-((4-(1-methyl-1H-indol-3-yl)-5-pivalamidopyrimidin-2-yl)amino)phenyl)acrylamide<br>$^1$H NMR: (CDCl$_3$) δ 9.64 (s, 1H), 9.23 (s, 1H), 8.41 (s, 1H), 7.74 (s, 1H), 7.56 (d, J = 7.9 Hz, 2H), 7.45 (s, 1H), 7.39 (d, J = 8.2 Hz, 1H), 7.24-7.29 (m, 2H), 7.15-7.21 (m, 1H), 6.53 (s, 1H), 6.39-6.45 (m, 1H), 6.26-6.35 (m, 1H), 5.73 (dd, J = 9.9, 1.3 Hz, 1H), 3.94 (s, 3H), 3.87 (s, 6H), 1.12 (s, 9H)<br>ESI-MS m/z: 529.5 [M + H]$^+$ | S11 |

Example 43

N-(5-((5-chloro-4-(1-methyl-1,6,7,8-tetrahydrocyclopenta[g]indol-3-yl)pyrimidin-2-yl)amino)-2-((2-(dimethylamino)ethyl)(methyl)amino)-4-methoxyphenyl)acrylamide

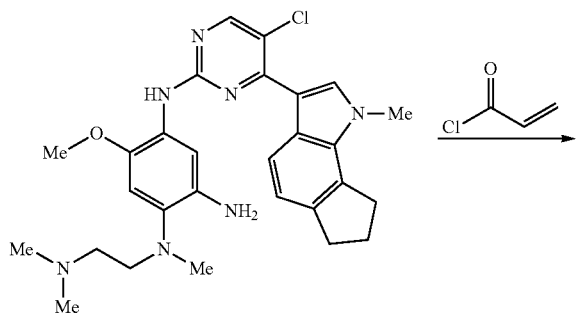

R7

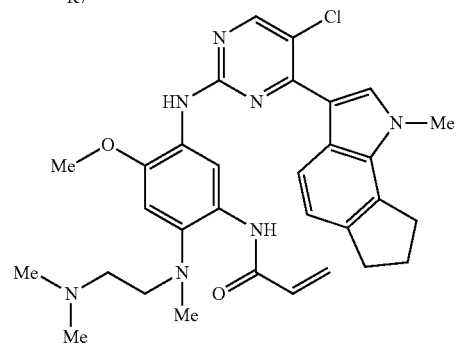

Example 43

A solution of N4-(5-chloro-4-(1-methyl-1,6,7,8-tetrahydrocyclopenta[g]indol-3-yl)pyrimidin-2-yl)-N1-(2-(dimethylamino)ethyl)-5-methoxy-N1-methylbenzene-1,2,4-triamine (R7) (190 mg, 0.20 mmol) and DCM (25 mL) was cooled to 0° C. Subsequently, acryloyl chloride (36 mg, 0.20 mmol) was added dropwise at 0° C. and stirred for 10 min before adding water (5 mL). The mixture was concentrated in vacuo and the resulting residue was purified by flash column chromatography on silica gel (5% to 10% MeOH/DCM) to afford N-(5-((5-chloro-4-(1-methyl-1,6,7,8-tetrahydrocyclopenta[g]indol-3-yl)pyrimidin-2-yl)amino)-2-((2-(dimethylamino)ethyl)-(methyl)amino)-4-methoxyphenyl) acrylamide (Example 43) as light brown solid. $^1$H-NMR: (CDCl$_3$) δ 10.06 (s, 1H), 9.55 (s, 1H), 8.45 (s, 1H), 8.22 (s, 1H), 8.18 (d, J=8.0 Hz, 1H), 7.58 (s, 1H), 7.12 (d, J=8.4 Hz, 1H), 6.81 (s, 1H), 6.42 (dd, J=16.8, 1.6 Hz, 1H), 6.34 (m, 1H), 5.69 (d, J=11.6 Hz, 1H), 4.09 (s, 3H), 3.90 (s, 3H), 3.48 (t, J=7.2 Hz, 2H), 3.04 (t, J=7.6 Hz, 2H), 2.91 (m, 2H), 2.73 (s, 3H), 2.30 (s, 6H), 2.26 (m, 2H), 2.22 (m, 2H). MS m/z 574.5 [M+H]$^+$.

The following example compounds, as shown in Table 27, were synthesized in analogous fashion to Example 43.

TABLE 27

| Ex. | Compound | Amine compound |
|-----|----------|----------------|
| 44 | 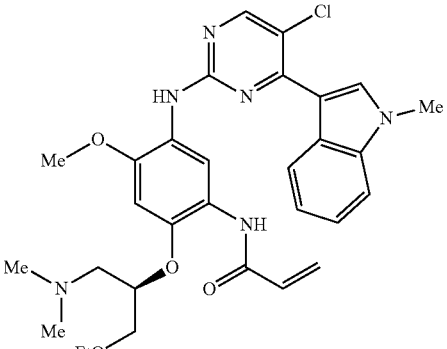<br>(R)-N-(5-((5-chloro-4-(1-methyl-1H-indol-3-yl)pyrimidin-2-yl)amino)-2-((1-(dimethylamino)-3-ethoxypropan-2-yl)oxy)-4-methoxyphenyl)acrylamide<br>$^1$H NMR: (CDCl$_3$) δ 9.84 (s, 1H), 9.37 (s, 1H), 8.34 (s, 1H), 8.32 (d, J = 8.0 Hz, 1H), 8.26 (s, 1H), 7.42 (s, 1H), 7.28 (d, J = 8.0 Hz, 1H), 7.20 (m, 1H), 7.14 (m, 1H), 6.90 (s, 1H), 6.33 (d, J = 15.6 Hz, 1H), 6.22 (dd, J = 16.8, 10.4 Hz, 1H), 5.62 (d, J = 8.8 Hz, 1H), 4.00 (m, 1H), 3.83 (s, 3H), 3.79 (s, 3H), 3.58-3.53 (m, 5H), 2.78 (m, 1H), 2.25 (s, 6H), 1.20 (t, J = 6.8 Hz, 3H)<br>ESI-MS m/z: 579.4 [M + H]$^+$ | 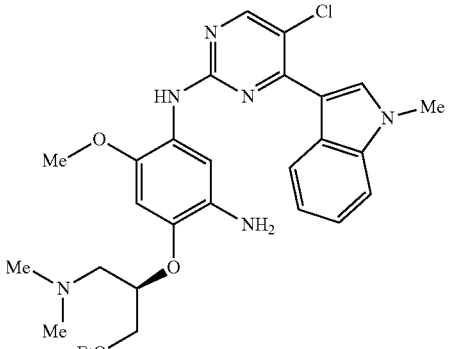<br>R8 |
| 45 | 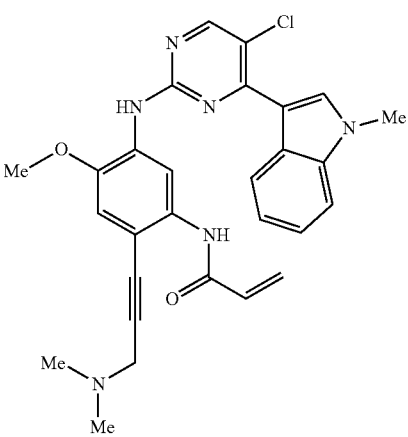 [SMILES: C=CC(=O)Nc1cc(Nc2ncc(Cl)c(-c3cn(C)c4ccccc34)n2)c(OC)cc1C#CCN(C)C]<br>N-(5-((5-chloro-4-(1-methyl-1H-indol-3-yl)pyrimidin-2-yl)amino)-2-(3-(dimethylamino)prop-1-yn-1-yl)-4-methoxyphenyl)acrylamide<br>$^1$H NMR: (CDCl$_3$) δ 9.59 (s, 1H), 8.49 (s, 1H), 8.45 (d, J = 8.0 Hz, 1H), 8.34 (s, 1H), 7.91 (s, 1H), 7.83 (s, 1H), 7.39 (d, J = 7.6 Hz, 1H), 7.34-7.25 (m, 2H), 6.95 (s, 1H), 6.40 (dd, J = 16.8, 1.6 Hz, 1H), 6.29 (dd, J = 16.8, 10.0 Hz, 1H), 5.76 (d, J = 9.6 Hz, 1H), 3.93 (s, 3H), 3.92 (s, 3H), 3.61 (s, 2H), 2.44 (s, 6H)<br>MS m/z 515.5 [M + H]$^+$ | 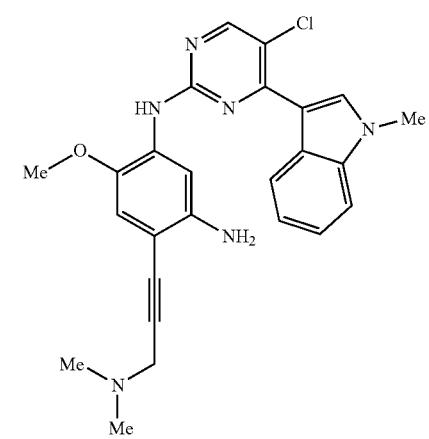<br>R9 |

TABLE 27-continued

| Ex. | Compound | Amine compound |
|---|---|---|
| 46 | 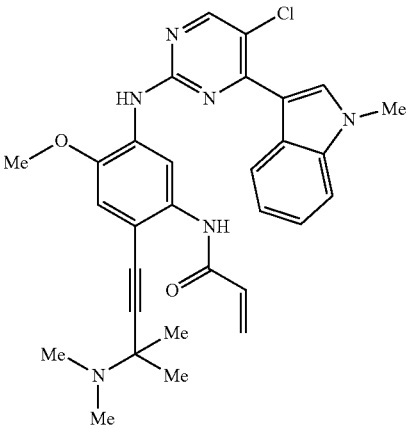 [SMILES: C=CC(=O)Nc1cc(Nc2ncc(Cl)c(-c3cn(C)c4ccccc34)n2)c(OC)cc1C#CC(C)(C)N(C)C]<br>N-(5-((5-chloro-4-(1-methyl-1H-indol-3-yl)pyrimidin-2-yl)amino)-2-(3-(dimethylamino)-3-methylbut-1-yn-1-yl)-4-methoxyphenyl)acrylamide<br>$^1$H NMR: (CDCl$_3$) δ 9.53 (s, 1H), 8.49 (s, 1H), 8.46 (d, J = 8.0 Hz, 1H), 8.39 (s, 1H), 8.00 (s, 1H), 7.85 (s, 1H), 7.40 (d, J = 8.0 Hz, 1H), 7.35-7.26 (m, 2H), 6.93 (s, 1H), 6.42-6.30 (m, 2H), 5.77 (dd, J = 10.4, 2.0 Hz, 1H), 3.95 (s, 3H), 3.94 (s, 3H), 2.51 (s, 6H), 1.61 (s, 6H)<br>MS m/z 543.5 [M + H]$^+$ | 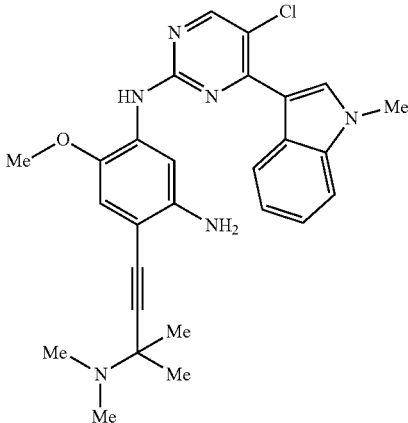<br>R10 |
| 47 | 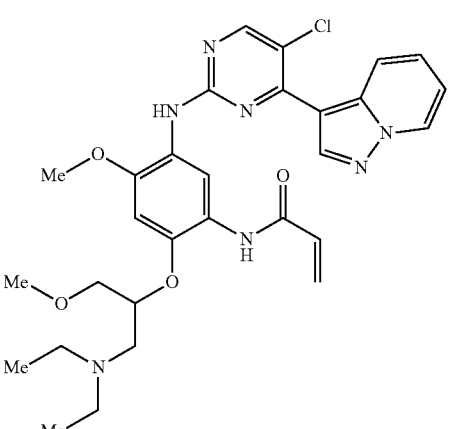<br>N-(5-((5-chloro-4-(pyrazolo[1,5-a]pyridin-3-yl)pyrimidin-2-yl)amino)-2-((1-(diethylamino)-3-methoxypropan-2-yl)oxy)-4-methoxyphenyl) acrylamide<br>$^1$H NMR: (CDCl$_3$) δ 9.29 (s, 2H), 8.93 (s, 1H), 8.53 (t, 2H), 8.43 (s, 1H), 7.38 (s, 1H), 7.32-7.26 (m, 1H), 6.98 (s, 1H), 6.90 (t, 1H), 6.33 (dd, 2H), 5.68 (d, 1H), 3.89 (s, 3H), 3.71-3.54 (m, 3H), 3.41 (s, 3H), 3.06-2.83 (m, 6H), 0.98-0.93 (m, 6H)<br>MS m/z 580.2 [M + H]$^+$ | 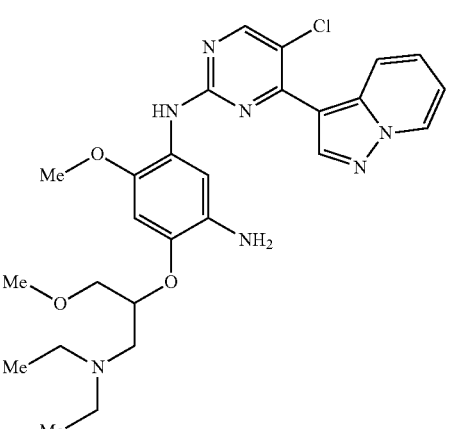<br>R27 |

TABLE 27-continued

| Ex. | Compound | Amine compound |
|---|---|---|
| 48 | 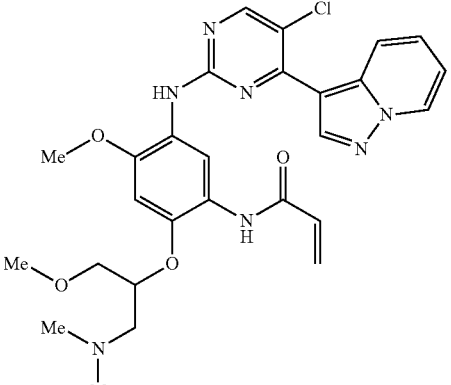<br>N-(5-((5-chloro-4-(pyrazolo[1,5-a]pyridin-3-yl)pyrimidin-2-yl)amino)-2-((1-(dimethylamino)-3-methoxypropan-2-yl)oxy)-4-methoxyphenyl)acrylamide<br>¹H NMR: (CDCl₃) δ 9.29 (s, 1H), 8.94 (s, 1H), 8.53 (t, 2H), 8.43 (s, 1H), 7.38 (s, 1H), 7.31 (t, 1H), 7.00 (s, 1H), 6.90 (t, 1H), 6.39-6.35 (m, 2H), 5.68 (d, 1H), 5.30 (s, 1H), 3.89 (s, 3H), 3.60-3.57 (m, 2H), 3.43 (s, 3H), 2.51 (br, 6H), 1.69 (br, 3H)<br>MS m/z 552.2 [M + H]⁺ | 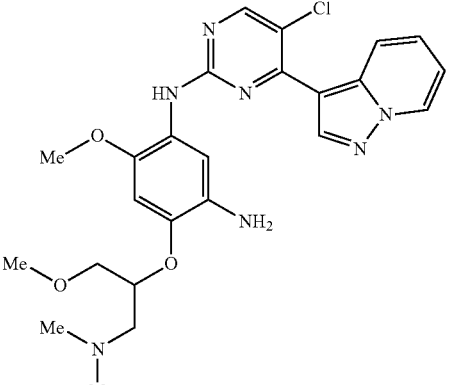<br>R28 |
| 49 | 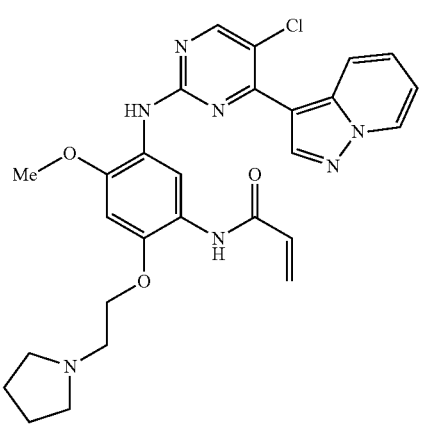 [SMILES: C=CC(=O)Nc1cc(Nc2ncc(Cl)c(-c3cnn4ccccc34)n2)c(OC)cc1OCCN1CCCC1]<br>N-(5-((5-chloro-4-(pyrazolo[1,5-a]pyridin-3-yl)pyrimidin-2-yl)amino)-4-methoxy-2-(2-(pyrrolidin-1-yl)ethoxy)phenyl)acrylamide<br>¹H NMR: (DMSO-d₆) δ 10.14 (s, 1H), 8.70 (s, 1H), 8.25 (d, J = 5.4 Hz, 1H), 7.98-7.85 (m, 2H), 7.13 (d, J = 5.4 Hz, 1H), 7.01 (s, 1H), 6.96-6.77 (m, 2H), 6.37 (dd, J = 16.9, 10.1 Hz, 1H), 6.17 (dd, J = 16.9, 2.0 Hz, 1H), 5.79-5.66 (m, 1H), 5.10 (d, J = 3.4 Hz, 1H), 4.53-4.02 (m, 4H), 3.81 (s, 3H), 3.27 (td, J = 20, 2.0 Hz, 1H), 3.15 (d, J = 4.4 Hz, 1H), 2.88 (s, 4H), 2.70 (d, J = 18.6 Hz, 3H), 2.30 (t, J = 4.0 Hz, 3H), 2.20 (s, 6H), 2.15-2.03 (m, 3H), 1.92-1.89 (m, 1H)<br>MS m/z 534.2 [M + H]⁺ | 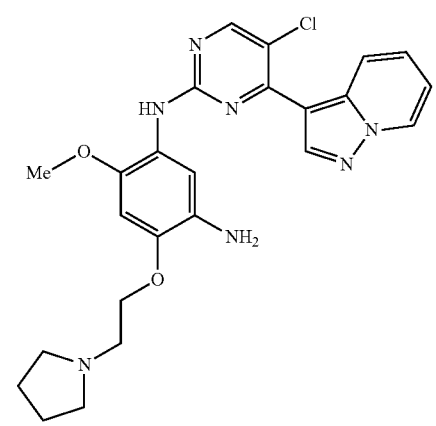<br>R29 |

TABLE 27-continued

| Ex. | Compound | Amine compound |
|---|---|---|

50

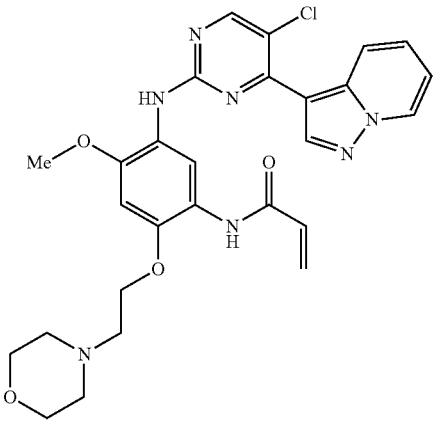 [SMILES: C=CC(=O)Nc1cc(Nc2ncc(Cl)c(-c3cnn4ccccc34)n2)c(OC)cc1OCCN1CCOCC1]

N-(5-((5-chloro-4-(pyrazolo[1,5-a]pyridin-3-yl)pyrimidin-2-yl)amino)-4-methoxy-2-(2-morpholinoethoxy)phenyl)acrylamide
$^1$H NMR: (CDCl$_3$) δ 9.21 (s, 1H), 8.93 (s, 1H), 8.53-8.51 (m, 2H), 8.41 (s, 1H), 8.32 (s, 1H), 7.29 (s, 1H), 6.90 (t, 1H), 6.62 (s, 1H), 6.36-6.34 (m, 2H), 5.73 (d, 1H), 4.20 (t, 2H), 3.88
(s, 3H), 3.77 (s, 4H), 2.73 (t, 2H), 2.57 (s, 4H)
MS m/z 550.2 [M + H]$^+$

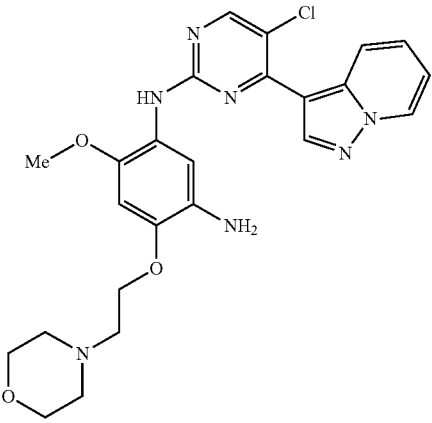

R30

51

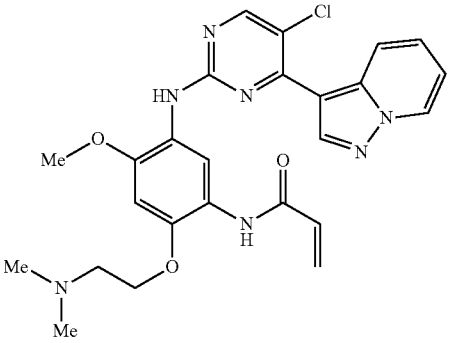 [SMILES: C=CC(=O)Nc1cc(Nc2ncc(Cl)c(-c3cnn4ccccc34)n2)c(OC)cc1OCCN(C)C]

N-(5-((5-chloro-4-(pyrazolo[1,5-a]pyridin-3-yl)pyrimidin-2-yl)amino)-2-(2-(dimethylamino)ethoxy)-4-methoxyphenyl)acrylamide
$^1$H NMR: (CDCl$_3$) δ 9.63 (s, 1H), 9.23 (s, 1H), 8.93 (s, 1H), 8.54-8.51 (m, 2H), 8.42 (s, 1H), 7.32-7.26 (m, 2H), 6.91-6.88 (m, 1H), 6.64 (s, 1H), 6.35 (s, 1H), 5.68 (t, 1H), 4.16 (t, 1H), 3.87 (s, 3H), 2.68 (br, 2H), 2.43 (s, 6H)
MS m/z 508.2 [M + H]$^+$

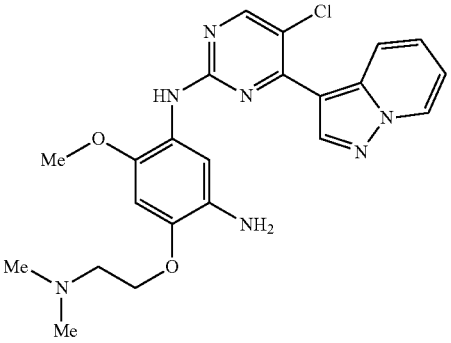

R31

TABLE 27-continued

| Ex. | Compound | Amine compound |
|---|---|---|
| 52 | 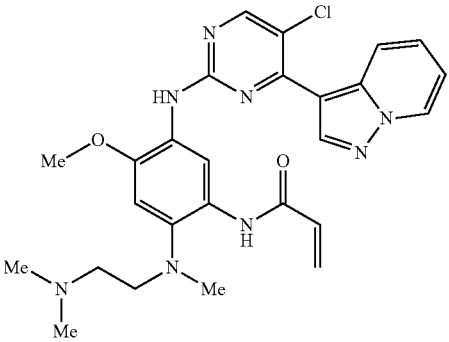 [SMILES: C=CC(=O)Nc1cc(Nc2ncc(Cl)c(-c3cnn4ccccc34)n2)c(OC)cc1N(C)CCN(C)C]<br>N-(5-((5-chloro-4-(pyrazolo[1,5-a]pyridin-3-yl)pyrimidin-2-yl)amino)-2-((2-(dimethylamino)ethyl)-(methyl)amino)-4-methoxyphenyl)-acrylamide<br>$^1$H NMR: (DMSO-d$_6$) δ 10.08 (s, 1H), 8.95 (s, 1H), 8.82 (d, 1H), 8.73 (s, 1H), 8.43-8.37 (m, 3H), 7.29 (t, 1H), 7.10 (t, 1H), 7.05 (s, 1H), 6.39 (dd, 1H), 6.17 (dd, 1H), 5.72 (d, 1H), 3.76 (s, 3H), 2.90 (t, 2H), 2.75 (s, 3H), 2.34 (t, 2H), 2.20 (s, 6H)<br>MS m/z 521.2 [M + H]$^+$ | 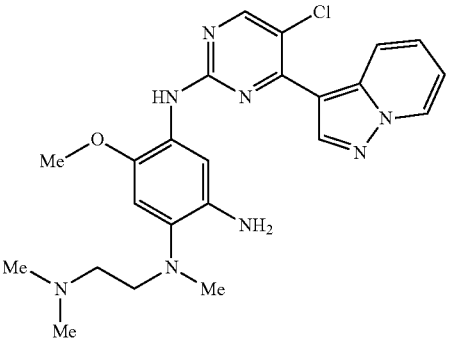<br>R32 |
| 53 | 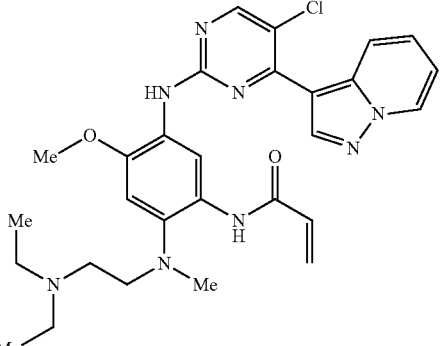<br>N-(5-((5-chloro-4-(pyrazolo[1,5-a]pyridin-3-yl)pyrimidin-2-yl)amino)-2-((2-(diethylamino)ethyl)-(methyl)amino)-4-methoxyphenyl)acrylamide<br>$^1$H NMR: (CDCl$_3$) δ 9.62 (s, 1H), 9.38 (s, 1H), 8.93 (s, 1H), 8.56-8.51 (m, 2H), 8.45 (s, 1H), 7.42 (s, 1H), 7.26 (t, 1H), 6.89 (d, 1H), 6.79 (s, 1H), 6.35-6.30 (m, 2H), 5.68 (t, 1H), 3.87 (s, 3H), 2.88 (t, 2H), 2.69 (s, 3H), 2.59 (dd, 4H), 2.47 (t, 2H), 1.03 (t, 6H)<br>MS m/z 549.4 [M + H]$^+$ | 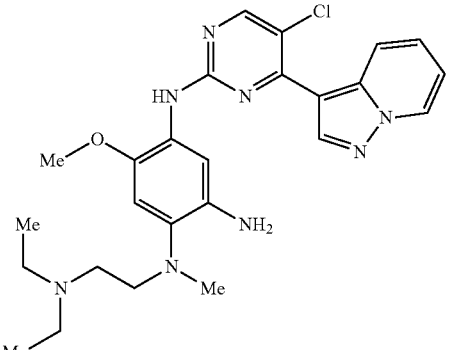<br>R35 |

TABLE 27-continued

| Ex. | Compound | Amine compound |
|---|---|---|
| 54 | 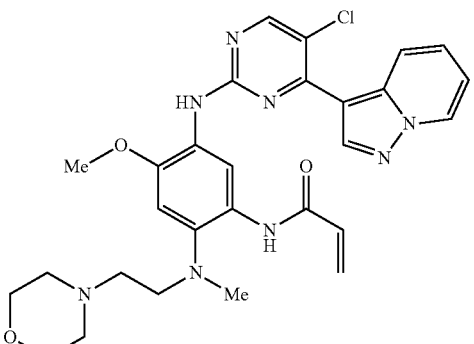<br>N-(5-((5-chloro-4-(pyrazolo[1,5-a]pyridin-3-yl)pyrimidin-2-yl)amino)-4-methoxy-2-(methyl(2-morpholinoethyl)amino)phenyl)-acrylamide<br>$^1$H NMR: (CDCl$_3$) δ 9.40 (s, 1H), 9.15 (s, 1H), 8.94 (s, 1H), 8.56-8.53 (m, 2H), 8.47 (s, 1H), 7.49 (s, 1H), 7.31-7.26 (m, 1H), 6.93-6.89 (m, 1H), 6.79 (s, 1H), 6.39 (s, 2H), 5.73 (t, 1H), 3.87 (s, 3H), 3.73 (s, 4H), 3.01 (s, 2H), 2.68 (s, 3H), 2.44-2.36 (m, 6H)<br>MS m/z 563.4 [M + H]$^+$ | 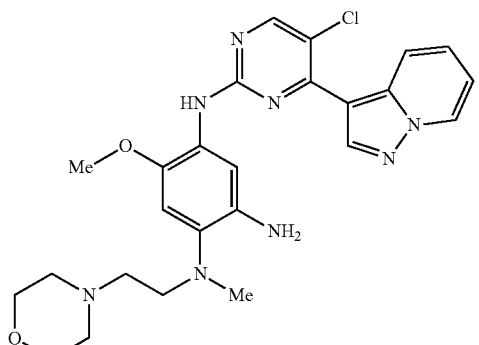<br>R37 |
| 55 | 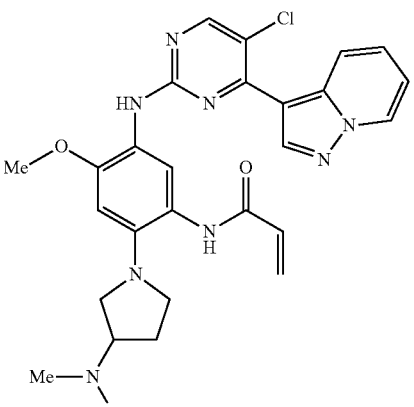<br>N-(5-((5-chloro-4-(pyrazolo[1,5-a]pyridin-3-yl)pyrimidin-2-yl)amino)-2-(3-(dimethylamino)pyrrolidin-1-yl)-4-methoxyphenyl)acrylamide<br>$^1$H NMR: (DMSO-d$_6$) δ 9.42 (s, 1H), 8.94 (s, 1H), 8.20 (d, 1H), 8.57 (s, 1H), 8.37 (s, 1H), 7.63 (s, 1H), 7.38 (t, 1H), 7.10 (t, 1H), 6.62 (s, 2H), 6.16 (d, 1H), 5.76 (s, 1H), 5.67 (d, 1H), 3.78 (s, 3H), 3.36-3.27 (m, 6H), 2.44 (s, 5H), 2.18 (s, 1H), 1.98 (s, 1H)<br>MS m/z 533.3 [M + H]$^+$ | 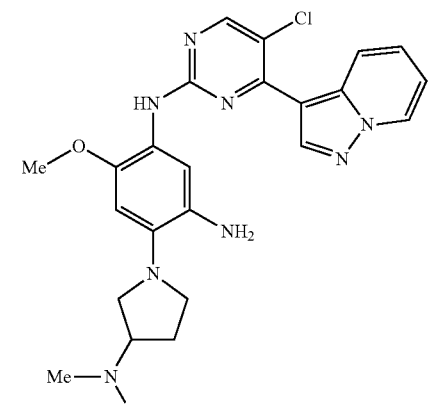<br>R38 |

TABLE 27-continued

| Ex. | Compound | Amine compound |
|---|---|---|
| 56 | 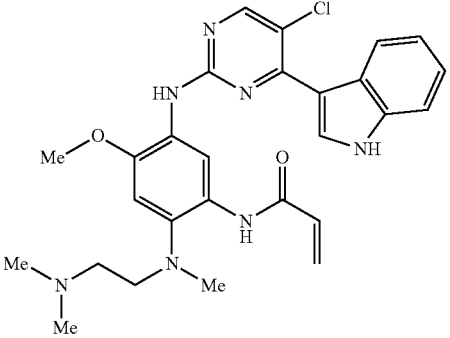<br>N-(5-((5-chloro-4-(1H-indol-3-yl)pyrimidin-2-yl)amino)-2-((2-(dimethylamino)ethyl)(methyl)amino)-4-methoxyphenyl)acrylamide<br>$^1$H NMR: (DMSO-d$_6$) δ 11.67 (s, 1H), 10.15 (s, 1H), 8.75 (s, 1H), 8.61 (s, 1H), 8.51 (s, 1H), 8.27 (d, 1H), 8.12 (s, 1H), 7.48 (d, 1H), 7.31 (s, 1H), 7.16 (m, 2H), 7.02 (s, 1H), 6.43 (m, 1H), 6.37 (m, 1H), 5.76 (m, 1H), 3.86 (s, 3H), 2.89 (m, 2H), 2.72 (s, 3H), 2.32 (m, 2H), 2.21 (s, 6H)<br>MS m/z 486.2 [M + H]$^+$ | 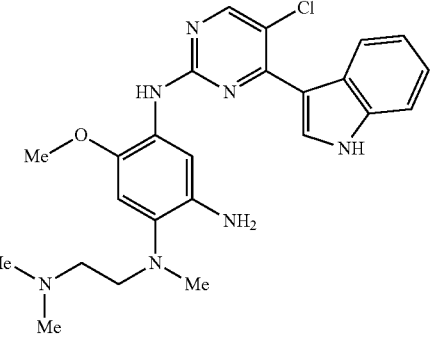<br>S2 |
| 59 | 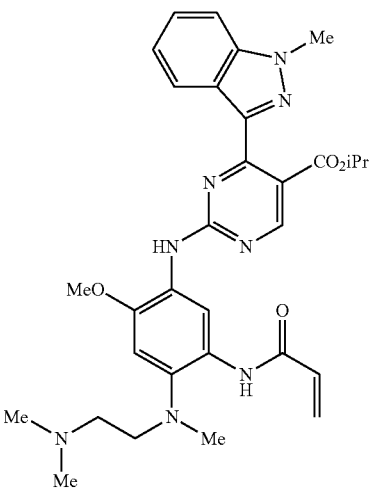<br>isopropyl 2-((5-acrylamido-4-((2-(dimethylamino)ethyl)(methyl)amino)-2-methoxyphenyl)amino)-4-(1-methyl-1H-indazol-3-yl)pyrimidine-5-carboxylate<br>$^1$H NMR: (CDCl$_3$) δ 9.84 (br. s., 1H), 9.56 (br. s., 1H), 8.95 (s, 1H), 8.04 (d, J = 7.9 Hz, 1H), 7.91 (s, 1H), 7.35-7.43 (m, 1H), 7.19 (m, 1H), 6.75 (s, 1H), 6.33-6.57 (m, 2H), 6.06-6.32 (m, 1H), 5.61-5.75 (m, 2H), 5.02-5.13 (m, 1H), 4.12 (s, 3H), 3.84 (s, 3H), 2.96 (t, J = 5.6 Hz, 2H), 2.66 (s, 3H), 2.51 (t, J = 5.6 Hz, 2H), 2.37 (s, 6H), 1.13 (d, J = 6.3 Hz, 6H)<br>ESI-MS m/z: 587.3 [M + H]$^+$ | 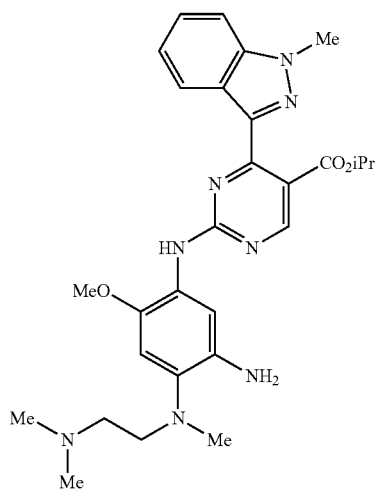<br>T1 |

| Ex. | Compound | Amine compound |
|---|---|---|
| 60 | 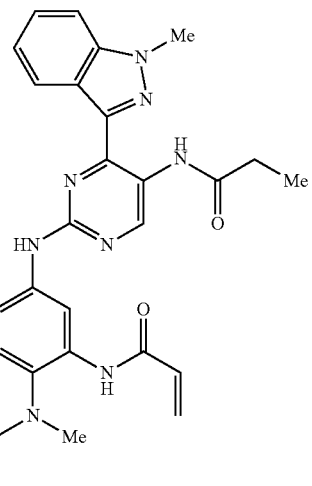<br>N-(2-((2-(dimethylamino)ethyl)(methyl)amino)-4-methoxy-5-((4-(1-methyl-1H-indazol-3-yl)-5-propionamidopyrimidin-2-yl)amino)phenyl)acrylamide<br>$^1$H NMR: (MeOH-d$_4$) δ 9.42 (s, 1H), 8.57 (d, J = 8.3 Hz, 1H), 8.39 (s, 1H), 7.63 (d, J = 8.5 Hz, 1H), 7.46 (ddd, J = 8.4, 7.1, 1.0 Hz, 1H), 7.21-7.27 (m, 1H), 6.98 (s, 1H), 6.78-6.79 (m, 1H), 6.44-6.49 (m, 2H), 5.79-5.86 (m, 1H), 4.20 (s, 3H), 4.01 (s, 3H), 3.48 (t, J = 5.6 Hz, 2H), 3.23-3.27 (m, 2H), 2.85 (s, 6H), 2.73 (s, 3H), 2.56 (q, J = 7.5 Hz, 2H), 1.33 (t, J = 7.6 Hz, 3H)<br>ESI-MS m/z: 572.3 [M + H]$^+$ | 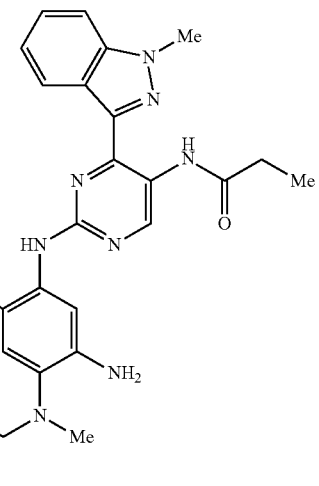<br>T2 |
| 61 | 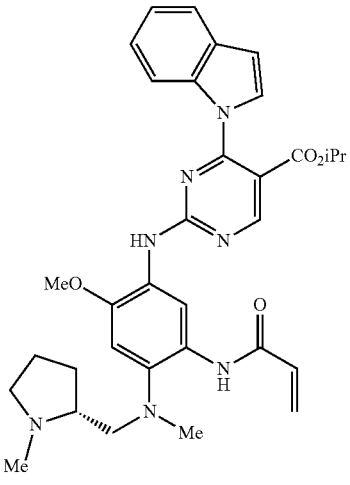<br>isopropyl (R)-2-((5-acrylamido-2-methoxy-4-(methyl((1-methylpyrrolidin-2-yl)methyl)amino)phenyl)amino)-4-(1H-indol-1-yl)pyrimidine-5-carboxylate<br>$^1$H NMR: (CDCl$_3$) δ 9.90 (br. s., 1H), 9.62 (s, 1H), 9.03 (br. s., 1H), 7.81 (br. s., 1H), 7.58 (d, J = 7.4 Hz, 2H), 7.50 (d, J = 17.4 Hz, 1H), 7.15 (br. s., 2H), 6.65-6.73 (m, 3H), 6.46-6.53 (m, 1H), 6.29-6.38 (m, 1H), 5.72 (d, J = 10.3 Hz, 1H), 4.90 (br. s., 1H), 3.87 (s, 3H), 3.10 (br. s., 1H), 2.85 (m, 1H), 2.74 (s, 3H), 2.66 (br. s., 2H), 2.56 (s, 3H), 2.36 (m, 2H), 1.98 (m, 1H), 1.73 (br. s., 2H), 1.39 (br. s., 1H)<br>ESI-MS m/z: 598.3 [M + H]$^+$ | 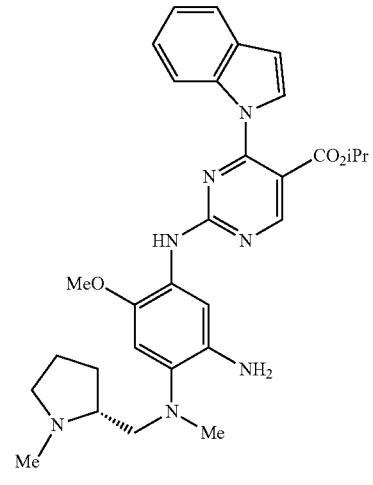 [SMILES: C=CC(=O)Nc1cc(Nc2ncc(C(=O)OC)c(-n3ccc4ccccc43)n2)c(OC)cc1N(C)C[C@H]1CCCN1C]<br>T3 |

TABLE 27-continued

| Ex. | Compound | Amine compound |
|---|---|---|
| 62 | isopropyl (R)-2-((5-acrylamido-2-methoxy-4-(methyl((1-methylpyrrolidin-2-yl)methyl)amino)phenyl)amino)-4-(benzofuran-3-yl)pyrimidine-5-carboxylate<br>$^1$H NMR: (CDCl$_3$) δ 9.79 (s, 1H), 9.36 (br. s., 1H), 9.03 (s, 1H), 8.72 (br. s., 1H), 7.91 (s, 1H), 7.57-7.66 (m, 1H), 7.53 (d, J = 8.0 Hz, 1H), 7.17-7.34 (m, 3H), 6.74-6.74 (m, 1H), 6.71 (s, 1H), 6.49-6.56 (m, 1H), 6.52 (dd, J = 16.8, 1.6 Hz, 1H), 5.73-5.80 (m, 1H), 4.95-5.04 (m, 1H), 3.89 (s, 3H), 3.14-3.31 (m, 2H), 2.75 (s, 3H), 2.57 (s, 3H), 2.15 (m, 3H), 1.75 (br. s., 1H), 0.95-1.13 (m, 6H)<br>ESI-MS m/z: 599.3 [M + H]$^+$ | T4 |
| 63 | methyl (R)-2-((5-acrylamido-2-methoxy-4-(methyl((1-methylpyrrolidin-2-yl)methyl)amino)phenyl)amino)-4-(1H-indol-1-yl)pyrimidine-5-carboxylate<br>$^1$H NMR: (MeOH-d$_4$) δ 8.93 (s, 1H), 8.75-8.75 (m, 1H), 8.73 (br. s., 1H), 7.66 (d, J = 7.3 Hz, 1H), 7.53-7.59 (m, 2H), 7.09-7.18 (m, 2H), 6.97 (s, 1H), 6.61-6.67 (m, 1H), 6.45-6.55 (m, 1H), 6.33-6.43 (m, 1H), 5.81 (dd, J = 10.0, 1.5 Hz, 1H), 3.93 (s, 3H), 3.63 (s, 3H), 3.11-3.05 (m, 3H), 2.73 (s, 3H), 2.63-2.69 (m, 1H), 2.56 (s, 3H), 2.13 (m, 1H), 1.84-1.95 (m, 2H), 1.60-1.70 (m, 1H)<br>ESI-MS m/z: 570.3 [M + H]$^+$ | T5 |

TABLE 27-continued

| Ex. | Compound | Amine compound |
|---|---|---|
| 64 | 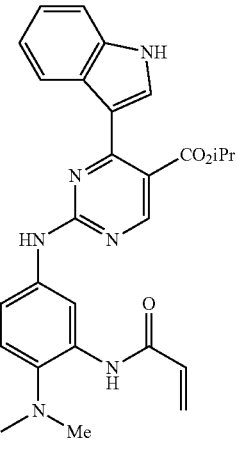<br>isopropyl (R)-2-((5-acrylamido-2-methoxy-4-(methyl((1-methylpyrrolidin-2-yl)methyl)amino)phenyl)amino)-4-(1H-indol-3-yl)pyrimidine-5-carboxylate<br>$^1$H NMR: (CDCl$_3$) δ 9.72 (s, 1H), 9.14 (br. s., 1H), 8.91 (s, 1H), 8.24 (br. s., 1H), 7.82 (s, 1H), 7.72 (d, J = 3.8 Hz, 1H), 7.30 (dd, J = 6.5, 2.0 Hz, 1H), 7.04-7.16 (m, 2H), 6.71 (s, 1H), 6.45 (d, J = 15.3 Hz, 1H), 5.62-5.74 (m, 1H), 4.92-5.05 (m, 1H), 3.85 (s, 3H), 3.09-3.21 (m, 1H), 2.92 (br. s., 1H), 2.71 (s, 3H), 2.50 (s, 3H), 2.33-2.40 (m, 1H), 1.96 (m, 1H), 1.74 (br. s., 2H), 1.45 (br. s., 1H), 1.04 (m, 6H)<br>ESI-MS m/z: 598.3 [M + H]$^+$ | T6 |
| 65 | 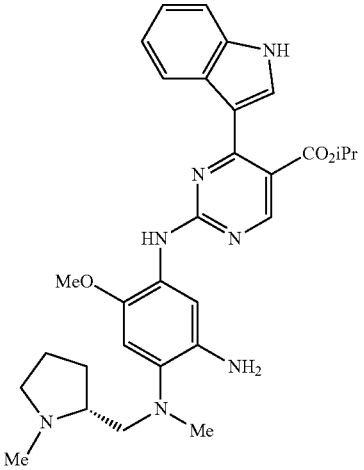<br>ethyl (R)-2-((5-acrylamido-2-methoxy-4-(methyl((1-methylpyrrolidin-2-yl)methyl)amino)phenyl)amino)-4-(1-methyl-1H-indol-3-yl)pyrimidine-5-carboxylate<br>$^1$H NMR: (CDCl$_3$) δ 9.80 (s, 1H), 9.75 (br. s., 1H), 8.90 (s, 1H), 8.68 (br. s., 1H), 7.84 (s, 1H), 7.53 (d, J = 10.5 Hz, 1H), 7.32 (d, J = 8.0 Hz, 2H), 7.16-7.24 (m, 1H), 7.08-7.15 (m, 1H), 6.73 (s, 1H), 6.43-6.51 (m, 1H), 6.38 (d, J = 10.0 Hz, 1H), 5.72 (d, J = 11.8 Hz, 1H), 4.11 (q, J = 7.0 Hz, 2H), 3.93 (s, 3H), 3.87 (s, 3H), 3.07 (m, 1H), 2.89 (m, 1H), 2.72 (s, 3H), 2.57-2.69 (m, 2H), 2.52 | T7 |

TABLE 27-continued

| Ex. | Compound | Amine compound |
|---|---|---|
| | (s, 3H), 2.26-2.37 (m, 1H), 1.87-2.01 (m, 1H), 1.72 (m, 2H), 1.37-1.47 (m, 1H), 0.94 (t, J = 6.7 Hz, 3H)<br>ESI-MS m/z: 598.3 [M + H]+ | |
| 66 | 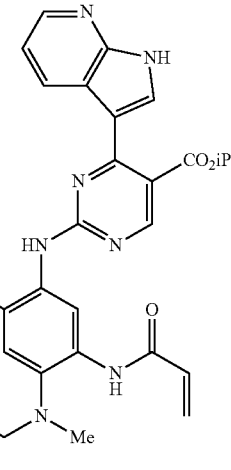<br>isopropyl 2-((5-acrylamido-4-((2-(dimethylamino)ethyl)(methyl)amino)-2-methoxyphenyl)amino)-4-(1H-pyrrolo[2,3-b]pyridin-3-yl)pyrimidine-5-carboxylate<br>1H NMR: (CDCl3) δ 10.09-10.19 (m, 1H), 9.71 (s, 1H), 8.97 (s, 1H), 8.65 (br. s., 1H), 8.32 (d, J = 3.6 Hz, 1H), 8.09 (br. s., 1H), 7.89 (s, 1H), 7.12 (dd, J = 7.8, 4.7 Hz, 1H), 6.80 (s, 1H), 6.41-6.50 (m, 1H), 6.24-6.38 (m, 1H), 5.61-5.75 (m, 1H), 5.05 (m, 1H), 3.88 (s, 3H), 2.87 (t, J = 5.5 Hz, 2H), 2.71 (s, 3H), 2.20-2.33 (m, 8H), 1.11 (d, J = 6.4 Hz, 6H)<br>ESI-MS m/z: 573.3 [M + H]+ | 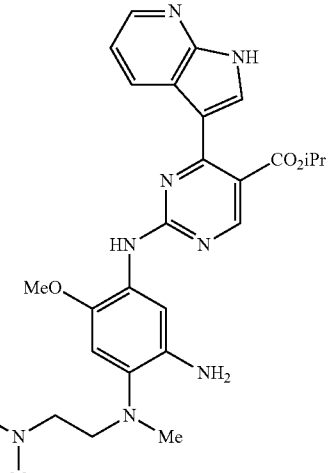<br>T8 |
| 67 | 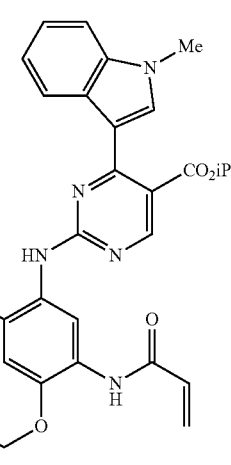<br>isopropyl 2-((5-acrylamido-4-(2-(dimethylamino)ethoxy)-2-methoxyphenyl)amino)-4-(1-methyl-1H-indol-3-yl)pyrimidine-5-carboxylate<br>1H NMR: (CDCl3) δ 9.67-9.79 (m, 2H), 8.88 (s, 1H), 8.59 (br. s., 1H), 7.81 (s, 1H), 7.59 (br. s., 1H), 7.32 (d, J = 8.2 Hz, 1H), 7.20 (td, J = 7.6, 0.9 Hz, 1H), 7.10-7.15 (m, 1H), 6.63 (s, 1H), 6.43-6.50 (m, 1H), 6.24-6.33 (m, 1H), 5.72 (dd, J = 10.2, 1.6 Hz, | 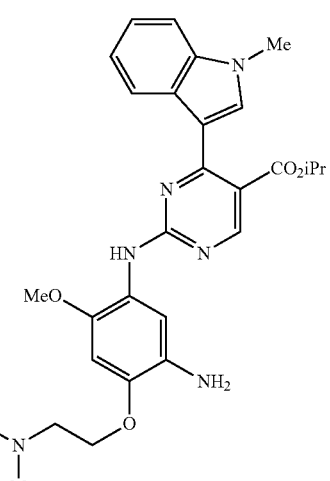<br>T9 |

TABLE 27-continued

| Ex. | Compound | | Amine compound |
|---|---|---|---|
| | 1H), 4.96-5.05 (m, 1H), 4.11 (t, J = 5.1 Hz, 2H), 3.92 (s, 3H), 3.86 (s, 3H), 2.54 (t, J = 5.1 Hz, 2H), 2.34 (s, 6H), 1.03 (d, J = 6.1 Hz, 6H) ESI-MS m/z: 573.3 [M + H]$^+$ | | |
| 68 | 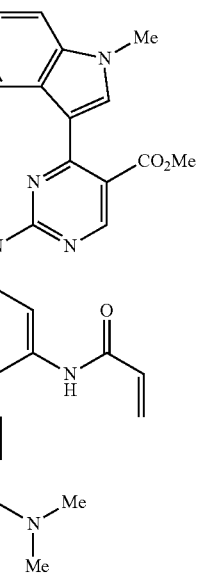 methyl 2-((5-acrylamido-4-(3-(dimethylamino)prop-1-yn-1-yl)-2-methoxyphenyl)amino)-4-(1-methyl-1H-indol-3-yl)pyrimidine-5-carboxylate $^1$H NMR: (CDCl$_3$) δ 9.77 (br. s., 1H), 8.91 (s, 1H), 8.55-8.69 (m, 1H), 8.62 (br. s., 1H), 7.97 (br. s., 1H), 7.54 (d, J = 6.9 Hz, 1H), 7.34 (d, J = 8.2 Hz, 1H), 7.22 (td, J = 7.6, 1.0 Hz, 1H), 7.13-7.18 (m, 1H), 6.91 (s, 1H), 6.41-6.47 (m, 1H), 6.27-6.35 (m, 1H), 5.78 (d, J = 10.2 Hz, 1H), 3.94 (s, 3H), 3.89 (s, 3H), 3.64 (s, 3H), 3.58 (s, 2H), 2.41 (s, 6H) ESI-MS m/z: 539.2 [M + H]$^+$ | | 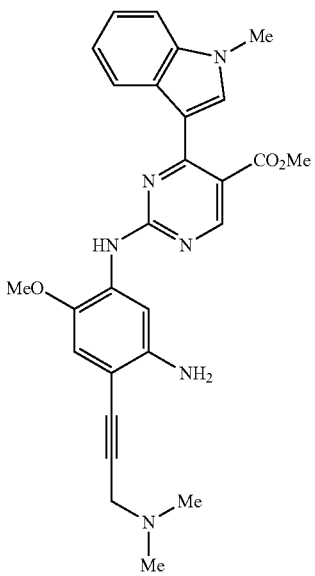 R47 |
| 69 | 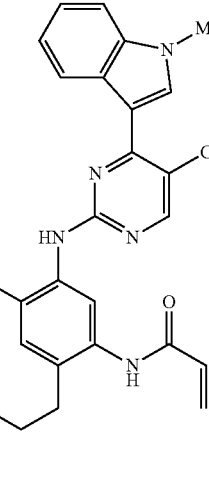 methyl 2-((5-acrylamido-4-(3-(dimethylamino)propyl)-2-methoxyphenyl)amino)-4-(1-methyl-1H-indol-3-yl)pyrimidine-5-carboxylate $^1$H NMR: (CDCl$_3$) δ 10.94 (br. s., 1H), 9.29 (br. s., 1H), 8.89 (s, 1H), 8.46-8.59 (m, 1H), | | 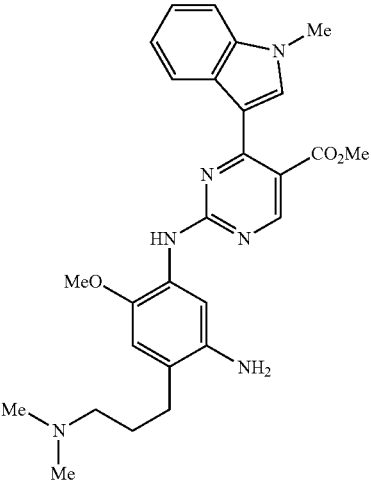 T10 |

TABLE 27-continued

| Ex. | Compound | Amine compound |
|---|---|---|
| | 7.96 (s, 1H), 7.53 (d, J = 9.8 Hz, 1H), 7.34 (d, J = 8.0 Hz, 1H), 7.22 (t, J = 7.0 Hz, 1H), 7.11-7.18 (m, 1H), 6.66 (s, 1H), 6.43-6.50 (m, 1H), 6.47 (dd, J = 16.9, 1.8 Hz, 1H), 6.22 (dd, J = 16.9, 10.2 Hz, 1H), 5.71 (dd, J = 10.2, 1.9 Hz, 1H), 3.94 (s, 3H), 3.88 (s, 3H), 3.63 (s, 3H), 2.65-2.71 (m, 2H), 2.26 (s, 6H), 2.13 (t, J = 5.6 Hz, 2H), 1.87 (m, 2H) ESI-MS m/z: 543.3 [M + H]+ | |
| 70 | 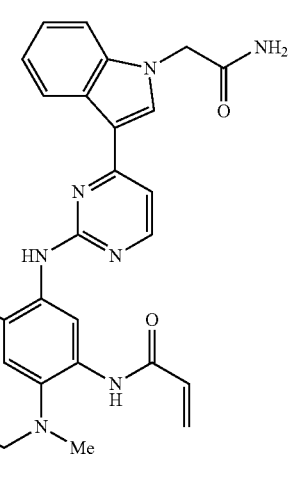 N-(5-((4-(1-(2-amino-2-oxoethyl)-1H-indol-3-yl)pyrimidin-2-yl)amino)-2-((2-(dimethylamino)ethyl)(methyl)amino)-4-methoxyphenyl)acrylamide <br> 1H NMR: (CDCl3): δ 10.27 (br. s., 1H), 9.77 (s, 1H), 9.32 (s, 1H), 8.39 (d, J = 5.3 Hz, 1H), 8.02 (dd, J = 6.1, 2.5 Hz, 1H), 7.76 (s, 1H), 7.44-7.51 (m, 1H), 7.28-7.33 (m, 2H), 7.21 (d, J = 5.3 Hz, 1H), 6.80 (s, 1H), 6.46 (br. s., 1H), 6.37 (m, 2H), 5.69-5.74 (m, 1H), 5.53 (br. s., 1H), 5.03 (s, 2H), 3.88 (s, 3H), 2.90 (t, J = 5.5 Hz, 2H), 2.70 (s, 3H), 2.25 (s, 8H) ESI-MS m/z: 543.4 [M + H]+ | 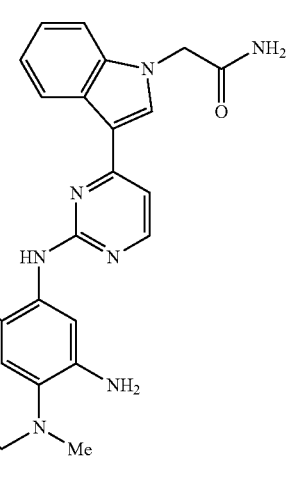 <br> T11 |
| 71 | 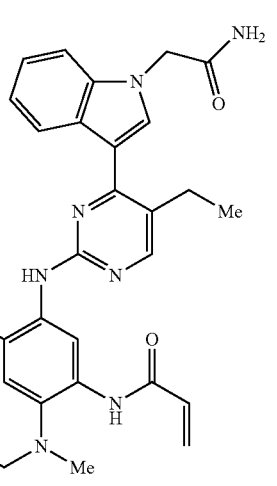 N-(5-((4-(1-(2-amino-2-oxoethyl)-1H-indol-3-yl)-5-ethylpyrimidin-2-yl)amino)-2-((2-(dimethylamino)ethyl)(methyl)amino)-4- | 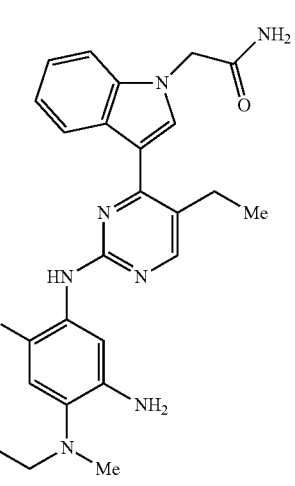 <br> T12 |

TABLE 27-continued

| Ex. | Compound | Amine compound |
|---|---|---|
| | methoxyphenyl)acrylamide<br>¹H NMR: (CDCl₃) δ 10.11 (br. s., 1H), 9.69 (s, 1H), 8.41 (s, 1H), 8.23 (s, 1H), 7.73 (d, J = 7.9 Hz, 1H), 7.63 (s, 1H), 7.40 (d, J = 8.2 Hz, 1H), 7.27-7.31 (m, 1H), 7.18-7.24 (m, 1H), 6.77 (s, 1H), 6.22-6.36 (m, 2H), 6.07 (br. s., 1H), 5.64-5.72 (m, 1H), 5.33 (br. s., 1H), 4.96 (s, 2H), 3.87 (s, 3H), 2.86 (t, J = 5.5 Hz, 2H), 2.79 (q, J = 7.6 Hz, 2H), 2.68 (s, 3H), 2.18-2.28 (m, 8H), 1.11 (t, J = 7.6 Hz, 3H)<br>ESI-MS m/z: 543.4 [M + H]⁺ | |
| 72 | 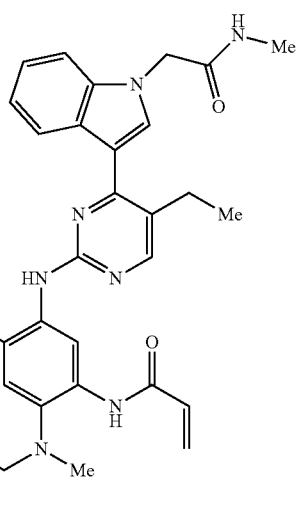<br>N-(2-((2-(dimethylamino)ethyl)(methyl)amino)-5-((5-ethyl-4-(1-(2-(methylamino)-2-oxoethyl)-1H-indol-3-yl)pyrimidin-2-yl)amino)-4-methoxyphenyl)acrylamide<br>¹H NMR: (CDCl₃) δ 10.12 (br. s., 1H), 9.70 (s, 1H), 8.42 (s, 1H), 8.22 (br. s., 1H), 7.75 (d, J = 7.8 Hz, 1H), 7.62 (s, 1H), 7.33-7.38 (m, 1H), 7.18-7.24 (m, 1H), 6.78 (s, 1H), 6.25-6.36 (m, 2H), 5.96 (br. s., 1H), 5.66-5.73 (m, 1H), 4.97 (s, 2H), 3.87 (s, 3H), 2.86 (br. s., 2H), 2.79 (q, J = 7.6 Hz, 2H), 2.66-2.69 (m, 6H), 2.23 (s, 8H), 1.14 (t, J = 7.6 Hz, 3H)<br>ESI-MS m/z: 585.3 [M + H]⁺ | 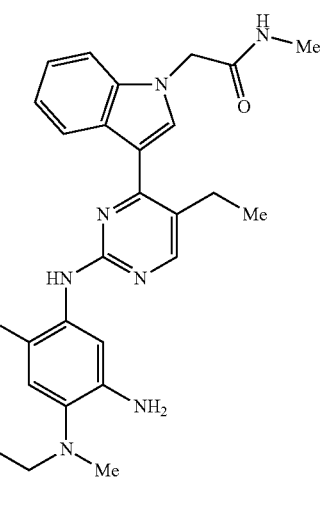<br>T13 |
| 75 | 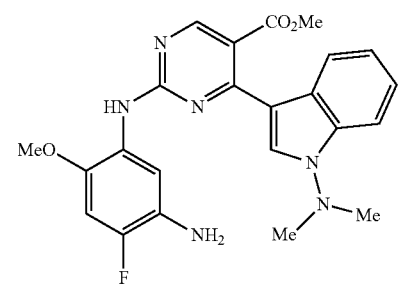<br>methyl 2-((5-acrylamido-4-fluoro-2-methoxyphenyl)amino)-4-(1-(dimethylamino)-1H-indol-3-yl)pyrimidine-5-carboxylate<br>¹H NMR: (CDCl₃) δ 9.45 (d, J = 8.8 Hz, 1H), 8.91 (s, 1H), 8.72 (s, 1H), 8.05 (s, 1H), 7.72 (s, 1H), 7.60 (d, J = 8.0 Hz, 1H), 7.26 (t, J = 8.4 Hz, 1H), 7.16 (t, J = 8.4 Hz, 1H), 6.75 (d, J = 12.0 Hz, 1H), 6.50 (dd, J = 17.2, 1.2 | R48 |

TABLE 27-continued

| Ex. | Compound | Amine compound |
|---|---|---|
| | Hz, 1H), 6.31 (dd, J = 17.2, 10.0 Hz, 1H), 5.84 (d, J = 10.0 Hz, 1H), 3.92 (s, 3H), 3.66 (s, 3H), 3.05 (s, 6H ESI-MS m/z: 505.1 [M + H]+ | |
| 76 | 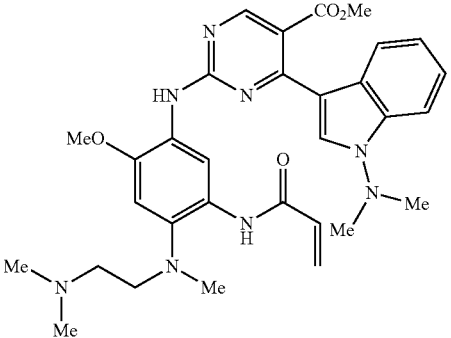 [SMILES: C=CC(=O)Nc1cc(Nc2ncc(C(=O)OC)c(-c3cn(N(C)C)c4ccccc34)n2)c(OC)cc1N(C)CCN(C)C]<br>methyl 2-((5-acrylamido-4-((2-(dimethylamino)ethyl)(methyl)amino)-2-methoxyphenyl)amino)-4-(1-(dimethylamino)-1H-indol-3-yl)pyrimidine-5-carboxylate<br>$^1$H NMR: (MeOH-d$_4$) δ 9.20 (s, 1H), 8.82 (s, 1H), 8.62 (m, 1H), 7.58 (dd, J = 8.0, 0.8 Hz, 1H), 7.21 (td, J = 7.2, 0.8 Hz, 1H), 7.10 (td, J = 8.0, 1.2 Hz, 1H), 7.00 (s, 1H), 6.57 (dd, J = 16.8, 10.0 Hz, 1H), 6.41 (dd, J = 16.8, 1.2 Hz, 1H), 5.83 (dd, J = 10.0, 1.6 Hz, 1H), 3.94 (s, 3H), 3.69 (s, 3H), 3.07 (t, J = 5.6 Hz, 2H), 3.00 (s, 6H), 2.71 (s, 3H), 2.48 (m, 2H), 2.32 (s, 6H)<br>ESI-MS m/z: 587.2 [M + H]+ | 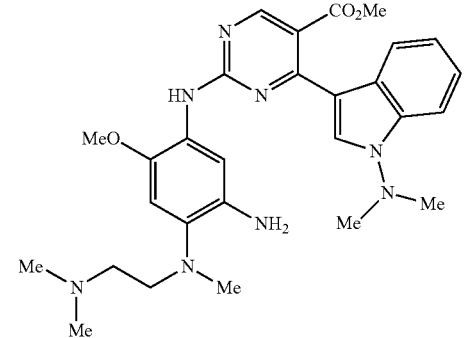<br>R49 |
| 77 | 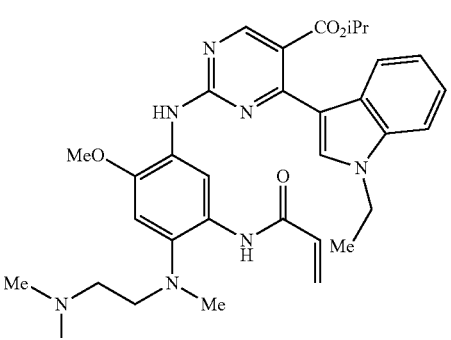<br>isopropyl 2-((5-acrylamido-4-((2-(dimethylamino)ethyl)(methyl)amino)-2-methoxyphenyl)amino)-4-(1-ethyl-1H-indol-3-yl)pyrimidine-5-carboxylate<br>$^1$H NMR: (MeOH-d$_4$) δ 9.32 (s, 1H), 8.77 (s, 1H), 8.34 (s, 1H), 7.64 (d, J = 8.0 Hz, 1H), 7.50 (d, J = 8.4 Hz, 1H), 7.23 (td, J = 8.0, 0.8 Hz, 1H), 7.12 (td, J = 8.4, 0.8 Hz, 1H), 7.00 (s, 1H), 6.58 (dd, J = 16.8, 10.0 Hz, 1H), 6.42 (dd, J = 16.8, 1.6 Hz, 1H), 5.82 (dd, J = 10.0, 1.6 Hz, 1H), 4.98 (sep, J = 6.4 Hz, 1H), 4.36 (q, J = 7.2 Hz, 2H), 3.96 (s, 3H), 3.07 (t, J = 5.6 Hz, 2H), 2.72 (s, 3H), 2.47 (m, 2H), 2.31 (s, 6H), 1.52 (t, J = 7.2 Hz, 3H), 1.06 (d, J = 6.4 Hz, 6H)<br>ESI-MS m/z: 600.3 [M + H]+ | 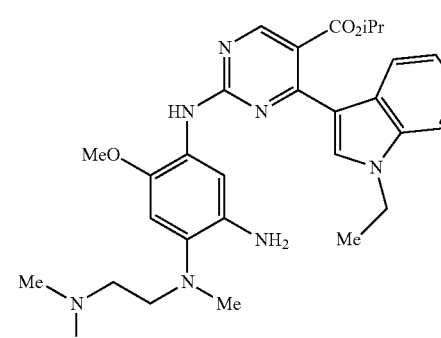<br>T16 |

TABLE 27-continued

| Ex. | Compound | Amine compound |
|---|---|---|
| 78 | 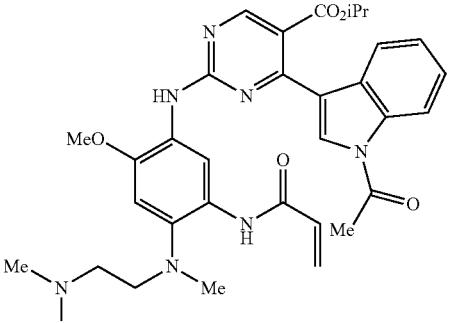<br>isopropyl 4-(1-acetyl-1H-indol-3-yl)-2-((5-acrylamido-4-((2-(dimethylamino)ethyl)(methyl)amino)-2-methoxyphenyl)amino)pyrimidine-5-carboxylate<br>$^1$H NMR: (MeOH-$d_4$) δ 9.25 (s, 1H), 8.94 (s, 1H), 8.47 (d, J = 8.4 Hz, 1H), 8.38 (s, 1H), 7.51 (d, J = 8.4 Hz, 1H), 7.36 (td, J = 8.4, 1.2 Hz, 1H), 7.28 (td, J = 8.0, 1.2 Hz, 1H), 7.00 (s, 1H), 6.58 (dd, J = 17.2, 10.0 Hz, 1H), 6.33 (dd, J = 17.2, 2.0 Hz, 1H), 5.80 (dd, J = 10.0, 2.0 Hz, 1H), 4.93 (sep, J = 6.0 Hz, 1H), 3.96 (s, 3H), 3.08 (m, 2H), 2.78 (s, 3H), 2.71 (s, 3H), 2.49 (m, 2H), 2.32 (s, 6H), 1.00 (d, J = 6.0 Hz, 6H)<br>ESI-MS m/z: 614.3 [M + H]$^+$ | 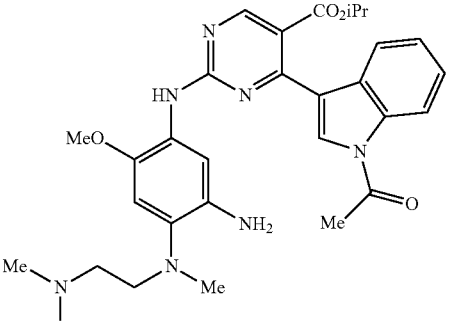<br>T17 |
| 79 | 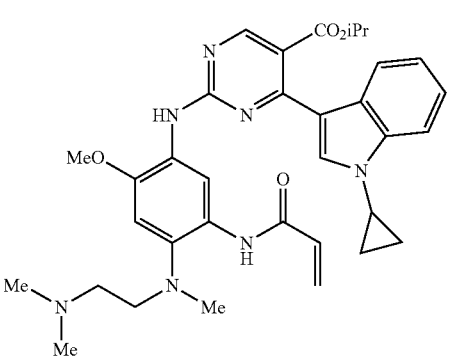<br>isopropyl 2-((5-acrylamido-4-((2-(dimethylamino)ethyl)(methyl)amino)-2-methoxyphenyl)amino)-4-(1-cyclopropyl-1H-indol-3-yl)pyrimidine-5-carboxylate<br>$^1$H NMR: (DMSO-$d_6$) δ 10.15 (s., 1H), 8.76 (d, J = 4.4 Hz, 1H), 1H), 8.68 (s, 1H), 8.01 (s, 1H), 7.70 (m, 1H), 7.61 (d, J = 4.4 Hz, 1H), 7.21 (t, J = 7.6 Hz, 1H), 7.07-7.02 (m, 2H), 6.42 (dd, J = 16.8, 5.6 Hz, 1H), 6.27 (dd, J = 16.8, 3.0 Hz, 1H), 5.78 (dd, J = 10.0, 3.0 Hz, 1H), 4.96 (sep, J = 6.0 Hz, 1H), 3.81 (s, 3H), 3.54 (m, 1H), 2.88 (t, J = 6.0 Hz, 2H), 2.73 (s, 3H), 2.32 (t, J = 5.6 HZ, 2H), 2.21 (s, 6H), 1.11 (d, J = 6.0 Hz, 6H), 1.08 (m, 2H), 0.98 (m, 2H).<br>ESI-MS m/z: 612.3 [M + H]$^+$ | 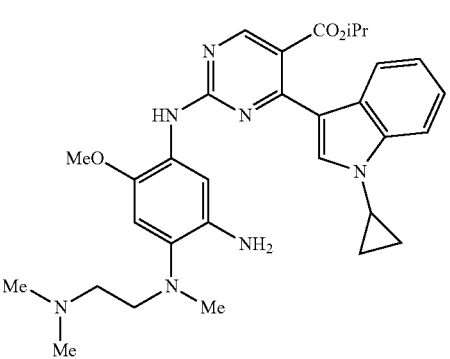<br>T18 |

TABLE 27-continued

| Ex. | Compound | Amine compound |
|---|---|---|
| 80 | 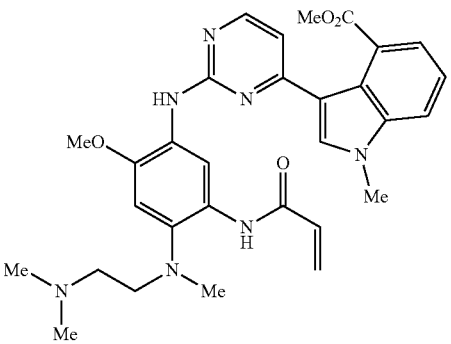 [SMILES: C=CC(=O)Nc1cc(Nc2nccc(-c3cn(C)c4cccc(C(=O)OC)c34)n2)c(OC)cc1N(C)CCN(C)C] methyl 3-(2-((5-acrylamido-4-((2-(dimethylamino)ethyl)(methyl)amino)-2-methoxyphenyl)amino)pyrimidin-4-yl)-1-methyl-1H-indole-4-carboxylate<br>$^1$H NMR: (MeOH-d$_4$) δ 9.26 (d, J = 5.6 Hz, 1H), 8.11 (s, 1H), 7.71 (dd, J = 8.4, 0.8 Hz, 1H), 7.53 (dd, J = 7.2, 0.8 Hz, 1H), 7.36 (dd, J = 8.4, 7.2 Hz, 1H), 6.98 (s, 1H), 6.90 (d, J = 5.6 Hz, 1H), 6.53 (dd, J = 16.8, 10.0 Hz, 1H), 6.33 (d, J = 16.8 Hz, 1H), 5.78 (d, J = 10.0 Hz, 1H), 3.984 (s, 3H), 3.976 (s, 3H), 3.61 (s, 3H), 3.08 (m, 2H), 2.71 (s, 3H), 2.48 (m, 2H), 2.34 (s, 6H)<br>ESI-MS m/z: 558.2 [M + H]$^+$ | 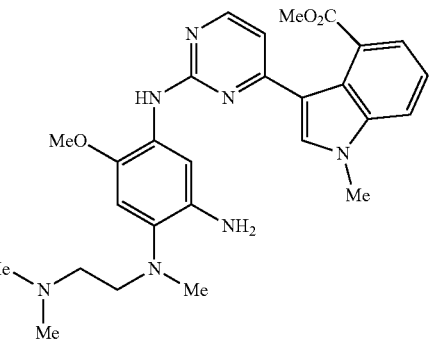<br>T19 |
| 81 | 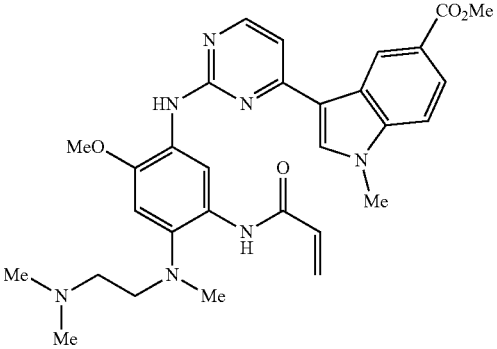 [SMILES: C=CC(=O)Nc1cc(Nc2nccc(-c3cn(C)c4ccc(C(=O)OC)cc34)n2)c(OC)cc1N(C)CCN(C)C] methyl 3-(2-((5-acrylamido-4-((2-(dimethylamino)ethyl)(methyl)amino)-2-methoxyphenyl)amino)pyrimidin-4-yl)-1-methyl-1H-indole-5-carboxylate<br>$^1$H NMR: (MeOH-d$_4$) δ 9.44 (s, 1H), 8.77 (s, 1H), 8.73 (s, 1H), 8.35 (d, J = 5.6 Hz, 1H), 7.94 (dd, J = 8.8, 1.6 Hz, 1H), 7.52 (d, J = 8.8 Hz, 1H), 7.25 (d, J = 5.6 Hz, 1H), 7.00 (s, 1H), 6.58 (dd, J = 16.8, 10.0 Hz, 1H), 6.38 (dd, J = 16.8, 1.6 Hz, 1H), 5.80 (dd, J = 10.0, 1.6 Hz, 1H), 3.983 (s, 3H), 3.976 (s, 3H), 3.96 (s, 3H), 3.08 (t, J = 6.0 Hz, 2H), 2.73 (s, 3H), 2.49 (t, J = 6.0 Hz, 2H), 2.33 (s, 6H)<br>ESI-MS m/z: 558.2 [M + H]$^+$ | 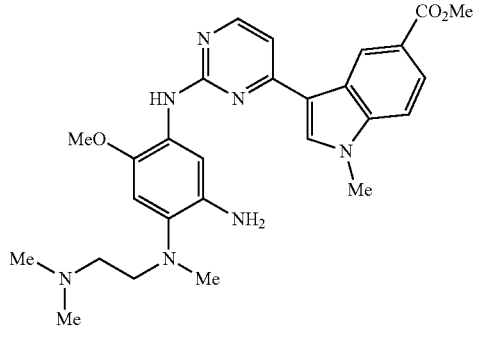<br>T20 |

TABLE 27-continued

| Ex. | Compound | Amine compound |
|---|---|---|
| 82 | 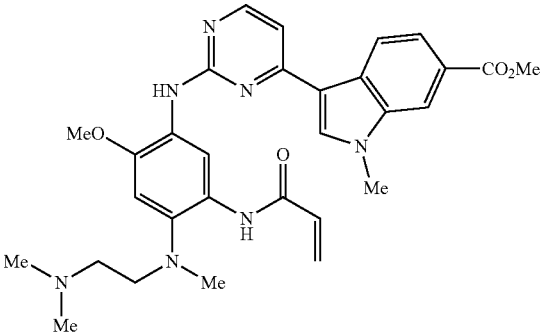 [SMILES: C=CC(=O)Nc1cc(Nc2nccc(-c3cn(C)c4cc(C(=O)OC)ccc34)n2)c(OC)cc1N(C)CCN(C)C]<br>methyl 3-(2-((5-acrylamido-4-((2-(dimethylamino)ethyl)(methyl)amino)-2-methoxyphenyl)amino)pyrimidin-4-yl)-1-methyl-1H-indole-6-carboxylate<br>$^1$H NMR: (DMSO-d$_6$) δ 10.22 (s, 1H), 9.08 (s, 1H), 8.84 (s, 1H), 8.37 (d, J = 5.2 Hz, 1H), 8.35 (d, J = 8.4 Hz, 1H), 8.16 (d, J = 1.6 Hz, 1H), 7.98 (s, 1H), 7.75 (dd, J = 8.4, 1.6 Hz, 1H), 7.26 (d, J = 5.2 Hz, 1H), 7.06 (s, 1H), 6.43 (dd, J = 16.8, 10.0 Hz, 1H), 6.25 (dd, J = 16.8, 2.0 Hz, 1H), 5.77 (dd, J = 10.0, 2.0 Hz, 1H), 4.00 (s, 3H), 3.90 (s, 3H), 3.86 (s, 3H), 2.97 (t, J = 5.6 Hz, 2H), 2.74 (s, 3H), 2.33 (m, 2H), 2.24 (s, 6H)<br>ESI-MS m/z: 558.2 [M + H]$^+$ | 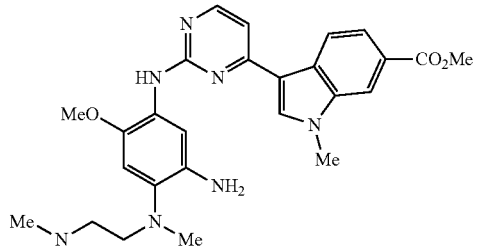<br>T21 |
| 83 | 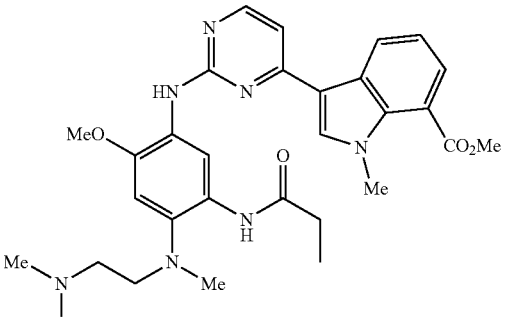<br>methyl 3-(2-((5-acrylamido-4-((2-(dimethylamino)ethyl)(methyl)amino)-2-methoxyphenyl)amino)pyrimidin-4-yl)-1-methyl-1H-indole-6-carboxylate<br>$^1$H NMR: (MeOH-d$_4$) δ 9.30 (s, 1H), 8.52 (s, 1H), 8.51 (d, J = 8.0 Hz, 1H), 8.32 (d, J = 5.6 Hz, 1H), 7.62 (dd, J = 7.2, 1.2 Hz, 1H), 7.25-7.20 (m 2H), 7.00 (s, 1H), 6.58 (dd, J = 16.8, 10.0 Hz, 1H), 6.38 (dd, J = 16.8, 1.6 Hz, 1H), 5.80 (dd, J = 10.0, 1.6 Hz, 1H), 4.00 (s, 3H), 3.99 (s, 3H), 3.96 (s, 3H), 3.09 (t, J = 6.0 Hz, 2H), 2.73 (s, 3H), 2.50 (m, 2H), 2.34 (s, 6H)<br>ESI-MS m/z: 558.2 [M + H]$^+$ | 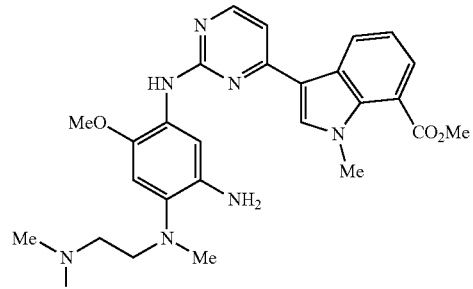<br>T22 |

TABLE 27-continued

| Ex. | Compound | Amine compound |
|---|---|---|
| 84 | 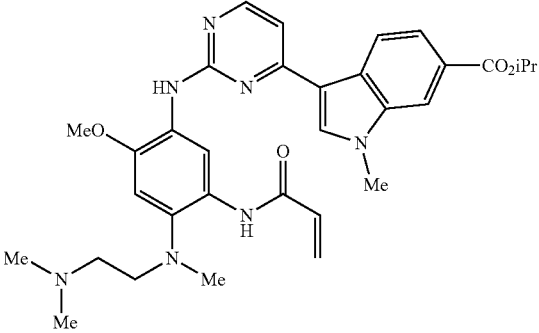<br>isopropyl 3-(2-((5-acrylamido-4-((2-(dimethylamino)ethyl)(methyl)amino)-2-methoxyphenyl)amino)pyrimidin-4-yl)-1-methyl-1H-indole-6-carboxylate<br><br>$^1$H NMR: (MeOH-$d_4$) δ 9.75 (s, 1H), 8.34 (d, J = 5.6 Hz, 1H), 8.31 (d, J = 8.4 Hz, 1H), 8.17 (d, J = 1.6 Hz, 1H), 7.87 (dd, J = 8.4, 1.6 Hz, 1H), 7.28 (d, J = 5.6 Hz, 1H), 7.25 (d, J = 5.6 Hz, 1H), 7.02 (s, 1H), 6.60 (dd, J = 17.2, 10.4 Hz, 1H), 6.38 (dd, J = 17.2, 1.6 Hz, 1H), 5.80 (dd, J = 10.4, 1.6 Hz, 1H), 5.29 (sep, J = 6.4 Hz, 1H), 4.04 (s, 3H), 3.97 (s, 3H), 3.11 (m, 2H), 2.74 (s, 3H), 2.50 (m, 2H), 2.3 (s, 6H), 1.44 (d, J = 6.4 Hz, 6H)<br>ESI-MS m/z: 586.2 [M + H]$^+$ | 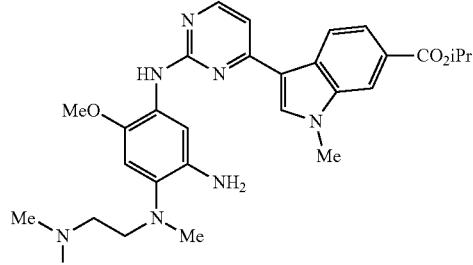<br>T23 |
| 85 | 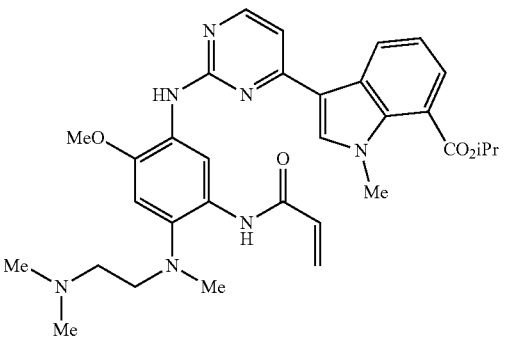<br>isopropyl 3-(2-((5-acrylamido-4-((2-(dimethylamino)ethyl)(methyl)amino)-2-methoxyphenyl)amino)pyrimidin-4-yl)-1-methyl-1H-indole-7-carboxylate<br><br>$^1$H NMR: (MeOH-$d_4$) δ 9.29 (s, 1H), 8.53-8.48 (m, 2H), 8.33 (d, J = 5.6 Hz, 1H), 7.59 (dd, J = 7.2, 0.8 Hz, 1H), 7.26 (d, J = 7.2 Hz, 1H), 7.22 (t, J = 7.2 Hz, 1H), 7.00 (s, 1H), 6.59 (dd, J = 17.2, 10.0 Hz, 1H), 6.38 (dd, J = 17.2, 1.6 Hz, 1H), 5.81 (dd, J = 10.0, 1.6 Hz, 1H), 5.32 (sep, J = 6.4 Hz, 1H), 4.00 (s, 3H), 3.96 (s, 3H), 3.10 (t, J = 6.0 Hz, 2H), 2.73 (s, 3H), 2.51 (m, 2H), 2.35 (s, 6H), 1.45 (d, J = 6.4 Hz, 6H)<br>ESI-MS m/z: 586.2 [M + H]$^+$ | 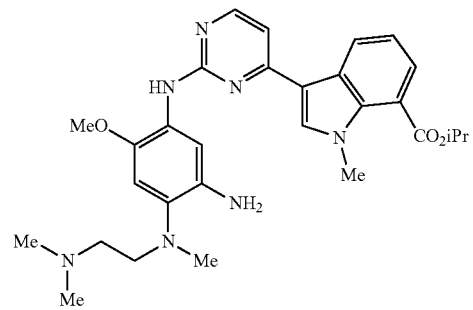<br>T24 |

TABLE 27-continued

| Ex. | Compound | Amine compound |
|---|---|---|

86

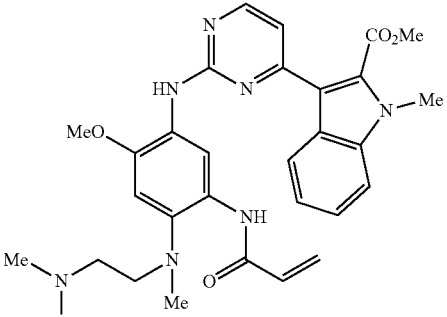

methyl 3-(2-((5-acrylamido-4-((2-(dimethylamino)ethyl)(methyl)amino)-2-methoxyphenyl)amino)pyrimidin-4-yl)-1-methyl-1H-indole-2-carboxylate $^1$H NMR: (MeOH-d$_4$) δ 9.02 (s, 1H), 8.47 (d, J = 5.2 Hz, 1H), 7.92 (d, J = 8.0 Hz, 1H), 7.57 (d, J = 8.4 Hz, 1H), 7.40 (td, J = 8.4, 1.2 Hz, 1H), 7.23 (td, J = 8.0, 1.2 Hz, 1H), 7.03 (d, J = 5.2 Hz, 1H), 6.97 (s, 1H), 6.51 (dd, J = 16.8, 10.4 Hz, 1H), 6.31 (dd, J = 16.8, 1.6 Hz, 1H), 5.77 (dd, J = 10.4, 1.6 Hz, 1H), 4.01 (s, 3H), 3.94 (s, 3H), 3.75 (s, 3H), 3.06 (t, J = 6.0 Hz, 2H), 2.71 (s, 3H), 2.46 (m, 2H), 2.32 (s, 6H)

ESI-MS m/z: 558.2 [M + H]$^+$

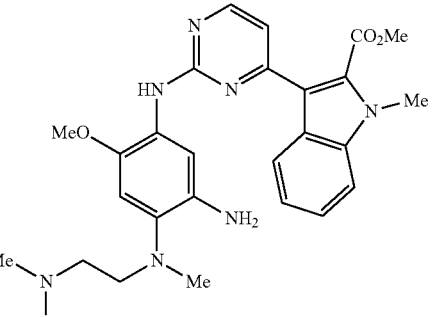

T25

87

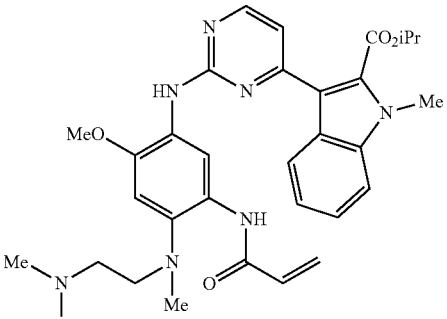

isopropyl 3-(2-((5-acrylamido-4-((2-(dimethylamino)ethyl)(methyl)amino)-2-methoxyphenyl)amino)pyrimidin-4-yl)-1-methyl-1H-indole-2-carboxylate $^1$H NMR: (MeOH-d$_4$) δ 9.10 (s, 1H), 8.48 (d, J = 5.2 Hz, 1H), 7.85 (d, J = 8.4 Hz, 1H), 7.55 (d, J = 8.4 Hz, 1H), 7.39 (ddd, J = 8.4, 6.8, 1.2 Hz, 1H), 7.22 (ddd, J = 8.4, 7.2, 1.2 Hz, 1H), 7.03 (d, J = 5.2 Hz, 1H), 6.96 (s, 1H), 6.51 (dd, J = 16.8, 10.0 Hz, 1H), 6.32 (d, J = 16.8, 1.2 Hz, 1H), 5.76 (dd, J = 10.0, 1.2 Hz, 1H), 5.08 (sep, J = 6.4 Hz, 1H), 4.01 (s, 3H), 3.92 (s, 3H), 3.04 (t, J = 6.0 Hz, 2H), 2.70 (s, 3H), 2.43 (t, J = 6.0 Hz, 2H), 2.30 (s, 6H), 1.20 (d, J = 6.4 Hz, 6H)

ESI-MS m/z: 586.2 [M + H]$^+$

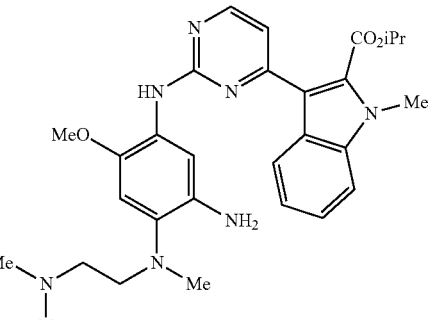

T26

TABLE 27-continued

| Ex. | Compound | Amine compound |
|---|---|---|
| 88 | 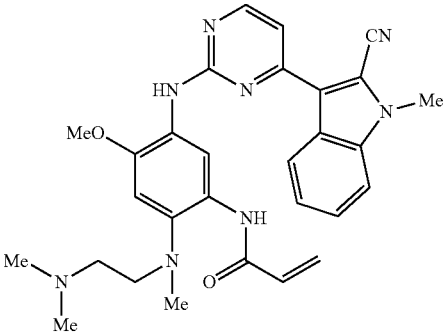<br>N-(5-((4-(2-cyano-1-methyl-1H-indol-3-yl)pyrimidin-2-yl)amino)-2-((2-(dimethylamino)ethyl)(methyl)amino)-4-methoxyphenyl)acrylamide<br>¹H NMR: (MeOH-d₄) δ 9.10 (s, 1H), 8.48 (d, J = 5.2 Hz, 1H), 7.85 (d, J = 8.4 Hz, 1H), 7.55 (d, J = 8.4 Hz, 1H), 7.39 (ddd, J = 8.4, 6.8, 1.2 Hz, 1H), 7.22 (ddd, J = 8.4, 7.2, 1.2 Hz, 1H), 7.03 (d, J = 5.2 Hz, 1H), 6.96 (s, 1H), 6.51 (dd, J = 16.8, 10.0 Hz, 1H), 6.32 (d, J = 16.8, 1.2 Hz, 1H), 5.76 (dd, J = 10.0, 1.2 Hz, 1H), 5.08 (sep, J = 6.4 Hz, 1H), 4.01 (s, 3H), 3.92 (s, 3H), 3.04 (t, J = 6.0 Hz, 2H), 2.70 (s, 3H), 2.43 (t, J = 6.0 Hz, 2H), 2.30 (s, 6H), 1.20 (d, J = 6.4 Hz, 6H)<br>ESI-MS m/z: 586.2 [M + H]⁺ | 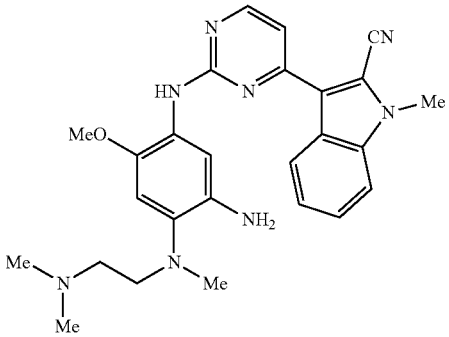<br>T27 |
| 89 | 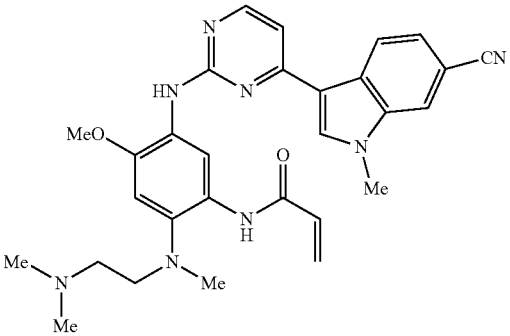<br>N-(5-((4-(6-cyano-1-methyl-1H-indol-3-yl)pyrimidin-2-yl)amino)-2-((2-(dimethylamino)ethyl)(methyl)amino)-4-methoxyphenyl)acrylamide<br>¹H NMR: (MeOH-d₄) δ 8.79 (s, 1H), 8.50 (d, J = 8.4 Hz, 1H), 8.49 (s, 1H), 8.33 (d, J = 5.2 Hz, 1H), 7.95 (s, 1H), 7.41 (dd, J = 8.4, 1.6 Hz, 1H), 7.23 (d, J = 5.2 Hz, 1H), 7.00 (s, 1H), 6.56-6.50 (m, 2H), 5.91-5.87 (m, 1H), 4.02 (s, 3H), 3.98 (s, 3H), 3.37 (s, 3H), 3.03 (m, 2H), 2.75 (s, 6H), 2.72 (m, 2H)<br>ESI-MS m/z: 586.2 [M + H]⁺ | 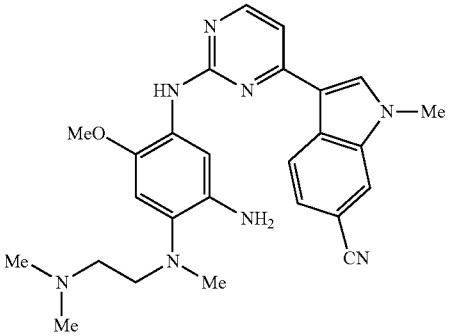<br>T28 |

TABLE 27-continued

| Ex. | Compound | Amine compound |
|---|---|---|
| 90 | 3-(2-((5-acrylamido-4-((2-(dimethylamino)ethyl)(methyl)amino)-2-methoxyphenyl)amino)pyrimidin-4-yl)-1-methyl-1H-indole-2-carboxamide<br>¹H NMR: (MeOH-d₄) δ 8.85 (s, 1H), 8.41 (d, J = 5.2 Hz, 1H), 8.13 (d, J = 8.0 Hz, 1H), 7.52 (d, J = 8.4 Hz, 1H), 7.34 (ddd, J = 8.4, 7.2, 1.2 Hz, 1H), 7.21 (ddd, J = 8.0, 7.2, 1.2 Hz, 1H), 7.15 (d, J = 5.2 Hz, 1H), 6.98 (s, 1H), 6.51 (dd, J = 16.8, 10.0 Hz, 1H), 6.30 (d, J = 16.8, Hz, 1H), 5.76 (d, J = 10.0 Hz, 1H), 3.95 (s, 6H), 3.10 (m, 2H), 2.72 (s, 3H), 2.50 (m, 2H), 2.34 (s, 6H)<br>ESI-MS m/z: 543.2 [M + H]⁺ | T29 |
| 91 | 3-(2-((5-acrylamido-4-((2-(dimethylamino)ethyl)(methyl)amino)-2-methoxyphenyl)amino)pyrimidin-4-yl)-N,1-dimethyl-1H-indole-2-carboxamide<br>¹H NMR: (MeOH-d₄) δ 8.92 (s, 1H), 8.41 (d, J = 5.2 Hz, 1H), 8.14 (d, J = 8.0 Hz, 1H), 7.53 (d, J = 8.4 Hz, 1H), 7.35 (ddd, J = 8.4, 7.2, 1.2 Hz, 1H), 7.22 (td, J = 8.0, 1.2 Hz, 1H), 7.06 (d, J = 5.2 Hz, 1H), 6.99 (s, 1H), 6.50 (dd, J = 17.2, 10.0 Hz, 1H), 6.27 (d, J = 17.2, Hz, 1H), 5.75 (d, J = 10.0 Hz, 1H), 3.95 (s, 3H), 3.89 (s, 3H), 3.10 (m, 2H), 2.80 (s, 3H), 2.72 (s, 3H), 2.50 (m, 2H), 2.33 (s, 6H)<br>ESI-MS m/z: 557.2 [M + H]⁺ | T30 |

TABLE 27-continued

| Ex. | Compound | Amine compound |
|-----|----------|----------------|
| 92 | 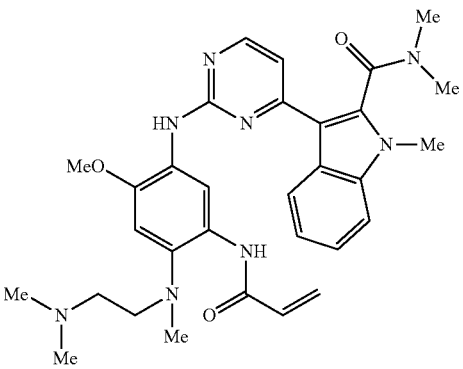 [SMILES: C=CC(=O)Nc1cc(Nc2nccc(-c3c(C(=O)N(C)C)n(C)c4ccccc34)n2)c(OC)cc1N(C)CCN(C)C]<br>3-(2-((5-acrylamido-4-((2-(dimethylamino)ethyl)(methyl)amino)-2-methoxyphenyl)amino)pyrimidin-4-yl)-N,N,1-trimethyl-1H-indole-2-carboxamide<br>$^1$H NMR: (MeOH-d$_4$) δ 8.95 (s, 1H), 8.41 (d, J = 5.2 Hz, 1H), 8.24 (d, J = 8.0 Hz, 1H), 7.55 (d, J = 8.4 Hz, 1H), 7.35 (ddd, J = 8.4, 7.2, 1.2 Hz, 1H), 7.26 (ddd, J = 8.4, 7.2, 1.2 Hz, 1H), 7.10 (d, J = 5.2 Hz, 1H), 6.99 (s, 1H), 6.50 (dd, J = 16.8, 10.0 Hz, 1H), 6.27 (d, J = 16.8, 1.2 Hz, 1H), 5.75 (dd, J = 10.0, 1.2 Hz, 1H), 3.96 (s, 3H), 3.80 (s, 3H), 3.17 (s, 3H), 3.10 (m, 2H),<br>2.80 (s, 3H), 2.84 (s, 3H), 2.72, (s, 3H), 2.50 (m, 2H), 2.34 (s, 6H)<br>ESI-MS m/z: 571.3 [M + H]$^+$ | 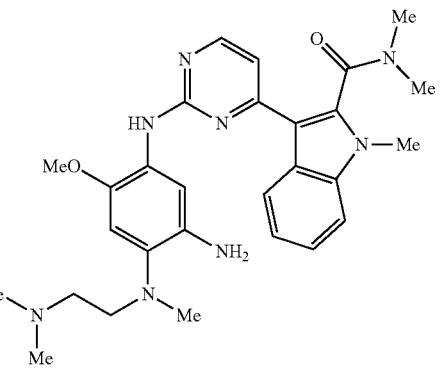<br>T31 |
| 93 | 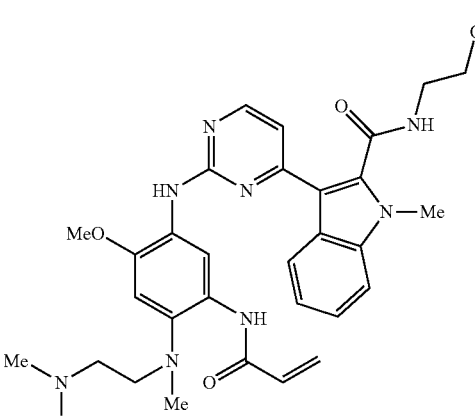<br>3-(2-((5-acrylamido-4-((2-(dimethylamino)ethyl)(methyl)amino)-2-methoxyphenyl)amino)pyrimidin-4-yl)-N-(2-methoxyethyl)-1-methyl-1H-indole-2-carboxamide<br>$^1$H NMR: (MeOH-d$_4$) δ 8.98 (s, 1H), 8.40 (d, J = 5.6 Hz, 1H), 8.12 (d, J = 8.0 Hz, 1H), 7.51 (d, J = 8.4 Hz, 1H), 7.34 (ddd, J = 8.4, 7.2, 1.2 Hz, 1H), 7.21 (ddd, J = 8.0, 7.2, 1.2 Hz, 1H), 7.10 (d, J = 5.6 Hz, 1H), 6.98 (s, 1H), 6.50 (dd, J = 16.8, 10.4 Hz, 1H), 6.27 (d, J = 16.8, 1.6 Hz, 1H), 5.74 (dd, J = 10.0, 1.6 Hz, 1H), 3.94 (s, 3H), 3.89 (s, 3H), 3.50 (s, 4H), 3.30 (s, 3H),<br>3.07 (t, J = 6.0 Hz, 2H), 2.80 (s, 3H), 2.71 (s, 3H), 2.47 (t, J = 6.0 Hz, 2H), 2.31 (s, 6H)<br>ESI-MS m/z: 601.2 [M + H]$^+$ | 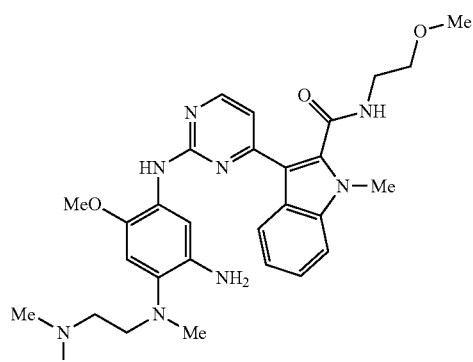<br>T32 |

TABLE 27-continued

| Ex. | Compound | Amine compound |
|---|---|---|
| 94 | 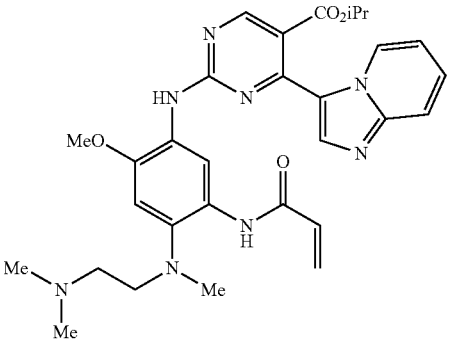<br>isopropyl 2-((5-acrylamido-4-((2-(dimethylamino)ethyl)(methyl)amino)-2-methoxyphenyl)amino)-4-(imidazo[1,2-a]pyridin-3-yl)pyrimidine-5-carboxylate<br>$^1$H NMR: (MeOH-d$_4$) δ 10.05 (br., s, 1H), 9.42 (s, 1H), 9.11 (d, dt, J = 6.8, 0.8 Hz, 1H), 9.01 (s, 1H), 8.20 (s, 1H), 7.70 (t, J = 0.8 Hz, 1H), 7.68 (s, 1H), 7.27 (m, 1H), 6.86 (t, J = 6.8 Hz, 1H), 6.80 (s, 1H), 6.45-6.40 (m, 2H), 5.72 (m, 1H), 5.19 (sep, J = 6.4 Hz, 1H), 3.89 (s, 3H), 2.96 (m, 2H), 2.74 (s, 3H), 2.37 (m, 2H), 1.26 (d, J = 6.4 Hz, 6H)<br>ESI-MS m/z: 573.3 [M + H]$^+$ | 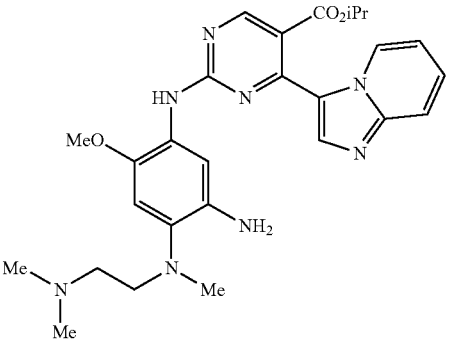<br>T33 |
| 95 | 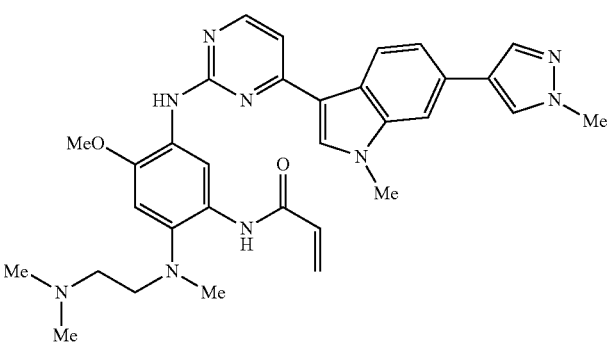 [SMILES: C=CC(=O)Nc1cc(Nc2nccc(-c3cn(C)c4cc(-c5cnn(C)c5)ccc34)n2)c(OC)cc1N(C)CCN(C)C]<br>N-(2-((2-(dimethylamino)ethyl)(methyl)amino)-4-methoxy-5-((4-(1-methyl-6-(1-methyl-1H-pyrazol-4-yl)-1H-indol-3-yl)pyrimidin-2-yl)amino)phenyl)acrylamide<br>$^1$H NMR: (MeOH-d$_4$) δ 9.39 (s, 1H), 8.58 (s, 1H), 8.31 (d, J = 5.6 Hz, 1H), 8.20 (d, J = 8.4 Hz, 1H), 8.00 (s, 1H), 7.89 (s, 1H), 7.64 (s, 1H), 7.42 (dd, J = 8.4, 1.6 Hz, 1H), 7.26 (d, J = 5.6 Hz, 1H), 7.01 (s, 1H), 6.61 (dd, J = 17.2, 10.0 Hz, 1H), 6.40 (dd, J = 17.2, 1.2 Hz, 1H), 5.80 (dd, J = 10.0, 1.6 Hz, 1H), 3.98 (s, 3H), 3.976 (s, 3H), 3.974 (s, 3H), 3.10 (t, J = 6.0 Hz, 2H), 2.74 (s, 3H), 2.50 (m, 2H), 2.34 (s, 6H)<br>ESI-MS m/z: 580.2 [M + H]$^+$ | 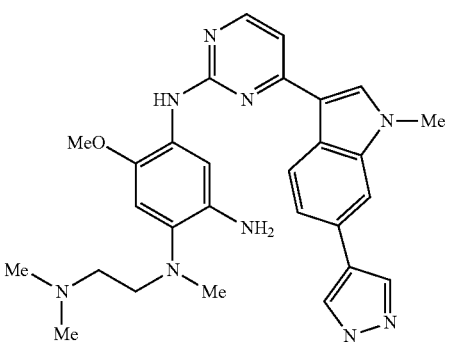<br>T34 |

TABLE 27-continued

| Ex. | Compound | Amine compound |
|---|---|---|

96

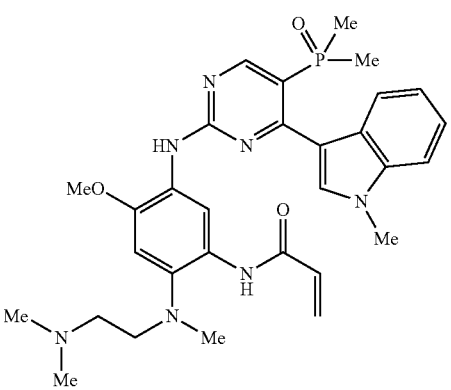 [SMILES: C=CC(=O)Nc1cc(Nc2ncc(P(C)(C)=O)c(-c3cn(C)c4ccccc34)n2)c(OC)cc1N(C)CCN(C)C]

N-(2-((2-(dimethylamino)ethyl)(methyl)amino)-5-((5-(dimethylphosphoryl)-4-(1-methyl-1H-indol-3-yl)pyrimidin-2-yl)amino)-4-methoxyphenyl)acrylamide $^1$H NMR: (MeOH-d$_4$) δ 8.80 (s, 1 H), 8.60 (d, J = 8.0 Hz, 1 H), 8.31 (s, 1 H), 8.03 (d, J = 8.0 Hz, 1 H), 7.35 (d, J = 8.0 Hz, 1 H), 7.14 (td, J = 8.0, 1.8 Hz, 1 H), 7.02 (t, J = 8.0 Hz, 1 H), 6.85 (s, 1H), 6.39 (dd, J = 17.2, 10.0 Hz, 1 H), 6.18 (dd, J = 17.2, 1.6 Hz, 1 H), 5.65 (dd, J = 10.0, 1.6 Hz, 1 H), 3.79 (s, 3 H), 3.78 (s, 3 H), 2.94 (t, J = 6.0 Hz, 2 H), 2.58 (s, 3 H), 2.35 (t, J = 6.0 Hz, 2 H), 2.18 (s, 6 H), 1.58 (s, 3 H), 1.55 (s, 3 H)
ESI-MS m/z: 576.2 [M + H]$^+$

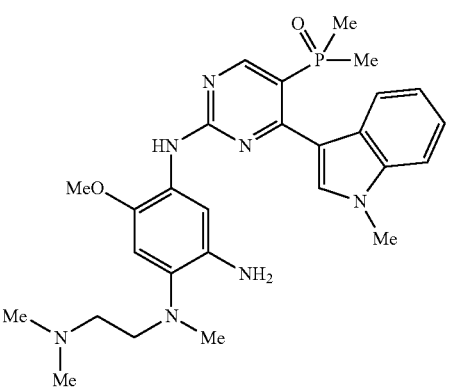

T35

97

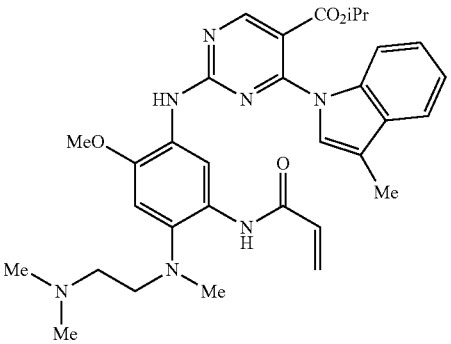

isopropyl 2-((5-acrylamido-4-((2-(dimethylamino)ethyl)(methyl)amino)-2-methoxyphenyl)amino)-4-(3-methyl-1H-indol-1-yl)pyrimidine-5-carboxylate $^1$H NMR: np
ESI-MS m/z: 576.2 [M + H]$^+$

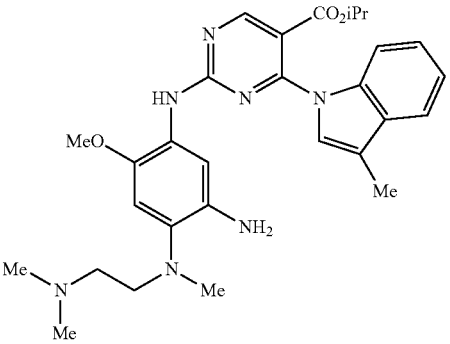

T36

TABLE 27-continued

| Ex. | Compound | Amine compound |
|---|---|---|
| 98 | N-(5-((5-cyano-4-(1-methyl-1H-indazol-3-yl)pyrimidin-2-yl)amino)-2-((2-(dimethylamino)ethyl)(methyl)amino)-4-methoxyphenyl)acrylamide<br>$^1$H NMR: (CDCl$_3$) δ 10.16 (s, 1H), 8.80 (m, 1H), 8.50 (d, 1H), 7.82 (m, 1H), 7.45 (m, 2H), 6.80 (m, 1H), 6.30 (m, 1H), 5.67 (d, 1H), 5.30 (m, 2H), 4.22 (s, 3H), 3.90 (s, 3H), 2.88 (m, 2H), 2.74 (s, 3H), 2.33 (m, 6H), 1.42 (m, 2H)<br>ESI-MS m/z: 526.2 [M + H]$^+$ | R50 |
| 99 | N-(2-((2-(dimethylamino)ethyl)(methyl)amino)-4-methoxy-5-((4-(1-methyl-1H-indol-3-yl)-5-(3-methylureido)pyrimidin-2-yl)amino)phenyl)acrylamide<br>$^1$H NMR: np<br>ESI-MS m/z: 572.2 [M + H]$^+$ | T37 |

TABLE 27-continued

| Ex. | Compound | Amine compound |
|---|---|---|
| 100 | 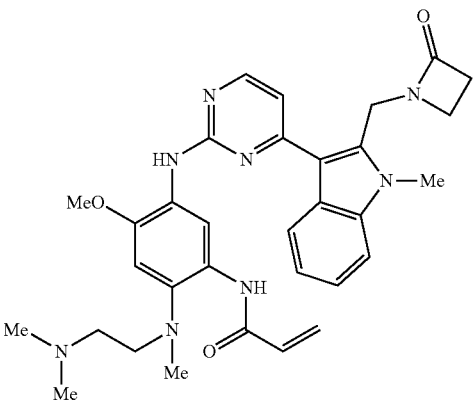 [SMILES: C=CC(=O)Nc1cc(Nc2nccc(-c3c(CN4CCC4=O)n(C)c4ccccc34)n2)c(OC)cc1N(C)CCN(C)C]<br>N-(2-((2-(dimethylamino)ethyl)(methyl)amino)-4-methoxy-5-((4-(1-methyl-2-((2-oxoazetidin-1-yl)methyl)-1H-indol-3-yl)pyrimidin-2-yl)amino)phenyl)acrylamide<br><sup>1</sup>H NMR: (MeOH-d$_4$) δ 8.88 (s, 1H), 8.41 (d, J = 5.27 Hz, 1H), 7.95 (d, J = 7.91 Hz, 1H), 7.48 (d, J = 8.28 Hz, 1H), 7.17-7.32 (m, 3H), 6.98 (s, 1H), 6.48-6.60 (m, 1H), 6.32-6.36 (m, 1H), 5.78 (dd, J = 1.57, 10.23 Hz, 1H), 5.08 (s, 2H), 3.92 (s, 3H), 3.82 (s, 3H), 3.05 (t, J = 6.02 Hz, 2H), 2.95 (t, J = 3.95 Hz, 2H), 2.79 (t, J = 3.95 Hz, 2H), 2.71 (s, 3H), 2.47 (t, J = 5.96 Hz, 2H), 2.31 (s, 6H)<br>ESI-MS m/z: 583.2 [M + H]<sup>+</sup> | 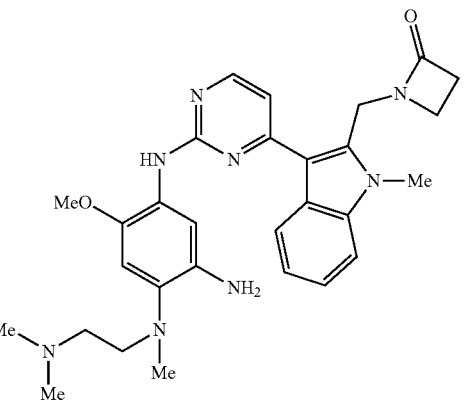<br>T38 |

Intermediate U1 tert-butyl (2-((2-acrylamido-5-methoxy-4-((4-(1-methyl-1H-indol-3-yl)pyrimidin-2-yl)amino)phenyl)(methyl)amino)ethyl)(methyl)carbamate

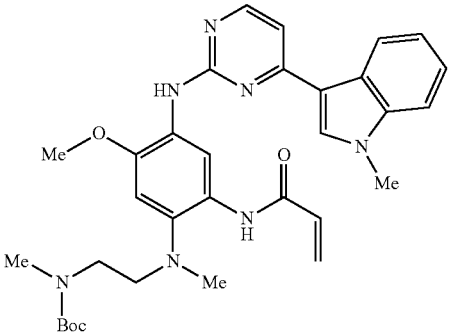

S3

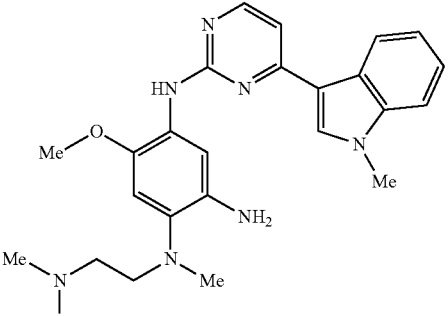

T1 tert-butyl (2-((2-acrylamido-5-methoxy-4-((4-(1-methyl-1H-indol-3-yl)pyrimidin-2-yl)amino)phenyl)(methyl)amino)ethyl)(methyl)carbamate was synthesized in analogous fashion to Example 1, except tert-butyl (2-((2-amino-5-methoxy-4-((4-(1-methyl-1H-indol-3-yl)pyrimidin-2-yl)amino)phenyl)(methyl)amino)ethyl)(methyl)carbamate (O3) was employed.

The following intermediate compounds, as shown in Table 28, were synthesized in analogous fashion to Example 1.

TABLE 28
| Intermediate U | Aniline |
|---|---|
| 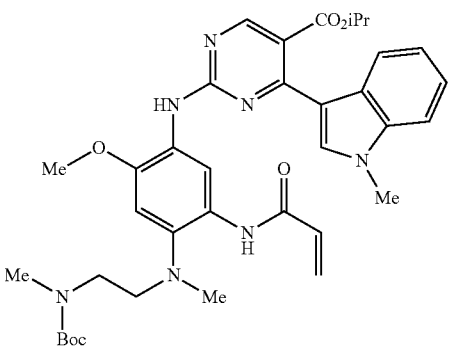<br>U2 | 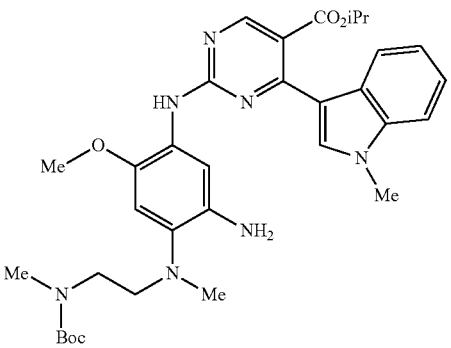<br>R46 |
| 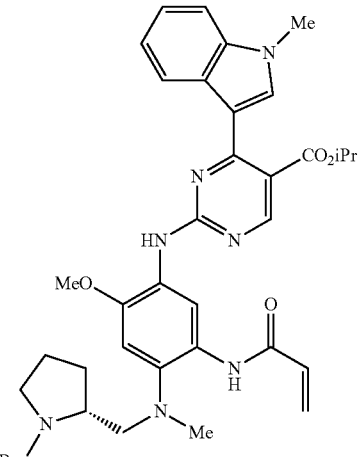<br>U3 | 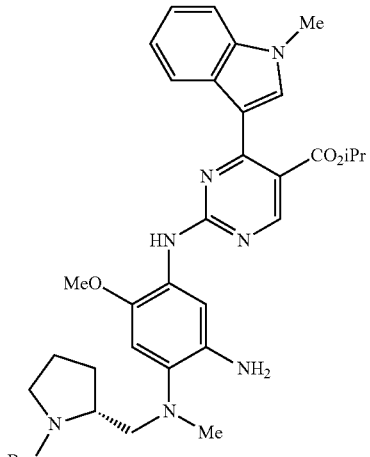<br>T14 |
| 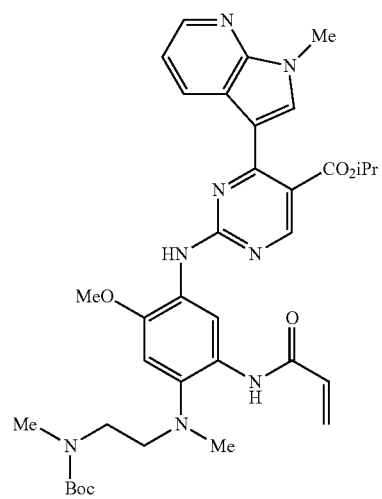<br>U4 | 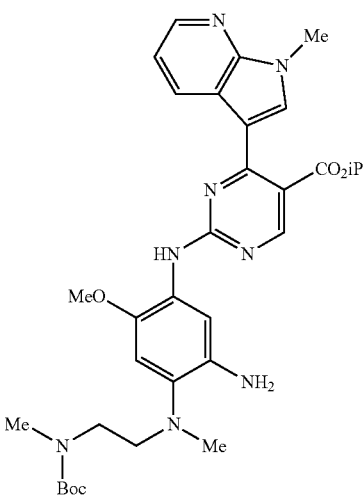<br>T15 |

Example 57

N-(4-methoxy-2-(methyl(2-(methylamino)ethyl)amino)-5-((4-(1-methyl-1H-indol-3-yl)pyrimidin-2-yl)amino)phenyl)acrylamide

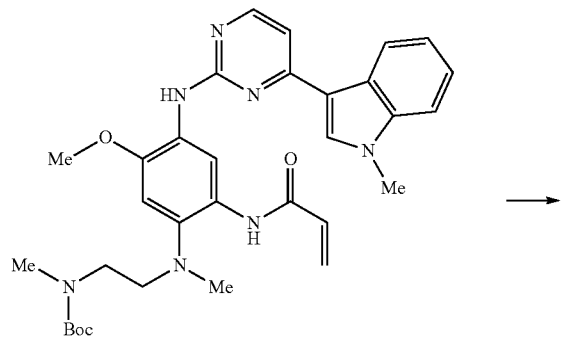

U1

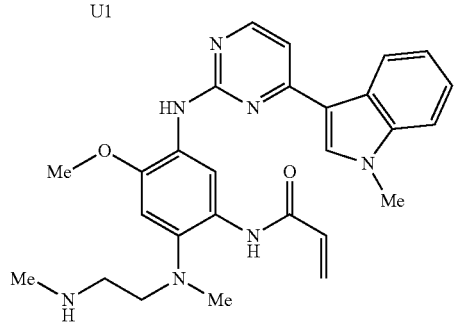

Example 57

To a solution of tert-butyl 2-((2-acrylamido-5-methoxy-4-(4-(1-methyl-1H-indol-3-yl)pyrimidin-2-ylamino)phenyl)(methyl)amino)ethyl(methyl)carbamate (U1) (130 mg, 0.22 mmol) in DCM (2 mL) was added TFA (1 mL). The mixture was stirred at rt for 10 min. Subsequently the mixture was concentrated in vacuo. The resulting residue was then diluted with DCM, washed with a saturated solution of potassium carbonate then brine, dried over sodium sulfate, filtered, and concentrated in vacuo. The resulting residue was purified by preparative thin layer chromatography on silica gel (5% MeOH/DCM) to afford N-(4-methoxy-2-(methyl(2-(methylamino)ethyl)amino)-5-((4-(1-methyl-1H-indol-3-yl)pyrimidin-2-yl)amino)phenyl)acrylamide (Example 57) as a yellow powder (52 mg, 48% yield). $^1$H-NMR (DMSO-$d_6$) δ 9.65 (s, 1H), 8.90 (br. s., 1H), 8.86 (s, 1H), 8.55 (s, 1H), 8.28-8.33 (m, 2H), 7.89 (s, 1H), 7.51 (d, 2H), 7.16-7.24 (m, 3H), 7.0 (m, 1H), 6.25-6.29 (d, 1H), 5.75 (m, 1H), 3.88 (s, 3H), 3.23 (m, 2H), 3.10 (m, 2H), 2.59 (s, 3H), 2.58 (s, 3H). MS m/z 574.5 [M+H]$^+$.

The following Example compounds, as shown in Table 29, were synthesized in analogous fashion to Example 57.

TABLE 29

| Example | Compound | Boc-protected Amine |
|---|---|---|
| 58 | isopropyl 2-((5-acrylamido-2-methoxy-4-(methyl(2-(methylamino)ethyl)-amino)phenyl)amino)-4-(1-methyl-1H-indol-3-yl)pyrimidine-5-carboxylate<br>$^1$H NMR: (CDCl$_3$) δ 7.82 (s, 1 H), 7.70 (br. s., 1 H), 7.33 (d, 1 H), 7.25 (d, 1 H), 7.18 (dd, 1 H), 7.00 (dd, 1 H), 6.53 (s, 1 H), 6.37 (d, 1 H), 5.70 (d, 1 H), 5.04 (m, 1 H), 3.87 (s, 6 H), 3.19 (s, 2 H), 2.84 (s, 2 H), 2.52 (s, 3 H), 2.44 (s, 3 H), 1.06 (d, 6 H)<br>MS m/z 573 [M + H]$^+$ | U2 |

TABLE 29-continued

| Example | Compound | Boc-protected Amine |
|---|---|---|
| 73 | 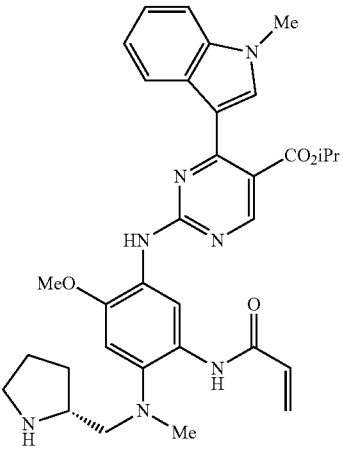<br>isopropyl 2-((5-acrylamido-2-methoxy-4-(methyl(2-(methylamino)ethyl)-amino)phenyl)amino)-4-(1-methyl-1H-indol-3-yl)pyrimidine-5-carboxylate<br>$^1$H NMR: (CDCl$_3$) δ 9.57 (br. s., 1H), 8.86 (s, 1H), 8.46 (br. s., 1H), 7.78 (s, 1H), 7.62 (br. s., 1H), 7.33 (d, J = 8.2 Hz, 1H), 7.22 (t, J = 7.1 Hz, 1H), 7.07-7.15 (m, 1H), 6.60-6.71 (m, 2H), 6.37 (d, J = 16.7 Hz, 1H), 5.64-5.73 (m, 1H), 5.01 (dt, J = 12.5, 6.2 Hz, 1H), 3.90 (s, 3H), 3.88 (s, 3H), 3.50 (m, 1H), 3.03-3.12 (m, 1H), 2.90-2.99 (m, 1H), 2.82 (br. s., 2H), 2.63 (s, 3H), 1.82-1.92 (m, 1H), 1.69-1.78 (m, 2H), 1.24-1.36 (m, 2H), 1.06 (d, J = 6.1 Hz, 6H)<br>ESI-MS m/z: 598.3 [M + H]$^+$ | 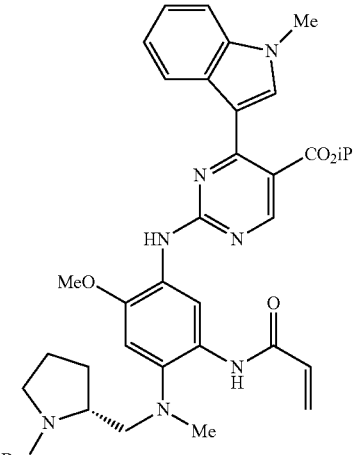<br>U3 |
| 74 | 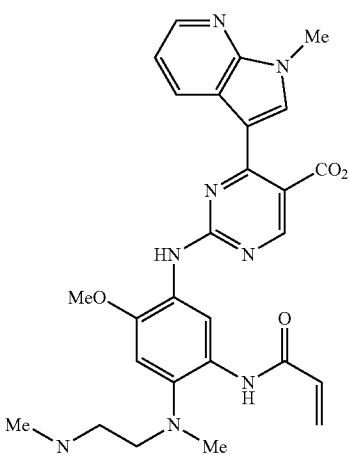<br>isopropyl 2-((5-acrylamido-2-methoxy-4-(methyl(2-(methylamino)ethyl)-amino)phenyl)amino)-4-(1-methyl-1H-pyrrolo[2,3-b]pyridin-3-yl)pyrimidine-5-carboxylate<br>$^1$H NMR: (CDCl$_3$) δ 9.61 (s, 1H), 8.89 (s, 1H), 8.71 (br. s., 1H), 8.54 (d, J = 4.4 Hz, 1H), 8.33 (dd, J = 4.6, 1.5 Hz, 1H), 7.93 (br. s., 1H), 7.87 (s, 1H), 7.09 (dd, J = 8.0, 4.7 Hz, 1H), 6.57-6.75 (m, 2H), 6.43 (dd, J = 16.9, 1.8 Hz, | 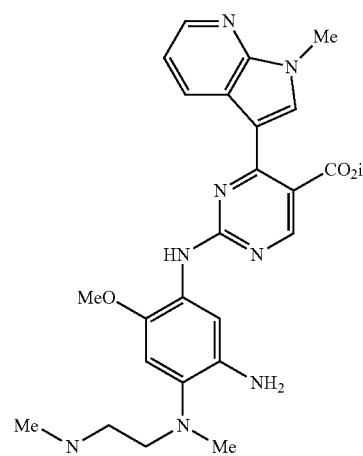<br>U4 |

TABLE 29-continued

| Example | Compound | Boc-protected Amine |
|---|---|---|
| | 1H), 5.65-5.77 (m, 1H), 5.05 (m, 1H), 4.00 (s, 3H), 3.87 (s, 3H), 2.86-3.02 (m, 2H), 2.73 (t, J = 5.3 Hz, 2H), 2.64 (s, 3H), 2.47 (s, 3H), 1.11 (d, J = 6.4 Hz, 6H) ESI-MS m/z: 573.3 [M + H]$^+$ | |

Biological Examples

Example 101: ASV & NPG EGFR Exon 20 Insertion Mutations

A compound's ability in selectively inhibiting EGFR exon 20 insertion mutations can be assessed using Ba/F3 cells, a murine pro-B cell line, which have been transduced with EGFR exon 20 insertions. An expression vector, pLVX-IRES puro (Clontech) coding for human EGFR exon 20 insertions NPG (H773_V774insNPG) or ASV (V769_D770insASV), was transfected into HEK293 cells by the Trans-Lentiviral ORF Packaging System (Thermo Scientific), to produce virus encoding EGFR exon 20 insertions. Ba/F3 (DSMZ) cells maintained in RPMI 1640 medium supplemented with 10% fetal bovine serum, 200 µM L-glutamine/l 200 µg/mL penicillin/200 µg/mL streptomycin (Life Technology) and 10 ng/mL IL-3 (R&D system), were infected by EGFR Exon20 virus and subsequently selected by puromycin (Life Technology) selection and IL-3 depletion. Ba/F3 cells expressing EGFR exon 20 insertions (named Ba/F3-EGFR-Exon20-NPG or Ba/F3-EGFR-Exon20-ASV) can proliferate in the absence of IL-3. The anti-proliferative activity of compounds were determined as follows: BaF3-EGFR-Exon20 cells (NPG or ASV) seeded in 96 well plates (2500 cells/well) were treated with test compound (dissolved in DMSO) at a series of concentrations (4-fold dilution, top concentration: 10,000 nM). The plates were incubated for 72 h in a 37° C. incubator with 5% $CO_2$, and the number of viable cells in each well were measured indirectly by CellTiter 96® Aqueous One Solution Cell Proliferation Assay (Promega) This assay is a colorimetric method for determining the number of viable cells through measurement of their metabolic activity by detection of enzymatic conversion of tetrazolium salts into blue formazan derivatives. Reagent (20 µL) was added into each well, and the plates were returned to the incubator for 2 h. The absorbance in each well was then measured at 490 nm using an Envision plate reader (Perkin Elmer). $IC_{50}$ values were calculated by determining the concentration of compound required to decrease the MTS signal by 50% comparing to the DMSO control in best-fit curves using Microsoft XLfit software or Accelrys Pipeline Pilot.

Example 102: EGFR Exon 19 Deletion and Exon 20 T790M Concurrent Mutations

A compound's ability in selectively inhibiting EGFR exon 19 deletion and T790M concurrent mutations can be assessed using Ba/F3 cells, a murine pro-B cell line, which have been transduced with EGFR exon 19 deletion and T790M mutation. An expression vector, pLVX-IRES puro (Clontech) coding for human EGFR E746-A750 deletion and T790M Mutation, was transfected into HEK293 cells by the Trans-Lentiviral ORF Packaging System (Thermo Scientific), to produce virus encoding EGFR exon 19 deletion and T790M mutations. Ba/F3 (DSMZ) cells maintained in RPMI 1640 medium supplemented with 10% fetal bovine serum, 200 µM L-glutamine/l 200 µg/mL penicillin/200 µg/mL streptomycin (Life Technology) and 10 ng/mL IL-3 (R&D system), were infected by EGFR E746-A750 deletion and T790M Mutation virus and subsequently selected by puromycin (Life Technology) selection and IL-3 depletion. Ba/F3 cells expressing EGFR E746-A750 deletion and T790M Mutation (named Ba/F3-EGFR-Del/T790M) can proliferate in the absence of IL-3. The anti-proliferative activity of compounds was determined as follows: BaF3-EGFR-Del/T790M cells seeded in 96 well plates (2500 cells/well) were treated with test compound (dissolved in DMSO) at a series of concentrations (4-fold dilution, top concentration: 10,000 nM). The plates were incubated for 72 h in a 37° C. incubator with 5% $CO_2$, and the number of viable cells in each well were measured indirectly by CellTiter 96® Aqueous One Solution Cell Proliferation Assay (Promega; this assay is a colorimetric method for determining the number of viable cells through measurement of their metabolic activity by detection of enzymatic conversion of tetrazolium salts into blue formazan derivatives). Reagent (20 µL) was added into each well, and the plates were returned to the incubator for 2 h. The absorbance in each well was then measured at 490 nm using an Envision plate reader (Perkin Elmer). $IC_{50}$ values were calculated by determining the concentration of compound required to decrease the MTS signal by 50% comparing to the DMSO control in best-fit curves using Microsoft XLfit software or Accelrys Pipeline Pilot.

Example 103: EGFR Exon 21 L858R and Exon 20 T790M Concurrent Mutations

A compound's ability in selectively inhibiting EGFR L858R and T790M concurrent mutations can be assessed using Ba/F3 cells, a murine pro-B cell line, which have been transduced with EGFR L858R and T790M double mutations. An expression vector, pLVX-IRES puro (Clontech) coding for human EGFR L858R and T790M double mutation, was transfected into HEK293 cells by the Trans-Lentiviral ORF Packaging System (Thermo Scientific), to produce virus encoding EGFR L858R and T790M double mutations. Ba/F3 (DSMZ) cells maintained in RPMI 1640 medium supplemented with 10% fetal bovine serum, 200 µM L-glutamine/l 200 µg/mL penicillin/200 µg/mL streptomycin (Life Technology) and 10 ng/mL IL-3 (R&D system), were infected by EGFR L858R and T790M double mutation virus and subsequently selected by puromycin (Life Technology) selection and IL-3 depletion. Ba/F3 cells expressing EGFR L858R and T790M double mutation (named Ba/F3-EGFR L858R/T790M) can proliferate in the absence of IL-3. The anti-proliferative activity of compounds was determined as follows: BaF3-EGFR L858R/T790M cells seeded in 96 well plates (2500 cells/well) were treated with test compound (dissolved in DMSO) at a series of concentrations (4-fold dilution, top concentration: 10,000 nM). The plates were incubated for 72 h in a 37° C. incubator with 5% $CO_2$, and the number of viable cells in each well were measured indirectly by CellTiter 96® Aqueous One Solution Cell Proliferation Assay (Promega; this assay is a colorimetric method for determining the number of viable cells through measurement of their metabolic activity by detection of enzymatic conversion of tetrazolium salts into blue formazan derivatives). Reagent (20 μL) was added into each well, and the plates were returned to the incubator for 2 h. The absorbance in each well was then measured at 490 nm using an Envision plate reader (Perkin Elmer). $IC_{50}$ values were calculated by determining the concentration of compound required to decrease the MTS signal by 50% comparing to the DMSO control in best-fit curves using Microsoft XLfit software or Accelrys Pipeline Pilot.

Example 104: HER2 Exon 20 YVMA Insertion Mutation

A compound's ability in selectively inhibiting Her2 exon 20 YVMA insertion mutations can be assessed using Ba/F3 cells, a murine pro-B cell line, which have been transduced with Her2 Exon20 YVMA insertions. An expression vector, pLVX-IRES puro (Clontech) coding for human EGFR exon 20 insertions YVMA (A775_G776ins YVMA), was transfected into HEK293 cells by the Trans-Lentiviral ORF Packaging System (Thermo Scientific), to produce virus encoding EGFR exon 20 insertions. Ba/F3 (DSMZ) cells maintained in RPMI 1640 medium supplemented with 10% fetal bovine serum, 200 μM L-glutamine/l 200 μg/mL penicillin/200 μg/mL streptomycin (Life Technology) and 10 ng/mL IL-3 (R&D system), were infected by EGFR Exon20 virus and subsequently selected by puromycin (Life Technology) selection and IL-3 depletion. Ba/F3 cells expressing Her2 Exon20 YVMA insertions (named Ba/F3-Her2 Exon20 YVMA) can proliferate in the absence of IL-3. The anti-proliferative activity of compounds was determined as follows: BaF3-Her2 Exon20 YVMA cells seeded in 96 well plates (2500 cells/well) were treated with test compound (dissolved in DMSO) at a series of concentrations (4-fold dilution, top concentration: 10,000 nM). The plates were incubated for 72 h in a 37° C. incubator with 5% $CO_2$, and the number of viable cells in each well were measured indirectly by CellTiter 96® Aqueous One Solution Cell Proliferation Assay (Promega; this assay is a colorimetric method for determining the number of viable cells through measurement of their metabolic activity by detection of enzymatic conversion of tetrazolium salts into blue formazan derivatives). Reagent (20 μL) was added into each well, and the plates were returned to the incubator for 2 h. The absorbance in each well was then measured at 490 nm using an Envision plate reader (Perkin Elmer). $IC_{50}$ values were calculated by determining the concentration of compound required to decrease the MTS signal by 50% comparing to the DMSO control in best-fit curves using Microsoft XLfit software or Accelrys Pipeline Pilot.

Table 30 provides the ASV and NPG insertion mutant exon 20 EGFR $IC_{50}$ data for exemplary compounds. $IC_{50}$ data on a DT mutation is provided, along with YVMA insertion mutant exon 20 HER2 $IC_{50}$ data for exemplary compounds. Group A compounds have an $IC_{50}$ value for the indicated mutant below about 100 nM. Group B compounds have an $IC_{50}$ value for the indicated mutant between about 100 to about 500 nM. Group C compounds have an $IC_{50}$ value for the indicated mutant between greater than about 500 to about 1 μM. Group D compounds have an $IC_{50}$ value for the indicated mutant greater than about 1 μM. "ND" indicates data not presented and should not be construed as the compound having any particular activity, such as, for example, Group D.

TABLE 30

| Ex. | EGFR exon 20 ASV insertion $IC_{50}$ | EGFR exon 20 NPG insertion $IC_{50}$ | EGFR exon 19 deletion and T790M mutation $IC_{50}$ | EGFR exon 21 L858R and T790M mutation $IC_{50}$ | Her2 exon 20 YVMA insertion $IC_{50}$ |
|---|---|---|---|---|---|
| 1 | ND | A | A | ND | B |
| 2 | A | A | A | ND | B |
| 3 | A | A | A | ND | B |
| 4 | B | A | B | ND | B |
| 5 | B | B | B | B | B |
| 6 | A | A | A | ND | B |
| 7 | B | A | A | A | B |
| 8 | A | A | A | ND | A |
| 9 | A | A | A | A | A |
| 10 | A | A | A | A | A |
| 11 | A | A | A | ND | A |
| 12 | D | D | D | ND | D |
| 13 | A | A | A | ND | A |
| 14 | A | A | A | ND | A |
| 15 | A | A | A | ND | A |
| 16 | A | A | A | ND | B |
| 17 | A | A | A | A | A |
| 18 | D | B | A | ND | D |
| 19 | B | A | A | ND | C |
| 20 | B | A | A | ND | C |
| 21 | C | A | A | ND | C |
| 22 | B | A | A | ND | B |
| 23 | B | A | A | ND | C |
| 24 | B | A | A | A | C |
| 25 | ND | B | A | ND | C |
| 26 | ND | C | A | ND | D |
| 27 | ND | C | A | ND | D |
| 28 | A | A | A | ND | B |
| 29 | A | A | A | ND | A |
| 30 | A | A | A | A | A |
| 31 | A | A | A | ND | A |
| 32 | A | A | A | ND | A |
| 33 | ND | B | A | ND | C |
| 34 | A | A | A | A | A |
| 35 | A | A | A | A | A |
| 36 | A | A | A | A | A |
| 37 | A | A | A | ND | B |
| 38 | A | A | A | ND | A |
| 39 | B | A | D | ND | D |
| 40 | B | B | C | ND | D |
| 41 | C | B | D | ND | D |
| 42 | D | D | D | ND | D |
| 43 | ND | A | A | ND | B |
| 44 | ND | B | A | ND | C |
| 45 | ND | B | A | ND | C |
| 46 | ND | B | A | ND | C |
| 47 | ND | B | A | ND | C |
| 48 | ND | A | A | ND | C |
| 49 | ND | B | A | ND | C |
| 50 | ND | D | A | ND | D |
| 51 | B | A | A | ND | B |
| 52 | A | A | A | A | B |
| 53 | ND | B | A | ND | C |
| 54 | ND | C | A | ND | D |
| 55 | D | B | A | ND | D |
| 56 | A | A | A | A | A |
| 57 | B | A | A | A | B |
| 58 | A | A | A | A | A |
| 59 | A | A | A | ND | A |
| 60 | A | A | A | ND | D |
| 61 | A | A | A | ND | B |
| 62 | A | A | A | ND | B |
| 63 | A | A | A | ND | C |
| 64 | A | A | A | ND | A |
| 65 | A | A | A | ND | A |
| 66 | A | A | A | A | A |

TABLE 30-continued

| Ex. | EGFR exon 20 ASV insertion IC$_{50}$ | EGFR exon 20 NPG insertion IC$_{50}$ | EGFR exon 19 deletion and T790M mutation IC$_{50}$ | EGFR exon 21 L858R and T790M mutation IC$_{50}$ | Her2 exon 20 YVMA insertion IC$_{50}$ |
|---|---|---|---|---|---|
| 67 | A | A | A | A | A |
| 68 | B | A | A | ND | C |
| 69 | B | A | A | ND | C |
| 70 | A | ND | A | A | B |
| 71 | A | ND | A | A | B |
| 72 | A | ND | A | A | B |
| 73 | A | A | A | A | A |
| 74 | A | A | A | B | B |
| 75 | D | C | B | ND | D |
| 76 | A | A | A | ND | A |
| 77 | A | A | A | A | A |
| 78 | A | A | A | ND | A |
| 79 | A | A | A | ND | B |
| 80 | D | D | D | ND | D |
| 81 | B | A | A | ND | C |
| 82 | B | A | A | ND | B |
| 83 | B | ND | A | A | B |
| 84 | C | ND | A | A | C |
| 85 | B | ND | A | A | B |
| 86 | A | ND | A | A | C |
| 87 | B | ND | A | A | C |
| 88 | A | ND | A | A | B |
| 89 | A | ND | A | A | B |
| 90 | B | ND | A | A | C |
| 91 | B | ND | A | B | C |
| 92 | A | ND | A | A | B |
| 93 | C | ND | B | C | D |
| 94 | A | A | A | ND | A |
| 95 | A | ND | A | A | B |
| 96 | D | ND | B | B | D |
| 97 | B | A | A | ND | B |
| 98 | A | A | A | ND | A |
| 99 | C | ND | D | D | D |
| 100 | ND | ND | ND | ND | ND |

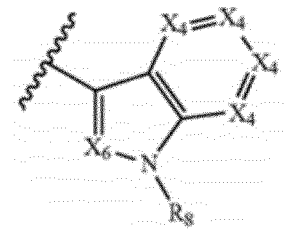

What is claimed is:

1. A compound selected from:

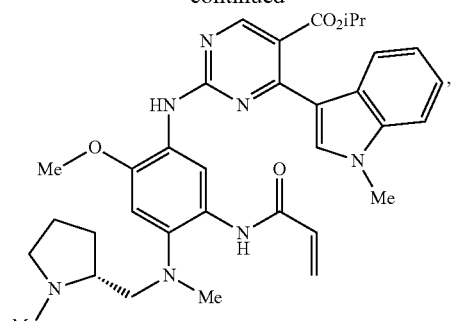

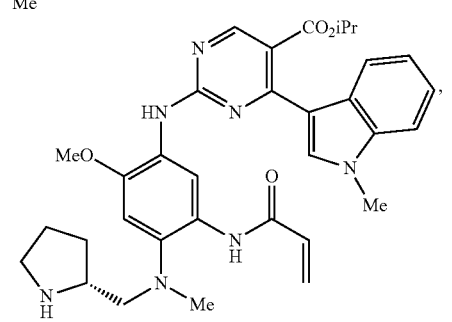

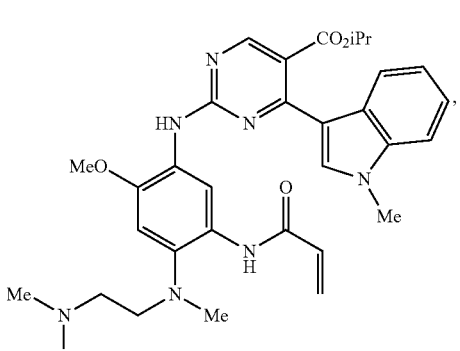

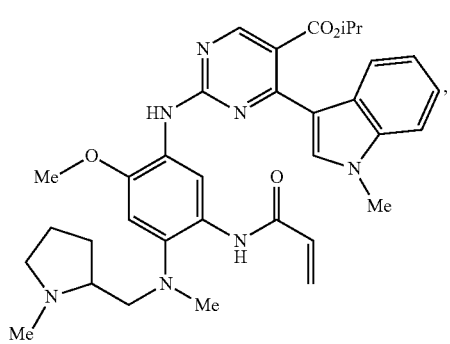

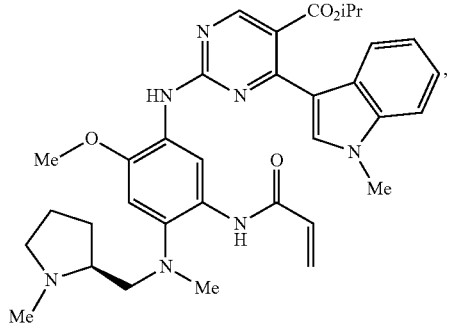

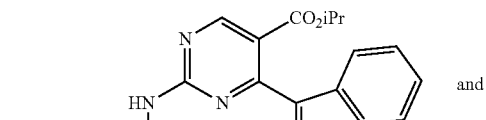

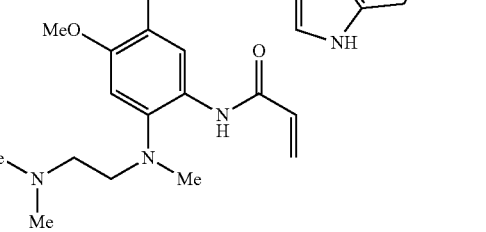

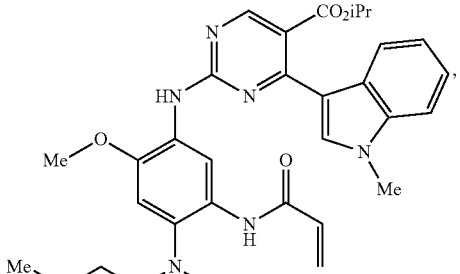

or a pharmaceutically acceptable salt thereof.

2. The compound or pharmaceutically acceptable salt of claim 1, which is

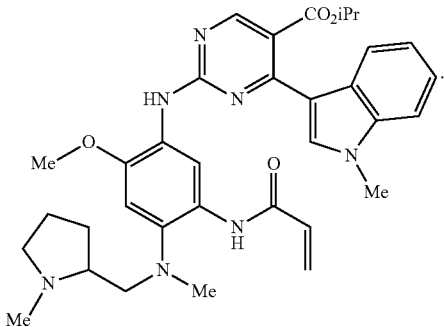

3. The compound or pharmaceutically acceptable salt of claim 1, which is

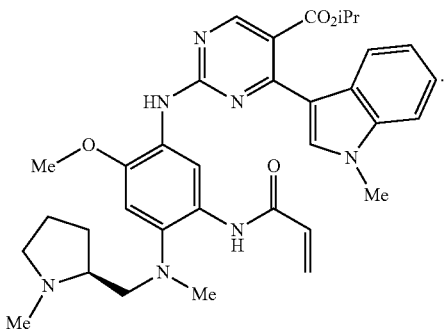

4. The compound or pharmaceutically acceptable salt of claim 1, which is

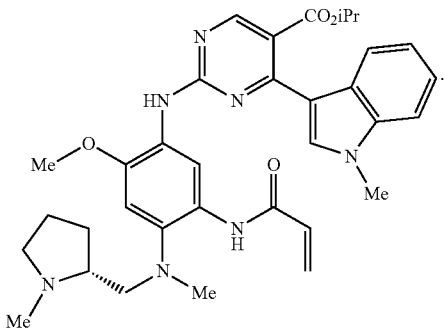

5. The compound or pharmaceutically acceptable salt of claim 1, which is

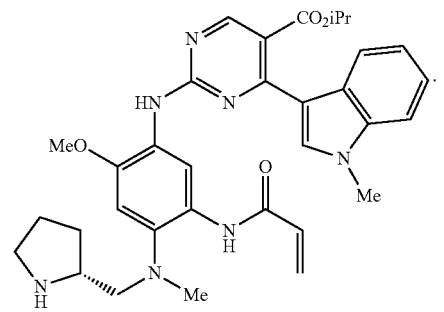

6. The compound or pharmaceutically acceptable salt of claim 1, which is

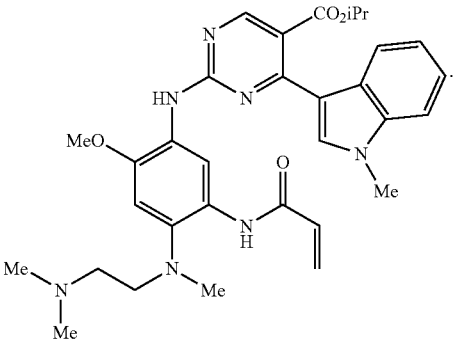

7. The compound or pharmaceutically acceptable salt of claim 1, which is

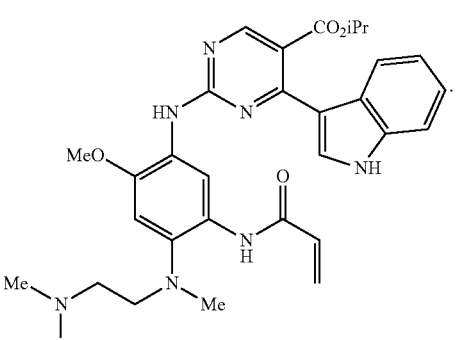

8. The compound or pharmaceutically acceptable salt of claim 1, which is

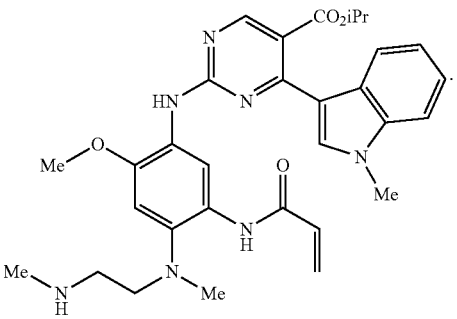

9. A pharmaceutical composition comprising a therapeutically effective amount of the compound of claim 2, or a pharmaceutically acceptable salt thereof, and a pharmaceutically acceptable carrier.

10. A pharmaceutical composition comprising a therapeutically effective amount of the compound of claim 3, or a pharmaceutically acceptable salt thereof, and a pharmaceutically acceptable carrier.

11. A pharmaceutical composition comprising a therapeutically effective amount of the compound of claim 4, or a pharmaceutically acceptable salt thereof, and a pharmaceutically acceptable carrier.

12. A pharmaceutical composition comprising a therapeutically effective amount of the compound of claim 5, or a pharmaceutically acceptable salt thereof, and a pharmaceutically acceptable carrier.

13. A pharmaceutical composition comprising a therapeutically effective amount of the compound of claim 6, or a pharmaceutically acceptable salt thereof, and a pharmaceutically acceptable carrier.

14. A pharmaceutical composition comprising a therapeutically effective amount of the compound of claim 7, or a pharmaceutically acceptable salt thereof, and a pharmaceutically acceptable carrier.

15. A pharmaceutical composition comprising a therapeutically effective amount of the compound of claim 8, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 9,796,712 B2
APPLICATION NO. : 15/600023
DATED : October 24, 2017
INVENTOR(S) : Wei-Shengh Huang et al.

Page 1 of 2

It is certified that error appears in the above-identified patent and that said Letters Patent is hereby corrected as shown below:

In the Specification

At Column 133, Lines 45-50:
The structure on the left reads as:   it should read as:

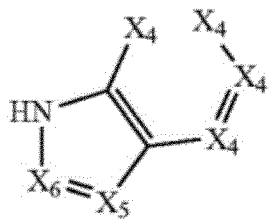   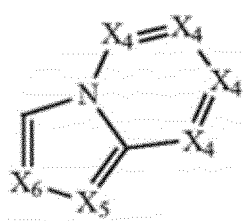

At Column 133, Lines 45-50:
The structure on the right reads as:   it should read as:

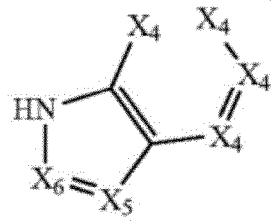   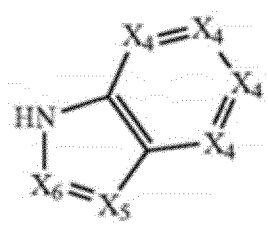

At Column 133, Lines 51-58:
The structure reads as:   it should read as:

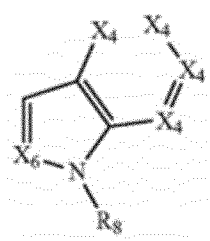   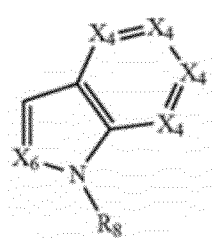

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 9,796,712 B2

At Column 134, Lines 34-40:
The structure reads as:

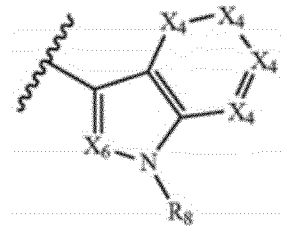

it should read as: